United States Patent [19]
Simons et al.

[11] Patent Number: 6,051,374
[45] Date of Patent: Apr. 18, 2000

[54] NON-A, NON-B, NON-C, NON-D, NON-E HEPATITIS REAGENTS AND METHODS FOR THEIR USE

[75] Inventors: John N. Simons, Grayslake; Tami J. Pilot-Matias, Green Oaks; George J. Dawson, Libertyville; George G. Schlauder, Skokie; Suresh M. Desai, Libertyville, all of Ill.; Thomas P. Leary; Anthony Scott Muerhoff, both of Kenosha, Wis.; James Carl Erker, Hainesville, Ill.; Sheri L. Buijk, Round Lake, Ill.; Isa K. Mushahwar, Grayslake, Ill.

[73] Assignee: Abbott Laboratories, Abbott Park, Ill.

[21] Appl. No.: 08/488,445

[22] Filed: Jun. 7, 1995

Related U.S. Application Data

[63] Continuation-in-part of application No. 08/377,557, Jan. 30, 1995, abandoned, which is a continuation-in-part of application No. 08/344,185, Nov. 23, 1994, abandoned, and application No. 08/344,190, Nov. 23, 1994, abandoned, which is a continuation-in-part of application No. 08/283,314, Jul. 29, 1994, abandoned, which is a continuation-in-part of application No. 08/242,654, May 13, 1994, abandoned, which is a continuation-in-part of application No. 08/196,030, Feb. 14, 1994, abandoned, said application No. 08/344,185, is a continuation-in-part of application No. 08/283,314.

[51] Int. Cl.[7] .............................. C12Q 1/70; C12P 19/34; C07H 21/02; C07H 21/04
[52] U.S. Cl. ................................ 435/5; 435/6; 435/91.2; 435/21.52; 435/810; 536/23.1; 536/24.32
[58] Field of Search ................................... 435/6, 5, 91.2, 435/91.52, 91.51, 91.5, 91.21, 810; 536/23.1, 24.32; 935/6, 77, 78

[56] References Cited

U.S. PATENT DOCUMENTS

| | | | |
|---|---|---|---|
| 4,743,535 | 5/1988 | Carrico | 435/6 |
| 4,876,187 | 10/1989 | Dick et al. | 435/6 |
| 5,275,947 | 1/1994 | Arima et al. | 435/252.33 |
| 5,399,346 | 3/1995 | Anderson et al. | 424/93.21 |
| 5,527,669 | 6/1996 | Resnick et al. | 435/5 |
| 5,576,302 | 11/1996 | Cook et al. | 514/44 |
| 5,766,840 | 6/1998 | Kim et al. | 435/5 |

FOREIGN PATENT DOCUMENTS

| | | |
|---|---|---|
| 0318216 | 5/1989 | European Pat. Off. |
| 9000597 | 1/1990 | WIPO |
| 9408002 | 4/1994 | WIPO |
| 9418217 | 8/1994 | WIPO |
| 9532290 | 11/1995 | WIPO |
| 9532291 | 11/1995 | WIPO |
| 9532292 | 11/1995 | WIPO |
| 9506266 | 5/1996 | WIPO |

OTHER PUBLICATIONS

T. Peters et al., Frequency of Hepatitis C in Acute Post–Transfusion Hepatitis After Open–Heart Surgery: A Prospective Study in 1,476 Patients, *Journal of Medical Virology* vol. 39: 139–145 (1993).

R. Purcell, The Discovery of the Hepatitis Viruses, *Gastroenterology* vol. 104 No. 4: 955–963 (1993).

G. Dawson et al., Solid–phase enzyme–linked immunosobent assay for hepatitis E virus IgG and IgM antibodies utilizing recombinant antigens and synthetic peptides, *Journal of Virological Methods* vol. 38: 175–186 (1992).

P. Yarbough et al., Hepatitis E Virus: Identification of Type–Common Epitopes, *Journal of Virology* vol. 65 No. 11: p. 5790–5797 (1991).

H. Alter et al., Detection of Antibody to Hepatitis C Virus in Prospectively Followed Transfusion Recipients with Acute and Chronic Non–A, Non–B Hepatitis, *The New England Journal of Medicine* vol. 321 No. 22: p. 1494–1500 (1989).

M. Alter et al., Risk Factors for Acute Non–A, Non–B Hepatitis in the United States and Association With Hepatitis C Virus Infection, *JAMA* vol. 264 No. 17: p. 2232–2235 (1990).

J. Dienstag, Hepatitis Non–A, Non–B: C at Last, *Gastroenterology* vol. 99 No. 4: p. 1177–1180 (1990).

G. Reyes et al., Isolation of a cDNA from the Virus Responsible for Enterically Transmitted Non–A, Non–B Hepatitis, *Science* vol. 247 : p. 1335–1339 (1990).

G. Kuo et al., An Assay for Circulating Antibodies to a Major Etiologic Virus of Human Non–A, Non–B Hepatitis, *Science* vol. 244 : p. 362–364 (1989).

A. Weiner et al., Detection of hepatitis C viral sequences in non–A, non–B hepatitis, *The Lancet* vol. 335: p. 1–3 (1990).

G. Schlauder et al., Viraemia in Egyptian children with hepatitis E virus infection, *The Lancet* vol. 341: p. 378 (1993).

N. Lisitsyn et at., Cloning the Differences Between Two Complex Genomes, *Science* vol. 259: p. 946–951 (1993).

V. Thiers et al., Post–transfusional anti–HCV–negative non–A non–B hepatitis (II) serological and polymerase chain reaction analysis for hepatitis C and hepatitis B viruses, *Journal of Hepatology* vol. 18: p. 34–39 (1993).

Hepatitis C virus upstanding, *The Lancet* vol. 335: p. 1431–1432 (1990).

W. Parks et al., Attempted Isolation of Hepatitis Viruses in Marmosets, *The Journal of Infectious Diseases* vol. 120 No. 5: 539–547 (1969).

A. Holmes et al., Specific Neutralization of Human Hepatitis Type A in Marmoset Monkeys, *Nature* vol. 243: p. 419–420 (1973).

(List continued on next page.)

*Primary Examiner*—Stephanie Zitomer
*Attorney, Agent, or Firm*—Cheryl L. Becker; Dianne Casuto; Priscilla Porembski

[57] ABSTRACT

Hepatitis GB Virus (HGBV) nucleic acid and amino acid sequences useful for a variety of diagnostic and therapeutic applications, kits for using the HGBV nucleic acid or amino acid sequences, HGBV immunogenic particles, and antibodies which specifically bind to HGBV. Also provided are methods for producing antibodies, polyclonal or monoclonal, from the HGBV nucleic acid or amino acid sequences.

35 Claims, 49 Drawing Sheets

OTHER PUBLICATIONS

P. Provost et al., Physical, Chemical and Morphologic Dimensions of Human Hepatitis A Virus Strain CR326 (38578), *Proceeding of the Society for Experimental Biology and Medicine* vol. 148: p. 532–539 (1975).

Q. Choo et al., Isolation of a cDNA Clone Derived from a Blood–Borne Non–A, Non–B Viral Hepatitis Genome, *Science* vol. 244: p. 359–361 (1989).

J. Almeida et al., Morphology of the GB hepatitis agent, *Nature* vol. 261: p. 608–609 (1976).

F. Deinhardt et al., Studies on the Transmission of Human Viral Heptitis to Marmoset Monkeys, *Journal of Experimental Medicine* vol. 125: p. 673–688, Plate 81–86 (1966).

J. Dienstag, Non–A, Non–B Hepatitis. II. Experimental Transmission, Putative Virus Agents and Markers, and Prevention, *Gastroenterology* vol. 85 No. 3: p. 743–768 (1983).

F. Hollinger et al., Transfusion–Transmitted Viruses Study: Experimental Evidence for Two Non–A, Non–B Hepatitis Agents, *Journal of Infectious Diseases* vol. 142 No. 3: p. 400–407 (1980).

D. Bradley, Transmission, Etiology, and Pathogenesis of Viral Hepatitis Non–A, Non–B in Non–Human Primates, *Advances in Hepatitis Research*: p. 268–280 (1984).

F. Deinhardt et al., Hepatitis in marmosets, *The American Journal of the Medical Sciences* vol. 270: p. 73–80 (1975).

S. Kalter, Comparison of Infectivity of Human Non–A/Non–B Hepatitis and the GB Hepatitis Agent in Marmosets, *Viral and Immunological Diseases in Nonhuman Primates;*: p. 221–224 (1983).

E. Tabor et al., Transmission of Human Non–A, Non–B Hepatitis to Chimpanzees Following Failure to Transmit GB Agent Hepatitis, *Journal of Medical Virology:* p. 103–108 (1980).

D. Bradley et al., Posttransfusion Non–A, Non–B Hepatitis: Physicochemical Properties of Two Distinct Agents, *The Journal of Infectious Diseases* vol. 148 No. 2: p. 254–265 (1983).

J. Dienstag, Virus–like particles and GB agent hepatitis, *Nature* vol. 264: p. 260–261 (1976).

P. Karayiannis et al., Studies of GB Hepatitis Agent in Tamarins, *Hepatology* vol. 9 No. 2: p. 186–192 (1989).

J. Melnick, Classification of Hepatitis A Virus as Enterovirus Type 72 and of Hepatitis B Virus as Hepadnavirus Type 1, *Intervirology* vol. 18: p. 105–106 (1982).

W. Parks et al., Characterization of Marmoset Hepatitis Virus, *The Journal of Infectious Diseases* vol. 120 No. 5: p. 548–559 (1969).

S. Feinstone et al., Hepatitis A: Detection by Immune Electron Microscopy of a Viruslike Antigen Associated with Acute Illness, *Science* vol. 182: p. 1026–1028 (1973).

E. Tabor et al., Lack of Susceptibility of Marmosets to Human Non–A, Non–B Hepatitis, *The Journal of Infectious Diseases* vol. 140 No. 5: p. 794–797 (1979).

E. Fagan et al., Toga Virus–Like Particles in Acute Liver Failure Attributed to Sporadic Non–A, Non–B Hepatitis and Recurrence After Liver Transplantation, *Journal of Medical Virology* vol. 38: p. 71–77 (1992).

J. Dienstag, Virus particles in marmoset hepatitis, *Nature* vol. 267: p. 729–730 (1977).

F. Deinhardt et al., Hepatitis in Marmosets, *The Journal of Infectious Diseases* vol. 121 No. 3: p. 351–354 (1970).

F. Deinhardt et al., The Mythology of Various Hepatitis A Virus Isolates, *International Symposium on Viral Hepatitis*: p. 390–404 (1975).

M. Alter et al., The Natural History of Community–Acquired Hepatitis C in the United States, *The New England Journal of Medicine* vol. 327 No. 27: p. 1899–1905 (1992).

R. Gibbs, Polymerase chain reaction techniques, *Analytical Biotechnology*: p. 69–75 (1991).

S. Friedman et al., The core element of the EcoRII methylase as defined by protease digestion and deletion analysis, *Nucleic Acids Research* vol. 19 No. 19: p. 5403–5408 (1991).

A. Rosenthal et al., Genomic walking and sequencing by oligo–cassette mediated polymerase chain reaction, *Nucleic Acids Research* vol. 18 No. 10: p. 3095–3096 (1990).

A. Akowitz, Protected endogenous retroviral sequences copurify with infectivity in experimental Creutzfeldt–Jakob disease, *Archives of Virology* vol. 130: p. 301–316 (1993).

Non–A, Non–B?, *The Lancet* vol. 2: p. 64–65 (1975).

F. Hollinger, Non–A, Non–B Hepatitis Viruses, *Virology* : p. 2239–2273 (1990).

J. Dienstag, Non–A, Non–B Hepatitis I. Recognition, Epidemiology, and Clinical Features, *Gastroenterology* vol. 85 No. 2: p. 439–462 (1983).

J. Strauss et al., Structure and Function of the Flavivirus and Pestivirus Genomes, *Viral Hepatitis and Liver Disease*: p. 333–344 (1990).

H. Alter et al., Posttransfusion Hepatitis After Exclusion of Commercial and Hepatitis–B Antigen–Positive Donors, *Annals of Internal Medicine* vol. 77 No. 5: p. 691–699 (1972).

H. Alter et al., Clinical and Serological Analysis of Transfusion–Associated Hepatitis, *The Lancet*: p. 838–841 (1975).

S. Feinstone et al., Transfusion–Associated Hepatitis Not Due To Viral Hepatitis Type A or B, *The New England Journal of Medicine* vol. 292 No. 15: p. 767–770 (1975).

J. Simons et al., Indentification of two flavivirus–like genomes in the GB Hepatitis agent, *Proc. Natl. Acad. Sci. USA* vol. 92: p. 3401–3405 (1995).

J. Simons et al., Isolation of novel virus–like sequences associated with human hepatitis, *Nature Medicine* vol. 1 No. 6: p. 564–568 (1995).

G. Schlauder et al., Molecular and Serologic Analysis in the Transmission of the GB Hepatitis Agents, *Journal of Medical Virology* vol. 46: p. 81–90 (1995).

M. Yoshiba et al., Detection of the GBV–C hepatitis virus genome in serum from patients with fulminant hepatitis of unknown aetiology, *The Lancet* vol. 346: p. 1131–1132 (1995).

J. Linnen et al., Molecular Cloning and Disease Association of Hepatitis G Virus: A Transfusion–Transmissible Agent, *Science* vol. 271: p. 505–508 (1996).

A. Zuckerman, The new GB hepatitis viruses, *The Lancet* vol. 345: p. 1453–1455 (1995).

L. Altman, Three Newly Discovered Viruses May Cause Unexplained Hepatitis, *The New York Times Medical Science,* Apr. 11, 1995.

L. Altman, Newly Found Viruses May Cause Hepatitis, *The New York Times Medical Science*, Apr. 10, 1995.

T. Leary et al., Sequence and Genomic Organization of GBV–C: A novel Member of the Flaviviridae Associated With Human Non–A–E Hepetitis, *Journal of Medical Virology* vol. 48: p. 80–87 (1996).

G. Caetano–Anolles et al., DNA Amplification Fingerprinting Using Arbitrary Oligonucleotide Primers, *Applied Biochemistry and Biotechnology* vol. 42: p. 189–200 (1993).

B. Bassam, DNA amplification fingerprinting of bacteria, *Applied Microbiology and Biotechnology* vol. 38: p. 70–76 (1992).

G. Caetano–Anolles et al., DNA Amplification Fingerprinting Using Very Short Arbitrary Oligonucleotide Primers, *Biotechnology* vol. 9: p. 553–557 (1991).

J. Welsh et al., Fingerprinting genomes using PCR with arbitrary primers*, *Nucleic Acids Research* vol. 18 No. 24: p. 7213–7218 (1990).

J. Welsh et al., Arbitrarily primed PCR fingerprinting of RNA, *Nucleic Acids Research* vol. 20 No. 19: p. 4965–4970 (1992).

J. Williams et al., DNA polymorphisms amplified by arbitrary primers are useful as genetic markers, *Nucleic Acids Research* vol. 18 No. 22: p. 6531–6535 (1990).

P. Liang et al., Differential Display of Eukaryotic Messenger RNA by Means of the Polymerase Chain Reaction, *Science* vol. 257: p. 967–971 (1992).

P. Liang et al., Distribution and cloning of eukaryotic mRNAs by means of differential display: refinements and optimization, *Nucleic Acids Research* vol. 21 No. 14: p. 3269–3275 (1993).

Chan et al. J. Gen. Virol. 73:1131–1141, May 1992.

Takamizawa et al., Journal of Virology 65(3):1105–1113, Mar. 1991.

A. Muerhoff et al., *Journal of Virology*, 69 (9), 5621–5630 (1995).

Gura, *Science*, vol. 270, pp. 575–577 (1995).

Brown, *Washington Post*, pp. 1 & A22 (Dec. 8, 1995).

Choo et al., *Proc. Natl. Acad. Sci. USA*, vol. 88, pp. 2451–22455 (1991).

Okamoto et al., "Polyprotein precursor—hepatitis C virus", EMBL Sequence Accession No. S40770, Submitted Mar. 1992.

Okamoto et al., *Virology*, vol. 188, pp. 331–341 (1992).

S. K. Kuwada et al., *The American Journal of Gastroenterology*, vol. 89, No. 1, pp 57–61 (1994).

A. S. Muerhoff et al., *Journal of Virological Methods*, vol. 62, No. 1, pp. 55–62 (1996).

S. Vijayasarathy, *Nucleic Acids Research*, vol. 18, pp. 2967–2975 (1990).

P. Tijssen, "Practice and Theory of Enzyme Immunoassays", Elsevier, Amsterdam pp. 333–340 (1985).

U.S. application No. 08/389,886, J. Kim et al., filed Jan. 15, 1995, issued Nov. 1994.

U.S. application No. 08/357,509, J. Kim et al., filed Dec. 16, 1994, issued Sep. 1994.

U.S. application No. 08/344,271, K. Fry et al., filed Nov. 23, 1994, issued Jun. 1994.

U.S. application No. 08/329,729, J. Kim et al., filed Oct. 26, 1994, issued Sep. 1994.

U.S. application No. 08/285,558, J. Kim et al., filed Aug. 3, 1994, issued May 1994.

U.S. application No. 08/246,985, J. Kim et al., filed May 20, 1994, issued Mar. 1994.

```
Contig B SEQ ID# 166(1297)  MYL..TGRCS RNYDVIICDE CHATDRTTVL GIGKVLTEAP SKNVRLVVLA
HCV-1    SEQ ID# 179(1298)  KFLADGGCSG GAYDIIICDE CHSTDATSIL GIGTVLDQAE TAGARLVVLA
Contig A SEQ ID# 157(1407)  RFMANPRKYL RGNDVICDE LHVTDPTSIL GMGRARLLAR ECGVRLLLFA
         Consensus          ---------- ---D--ICDE -H-TD-T--L G-G------A- ----RL---A
                                          **   *

Contig B SEQ ID# 166(1345)  TATPPGVIPT PHANITEIQL TDEGTIPFHG KKIKEENLKK GRHLIFEATK
HCV-1    SEQ ID# 179(1348)  TATPPGSVTV PHPNIEEVAL STTGEIPFYG KAIPLEVIKG GRHLIFCHSK
Contig A SEQ ID# 157(1457)  TATPPVSPMA KHESIHEEML GSEGEVPFYC QFLPLSRYAT GRHLLFCHSK
         Consensus          TATPP----- -H--I-E--L ---G--PF-- ---------- GRHL-F---K
                            ***                       *

Contig B SEQ ID# 166(1395)  KHCDELANEL ARKGITAVSY YRGCDISKMP .EGDCVVVAT DALCTGYTGD
HCV-1    SEQ ID# 179(1398)  KKCDELAAKL VALGINAVAY YRGLDVSVIP TSGDVVVVAT DALMTGYTGD
Contig A SEQ ID# 157(1507)  VECTRLSSAL ASFGVNTVVY FRGKETDI.. PTGDVCVCAT DALSTGYTGN
         Consensus          --C--L---L ---G---V-Y -RG------- --GD--V-AT DAL-TGYTG-
                                *                                    *

Contig B SEQ ID# 166(1444)  FDSVYDCSLM VEGTCHVDLD PTFTMGVRVC GVSAIVKGQR RGRTGRGRAG
HCV-1    SEQ ID# 179(1448)  FDSVIDCNTC VTQTVDFSLD PTFTIETITL PQDAVSRTQR RGRTGRGKPG
Contig A SEQ ID# 157(1555)  FDTVTDCGLM VEEVEVTLD PTITIGVKTV PAPAELRAQR RGRCGRGKAG
         Consensus          FD-V-DC--- V-------LD PT-T------ ---A----QR RGR-GRG--G
                            *                                         *  ** **
```

FIG. 24A

```
Contig B SEQ ID# 166(2599)  AAKLSDQHRA GIHTIARQYH AGGPMIAYDG REIGYRRCRS SGVYTTSSSN
HCV-1    SEQ ID# 180(2662)  CCDLDPQARV AIKSLTERLY VGGPLTNSRG ENCGYRRCRA SGVLTTSCGN
Contig A SEQ ID# 157(2798)  AA...SDNPS MVHALC.KKY SGGPMVSPDG VPLGYRQCRS SGVLTTSSAN
                 Consensus  ---------- ---------- -GGP-----G ---GYR-CR- SGV-TTS--N
                                                                        *   *   *

Contig B SEQ ID# 166(2649)  SLTCWLKVNA AAEQAGMKNP RFLICGDDCT VIWKSAGADA DKQAMRVFAS
HCV-1    SEQ ID# 180(2712)  TLTCYIKARA ACRAAGLQDC TMLVCGDDLV VICESAGVQE DAASLRAFTE
Contig A SEQ ID# 157(2844)  SITCYIKVSA ACRRVGIKAP SFFIAGDDCL IIYENDGTDP CPALKAALAN
                 Consensus  --TC--K--A A----G---- -----GDD-- -I----G--- ----------
                                                      ***
```

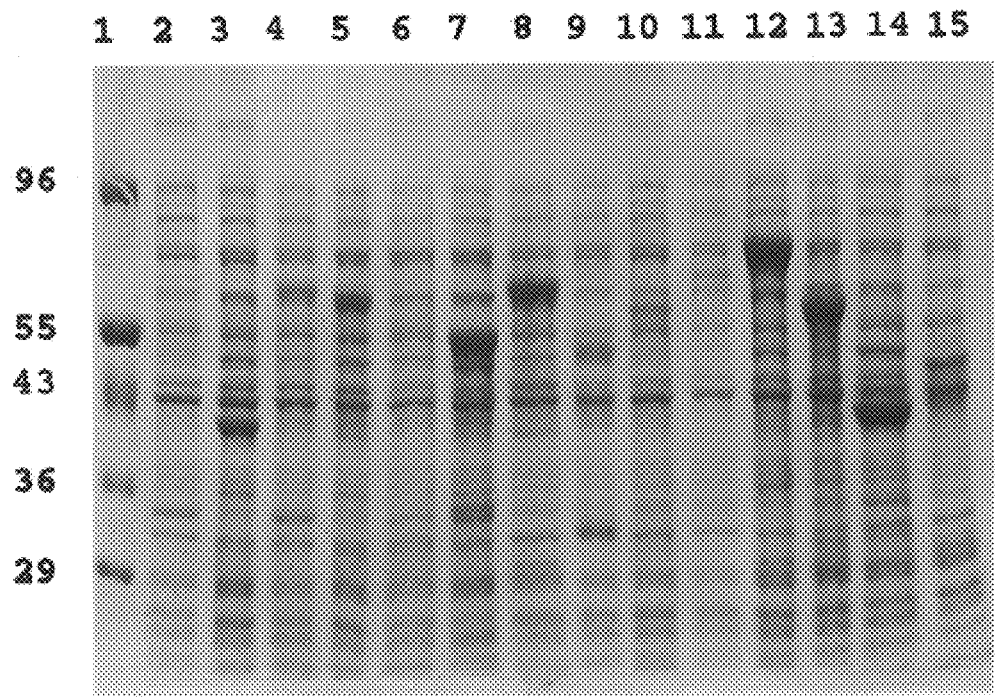
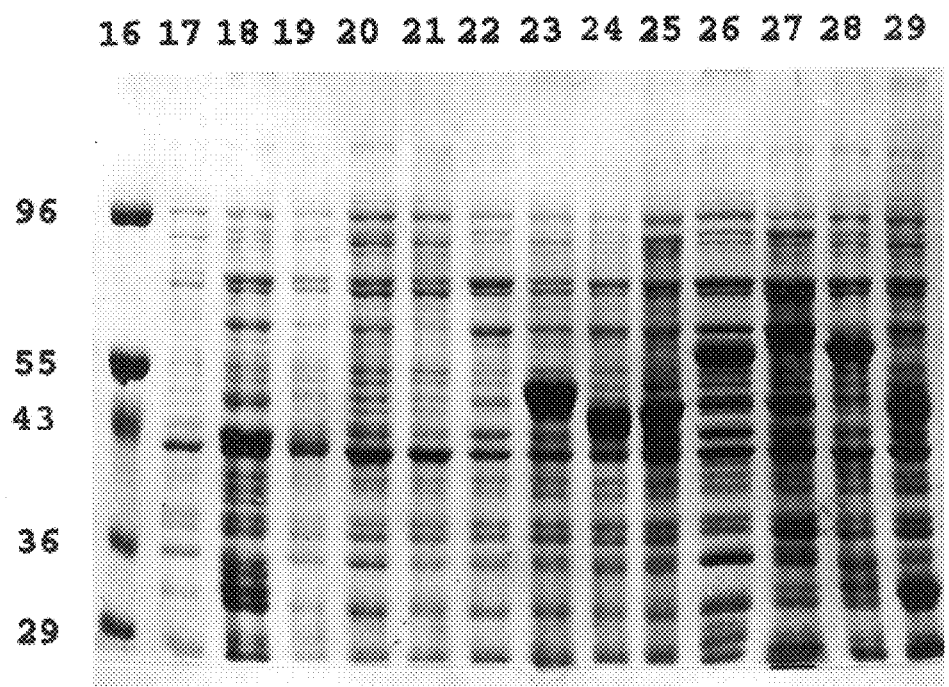
FIG.25A

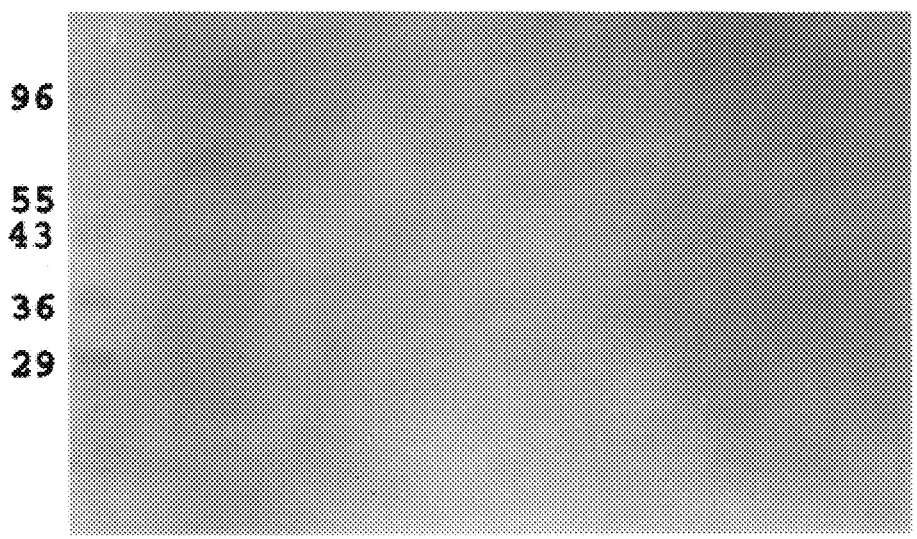
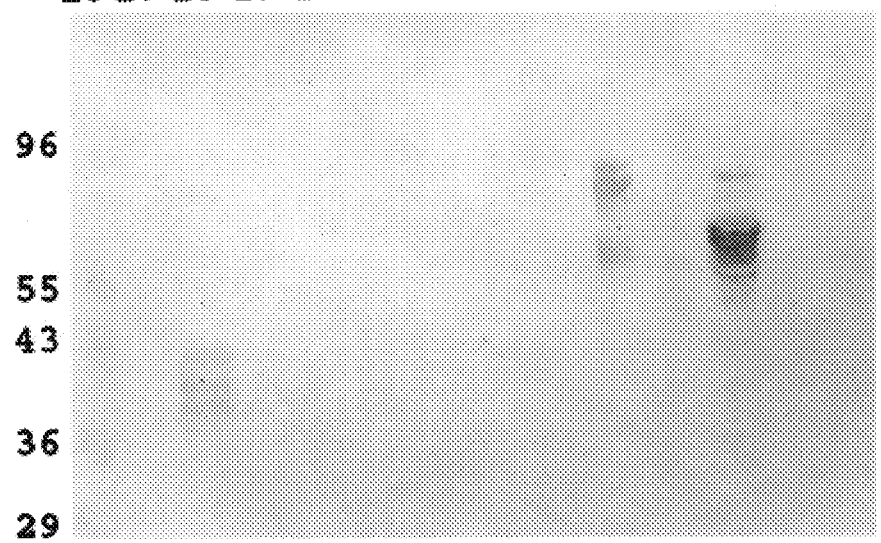
FIG.25B

```
Contig B SEQ ID# 166(1297)   MYL..TGRCS RNYDVIICDE CHATDRTTVL GIGKVLTEAP SKNVRLVVLA
        HCV-1 SEQ ID# 179(1298)   KFLADGGCSG GAYDIIICDE CHSTDATSIL GIGTVLDQAE TAGARLVVLA
Contig A SEQ ID# 157(1407)   RFMANPRKYL RGNDVIICDE LHVTDPTSIL GMGRARLLAR ECGVRLLLFA
                 Consensus   ---------- ---D--ICDE -H-TD-T--L G-G------A- ----RL---A
                                          **         *

Contig B SEQ ID# 166(1345)   TATPPGVIPT PHANITEIQL TDEGTIPFHG KKIKEENLKK GRKLIFEATK
        HCV-1 SEQ ID# 179(1348)   TATPPGSVTV PHPNIEEVAL STTGEIPFYG KAIPLEVIKG GRHLIFCHSK
Contig A SEQ ID# 157(1457)   TATPPVSPMA KHESIHEEML GSEGEVPFYC QFLPLSRYAT GRHLLFCHSK
                 Consensus   TATPP----- -H-I-E--L ---G--PF-- ---------- GRHL-F---K
                             ***                    *

Contig B SEQ ID# 166(1395)   KHCDELANEL ARKGITAVSY YRGCDISKMP .EGDCVVVAT DALCTGYTGD
        HCV-1 SEQ ID# 179(1398)   KKCDELAAKL VALGINAVAY YRGLDVSVIP TSGDVVVVAT DALMTGYTGD
Contig A SEQ ID# 157(1507)   VECTRLSSAL ASFGVNTVVY FRGKETDI.. PTGDVCVCAT DALSTGYTGN
                 Consensus   --C--L---L ---G---V-Y -RG------- ---GD--V-AT DAL-

```
Contig B SEQ ID# 166(2599)  AAKLSDQHRA GIHTIARQYH AGGPMIAYDG REIGYRRCRS SGVYTTSSSN
        HCV-1 SEQ ID# 180(2662)  CCDLDPQARV AIKSLTERLY VGGPLTNSRG ENCGYRRCRA SGVLTTSCGN
Contig A SEQ ID# 152(2798)  AA...SDNPS MVHALC.KYY SGGPMVSPDG VPLGYRQCRS SGVLTTSSAN
        Consensus           ---------- ---------- -GGP------G ---GYR-CR- SGV-TTS--N
                                                      ***                    *  *

Contig B SEQ ID# 166(2649)  SLTCWLKVNA AAEQAGMKNP RFLICGDDCT VIWKSAGADA DKQAMRVFAS
        HCV-1 SEQ ID# 180(2712)  TLTCYIKARA ACRAAGLQDC TMLVCGDDLV VICESAGVQE DAASLRAFTE
Contig A SEQ ID# 157(2844)  SITCYIKVSA ACRRVGIKAP SFFIAGDDCL IIYENDGTDP CPALKAALAN
        Consensus           --TC--K--A A--------- ----GDD--- -I------G- ----------
                                                      ***
```

FIG.35B

```
SEQ ID 76    agcCtActgC GActcCCCcg GGCTCgCCTA TGACTCAGCA tCCATCCATA aTTGAGAGAA AGcTGGac.. .gTTGGTGAG ATCCCCTTTT ATGGGcaTGG
SEQ ID 37    TCGCTACGGC GACCCCACCG GTCTCTCCGA TGGCGAAGCA TGAATCTATT CATGAGGAGA TGTTGGGCAG TGAGGGGGAG GTCCCCTTCT ATTGCCAATT
SEQ ID 44    TTGCCACGGC tACCCCCCCT GGAGTAATCC CTACACCACA TgCCAAcAtA acTGAGATtC AATTAACCGA TGAAGGCACT ATcCCCTTTC ATGGAAAAAA
SEQ ID 100   TCGCCACTGC TACCCCTCCG GGCTCCGTCA CTGTGTCCCA TCCTAACATC GAGGAGGTTG CTCGTGTCAC CACCGGAGAG ATCCCCTTTT ACGGCAAGGC SEQ ID 76    TATCCCCCTc gAGcG.TATg aGGACTGGT. CGCCACCTTG TATtCTGccA TtccaAGGCG GAGTGCGAGA GaTGGCCCgA CCAGTTCTCC GcgcGGgGGG
SEQ ID 37    CCTCCCACTG AGTAGGTATG CTACTGGG.. AGACACCTGC TGTTTTGTCA TTCCAAGGTA GArTGCACTA CACTGTGAtg AGCTTGCTAA AGCTTTGGCC AGCTTTGGTG
SEQ ID 44    GATTAaGGAG GAAAATCTGA aGAAAGGG.. AGACACCTTA TCTTTGAGGC TACCAAAAAA CACTGTGATg AGCTtGCTAA CGAGTTAGCT CGAAAGGGAA
SEQ ID 100   TATCCCCCTC GAGGTGATCA AGGGGGGA.. AGACATCTCA TCTTCTGCCA CTCAAAGAAG AAGTGCGACG AGCTCGCCGC GAAGCTGGTC GCATTGGGCA SEQ ID 76    TtAATgCcAT CgcC.TATTA TAGGGGTAAG GACAGTTCCA TCATCAAAGa CGgAgacCTg GTGGtTTGTG .CGACAGACG .Cg.CTCTCT ACCGGGTACA
SEQ ID 37    TCAACACCGT TGTGTACTTC AGAGCAAAAG AA....ACTG ACATTCCAAC AAATCC...C TGGTGACGTG TGCGTTTG.. .CGCCACAGA CGCACTTTCC ACTGGTTACA
SEQ ID 44    TAACAGCTGT CtCTTAC.TA TAGGGGATGT GACATCTCAA ACATCCCGAC TGAGGGCGAc tGtGtaGTaG tTGccaCTGa TGCCTTgtGT aCaGgGTaCa
SEQ ID 100   TCAATGCCGT GGCCTAC.TA CCGGGGTCTT GACGTGTCTG TCATCCCGAC CAGCGGCGAT GTTGTCGTCG TGTGTCGACGA TGCTCTCATG ACTGGCTTTA SEQ ID 76    CAGgAAACTT CGATTCTGTC ACCGACTGTG GGTTGGTGGT GGAGGAGGTC GTTGAGGTGA CCCTtGAtCC cACCaT
SEQ ID 37    CTGGCAATTT TGACACCGTA ACAGACTGTG GTTTAATGGT TGAGGAGGTA GTGGAAGTGA CCCTGGACCC GACCAT
SEQ ID 44    CTGGTGACTT TGaTTCCGTG TaTGaCTGCa GcCTCaTGCa AGAaGGCaca TGCCaTGTTG aCCTTGaCCC TaCTTT
SEQ ID 100   CCGGCGACTT CGACTCTGTG ATAGACTGCA ACACGTGTGT CACTCAGACA GTCGATTTTA GCCTTGACCC TACCTT
```

FIG. 36

```
SEQ ID 98    ATC CCC TTT TAT GGG CAT GGC ATA CCC CTG GAG AGG ATG CGG ACC GGC AGG CAC CTC GTA
SEQ ID 97    ATC CCC TTT TAT GGG CAT GGA ATC CCC CTC GAG CGG ATG CGG ACC GGG CGC CAC CTC GTG
SEQ ID 76    ATC CCC TTT TAT GGG CAT GGT ATC CCC CTC GAG CGT ATG AGG ACT GGT CGC CAC CTT GTA
Consensus    ATC CCC TTT TAT GGG CAT GG- AT- CCC CT- GAG -G- ATG AC- GG- -G- CAC CT- GT-
translat.     I   P   F   Y   G   H   G   I   P   L   E   R   M   R   T   G   R   H   L   V SEQ ID 98    TTC TGC CAT TCA AAG GCG GAG TGC GAG CGG CTT GCT GGC CAG TTC TCA GCC CGG GGA GTA
SEQ ID 97    TTC TGC CAT TCA AAG GCG GAG TGC GAG CGG TTG GCT GGC CAG TTC TCT TCG CGG GGG GTG
SEQ ID 76    TTC TGC CAT TCC AAG GCG GAG TGC GAG AGA TTG GCC GGC CAG TTC TCC GCr CGG GGG GTG
Consensus    TTC TGC CAT TC- AAG GCG GAG TGC GAG -G- -T- GC- GGC CAG TTC TC- -C- CGG GGG GT-
translat.     F   C   H   S   K   A   E   C   E   R   L   A   G   Q   F   S  A/S  R   G   V SEQ ID 98    AAT GCC ATT GCC TAT TAT AGG GGG AAA GAC AGT TCT
SEQ ID 97    AAT GCC ATT GCC ATC GCC TAT TAC AGG GGG AAA GAC AGT TCC
EQ ID 76     AAT GCC AT- GCC TAT TAT AGG GGT AAG GAC AGT TCC
Consensus    AAT GCC AT- GCC TAT TA- AGG GG- AA- GAC AGT TC-
translat.     N   A   N   A   Y   Y   R   G   K   D   S   S
```

FIG.38

```
  GB-C  T TAT GGG CAT GGT ATC CCC CTC GAG CGT ATG AGG ACT GGT CGC CAC
CTT GTA TTC TGC CAT TCC AAG GCG GAG TGC GAG AGA
GB-C.4 - --- --- --- --C --- --- --G --- --G --- --- --C --- A-G ---
--G --- --- --- --C --A --- --- --- --T --- --G
GB-C.5 - --- --- --- --C --A --T --- --A --G --- C-- --C --A A-G ---
--C --G --- --- --- --A --- --- --- --- --- C-G
GB-C.6 - --- --- --- --C --T --T --G --- --G --- CA- --C --- A-A --T
--- --G --- C-- --C --G --- --- --- --- --- C-G
GB-C.7 - --- --- --- --C --A --- --- --A --G --- C-A --C --A G-G ---
--C --G --- --T --- --- --- --- --- --- --- C-G

GB-C  TTG GCC GGC CAG TTC TCC GCG CGG GGG GTT AAT GCC ATC GCC TAT
TAT AGG GGT AAG GAC AGT TCC ATC ATC AAA GAC GGA GAC
GB-C.4 C-- --- --- --A --- --- T-A --- --- --- --- --T G-T --- ---
--- --- --- --- --- --- --A --- --- --G --T --T ---
GB-C.5 C-C --T --T --- --T --T --- A-- --- --A --C --- --T --T ---
--- --- --C --A --- --- --- --- --- --G --- --- ---
GB-C.6 C-T --- --- --- --- --- T-T A-- --- --C --C --- --T --- ---
--C --- --- --- --- --C --- --- --G --- --- --- ---
GB-C.7 C-T --T --- --- --- --T --- A-- --- --G --- --- --T --- ---
--- --- --C --A --- --- --- --- --G --T --C ---

GB-C  CTG GTG GTT TGT GCG ACA GAC GCG CTC TCT ACC
GB-C.4 --- --- --G --C --T --T --- --- --A --- ---
GB-C.5 --A --- --G --C --C --- --- --- --A --C --G
GB-C.6 --C --T --G --C --C --T --T --- --- --- --G
GB-C.7 --- --- --G --C --T --G C-- --- --A --C ---
```

FIG.40

NON-A, NON-B, NON-C, NON-D, NON-E HEPATITIS REAGENTS AND METHODS FOR THEIR USE

This application is a continuation-in-part application of U.S. Ser. No. 08/377,557 filed Jan. 30, 1995, which is a continuation-in-part of U.S. Ser. No. 08/344,185 filed Nov. 23, 1994 and U.S. Ser. No. 08/344,190 filed Nov. 23, 1994, which are each continuation-in-part applications of Ser. No. 08/283,314 filed Jul. 29, 1994, which is a continuation-in-part application of U.S. Ser. No. 08/242,654, filed May 13, 1994, which is a continuation-in-part application of U.S. Ser. No. 08/196,030 filed Feb. 14, 1994, all of which are abandoned, all of which enjoy common ownership and each of which is incorporated herein by reference.

BACKGROUND OF THE INVENTION

This invention relates generally to a group of infectious viral agents causing hepatitis in man, and more particularly, relates to materials such as polynucleotides derived from this group of viruses, polypeptides encoded therein, antibodies which specifically bind to these polypeptides, and diagnostics and vaccines that employ these materials.

Hepatitis is one of the most important diseases transmitted from a donor to a recipient by transfusion of blood products, organ transplantation and hemodialysis; it also can be transmitted via ingestion of contaminated food stuffs and water, and by person to person contact. Viral hepatitis is known to include a group of viral agents with distinctive viral genes and modes of replication, causing hepatitis with differing degrees of severity of hepatic damage through different routes of transmission. In some cases, acute viral hepatitis is clinically diagnosed by well-defined patient symptoms including jaundice, hepatic tenderness and an elevated level of liver transaminases such as aspartate transaminase (AST), alanine transaminase (ALT) and isocitrate dehydrogenase (ISD). In other cases, acute viral hepatitis may be clinically inapparent. The viral agents of hepatitis include hepatitis A virus (HAV), hepatitis B virus (HBV), hepatitis C virus (HCV), hepatitis delta virus (HDV), hepatitis E virus (HEV), Epstein-Barr virus (EBV) and cytomegalovirus (CMV).

Although specific serologic assays available by the late 1960's to screen blood donations for the presence of HBV surface antigen (HBsAg) were successful in reducing the incidence of post-transfusion hepatitis (PTH) in blood recipients, PTH continued to occur at a significant rate. H. J. Alter et al., *Ann. Int. Med.* 77:691–699 (1972); H. J. Alter et al., *Lancet* ii:838–841 (1975). Investigators began to search for a new agent, termed "non-A, non-B hepatitis" (NANBH), that caused viral hepatitis not associated with exposure to viruses previously known to cause hepatitis in man (HAV, HBV, CMV and EBV). See, for example, S. M. Feinstone et al., *New Engl. J. Med.* 292:767–770 (1975); Anonymous editorial, *Lancet* ii:64–65 (1975); F. B. Hollinger in B. N. Fields and D. M. Knipe et al., *Virology*, Raven Press, New York, pp. 2239–2273 (1990).

Several lines of epidemiological and laboratory evidence have suggested the existence of more than one parenterally transmitted NANB agent, including multiple attacks of acute NANBH in intraveneous by drug users; distinct incubation periods of patients acquiring NANBH post-transfusion; the outcome of cross-challenge chimpanzee experiments; the ultrastructural liver pathology of infected chimpanzees; and the differential resistance of the putative agents to chloroform. J. L. Dienstag, *Gastroenterology* 85:439–462 (1983); J. L. Dienstag, *Gastroenterology* 85:743–768 (1983); F. B. Hollinger et al., *J. Infect. Dis.* 142:400–407 (1980); D. W. Bradley in F. Chisari, ed., *Advances in Hepatitis Research*, Masson, New York, pp. 268–280 (1984); and D. W. Bradley et al., *J. Infect. Dis.* 148:254–265 (1983).

A serum sample obtained from a surgeon who had developed acute hepatitis was shown to induce hepatitis when inoculated into tamarins (Saguinus species). Four of four tamarins developed elevated liver enzymes within a few weeks following their inoculation, suggesting that an agent in the surgeon's serum could produce hepatitis in tamarins. Serial passage in various non-human primates demonstrated that this hepatitis was caused by a transmissible agent; filtration studies suggested the agent to be viral in nature. The transmissable agent responsible for these cases of hepatitis in the surgeon and tamarins was termed the "GB agent." F. Deinhardt et al., *J. Exper. Med.* 125:673–688 (1967). F. Deinhardt et al., *J. Exper. Med.*, supra; E. Tabor et al., *J. Med. Virol.* 5:103–108 (1980); R. O. Whittington et al., *Viral and Immunological Diseases in Nonhuman Primates*, Alan R. Liss, Inc., New York, pp. 221–224 (1983).

Although it was suggested that the GB agent may be an agent causing NANBH in humans and that the GB agent was not related to the known NANBH agents studied in various laboratories, no definitive or conclusive studies on the GB agent are known, and no viral agent has been discovered or molecularly characterized. F. Deinhardt et al., *Am. J. Med. Sci.* 270:73–80 (1975); and J. L. Dienstag et al., *Nature* 264:260–261 (1976). See also E. Tabor et al., *J. Med. Virol.*, supra; E. Tabor et al., *J. Infect. Dis.* 140:794–797 (1979); R. O. Whittington et al., supra; and P. Karayiannis et al., *Hepatology* 9:186–192 (1989).

Early studies indicated that the GB agent was unrelated to any known human hepatitis virus. S. M. Feinstone et al., *Science* 182:1026–1028 (1973); P. J. Provost et al., *Proc. Soc. Exp. Biol. Med.* 148:532–539 (1975); J. L. Melnick, *Intervirology* 18:105–106 (1982); A. W. Holmes et al., *Nature* 243:419–420 (1973); and F. Deinhardt et al., *Am. J. Med. Sci.*, supra. However, questions were raised regarding whether the GB agent was a virus which induced hepatitis infection in humans, or a latent tamarin virus activated by the GB serum and once activated, easily passaged to other tamarins, inducing hepatitis in them. Also, a small percentage of marmosets inoculated with GB-positive serum did not develop clinical hepatitis (4 of 52, or 7.6%), suggesting that these animals may have been naturally immune and thus, that the GB agent may be a marmoset virus. W. P. Parks et al., *J. Infect. Dis.* 120:539–547 (1969); W. P. Parks et al., *J. Infect. Dis.* 120:548–559 (1969). Morphological studies have been equivocal, with immune electron microscopy studies in one report indicating that the GB agent formed immune complexes with a size distribution of 20–22 nm and resembling the spherical structure of a parvovirus, while another study reported that immune electron microscopy data obtained from liver homogenates of GB-positive tamarins indicated that aggregates of 34–36 nm with icosahedral symmetry were detected, suggesting that the GB agent was a calici-like virus. See, for example, J. D. Almeida et al., *Nature* 261:608–609 (1976); J. L. Dienstag et al., *Nature*, supra.

Two hepatitis-causing viruses recently have been discovered and reported: HCV, which occurs primarily through parenteral transmission, and HEV, which is transmitted enterically. See, for example, Q. L. Choo et al., *Science* 244:359–362 (1989), G. Kuo et al., *Science* 244:362–364 (1989), E. P. Publication No. 0 318 216 (published May 31, 1989), G. R. Reyes et al., *Science* 247:1335–1339 (1990).

HCV is responsible for a majority of PTH ascribed to the NANBH agent(s) and many cases of acute NANBH not acquired by transfusion. Anonymous editorial, *Lancet* 335:1431–1432 (1990); J. L. Dienstag, *Gastroenterology* 99:1177–1180 (1990); and M. J. Alter et al., *JAMA* 264:2231–2235 (1990).

While the detection of HCV antibody in donor samples eliminates 70 to 80% of NANBH infected blood in the blood supply system, the discovery and detection of HCV has not totally prevented the transmission of hepatitis. H. Alter et al., *New Eng. J. Med.* 321:1494–1500 (1989). Recent publications have questioned whether additional hepatitis agents may be responsible for PTH and for community acquired acute and/or chronic hepatitis that is not associated with PTH. For example, of 181 patients monitored in a prospective clinical survey conducted in France from 1988 to 1990, investigators noted a total of 18 cases of PTH. Thirteen of these 18 patients tested negative for anti-HCV antibodies, HBsAg, HBV and HCV nucleic acids. The authors speculated as to the potential importance of a non-A, non-B, non-C agent causing PTH. V. Thiers et al., *J. Hepatology* 18:34–39 (1993). Also, of 1,476 patients monitored in another study conducted in Germany from 1985 to 1988, 22 cases of documented cases of PTH were not related to infection with HBV or HCV. T. Peters et al., *J. Med. Virol.* 39:139–145 (1993).

It would be advantageous to identify and provide materials derived from a group of novel and unique viruses causing hepatitis, such as, polynucleotides, recombinant and synthetic polypeptides encoded therein, antibodies which specifically bind to these polypeptides, and diagnostics and vaccines that employ these materials. Such materials could greatly enhance the ability of the medical community to more accurately diagnose acute and/or chronic viral hepatitis and could provide a safer blood and organ supply by detecting non-A, non-B and non-C hepatitis in these blood and organ donations.

SUMMARY OF THE INVENTION

The present invention provides a purified polynucleotide or fragment thereof derived from hepatitis GB virus (HGBV) capable of selectively hybridizing to the genome of HGBV or the complement thereof, wherein said polynucleotide is characterized by a positive stranded RNA genome wherein said genome comprises an open reading frame (ORF) encoding a polyprotein wherein said polyprotein comprises an amino acid sequence having at least 35% identity, more preferably, 40% identity, even more preferably, 60% identity, and yet more preferably, 80% identity to an amino acid sequence selected from the group consisting of HGBV-A, HGBV-B and HGBV-C. Also provided is a recombinant polynucleotide or fragment thereof derived from hepatitis GB virus (HGBV) capable of selectively hybridizing to the genome of HGBV or the complement thereof, wherein said nucleotide comprises a sequence that encodes at least one epitope of HGBV, and wherein said recombinant nucleotide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. Such a recombinant polynucleotide is contained within a recombinant vector and further comprises a host cell transformed with said vector.

The present invention also provides a hepatitis GB virus (HGBV) recombinant polynucleotide or fragment thereof comprising a nucleotide sequence derived from an HGBV genome, wherein said polynucleotide is contained within a recombinant vector and further comprises a host cell transformed with said vector. and further wherein said sequence encodes an epitope of HGBV. The HGBV recombinant polynucleotide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. The present invention provides a recombinant expression system comprising an open reading frame of DNA or RNA derived from hepatitis GB virus (HGBV) wherein said open reading frame comprises a sequence of HGBV genome or cDNA and wherein said open reading frame is operably linked to a control sequence compatible with a desired host, and further comprises a cell transformed with said recombinant expression system and a polypeptide of at least about eight amino acids in length produced by said cell.

The present invention additionally provides a purified hepatitis GB virus (HGBV) comprising a preparation of HGBV polypeptide or fragment thereof, a recombinant polypeptide comprising an amino acid sequence or fragment thereof wherein said sequence is characterized by a positive stranded RNA genome wherein said genome comprises an open reading frame (ORF) encoding a polyprotein wherein said polyprotein comprises an amino acid sequence having at least 35% identity, more preferably 40% identity and yet more preferably 60% identity to an amino acid sequence selected from the group consisting of HGBV-A, HGBV-B and HGBV-C. Antibodies, both polyclonal and monoclonal, are provided by the present invention, as well as, a fusion polypeptide comprising at least one hepatitis GB virus (HGBV) polypeptide or fragment thereof, a particle that is immunogenic against hepatitis GB virus (HGBV) infection, comprising a non-HGBV polypeptide having an amino acid sequence capable of forming a particle when said sequence is produced in a eukaryotic or prokaryotic host, and at least one HGBV epitope, and a polynucleotide probe for hepatitis GB virus (HGBV) wherein said polynucleotide probe is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C.

Assay kits also are provided, as well as methods for producing a polypeptide containing at least one hepatitis GB virus (HGBV) epitope comprising incubating host cells transformed with an expression vector comprising a sequence encoding a polypeptide characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. Also provided are methods of detecting HGBV nucelic acids, antigens and antibodies in test samples, including methods which utilize solid phases, recombinant or synthetic peptides, or probes. Vaccines also are provided by the present invention, as are tissue culture grown cell infected with hepatitis GB virus (HGBV), a method for producing antibodies to hepatitis GB virus (HGBV) comprising administering to an individual an isolated immunogenic polypeptide or fragment thereof comprising at least one HGBV epitope in an amount sufficient to produce an immune response. Diagnostic reagents also are provided herein which comprises polynucleotides or polypeptides or fragments thereof.

BRIEF DESCRIPTION OF THE DRAWINGS

FIGS. 1–12 are graphs of individual tamarins which plot the amount of liver enzyme (ALT or ICD) as measured in mU/ml against time (weeks post inoculation), where ALT CO indicates the cutoff value for ALT, and ICD CO indicates the cutoff value of ICD, wherein FIG. 1 shows the graph of tamarin T-1053;

FIG. 2 shows the graph of tamarin T-1048;

FIG. 3 shows the graph of tamarin T-1057;

FIG. 4 shows the graph of tamarin T-1061;

FIG. 5 shows the graph of tamarin T-1047;

FIG. 6 shows the graph of tamarin T-1042;

FIG. 7 shows the graph of tamarin T-1044;

FIG. 8 shows the graph of tamarin T-1034;

FIG. 9 shows the graph of tamarin T-1055;

FIG. 10 shows the graph of tamarin T-1051;

FIG. 11 shows the graph of tamarin T-1038; and

FIG. 12 shows the graph of tamarin T-1049.

FIGS. 23A–C show dot plot analyses of the nucleic acid sequences wherein:

FIG. 23A shows a dot blot comparison of HGBV-A;

FIG. 23B shows a dot blot comparison of HGBV-B;

FIG. 23C shows a dot blot comparison of HGBV-A v. HGBV-B.

FIGS. 24A–B show the conserved residues as follows:

FIG. 24A shows the conserved residues in the putative NTP-binding helicase domain of predicted translation products of HGBV-A, HGBV-B and HCV-1 NS3, FIG. 24B shows the conserved residues of the RNA-dependent RNA polymerase domain of predicted translation products of HGBV-A, HGBV-B and HCV-1 NS5b.

FIGS. 25A–B show Coomassie-stained 10% SDS-polyacrylamide gels of CKS fusion protein whole cell lysates; three CKS fusion proteins demonstrate immunoreactivity with HGBV-infected tamarin sera.

FIGS. 26 to 30 are graphs of individual tamarins which plot 1) the amount of liver enzyme (ALT) as measured in mU/ml against time (weeks post inoculation) as shown by a solid line; 2) ELISA absorbance values for the CKS-1.7 recombinant protein as shown by filled circles connected by dotted lines; 3) ELISA absorbance values for the CKS-1.4 recombinant protein as shown by open circles connected by dotted lines; 4) ELISA absorbance values for the CKS4.1 recombinant protein as shown by crosses connected by dotted lines; 5) negative PCR results using Sequence I.D. NO. 21 primers as shown by empty squares; 6) positive PCR results using Sequence I.D. NO. 21 primers as shown by filled squares; 7) negative PCR results using Sequence I.D. NO. 26 primers as shown by empty diamonds; 8) positive PCR results using Sequence I.D. NO. 26 primers as shown by filled diamonds; 9) inoculation dates are indicated by the arrowheads, wherein FIG. 26 shows the graph of tamarin T-1048;

FIG. 27 shows the graph of tamarin T-1057;

FIG. 28 shows the graph of tamarin T-1061;

FIG. 29 shows the graph of tamarin T-1051; and

FIG. 30 shows the graph of tamarin T-1034.

FIGS. 31–34 are graphs of a human test specimens which plots 1) the amount of liver enzyme (ALT) as measured in mU/ml against time (weeks post inoculation) as shown by a solid line; 2) ELISA absorbance values for the CKS-1.7 recombinant protein as shown by dotted lines, filled circles; 3) ELISA absorbance values for the CKS-1.4 recombinant protein as shown by dotted lines, open circles, wherein FIG. 31 shows a graph of patient 101;

FIG. 32 shows a graph of patient 257;

FIG. 33 shows a graph of patient 260; and

FIG. 34 shows a graph of patient 340.

FIG. 35 shows conserved residues, wherein

FIG. 35A shows the conserved residues in the putative NTP-binding helicase domain of predicted translation products of Contig. A, Contig. B and HCV-1 NS3, and FIG. 35B shows the conserved residues of the RNA-dependent RNA polymerase domain of predicted translation products of Contig. A, Contig. B and HCV-1 NS5b.

FIG. 36 shows a nucleotide alignment of HGBV-A, HGBV-B, HGBV-C and HCV-1.

FIG. 38 shows a nucleotide alignment of HGBV-C with two variant clones.

FIG. 40 shows a nucleotide alignment of HGBV-C with four variant clones.

DETAILED DESCRIPTION OF THE INVENTION

Figure 1:
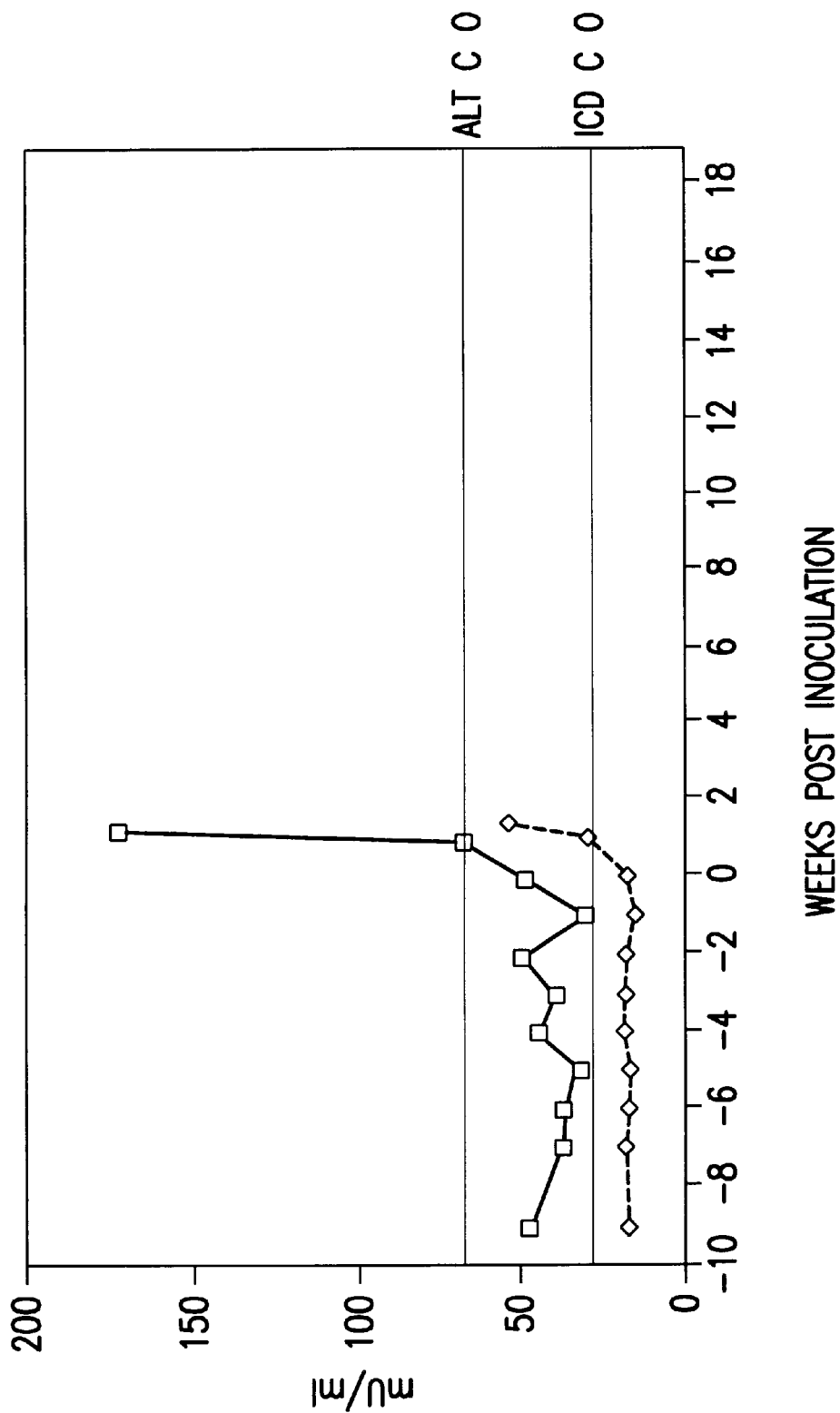

The present invention provides characterization of a newly ascertained etiological agents of non-A, non-B, non-C, non-D and non-E hepatitis-causing agents, collectively so-termed "Hepatitis GB Virus," or "HGBV." The present invention provides a method for determining the presence of the HGBV etiological agents, methods for obtaining the nucleic acid of this etiological agents created from infected serum, plasma or liver homogenates from individuals, either humans or tamarins, with HGBV to detect newly synthesized antigens derived from the genome of heretofore unisolated viral agents, and of selecting clones which produced products which are only found in infectious individuals as compared to non-infected individuals.

Portions of the nucleic acid sequences derived from HGBV are useful as probes to determine the presence of HGBV in test samples, and to isolate naturally occurring variants. These sequences also make available polypeptide sequences of HGBV antigens encoded within the HGBV genome(s) and permit the production of polypeptides which are useful as standards or reagents in diagnostic tests and/or as components of vaccines. Monoclonal and polyclonal antibodies directed against at least one epitope contained within these polypeptide sequences also are useful for diagnostic tests as well as therapeutic agents, for screening of antiviral agents, and for the isolation of the HGBV agent from which these nucleic acid sequences are derived. Isolation and sequencing of other portions of the HGBV genome also can be accomplished by utilizing probes or PCR primers derived from these nucleic acid sequences, thus allowing additional probes and polypeptides of the HGBV to be established, which will be useful in the diagnosis and/or treatment of HGBV, both as a prophylactic and therapeutic agent.

According to one aspect of the invention, there will be provided a purified HGBV polynucleotide, a recombinant HGBV polynucleotide, a recombinant polynucleotide comprising a sequence derived from an HGBV genome; a recombinant polypeptide encoding an epitope of HGBV; a synthetic peptide encoding an epitope of HGBV; a recombinant vector containing any of the above described recombinant polypeptides, and a host cell transformed with any of these vectors. These recombinant polypeptides and synthetic peptides may be used alone or in combination, or in conjunction with other substances representing epitopes of HGBV.

In another aspect of the invention there will be provided purified HGBV; a preparation of polypeptides from the purified HGBV; a purified HGBV polypeptide; a purified polypeptide comprising an epitope which is immunologically identical with an epitope contained in HGBV.

In yet another aspect of the invention there will be provided a recombinant expression system comprising an open reading frame (ORF) of DNA derived from an HGBV genome or from HGBV cDNA, wherein the ORF is operably linked to a control sequence compatible with a desired host, a cell transformed with the recombinant expression system, and a polypeptide produced by the transformed cell.

Additional aspects of the present invention include at least one recombinant HGBV polypeptide, at least one recombinant polypeptide comprised of a sequence derived from an HGBV genome or from HGBV cDNA; at least one recombinant polypeptide comprised of an HGBV epitope and at least one fusion polypeptide comprised of an HGBV polypeptide.

The present invention also provides methods for producing a monoclonal antibody which specifically binds to at least one epitope of HGBV; a purified preparation of polyclonal antibodies which specifically bind to at least one HGBV epitope; and methods for using these antibodies, which include diagnostic, prognostic and therapeutic uses.

In still another aspect of the invention there will be provided a particle which immunizes against HGBV infection comprising a non-HGBV polypeptide having an amino acid sequence capable of forming a particle when said sequence is produced in an eukaryotic host, and an HGBV epitope.

A polynucleotide probe for HGBV also will be provided.

The present invention provides kits containing reagents which can be used for the detection of the presence and/or amount of polynucleotides derived from HGBV, such reagents comprising a polynucleotide probe containing a nucleotide sequence from HGBV of about 8 or more nucleotides in a suitable container; a reagent for detecting the presence and/or amount of an HGBV antigen comprising an antibody directed against the HGBV antigen to be detected in a suitable container; a reagent for detecting the presence and/or amount of antibodies directed against an HGBV antigen comprising a polypeptide containing an HGBV epitope present in the HGBV antigen, provided in a suitable container. Other kits for various assay formats also are provided by the present invention as described herein.

Other aspects of the present invention include a polypeptide comprising at least one HGBV epitope attached to a solid phase and an antibody to an HGBV epitope attached to a solid phase. Also included are methods for producing a polypeptide containing an HGBV epitope comprising incubating host cells transformed with an expression vector containing a sequence encoding a polypeptide containing an HGBV epitope under conditions which allow expression of the polypeptide, and a polypeptide containing an HGBV epitope produced by this method.

The present invention also provides assays which utilize the recombinant or synthetic polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of HGBV infection comprising an immunogenic peptide containing an HGBV epitope, or an inactivated preparation of HGBV, or an attenuated preparation of HGBV, or the use of recombinant vaccines that express HGBV epitope(s) and/or the use of synthetic peptides, also are included in the present invention. An effective vaccine may make use of combinations of these immunogenic peptides (such as, a cocktail of recombinant antigens, synthetic peptides and native viral antigens administered simultaneously or at different times); some of these may be utilized alone and be supplemented with other representations of immunogenic epitopes at later times. Also included in the present invention is a method for producing antibodies to HGBV comprising administering to an individual an isolated immunogenic polypeptide containing an HGBV epitope in an amount sufficient to produce an immune response in the inoculated individual.

Also provided by the present invention is a tissue culture grown cell infected with HGBV.

In yet another aspect of the present invention is provided a method for isolating DNA or cDNA derived from the genome of an unidentified infectious agent, which is a unique modification of representational difference analysis (RDA), and which is described in detail hereinbelow.

Definitions

The term "Hepatitis GB Virus" or "HGBV", as used herein, collectively denotes a viral species which causes non-A, non-B, non-C, non-D, non-E hepatitis in man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intravenous drug use. The methods as described herein will allow the identification of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera: Flavivirus, Pestivirus, and the hepatitis C group. Similarity searches at the amino acid level reveal that the hepatitis GB virus subclones have some, albeit low, sequence resemblance to hepatitis C virus. The information provided herein is sufficient to allow classification of other strains of HGBV.

Several lines of evidence demonstrate that HGBV-C is not a genotype of HCV. First, sera containing HGB-C sequences were tested for the presence of HCV antibody. Routine detection of individuals exposed to or infected with HCV relies upon antibody tests which utilize antigens derived from three or more regions from HCV-1. These tests allow detection of antibodies to the known genotypes of HCV (See, for example, Sakamoto et al., *J. Gen. Virol.* 75:1761–1768 (1994) and Stuyver et al., *J. Gen. Virol.* 74:1093–1102 (1993). HCV-specific ELISAs failed to detect sera containing GB-C sequences in six of eight cases (TABLE A). Second, several human sera that were seronegative for HCV antibodies have been shown to be positive for HCV genomic RNA by a highly sensitive RT-PCR assay (Sugitani, *Lancet* 339:1018–1019 (1992). This assay failed to detect HCV RNA in seven of eight sera containing HGB-C sequences (TABLE A). Thus, HGBV-C is not a genotype of HCV based on both serologic and molecular assays.

The alignment of a portion of the predicted translation product of HGB-C within the helicase region with the homologous region of HGBV-A, HGBV-B, HCV-1 and additional members of the Flaviviridae, followed by phylogenetic analysis of the aligned sequences suggests that HGBV-C is more closely related to HGBV-A than to any member of the HCV group. The sequences of HGBV-C and HGBV-A, while exhibiting an evolutionary distance of 0.42, are not as divergent as HGBV-C is from HGBV-B, which shows an evolutionary distance of 0.92 (TABLE 33, infra.). Thus, HGBV-A and HGBV-C may be considered to be members of one subgroup of the GB viruses and GBV-B a member of its own subgroup. The phylogenetic analysis of the helicase sequences from various HCV isolates show that they form a much less diverged group, exhibiting a maximum evolutionary distance of 0.20 (TABLE 32, infra.). A comparison of the HCV group and the HGBV group shows a minimum evolutionary distance between any two sequences from each group of 0.69. The distance values reported hereinabove were used to generate a phylogenic tree presented in FIG. 42. The relatively high degree of divergence among these viruses suggests that the GB viruses are not merely types or subtypes within the hepatitis C group; rather, they constitute their own phyletic group (or groups). Phylogenetic analysis using sequence information derived from a small portion of HCV viral genomes has been shown to be an acceptable method for the assignment of new isolates into genotypic groups (Simmonds et al., *Hepatology* 19:1321–1324 (1994). In the current analysis, the use of a 110 amino acid sequence within the helicase gene from representative HCV isolates has properly grouped them into their respective genotypes (Simmonds et al., *J. Gen. Virol.* 75:1053–1061 (1994). Therefore, the evolutionary distances shown, in all likelihood, accurately reflect the high degree of divergence between the GB viruses and the hepatitis C virus.

In previous applications, it was stated that "HGBV strains are identifiable on the polypeptide level and that HGBV strains are more than 40% homologous, preferably more than about 60% homologous, and even more preferably more than about 80% homologous at the polypeptide level." As it is used, the term "homologous," when referring to the degree of relatedness of two polynucleotide or polypeptide sequences, can be ambiguous and actually implies an evolutionary relationship. As is now the current convention in the art, the term "homologous" is no longer used; instead the terms "similarity" and/or "identity" are used to describe the degree of relatedness between two polynucleotides or polypeptide sequences. The techniques for determining amino acid sequence "similarity" and/or "identity" are well-known in the art and include, for example, directly determining the amino acid sequence and comparing it to the seqeunces provided herein; determining the nucleotide sequence of the genomic material of the putative HGBV (usually via a cDNA intermediate), and determining the amino acid sequence encoded therein, and comparing the corresponding regions. In general, by "identity" is meant the exact match-up of either the nucleotide sequence of HGBV and that of another strain(s) or the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

The compositions and methods described herein will enable the propagation, identification, detection and isolation of HGBV and its possible strains. Moreover, they also will allow the preparation of diagnostics and vaccines for the possible different strains of HGBV, and will have utility in screening procedures for anti-viral agents. The information will be sufficient to allow a viral taxonomist to identify other strains which fall within the species. We believe that HGBV encodes the sequences that are included herein. Methods for assaying for the presence of these sequences are known in the art and include, for example, amplification methods such as ligase chain reaction (LCR), polymerase chain reaction (PCR) and hybridization. In addition, these sequences contain open reading frames from which an immunogenic viral epitope may be found. This epitope is unique to HGBV when compared to other known hepatitis-causing viruses. The uniqueness of the epitope may be determined by its immunological reactivity with HGBV and lack of immunological reactivity with Hepatitis A, B, C, D and E viruses. Methods for determining immunological reactivity are known in the art and include, for example, radioimmunoassay (RIA), enzyme-linked immunosorbant assay (ELISA), hemagglutination (HA), fluorescence polarization immunoassay (FPIA) and several examples of suitable techniques are described herein.

A polynucleotide "derived from" a designated sequence for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

A "polypeptide" or "amino acid sequence derived from a designated nucleic acid sequence or from the HGBV genome refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide of genomic, semisynthetic or synthetic origin which by virtue of its origin or manipulation is not associated with all or a portion of the polypeptide with which it is associated in nature or in the form of a library and/or is linked to a polynucleotide other than that to which it is linked in nature. A recombinant or derived polypeptide is not necessarily translated from a designated nucleic acid sequence of HGBV or from an HGBV genome. It also may be generated in any manner, including chemical synthesis or expression of a recombinant expression system, or isolation from mutated HGBV.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"HGBV containing a sequence corresponding to a cDNA" means that the HGBV contains a polynucleotide sequence which is similar to or complementary to a sequence in the designated DNA. The degree of similarity or complementarity to the cDNA will be approximately 50% or greater, will preferably be at least about 70%, and even more preferably will be at least about 90%. The sequence which corresponds will be at least about 70 nucleotides, preferably at least about 80 nucleotides, and even more preferably at least about 90 nucleotides in length. The correspondence between the HGBV and the cDNA can be determined by methods known in the art, and include, for example, a direct comparison of the sequenced material with the cDNAs described, or hybridization and digestion with single strand nucleases, followed by size determination of the digested fragments.

"Purified viral polynucleotide" refers to an HGBV genome or fragment thereof which is essentially free, i.e., contains less than about 50%, preferably less than about 70%, and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means an HGBV polypeptide or fragment thereof which is essentially free, that is, contains less than about 50%, preferably less than about 70%, and even more preferably, less than about 90% of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eucaryotic cell lines cultured as unicellular entities refer to cells which can be, or have been, used as recipients for recombinant vector or other transfer DNA, and include the original progeny of the original cell which has been transfected.

As used herein "replicon" means any genetic element, such as a plasmid, a chromosome or a virus, that behaves as an autonomous unit of polynucleotide replication within a cell. That is, it is capable of replication under its own control.

A "vector" is a replicon in which another polynucleotide segment is attached, such as to bring about the replication and/or expression of the attached segment.

The term "control sequence refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an HGBV epitope" means naturally occurring HGBV polypeptides or fragments thereof, as well as polypeptides prepared by other means, for example, chemical synthesis or the expression of the polypeptide in a recombinant organism.

The term "transformation" refers to the insertion of an exogenous polynucleotide into a host cell, irrespective of the method used for the insertion. For example, direct uptake, transduction, or f-mating are included. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to tamarins and humans.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and which encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

"Purified HGBV" refers to a preparation of HGBV which has been isolated from the cellular constituents with which the virus is normally associated, and from other types of viruses which may be present in the infected tissue. The techniques for isolating viruses are known to those skilled in the art and include, for example, centrifugation and affinity chromatography.

"PNA" denotes a "peptide nucleic analog" which may be utilized in a procedure such as an assay to determine the presence of a target. PNAs are neutrally charged moieties which can be directed against RNA targets or DNA. PNA probes used in assays in place of, for example, DNA probes, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as flouorescein, radionucleotides, chemiluminescent compounds, and the like. PNAs thus can be used in methods in place of DNA or RNA. Although assays are described herein utilizing DNA, it is within the scope of the routineer that PNAs can be substituted for RNA or DNA with appropriate changes if and as needed in assay reagents.

General Uses

After preparing recombinant proteins, synthetic peptides, or purified viral polypeptides of choice as described by the present invention, the recombinant or synthetic peptides can be used to develop unique assays as described herein to detect either the presence of antigen or antibody to HGBV. These compositions also can be used to develop monoclonal and/or polyclonal antibodies with a specific recombinant protein or synthetic peptide which specifically bind to the immunological epitope of HGBV which is desired by the routineer. Also, it is contemplated that at least one polynucleotide of the invention can be used to develop vaccines by following methods known in the art.

It is contemplated that the reagent employed for the assay can be provided in the form of a test kit with one or more containers such as vials or bottles, with each container containing a separate reagent such as a monoclonal antibody, or a cocktail of monoclonal antibodies, or a polypeptide (either recombinant or synthetic) employed in the assay. Other components such as buffers, controls, and the like, known to those of ordinary skill in art, may be included in such test kits.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, Duracytes® (derviatized red blood cells, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272.

The "indicator reagent" comprises a "signal generating compound" (label) which is capable of generating and generates a measurable signal detectable by external means conjugated (attached) to a specific binding member for HGBV. "Specific binding member" as used herein means a member of a specific binding pair. That is, two different molecules where one of the molecules through chemical or physical means specifically binds to the second molecule. In addition to being an antibody member of a specific binding pair for HGBV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HGBV as in a sandwich assay, to the capture reagent as in a competitive assay, or to the ancillary specific binding member as in an indirect assay.

The various "signal generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten," as used herein, refers to a partial antigen or non-protein binding member which is capable of binding to an antibody, but which is not capable of eliciting antibody formation unless coupled to a carrier protein.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278 corresponding to EP publication 0326100 and U.S. patent application Ser. No. 375,029 (EP publication no. 0406473), can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No. 921,979 corresponding to EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in pending U.S. patent application Ser. Nos. 425,651 and 425,643, which correspond to published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 662,147. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the binding partner directly (in the cases of amino or thiol) or the activated surface can be further reacted with linkers such as glutaraldehyde, bis (succinimidyl) suberate, SPPD 9 succinimidyl 3-[2-pyridyldithio]propionate), SMCC (succinimidyl-4-[N-maleimidomethyl]cyclohexane-1-carboxylate), SIAB (succinimidyl [4-iodoacetyl] aminobenzoate), and SMPB (succinimidyl 4-[1-maleimidophenyl]butyrate) to separate the binding partner from the surface. The vinyl group can be oxidized to provide a means for covalent attachment. It also can be used as an anchor for the polymerization of various polymers such as poly acrylic acid, which can provide multiple attachment points for specific binding partners. The amino surface can be reacted with oxidized dextrans of various molecular weights to provide hydrophilic linkers of different size and capacity. Examples of oxidizable dextrans include Dextran T-40 (molecular weight 40,000 daltons), Dextran T-10 (molecular weight 10,000 daltons), Dextran T-500 (molecular weight 500,000 daltons), Dextran T-2M (molecular weight 2,000,000 daltons) (all of which are available from Pharmacia), or Ficoll (molecular weight 70,000 daltons (available from Sigma Chemical Co., St. Louis, Mo.). Also, polyelectrolyte interactions may be used to immobilize a specific binding partner on a surface of a test piece by using techniques and chemistries described by pending U.S. patent applications Ser. No. 150,278, filed Jan. 29, 1988, and Ser. No. 375,029, filed Jul. 7, 1989. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and probe assays. For example, the monoclonal antibodies of the present invention can be employed in various assay systems to determine the presence, if any, of HGBV proteins in a test sample. Fragments of these monoclonal antibodies provided also may be used. For example, in a first assay format, a polyclonal or monoclonal anti-HGBV antibody or fragment thereof, or a combination of these antibodies, which has been coated on a solid phase, is contacted with a test sample which may contain HGBV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to an HGBV region, or a combination of these antibodies, to which a signal generating compound has been attached, is contacted with the antigen/antibody complexes to form a second mixture. This second mixture then is incubated for a time and under conditions sufficient to form antibody/antigen/antibody complexes. he presence of HGBV antigen present in the test sample and captured on the solid phase, if any, is determined by detecting the measurable signal generated by the signal generating compound. The amount of HGBV antigen present in the test sample is proportional to the signal generated.

Alternatively, a polyclonal or monoclonal anti-HGBV antibody or fragment thereof, or a combination of these antibodies which is bound to a solid support, the test sample and an indicator reagent comprising a monoclonal or polyclonal antibody or fragments thereof, which specifically binds to HGBV antigen, or a combination of these antibodies to which a signal generating compound is attached, are contacted to form a mixture. This mixture is incubated for a time and under conditions sufficient to form antibody/antigen/antibody complexes. The presence, if any, of HGBV proteins present in the test sample and captured on the solid phase is determined by detecting the measurable signal generated by the signal generating compound. The amount of HGBV proteins present in the test sample is proportional to the signal generated.

In another alternate assay format, one or a combination of at least two monoclonal antibodies of the invention can be employed as a competitive probe for the detection of antibodies to HGBV protein. For example, HGBV proteins, either alone or in combination, can be coated on a solid phase. A test sample suspected of containing antibody to HGBV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB, non-C, non-D, non-E hepatitis test sample indicates the presence of anti-HGBV antibody in the test sample.

In yet another detection method, each of the monoclonal or polyclonal antibodies of the present invention can be employed in the detection of HGBV antigens in fixed tissue sections, as well as fixed cells by immunohistochemical analysis. Cytochemical analysis wherein these antibodies are labeled directly (fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific HGBV proteins from cell cultures, or biological tissues such as blood and liver such as to purify recombinant and native viral HGBV antigens and proteins.

The monoclonal antibodies of the invention can also be used for the generation of chimeric antibodies for therapeutic use, or other similar applications.

The monoclonal antibodies or fragments thereof can be provided individually to detect HGBV antigens. Combinations of the monoclonal antibodies (and fragments thereof) provided herein also may be used together as components in a mixture or "cocktail" of at least one anti-HGBV antibody of the invention with antibodies to other HGBV regions, each having different binding specificities. Thus, this cocktail can include the monoclonal antibodies of the invention which are directed to HGBV proteins and other monoclonal antibodies to other antigenic determinants of the HGBV genome.

The polyclonal antibody or fragment thereof which can be used in the assay formats should specifically bind to a specific HGBV region or other HGBV proteins used in the assay. The polyclonal antibody used preferably is of mammalian origin; human, goat, rabbit or sheep anti-HGBV polyclonal antibody can be used. Most preferably, the polyclonal antibody is rabbit polyclonal anti-HGBV antibody. The polyclonal antibodies used in the assays can be used either alone or as a cocktail of polyclonal antibodies. Since the cocktails used in the assay formats are comprised of either monoclonal antibodies or polyclonal antibodies having different HGBV specificity, they would be useful for diagnosis, evaluation and prognosis of HGBV infection, as well as for studying HGBV protein differentiation and specificity.

It is contemplated and within the scope of the present invention that the HGBV group of viruses may be detectable in assays by use of a synthetic, recombinant or native peptide that is common to all HGBV viruses. It also is within the scope of the present invention that different synthetic, recombinant or native peptides identifying different epitopes from HGBV-A, HGBV-B, HGBV-C, or yet other HGBV viruses, can be used in assay formats. In the later case, these can be coated onto one solid phase, or each separate peptide may be coated on separate solid phases, such as microparticles, and then combined to form a mixture of peptides which can be later used in assays. Such variations of assay formats are known to those of ordinary skill in the art and are discussed hereinbelow.

In another assay format, the presence of antibody and/or antigen to HGBV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, which corresponds to EP Publication No. 0473065.

In yet other assay formats, recombinant proteins and/or synthetic peptides may be utilized to detect the presence of anti-HGBV in test samples. For example, a test sample is incubated with a solid phase to which at least one recombinant protein or synthetic peptide has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein or synthetic peptide produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HGBV antibody. Other assay formats utilizing the proteins of the present invention are contemplated. These include contacting a test sample with a solid phase to which at least one antigen from a first source has been attached, incubating the solid phase and test sample for a time and under conditions sufficient to form antigen/antibody complexes, and then contacting the solid phase with a labelled antigen, which antigen is derived from a second source different from the first source. For example, a recombinant protein derived from a first source such as E. coli is used as a capture antigen on a solid phase, a test sample is added to the so-prepared solid phase, and a recombinant protein derived from a different source (i.e., non-E. coli) is utilized as a part of an indicator reagent. Likewise, combinations of a recombinant antigen on a solid phase and synthetic peptide in the indicator phase also are possible. Any assay format which utilizes an antigen specific for HGBV from a first source as the capture antigen and an antigen specific for HGBV from a different second source are contemplated. Thus, various combinations of recombinant antigens, as well as the use of synthetic peptides, purified viral proteins, and the like, are within the scope of this invention. Assays such as this and others are described in U.S. Pat. No. 5,254,458, which enjoys common ownership and is incorporated herein by reference.

Other assay systems which utilize an antibody (polyclonal, monoclonal or naturally-occurring) which specifically binds HGBV viral particles or sub-viral particles housing the viral genome (or fragments thereof) by virtue of a contact between the specific antibody and the viral protein (peptide, etc.). This captured particle then can be analyzed by methods such as LCR or PCR to determine whether the viral genome is present in the test sample. Test samples which can be assayed according to this method include blood, liver, sputum, urine, fecal material, saliva, and the like. The advantage of utilizing such an antigen capture amplification method is that it can separate the viral genome from other molecules in the test specimen by use of a specific antibody. Such a method has been described in pending U.S. patent application Ser. No. 08/141,429.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

Materials and Methods

General Techniques

Conventional and well-known techniques and methods in the fields of molecular biology, microbiology, recombinant DNA and immunology are employed in the practice of the invention unless otherwise noted. Such techniques are explained and detailed in the literature. See, for example, J. Sambrook et al., *Molecular Cloning: A Laboratory Manual*, 2nd edition, Cold Spring Harbor Press, Cold Spring Harbor, N.Y. (1989); D. N. Glover, ed., *DNA Cloning, Volumes I and II* (1985); M. J. Gait ed., *Oligonucleotide Synthesis*, (1984); B. D. Hames et al., eds., *Nucleic Acid Hybridization*, (1984); B. D. Hames et al., eds., *Transcription and Translation*, (1984); R. I. Freshney ed., *Animal Cell Culture*, (1986); *Immobilized Cells and Enzymes*, IRL Press (1986); B. Perbal, *A Practical Guide to Molecular Cloning*, (1984); the series, *Methods in Enzymology*, Academic Press, Inc., Orlando, Fla.; J. H. Miller et al., eds., *Gene Transfer Vectors For Mammalian Cells*, Cold Spring Harbor Laboratory, Cold Spring Harbor, N.Y. (1987); Wu et al., eds., Methods in Enzymology, Vol. 154 and 155; Mayer et al., eds., *Immunological Methods In Cell and Molecular Biology*, Academic Press, London (1987); Scopes, *Protein Purification: Principles and Practice,* 2nd ed., Springer-Verlag, N.Y.; and D. Weir et al., eds., *Handbook Of Experimental Immunology*, Volumes I–IV (1986); N. Lisitisyn et al., *Science* 259:946–951 (1993).

The reagents and methods of the present invention are made possible by the provision of a family of closely related nucleotide sequences, isolated by representational difference analysis modified as described herein, present in the plasma, serum or liver homogenate of an HGBV infected individual, either tamarin or human. This family of nucleotide sequences is not of human or tamarin origin, since it will be shown that it hybridizes to neither human nor tamarin genomic DNA from uninfected individuals, since nucleotides of this family of sequences are present only in liver (or liver homogenates), plasma or serum of individuals infected with HGBV, and since the sequence is not present in GenBank. In addition, the family of sequences will show no significant identity at the nucleic acid level to sequences contained within the HAV, HBV, HCV, HDV and HEV genome, and low level identity, considered not significant, as translation products. Infectious sera, plasma or liver homogenates from HGBV infected humans contain these polynucleotide sequences, whereas sera, plasma or liver homogenates from non-infected humans do not contain these sequences. Northern blot analysis of infected liver with some of these polynucleotide sequences demonstrate that they are derived from a large RNA transcript similar in size to a viral genome. Sera, plasma or liver homogenates from HGBV-infected humans contain antibodies which bind to this polypeptide, whereas sera, plasma or liver homogenates from non-infected humans do not contain antibodies to this polypeptide; these antibodies are induced in individuals following acute non-A, non-B, non-C, non-D and non-E infection. By these criteria, it is believed that the sequence is a viral sequence, wherein the virus causes or is associated with non-A, non-B, non-C, non-D and non-E hepatitis.

The availability of this family of nucleic acid sequences permits the construction of DNA probes and polypeptides useful in diagnosing non-A, non-B, non-C, non-D, non-E hepatitis due to HGBV infections, and in screening blood donors, donated blood, blood products and individuals for infection. For example, from the sequence it is possible to synthesize DNA oligomers of about eight to ten nucleotides, or larger, which are useful as hybridization probes or PCR primers to detect the presence of the viral genome in, for example, sera of subjects suspected of harboring the virus, or for screening donated blood for the presence of the virus. The family of nucleic acid sequences also allows the design and production of HGBV specific polypeptides which are useful as diagnostic reagents for the presence of antibodies raised during infection with HGBV. Antibodies to purified polypeptides derived from the nucleic acid sequences may also be used to detect viral antigens in infected individuals and in blood. These nucleic acid sequences also enable the design and production of polypeptides which may be used as vaccines against HGBV, and also for the production of antibodies, which then may be used for protection of the disease, and/or for therapy of HGBV infected individuals.

The family of nucleic acid sequences also enables further characterization of the HGBV genome. Polynucleotide probes derived from these sequences may be used to screen genomic or cDNA libraries for additional overlapping nucleic acid sequences which then may be used to obtain more overlapping sequences. Unless the genome is segmented and the segments lack common sequences, this technique may be used to gain the sequence of the entire genome. However, if the genome is segmented, other segments of the genome can be obtained by either repeating the RDA cloning procedure as described and modified hereinbelow or by repeating the lambda-gt11 serological screening procedure discussed hereinbelow to isolate the clones which will be described herein, or alternatively by isolating the genome from purified HGBV particles.

The family of cDNA sequences and the polypeptides derived from these sequences, as well as antibodies directed against these polypeptides, also are useful in the isolation and identification of the HGBV etiological agent(s). For example, antibodies directed against HGBV epitopes contained in polypeptides derived from the nucleic acid sequences may be used in methods based upon affinity chromatography to isolate the virus. Alternatively, the antibodies can be used to identify viral particles isolated by other techniques. The viral antigens and the genomic material within the isolated viral particles then may be further characterized.

The information obtained from further sequencing of the HGBV genome(s), as well as from further characterization of the HGBV antigens and characterization of the genome enables the design and synthesis of additional probes and polypeptides and antibodies which may be used for diagnosis, prevention and therapy of HGBV induced non-A, non-B, non-C non-D, non-E hepatitis, and for screening of infected blood and blood-related products.

The availability of probes for HGBV, including antigens, antibodies and polynucleotides derived from the genome from which the family of nucleic acid sequences is derived also allows for the development of tissue culture systems which will be of major use in elucidating the biology of HGBV. Once this is known, it is contemplated that new treatment regimens may be developed based upon antiviral compounds which preferentially inhibit the replication of or infection by HGBV.

In one method used to identify and isolate the etiological agent of HGBV, the cloning/isolation of the GB agent was achieved by modifying the published procedure known as representational difference analysis (RDA), as reported by N. Lisitsyn et al., *Science* 259: 946–951 (1993). This method is based upon the principles of subtractive hybridization for cloning DNA differences between two complex mammalian genomes. Briefly, in this procedure, the two genomes under evaluation are identified generically as the "tester" (containing the target sequence of interest) and the "driver" (representing normal DNA). Lisitsyn et al.'s description of RDA is limited to identifying and cloning DNA differences between complex, but similar DNA backgrounds. These differences may include any large DNA viruses (eg. ≧75,000 base pairs of DNA) that is present in a cell line, blood, plasma or tissue sample and absent in an uninfected cell line, blood, plasma or tissue sample. Because previous literature suggested that HGBV may be a small virus containing either a DNA or RNA genome of ≦10,000 bases, the RDA protocol was modified such as to allow the detection of small viruses. The major steps of the procedure are described hereinbelow and are diagrammed in FIG. 13.

Briefly, in step 1, total nucleic acid (DNA and RNA) is isolated using commercially available kits. RDA requires that the sample be highly matched. Ideally, tester and driver nucleic acid samples should be obtained from the same source (animal, human or other). It may be possible to use highly related, but non-identical, material for the source of the tester and driver nucleic acids. Double stranded DNA is generated from the total nucleic acid by random primed reverse transcription of the RNA followed by random primed DNA synthesis. This treatment converts single strand RNA viruses and single strand DNA viruses to double strand DNA molecules which are amenable to RDA. If one chooses to assume that an unknown virus has a DNA or an RNA genome, a DNA-only or RNA-only extraction procedure can be employed and double-stranded DNA can be generated as described in the art.

In step 2, the tester and driver nucleic acids are amplified to generate an abundant amount of material which represents the total nucleic acid extracted from the pre-inoculation and infectious plasma sources (i.e. the tester amplicon and the driver amplicon). This is achieved by cleaving double-stranded DNA prepared as described above with a restriction endonuclease which has a 4 bp recognition site (such as Sau3A I). The DNA fragments are ligated to oligonucleotide adaptors (set #1). The DNA fragments are end-filled and PCR amplified. Following PCR amplification, the oligonucleotide adaptor (set #1) is then removed by restriction endonuclease digestion (for example, with Sau3A I), liberating a large amount of tester and driver nucleic acid to be used in subsequent subtractive hybridization techniques.

In step 3, the experimental design is to enrich for DNA unique to the tester genome. This is achieved by combining subtractive hybridization and kinetic enrichment into a single step. Briefly, an oligonucleotide adaptor set (#2 or #3) is ligated to the 5' ends of the tester amplicon. The tester amplicon and an excess of driver amplicon are mixed, denatured and allowed to hybridized for 20 hours. A large amount of the sequences that are held in common between the tester and driver DNA will anneal during this time. In addition, sequences that are unique to the tester amplicon will reanneal. However, because of the limited time of hybridization, some single-stranded tester and driver DNA will remain.

In step 4, the 3' ends of the reannealed tester and driver DNA are filled in using a thermostable DNA polymerase at elevated temperature as described in the art. The reannealed sequences that are unique to the tester contain the ligated adaptor on both strands of the annealed sequence. Thus, 3' end-filling of these molecules creates sequences complementary to PCR primers on both DNA strands. As such, these DNA species will be amplified exponentially when subjected to PCR. In contrast, the relatively large amount of hybrid molecules containing sequences held in common between tester and driver amplicons (i.e. one strand was derived from the tester amplicon and one strand was derived from the driver amplicon) will be amplified linearly when subjected to PCR. This is because only one strand (derived from the tester amplicon) contains the ligated adaptor sequence, and 3' end filling will only generate sequences complementary to the PCR primer on the strand derived from the driver amplicon.

In step 5, the double-strand DNA of interest is enriched quantitatively using PCR for 10 cycles of amplification. As stated above in step 4, reannealed tester sequences will be amplified exponentially whereas sequences held in common between tester and driver amplicons will be amplified linearly.

In step 6, single-strand DNA which remains is removed by a single strand DNA nuclease digestion using mung bean nuclease as described in the art.

In step 7, double-stranded DNA which remains after nuclease digestion is PCR amplified an additional 15 to 25 cycles.

Finally in step 8, these DNA products are cleaved with restriction endonuclease to remove the oligonucleotide adaptors. These DNA products can then be subjected to subsequent rounds of amplification (beginning at step #3 using the oligonucleotide adaptor set that was not used in the previous cycle of RDA) or cloned into a suitable plasmid vector for further analysis.

The RDA procedure as described supra is a modification of the representational difference analysis known in the art. The method was modified to isolate viral clones from pre-inoculation and infectious sera sources. These modifications are discussed further below and relate to the preparation of amplicons for both tester and driver DNA. First, the starting material was not double-stranded DNA obtained from the genomic DNA of mammalian cells as reported previously, but total nucleic acid extracted from infectious and pre-inoculation biological blood samples obtained from tamarins. It is possible that other biological samples (for example, organs, tissue, bile, feces or urine) could be used as sources of nucleic acid from which tester and driver amplicons are generated. Second, the amount of starting nucleic acid is substantially less than that described in the art. Third, a restriction endonuclease with a 4 bp instead of a 6 bp recognition site was used. This is substantially different from the prior art. Lisitsyn et al. teach that RDA works because the generation of amplicons (i.e. representations) decreases the complexity of the DNA that is being hybridized (i.e. subtracted).

In the prior art, restriction enzymes that have 6 bp recognition sites were used to fragment the genome. These restriction endonucleases cleave approximately every 4000 bp. However, the PCR conditions described in the prior art amplify sequences ≦1500 bp in size. Therefore, subsequent PCR amplification of a complex species of DNA (such as a genome) that has been fragmented with a restriction enzyme that recognizes a 6 bp sequence results in the generation of amplicons that contain the fraction of the DNA that was ≦1500 bp in size after restriction endonuclease digestion. This reduction in DNA complexity (estimated to be a 10- to 50-fold reduction) is reported to be necessary for the hybridization step of RDA to work. If the complexity is not reduced, unique sequences in the tester will not be able to efficiently hybridize during the subtraction step, and therefore, these unique sequences will not be amplified exponentially during the subsequent PCR steps of RDA.

The reduction of complexity of the nucleic acid sequences being subjected to RDA undermines using RDA effectively to isolate relatively small viruses. The odds of two 6 bp-recognition sites occurring within 1.5 kb of each other is sufficiently rare that one might miss a small (≦10 kb) virus (TABLE 1).

TABLE 1

| Virus | Enzyme | # of Fragments <1.5kb |
|---|---|---|
| λ | BamH I | 0 |
| (~50 kb) | Bgl II | 3 |
|  | Hind III | 1 |
| Parvo B19 | BamH I | 0 |
| (~5 kb) | Bgl II | 0 |
|  | Hind III | 2 |
|  | Sau3A I (4 bp site) | 5–7 |
| HBV | BamH I | 1–2 |
| (~3.2 kb) | Bgl II | 1–2 |
|  | HindIII | 0 |
|  | Sau3A I (4 bp site) | 12 |

However, we have discovered that RDA may be useful in cloning small viruses if a more frequently cutting restriction endonuclease is used to fragment the DNA being subjected to RDA. As shown in TABLE 1, amplicons based on 4 bp recognition site enzymes will almost certainly contain several fragments from any small virus, as restriction endonucleases which have 4 bp recognition sites fragment DNA approximately every 250 base pairs. However, it is likely that amplicons will be as complex as the source of the nucleic acid from which they were generated because nearly all of the DNA species will be ≦1500 bp after digestion with a 4 bp recognizing restriction endonuclease and thus, subject to PCR amplification. Since the relative viral sequence copy number is predicted to be higher than any specific or endogenous sequence copy number, the unique viral sequences that are present in the tester amplicon should be able to form double stranded molecules during the hybridization step (step 3, above). Therefore, these sequences will be amplified exponentially as described above. It is reasoned that as the relative viral sequence copy number becomes closer to that of the background or endogenous nucleic acid sequence copy number, a restriction endonuclease which recognizes a redundant 6 bp sequence (for example BstYI or HincII) and cleaves approximately every 1000 bp, or the simultaneous use of several restriction endonuclease which recognizes 6 bp sequences, may be used to fragment the DNA prior to amplification by PCR. In this way, one can moderately reduce the complexity of the amplicons being subjected to RDA while minimizing the risk of excluding viral sequences from the tester amplicon. The utility of this procedure is demonstrated by the cloning of HGBV sequences from infectious tamarin plasma described herein.

Immunoscreening to Identify HGBV Immunoreactive epitopes

Immunoscreening as described herein as follows also provided an additional means of identifying HGBV sequences. Pooled or individual serum, plasma or liver homogenates from an individual meeting the criteria and within the parameters set forth below with acute or chronic HGBV infection is used to isolate viral particles. Nucleic acids isolated from these particles are used as the template in the construction of a genomic and/or cDNA library to the viral genome. The procedures used for isolation of putative HGBV particles and for constructing the genomic and/or cDNA library in lambda-gt11 or similar systems known in the art is discussed hereinbelow. Lambda-gt11 is a vector that has been developed specifically to express inserted cDNAs as fusion polypeptides with beta-galactosidase and to screen large numbers of recombinant phage with specific antisera raised against a defined antigen. The lambda-gt11 cDNA library generated from a cDNA pool containing cDNA is screened for encoded epitopes that can bind specifically with sera derived from individuals who previously had experienced non-A, non-B, non-C, non-D and non-E hepatitis. See V. Hunyh et al., in D. Glover, ed., *DNA Cloning Techniques; A Practical Approach*, IRL Press, Oxford, England, pp. 49–78 (1985). Approximately $10^6$–$10^7$ phage are screened, from which positive phage are identified, purified, and then tested for specificity of binding to sera from different individuals previously infected with the HGBV agent. Phage which selectively bind sera or plasma from patients meeting the criteria described hereinbelow and not in patients who did not meet these described criteria, are preferred for further study. By utilizing the technique of isolating overlapping nucleic acid sequences, clones containing additional upstream and downstream HGBV sequences are obtained. Analysis of the nucleotide sequences of the HGBV nucleic acid sequences encoded within the isolated clones is performed to determine whether the composite sequence contains one long continuous ORF.

The sequences (and their complements) retrieved from the HGBV sequence as provided herein, and the sequences or any portion thereof, can be prepared using synthetic methods or by a combination of synthetic methods with retrieval of partial sequences using methods similar to those described herein. This description thus provides one method by which genomic or cDNA sequences corresponding to the entire HGBV genome may be isolated. Other methods for isolating these sequences, however, will be obvious to those skilled in the art and are considered to be within the scope of the present invention.

Deposit of Strains

Strains replicated (clones 2, 4, 10, 16, 18, 23 and 50) from the HGBV nucleic acid sequence library have been deposited at the American Type Culture Collection, 10801 University Boulevard, Manassas, Va. 20110-2209, as of Feb. 10, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 2 was accorded A.T.C.C. Deposit No. 69556; Clone 4 was accorded A.T.C.C. Deposit No. 69557; Clone 10 was accorded A.T.C.C. Deposit No. 69558; Clone 16 was accorded A.T.C.C. Deposit No. 69559; Clone 18 was accorded A.T.C.C. Deposit No. 69560; Clone 23 was accorded A.T.C.C. Deposit No. 69561; and Clone 50 was accorded A.T.C.C. Deposit No. 69562.

Strains replicated (clones 11, 13, 48 and 119) from the HGBV nucleic acid sequence library have been deposited at the American Type Culture Collection, 10801 University Boulevard, Manassas, Va. 20110-2209, as of Apr. 29, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 11 was accorded A.T.C.C. Deposit No. No. 69613; Clone 13 was accorded A.T.C.C. Deposit No. 69611; Clone 48 was accorded A.T.C.C. Deposit No. 69610; and Clone 119 was accorded A.T.C.C. Deposit No. 69612.

Additional strains (clones 4-B1.1, 66-3A1.49, 70-3A1.37 and 78-1C1.17) from the HGBV nucleic acid sequence library have been deposited at the American Type Culture Collection, 10801 University Boulevard, Manassas, Va. 20110-2209, as of Jul. 28, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. The HGBV cDNA sequences in all of the deposited materials are incorporated herein by reference. The plasmids were accorded the following A.T.C.C. deposit numbers: Clone 4-B1.1 was accorded A.T.C.C. Deposit No. No. 69666; Clone 66-3A1.49 was accorded A.T.C.C. Deposit No. 69665; Clone 70-3A1.37 was accorded A.T.C.C. Deposit No. 69664; and Clone 78-1C1.17 was accorded A.T.C.C. Deposit No. 69663.

Clone pHGBV-C clone #1 was deposited at the American Type Culture. Collection, 10801 University Boulevard, Manassas, Va. 20110-2209 as of Nov. 8, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. pHGBV-C clone #1 was accorded A.T.C.C. Deposit No. 69711. The HGBV cDNA sequences in all of the deposited materials are incorporated herein by reference.

Preparation of Viral Polypeptides and Fragments

The availability of nucleic acid sequences permits the construction of expression vectors encoding antigenically active regions of the polypeptide encoded in either strand. These antigenically active regions may be derived from structural regions of the virus, including, for example, envelope (coat) or core antigens, in addition to nonstructural regions of the virus, including, for example, polynucleotide binding proteins, polynucleotide polymerase(s), and other viral proteins necessary for replication and/or assembly of the viral particle. Fragments encoding the desired polypeptides are derived from the genomic or cDNA clones using conventional restriction digestion or by synthetic methods, and are ligated into vectors which may, for example, contain portions of fusion sequences such as beta-galactosidase (β-gal) or superoxide dismutase (SOD) or CMP-KDO synthetase (CKS). Methods and vectors which are useful for the production of polypeptides which contain fusion sequences of SOD are described in EPO 0196056, published Oct. 1, 1986, and those of CKS are described in EPO Publication No. 0331961, published Sep. 13, 1989. Any desired portion of the nucleic acid sequence containing an open reading frame, in either sense strand, can be obtained as a recombinant protein, such as a mature or fusion protein; alternatively, a polypeptide encoded in the HGBV genome or cDNA can be provided by chemical synthesis.

The nucleic acid sequence encoding the desired polypeptide, whether in fused or mature form, and whether or not containing a signal sequence to permit secretion, may be ligated into expression vectors suitable for any convenient host. Both eucaryotic and prokaryotic host systems are used in the art to form recombinant proteins, and some of these are listed herein. The polypeptide then is isolated from lysed cells or from the culture medium and purified to the extent needed for its intended use. Purification can be performed by techniques known in the art, and include salt fractionation, chromatography on ion exchange resins, affinity chromatography, centrifugation, among others. Such polypeptides may be used as diagnostic reagents, or for passive immunotherapy. In addition, antibodies to these polypeptides are useful for isolating and identifying HGBV particles. The HGBV antigens also may be isolated from HGBV virions. These virions can be grown in HGBV infected cells in tissue culture, or in an infected individual.

Preparation of Antigenic Polypeptides and Conjugation With Solid Phase

An antigenic region or fragment of a polypeptide generally is relatively small, usually about 8 to 10 amino acids or less in length. Fragments of as few as 5 amino acids may characterize an antigenic region. These segments may correspond to regions of HGBV antigen. By using the HGBV genomic or cDNA sequences as a basis, nucleic acid sequences encoding short segments of HGBV polypeptides can be expressed recombinantly either as fusion proteins or as isolated polypeptides. These short amino acid sequences also can be obtained by chemical synthesis. The small chemically synthesized polypeptides may be linked to a suitable carrier molecule when the synthesized polypeptide provided is correctly configured to provide the correct epitope but too small to be antigenic. Linking methods are known in the art and include but are not limited to using N-succinimidyl-3-(2-pyrdylthio)propionate (SPDP) and succinimidyl 4-(N-maleimidomethyl)cyclohexane-1-carboxylate (SMCC). Polypeptides lacking sulfhydryl groups can be modified by adding a cysteine residue. These reagents create a disulfide linkage between themselves and peptide cysteine residues on one protein and an amide linkage through the epsilon-amino on a lysine, or other free amino group in the other. A variety of such disulfide/amide-forming agents are known. Other bifunctional coupling agents form a thioester rather than a disulfide linkage. Many of these thio-ether-forming agents are commercially available and are known to those of ordinary skill in the art. The carboxyl groups can be activated by combining them with succinimide or 1-hydroxyl-2-nitro-4-sulfonic acid, sodium salt. Any carrier which does not itself induce the production of antibodies harmful to the host can be used. Suitable carriers include proteins, polysaccharides such as latex functionalized sepharose, agarose, cellulose, cellulose beads, polymeric amino acids such as polyglutamic acid, polylysine, amino acid copolymers and inactive virus particles, among others. Examples of protein substrates include serum albumins, keyhole limpet hemocyanin, immunoglobulin molecules, thyroglobulin, ovalbumin, tetanus toxoid, and yet other proteins known to those skilled in the art.

Preparation of Hybrid Particle Immunogens Containing HGBV Epitopes

The immunogenicity of HGBV epitopes also may be enhanced by preparing them in mammalian or yeast systems fused with or assembled with particle-forming proteins such as those associated with HBV surface antigen. Constructs wherein the HGBV epitope is linked directly to the particle-forming protein coding sequences produce hybrids which are immunogenic with respect to the HGBV epitope. In addition, all of the vectors prepared include epitopes specific for HGBV, having varying degrees of immunogenicity.

Particles constructed from particle forming protein which include HGBV sequences are immunogenic with respect to HGBV and HBV.

Hepatitis B surface antigen has been determined to be formed and assembled into particles in *S. cerevisiae* and mammalian cells; the formation of these particles has been reported to enhance the immunogenicity of the monomer subunit. P. Valenzuela et al., *Nature* 298:334 (1982); P. Valenzuela et al., in I. Millman et al., eds., *Hepatitis B*, Plenum Press, pp. 225–236 (1984). The constructs may include immunodominant epitopes of HBsAg. Such constructs have been reported expressible in yeast, and hybrids including heterologous viral sequences for yeast expression have been disclosed. See, for example, EPO 174, 444 and EPO 174,261. These constructs also have been reported capable of being expressed in mammalian cells such as Chinese hamster ovary (CHO) cells. Michelle et al., *International Symposium on Viral Hepatitis*, 1984. In HGBV, portions of the particle-forming protein coding sequence may be replaced with codons encoding an HGBV epitope. In this replacement, regions that are not required to mediate the aggregation of the units to form immunogenic particles in yeast or mammals can be deleted, thus eliminating additional HGBV antigenic sites from competition with the HGBV epitope.

Vaccine Preparation

Vaccines may be prepared from one or more immunogenic polypeptides or nucleic acids derived from HGBV nucleic acid sequences or from the HGBV genome to which they correspond. Vaccines may comprise recombinant polypeptides containing epitope(s) of HGBV. These polypeptides may be expressed in bacteria, yeast or mammalian cells, or alternatively may be isolated from viral preparations. It also is anticipated that various structural proteins may contain epitopes of HGBV which give rise to protective anti-HGBV antibodies. Synthetic peptides therefore also can be utilized when preparing these vaccines. Thus, polypeptides containing at least one epitope of HGBV may be used, either singly or in combinations, in HGBV vaccines. It also is contemplated that nonstructural proteins as well as structural proteins may provide protection against viral pathogenicity, even if they do not cause the production of neutralizing antibodies.

Considering the above, multivalent vaccines against HGBV may comprise one or more structural proteins, and/or one or more nonstructural proteins. These vaccines may be comprised of, for example, recombinant HGBV polypeptides and/or polypeptides isolated from the virions and/or synthetic peptides. These immunogenic epitopes can be used in combinations, i.e., as a mixture of recombinant proteins, synthetic peptides and/or polypeptides isolated from the virion; these may be administered at the same or different time. Additionally, it may be possible to use inactivated HGBV in vaccines. Such inactivation may be by preparation of viral lysates, or by other means known in the art to cause inactivation of hepatitis-like viruses, for example, treatment with organic solvents or detergents, or treatment with formalin. Attenuated HGBV strain preparation also is disclosed in the present invention. It is contemplated that some of the proteins in HGBV may cross-react with other known viruses, and thus that shared epitopes may exist between HGBV and other viruses which would then give rise to protective antibodies against one or more of the disorders caused by these pathogenic agents. It is contemplated that it may be possible to design multiple purpose vaccines based upon this belief.

The preparation of vaccines which contain at least one immunogenic peptide as an active ingredient is known to one skilled in the art. Typically, such vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy) ethylamine (CGP 19835A, also referred to as MTP-PE), and RIBI (MPL+TDM+CWS) in a 2% squalene/Tween-80® emulsion. The effectiveness of an adjuvant may be determined by measuring the amount of antibodies directed against an immunogenic polypeptide containing an HGBV antigenic sequence resulting from administration of this polypeptide in vaccines which also are comprised of the various adjuvants.

The vaccines usually are administered by intravenous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic HGBV antigen(s) may be administered in conjunction with other immunoregulatory agents, for example, with immune globulins.

Preparation of Antibodies Against HGBV Epitopes

The immunogenic peptides prepared as described herein are used to produce antibodies, either polyclonal or monoclonal. When preparing polyclonal antibodies, a selected mammal (for example, a mouse, rabbit, goat, horse or the like) is immunized with an immunogenic polypeptide bearing at least one HGBV epitope. Serum from the immunized animal is collected after an appropriate incubation period and treated according to known procedures. If serum containing polyclonal antibodies to an HGBV epitope contains antibodies to other antigens, the polyclonal antibodies can be purified by, for example, immunoaffinity chromatography. Techniques for producing and processing polyclonal antibodies are known in the art and are described in, among others, Mayer and Walker, eds., *Immunochemical Methods In Cell and Molecular Biology*, Academic Press, London (1987). Polyclonal antibodies also may be obtained from a mammal previously infected with HGBV. An example of a method for purifying antibodies to HGBV epitopes from serum of an individual infected with HGBV using affinity chromatography is provided herein.

Monoclonal antibodies directed against HGBV epitopes also can be produced by one skilled in the art. The general methodology for producing such antibodies is well-known and has been described in, for example, Kohler and Milstein, *Nature* 256:494 (1975) and reviewed in J. G. R. Hurrel, ed., *Monoclonal Hybridoma Antibodies: Techniques and Applications*, CRC Press Inc., Boco Raton, Fla. (1982), as well as that taught by L. T. Mimms et al., *Virology* 176:604–619 (1990). Immortal antibody-producing cell lines can be created by cell fusion, and also by other techniques such as direct transformation of B lymphocytes with oncogenic DNA, or transfection with Epstein-Barr virus. See also, M. Schreier et al., Hybridoma Techniques, Scopes (1980) Protein Purification, Principles and Practice, 2nd Edition, Springer-Verlag, New York (1984); Hammerling et al., Monoclonal Antibodies and T-Cell Hybridomas (1981); Kennet et al., Monoclonal Antibodies (1980). Examples of uses and techniques of monoclonal antibodies are disclosed in U.S. patent applications Ser. Nos. 748,292; 748,563; 610,175, 648,473; 648,477; and 648,475.

Monoclonal and polyclonal antibodies thus developed, directed against HGBV epitopes, are useful in diagnostic and prognostic applications, and also, those which are neutralizing are useful in passive immunotherapy. Monoclonal antibodies especially can be used to produce anti-idiotype antibodies. These anti-idiotype antibodies are immunoglobulins which carry an "internal image" of the antigen of the infectious agent against which protection is desired. See, for example, A. Nisonoff et al., *Clin. Immunol. Immunopath.* 21:397–406 (1981), and Dreesman et al., *J. Infect. Dis.* 151:761 (1985). Techniques for raising such idiotype antibodies are known in the art and exemplified, for example, in Grych et al., *Nature* 316:74 (1985); MacNamara et al., *Science* 226:1325 (1984); and Uytdehaag et al., *J. Immunol.* 134:1225 (1985). These anti-idiotypic antibodies also may be useful for treatment of HGBV infection, as well as for elucidation of the immunogenic regions of HGBV antigens.

Diagnostic Oligonucleotide Probes and Kits

Using determined portions of the isolated HGBV nucleic acid sequences as a basis, oligomers of approximately eight nucleotides or more can be prepared, either by excision or synthetically, which hybridize with the HGBV genome and are useful in identification of the viral agent(s), further characterization of the viral genome, as well as in detection of the virus(es) in diseased individuals. The natural or derived probes for HGBV polynucleotides are a length which allows the detection of unique viral sequences by hybridization. While six to eight nucleotides may be a workable length, sequences of ten to twelve nucleotides are preferred, and those of about 20 nucleotides may be most preferred. These sequences preferably will derive from regions which lack heterogeneity. These probes can be prepared using routine, standard methods including automated oligonucleotide synthetic methods. A complement of any unique portion of the HGBV genome will be satisfactory. Complete complementarity is desirable for use as probes, although it may be unnecessary as the length of the fragment is increased.

When used as diagnostic reagents, the test sample to be analyzed, such as blood or serum, may be treated such as to extract the nucleic acids contained therein. The resulting nucleic acid from the sample may be subjected to gel electrophoresis or other size separation techniques; or, the nucleic acid sample may be dot-blotted without size separation. The probes then are labeled. Suitable labels and methods for attaching labels to probes are known in the art, and include but are not limited to radioactive labels incorporated by nick translation or kinasing, biotin, fluorescent and chemiluminescent probes. Examples of many of these labels are disclosed herein. The nucleic acids extracted from the sample then are treated with the labeled probe under hybridization conditions of suitable stringencies.

The probes can be made completely complementary to the HGBV genome. Therefore, usually high stringency conditions are desirable in order to prevent false positives. However, conditions of high stringency should be used only if the probes are complementary to regions of the HGBV genome which lack heterogeneity. The stringency of hybridization is determined by a number of factors during the washing procedure, including temperature, ionic strength, length of time and concentration of formamide. See, for example, J. Sambrook (supra). Hybridization can be carried out by a number of various techniques. Amplification can be performed, for example, by Ligase Chain Reaction (LCR), Polymerase Chain Reaction (PCR), Q-beta replicase, NASBA, etc.

It is contemplated that the HGBV genome sequences may be present in serum of infected individuals at relatively low levels, for example, approximately $10^2$–$10^3$ sequences per ml. This level may require that amplification techniques be used in hybridization assays, such as the Ligase Chain Reaction or the Polymerase Chain Reaction. Such techniques are known in the art. For example, the "Bio-Bridge" system uses terminal deoxynucleotide transferase to add unmodified 3'-poly-dT-tails to a nucleic acid probe (Enzo Biochem. Corp.). The poly dt-tailed probe is hybridized to the target nucleotide sequence, and then to a biotin-modified poly-A. Also, in EP 124221 there is described a DNA hybridization assay wherein the analyte is annealed to a single-stranded DNA probe that is complementary to an enzyme-labeled oligonucleotide, and the resulting tailed duplex is hybridized to an enzyme-labeled oligonucleotide. EP 204510 describes a DNA hybridization assay in which analyte DNA is contacted with a probe that has a tail, such as a poly-dT-tail, an amplifier strand that has a sequence that hybridizes to the tail of the probe, such as a poly-A sequence, and which is capable of binding a plurality of labeled strands. The technique first may involve amplification of the target HGBV sequences in sera to approximately $10^6$ sequences/ml. This may be accomplished by following the methods described by Saiki et al., *Nature* 324:163 (1986). The amplified sequence(s) then may be detected using a hybridization assay such as those known in the art. The probes can be packaged in diagnostic kits which include the probe nucleic acid sequence which sequence may be labeled; alternatively, the probe may be unlabeled and the ingredients for labeling could be included with the kit. The kit also may contain other suitably packaged reagents and materials needed or desirable for the particular hybridization protocol, for example, standards as well as instructions for performing the assay.

Other known amplification methods which can be utilized herein include but are not limited to the so-called "NASBA" or "3SR" technique taught in *PNAS USA* 87:1874–1878 (1990) and also discussed b in *Nature:*350 (No. 6313):91–92 (1991) and Q-beta replicase.

Fluorescence in situ hybridization ("FISH") also can be performed utilizing the reagents described herein. In situ hybridization involves taking morphologically intact tissues, cells or chromosomes through the nucleic acid hybridization process to demonstrate the presence of a particular piece of genetic information and its specific location within individual cells. Since it does not require homogenization of cells and extraction of the target sequence, it provides precise localization and distribution of a sequence in cell populations. In situ hybridization can identify the sequence of interest concentrated in the cells containing it. It also can identify the type and fraction of the cells in a heterogeneous cell population containing the sequence of interest. DNA and RNA can be detected with the same assay reagents. PNAs can be utilized in FISH methods to detect targets without the need for amplification. If increased signal is desired, multiple fluorophores can be used to increase signal and thus, sensitivity of the method. Various methods of FISH are known, including a one-step method using multiple oligonucleotides or the conventional multi-step method. It is within the scope of the present invention that these types of methods can be automated by various means including flow cytometry and image analysis.

Immunoassay and Diagnostic Kits

Both the polypeptides which react immunologically with serum containing HGBV antibodies and composites thereof, and the antibodies raised against the HGBV specific epitopes in these polypeptides are useful in immunoassays to detect the presence of HGBV antibodies, or the presence of the virus and/or viral antigens in biological test samples. The design of these immunoassays is subject to variation, and a variety of these are known in the art; a variety of these have been described herein. The immunoassay may utilize one viral antigen, such as a polypeptide derived from any clone-containing HGBV nucleic acid sequence, or from the composite nucleic acid sequences derived from the HGBV nucleic acid sequences in these clones, or from the HGBV genome from which the nucleic acid sequences in these clones is derived. Or, the immunoassay may use a combination of viral antigens derived from these sources. It may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785. Recombinant polypeptides which include epitopes from immunodominant regions of HGBV may be useful for the detection of viral antibodies in biological test samples of infected individuals. It also is contemplated that antibodies may be useful in discriminating acute from non-acute infections. Kits suitable for immunodiagnosis and containing the appropriate reagents are constructed by packaging the appropriate materials, including the polypeptides of the invention containing HGBV epitopes or antibodies directed against HGBV epitopes in suitable containers, along with the remaining reagents and materials required for the conduct of the assay, as well as suitable assay instructions.

Assay formats can be designed which utilize the recombinant proteins detailed herein, and although we describe and detail CKS proteins, it also is contemplated that other expression systems, such as superoxide dismutase (SOD), and others, can be used in the present invention to generate fusion proteins capable of use in a variety of ways, including as antigens in immunoassays, immunogens for antibody production, and the like. In an assay format to detect the presence of antibody against a specific analyte (for example, an infectious agent such as a virus) in a human test sample, the human test sample is contacted and incubated with a solid phase coated with at least one recombinant protein (polypeptide). If antibodies are present in the test sample, they will form a complex with the antigenic polypeptide and become affixed to the solid phase. After the complex has formed, unbound materials and reagents are removed by washing the solid phase. The complex is reacted with an indicator reagent and allowed to incubate for a time and under conditions for second complexes to form. The presence of antibody in the test sample to the CKS recombinant polypeptide(s) is determined by detecting the signal generated. Signal generated above a cut-off value is indicative of antibody to the analyte present in the test sample. With many indicator reagents, such as enzymes, the amount of antibody present is proportional to the signal generated. Depending upon the type of test sample, it may be diluted with a suitable buffer reagent, concentrated, or contacted with the solid phase without any manipulation ("neat"). For example, it usually is preferred to test serum or plasma samples which previously have been diluted, or concentrate specimens such as urine, in order to determine the presence and/or amount of antibody present.

In addition, more than one recombinant protein can be used in the assay format just described to test for the presence of antibody against a specific infectious agent by utilizing CKS fusion proteins against various antigenic epitopes of the viral genome of the infectious agent under study. Thus, it may be preferred to use recombinant polypeptides which contain epitopes within a specific viral antigenic region as well as epitopes from other antigenic regions from the viral genome to provide assays which have increased sensitivity and perhaps greater specificity than using a polypeptide from one epitope. Such an assay can be utilized as a confirmatory assay. In this particular assay format, a known amount of test sample is contacted with (a) known amount(s) of at least one solid support coated with at least one recombinant protein for a time and under conditions sufficient to form recombinant protein/antibody complexes. The complexes are contacted with known amount(s) of appropriate indicator reagent(s)s for a time and under suitable conditions for a reaction to occur, wherein the resultant signal generated is compared to a negative test sample in order to determine the presence of antibody to the analyte in the test sample. It further is contemplated that, when using certain solid phases such as microparticles, each recombinant protein utilized in the assay can be attached to a separate microparticle, and a mixture of these microparticles made by combining the various coated microparticles, which can be optimized for each assay.

Variations to the above-described assay formats include the incorporation of CKS-recombinant proteins of different analytes attached to the same or to different solid phases for the detection of the presence of antibody to either analyte (for example, CKS-recombinant proteins specific for certain antigenic regions of one infective agent coated on the same or different solid phase with CKS-recombinant proteins specific for certain antigenic region(s) of a different infective agent, to detect the presence of either (or both) infective agents.

In yet another assay format, CKS recombinant proteins containing antigenic epitopes are useful in competitive assays such as neutralization assays. To perform a neutralization assay, a recombinant polypeptide representing epitopes of an antigenic region of an infectious agent such as a virus, is solubilized and mixed with a sample diluent to a final concentration of between 0.5 to 50.0 $\mu$g/ml. A known amount of test sample (preferably 10 $\mu$l), either diluted or non-diluted, is added to a reaction well, followed by 400 $\mu$l of the sample diluent containing the recombinant polypeptide. If desired, the mixture may be preincubated for approximately 15 minutes to two hours. A solid phase coated with the CKS recombinant protein described herein then is added to the reaction well, and incubated for one hour at approximately 40° C. After washing, a known amount of an indicator reagent, for example, 200 $\mu$l of a peroxidase labeled goat anti-human IgG in a conjugate diluent is added and incubated for one hour at 40° C. After washing and when using an enzyme conjugate such as described, an enzyme substrate, for example, OPD substrate, is added and incubated at room temperature for thirty minutes. The reaction is terminated by adding a stopping reagent such as 1N sulfuric acid to the reaction well. Absorbance is read at 492 nm. Test samples which contain antibody to the specific polypeptide generate a reduced signal caused by the competitive binding of the peptides to these antibodies in solution. The percentage of competitive binding may be calculated by comparing absorbance value of the sample in the presence of recombinant polypeptide to the absorbance value of the sample assayed in the absence of a recombinant polypeptide at the same dilution. Thus, the difference in the signals generated between the sample in the presence of recombinant protein and the sample in the absence of recombinant protein is the measurement used to determine the presence or absence of antibody.

In another assay format, the recombinant proteins can be used in immunodot blot assay systems. The immunodot blot assay system uses a panel of purified recombinant polypeptides placed in an array on a nitrocellulose solid support. The prepared solid support is contacted with a sample and captures specific antibodies (specific binding member) to the recombinant protein (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988. The related U.S. patent application Ser. Nos. 07/227,586 and 07/227,590 (both of which were filed on Aug. 2, 1988) further described specific methods and apparatus useful to perform an immunodot assay, as well as U.S. Pat. No. 5,075,077 (U.S. Ser. No. 07/227,272 filed Aug. 2, 1988), which enjoys common ownership and is incorporated herein by reference. Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

CKS fusion proteins can be used in assays which employ a first and second solid support, as follow, for detecting antibody to a specific antigen of an analyte in a test sample. In this assay format, a first aliquot of a test sample is contacted with a first solid support coated with CKS recombinant protein specific for an analyte for a time and under conditions sufficient to form recombinant protein/analyte antibody complexes. Then, the complexes are contacted with an indicator reagent specific for the recombinant antigen. The indicator reagent is detected to determine the presence of antibody to the recombinant protein in the test sample. Following this, the presence of a different antigenic determinant of the same analyte is determined by contacting a second aliquot of a test sample with a second solid support coated with CKS recombinant protein specific for the second antibody for a time and under conditions sufficient to form recombinant protein/second antibody complexes. The complexes are contacted with a second indicator reagent specific for the antibody of the complex. The signal is detected in order to determine the presence of antibody in the test sample, wherein the presence of antibody to either analyte recombinant protein, or both, indicates the presence of anti-analyte in the test sample. It also is contemplated that the solid supports can be tested simultaneously.

The use of haptens is known in the art. It is contemplated that haptens also can be used in assays employing CKS fusion proteins in order to enhance performance of the assay. Further Characterization of the HGBV Genome, Virions, and Viral Antigens Using Probes The HGBV nucleic acid sequences may be used to gain further information on the sequence of the HGBV genome, and for identification and isolation of the HGBV agent. Thus, it is contemplated that this knowledge will aid in the characterization of HGBV including the nature of the HGBV genome, the structure of the viral particle, and the nature of the antigens of which it is composed. This information, in turn, can lead to additional polynucleotide probes, polypeptides derived from the HGBV genome, and antibodies directed against HGBV epitopes which would be useful for the diagnosis and/or treatment of HGBV caused non-A, non-B, non-C, non-D and non-E hepatitis.

The nucleic acid sequence information is useful for the design of probes or PCR primers for the isolation of additional nucleic acid sequences which are derived from yet undefined regions of the HGBV genome. For example, PCR primers or labeled probes containing a sequence of 8 or more nucleotides, and preferably 20 or more nucleotides, which are derived from regions close to the 5'-termini or 3'-termini of the family of HGBV nucleic acid sequences may be used to isolate overlapping nucleic acid sequences from HGBV genomic or cDNA libraries or directly from viral nucleic acid. These sequences which overlap the HGBV nucleic acid sequences, but which also contain sequences derived from regions of the genome from which the above-mentioned HGBV nucleic acid sequence are not derived, may then be used to synthesize probes for identification of other overlapping fragments which do not necessarily overlap the nucleic acid sequences in the clones. Unless the HGBV genome is segmented and the segments lack common sequences, it is possible to sequence the entire viral genome(s) utilizing the technique of isolation of overlapping nucleic acid sequences derived from the viral genome(s). Characterization of the genomic segments alternatively could be from the viral genome(s) isolated from purified HGBV particles. Methods for purifying HGBV particles and for detecting them during the purification procedure are described herein. Procedures for isolating polynucleotide genomes from viral particles are well-known in the art. The isolated genomic segments then could be cloned and sequenced. Thus, it is possible to clone and sequence the HGBV genome(s) irrespective of their nature.

Methods for constructing HGBV genomic or cDNA libraries are known in the art, and vectors useful for this purpose are known in the art. These vectors include lambda-gt11, lambda-gt10, and others. The HGBV derived nucleic acid sequence detected by the probes derived from the HGBV genomic or cDNAs, may be isolated from the clone by digestion of the isolated polynucleotide with the appropriate restriction enzyme(s), and sequenced.

The sequence information derived from these overlapping HGBV nucleic acid sequences is useful for determining areas of homology and heterogeneity within the viral genome(s), which could indicate the presence of different strains of the genome and or of populations of defective particles. It is also useful for the design of hybridization probes to detect HGBV or HGBV antigens or HGBV nucleic acids in biological samples, and during the isolation of HGBV, utilizing the techniques described herein. The overlapping nucleic acid sequences may be used to create expression vectors for polypeptides derived from the HGBV genome(s). Encoded within the family of nucleic acid sequences are antigen(s) containing epitopes which are contemplated to be unique to HGBV, i.e., antibodies directed against these antigens are absent from individuals infected with HAV, HBV, HCV, and HEV, and with the genomic sequences in GenBank are contemplated to indicate that minimal homology exists between these nucleic acid sequences and the polynucleotide sequences of those sources. Thus, antibodies directed against the antigens encoded with the HGBV nucleic acid sequences may be used to identify the non-A, non-B, non-C, non-D and non-E particle isolated from infected individuals. In addition, they also are useful for the isolation of the HGBV agent(s).

HGBV particles may be isolated from the sera of infected individuals or from cell cultures by any of the methods known in the art, including, for example, techniques based on size discrimination such as sedimentation or exclusion methods, or techniques based on density such as ultracentrifugation in density gradients, or precipitation with agents such as polyethylene glycol (PEG), or chromatography on a variety of materials such as anionic or cationic exchange materials, and materials which bind due to hydrophobic interactions, as well as affinity columns. During the isolation procedure the presence of HGBV may be detected by hybridization analysis of the extracted genome, using probes derived from HGBV nucleic acid sequences or by immunoassay which utilize as probes antibodies directed against HGBV antigens encoded within the family of HGBV nucleic acid sequences. The antibodies may be polyclonal or monoclonal, and it may be desirable to purify the antibodies before their use in the immunoassay. Such antibodies directed against HGBV antigens which are affixed to solid phases are useful for the isolation of HGBV by immunoaffinity chromatography. Methods for immunoaffinity chromatography are known in the art, and include methods for affixing antibodies to solid phases so that they retain their immunoselective activity. These methods include adsorption, and covalent binding. Spacer groups may be included in the bifunctional coupling agents such that the antigen binding site of the antibody remains accessible.

During the purification procedure the presence of HGBV may be detected and/or verified by nucleic acid hybridization or PCR, utilizing as probes or primers polynucleotides derived from a family of HGBV genomic or cDNA sequences, as well as from overlapping HGBV nucleic acid sequences. Fractions are treated under conditions which would cause the disruption of viral particles, such as by use of detergents in the presence of chelating agents, and the presence of viral nucleic acid determined by hybridization techniques or PCR. Further confirmation that the isolated particles are the agents which induce HGBV infection may be obtained by infecting an individual which is preferably a tamarin with the isolated virus particles, followed by a determination of whether the symptoms of non-A, non-B, non-C, non-D and non-E hepatitis, as described herein, result from the infection.

Such viral particles obtained from the purified preparations then may be further characterized. The genomic nucleic acid, once purified, can be tested to determine its sensitivity to RNAse or DNAse I; based on these tests, the determination of HGBV as a RNA genome or DNA genome may be made. The strandedness and circularity or non-circularity can be determined by methods known in the art including its visualization by electron microscopy, its migration in density gradients and its sedimentation characteristics. From hybridization of the HGBV genome, the negative or positive strandedness of the purified nucleic acid can be determined. In addition, the purified nucleic acid can be cloned and sequenced by known techniques, including reverse transcriptase, if the genomic material is RNA. Utilizing the nucleic acid derived from the viral particles, it then is possible to sequence the entire genome, whether or not it is segmented.

Determination of polypeptides containing conserved sequences may be useful for selecting probes which bind the HGBV genome, thus allowing its isolation. In addition, conserved sequences in conjunction with those derived from the HGBV nucleic acid sequences, may be used to design primers for use in systems which amplify genomic sequences. Further, the structure of HGBV also may be determined and its components isolated. The morphology and size may be determined by electron microscopy, for example. The identification and localization of specific viral polypeptide antigens such as envelope (coat) antigens, or internal antigens such as nucleic acid binding proteins or core antigens, and polynucleotide polymerase(s) also may be determined by ascertaining whether the antigens are present in major or minor viral components, as well as by utilizing antibodies directed against the specific antigens encoded within isolated nucleic acid sequences as probes. This information may be useful for diagnostic and therapeutic applications. For example, it may be preferable to include an exterior antigen in a vaccine preparation, or perhaps multivalent vaccines may be comprised of a polypeptide derived from the genome encoding a structural protein as well as a polypeptide from another portion of the genome, such as a nonstructural polypeptide.

Cell Culture Systems and Animal Model Systems for HGBV Replication

Generally, suitable cells or cell lines for culturing HGBV may include the following: monkey kidney cells such as MK2 and VERO, porcine kidney cell lines such as PS, baby hamster kidney cell lines such as BHK, murine macrophage cell lines such as P388D1, MK1 and Mm1, human macrophage cell lines such as U-937, human peripheral blood leukocytes, human adherent monocytes, hepatocytes or hepatocytic cell lines such as HUH7 and HepG2, embryos or embryonic cell such as chick embryo fibroblasts or cell lines derived from invertebrates, preferably from insects such as Drosophia cell lines or more preferably from arthropods such as mosquito cell lines or tick cell lines. It also is possible that primary hepatocytes can be cultured and then infected with HGBV. Alternatively, the hepatocyte cultures could be derived from the livers of infected individuals (human or tamarins). That latter case is an example of a cell line which is infected in vivo being passaged in vitro. In addition, various immortalization methods can be used to obtain cell lines derived from hepatocyte cultures. For example, primary liver cultures (before and after enrichment of the hepatocyte population) may be fused to a variety of cells to maintain stability. Also, cultures may be infected with transforming viruses, or transfected with transforming genes in order to create permanent or semipermanent cell lines. In addition, cells in liver cultures may be fused to established cell lines such as PehG2. Methods for cell fusion are well-known to the routineer, and include the use of fusion agents such as PEG and Sendai Virus, among others.

It is contemplated that HGBV infection of cell lines may be accomplished by techniques such as incubating the cells with viral preparations under conditions which allow viral entry into the cell. It also may be possible to obtain viral production by transfecting the cells with isolated viral polynucleotides. Methods for transfecting tissue culture cells are known in the art and include but are not limited to techniques which use electroporation and precipitation with DEAE-Dextran or calcium phosphate. Transfection with cloned HGBV genomic or cDNA should result in viral replication and the in vitro propagation of the virus. In addition to cultured cells, animal model systems may be used for viral replication. HGBV replication thus may occur in chimpanzees and also in, for example, marmosets and suckling mice.

Screening for Anti-Viral Agents for HGBV

The availability of cell culture and animal model systems for HGBV also renders screening for anti-viral agents which inhibit HGBV replication possible, and particularly for those agents which preferentially allow cell growth and multiplication while inhibiting viral replication. These screening methods are known in the art. Generally, the anti-viral agents are tested at a variety of concentrations, for their effect on preventing viral replication in cell culture systems which support viral replication, and then for an inhibition of infectivity or of viral pathogenicity, and a low level of toxicity, in an animal model system. The methods and composition provided herein for detecting HGBV antigens and HGBV polynucleotides are useful for screening of anti-viral agents because they provide an alternative, and perhaps a more sensitive means, for detecting the agent's effect on viral replication than the cell plaque assay or $ID_{50}$ assay. For example, the HGBV polynucleotide probes described herein may be used to quantitate the amount of viral nucleic acid produced in a cell culture. This could be performed by hybridization or competition hybridization of the infected cell nucleic acids with a labeled HGBV polynucleotide probe. Also, anti-HGBV antibodies may be used to identify and quantitate HGBV antigen(s) in the cell culture utilizing the immunoassays described herein. Also, since it may be desirable to quantitate HGBV antigens in the infected cell culture by a competition assay, the polypeptides encoded within the HGBV nucleic acid sequences described herein are useful for these assays. Generally, a recombinant HGBV polypeptide derived from the HGBV genomic or cDNA would be labeled, and the inhibition of binding of this labeled polypeptide to an HGBV polypeptide due to the antigen produced in the cell culture system would be monitored. These methods are especially useful in cases where the HGBV may be able to replicate in a cell lines without causing cell death.

Preparation of Attenuated Strains of HGBV

It may be possible to isolate attenuated strains of HGBV by utilizing the tissue culture systems and/or animal models systems provided herein. These attenuated strains would be useful for vaccines, or for the isolation of viral antigens. Attenuated strains are isolatable after multiple passages in cell culture and/or an animal model. Detection of an attenuated strain in an infected cell or individual is achievable by following methods known in the art and could include the use of antibodies to one or more epitopes encoded in HGBV as a probe or the use of a polynucleotide containing an HGBV sequence of at least about 8 nucleotides in length as a probe. Also or alternatively, an attenuated strain may be constructed utilizing the genomic information of HGBV provided herein, and utilizing recombinant techniques. Usually an attempt is made to delete a region of the genome encoding a polypeptide related to pathogenicity but not to viral replication. The genomic construction would allow the expression of an epitope which gives rise to neutralizing antibodies for HGBV. The altered genome then could be used to transform cells which allow HGBV replication, and the cells grown under conditions to allow viral replication. Attenuated HGBV strains are useful not only for vaccine purposes, but also as sources for the commercial production of viral antigens, since the processing of these viruses would require less stringent protection measures for the employees involved in viral production and/or the production of viral products.

Hosts and Expression Control Sequences

Although the following are known in the art, included herein are general techniques used in extracting the genome from a virus, preparing and probing a genomic library, sequencing clones, constructing expression vectors, transforming cells, performing immunological assays, and for growing cell in culture.

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotics include promoters, optionally containing operator portions, and ribosome binding sites. Transfer vectors compatible with prokaryotic hosts are commonly derived from the plasmid pBR322 which contains operons conferring ampicillin and tetracycline resistance, and the various pUC vectors, which also contain sequences conferring antibiotic resistance markers. These markers may be used to obtain successful transformants by selection. Commonly used prokaryotic control sequences include the beta-lactamase (penicillinase), lactose promoter system (Chang et al., *Nature* 198:1056 [1977]) the tryptophan promoter system (reported by Goeddel et al., *Nucleic Acid Res* 8:4057 [1980]) and the lambda-derived P1 promoter and N gene ribosome binding site (Shimatake et al., *Nature* 292:128 [1981]) and the hybrid Tac promoter (De Boer et al., *Proc. Natl. Acad. Sci. USA* 292:128 [1983]) derived from sequences of the trp and lac UV5 promoters. The foregoing systems are particularly compatible with *E. coli*; however, other prokaryotic hosts such as strains of Bacillus or Pseudomonas may be used if desired, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring protrophy to auxotrophic mutants or resistance to heavy metals on wild-type strains. Yeast compatible vectors may employ the 2 micron origin of replication (as described by Broach et al., *Meth. Enz.* 101:307 [1983]), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes, including the promoter for 3 phosphophycerate kinase. See, for example, Hess et al., *J. Adv. Enzyme Reg.* 7: 149 (1968), Holland et al., *Biochemistry* 17:4900 (1978) and Hitzeman *J. Biol. Chem.* 255:2073 (1980). Terminators also may be included, such as those derived from the enolase gene as reported by Holland, *J. Biol. Chem.* 256:1385 (1981). It is contemplated that particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines which are available from the American Type Culture Collection. These include HeLa cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV), cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which insure integration of the appropriate sequences encoding non-A, non-B, non-C, non-D, non-E epitopes into the host genome. An example of a mammalian expression system for HCV is described in U.S. patent application Ser. No. 07/830,024, filed Jan. 31, 1992.

Transformations

Transformation may be by any known method for introducing polynucleotides into a host cell, including packaging the polynucleotide in a virus and transducing a host cell with the virus, and by direct uptake of the polynucleotide. The transformation procedures selected depends upon the host to be transformed. Bacterial transformation by direct uptake generally employs treatment with calcium or rubidium chloride. Cohen, *Proc. Natl. Acad. Sci. USA* 69:2110 (1972). Yeast transformation by direct uptake may be conducted using the calcium phosphate precipitation method of Graham et al., *Virology* 52:526 (1978), or modification thereof.

Vector Construction

Vector construction employs methods known in the art. Generally, site-specific DNA cleavage is performed by treating with suitable restriction enzymes under conditions which generally are specified by the manufacturer of these commercially available enzymes. Usually, about 1 microgram (μg) of plasmid or DNA sequence is cleaved by 1–10 units of enzyme in about 20 μl of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis methods, according to methods known by the routineer.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Sticky end ligations require less ATP and less ligase than blunt end ligations. When vector fragments are used as part of a ligation mixture, the vector fragment often is treated with bacterial alkaline phosphatase (BAP) or calf intestinal alkaline phosphatase to remove the 5'-phosphate and thus prevent religation of the vector. Or, restriction enzyme digestion of unwanted fragments can be used to prevent ligation. Ligation mixtures are transformed into suitable cloning hosts such as *E. coli* and successful transformants selected by methods including antibiotic resistance, and then screened for the correct construction.

Construction of Desired DNA Sequences

Synthetic oligonucleotides may be prepared using an automated oligonucleotide synthesizer such as that described by Warner, *DNA* 3:401 (1984). If desired, the synthetic strands may be labeled with $^{32}P$ by treatment with polynucleotide kinase in the presence of $^{32}P$-ATP, using standard conditions for the reaction. DNA sequences including those isolated from genomic or cDNA libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions suitable for hybridization with the correct strand, but not with the unmodified sequence. The sequences which have been identified by hybridization are recovered and cloned.

Hybridization With Probe

HGBV genomic or DNA libraries may be probed using the procedure described by Grunstein and Hogness, *Proc. Natl. Acad. Sci. USA* 73:3961 (1975). Briefly, the DNA to be probed is immobilized on nitrocellulose filters, denatured and prehybridized with a buffer which contains 0–50% formamide, 0.75 M NaCl, 75 mM Na citrate, 0.02% (w/v) each of bovine serum albumin (BSA), polyvinyl pyrollidone and Ficoll, 50 mM Na Phosphate (pH 6.5), 0.1% SDS and 100 μg/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, for example, about 40 to 42° C., and a high percentage, for example, 50% formamide. Following prehybridization, a $^{32}$P-labeled oligonucleotide probe is added to the buffer, and the filters are incubated in this mixture under hybridization conditions. After washing, the treated filters are subjected to autoradiography to show the location of the hybridized probe. DNA in corresponding locations on the original agar plates is used as the source of the desired DNA.

Verification of Construction and Sequencing

For standard vector constructions, ligation mixtures are transformed into *E. coli* strain XL-1 Blue or other suitable host, and successful transformants selected by antibiotic resistance or other markers. Plasmids from the transformants then are prepared according to the method of Clewell et al., *Proc. Natl. Acad. Sci. USA* 62:1159 (1969) usually following chloramphenicol amplification as reported by Clewell et al., *J. Bacteriol.* 110:667 (1972). The DNA is isolated and analyzed usually by restriction enzyme analysis and/or sequencing. Sequencing may be by the well-known dideoxy method of Sanger et al., *Proc. Natl. Acad. Sci. USA* 74:5463 (1977) as further described by Messing et al., *Nucleic Acid Res.* 9:309 (1981), or by the method reported by Maxam et al., *Methods in Enzymology* 65:499 (1980). Problems with band compression, which are sometimes observed in GC rich regions, are overcome by use of T-deazoguanosine according to the method reported by Barr et al., *Biotechniques* 4:428 (1986).

Enzyme-Linked Immunosorbent Assay

Enzyme-linked immunosorbent assay (ELISA) can be used to measure either antigen or antibody concentrations. This method depends upon conjugation of an enzyme label to either an antigen or antibody, and uses the bound enzyme activity (signal generated) as a quantitative label (measurable generated signal). Methods which utilize enzymes as labels are described herein, as are examples of such enzyme labels.

Preparation of HGBV Nucleic Acid Sequences

The source of the non-A, non-B, non-C, non-D, non-E agent is an individual or pooled plasma, serum or liver homogenate from a human or tamarin infected with the HGBV virus meeting the clinical and laboratory criteria described herein. A tamarin alternatively can be experimentally infected with blood from another individual with non-A, non-B, non-C, non-E hepatitis meeting the criteria described hereinbelow. A pool can be made by combining many individual plasma, serum or liver homogenate samples containing high levels of alanine transferase activity; this activity results from hepatic injury due to HGBV infection. The TID (tamarin infective dose) of the virus has been calculated from one of our experiments to be $\geq 4 \times 10^5$/ml (see Example 2, below).

For example, a nucleic acid library from plasma, serum or liver homogenate, preferably but not necessarily high titer, is generated as follows. First, viral particles are isolated from the plasma, serum or liver homogenate; then an aliquot is diluted in a buffered solution, such as one containing 50 mM Tris-HCl, pH 8.0, 1 mM EDTA, 100 mM NaCl. Debris is removed by centrifugation, for example, for 20 minutes at 15,000×g at 20° C. Viral particles in the resulting supernatant then are pelleted by centrifugation under appropriate conditions which can be determined routinely by one skilled in the art. To release the viral genome, the particles are disrupted by suspending the pellets in an aliquot of an SDS suspension, for example, one containing 1% SDS, 120 mM EDTA, 10 mM Tris-HCl, pH 7.5, which also contains 2 mg/ml proteinase K, which is followed by incubation at appropriate conditions, for example, 45° C. for 90 minutes. Nucleic acids are isolated by adding, for example, 0.8 μg MS2 bacteriophage RNA as carrier, and extracting the mixture four times with a 1:1 mixture of phenol:chloroform (phenol saturated with 0.5M Tris-HCl, pH 7.5, 0.1% (v/v) beta-mercaptoethanol, 0.1% (w/v) hydroxyquinolone, followed by extraction two times with chloroform. The aqueous phase is concentrated with, for example, 1-butanol prior to precipitation with 2.5 volumes of absolute ethanol overnight at −20° C. Nucleic acids are recovered by centrifugation in, for example, a Beckman SW41 rotor at 40,000 rpm for 90 min at 4° C., and dissolved in water that is treated with 0.05% (v/v) diethylpyrocarbonate and autoclaved.

Nucleic acid obtained by the above procedure is denatured with, for example, 17.5 mM $CH_3HgOH$; cDNA then is synthesized using this denatured nucleic acid as template, and is cloned into the EcoRI site of phage lambda-gt11, for example, by using methods described by Huynh (1985) supra, except that random primers replace oligo(dT) 12–18 during the synthesis of the first nucleic acid strand by reverse transcriptase (see Taylor et al., [1976]). The resulting double stranded nucleic acid sequences are fractionated according to size on a Sepharose CL-4B column, for example. Eluted material of approximate mean size 400, 300, 200 and 100 base-pairs are pooled into genomic pools. The lambda-gt11 cDNA library is generated from the cDNA in at least one of the pools. Alternatively, if the etiological agent is a DNA virus, methods for cloning genomic DNA may be useful and are known to those skilled in the art.

The so-generated lambda-gt11 genomic library is screened for epitopes that can bind specifically with serum, plasma or a liver homogenate from an individual who had previously experienced non-A, non-B, non-C, non-E hepatitis (one which meets the criteria as set forth hereinbelow. About $10^4$–$10^7$ phage are screened with sera, plasma, or liver homogenates using the methods of Huyng et al. (supra). Bound human antibody can be detected with sheep anti-human Ig antisera that is radio-labeled with $^{125}$I or other suitable reporter molecules including HRPO, alkaline phosphatase and others. Positive phage are identified and purified. These phage then are tested for specificity of binding to sera from a pre-determined number of different humans previously infected with the HGBV agent, using the same method. Ideally, the phage will encode a polypeptide that reacts with all or a majority of the sera, plasma or liver homogenates that are tested, and will not react with sera, plasma or liver homogenates from individuals who are determined to be "negative" according to the criteria set forth herein for the HGBV agent as well as hepatitis A, B, C, D and E. By following these procedures, a clone that encodes a polypeptide which is specifically recognized immunologically by sera, plasma or liver homogenates from non-A, non-B, non-C, non-D and non-E-identified patients can be isolated.

The present invention will now be described by way of examples, which are meant to illustrate, but not to limit, the spirit and scope of the invention.

EXAMPLES

The examples provided herein describe in detail methods which led to the discovery of the HGBV group of viruses. The examples are provided in chronological order so that the discovery of the HGBV-A, HGBV-B and HGBV-C viruses of the HGBV group can be followed. Generally, transmissibility and infectivity studies were initially performed; these studies and subsequent ones described herein led to evidence for the existence of two HCV-like viruses in HGBV: GB-A and GB-B. Subsequent experiments also detailed herein utilizing degenerative primers led to the discovery of HGBV-C. The prevalence of this group of viruses in humans as evidenced by serological studies, the viral characterization of this group of viruses, the relatedness of HGBV to other viruses in its proposed genus and the interrelatedness of HGBV-A, HGBV-B and HGBV-C also is taught.

Example 1

Transmissibility of HGBV

A. Experimental Protocol

Sixteen tamarins (*Saguinus labiatus*) were secured through LEMSIP (Laboratory for Experimental Medicine and Surgery in Primates, Tuxedo, N.Y.) for the transmissibility and infectivity studies. All animals were maintained and monitored at LEMSIP according to protocols approved by LEMSIP. (Note: one animal died of natural causes and one ailing animal was euthanized prior to the initiation of infectivity studies). Baseline serum liver enzyme values were established for serum liver enzymes alanine transaminase (ALT), gamma-glutamyltransferase (GGT) and isocitric dehydrogenase (ICD) for two to three months on serum specimens obtained weekly or bi-weekly. A minimum of eight serum liver enzyme values were obtained for each animal prior to inoculation. Cutoff values (CO) were determined for each animal, based on the mean liver enzyme value plus 3.75 times the standard deviation. Liver enzyme values above the cutoff value were interpreted as abnormal and suggestive of liver damage. Several tamarins were inoculated as described hereinbelow and monitored for changes in ALT, GGT and ICD serum levels. At specified times thereafter during the monitoring process, certain animals were sacrificed in order to obtain serum and tissues for further studies.

B. Inoculation of Animals (Initial Study)

A pool of known infectious tamarin GB serum (passage 11, designated as H205 GB pass 11) was prepared from serum collected during the early acute phase (19–24 days post inoculation) of hepatitis from nine tamarins inoculated with the HGBV. This pool had been previously described and studied in an effort to determine the etiological agent involved. J. L. Dienstag et al., *Nature* 264 supra; E. Tabor et al., J. Med. Virol. 5, supra. Aliquots of this pool were maintained at Abbott Laboratories (North Chicago, Ill. 60064) under liquid nitrogen storage conditions until utilized in this study. Other aliqouts of HGBV are available from the American Type Culture Collection (A.T.C.C.), 10801 University Boulevard, Manassas, Va. 20110-2209, under A.T.C.C. Deposit. No. VR-806.

On day one, four tamarins of the initial group of remaining 14 tamarins, identified as T-1053, T-1048, T-1057 and T-1061, were inoculated intravenously with 0.25 ml of pool H205, passage 11, previously diluted 1:50. These animals were monitored weekly for changes in the liver enzymes ALT, GGT and ICD. TABLE 2 presents the pre- and post-inoculation liver enzyme data on these four tamarins (T-1053, T-1048, T-1057 and T-1061); FIGS. 1–4 present the pre- and post-inoculation ALT and ICD levels of these four tamarins. As the data demonstrate, significant rises in ALT, GGT and ICD above the CO were obtained in the four tamarins inoculated with the 1:50 dilution of pool H205.

On the same day (day one), one tamarin (T-1047) was inoculated intravenously with 0.25 ml of pooled normal tamarin serum and used as a negative control, and another tamarin (T-1042) was inoculated intravenously with 0.25 ml of pooled normal human serum and served as an additional negative control. FIGS. 5–6 and TABLE 3 present the pre- and post-inoculation ALT and ICD levels of the two control tamarins (T-1047 and T-1042). As the data demonstrate, no rise in ALT or ICD was documented post-inoculation for the two control tamarins for a period of eight weeks.

On the same day (day one), one tamarin (T-1044) was inoculated intravenously with 0.2 ml of convalescent sera obtained from the surgeon (original GB source) approximately three weeks following the onset of acute hepatitis. This specimen had been stored at −20° C. F. Deinhardt et al., *J. Exper. Med.* 125:673–688 (1967). Another tamarin (T-1034) was inoculated with 0.1 ml of this convalescent sera. As FIGS. 7–8 and TABLE 4 demonstrate, no rise in serum liver enzymes was observed in these tamarins for a period of eleven weeks post inoculation. Thus, these data demonstrate that infective HGBV was not detectable in the convalescent sera obtained from the original patient and stored at −20° C., which could indicate that the individual had recovered from infection and that the virus had been cleared from the patient's serum or that the viral titer had been reduced to non-detectable levels upon storage at −20° C.

C. Further Studies

Tamarin T-1053 showed a significant rise in serum liver enzymes one week post-inoculation, and was retested for liver enzymes on day 11 post-inoculation. At day 12 it was determined that significant elevations in serum liver enzymes were present, and the animal was sacrificed on that day. Plasma, liver and spleen tissue samples were obtained for further studies. The plasma from T-1053 served as the source for the RDA procedure discussed in Example 3 below; the liver tissue was utilized in Example 8 below.

Tamarins T-1048, T-1057 and T-1061 were monitored for serum liver enzyme values; all were observed to exhibit elevated serum liver enzyme levels within two weeks following inoculation; these elevated values were noted for six or more weeks post inoculation. All three tamarins were observed to have decreasing serum liver enzyme levels below the CO by 84 days post inoculation. On day 97 post inoculation, these three tamarins (T-1048, T-1057 and T-1061) were re-challenged with 0.10 ml of neat plasma obtained from tamarin T-1053 (shown to be infectious, see Example 2) to determine whether hepatitis as documented by elevations in serum liver enzymes could be re-induced. The data are presented in TABLE 2 and FIGS. 1, 3 and 4. As the data indicates, serum liver enzyme levels of two tamarins (T-1057 and T-1061) remained below the CO for three weeks post reinoculation. One tamarin (T-1048) exhibited mild elevations in serum liver enzyme levels two weeks immediately post-reinoculation. It was hypothesized that the mild elevations in T-1048 were attributable to either reinfection of liver tissue by HGBV or incomplete recovery from the initial inoculation with H205.

Example 2

Infectivity Studies

A. Experimental Protocol

Baseline readings on four tamarins were obtained as described in Example 1(A). Briefly, baseline serum liver enzymes (ALT, GGT and ICD) were established for each animal prior to inoculation. Cutoff values (CO) were determined for each animal, based on the mean liver enzyme value plus 3.75 times the standard deviation. Liver enzyme values above the cutoff were interpreted as abnormal and suggestive of liver damage.

B. Inoculation of Tamarins

The plasma from Tamarin T-1053, sacrificed at day 12 post inoculation (see Example 1[C]), was used as the inoculum for further studies. On day one, one tamarin (T-1055) was inoculated intravenously with 0.25 ml of neat T-1053 plasma. On the same day, two tamarins (T-1038 and T-1051) were inoculated intravenously with 0.25 ml of T-1053 plasma which had been serially diluted to either $10^{-4}$ (T-1038) or $10^{-5}$ (T-1051) in pooled normal tamarin plasma. On the same day, tamarin T-1049 was inoculated intravenously with 0.25 ml of plasma T-1053 which had been filtered through a series of filters of decreasing pore size (0.8 μm, 0.45 μm, 0.22 μm and 0.10 μm) and diluted at $10^{-4}$ in pooled normal tamarin plasma.

Figure 9:
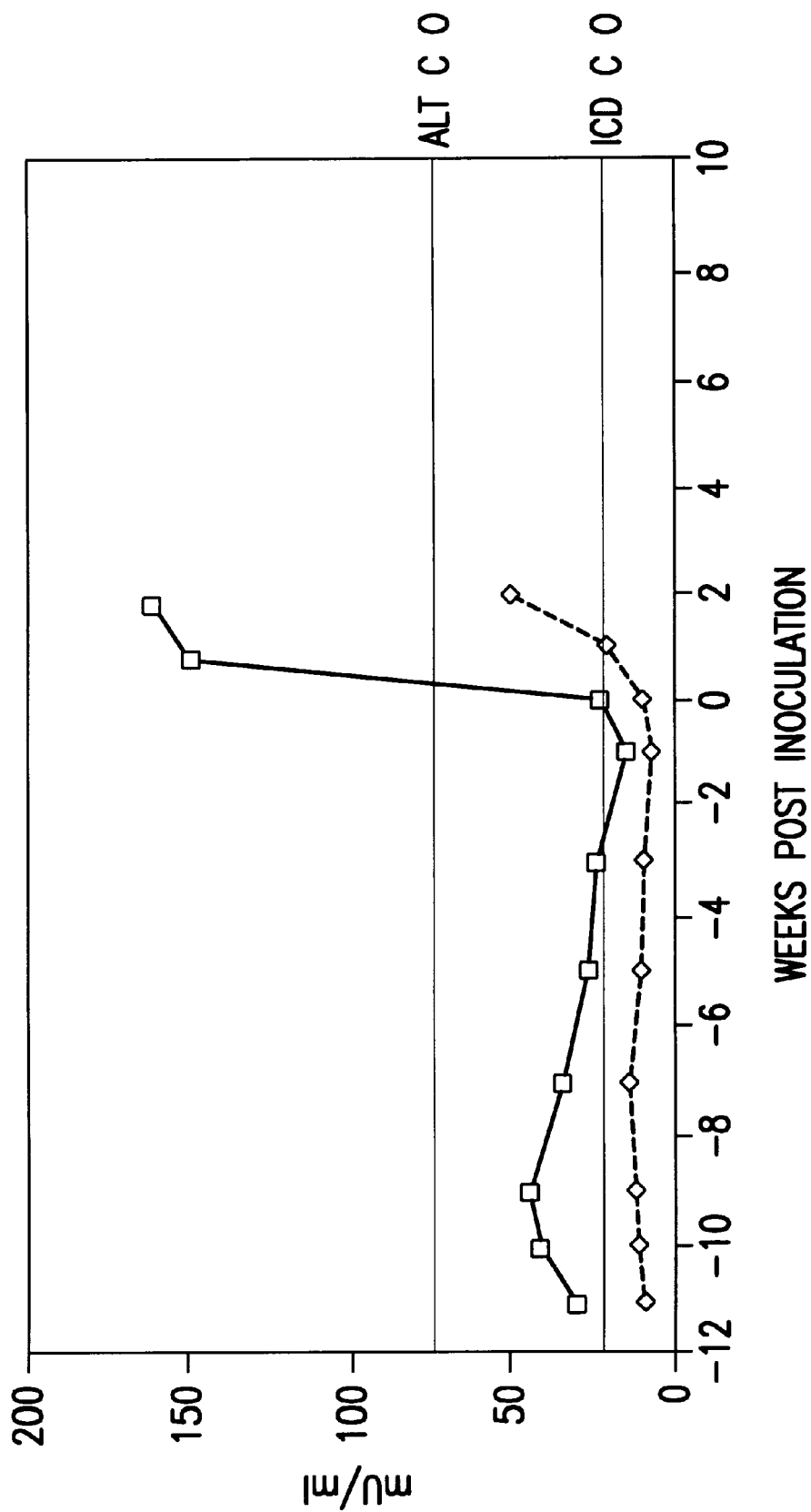
Figure 10:
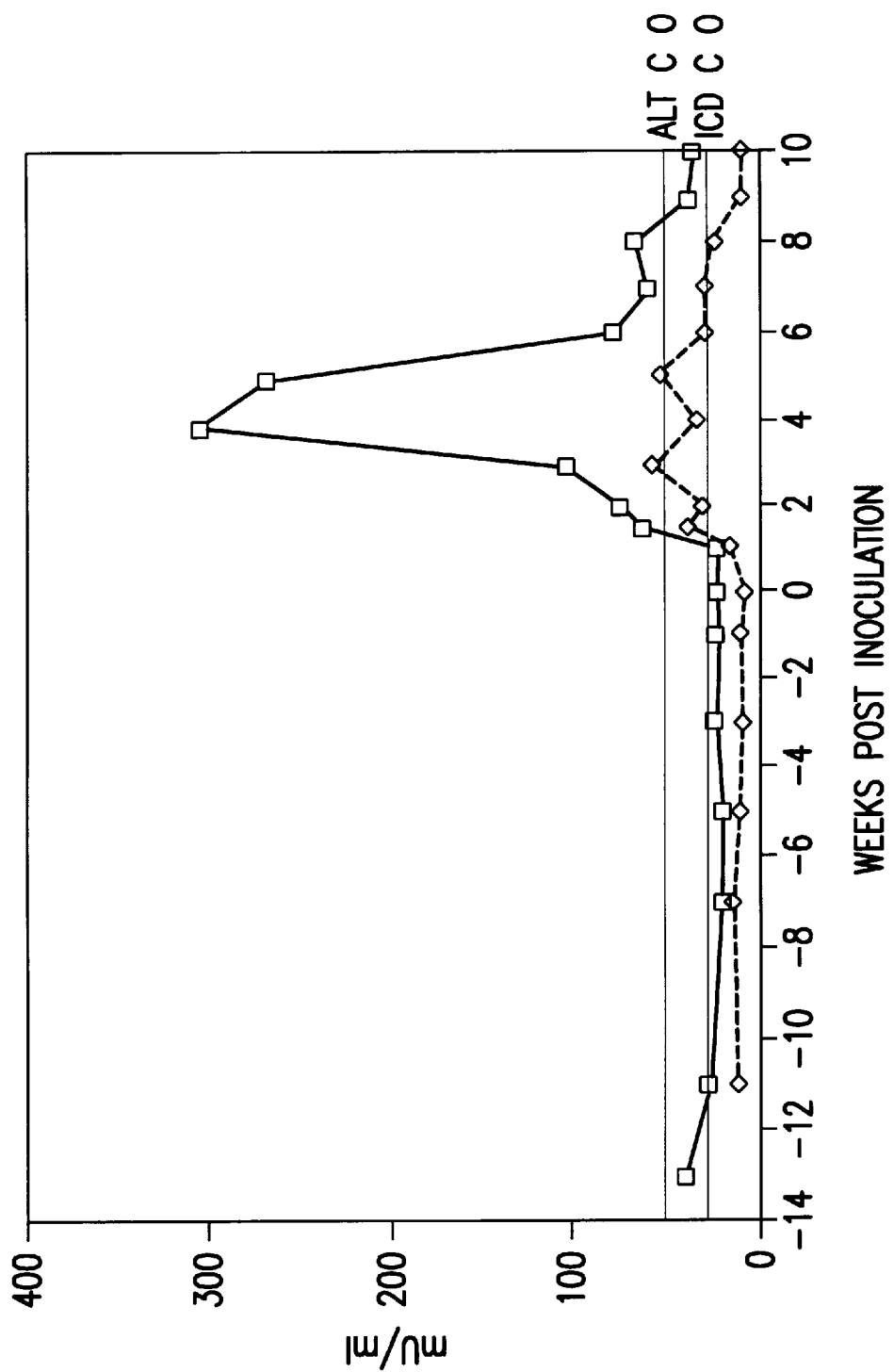
Figure 11:
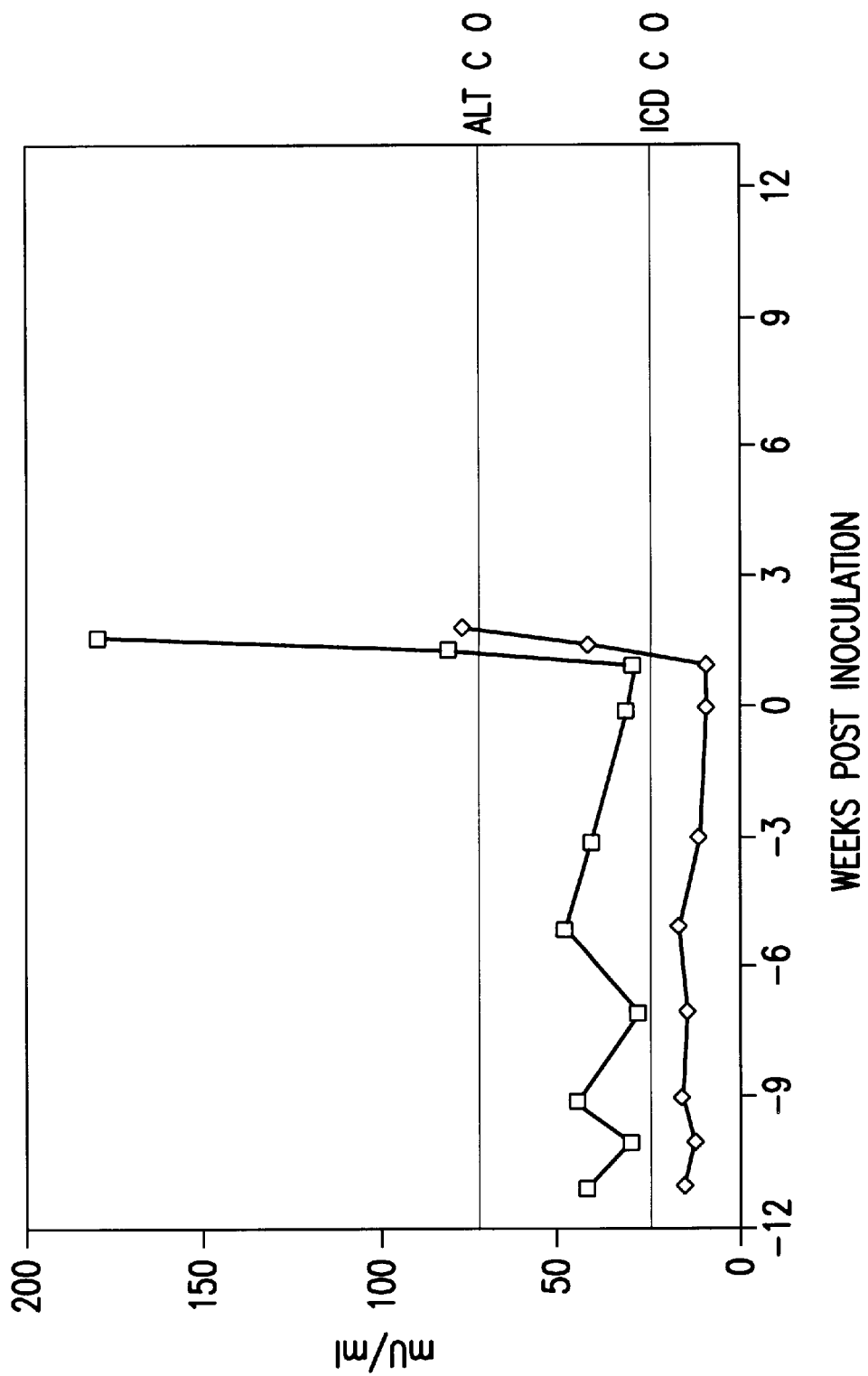
Figure 12:
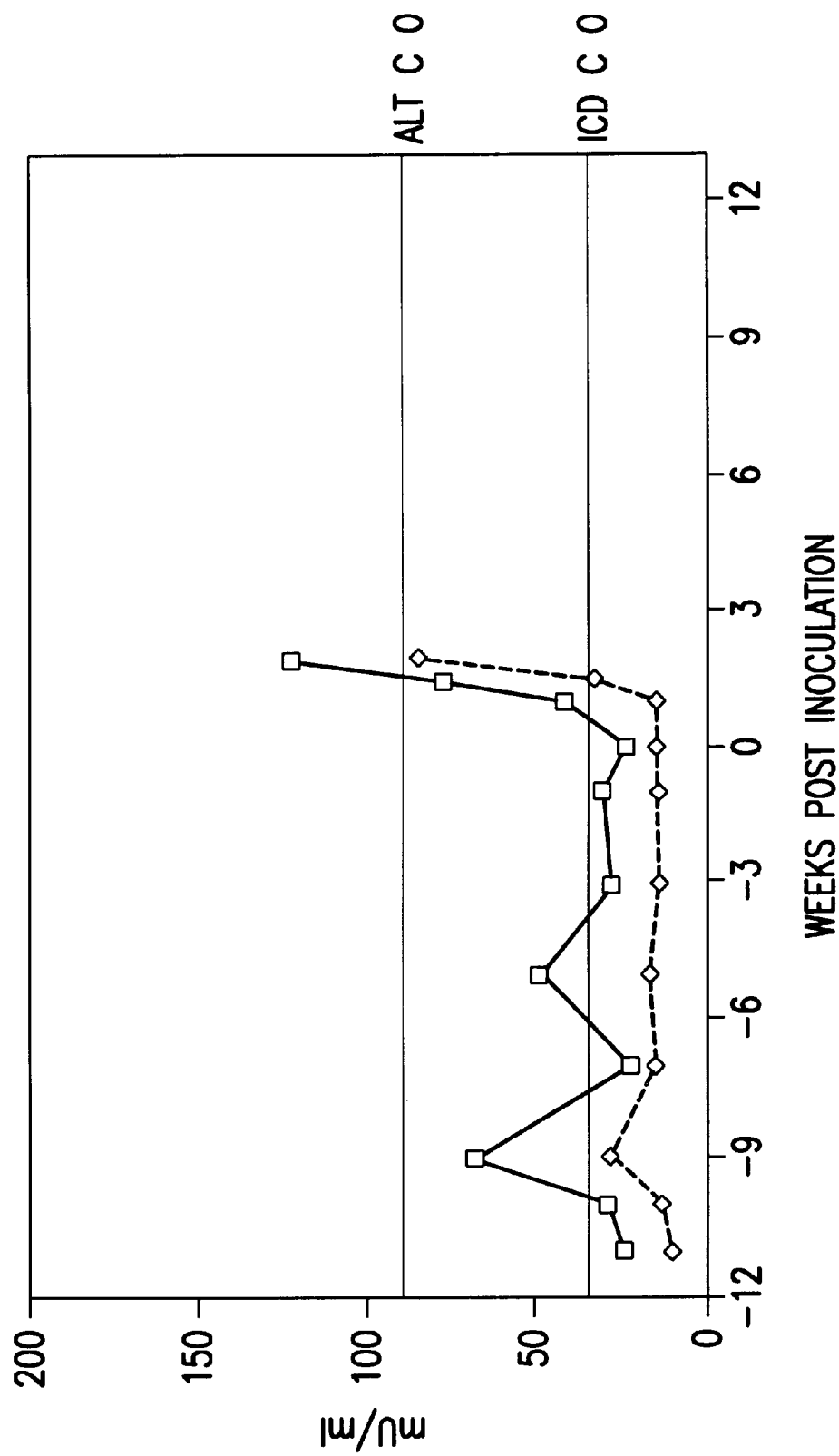

All tamarins (T-1055, T-1038, T-1051 and T-1049) were monitored weekly as described in Example 1 for changes in serum liver enzymes ALT, GGT and ICD. TABLE 5 presents the pre- and post-inoculation liver enzyme data on these four tamarins. FIG. 9 presents the pre- and post-inoculation ALT and ICD values T-1055. Referring to FIG. 9, it can be seen that elevations above the CO in serum liver enzymes ALT and ICD occurred. This tamarin was sacrificed on day 12 post-inoculation. FIGS. 10 and 11 present the pre- and post-inoculation serum levels of ALT and ICD for tamarins T-1051 and T-1038, respectively. Referring to FIGS. 10 and 11, it can be seen that elevations in serum liver enzymes ALT and ICD occurred in both animals by 11 days post-inoculation. T-1038 was sacrificed on day 14 post inoculation. TABLE 5 and FIG. 12 present the data obtained on T-1049. As can be seen from TABLE 5 and FIG. 12, elevations in serum liver enzymes above the CO were observed in T-1049 within 11 days post-inoculation.

The filtration study conducted on T-1049 indicates that HGBV can pass through a 0.10 μm filter, thereby suggesting that HGBV is likely to be viral in nature, and less than 0.1 μm in diameter. In addition, the infectivity titration experiment conducted on T-1038 demonstrates that the T 1053 serum contains at least $4 \times 10^5$ tamarin infectious doses per ml.

In order to show the transmissibility of a single HGBV agent, tamarin T-1044 was inoculated with 0.25 ml of an inoculum consisting of T-1057 serum that had been obtained 7 days after the H205 inoculation and diluted 1:500 in normal tamarin serum. Mild elevations in ALT levels above the cutoff were observed from days 14–63 PI (that it, elevations in the range of 82 to 106).

Tamarins T-1047 and T-1056 were subsequently inoculated with 0.25 ml of T-1044 serum obtained 14 days PI and diluted 1:2 in normal tamarin serum. Elevations in ALT levels above the cutoff were first observed in T-1047 and T-1056 at 42 days PI and returned to normal levels at days 64 and 91 PI, respectively. Tamarin T-1058 was inoculated with 0.23 ml of neat T-1057 serum obtained 22 days after the challenge with T-1053 serum. Elevations in ALT levels have not been observed for 112 days PI.

Example 3

Representational Difference Analysis (Subtractive Hybridization)

A. Generation of Double-Stranded DNA for Amplicons

Figure 13:
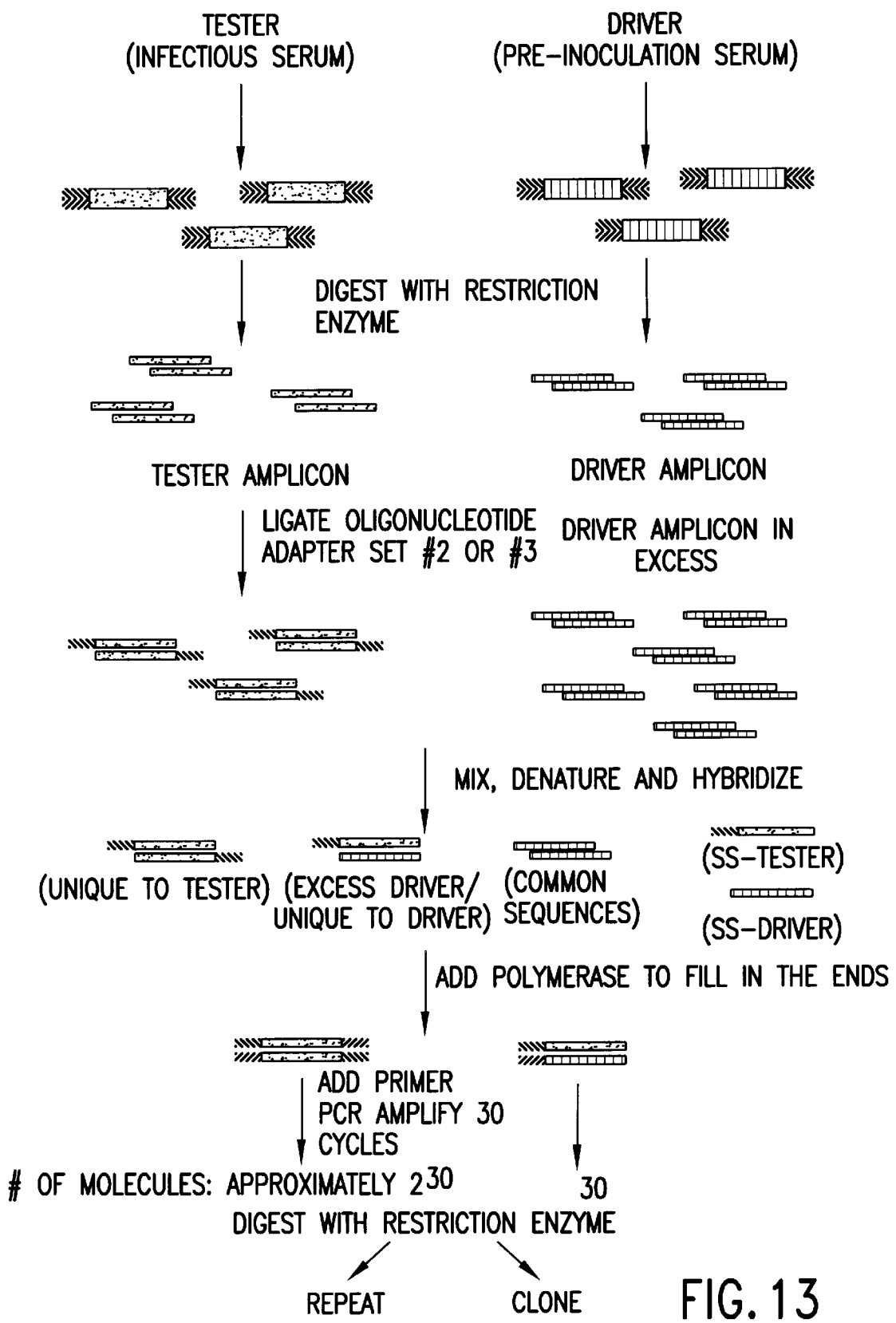
FIG. 13 presents a flow diagram of the steps involved in representational difference analysis (RDA), the procedure used for identifying clones.

Using the procedure described herein in Materials and Methods above and referring to FIG. 13, tester amplicon was prepared from total nucleic acid obtained from tamarin T-1053 infectious plasma on day 12 post inoculation with H205 serum (see Examples 1C and 2B). Driver amplicon was prepared from Tamarin T-1053 pre-inoculation plasma pooled from days −17 to −30 (see Example 1A). Briefly, both plasmas were filtered through a 0.1 μm filter as described in Example 2B. Next, 50 μl of each filtered plasma was extracted using a commercially available kit [United States Biochemical (USB), Cleveland, Ohio, cat. #73750] and 10 μg yeast tRNA as a carrier. This nucleic acid was subjected to random primed reverse transcription followed by random primed DNA synthesis using commercially available kits. Briefly, an 80 μl reverse transcription reaction was performed using Perkin Elmer's (Norwalk, Conn.) RNA PCR kit (cat. # N808-0017) as directed by the manufacturer using random hexamers and incubating for 10 minutes at 20° C. followed by 2 hours incubation at 42° C. The reactions then were terminated and cDNA/RNA duplexes denatured by incubation at 99° C. for 2 minutes. The reactions were supplemented with 10 μl 10× RP buffer [100 mM NaCl, 420 mM Tris (pH 8.0), 50 mM DTT, 100 μg/ml BSA], 250 pmoles random hexamers and 13 units Sequenase® version 2.0 polymerase (USB, cat. #70775) in a total volume of 20 μl. The reactions were incubated at 20° C. for 10 minutes followed by 37° C. for 2 hours. After phenol:chloroform extraction and ethanol precipitation, the double stranded DNA products of these reactions were digested with 4 units of restriction endonuclease Sau3A I (New England Biolabs [NEB], cat. #169L) in 30 μl reaction volumes for 30 minutes, as directed by the supplier.

B. Generation of Amplicons

Sau3AI-digested DNA was extracted and precipitated as described above. The entire Sau3AI-digested product was annealed to 465 pmoles R Bgl 24 (SEQUENCE I.D. NO. 1) and 465 pmoles R Bgl 12 (SEQUENCE I.D. NO. 2) in a 30 μl reaction volume buffered with 1× T4 DNA ligase buffer (NEB) by placing the reaction in a 50–55° C. dry heat block which was then incubated at 4° C. for 1 hour. The annealed product was ligated by adding 400 units T4 DNA ligase (NEB, cat. # 202S). After incubation for 14 hours at 16° C., a small scale PCR was performed. Briefly, 10 μl of the ligation reaction was added to 60 μl H$_2$O, 20 μl 5× PCR buffer (335 mM Tris, pH 8.8, 80 mM [NH$_4$]$_2$SO$_4$, 20 mM MgCl$_2$, 0.5 μg/ml bovine serum albumin, and 50 mM 2-mercaptoethanol), 8 μl of 4 mM dNTP stock, 2 μl (124 pmoles) R Bgl 24 (SEQUENCE I.D. NO. 3) and 3.75 units of AmpliTaq® DNA polymerase (Perkin Elmer, cat. #

N808-1012). The PCR amplification was performed in a GeneAmp® 9600 thermocycler (Perkin Elmer). Samples were incubated for 5 min. at 72° C. to fill-in the 5'-protruding ends of the ligated adaptors. The samples were amplified for 25 to 30 cycles (1 min. at 95° C. and 3 min. at 72° C.) followed by extension of 72° C. for 10 min. After agarose gel confirmation of successful amplicon generation (i.e. a smear of PCR products ranging from approximately 100 bp to over 1500 bp), a large scale amplification of tester and driver amplicons was performed. Forty 100 µl PCRs and eight 100 µl PCRs were set up as described above for the preparation of driver and tester amplicons, respectively. Two µl from the small scale PCR product per 100 µl reaction served as the template for the large scale amplicon generation. Thermocycling was performed as described above for an additional 15 to 20 cycles of amplification. The PCR reactions for both driver and tester DNA were then phenol/chloroform extracted twice, isopropanol precipitated, washed with 70% ethanol and digested with Sau3AI to cleave away the adaptors. The tester amplicon was further purified on a low melting point agarose gel. Briefly, 10 µg of tester amplicon DNA was run on a 2% SeaPlaque® gel (FMC Bioproducts, Rockland, Me.). Fragments of 150–1500 base pairs were excised from the gel, the gel slice was melted at 72° C. for 20 minutes with 3 ml $H_2O$, 400 µl 0.5 M MOPS and 400 µl NaCl. DNA was recovered from the melted gel slice using a Qiagen-tip 20 (Qiagen, Inc., Chatsworth, Calif.) as directed by the manufacturer.

C. Hybridization and Selective Amplification of Amplicons

Approximately 2 µg of purified tester DNA amplicon was ligated to N Bgl 24 (SEQUENCE I.D. NO. 3) and N Bgl 12 (SEQUENCE I.D. NO. 4) as described above. For the first subtractive hybridization, tester amplicon ligated to the N Bgl primer set (0.5 µg) and driver amplicon (20 µg) were mixed, phenol/chloroform extracted and ethanol precipitated. The DNA was resuspended in 4 µl of EEx3 buffer (30 mM EPPS, pH 8.0 at 20° C. [Sigma, St. Louis, Mo.], 3 mM EDTA) and overlaid with 35 µl of mineral oil. Following heat denaturation (3 min at 99° C.), 1 µl of 5 M NaCl was added to the denatured DNA and the DNA was allowed to hybridize at 67° C. for 20 hours. The aqueous phase was removed to a new tube and 8 µl of tRNA (5 mg/ml) was added to the sample followed by 390 µl TE (10 mM Tris, pH 8.0 and 1 mM EDTA). Eighty µl of the hybridized DNA solution was added to 480 µl $H_2O$, 160 µl 5× PCR buffer (above), 64 µl 4 mM dNTPs and 6 µl (30 units) AmpliTaq® polymerase. This solution was incubated at 72° C. for 5 min. to fill in the 5' overhangs created by the ligated N Bgl 24 primer. N Bgl 24 (SEQUENCE I.D. NO. 3, 1.24 nmoles in 20 µl $H_2O$) was added, the reaction was aliquoted (100 µl/tube) and subjected to 10 cycles of amplification as described above. The reaction was pooled, phenol/chloroform extracted twice, isopropanol precipitated, washed with 70% ethanol and resuspended in 40 µl $H_2O$. Single-stranded DNA was removed by mung bean nuclease (MBN). Briefly, 20 µl amplified DNA was digested with 20 units MBN (NEB) in a 40 µl reaction as described by the supplier. One hundred and sixty µl 50 mM Tris, pH 8.8 was added to the MBN digest. The enzyme was heat inactivated at 99° C. for 5 min. Eighty µl of the MBN-digested DNA was PCR amplified as described above for an additional 15 cycles. Again, the reaction was pooled, phenol/chloroform extracted twice, isopropanol precipitated, washed with 70% ethanol and resuspended in $H_2O$. The amplified DNA (3 to 5 µg) was then digested with Sau3A I, extracted and precipitated as described above. The final DNA pellet was resuspended in 100 µl TE.

D. Subsequent Hybridization/Amplification Steps

One hundred ng of the DNA from the previous hybridization/selective amplification was ligated to the J Bgl primer set (SEQUENCE I.D. NO. 5 and SEQUENCE I.D. NO. 6) as described previously. This DNA (50 ng) was mixed with 20 µg of driver amplicon and the hybridization and amplification procedures were repeated as described above except that the extension temperature during the thermocycling was 70° C. and not 72° C. as for the N Bgl primer set (SEQUENCE I.D. NO. 3 and SEQUENCE I.D. NO. 4) and the final amplification step (after MBN digestion) was for 25 cycles. One hundred ng of the second hybridization-amplification product was then ligated to the N Bgl primer set (SEQUENCE I.D. NO. 3 and SEQUENCE I.D. NO. 4), and 200 pg of this material together with 20 µg of driver amplicon was taken for the third round of hybridization/amplification as described above with the final amplification for 25 cycles.

Figure 14:
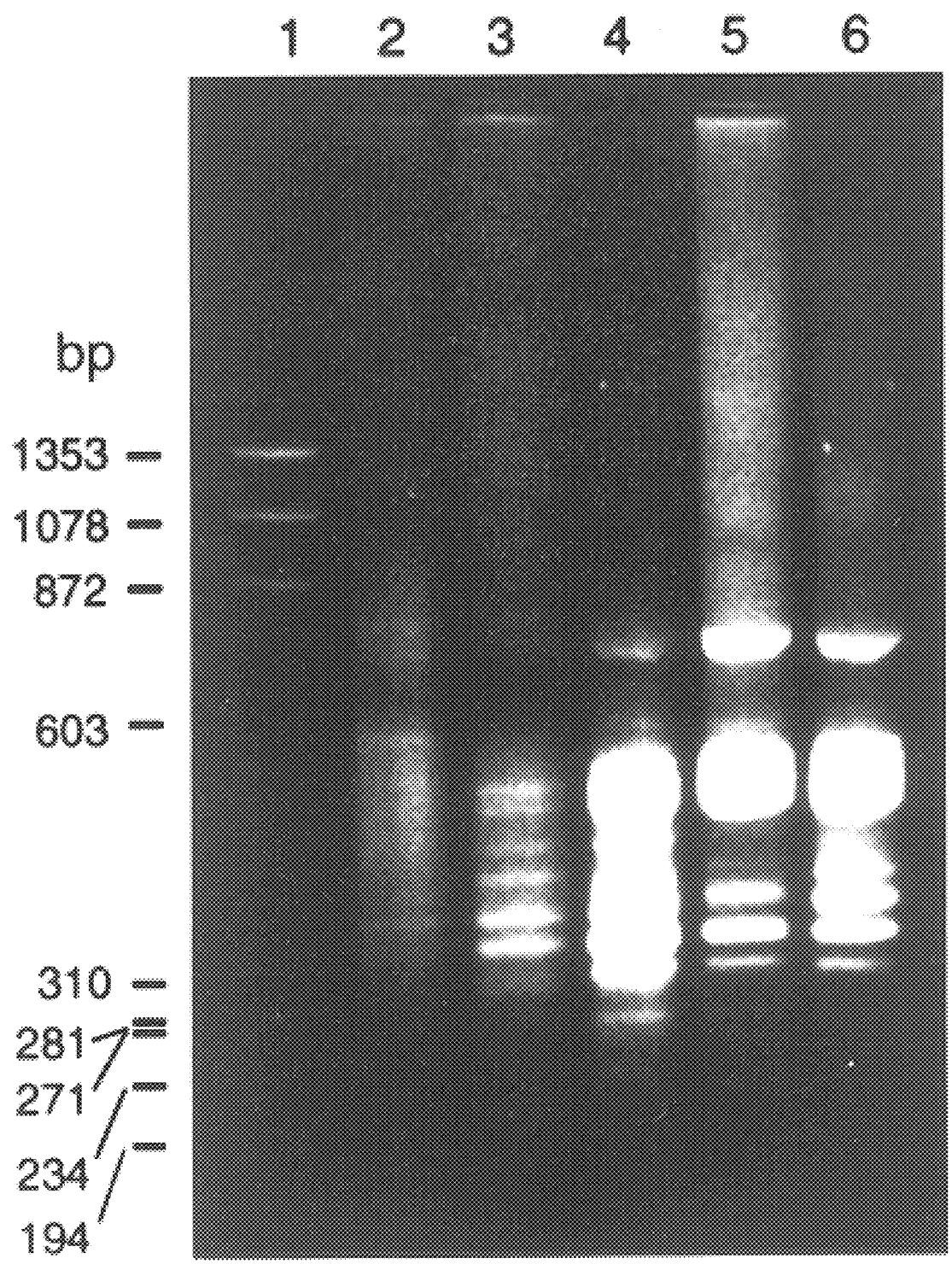
FIG. 14 shows an ethidium bromide stained 2.0% agarose gel of the products from the representational difference analysis (RDA) performed on pre-inoculation and acute phase HGBV-infected tamarin plasma.

A 2% agarose gel of the products from the representational difference analysis (RDA) performed on pre-HGBV inoculated and acute phase T-1053 plasma is shown in FIG. 14. Referring to FIG. 14, Lane 1 contains 150 ng of HaeIII digested Phi-X174 DNA marker (NEB) with the appropriate size (in bp) of the DNA fragments. The complexity of the driver amplicon (lane 2) and the tester amplicon (lane 3) is evidenced by the smear of DNA products seen in these samples. This complexity drops dramatically as the tester sequences are subjected to one (lane 4), two (lane 5) or three (lane 6) rounds of hybridization/selective amplification.

E. Cloning of the Difference Products

The difference products were cloned into the BamHI site of pBluescript II KS+ (Stratagene, La Jolla, Calif., cat. # 212207), as follows. Briefly, 0.5 µg pBluescript II was digested with BamHI (10 units, NEB) and 5' dephosphorylated with calf intestinal phosphatase (10 units, NEB) as directed by the supplier. The plasmid was phenol:chloroform extracted, ethanol precipitated, washed with 70% ethanol and resuspended in 10 µl $H_2O$ (final concentration approximately 50 ng pBluescript II per µl). The four largest bands from the second hybridization/amplification products were excised from a 2% low melting point agarose gel as described above. Four µl of the melted (72° C., 5 min.) gel slices were ligated to 50 ng of the BamHI-cut, dephosphorylated pBluescript II in a 50 µl reaction using the Takara DNA ligation kit (Takara Biochemical, Berkeley, Calif.). After incubating at 16° C. for 3.5 hours, 8 µl of the ligation reactions were used to transform E. coli competent XL-1 Blue cells (Stratagene) as directed by the supplier. The transformation mixtures were plated on LB plates supplemented with ampicillin (150 µg/ml) and incubated overnight at 37° C. The resulting colonies were grown up in liquid culture and miniprep plasmid DNA was analyzed as described in the art to confirm the existence of cloned product.

In addition to the cloning of the four largest products from the second hybridization/amplification step, the entire population of products from the third hybridization/amplification step was cloned into pBluescript II. Briefly, 50 ng pBluescript II vector (prepared as above) was ligated to 10 ng of the third hybridization/amplification products in a 50 µl reaction as described above. After incubation at 16° C. for 2 hours, 10 µl ligation product was used to transform E. coli competent XL-1 Blue cells as before. Sixty colonies from the resultant transformation were grown up, and miniprep DNA was prepared and analyzed as described and known in the art. Restriction endonuclease digestion and dot blot hybridization experiments were used to identify unique clones.

Example 4

Immunoisolation of a cDNA Clone Encoding an Antigenic Region of the HGBV Genome

A. Preparation of Concentrated Virus as a Source of Cloning Material

The following isolation scheme was employed to isolate the HGBV genome in addition to the procedures exemplified in Example 3. Three tamarins (T-1055, T-1038 and T-1049) were inoculated with serum prepared from tamarin T-1053 as described in Example 2. Referring to TABLE 5, elevated liver enzyme values were noted in all 3 tamarins by day 11 PI. Tamarin T-1055 was sacrificed on day 12 PI and tamarins T-1038 and T-1049 were sacrificed on day 14 PI. Approximately 3–4 ml of serum from each of these three tamarins were pooled, providing a total volume of approximately 11.3 ml. The pooled serum was clarified by centrifugation at 10,000×g for 15 min at 15° C. It was then passed successively through 0.8, 0.45, 0.2, and 0.1 μm syringe filters. This filtered material was then concentrated by centrifugation through a 0.3 ml CsCl cushion (density 1.6 g/ml, in 10 mM Tris, 150 mM NaCl, 1 mM EDTA, pH 8.0) in a SW41-Ti rotor at 41,000 rpm at 4° C. for 68 min. The CsCl layer, approximately 0.6 ml, was removed following centrifugation and stored in three 0.2 ml aliquots at −70° C.

Tamarin T-1034 was subsequently inoculated with 0.25 ml of a $10^{-6}$ dilution of this pelleted material (prepared in normal tamarin serum). Elevated ALT liver enzyme values were first noted in T-1034 at 2 weeks PI, and remained elevated for the next 7 weeks, finally normalizing by week 10 PI (see FIG. 30, Example 14). This experiment demonstrated the infectivity of the material concentrated from the pooled tamarin sera. Since this material was shown to be of a relatively high titer, this concentrated source of virus was used as the source of nucleic acid for the preparation of a cDNA library, as described below.

B. cDNA Library Construction

An aliquot (0.2 ml) of the concentrated virus (described above) was extracted for RNA using a commercially available RNA extraction kit (Stratagene, La Jolla, Calif.) as instructed by the supplier. The sample was divided into four equal aliquots prior to the final precipitation step, and then precipitated in the presence of 5 μg/ml yeast tRNA. Only one of these aliquots was used for cDNA synthesis; the others were stored at −80° C. Phosphorylated, blunt-ended, double-stranded cDNA was prepared from the RNA using a commercially available kit (Stratagene, La Jolla, Calif.) as directed by the manufacturer. A double-stranded linker/primer was then ligated to the cDNA ends (sense strand, SEQUENCE I.D. NO. 7; antisense strand, SEQUENCE I.D. NO. 8) in a 10 μl reaction volume using a T4 DNA ligase kit (Stratagene, La Jolla, Calif.) as directed by the manufacturer. This provided all cDNAs in the mixture with identical 5' and 3' ends containing Not I and Eco RI restriction enzyme recognition sites. G. Reyes and J. Kim, *Mol. Cell. Probes* 5:473–481 (1991); A. Akowitz and L. Manuelidis, *Gene* 81:295–306 (1989); and G. Inchauspe et al., in *Viral Hepatitis and Liver Disease*, F. B. Hollinger et al., Eds., pp. 382–387 (1991). The sense-strand oligonucleotide of the linker/primer was then used as a primer in a PCR reaction such that all cDNAs were amplified independent of their sequence. This procedure allowed for the amplification of rare cDNAs present within the total cDNA population to a level which allowed them to be efficiently cloned, thus producing a cDNA library that is representative of the sequences within the starting material.

PCR was performed on a 1 μl aliquot of the above ligate in the presence of the sense-strand oligonucleotide primer (final concentration: 1 μM; reaction volume: 50 μl) using the GeneAmp PCR kit (Perkin-Elmer) as directed by the manufacturer in a PE-9600 thermocycler. Thirty cycles of PCR were performed as follows: denaturation at 94° C. for 0.5 min, annealing at 55° C. for 0.5 min, and extension at 72° C. for 1.5 min. A 1 μl aliquot of the resulting products was then re-amplified as described above. The final PCR reaction products were then extracted once with an equal volume of phenol-chloroform (1:1, v/v) and once with an equal volume of chloroform, and then precipitated on dry ice for 10 min following the addition of sodium acetate (final concentration, 0.3 M) and 2.5 volumes of absolute ethanol. The resulting DNA pellet was resuspended in water and digested with the restriction enzyme Eco RI (New England Biolabs) as directed by the manufacturer. The digested cDNAs were then purified from the reaction mixture using a DNA binding resin (Prep-a-Gene, BioRad Laboratories) as directed by the manufacturer and eluted in 20 μl of distilled water.

The cDNAs (8 μl) were ligated-to 3 μg lambda gt11 vector DNA arms (Stratagene, La Jolla, Calif.) in a reaction volume of 30 μl at 4° C. for 1–5 days. Eleven microliters of the ligate was packaged into phage heads using GigaPack III Gold packaging extract (Stratagene, La Jolla, Calif.) as directed by the manufacturer. The resulting library contained a total of approximately 1.73 million members (PFU) at a recombination frequency of 89.3% with an average insert size of approximately 350 base pairs.

C. Immunoscreening of the Recombinant GB cDNA Library

The antiserum used for immunoscreening of the cDNA library was obtained from tamarins that had demonstrated elevations in their serum liver enzyme levels following inoculation. Two separate pools of antisera were used for immunoscreening. The first pool contained serum from two animals (T-1048 and T-1051; see Example 1, TABLE 2, and Example 2, TABLE 5, respectively) while the second pool contained serum from a single animal (T1034; see FIG. 30, Example 14). The specific sera used are shown in TABLE 6.

At the time that these samples were chosen for use in cDNA library immunoscreening, they had not been tested for their immunoreactivity with either the 1.4 or 1.7 recombinant CKS proteins (Example 13). Therefore, the results shown herein were obtained independent of any information regarding the presence or absence of HGBV antibodies against these recombinant proteins within the antiserum used.

TABLE 6

Tamarin Sera used for Immunoscreening of GB cDNA Library

| Tamarin 1048[a] | | Tamarin 1051[b] | | Tamarin 1034[c] | |
|---|---|---|---|---|---|
| Days Post-Inoculate | Volume in Pool | Days Post-Inoculate | Volume in Pool | Days Post-Inoculate | Volume in Pool |
| 63 | 0.2 ml | 63 | 0.2 ml | 42 | 0.1 ml |
| 77 | 0.2 ml | 69 | 0.1 ml | 49 | 0.1 ml |
| 91 | 0.2 ml | 91 | 0.2 ml | 63 | 0.1 ml |
| 97 | 0.2 ml | 98 | 0.2 ml | 70 | 0.1 ml |
| 126 | 2.0 ml | 105 | 0.2 ml | 77 | 0.08 ml |
| | | 109 | 5.3 ml | | |

[a]Total T-1048 pool volume is 2.8 ml.
[b]Total T-1051 pool volume is 6.4 ml. One ml of each pool was saved and the remainder of each was combined and used as the primary antiserum for immunoscreening.
[c]Total T-1034 pool volume is 0.48 ml; the entire pool was used for immunoscreening.

The procedure used for the immunoisolation of recombinant phage was based upon the method described by Young and Davis with modifications as described below. R. A. Young and R. W. Davis, *PNAS* 80:1194–1198 (1983). Two immunoscreening experiments were performed, one utilizing antiserum pooled from T-1048 and T-1051 and the other utilizing antiserum from T-1034. In both cases, the primary antiserum was pre-adsorbed against *E. coli* extract prior to use in order reduce non-specific interactions of antibody with *E. coli* proteins. In the first experiment, 1.29 million recombinant phage were immunoscreened with the T-1048/ T-1051 antiserum pool; in the second experiment 0.30 million recombinant phage were immunoscreened with T-1034 antiserum. The recombinant phage library was plated on a lawn of *E. coli* strain Y1090r- and grown at 37° C. for 3.5 hours. The plates were then overlaied with nylon filters that were saturated with IPTG (10 mM) and the plates incubated at 42° C. for 3.5 hours. The filters were then blocked in Tris-saline buffer containing 1% BSA, 1% gelatin, and 3% Tween-20 ("blocking buffer") for 1 hour at 22° C. The filters were then incubated in primary antiserum (1:100 dilution in blocking buffer) at 4° C. for 16 hours. Primary antiserum was then removed and saved for subsequent rounds of plaque purification, and the filters washed four times in Tris-saline containing 0.1% Tween-20. The filters were then incubated in blocking buffer containing 125I-labeled (or alkaline-phosphatase conjugated) goat anti-human IgG (available from Jackson ImmunoResearch, West Grove, Pa.) for 60 min at 22° C., washed as described above, and then exposed to x-ray film (or subjected to color development according to established procedures, as in J. Sambrook et al., *Molecular Cloning: A Laboratory Manual*, 2nd edition, Cold Spring Harbor Press, Cold Spring Harbor, N.Y., 1989). Five immunopositive phage (4-3B1, 48-1A1, 66-3A1, 70-3A1, 78-1C1) were isolated from this library and subsequently tested for specificity of binding to antisera from three infected tamarins (T-1048, T-1051, T-1034) using the method described above. These recombinants encoded polypeptides that reacted with convalescent sera, but not with pre-inoculation sera, from each of the three infected tamarins (data not shown).

In order to verify the specificity of the immunological reactivity of the polypeptide encoded by the recombinant phage, each cDNA was rescued from the lambda phage genome by PCR using primers located 5' (SEQUENCE I.D. NO. 9) and 3' (SEQUENCE I.D. NO. 10) to the Eco RI cloning site. The PCR products were then digested with Eco RI and subsequently ligated into the *E. coli* expression plasmid pJO201 as described in Example 13. Insertion of the cDNAs into the Eco RI site of pJO201 maintained the translational reading frame of this cDNA as present in the lambda phage clone. The subclones in the pJO201 expression vector were designated 4-3B1.1, 48-1A1.1, 66-3A1.49, 70-3A1.37, and 78-1C1.17. Immunoblot analysis (as in Example 13) of *E. coli* lysates prepared from cultures expressing these cDNAs with convalescent sera from tamarins T-1034, T-1048, and T-1051 (1:100 dilution) demonstrated specific immunologic reactivity with a protein of the size predicted for each CKS-fusion protein. (data not shown). The DNA sequence of each of the cDNAs was determined and it was found that these clones possessed nearly 100% sequence identity with that of HGBV-B virus (SEQUENCE I.D. NO. 11). The sequence of the 4-3B1.1 insert (SEQUENCE I.D. NOS. 12 and 13), although not determined in its entirety, those portions that have been sequenced exhibit 99.5% Sequence identity to a portion of the sequence within HGBV-B (SEQUENCE I.D. NO. 11) from base pairs 6834–7458. This region of the HGBV-B (SEQUENCE I.D. NO. 11) sequence showing identity with that of the sequence obtained from clone 4-3B1.1 was translated into the +1 reading frame and is presented in the sequence listing as SEQUENCE I.D. NO. 14. The sequence of the 48-1A1.1 insert (SEQUENCE I.D. NO. 15) exhibits 100% Sequence identity to a portion of the sequence from HGBV-B (SEQUENCE I.D. NO. 11, see Example 9) from base pairs 4523–4752. The DNA sequence corresponding to SEQUENCE I.D. NO. 15 was translated into the +1 reading frame and is presented in the sequence listing as SEQUENCE I.D. NO. 16. The sequence of the 66-3A1.49 insert (SEQUENCE I.D. NO. 17) exhibits essentially 100% sequence identity to that of clone 48-1A1.1 and thus no protein translation is shown in the sequence listing. The sequence of the 70-3A1.37 insert (SEQUENCE I.D. NO. 18) exhibits 100% sequence identity to a portion of the sequence from HGBV-B (SEQUENCE I.D. NO. 11) from base pairs 6450–6732 except for a three base-pair deletion corresponding to bases 6630–6632 of the HGBV-B sequence (SEQUENCE I.D. NO. 11). The DNA sequence corresponding to SEQUENCE I.D. NO. 18 was translated into the +2 reading frame and is presented in the sequence listing as SEQUENCE I.D. NO. 19. The sequence of the 78-1C1.17 insert (SEQUENCE I.D. NO. 20) exhibits 100% sequence identity to that of clone 70-3A1.37 and thus no protein translation is shown in the sequence listing. These data demonstrate that the cDNA clones isolated from the lambda gt11 cDNA library are derived from the genome of the HGBV agent and that it encodes polypeptides which are specifically recognized immunologically by sera from GB-infected tamarins. Clones 48-1A1.1("clone 48") 4-3B1.1, 66-3A1.49, 70-3A1.37, and 78-1C1.17 have been deposited at the American Type Culture Collection as provided hereinabove.

Example 5

DNA Sequence Analysis of HGBV Clones

Unique clones obtained in Example 3 were sequenced using the dideoxynucleotide chain termination technique (Sanger, et al., supra) in a kit form (Sequenase® version 2.0, USB). These sequences are non-overlapping and are presented in the Sequence Listing as clone 4 (SEQUENCE I.D. NO. 21), clone 2 (SEQUENCE I.D. NO. 22), clone 10 (SEQUENCE I.D. NO. 23), clone 11 (SEQUENCE I.D. NO. 24), clone 13 (SEQUENCE I.D. NO. 25), clone 16 (SEQUENCE I.D. NO. 26), clone 18 (SEQUENCE I.D. NO. 27), clone 23 (SEQUENCE I.D. NO. 28), clone 50 (SEQUENCE I.D. NO. 29) and clone 119 (SEQUENCE I.D. No. 30). Clones 4, 2, 10, 11, 13, 16, 18, 23, 50 and 119 have been deposited at the A.T.C.C. Clone 2 was accorded A.T.C.C. Deposit No. 69556; Clone 4 was accorded A.T.C.C. Deposit No. 69557; Clone 10 was accorded A.T.C.C. Deposit No. 69558; Clone 16 was accorded A.T.C.C. Deposit No. 69559; Clone 18 was accorded A.T.C.C. Deposit No. 69560; Clone 23 was accorded A.T.C.C. Deposit No. 69561; and Clone 50 was accorded A.T.C.C. Deposit No. 69562; Clone 11 was accorded A.T.C.C. Deposit No. No. 69613; Clone 13 was accorded A.T.C.C. Deposit No. 69611; and Clone 119 was accorded A.T.C.C. Deposit No. 69612.

The sequences were searched against the GenBank database using the BLASTN algorithm (Altschul et al, *J. Mol. Biol.* 215:403–410 [1990]). None of these sequences were found in GenBank, indicating that these sequences have not been previously characterized in the literature. The DNA sequences were translated into the six possible reading frames and are presented in the sequence listing (SEQUENCE I.D. NO. 21 translates to SEQUENCE I.D. NOS. 31–36, SEQUENCE I.D. NO. 22 translates to SEQUENCE I.D. NOS. 37–42, SEQUENCE I.D. NO. 23 translates to SEQUENCE I.D. NOS. 43–48, SEQUENCE I.D. NO. 26 translates to SEQUENCE I.D. NOS. 49–54, SEQUENCE I.D. NO. 27 translates to SEQUENCE I.D. NOS. 55–60, SEQUENCE I.D. NO. 28 translates to SEQUENCE I.D. NOS. 61–66, and SEQUENCE I.D. NO. 29 translates to SEQUENCE I.D. NOS. 67–72). SEQUENCE I.D. NO. 24 is contained within SEQUENCE I.D. NO. 73 (described in Example 9), which translates to SEQUENCE I.D. NOS. 74–79. SEQUENCE I.D. NOS. 25 and 30 are contained within SEQUENCE I.D. NO. 80 (described in Example 9), which translates to SEQUENCE I.D. NO. 81–86. The translated sequences were used to search the SWISS-PROT database using the BLASTX algorithm (Gish et al., Nature Genetics 3:266–272 [1993]). Again, none of these sequences were found in SWISS-PROT indicating that these sequences have not been previously characterized in the literature.

Homology searches conducted using the BLASTN, BLASTX and FASTdb algorithms demonstrate some, albeit low, sequence resemblance to hepatitis C virus (TABLE 7, below). Specifically, translations of clones 4 (SEQUENCE I.D. NO. 35), 10 (SEQUENCE I.D. NO. 44), 11 (residues 1–166 of GB-A, frame 3 [SEQUENCE I.D. NO. 76]), 16 (SEQUENCE I.D. NO. 50), 23 (SEQUENCE I.D. NO. 65), 50 (SEQUENCE I.D. NOS. 70 and 72) and 119 (residues 912–988 of GB-A, frame 3 [SEQUENCE I.D. NO. 83]), are between 24.1% and 45.1% homologous to various HCV isolates at the amino acid level. Of particular interest, translation of clone 10 (SEQUENCE I.D. NO. 44) showed limited homology to the putative RNA-dependent RNA polymerase of HCV. A comparison of the conserved amino acids present in the putative RNA-dependent RNA polymerase of other positive strand viruses (Jiang et al. PNAS 90:10539–10543 [1993]) with the putative amino acid translation of clone 10 (SEQUENCE I.D. NO. 44) revealed that conserved amino acid residues of other RNA-dependent RNA polymerases are also conserved in clone 10 (SEQUENCE I.D. NO. 44). This includes the canonical GDD (Gly-Asp-Asp) signature sequence of RNA-dependent RNA polymerases. Thus, clone 10 (SEQUENCE I.D. NO. 44) appears to encode a viral RNA-dependent RNA polymerase. Surprisingly, only clone 10 (SEQUENCE I.D. NO. 44) showed any sequence homology with HCV at the nucleotide level when the BLASTN algorithm was used. Clones 4 (SEQUENCE I.D. NO. 21), 16 (SEQUENCE I.D. NO. 26), 23 (SEQUENCE I.D. NO. 28) and 50 (SEQUENCE I.D. NO. 29) and 119 (SEQUENCE ID. NO. 30) which have low HCV homology at the amino acid level, were not detected by BLASTN in searches of GenBank. In addition, clones 2 (SEQUENCE I.D. NOS. 37–42), 13 (SEQUENCE I.D. NO. 25 and 37–42) and 18 (SEQUENCE I.D. NOS. 27 and 55–60) showed no significant nucleotide or amino acid homology to HCV when searched against GenBank or SWISS-PROT as described hereinabove.

TABLE 7

HCV Homology of HGBV Clones

| Clone | Homology | | Strain[c] | Region[d] | Function[e] |
|---|---|---|---|---|---|
| | Nucleotide[a] | Amino Acid[b] | | | |
| 4 | none | 28/73 (38.4%) | HCVTW | NS4 | unknown |
| 10 | 134/307 (43.6%)[f] | 46/102 (45.1%) | HCVJ6 | NS5 | replicase |
| 11 | none | 40/166 (24.1%) | HCVJT | NS5 | replicase |
| 16 | none | 55/177 (31.1%) | HCVJ8 | NS2/3 | protease |
| 23 | none | 44/121 (36.4%) | HCVJA | NS3 | helicase |
| 50 | none | 29/112 (25.9%) | HCVH | NS4/5 | unknown |
| 119 | none | 27/77 (35.1%) | HCVTW | NS5 | replicase |

[a]Homology found to HCV when GB clones were searched against GenBank using the BLAST algorithm.
[b]Homology found to HCV when translated GB clone sequences were searched against SWISS-PROT using the FASTdb algorithm.
[c]Most homologous strain of HCV (SWISS-PROT designation)
[d,e]Region of homology and reputed function of clone compared with HCV according to Houghton et al., Hepatology 14(2): 381–388 (1991).
[f]BLASTN detected a segment of clone 10 that was 64% homologous with HCV NS5 over 132 nucleotides. Alignment of the entire clone 10 sequences with the homologous nucleotide sequence of HCVJ6 shows 43.6% homology.

Example 6

Exogenicity of HGBV Clones

The HGBV clones were not detected in normal or HGBV-infected tamarin liver DNA, normal human lymphocyte DNA, yeast DNA or E. coli DNA. This was demonstrated for HGBV clones 2 (SEQUENCE I.D. NO. 22) and 16 (SEQUENCE I.D. NO. 26) by Southern blot analysis. In addition, all HGBV clones were analyzed by genomic PCR to confirm the exogenous origin of the HGBV sequences with respect to the tamarin, human, yeast and E. coli genomes. These data are consistent with the viral nature of the HGBV sequences described in Example 5.
A. Southern Blot Analysis Tamarin liver nuclei were obtained from low speed pelleting of liver homogenates of HGBV-infected and normal tamarins (described hereinbelow). DNA was extracted from nuclei using a commercially available kit (USB cat. # 73750) as directed by the supplier. The tamarin DNA was treated with RNase during the extraction procedure. Human placental DNA (Clontech, Palo Alto, Calif.), yeast DNA (Saccharomyces cerevisiae, Clontech) and E. coli DNA (Sigma) were obtained from commercial sources.

Each DNA sample was digested with BamHI (NEB) according to the suppliers direction. Digested DNAs (10 µg) and RDA products (0.5 µg each from Example 3B) were electrophoresed on 1% agarose gels and capillary blotted to Hybond-N+ nylon membranes (Amersham, Arlington Heights, Ill.) as described in Sambrook et al. (pp. 9.34 ff). DNA was fixed to the membrane by alkali treatment as directed by the membrane supplier. Membranes were prehybridized in Rapid Hyb solution (Amersham) at 65° C. for 30 min.

Radiolabeled probes of the HGBV sequences were prepared by PCR. Briefly, 50 µl PCRs were set up using 1× PCR buffer II (Perkin Elmer), 2 mM MgCl$_2$, 20 µM dNTPs, 1 µM each of clone specific sense and antisense primers (for clone 2, SEQUENCE I.D. NOS. 87 and 88; for clone 4, SEQUENCE I.D. NOS. 89 and 90; for clone 10, SEQUENCE I.D. NOS. 91 and 92; for clone 16, SEQUENCE I.D. NOS. 93 and 94; for clone 18, SEQUENCE I.D. NOS. 95 and 96; for clone 23, SEQUENCE I.D. NOS. 97 and 98; and for clone 50, SEQUENCE I.D. NOS. 99 and 100), 1 ng HGBV clone plasmid (described in Example 3[E]), 60 μCi α-$^{32}$P-dATP (3000 Ci/mmol) and 1.25 units of AmpliTaq® polymerase (Perkin Elmer). The reactions were incubated at 94° C. for 30 sec., 55° C. for 30 sec., and 72° C. for 30 sec. for a total of 30 cycles of amplification followed by a final extension at 72° C. for 3 minutes. Unincorporated label was removed by Quick-Spin® G-50 spin columns (Boehringer Mannheim, Indianapolis, Ind.) as directed by the supplier. The probes were denatured (99° C., 2 min.) prior to addition to the pre-hybridized membranes.

Radiolabeled probes were added to the prehybridized membranes (2×10$^6$ dpm/ml) and filters were hybridized at 65° C. for 2.5 hours as directed by the Rapid Hyb® supplier. The hybridized membranes were washed under conditions of moderate stringency (1× SSC, 0.1% SDS at 65° C.) before being exposed to autoradiographic film for 72 hours at −80° C. with an intensifying screen. These conditions were designed to detect a single copy gene with a similar radiolabeled probe.

Figure 15A:
FIGS. 15A and B show autoradiograms from a Southern blots of genomic DNA, amplicon DNA and products from the first three rounds of subtraction/hybridization.
Figure 15B:
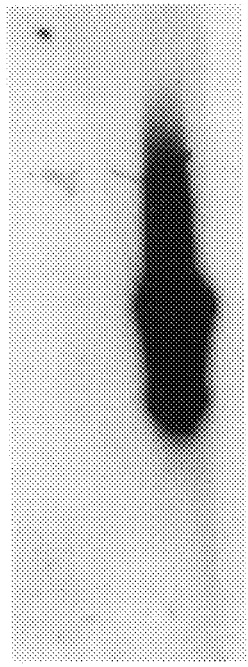
Figure 16A:
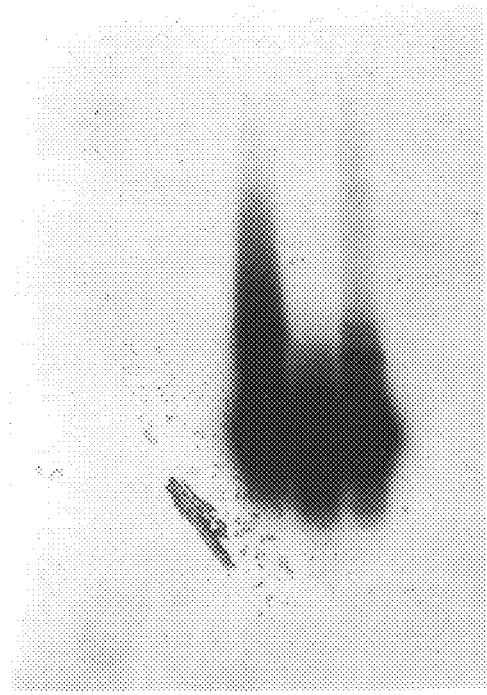
FIGS. 16A and B show the same autoradiograms as described in FIGS. 15 A and B, respectively, except that an alternative radiolabeled probe is used.
Figure 16B:
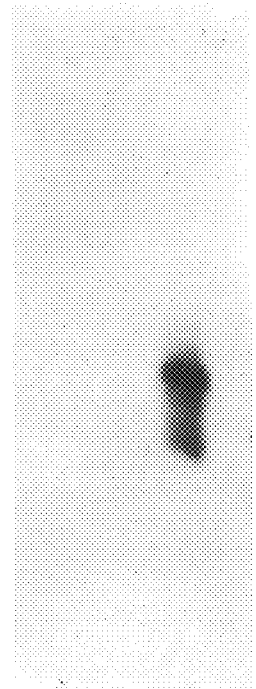

The results show that clone 2 (SEQUENCE I.D. NO. 22) and clone 16 (SEQUENCE I.D. NO. 26) sequences did not hybridize to DNA from normal or HGBV-infected tamarin liver (FIGS. 15 and 16, lanes 1B and 3B, respectively), human DNA (FIGS. 15 and 16, lane 1A), yeast DNA (FIGS. 15 and 16, lane 2A) or E. coli DNA (FIGS. 15 and 16, lane 3A). In addition, no hybridization was detected with the driver amplicon DNA (FIGS. 15 and 16, lanes 4A, derived from pre-HGBV-inoculated tamarin plasma as described in Example 2.B). In contrast, strong hybridization signals were seen with the tester amplicon (FIGS. 15 and 16, lane 6A, derived from infectious HGBV tamarin plasma using total nucleic acid extraction and reverse transcription steps as described in Example 2.B) and the products of the three rounds of subtraction/selective amplification (FIGS. 15 and 16, lanes 7A, 8A and 4B referring to the products from the first, second and third rounds of subtraction/selective amplification, respectively). These data demonstrate that HGBV clones 2 (SEQUENCE I.D. NO. 22) and 16 (SEQUENCE I.D. NO. 26) can be detected in nucleic acid sequences amplified from infectious sources; HGBV clones 2 (SEQUENCE I.D. NO. 22) and 16 (SEQUENCE I.D. NO. 26) are not derived from tamarin, human, yeast or E. coli genomic DNA sequences.

B. Genomic PCR Analysis

To further demonstrate the exogenicity of the HGBV sequences and support their viral origin, PCR was performed on genomic DNA from tamarin, human, yeast and E. coli. DNA from normal tamarin kidney and liver tissue was prepared as described by J. Sambrook et al., supra. Yeast, Rhesus monkey kidney and human placental DNAs were obtained from Clontech. E. coli DNA was obtained from Sigma.

PCR was performed using GeneAmp® reagents from Perkin-Elmer-Cetus essentially as directed by the supplier's instructions. Briefly, 300 ng of genomic DNA was used for each 100 μl reaction. PCR primers derived from HGBV cloned sequences (for clone 2, SEQUENCE I.D. NOS. 87 and 88; for clone 4, SEQUENCE I.D. NOS. 89 and 90; for clone 10, SEQUENCE I.D. NOS. 91 and 92; for clone 16, SEQUENCE I.D. NOS. 93 and 94; for clone 18, SEQUENCE I.D. NOS. 95 and 96; for clone 23, SEQUENCE I.D. NOS. 97 and 98; and for clone 50, SEQUENCE I.D. NOS. 99 and 100) were used at a final concentration of 0.5 μM. PCR was performed for 35 cycles (94° C., 1 min; 55° C., 1 min; 72° C., 1 min) followed by an extension cycle of 72° C. for 7 min. The PCR products were separated by agarose gel electrophoresis and visualized by UV irradiation after direct staining of the nucleic acid with ethidium bromide and/or hybridization to a radiolabeled probe after Southern blot transfer to a nitrocellulose filter. Probes were generated as described in Example 6A. Filters were prehybridized in Fast-Pair Hybridization Solution from Digene (Belstville, Md.) for 3–5 hours and then hybridized in Fast-Pair Hybridization Solution with 100–200 cpm/cm$^2$ at 42° C. for 15–25 hours. Filters were washed as described in G. G. Schlauder et al., J. Virol. Methods 37:189–200 (1992) and exposed to Kodak X-Omat-AR film for 15 to 72 hours at −70° C. with intensifying screens.

Figure 17:
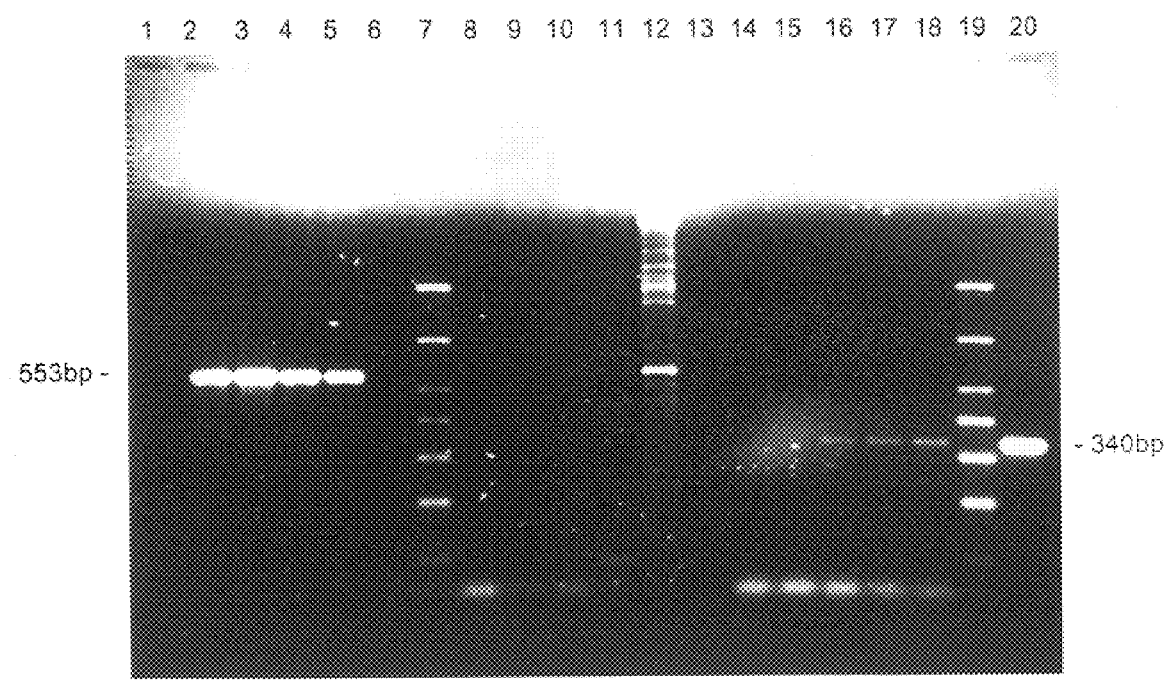
FIG. 17 shows an ethidium bromide stained 1.5% agarose gel of polymerase chain reaction (PCR) amplified product from genomic DNA.
Figure 18:
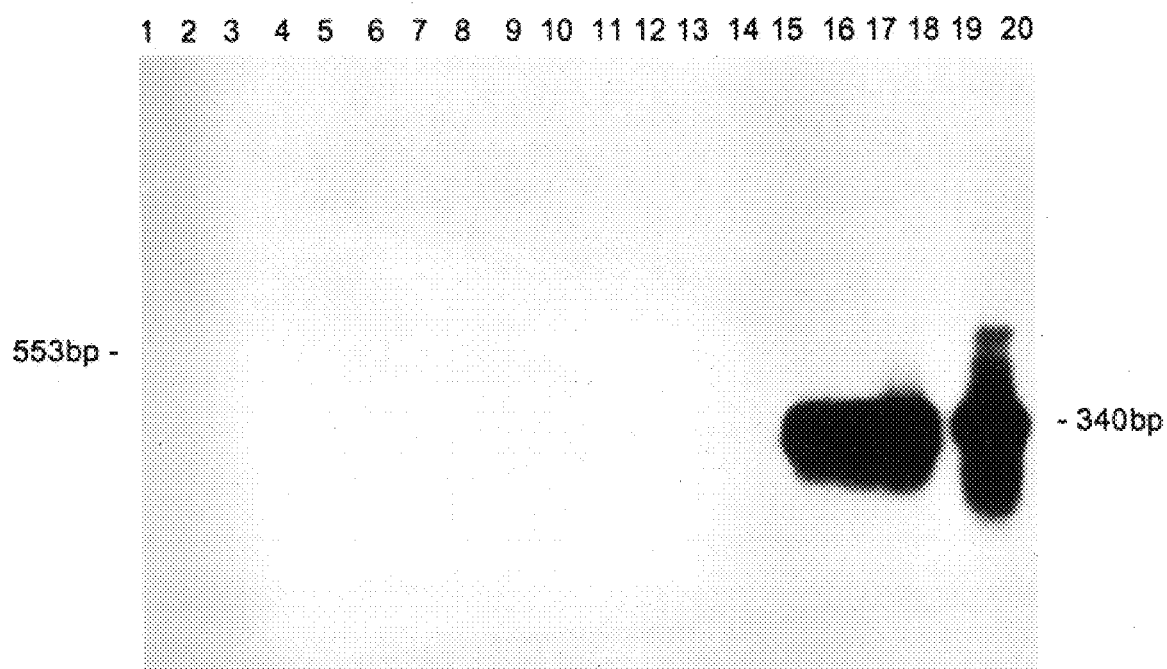
FIG. 18 shows an autoradiogram from a Southern blot of the 1.5% agarose gel in FIG. 17.

FIG. 17 shows an ethidium bromide stained 1.5% agarose gel. FIG. 18 shows an autoradiogram from a Southern blot from the same gel after hybridization to the radiolabeled probe from clone 16 (SEQUENCE I.D. NO. 26). Consistent with its exogenous nature, clone 16 (SEQUENCE I.D. NO. 26) sequences were not detected in tamarin (FIGS. 17 and 18, lanes 9 and 10), Rhesus monkey (lane 11) or human genomic DNAs (lane 12) or in yeast or E. coli DNAs (data not shown) by genomic PCR analysis despite being able to detect clone 16 (SEQUENCE I.D. NO. 26) sequences that have been spiked into normal tamarin liver and kidney DNA at 0.05 genome equivalents (lanes 17 and 18). In addition, primers derived from the human dopamine D1 receptor gene, 1000–1019 base pairs (sense primer) and 1533–1552 base pairs (antisense primer) (GenBank accession number X55760, R. K. Sunahara. et al., Nature 347:80–83 [1990]) successfully amplified the dopamine D1 receptor DNA from the primate genomic DNAs (FIG. 17 lanes 2, 3, 4 and 5 corresponding to tamarin kidney, tamarin liver, rhesus monkey and human DNAs) demonstrating the utility of this method for detecting low copy number (i.e. single copy) sequences. Lanes 1 and 8 are H$_2$O controls for dopamine D1 receptor and clone 16 primers (SEQUENCE I.D. NOS. 93 and 94), respectively. Lane 6 contains 100 fg of clone 16 (SEQUENCE I.D. NO. 26) plasmid DNA amplified with the dopamine receptor primers. Lanes 14, 15, 16 and 20 contain 1, 3, 10, and 100 fg, respectively, of clone 16 (SEQUENCE I.D. NO. 26) plasmid DNA. Lanes 7 and 19 are markers. Similar results were obtained using PCR primers specific for clones 2, 4, 10, 18, 23 and 50 described above (data not shown). Clones 2 (SEQUENCE I.D. NO. 22), 4 (SEQUENCE I.D. NO. 21), 10 (SEQUENCE I.D. NO. 23), 18 (SEQUENCE I.D. NO. 27), 23 (SEQUENCE I.D. NO. 28) and 50 (SEQUENCE I.D. NO. 29) are inconclusive at this time. However, clones 4 (SEQUENCE I.D. NO. 21), 10 (SEQUENCE I.D. NO. 23), 18 (SEQUENCE I.D. NO. 27) and 50 (SEQUENCE I.D. NO. 29) sequences were not detected in tamarin, human, yeast and E. coli DNA, (Rhesus monkey was not tested) indicating that these sequences are exogenous to the genomic DNA sources tested and supporting the viral origin of these sequences.

Example 7

Presence of HGBV Sequences in Tamarin Sera

The presence of the HGBV clone sequences in pre-inoculation and acute phase T-1053 plasma was examined by PCR. Because the HGBV genome could be DNA or RNA, PCR and RT-PCR was performed. Specifically, total nucleic acids were extracted from plasma as described in Example 3(A). PCR was performed on the equivalent of 5 μl plasma nucleic acids as described in Example 6(B) and RT-PCR was performed using the GeneAmp® RNA PCR Kit from Perkin-Elmer-Cetus essentially according to the manufacturer's instructions using 1 μM concentration of primers (for clone 2, SEQUENCE I.D. NOS. 87 and 88; for clone 4, SEQUENCE I.D. NOS. 89 and 90; for clone 10, SEQUENCE I.D. NOS. 91 and 92; for clone 16, SEQUENCE I.D. NOS. 93 and 94; for clone 18, SEQUENCE I.D. NOS. 95 and 96; for clone 23, SEQUENCE I.D. NOS. 97 and 98; and for clone 50, SEQUENCE I.D. NOS. 99 and 100) in the PCRs. cDNA synthesis was primed with random hexamers.

Ethidium bromide staining and hybridization of the PCR products demonstrated the presence of HGBV clone sequences 2 (SEQUENCE I.D. NO. 22), 4 (SEQUENCE I.D. NO. 21), 10 (SEQUENCE I.D. NO. 23), 16 (SEQUENCE I.D. NO. 26), 18 (SEQUENCE I.D. NO. 27), 23 (SEQUENCE I.D. NO. 28) and 50 (SEQUENCE I.D. NO. 29) in the acute phase T-1053 plasma and not the pre-inoculation T-1053 plasma (data not shown). In addition, HGBV clones 2 (SEQUENCE I.D. NO. 22), 4 (SEQUENCE I.D. NO. 21), 10 (SEQUENCE I.D. NO. 23), 18 (SEQUENCE I.D. NO. 27), 23 (SEQUENCE I.D. NO. 28) and 50 (SEQUENCE I.D. NO. 29) sequences could be detected in H205, the HGBV inoculum that was injected into tamarin T-1053 (see Example 1B). These results are summarized in TABLE 8. It should be noted that the HGBV clone sequences were only detected by RT-PCR in the acute phase plasma. The fact that the HGBV clone sequences were detected in the acute phase plasma by PCR only after a reverse transcription step to convert RNA to cDNA, taken together with the limited homology of some of these clones with HCV isolates, and the presence of the sequences coding for the conserved amino acids found in the RNA-dependent RNA polymerase in HGBV clone 10 (SEQUENCE I.D. NO. 23; Example 5) suggest that HGBV is an RNA virus.

RT-PCR analysis of a panel of tamarin plasmas with HGBV clone 16 sequence (SEQUENCE I.D. NO. 26) was undertaken to confirm the presence of HGBV clone 16 (SEQUENCE I.D. NO. 26) in other individuals who had been experimentally infected with HGBV. Briefly, nucleic acids were isolated as previously described (G. G. Schlauder et al., *J. Virological Methods* 37:189–200 [1992]) from 25 μl of plasma from tamarins obtained prior to and after experimental infection with the H205 inoculum. Ethanol precipitated nucleic acids were resuspended in 3 μl of DEPC-treated $H_2O$. cDNA synthesis and PCR were performed using the GeneAmp RNA PCR Kit from Perkin-Elmer-Cetus essentially according to the manufacturer's instructions. cDNA synthesis was primed with random hexamers. The resulting cDNA was subjected to PCR using clone 16 primers (SEQUENCE I.D. NOS. 93 and 94) at a final concentration of 0.5 μM. PCR was performed for 35 cycles (94° C., 1 min; 55° C., 1 min; 72° C., 1 min) followed by an extension cycle of 72° C. for 7 min. The PCR products were separated by agarose gel electrophoresis and visualized by UV irradiation after direct staining of the nucleic acid with ethidium bromide and/or hybridization to a radiolabeled probe after Southern blot transfer to a nitrocellulose filter as describes in Example 6B.

Figure 19:
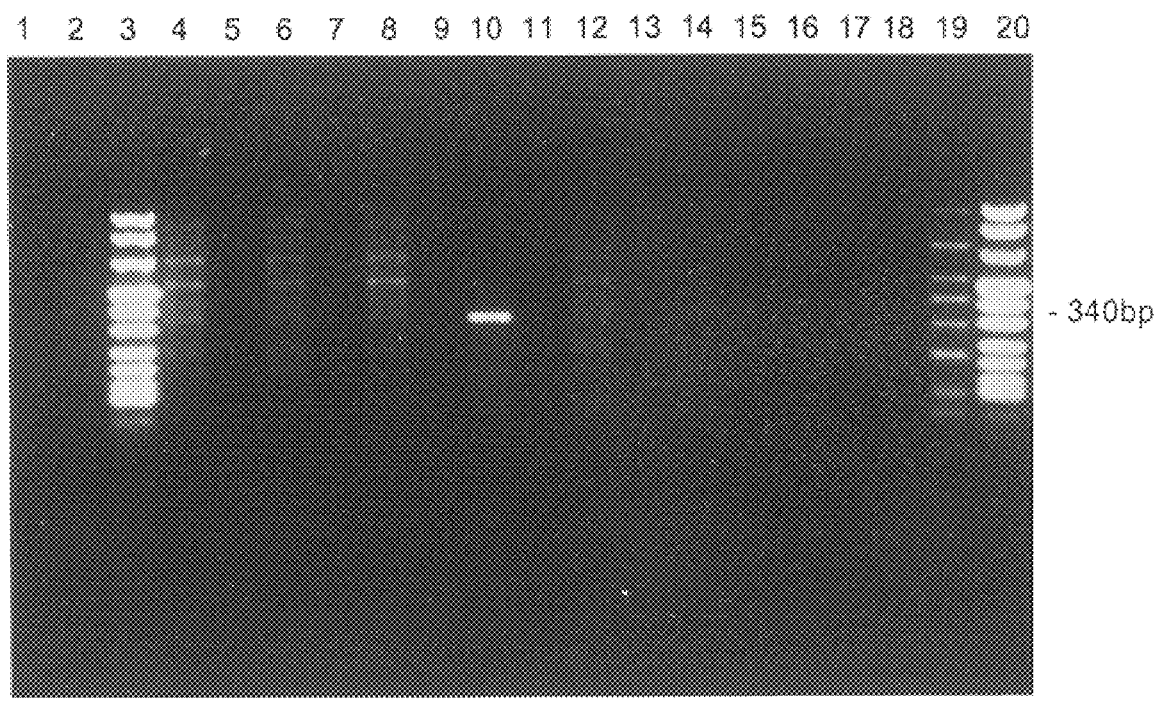
FIG. 19 shows an ethidium bromide stained 1.5% agarose gel of RT-PCR product obtained from normal human serum and pre-inoculation and acute phase tamarin plasmas.
Figure 20:
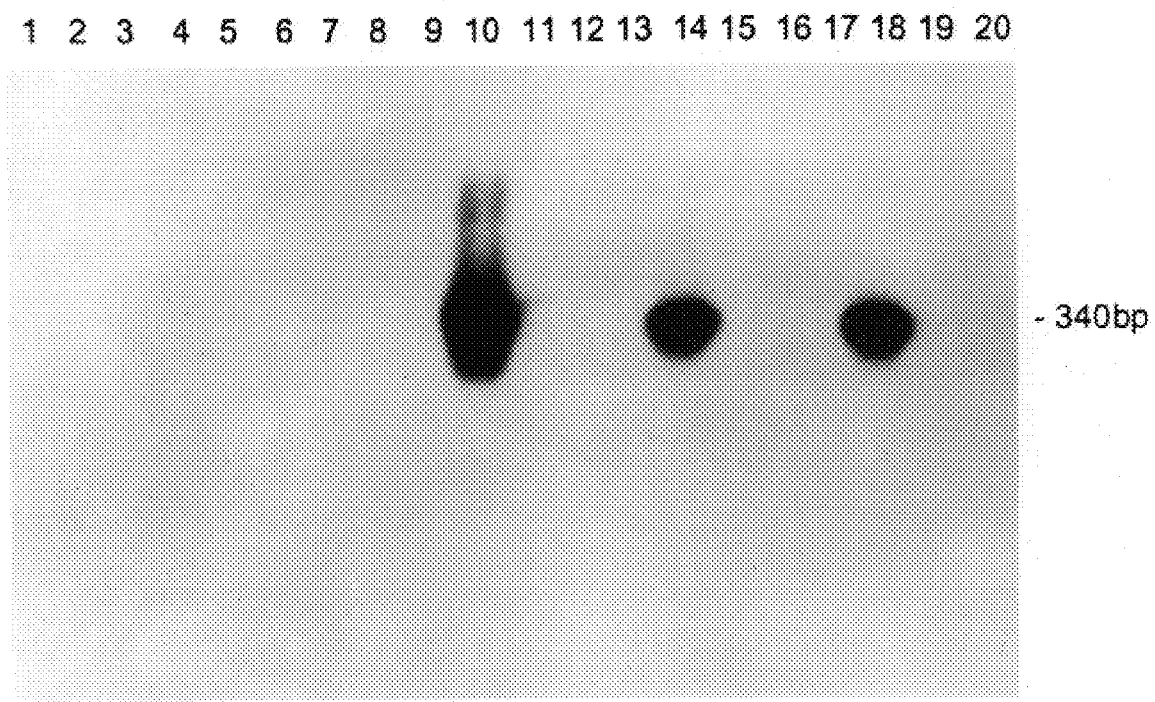
FIG. 20 shows an autoradiogram from a Southern blot of the same gel described in FIG. 19.

FIG. 19 shows an ethidium bromide stained 1.5% agarose gel. FIG. 20 shows an autoradiogram from a Southern blot from the same gel after hybridization to the radiolabeled probe from clone 16 (SEQUENCE I.D. NO. 26). $H_2O$ and normal human serum are shown in lanes 1 and 2. Lanes 3, 19 and 20 are markers. Lanes 4, 8, 12, and 16 are from uninfected tamarin sera while lanes 6, 10, 14 and 18 are from infected tamarin sera. These results show that HGBV clone 16 sequence (SEQUENCE I.D. NO. 26) was detected in other individuals infected with HGBV, in addition to tamarin T-1053, and not in uninfected individuals. Acute phase sera from five H205-infected animals were tested. Clone 16 sequences (SEQUENCE I.D. NO. 26) were detected in sera from three of these animals [lane 10, T-1049, 14 days post-inoculation (dpi); lane 14, T-1051, 28 dpi; lane 18, T-1055, 16 dpi.]. The clone 16 sequence (SEQUENCE I.D. NO. 26) was not detected in pre-inoculation sera from any of the five animals (lane 4, T-1048; lane 8, T1049; lane 12, T-1051; lane 16, T-1055; T-1057 not shown). These results suggest that the clone 16 sequence (SEQUENCE I.D. NO. 26) may be derived from the infectious HGBV agent. The absence of clone 16 sequence (SEQUENCE I.D. NO. 26) in two of five acute phase plasmas (lane 6, T-1048, 28 dpi; T-1057, 14 dpi, not shown) may be explained by the relative low sensitivity of the clone 16 RT-PCR (estimated to be able to detect approximately ≧1000 copies of clone 16 sequence (SEQUENCE I.D. NO. 26) coupled with the acute resolving nature of HGBV infection in tamarins. Thus, the acute plasma from the two negative animals may contain a titer of HGBV that is below the detection level of the RT-PCR assay employed. The observation that these two animals were positive for clone 4 (SEQUENCE I.D. NO. 21) by RT-PCR (Example 14) may reflect the presence of RNA sequences of one virus (containing clone 4) and the absence of detectable RNA sequences from a second virus (containing clone 16).

Example 8

Northern Blot Analysis of HGBV Sequences in Infected Tamarin Liver

Figure 21A:
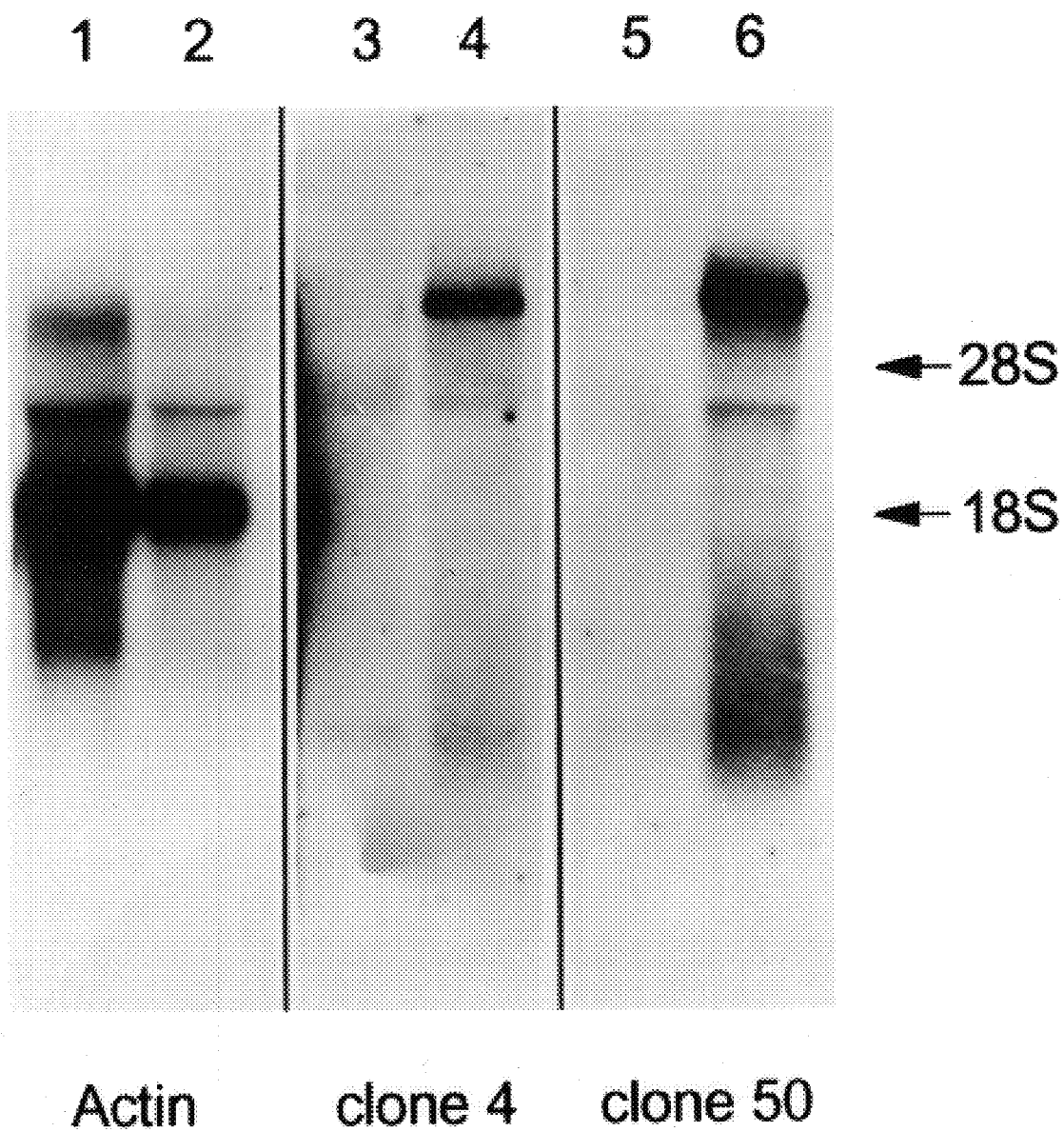
FIGS. 21A and B show autoradiograms from Northern blots of total cellular RNA extracted from the liver of an uninfected tamarin and an HGBV-infected tamarin.

Because the HGBV clone sequences were detectable by RT-PCR in the acute phase tamarin plasma and the H205 inoculum, it was likely that these sequences originate from the HGBV genome. Additional RT-PCR studies demonstrated the presence of the HGBV sequences in liver RNA extracted from the H205-infected tamarin, T-1053 (data not shown). Therefore, to determine the size of the HGBV genome, Northern analysis of H205-infected and uninfected tamarin liver RNA was performed. Total cellular RNA was extracted from 1.25 g liver of H205-infected tamarin T-1053 and from 1.0 g of liver from a control (i.e. uninfected) tamarin T-1040 using an RNA isolation kit (Stratagene, La Jolla, Calif.) as directed by the manufacturer. Total RNA (30 μg) was electrophoresed through a 1% agarose gel containing 0.6 M formaldehyde (R. M. Fourney, et al., *Focus* 10: 5–7, [1988]) and then transferred to Hybond-N nylon membrane (Amersham) by capillary action in 20× SCC (pH 7.0) as previously described. J. Sambrook, et al., *Molecular Cloning—A Laboratory Manual*, 2nd Edition (1989). The RNA was UV-crosslinked to the nylon membrane which was then baked in a vacuum oven at 80° C. for 60 min. The blots were prehybridized at 60° C. for 2 hours in 25 ml of a solution containing 0.05 M PIPES, 50 mM sodium phosphate, 100 mM NaCl, 1 mM EDTA, and 5% SDS. G. D. Virca, et al., *Biotechniques* 8:370–371 (1990). Prior to hybridization with the radiolabeled DNA probe, the solution was removed and 10 ml of fresh solution was added. The probes used for hybridization were clone 4 (SEQUENCE I.D. NO. 21; 221 bp) and clone 50 (SEQUENCE I.D. NO. 29; 337 bp) and the 2000 bp cDNA encoding human β-actin. P. Gunning, et al., *Mol. and Cell. Biol.* 3:787–795 (1983). The probes (50 ng) were radiolabeled using a random primer labeling kit (Stratagene. La Jolla, Calif.) in the presence of [α-$^{32}$P]dATP as directed by the manufacturer. The specific activity of each probe was approximately $10^9$ cpm/μg. The blots were hybridized at 60° C. for 16 hours and washed as described (G. D. Virca, et al., supra) and then exposed to Kodak X-Omat-AR film at −80° C. Photographs of the resulting autoradiographs are shown in FIG. 21A. Lanes 1, 3, and 5 contain liver RNA from T-1040 and lanes 2, 4, and 6 contain liver RNA from T-1053. Lanes 1 and 2 were hybridized with the human β-actin cDNA probe; lanes 3 and 4 were hybridized with the clone 4 probe (SEQUENCE I.D. NO. 21); and lanes 5 and 6 were hybridized with the clone 50 probe (SEQUENCE I.D. NO. 29). Exposure times were as follows: lanes 1 and 2, 5 hours at −80° C.; lanes 3–6, 56 hours at −80° C. The positions of the 28S and 18S ribosomal RNAs are indicated by the arrows. The relative sizes of these ribosomal RNAs are 6333 and 2366 nucleotides, respectively. J. Sambrook, et al., supra.

Clone 4 (SEQUENCE I.D. NO. 21) and clone 50 probes (SEQUENCE I.D. NO. 29) hybridized with an RNA species present in RNA extracted from the liver of the infected tamarin (T-1053) (FIG. 21A, lanes 4 and 6). The size of this hybridizable RNA species was calculated at approximately 8300 nucleotides based on its relative mobility with respect to 28S and 18S ribosomal RNAs. Both probes appear to hybridize to the same RNA species. Neither probe hybridized with RNA extracted from the liver of the uninfected tamarin (T-1040) (FIG. 21A, lanes 3 and 5). These results suggest that the sequences of clones 4 (SEQUENCE I.D. NO. 21) and 50 (SEQUENCE I.D. NO. 29) are present within the same 8.3 Kb transcript.

Figure 21B:
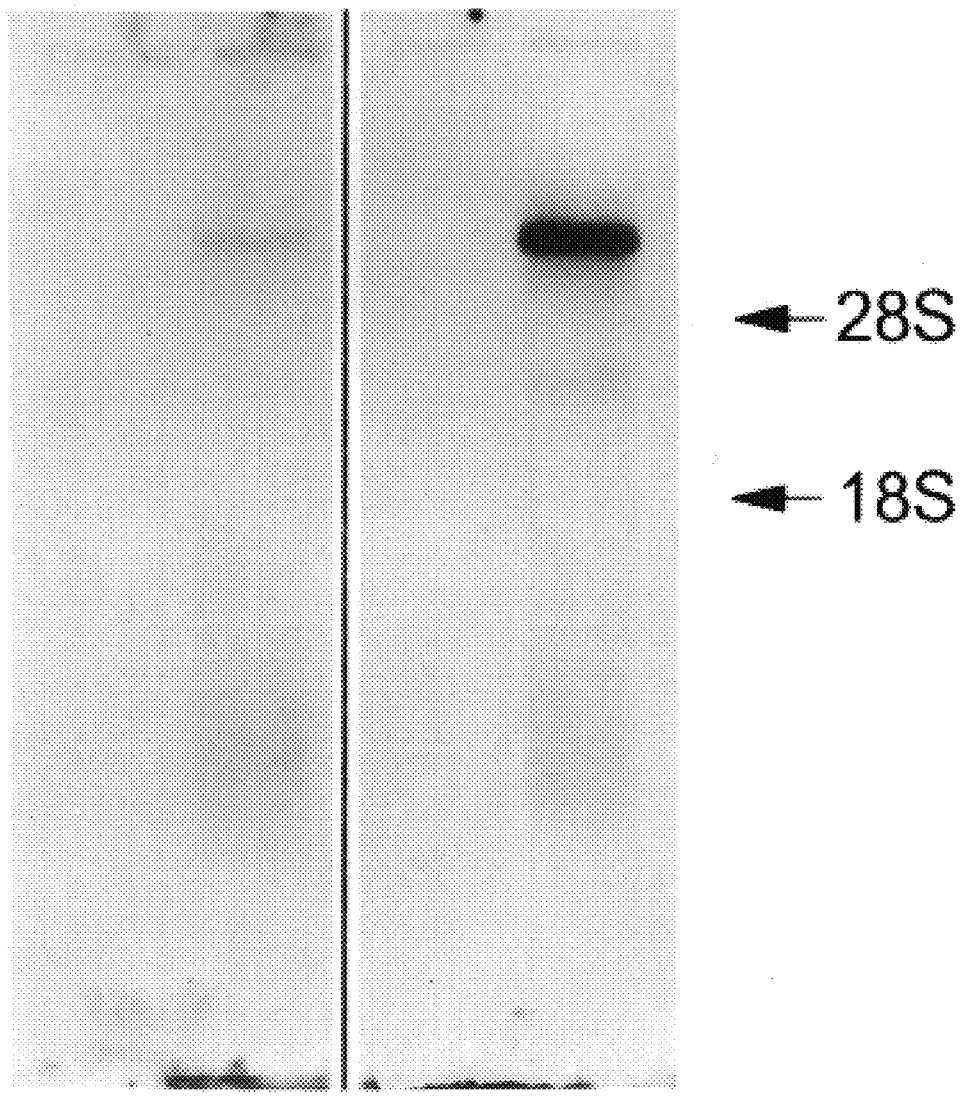

In order to determine the strandedness of the HGBV RNA genome, strand-specific radiolabeled DNA probes were prepared by asymmetric PCR using the GeneAmp® PCR kit from Perkin-Elmer essentially according to the manufacturer's instructions. Purified clone 50 DNA (SEQUENCE I.D. NO. 29) was used as template in separate reactions containing either the clone 50 negative strand-specific primer (SEQUENCE I.D. NO. 99) or the clone 50 positive strand-specific primer (SEQUENCE I.D. NO. 100) at 1 μM final concentrations. The reaction mixture contained [α$^{32}$P-dATP] (Amersham; 3000 Ci/mmol) in place of the dATP normally included in the reaction mixture. Following 30-cycles of linear amplification of the template, the unincorporated [α$^{32}$P-dATP] was removed by Quick-Spin® Sephadex G50 spin columns (Boehringer-Mannheim, Indianapolis, Ind.) according to the manufacturer's instructions. Hybridization of the radiolabeled probes to DNA dot blots containing ten-fold serial dilutions of double-stranded clone 50 DNA (SEQUENCE I.D. NO. 29) demonstrated that the two probes possessed nearly identical sensitivities (data not shown). The radiolabeled probes were then hybridized to RNA blots containing 30 μg of total liver RNA extracted from uninfected tamarin T-1040 and from infected tamarin T-1053 as described above. Photographs of the resulting autoradiographs are shown in FIG. 21B. Lanes 1 and 3 contain liver RNA from T-1040 and lanes 2 and 4 contain liver RNA from T-1053. Lanes 1 and 2 were hybridized with the clone 50 positive strand probe (i.e., the positive strand is radiolabeled and will detect the negative strand; SEQUENCE I.D. NO. 100); lanes 3 and 4 were hybridized with the clone 50 negative strand probe (i.e., the negative strand is radiolabeled and will detect the positive strand; SEQUENCE I.D. NO. 99). The blots were exposed for 18 hours at −80° C. The positions of the 28S and 18S ribosomal RNAs are indicated by the arrows.

As shown in FIG. 21B, the clone 50 positive and negative strand probes (SEQUENCE I.D. NOS. 100 and 99, respectively) hybridized to an RNA species of approximately 8.3 kilobases extracted from the liver of the infected tamarin T-1053 (FIG. 21B, lanes 2 and 4), but not to RNA extracted from the liver of the uninfected tamarin T-1040 (FIG. 21B, lanes 1 and 3). This is consistent with the Northern blot results obtained with the clone 4 (SEQUENCE I.D. NO. 21) and clone 50 (SEQUENCE I.D. NO. 29) double-stranded probes shown above. The more intense signal obtained with the clone 50 negative strand probe (SEQUENCE I.D. NO. 99) (FIG. 21B, lane 4 vs. lane 2) suggests that the predominant RNA species present in the liver of infected tamarins is the positive (i.e. coding) strand.

Example 9

Extending the HGBV Clone Sequence

A. Generation of HGBV Sequences

The clones obtained as described in Example 3 and sequenced as described in Example 5 hereinabove appear to be derived from separate regions of the HGBV genome. Therefore, to obtain sequences from additional regions of the HGBV genome that reside between the previously identified clones, and to confirm the sequence of the RDA clones, several PCR walking experiments were performed.

Total nucleic acids were extracted from 50 μl aliquots of infectious T-1053 plasma as described in Example 3(A). Briefly, precipitated nucleic acids were resuspended in 10 μl DEPC-treated H$_2$O. Standard RT-PCR was performed using the GeneAmp® RNA PCR kit (Perkin Elmer) as directed by the manufacturer. Briefly, PCR was performed on the cDNA products of random primed reverse transcription reactions of the extracted nucleic acids with 2 mM MgCl$_2$ and 1 μM primers. Reactions were subjected to 35 cycles of denaturation-annealing-extension (94° C., 30 sec; 55° C., 30 sec; 72° C. 2 min) followed by a 3 min extension at 72° C. The reactions were held at 4° C. prior to agarose gel analysis. These products were cloned into pT7 Blue T-vector plasmid (Novagen) as described in the art. TABLE 9 presents the results obtained when these reactions were performed.

TABLE 9

| Reaction | Primer 1 | Primer 2 | Product Size |
|---|---|---|---|
| 1.1 | SEQ ID #88 | comp. of SEQ ID #93 | 878 bp |
| 1.2 | comp. of SEQ ID #87 | SEQ ID #97 | 1191 bp |
| 1.3 | SEQ ID #90 | SEQ ID #101 | 864 bp |
| 1.4 | comp. of SEQ ID #99 | comp. of SEQ ID #102 | 1.4 kb |
| 1.5 | SEQ ID #102 | SEQ ID #91 | 672 bp |
| 1.6 | SEQ ID #98 | SEQ ID #99 | 2328 bp |
| 1.7 | comp of SEQ ID #103 | SEQ ID #104 | 1300 bp |
| 1.8 | comp. of SEQ ID #105 | SEQ ID #87 | 900 bp |
| 1.9 | SEQ. ID. #93 | SEQ. ID. #99 | 2323 bp |
| 1.10 | SEQ. ID. #92 | SEQ. ID. #91 | 1216 bp |
| 1.11 | SEQ. ID. #90 | SEQ. ID. #92 | 1570 bp |
| 1.12 | comp. of SEQ ID #106 | SEQ ID #103 | 550 bp |
| 1.13 | comp. of SEQ ID #107 | SEQ ID #108 | 900 bp |
| 1.14 | SEQ ID #107 | comp. of SEQ ID #96 | 1100 bp |
| 1.15 | comp. of SEQ ID #109 | SEQ ID #110 | 410 bp |
| 1.16 | SEQ ID #111 | comp. of SEQ #112 | 600 bp |
| 1.17 | comp. of SEQ ID #113 | SEQ ID #114 | 1000 bp |
| 1.18 | SEQ ID #98 | comp. of SEQ ID #115 | 720 bp |
| 1.19 | comp. of SEQ ID #116 | comp. of SEQ ID #117 | 825 bp |
| 1.20 | SEQ ID #118 | comp. of SEQ ID #119 | 700 bp |
| 1.21 | SEQ ID #120 | SEQ ID #95 | 900 bp |
| 1.22 | SEQ ID #121 | comp. of SEQ ID #122 | 950 bp |
| 1.23 | SEQ ID #123 | SEQ ID #124 | 420 bp |
| 1.24 | SEQ. ID #87 | SEQ. ID #88 | 130 bp |
| 1.25 | SEQ. ID #55 | SEQ. ID #89 | 450 bp |

A modification of a PCR walking technique described by Sorensen et al. (J. Virol. 67:7118–7124 [1993]) was utilized to obtain additional HGBV sequences. Briefly, total nucleic acid were extracted from infectious tamarin T-1053 plasma and reverse transcribed. The resultant cDNAs were amplified in 50 μl PCR reactions (PCR 1) as described by Sorensen et al. (supra) except that 2 mM MgCl$_2$ was used. The reactions were subjected to 35 cycles of denaturation-annealing-extension (94° C., 30 sec; 55° C., 30 sec; 72° C., 2 min) followed by a 3 min extension at 72° C. Biotinylated products were isolated using streptavidin-coated paramagnetic beads (Promega) as described by Sorensen et al. (supra). Nested PCRs (PCR 2) were performed on the streptavidin-purified products as described by Sorensen et al. for a total of 20 to 35 cycles of denaturation-annealing-extension as described above. The resultant products and the PCR primers used to generate them are listed in TABLE 10.

TABLE 10

| Reaction product | Primer set PCR 1 | Primer set PCR 2 | Size of PCR |
|---|---|---|---|
| 2.1 | SEQ ID #103/SEQ ID #125 | SEQ ID #668/SEQ ID #126 | 500 bp |
| 2.2 | SEQ ID #114/SEQ ID #125 | SEQ ID #105/SEQ ID #126 | 1000 bp |
| 2.3 | SEQ ID #92/SEQ ID #125 | SEQ ID #123/SEQ ID #126 | 400 bp |
| 2.4 | SEQ ID #127/SEQ ID #128 | comp. of SEQ ID #88/ SEQ ID #126 | 420 bp |
| 2.5 | SEQ ID #108/SEQ ID #128 | SEQ ID #106/SEQ ID #126 | 900 bp |
| 2.6 | SEQ ID #129/SEQ ID #125 | SEQ ID #98/SEQ ID #126 | 750 bp |
| 2.7 | SEQ ID #116/SEQ ID #128 | SEQ ID #115/SEQ ID #126 | 825 bp |
| 2.8 | SEQ ID #130/SEQ ID #125 | SEQ ID #107/SEQ ID #126 | 630 bp |
| 2.9 | SEQ ID #110/SEQ ID #135 | SEQ ID #131/SEQ ID #126 | 390 bp |
| 2.10 | SEQ ID #132/SEQ ID #125 | SEQ ID #109/SEQ ID #126 | 1000 bp |
| 2.11 | SEQ ID #111/SEQ ID #128 | SEQ ID #133/SEQ ID #126 | 600 bp |
| 2.12 | SEQ ID #134/SEQ ID #135 | SEQ ID #112/SEQ ID #126 | 580 bp |
| 2.13 | SEQ ID #136/SEQ ID #125 | SEQ ID #137/SEQ ID #126 | 400 bp |
| 2.14 | SEQ ID #138/SEQ ID #128 | SEQ ID #113/SEQ ID #126 | 500 bp |
| 2.15 | SEQ ID #139/SEQ ID #128 | SEQ ID #140/SEQ ID #126 | 900 bp |
| 2.16 | SEQ ID #121/SEQ ID #135 | SEQ ID #141/SEQ ID #126 | 400 bp |
| 2.17 | SEQ ID #142/SEQ ID #125 | comp. of SEQ ID #102/ SEQ ID #126 | 1000 bp |
| 2.18 | SEQ ID #143/SEQ ID #135 | SEQ ID #144/SEQ ID#126 | 550 bp |
| 2.19 | SEQ. ID #87/SEQ ID #125 | SEQ. ID #90/SEQ ID #126 | 220 bp |

These products were isolated from low melting point agarose gels and cloned into pT7 Blue T-vector plasmid (Novagen) as described in the art.

RNA ligase-mediated 5' RACE (rapid amplification of cDNA ends) was employed to obtain the 5' end sequences from viral genomic RNAs as described hereinabove. Briefly, the 5' AmpliFINDER™ RACE kit (Clontech, Palo Alto, Calif.) was used as directed by the manufacturer. The source of the viral RNA was acute phase T-1053 plasma that was extracted as described above. The virus-specific oligonucleotides utilized for the reverse transcription (RT), the first PCR amplification (PCR 1) and the second PCR amplification (PCR 2) are listed in TABLE 11. The ligated anchor primer and its complementary PCR primer were provided by the manufacturer. PCRs were performed with the Gene-Amp® PCR kit (Perkin Elmer) as directed by the manufacturer.

TABLE 11

| Reaction product | RT primer | PCR 1 primer | PCR 2 primer | Size of PCR 2 |
|---|---|---|---|---|
| 3.1 | SEQ ID #145 | SEQ ID #146 | SEQ ID #147 | 190 bp |
| 3.2 | SEQ ID #148 | SEQ ID #149 | SEQ ID #150 | 620 bp |

The products generated by RNA ligase-mediated 5' RACE were isolated from low melting point agarose gels and cloned into pT7 Blue T-vector plasmid (Novagen) as described in the art.

To obtain additional sequence at the 5' and 3' ends of HGBV-B SEQUENCE (see below, *Evidence for the existence of two HCV-like flaviviruses in HGBV*), an RNA circularization experiment was performed. (This method is based on that described by C. W. Mandl et al. (1991) *Biotechniques*, Vol. 10 (4): 485–486.) Total nucleic acids were purified from 50 μl of T-1057 plasma (14 days post H205 inoculation except that 1 μg glycogen replaced the tRNA in the precipitation. The nucleic acid pellet was dissolved in 16.3 μl of DEPC-treated water, and 25 μl of 2× TAP buffer (1×=50 mM NaOAC, pH 5.0, 1 mM EDTA, 10 mM 2-mercaptoethanol, 2 mM ATP) and 8.7 μl of tobacco acid pyrophophatase (20 Units; Sigma) were added. The mixture was incubated at 37° C. for 60 min. The sample was extracted with phenol (water-saturated) followed by chloroform and then precipitated with NaOAC/EtOH in the presence of glycogen (1 μg). The pellet was dissolved in 83 μl of DEPC water and 10 μl of 10× RNA ligase buffer (New England Biolabs, NEB), 2 μl of RNase inhibitor (Perkin Elmer), and 5 μl of T4 RNA ligase (NEB) was then added. The mixture was incubated at 4° C. for 16 hours. The sample was then extracted with phenol (water-saturated) and then chloroform as before and then precipitated with NaOAC/EtOH.

One-tenth of the ligated RNA was used in the reverse transcriptase (RT) reaction using Superscript RT (GIBCO/BRL) and SEQUENCE ID. NO. 146 as the primer as directed by the manufacturer. One-half of the RT reaction mix was used for PCR1 in the presence of a biotinylated oligonucleotide primer (SEQUENCE ID. NO.146) and a second oligonucleotide primer (SEQUENCE ID. NO.133) as described above. PCR1 products were purified from the reaction mixture using streptavidin-magnetic beads as described by Sorensen et al. Purified PCR1 products (2 μl out of 30 μl) were used as the template for PCR2. PCR2 using oligonucleotide primers (SEQUENCE ID. NOS. 147 and 154) yielded a 1200 bp product that was cloned into pT7 Blue T-vector plasmid and sequenced as described below. Sequence analysis of two independent clones from this experiment demonstrated 100% identity in the region of overlap with known sequence (although one clone possessed a sequence of 18 T residues and the other a sequence of 27 T residues), and an additional 270 bases of new sequence.

The above circularization experiment provided sequence from both the 5'- and 3'-ends of the HGBV-B viral genome that was not obtained using standard 3'- or 5'-RACE techniques. However, the exact 5'-3' junction is difficult to determine even after additional PCR experiments are performed using primers designed from the newly obtained sequence. Thus, in order to better characterize the 5'-end of the HGBV-B RNA genome a primer extension experiment was performed using RNA isolated from the liver of T-1053.

Total cellular RNA was isolated from the liver of T-1053 and a control (i.e. uninfected) animal (T-1040) as described in Example 7. An antisense oligonucleotide (SEQUENCE I.D. NO. 155) was endlabeled with γ-$^{32}$P-ATP using T4 polynucleotide kinase (NEB) to a specific activity of approximately $9.39\times10^7$ CPM/μg as described (Sambrook et al.). The primer was annealed to 30 μg of T-1053 and T-1040 liver RNA in separate reactions and then extended using MMLV reverse transcriptase (Perkin-Elmer) as previously described (Sambrook et al). The products were analyzed on a 6% sequencing gel. A sequence ladder generated from one of the HGBV-B circularization clones using the same primer as that utilized for the primer extension served as a size standard.

Primer extension products of 176 bp were obtained from T-1053. These products were not obtained when primer extension was performed using liver RNA from an uninfected animal (T-1040) and therefore represent products derived from the HGBV-B genome. The length of the products obtained indicate that the 5'-end of the genome, as present in the liver of infected animals, is located 442 nucleotides upstream of the initiator AUG codon.

To confirm the 3' location of the sequence obtained in the circularization experiment, RT-PCRs were performed using primers designed to the predicted 3' termini (see reaction 1.25, TABLE 2). RT-PCR of infectious T-1053 plasma as (described above) using SEQUENCE ID. NOS. 156 and SEQUENCE ID. NO. 157 yielded a product of 450 bp. In contrast, RT-PCR using the complement of SEQUENCE ID. NO. 157 and SEQUENCE ID. NO. 147 did not yield a detectable PCR product (data not shown). These data suggest that the 3' end of the genome is located 50 nucleotides downstream of the poly T tract.

Figure 22:
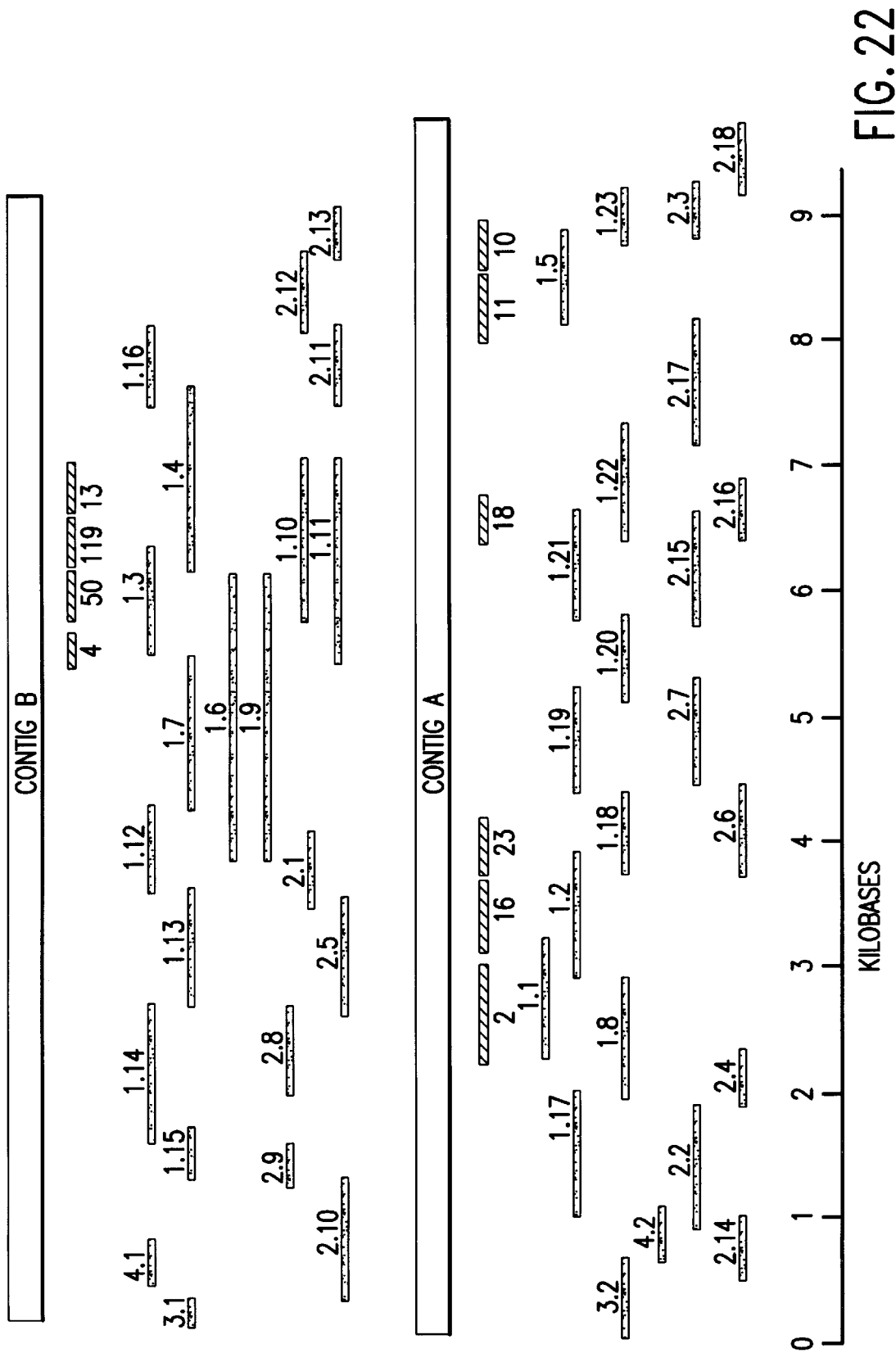
FIG. 22 shows a diagram that demonstrates each of the recombinant polynucleotide isolates are present on contiguous RNA species.

The cloned products from TABLES 9, 10 and 11, and the RNA circularization experiment were sequenced as previously described in Example 5. Interestingly, the cloned products of reactions 1.4, 1.6, 1.9, 1.10 and 1.11 were found to contain only one of the two primer sequences at the termini, suggesting that these products were the result of false priming events. PCR/sequencing experiments have linked sequences detected in products 1.4, 1.6, 1.9, 1.10 and 1.11 with clone 4 (SEQUENCE I.D. NO. 21) and/or clone 50 (SEQUENCE I.D. NO. 29). In addition, sequences derived from each of these reactions contain limited HCV identity. Thus, these products, although a result of false priming at one end of the PCR product, appear to contain authentic HGBV sequence. The product from reaction 1.14 also appeared to be a result of false priming. Here, the complement of SEQUENCE I.D. NO. 160 is found at the 5' end of the product from reaction 1.14 (GB-B, FIG. 22). This was unexpected because SEQUENCE I.D. NO. 160 was derived from SEQUENCE I.D. NO. 161 which resides in GB-A. However, the sequence identity between products from reactions 1.14 and 2.8, together with additional PCRs/sequencing experiments (data not shown), demonstrate that reaction 1.14 contains authentic HGBV sequence. Apparently, the complement of SEQUENCE I.D. NO. 160 had enough identity to GB-B sequences upstream of SEQUENCE I.D. NO. 162 to act as a PCR primer.

The sequences obtained from the products described in TABLES 9, 10 and 11 hereinabove, and the RNA circularization experiment were assembled into contigs using the GCG Package (version 7) of programs. A schematic of the assembled contigs is presented in FIG. 22). GB contig A (GB-A) is 9493 bp in length, all of which has been sequenced and is presented in SEQUENCE I.D. NO. 163. GB-A includes clones 2 (SEQUENCE I.D. NO. 22), 16 (SEQUENCE I.D. NO. 26), 23 (SEQUENCE I.D. NO. 28), 18 (SEQUENCE I.D. NO. 27), 11 (SEQUENCE I.D. NO. 24) and 10 (SEQUENCE I.D. NO. 23). SEQUENCE I.D. NO. 163 was translated into three possible reading frames and is presented in the Sequence Listing as SEQUENCE I.D. NOS. 165–389. GB contig B (GB-B) is 9143 bp and is presented in SEQUENCE I.D. NO. 390. GB-B (SEQUENCE I.D. NO. 390) includes clones 4 (SEQUENCE I.D. NO. 21), 50 (SEQUENCE I.D. NO. 29), 119 (SEQUENCE I.D. NO. 30) and 13 (SEQUENCE I.D. NO. 25). SEQUENCE I.D. NO. 390 was translated into one open reading frame and is presented in the Sequence Listing as SEQUENCE I.D. 393 and 394. The UTRs from the 5' and the 3' ends can each be translated into six reading frames.

B. Evidence for the Existence of Two HCV-Like Viruses in HGBV

1. Evidence for GB-A and GB-B Representing Two Distinct RNA Species

Figure 23A:
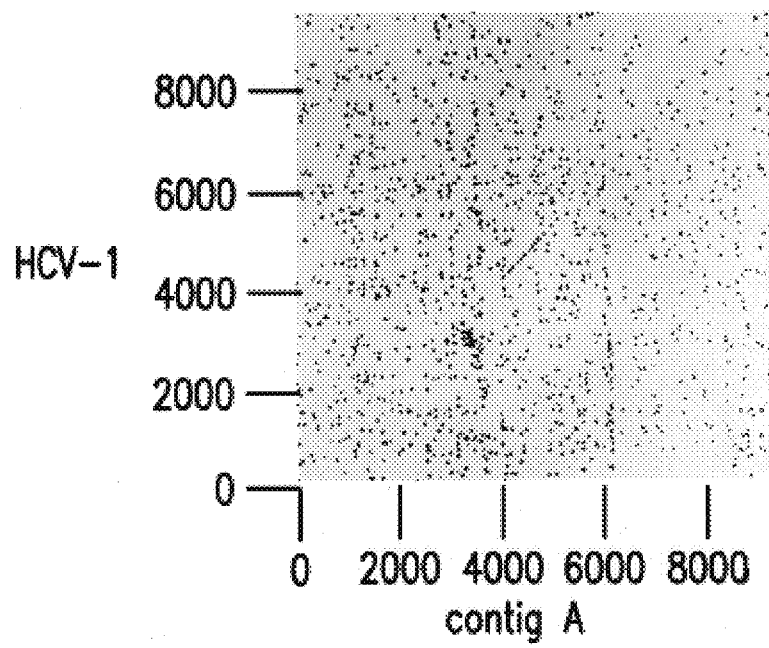
Figure 23B:
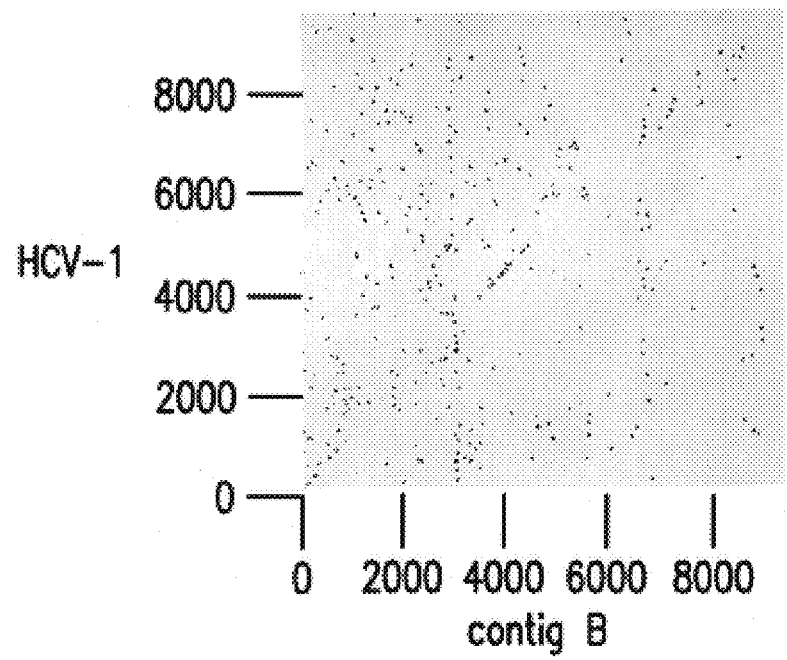
Figure 23C:
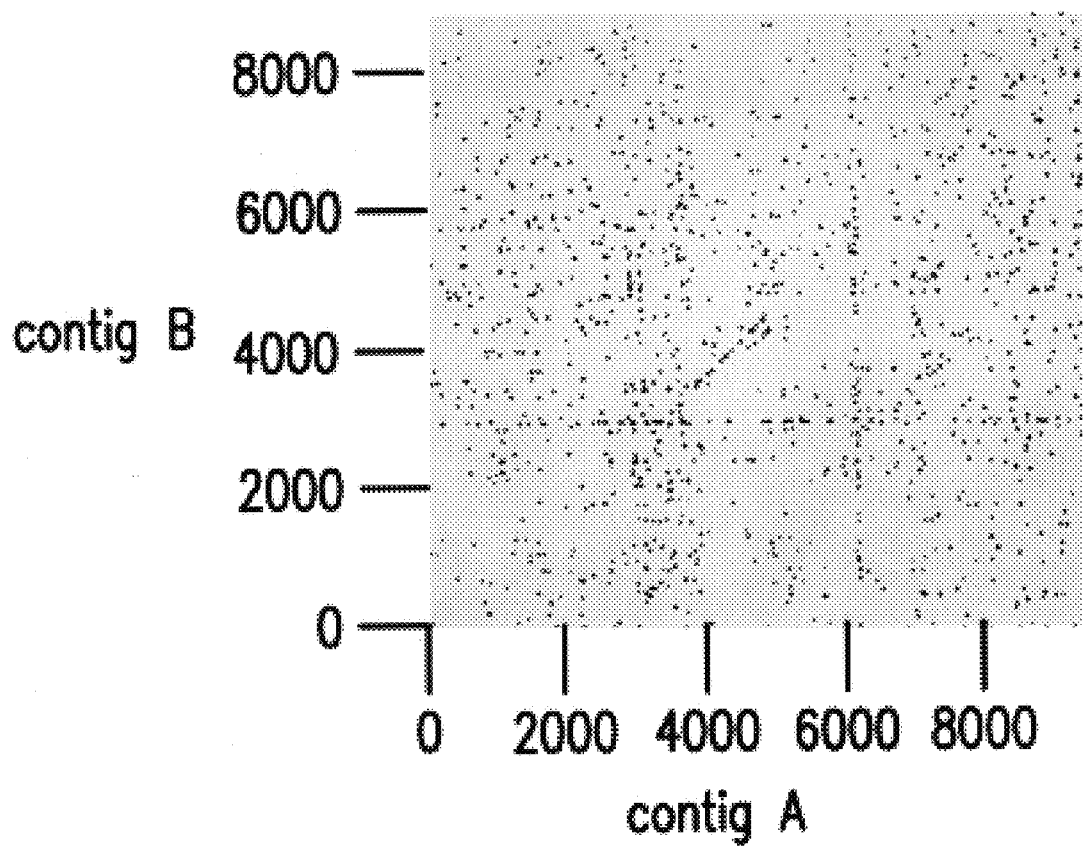

Comparison of GB-A (SEQUENCE I.D. NO. 163) GB-B (SEQUENCE I.D. NO. 390) and HCV-1 (GenBank accession # M67463) demonstrate that GB-A (SEQUENCE I.D. NO. 163), GB-B (SEQUENCE I.D. NO. 390) and HCV-1 are all distinct sequences. Dot plot analyses of the nucleic acid sequences of GB-A (SEQUENCE I.D. NO. 163), GB-B (SEQUENCE I.D. NO. 390) and HCV-1 were performed using the GCG Package (version 7). Using a window size of 21 and a stringency of 14, GB-A (SEQUENCE I.D. NO. 163), GB-B (SEQUENCE I.D. NO. 390) and HCV-1 were found to clearly contain different nucleotide sequences (FIG. 23). Therefore, GB-A (SEQUENCE I.D. NO. 163) and GB-B (SEQUENCE I.D. NO. 390) do not represent different strains or genotypes of HCV or of each other. Short regions of limited nucleotide identity are found in the putative NS3-like and NS5b-like sequences of GB-A (SEQ. ID. NO. 163) and GB-B (SEQ. ID. NO. 390) and the NS3 and NS5b sequences of HCV by this analysis. However, nucleotide identity in these regions is not surprising because NS3 and NS5b code for the putative NTP-binding helicase and the RNA-dependent RNA polymerase, respectively, which are conserved in all flaviviruses (see below). That GB-A (SEQUENCE I.D. NO. 163) and GB-B (SEQUENCE I.D. NO. 390) represent separate RNA molecules and not different regions of the same RNA molecule is evidenced by the 5' RACE experiments (above) and supported by the Northern blot data (as described in Example 8. First, the 5' RACE experiments show distinct 5' ends for GB-A (SEQUENCE I.D. NO. 163) and GB-B (SEQUENCE I.D. NO. 390). Because RNA molecules can contain only one 5' end, GB-A (SEQUENCE I.D. NO. 163) and GB-B (SEQUENCE I.D. NO. 390) represent separate RNA molecules. Second, the 8300 base RNA molecule detected in infected tamarin liver RNA by probing Northern blots with clones 4 and 50 (SEQUENCE I.D. NOS. 21 and 29, respectively), both from GB-B [SEQUENCE I.D. NO. 390], see Example 8, corresponds closely to the size of GB-B (SEQUENCE I.D. NO. 390, 9143 bp). If GB-A and GB-B were part of the same RNA molecule, one would expect a Northern blot product of at least 17,000 bases. These data demonstrate that GB-A (SEQUENCE I.D. NO. 163) and GB-B (SEQUENCE I.D. NO. 390) represent the nucleotide sequences of two distinct RNA molecules that are not variants of HCV or each other.

Northern blot analysis and PCR studies of T-1053 provided evidence that the two RNA species corresponding to GB-A (SEQUENCE I.D. NO. 163) and GB-B (SEQUENCE I.D. NO. 390) were not at equivalent levels in the liver. As stated above, clones 4 and 50 (SEQUENCE I.D. NOS. 21 and 29, respectively), both from the GB-B (SEQUENCE I.D. NO. 390), hybridized to an 8.3 kb RNA species present in infected liver of T-1053 (as described in Example 8). In contrast, clones 2 (SEQUENCE I.D. NO. 22), 10 (SEQUENCE I.D. NO. 23), 16 (SEQUENCE I.D. NO. 26 and 23 (SEQUENCE I.D. NO. 28), all from GB-A (SEQUENCE ID. NO. 163), showed no hybridization with T-1053 liver RNA in identical experiments (data not shown). In addition, clone 16 PCR generated much less product than clone 4 PCR on cDNAs generated from T-1053 liver RNA by ethidium staining, despite equivalent sensitivities of clone 4 and clone 16 PCRs demonstrated using plasmid templates (data not shown). This is in contrast to what is found in T-1053 plasma at the time of sacrifice. PCR titration experiments for clone 4 (GB-B-specific, SEQUENCE I.D.

NO. 390) and clone 16 (GB-A-specific, SEQUENCE I.D. NO. 163) PCR on cDNAs generated from T-1053 plasma RNA suggest that equivalent amounts of GB-A (SEQUENCE I.D. NO. 163) RNA and GB-B (SEQUENCE I.D. NO. 390) RNA are present in T-1053 plasma (Example 4, E.2). Thus, although GB-A (SEQUENCE I.D. NO. 163) RNA and GB-B (SEQUENCE I.D. NO. 390) RNA were at equivalent levels in T-1053 plasma, there appeared to be a greater amount of GB-B (SEQUENCE I.D. NO. 390) RNA relative to GB-A (SEQUENCE I.D. NO. 163) RNA present in T-1053 liver at the time of sacrifice. Together, these results provide further evidence for the existence of two different RNA molecules corresponding to GB-A (SEQUENCE I.D. NO. 163) and GB-B (SEQUENCE I.D. NO. 390) in T-1053 plasma and suggest that these RNAs are not necessarily present at equivalent levels in infected liver RNA. Therefore, it is unlikely that GB-A (SEQUENCE I.D. NO. 163) and GB-B (SEQUENCE I.D. NO. 390) make up individual segments of a single viral genome.

2. Evidence that GB-A (SEQUENCE I.D. NO. 163) and GB-B (SEQUENCE I.D. NO. 390) Represent the Genomes of Two Distinct Viruses Infectivity and PCR studies provide evidence for the viral nature of GB-A (SEQUENCE I.D. NO. 163) and B (SEQUENCE I.D. NO. 390). Specifically, tamarins T-1049 and T-1051 which were inoculated with T-1053 plasma that had been filtered (0.1 μm) and diluted to $10^{-4}$, or unfiltered and diluted to $10^{-5}$, respectively, were positive for both clone 4 (GB-B [SEQUENCE I.D. NO. 390) and clone 16 (GB-A [SEQUENCE I.D. NO. 163]) sequences. Prior to inoculation, both of these animals were negative for clones 4 and 16 (Examples 4, E.4 and 4, E.5). Therefore, the two RNA species present in the acute phase T-1053 plasma corresponding to GB-A and GB-B can be filtered, diluted and passaged to other animals consistent with the proposed viral nature of GB-A (SEQUENCE I.D. NO. 163) and GB-B (SEQUENCE I.D. NO. 390). That GB-A and GB-B represent RNA molecules from separate viral particles is evidenced by PCR studies of the H205-inoculated tamarins. Specifically, four of four tamarins became positive for clone 4 (GB-B [SEQUENCE I.D. NO. 390]) by RT-PCR after H205 inoculation. In contrast, only one of 4 H205-inoculated tamarins (T-1053) became positive for clone 16 (GB-A [SEQUENCE I.D. NO. 163]) by RT-PCR (Example 4.E.2). Therefore, assuming that GB-A (SEQUENCE I.D. NO. 163) sequences were truly absent from T-1048, T-1057 and T-1061, and that the negative clone 16 PCR results were not due to poor sensitivity, it would appear that the virus corresponding to GB-B (SEQUENCE I.D. NO. 390) sequences (i.e. hepatitis GB virus B [HGBV-B]) can be passaged independent of GB-A (SEQUENCE I.D. NO. 163) sequences. An HGBV-B only sample from T-1057 has been passaged two additional times (Example 4). GB-A (SEQUENCE I.D. NO. 163) sequences have not been detected in these animals by RT-PCR. In addition, significant liver enzyme elevations have been noted in these animals (Example 4), demonstrating that HGBV-B alone caused hepatitis in tamarins. GB-A (SEQUENCE I.D. NO. 163) sequences have been identified in tamarins lacking detectable GB-B (SEQUENCE I.D. NO. 390) sequences. Specifically, GB-B only animals (T-1048, T-1057 and T-1061) challenged with T-1053 plasma developed GB-A (SEQUENCE I.D. NO. 163) only viremias as detected by clone 16 specific RT-PCR. The GB-A only plasma from T-1057 has been passaged one additional time (Example 4). Thus, it appears that a virus corresponding to GB-A (SEQUENCE I.D. NO. 163) sequences (hepatitis GB virus A [HGBV-A]) can replicate independent of HGBV-B. Additional passages of HGBV-A in the absence of HGBV-B is ongoing. At this time it is not known whether HGBV-A causes hepatitis in tamarins. However, the lack of elevated liver enzymes noted in the T-1053 challenged tamarins with HGBV-A viremias and in the passage of the HGBV-A only serum from T-1057 argue against the hepatotropic nature of HGBV-B in tamarins.

The presence of two viruses in acute phase T-1053 plasma can be traced back to the H205 inoculum. Specifically, data from Example 7 showed that clone 16 (SEQUENCE I.D. NO. 26, found in GB-A [SEQUENCE I.D. NO. 163]) was absent in the preinoculation plasma from all 7 tamarins tested. In addition, clones 2, 10, 18 and 23 (SEQUENCE I.D. NOS. 22, 23, 27 and 28, respectively, all from GB-A [SEQUENCE I.D. NO. 163]) have not been detected in any pre-HGBV-inoculated tamarin plasma tested (Example 7. Similar negative results were found when preinoculation tamarin plasma were tested for clones 4 and 50 (SEQUENCE I.D. NOS. 21 and 29, respectively, all from GB-B [SEQUENCE I.D. NO. 390]). Thus, both HGBV-A and HGBV-B were absent in the preinoculation tamarin plasma. In contrast, all of these clones (i.e. clones 2, 10, 16, 18 and 23 from GB-A [SEQUENCE I.D. NO. 163], and clones 4 and 50 from GB-B [SEQUENCE I.D. NO. 390]) were detected in the H205 inoculum (TABLE 7). Interestingly, as found in cDNA made from T-1053 liver (above), several different PCR targets in GB-A (SEQUENCE I.D. NO. 163) all generated less product than similar PCR targets in GB-B (SEQUENCE I.D. NO. 390) using the same random primed cDNAs from H205 (data not shown). Thus, we conclude that HGBV-A and HGBV-B are present in the original GB inoculum, H205. However, HGBV-B appears to be more abundant than HGBV-A in H205. The low relative amount of HGBV-A in the H205 inoculum may explain why only one of four tamarins were positive for the HGBV-A after H205 inoculation (Example 4.E.2).

3. Evidence That HGBV-A and HGBV-B are Members of the Flaviviridae

Searches of the SWISS-PROT database with the three frame translation products of GB-A (SEQUENCE I.D. NO. 164–396) and GB-B (SEQUENCE I.D. NO. 394) as described in Example 5 show limited, but significant amino acid sequence identity with various strains of HCV. Translation products from GB-A (SEQUENCE I.D. NO. 163) and GB-B (SEQUENCE I.D. NO. 390) show the closest homology to regions of the nonstructural proteins of various HCV isolates (i.e. NS2, NS3, NS4 and NS5). For example, as shown in FIG. 24, the conserved residues (indicated by *) in the putative NTP-binding helicase domain of flaviviruses (FIG. 24A) and in the RNA-dependent RNA polymerase domain of all viral RNA-dependent RNA polymerases (FIG. 24B) are held in common between HCV-1 NS3 and NS5b (SWISS-PROT accession number p26664), respectively, and the predicted translation products of GB-A (SEQUENCE I.D. NO. 390) and GB-B (SEQUENCE I.D. NO. 397). (See Choo et al., *PNAS* 88:2451–2455 [1991] and Domier et al., *Virology* 158:20–27 [1987]). Therefore, it appears that both GB-A virus and GB-B virus encode functional NTP-binding helicases and RNA-dependent RNA polymerases. However, GB-A (SEQUENCE I.D. NO. 390) and GB-B (SEQUENCE I.D. NO. 394) do not share complete amino acid identity to each other and/or to HCV in other regions of HCV NS3 and NS5b. Specifically, over the 200 residue region of NS3 shown in FIG. 24A, GB-A (SEQUENCE I.D. NO. 390, residues 1252–1449) virus and HCV-1 (SEQ. ID. NO. 395), GB-B (SEQUENCE I.D. NO. 397, residues 1212–1408) virus and HCV-1 (SEQUENCE I.D. NO. 395), and GB-A (SEQUENCE I.D. NO. 390, residues 1252–1449) virus and GB-B (SEQUENCE I.D. NO. 394, residues 1212–1408) virus are 47%, 55% and 43.5% identical, respectively. In addition, over the 100 residue region of NS5b shown in FIG. 24B, GB-A (SEQUENCE I.D. NO. 390, residues 2644–2739) virus and HCV-1 (SEQUENCE I.D. NO. 395), GB-B (SEQUENCE I.D. NO. 394, residues 2513–1612) virus and HCV-1 (SEQUENCE I.D. NO. 395), and GB-A (SEQUENCE I.D. NO. 390, residues 2644–2739) virus and GB-B (SEQUENCE I.D. NO. 394, residues 2599–2698) virus are 36%, 41% and 44% identical, respectively. Lower levels of homology are found in other putative nonstructural genes of GB-A (SEQUENCE I.D. NO. 390) and GB-B (SEQUENCE I.D. NO. 394) when compared to HCV. The overall level of homology of the putative nonstructural proteins of GB-A virus and GB-B virus compared with HCV sequences present in GenBank suggests that both GB-A (SEQUENCE I.D. NO. 163) and GB-B (SEQUENCE I.D. NO. 390) are derived from two separate members of the Flaviviridae. Flaviviruses contain a single genomic RNA molecule which code for one NTP-binding helicase domain and one RNA-dependent RNA polymerase domain. The presence of two contigs, each containing a putative RNA helicase domain and a putative RNA-dependent RNA polymerase is consistent with the presence of two HCV-like flaviviruses in the acute phase T-1053 plasma.

Example 10

PCR

In order to determine the sequence relatedness of HGBV to hepatitis C virus the following PCR-based experiment was performed. PCR primers based on the 5'-untranslated region (UTR) sequence of the HCV genome (J. H. Han, *PNAS* 88:1711–1715 [1991]), which are highly conserved in HCV isolates from a variety of geographic origins (Cha, T.-A., et al., *J. Clin. Microbiol.* 29:2528–2534 [1991]) were utilized in attempts to detect similar sequences in H205-infected tamarin T-1053 liver RNA. Total cellular RNA was extracted from the liver of infected tamarin T1053 and from the liver of an uninfected tamarin (T-1040) as described in Example 8A. Thirty micrograms of each RNA sample was reverse transcribed and PCR amplified using a kit available from Perkin-Elmer essentially as described in the manufacturer's instructions. An antisense primer (primer 1) was used for the reverse transcriptase reaction and comprised bases 249–268 of the HCV 5'-UTR. Primer 1 and a primer comprising bases 13–46 of the HCV 5'-UTR (primer 2) were then used for PCR amplification of the intervening sequence. The conditions used for thermocycling were essentially as described by Cha et al., supra.

In order to increase the sensitivity of this assay for the detection of HCV 5'-UTR sequences in H205 infected tamarin T-1053, the above PCR reaction was subjected to a second amplification reaction which utilized "nested" PCR primers. These primers are derived from sequences found internal to the sequences of primers 1 and 2 above in the HCV 5'-UTR: Primer 3 comprised sequences from 47–69 and primer 4, an antisense primer, comprised bases 188–210 of the HCV 5'-UTR. In this "nested" PCR reaction, PCR products (2 μl out of a total of 100 μl reaction volume) from the first PCR reaction were used as the source of DNA template. The thermocycling parameters were essentially the same as described above except that the annealing temperature was 55° C. instead of 60° C. The resulting PCR products from the second PCR reaction were then analyzed for the expected DNA products by agarose gel electrophoresis and ethidium bromide staining. The expected DNA fragment sizes, based on the sequence of the HCV 5'UTR (Han et al., supra) is 253 bp for the product of the first PCR reaction and 163 bp for the product of the nested PCR reaction. PCR products of the anticipated size were obtained in control experiments performed using 30 μg of total cellular RNA extracted form the liver of an HCV infected chimpanzee as described in Example 8A (data not shown), thus demonstrating that this experimental procedure was able to detect the 5-UTR of HCV. However, neither of the expected products were observed on the resulting ethidium bromide stained agarose gel when either T-1053 liver RNA or T-1040 liver RNA were used (data not shown). This inability to produce the predicted result may suggest that (i) the sequence of the 5'-UTR of the agent differs significantly from that of HCV such that the oligonucleotide primers used would not be able to anneal efficiently thereby disallowing PCR amplification from occurring or (ii) the agent lacks a 5'-UTR. In either case it appears from these results that the nucleotide sequence of the agent is significantly different from that of HCV.

In addition, nucleic acids were isolated as in Example 7 from a chimpanzee plasma pool obtained during the acute phase of an experimental infection of HCV (G. Schlauder et al., *J. Clin. Microbiology* 29:2175–2179 [1991]). RT-PCR was performed as described in Example 7 using clone 16 primers (SEQUENCE I.D. NOS. 93 and 94). No bands of the expected size for these primers were detected by ethidium bromide staining or after hybridization to a clone 16 specific probe (data not shown). These results support the unrelatedness of clone 16 sequence (SEQUENCE I.D. NO. 26) to HCV.

Example 11

Reactivity of HGBV Infected Serum to Other Hepatitis Viruses

Serum specimens were obtained prior to, and after, inoculation with HGBV using either the H205 inoculum (T-1048, T-1057, T-1061) or the T-1053 inoculum (T-1051) and tested for antibodies frequently detected following exposure to known hepatitis viruses. Specimens were tested for antibodies to hepatitis A virus (using the HAVAB assay, available from Abbott Laboratories, Abbott Park, Ill.), the core protein of hepatitis B core (using the Corzyme® test available from Abbott Laboratories, Abbott Park, Ill.), hepatitis E virus (HEV) (using the HEV EIA,-available from Abbott Laboratories, Abbott Park, Ill.) and hepatitis C virus (HCV) (utilizing HCV second generation test, available from Abbott Laboratories, Abbott Park, Ill.). These tests were performed according to the manufacturer's package inserts.

None of the tamarins tested positive for antibodies to HCV or to HEV either prior to or after HGBV inoculation (see TABLE 12). Therefore, HGBV infection does not elicit detectable antisera against HCV or HEV.

One of the tamarins (T-1061) was positive for antibodies to HAV prior to and after inoculation with HGBV, suggesting a previous exposure to HAV (TABLE 9, T-1061). However, the three remaining tamarins (T-1048, T-1057 and T-1051) show no HAV-specific antibodies after HGBV inoculation. Therefore, HGBV infection does not elicit an anti-HAV response. One of the tamarins (T-1048) was negative for antibodies to HBV core both prior to and after inoculation with HGBV. Two of the tamarins (T-1061 and T-1057) were positive prior to inoculation with HGBV. One of the tamarins (T-1051) was borderline positive for antibodies to HBV prior to inoculation, but was negative after inoculation. Based on these data, there is no evidence that infection with the HGBV agent induces an immune response to HBV core. Taken together, these data support that the HGBV agent is a unique viral agent, and is not related to any of the viral agents commonly associated with hepatitis in man.

Example 12

Western Blot Analysis of HGBV Infected Liver

As noted in Examples 1 and 2 above, elevated liver enzyme values are noted in tamarins inoculated with HGBV. If HGBV is indeed a hepatotropic virus, it would be expected that viral protein(s) would be produced in infected liver cells, and that an immune response to those proteins would be generated. In this example, evidence is presented which suggests that a unique protein appears in livers obtained from HGBV-infected tamarins; this protein appears to be specifically recognized via Western blot utilizing tamarin serum obtained in the convalescent stage following infection with HGBV.

HGBV-infected tamarin livers and various control tamarin and chimpanzee livers were diced and homogenized in PBS (approximately 1 g liver to 5 ml) using a Omni-mixer homogenizer. The resulting suspension was clarified by centrifugation (10,000×g, 1 hour, 4° C.) and by microfiltration through 5 µm, 0.8 µm and 0.45 µm filters. The clarified homogenate was centrifuged under conditions pelleting all components of 100S or greater. Pellets (100S liver fractions) were taken up in a small volume of buffer and stored at −70° C.

SDS polyacrylamide gel electrophoresis (PAGE) was carried out using standard methods and reagents (Laemmli discontinuous gels). 100S liver fractions were diluted 1:20 in a sample buffer containing SDS and 2-mercaptoethanol and heated at 95° C. for 5 minutes. The proteins were electrophoresed through either 12% acrylamide or 4–15% acrylamide linear gradient gels, 7 cm×8 cm, at 200 volts for 30 to 45 minutes. Proteins were electro-transferred to nitrocellulose membranes using standard methods and reagents.

Western blots were developed using standard methods. Briefly, the nitrocellulose membrane was briefly rinsed in TBS/Tween and blocked overnight in TBS/CS (100 mM Tris, 150 mM NaCl, 10 mM EDTA, 0.18% Tween-20, 4.0% calf serum, pH 8.0) at 4° C. The nitrocellulose was placed in the Multi-screen apparatus and 600 µl of sera was placed in the channels and followed with a 2 hour room temperature and an overnight 4° C. incubation. After removing the membrane from the Multi-screen apparatus, it was washed 3 times, 5 minutes each, in 15 ml TBS/Tween (50 mM Tris, 150 mM NaCl, 0.05% Tween-20, pH 8.0). The membrane was incubated for 1 hour at room temperature in 15 ml goat anti-human:HRPO conjugate (0.2 µg/ml TBS/CS). After washing as before, the membrane was incubated in the TMB enzyme substrate solution, rinsed in water and dried.

Proteins isolated from T-1053 liver at sacrifice (12 days post-GB inoculation) and blotted as described above showed a unique immunogenic protein with an apparent molecular weight of approximately 50 to 80 kDa when reacted with T-1057 sera from 5, 6, 7, 9 or 11 weeks post-GB inoculation. The band was not present when reacted with T-1057 sera pre-inoculation or 3 weeks post-GB inoculation. This band did not appear in the lanes containing liver proteins obtained from an uninoculated tamarin (T-1040) when reacted with any of these T-1057 sera. In addition, a protein of the same size (50 to 80 kDa) was visible when the T-1053 liver proteins were reacted with other post-GB inoculation sera (T-1048 at 11 weeks post-GB inoculation and T-1051 at 8 weeks post-GB inoculation) but not when they were reacted with pre-inoculation sera from these same animals.

An additional Western blot experiment was performed to determine if this immunoreactive band would be detected in liver tissues from other GB-inoculated tamarins, or in liver tissues of chimpanzees infected either with HCV or HBV. In each case, the nitrocellulose strips containing the liver proteins were reacted with a pool of sera from T-1048 (5, 8, and 16 weeks post-GB inoculation) and T-1051 (8 and 12 weeks post-GB inoculation). All 5 sera in the pool were mixed in equal proportion. A reactive protein band of 50–80 kDa was seen with all of the tamarin liver samples obtained from GB inoculated tamarins (T-1038, T-1049, and T-1055 obtained at 14 days post-GB inoculation and T-1053 obtained at 12 days post-GB inoculation). This immunoreactive band was not detected in the liver preparations obtained from T-1040 (uninoculated) nor in any of the chimp liver preparations (CHAS-457 (pre-HCV inoculation), CHAS-457 (HCV+), CRAIG-454 (HCV+) and MUNA-376 (HBV+).

Taken together, these data demonstrate the existence of an immunogenic and antigenic protein with an apparent molecular weight of approximately 50 to 80 kDa specifically associated with HGBV-infected tamarin liver. The nature of this HGBV-associated protein (i.e. whether it is viral encoded or of host origin) is currently under investigation. Regardless of the source of the HGBV-associated protein, these result are consistent with HGBV infection inducing an antibody response to an antigen which is present in HGBV-infected tamarin liver.

Example 13

CKS-Based Expression and Detection of Immunogenic HGBV-A and HGBV-B Polypeptides A. Cloning of HGBV-A and HGBV-B Sequences The cloning vectors pJO200, pJO201, and pJO202 allow the fusion of recombinant proteins to the CMP-KDO synthetase (CKS) protein. Each of these plasmids consists of the plasmid pBR322 with a modified lac promoter fused to a kdsB gene fragment (encoding the first 239 of the entire 248 amino acids of the *E. coli* CKS protein), and a synthetic linker fused to the end of the kdsB gene fragment. The synthetic linkers include: multiple restriction sites for insertion of genes, translational stop signals, and the trpA rho-independent transcriptional terminator. The unique restriction sites in this linker region include, from 5' to 3', EcoRI, SacI, KpnI, SmaI, BamHI, XbaI, PstI, SphI, and HindIII. Each plasmid allows for insertion in a different reading frame within the multiple cloning site. The CKS method of protein synthesis as well as CKS vectors are disclosed in U.S. Pat. No. 5,124,255, which enjoys common ownership and is incorporated herein by reference, and the use of CKS fusion proteins in assay formats and test kits is described in U.S. Ser. No. 07/903,043, which enjoys common ownership and is incorporated herein by reference.

The HGBV-A and HGBV-B sequences obtained from the walking experiments described in TABLES 9 and 10 (Example 9) were liberated from the appropriate pT7Blue T-vector clones using restriction enzymes listed in TABLES 13 and 14 (10 units, NEB), and purified from 1% low melting point agarose gels as described in Example 3B. Plasmids pJO200, pJO201, and pJO202 were digested with the same restriction enzymes (10 units, NEB) and dephosphorylated with bacterial alkaline phosphatase (GIBCO BRL, Grand Island, N.Y.). Each purified HGBV fragment was ligated into the digested, dephosphorylated pJO200, pJO201, and pJO202 and transformed into *E. coli* XL1 Blue as described in Example 3B. Standard miniprep analyses confirmed the successful construction of the CKS/HGBV expression vectors.

Two additional PCR products were generated specifically for expression. The 2 products, designated 4.1 and 4.2, were predicted to encode the HGBV-B and HGBV-A core regions, respectively (see FIG. 22). PCR product 4.1 was generated using primers coreB-s and coreB-a1 (SEQUENCE I.D. NOS. 702 and 703) and PCR product 4.2 was generated using primers coreA-s and 2.2.1' (SEQUENCE I.D. NOS. 704 and 138), as described in Example 9. The 4.1 sense and antisense primers had EcoRI and BamHI restriction sites, respectively, designed into the ends. The 4.1 PCR product was digested, gel isolated, and ligated to pJO200, pJO201, and pJO202 as described above. The sense primer for the 4.2 PCR product had an EcoRI restriction site designed into the end, but the antisense primer did not have a restriction site. Thus, the product was cut with EcoRI, gel isolated, and ligated to pJO200, pJO201, and pJO202 which had been digested with BamHI, end-filled with the Klenow fragment of DNA polymerase and dNTPs, digested with EcoRI, and dephosphorylated with bacterial alkaline phosphatase as described in the art.

B. Expression of HGBV-A and HGBV-B Sequences

*E. coli* XL1 Blue cultures containing the CKS/HGBV expression vectors were grown at 37° C. with shaking in media containing 32 gm/L tryptone, 20 gm/L yeast extract, 5 gm/L NaCl, pH7.4, plus 100 mg/L ampicillin and 3 mM glucose. When the cultures reached an OD600 of between 1.0 and 2.0, IPTG was added to a final concentration of 1 mM to induce expression from the modified lac promoter. Cultures were allowed to grow at 37° C. with shaking for an additional 3 hours, and were then harvested. The cell pellets were resuspended to an OD600 of 10 in SDS/PAGE loading buffer (62.5 mM Tris pH6.8, 2% SDS, 10% glycerol, 5% 2-mercaptoethanol, and 0.1 mg/ml bromophenol blue), and boiled for 5 minutes. Aliquots of the prepared whole cell lysates were run on a 10% SDS-polyacrylamide gel, stained in a solution of 0.2% Coomassie blue dye in 40% methanol/10% acetic acid and destained in 16.5% methanol/5% acetic acid until a clear background was obtained.

The whole cell lysates were run on a second 10% SDS-polyacrylamide gel, and electrophoretically transferred to nitrocellulose for immunoblotting. The nitrocellulose sheet containing the transferred proteins was incubated in blocking solution (5% Carnation nonfat dry milk in Tris-buffered saline) for 30 minutes at room temperature followed by incubation for 1 hour at room temperature in goat anti-CKS sera which had been preblocked against *E. coli* cell lysate then diluted 1:1000 in blocking solution. The nitrocellulose sheet was washed two times with Tris-buffered saline (TBS), then incubated for 1 hour at room temperature with alkaline phosphatase-conjugated rabbit anti-goat IgG, diluted 1:1000 in blocking solution. The nitrocellulose was washed two times with TBS and the color was developed in TBS containing nitroblue tetrazolium and 5-bromo-4-chloro-3-indolyl phosphate. The appropriate reading frame for each fragment was identified based on expression of an immunoreactive CKS fusion protein of the correct predicted size, and further confirmed by DNA sequencing across the vector-insert junction.

After determining the appropriate reading frame for each of the fragments, samples from cultures containing the appropriate constructs were analyzed by SDS-polyacrylamide gel electrophoresis and Western blot. FIG. 25A shows 2 Coomassie-stained 10% SDS-polyacrylamide gels containing the CKS fusion protein whole cell lysates. Lanes 1 and 16 contain molecular weight standards with the sizes in kilodaltons shown on the left. The loading order on gel 1 (HGBV-A samples) is as follows: lane 2, clone 1.17 prior to induction; lanes 3–15, clone 4.2, clone 1.17, clone 1.8, clone 1.2, clone 1.18 (SEQUENCE I.D. NO. 387), clone 1.19, clone 1.20, clone 1.21, clone 1.22 (SEQUENCE I.D. NO. 387), clone 2.12, clone 1.5, clone 1.23, and clone 2.18 respectively, all after 3 hours of induction. The loading order on gel 2 (HGBV-B samples) is as follows: lane 17, clone 4.1 prior to induction; lanes 18–29, clone 4.1, clone 1.15, clone 1.14, clone 2.8, clone 1.13, clone 1.12, clone 2.1, clone 1.7, clone 1.3, clone 1.4, clone 1.16, and clone 2.12 respectively, all after 3 hours of induction. These proteins were run on 2 additional 10% gels, in the same loading order, and transferred to nitrocellulose as described above. The samples were analyzed by Western blot using a pool of sera from 2 convalescent tamarins, T-1048 and T-1051, as follows: The nitrocellulose sheets containing the samples were incubated for 30 minutes in blocking solution, followed by transfer to blocking solution containing 10% *E. coli* lysate, 6 mg/ml XL1-Blue/CKS lysate, and a 1:100 dilution of the pooled convalescent tamarin sera described in TABLE 6 (Example 4). After overnight incubation at room temperature, the nitrocellulose sheets were washed two times in TBS and then incubated for 1 hour at room temperature in HRPO-conjugated goat anti-human IgG, diluted 1:500 in blocking solution. The nitrocellulose sheets were washed two times in TBS and the color was developed in TBS containing 2 mg/ml 4-chloro-1-napthol, 0.02% hydrogen peroxide and 17% methanol. As shown in FIG. 25B, three HGBV-B proteins demonstrated immunoreactivity with the pooled tamarin sera; CKS fusions of clones 1.4, 1.7, and 4.1. Clone 1.7 contains the sequence encoding an HGBV-B immunogenic region (SEQUENCE I.D. NO. 604) and clone 1.4 contains the sequence encoding two HGBV-B immunogenic regions (SEQ. ID. NOS. 12, 13 and 18), identified by immunoscreening of a cDNA library (Example 4) using the same pool of convalescent tamarin sera.

The samples described in the previous paragraph were also analyzed by Western blot as above using a 1:100 dilution of convalescent serum obtained approximately three weeks following the onset of acute hepatitis from the surgeon GB. The reactivities of the fusion proteins from HGBV-A and HGBV-B with this serum are indicated in TABLES 13 and 14. Only one HGBV-B protein (2.1) showed reactivity with this serum, and the reactivity was quite weak, while two HGBV-A proteins (1.22 [SEQUENCE I.D. NO. 389] and 2.17) exhibited strong reactivity with this serum. These two HGBV-A proteins overlap by 40 amino acids, so this may reflect reactivity with one epitope or more than one epitope. These two HGBV-A proteins were chosen for use in ELISA assays as described in Example 16. It is of interest to note that although tamarins infected with the eleventh passage GB material (H205 GB pass 11) demonstrate an immune response to several HGBV-B epitopes but no HGBV-A epitopes, serum from the original GB source demonstrates significant reactivity with at least one HGBV-A epitope. This suggests that HGBV-A may have been the causative agent of hepatitis in the surgeon GB.

Four additional human sera which had indicated the presence of antibodies to one or more of the CKS/HGBV-A or CKS/HGBV-B fusion proteins by the 1.4, 1.7, or 2.17 ELISAS (see Examples 15 and 16) were chosen for Western blot analysis. Three of these sera (G1-41, G1-14 and G1-31) are from the West African "at risk" population and the fourth (341C) is from a non A–E hepatitis (Egypt) sample (see Example 15 for detailed description of these populations). Additional 10% SDS-polyacrylamide gels containing the whole cell lysates from some of the CKS fusion proteins discussed above were run and transferred to nitrocellulose as described previously. Each of these blots was preblocked as described, then incubated overnight with one of the human serum sample diluted 1:100 in blocking buffer containing 10% E. coli lysate and 6 mg/ml XL1-Blue/CKS lysate. The blots were washed two times in TBS, then reacted with HRPO-conjugated goat anti-human IgG and developed as indicated above.

The CKS/HGBV-B proteins were analyzed with two of these sera, G1-41 and G1-14, and the reactivities are indicated in TABLE 13. In addition to the three proteins which showed reactivity with the tamarin sera, two additional proteins (1.16 and 2.1) showed reactivity with one or the other of the two human sera. The CKS/HGBV-A proteins were analyzed with all four of these human sera and the reactivities are indicated in TABLE 14. In addition to the two proteins which showed reactivity with GB serum, three additional proteins (1.5, 1.18, and 1.19) showed reactivity with one or more of the human sera. Two of these (1.5 and 1.18) were chosen for use in ELISA assays as described in Example 16. It is of particular interest to note that the G1-31 serum, which shows reactivity by Western blot and/or ELISA (Examples 15 and 16) with two HGBV-A proteins (1.18 and 2.17) and one HGBV-B protein (1.7), is the serum from which the GB-C sequence (SEQUENCE I.D. No. 667, residues 2274–2640) was isolated (Example 17).

TABLE 13

HGBV-B Samples

| PCR product[a] | Restriction digest[b] | Reactivity with T4048 + T1051 sera | Reactivity with GB sera | Reactivity with human G1-41 sera | Reactivity with human G1-14 sera |
|---|---|---|---|---|---|
| 1.3 | EcoRI, PstI | – | – | – | – |
| 1.4 | EcoRI, XbaI | + | – | + | + |
| 1.7 | EcoRI, HindIII | + | – | + | – |
| 1.12 | KpnI, PstI | – | – | – | – |
| 1.13 | EcoRI, XbaI | – | – | – | – |
| 1.14 | BamHI, HindIII | – | – | – | – |
| 1.15 | EcoRI, PstI | – | – | – | – |
| 1.16 | EcoRI, XbaI | – | – | + | – |
| 2.1 | EcoRI, HindIII | – | +/– | – | + |
| 2.8 | EcoRI, XbaI | – | – | – | – |
| 2.12 | KpnI, PstI | – | – | – | – |
| 4.1 | EcoRI, BamHI | + | – | – | – |

[a]PCR product is as indicated in TABLE 9, TABLE 10, or Example 13.
[b]Restriction digests used to liberate the PCR fragment from pT7Blue T-vector or for direct digestion of 4.1 PCR product.

Example 14

Epitope Mapping of Immunoreactive HGBV-A and HGBV-B Proteins

A. Epitope Mapping of HGBV-B Protein 1.7

Overlapping subclones within the HGBV-B immunogenic protein 1.7 were generated by RT-PCR from T1053 serum as described in Example 7 in order to determine the location of the immunogenic region or regions. Each PCR primer had six extra bases on the 5' end to facilitate restriction enzyme digestion, followed by either an EcoRI site (sense primers) or a HindIII site (antisense primers). In addition, each antisense primer contained a stop codon just after the coding region. After digestion, each fragment was cloned into EcoRI/HindIII-digested pJO201 as described in Example 13. The CKS fusion proteins were expressed and analyzed by Western blot with tamarin T1048/T1051 sera as described in Example 13. Five overlapping clones, designated 1.7-1 through 1.7-5, were generated. The clones encoded regions of the 1.7 protein ranging in size from 104 to 110 amino acids. The PCR primers used to generate each clone, the sizes of the encoded polypeptides, the location within the 1.7 sequence and the reactivity with tamarin T1048/T1051 sera are shown in TABLE 15. Two further overlapping clones were generated which encompassed the immunogenic region (SEQUENCE I.D. NO. 672) identified by immunoscreening of a cDNA library (Example 4). Each of these clones, designated 1.7-6 and 1.7-7, encoded polypeptides of 75 amino acids. The PCR primers, sizes of encoded polypeptides, location within the 1.7 sequence and reactivity with tamarin T1048/T1051 sera are shown in TABLE 15. Two immunogenic regions were identified within the 507 amino acid long 1.7 protein; one near the N-terminus within residues 1–105, and another near the middle of the protein, encompassing residues 185 to 410. It remains to be determined whether there is a single epitope or multiple epitopes within each of these regions.

B. Epitope Mapping of HGBV-B Protein 1.4

Overlapping subclones within the HGBV-B immunogenic protein 1.4 were generated by RT-PCR from T1053 serum as above in order to determine the location of the immunoreactive region or regions. Each PCR primer had six extra bases on the 5' end to facilitate restriction enzyme digestion, followed by either an EcoRI site (sense primers) or a BamHI site (antisense primers). In addition, each antisense primer contained a stop codon just after the coding region. After digestion, each fragment was cloned into EcoRI/BamHI-digested pJO201 as described in Example 13. The CKS fusion proteins were expressed and analyzed by Western blot with tamarin T1048/T1051 sera as described in Example 13. Four overlapping clones, designated 1.4-1 through 1.4-4, were generated. The clones encoded regions of the 1.4 protein ranging in size from 137 to 138 amino acids. The PCR primers used to generate each clone, the sizes of the encoded polypeptides, the location within the 1.4 sequence and the reactivity with tamarin T1048/T1051 sera are shown in TABLE 15. Two further overlapping clones were generated which encompassed an immunogenic region identified by immunoscreening of a cDNA library (Example 4). Each of these clones, designated 1.4-5 and 1.4-6, encoded polypeptides of 75 amino acids. The PCR primers, sizes of encoded polypeptides, location within the 1.4 sequence and reactivity with tamarin T1048/T1051 sera are shown in TABLE 15. A 265 amino acid sequence was identified as being the immunogenic region within the 522 amino acid long 1.4 protein, encompassing residues 129 to 393. It is likely that there are at least two epitopes within this region, since library immunoscreening (Example 4) identified two immunogenic non-contiguous clones within this sequence.

C. Epitope Mapping of HGBV-A Proteins 1.22 (SEQUENCE I.D. NO. 387) and 2.17

The HGBV-A proteins 1.22 (SEQUENCE I.D. NO. 387) and 2.17 (SEQUENCE I.D. NO. 613) both showed immunoreactivity with GB serum by Western blot (Example 13). Since these two proteins overlap by 40 amino acids, the observed immunoreactivity may have resulted from the presence of one epitope or more than one epitope. The complete 1.22/2.17 sequence is 641 amino acids long.

Overlapping subclones within this region were generated by RT-PCR from T1053 serum as above in order to determine the location of the immunogenic region or regions. Each PCR primer had six extra bases on the 5' end to facilitate restriction enzyme digestion, followed by either an EcoRI site (sense primers) or a BamHI site (antisense primers) for 1.22/2.17-2 through 1.22/2.17-6. However, since clone 1.22/2.17-1 had an internal EcoRI site, a BamHI site was used in the sense primer and a HindIII site was used in the antisense primer. In addition, each antisense primer contained a stop codon just after the coding region. After digestion, each fragment was cloned into EcoRI/BamHI-digested (or BamHI/HindIII-digested for 1.22/2.17-1) pJO201 as described in Example 13. The CKS fusion proteins were expressed and analyzed by Western blot with GB serum as described in Example 13. The clones encoded regions of 1.22/2.17 ranging in size from 115 to 116 amino acids. The PCR primers used to generate each clone, the sizes of the encoded polypeptides, the location within the HGBV-A polypeptide sequence and the reactivity with GB serum are shown in TABLE 15. The immunogenic region was narrowed down to a 220 amino acid long region in the middle of the 1.22/2.17 protein. This encompassed the 40 amino acid region of overlap between 1.22 and 2.17, and thus the immunoreactivity seen with the two proteins individually may have been due to a shared epitope or to multiple epitopes.

protease inhibitors to produce mixtures of the individual recombinant antigen and E. coli proteins. Individually for each of the three cultures, the insoluble recombinant antigen was concentrated by centrifugation and subjected to a series of sequential washes to eliminate the majority of non-recombinant E. coli proteins. The washes used in this protocol included distilled water, 5% Triton X-100 and 50 mM Tris (pH 8.5). The resulting pellets were solubilized in the presence of sodium dodecyl sulfate (SDS). After determining protein concentration, 2-mercaptoethanol was added and the mixtures were subjected to gel filtration column chromatography, with Sephacryl S300 resin used to size and separate the various proteins. Fractions were collected and analyzed by SDS-polyacrylamide gel electrophoresis (SDS-PAGE) The electrophoretically separated proteins were then stained with Coomassie Brilliant Blue R250 and examined for the presence of a protein having a molecular weight of approximately 75 kD (CKS-1.7/SEQUENCE I.D. NO. 604), 80 kD (CKS-1.4/SEQUENCE I.D. NO. 605), 42 kD (CKS-4.1/SEQUENCE I.D. NO. 606). Fractions containing the protein of interest were pooled and re-examined by SDS-PAGE.

The immunogenicity and structural integrity of the pooled fractions containing the purified antigen were determined by immunoblot following electrotransfer to nitrocellulose as described in Example 13. In the absence of a qualified positive control, the recombinant proteins were identified by

TABLE 15

| CLONE | SIZE OF ENCODED POLYPEPTIDE | PRIMER SET | T1048/T1051 REACTIVITY | RESIDUES IN SEQ ID NO. 120 |
|---|---|---|---|---|
| 1.7-1 | 105 aa | SEQ ID #609/SEQ ID #610 | + | 1–105 |
| 1.7-2 | 109 aa | SEQ ID #611/SEQ ID #612 | − | 98–206 |
| 1.7-3 | 110 aa | SEQ ID #613/SEQ ID #614 | + | 199–308 |
| 1.7-4 | 110 aa | SEQ ID #615/SEQ ID #616 | +/− | 301–410 |
| 1.7-5 | 104 aa | SEQ ID #617/SEQ ID #618 | − | 403–507 |
| 1.7-6 | 75 aa | SEQ ID #619/SEQ ID #620 | + | 185–259 |
| 1.7-7 | 75 aa | SEQ ID #621/SEQ ID #622 | + | 251–325 |

| CLONE | SIZE OF ENCODED POLYPEPTIDE | PRIMER SET | T1048/T1051 REACTIVITY | RESIDUES IN SEQ ID NO. 119 |
|---|---|---|---|---|
| 1.4-1 | 137 aa | SEQ ID #623/SEQ ID #624 | − | 1–137 |
| 1.4-2 | 137 aa | SEQ ID #625/SEQ ID #626 | + | 129–265 |
| 1.4-3 | 137 aa | SEQ ID #627/SEQ ID #628 | + | 257–393 |
| 1.4-4 | 138 aa | SEQ ID #629/SEQ ID #630 | − | 385–522 |
| 1.4-5 | 75 aa | SEQ ID #631/SEQ ID #632 | + | 138–212 |
| 1.4-6 | 75 aa | SEQ ID #633/SEQ ID #634 | + | 204–278 |

| CLONE | SIZE OF ENCODED POLYPEPTIDE | PRIMER SET | GB SERUM REACTIVITY | RESIDUES IN SEQ ID NO. 390 |
|---|---|---|---|---|
| 1.22/2.17-1 | 115 aa | SEQ ID #635/SEQ ID #636 | − | 1862–1976 |
| 1.22/2.17-2 | 115 aa | SEQ ID #637/SEQ ID #638 | − | 1967–2081 |
| 1.22/2.17-3 | 115 aa | SEQ ID #639/SEQ ID #640 | + | 2072–2186 |
| 1.22/2.17-4 | 115 aa | SEQ ID #641/SEQ ID #642 | + | 2177–2291 |
| 1.22/2.17-5 | 115 aa | SEQ ID #643/SEQ ID #644 | − | 2282–2396 |
| 1.22/2.17-6 | 116 aa | SEQ ID #645/SEQ ID #646 | − | 2387–2505 |

Example 15

Serological Studies HGBV-B

A. Recombinant Protein Purification Protocol

Bacterial cell cultures expressing the CKS fusion proteins were frozen and stored at −70° C. The bacterial cells from each of the three constructs were thawed and disrupted by treating with lysozyme and DNAse, followed by sonication in the presence of phenylmethanesulfonyl fluoride and other their reactivity with a monoclonal antibody directed against the CKS portion of each fusion protein. When the CKS-1.7 protein (SEQUENCE I.D. NO. 604) was examined by Western blot, using the anti-CKS monoclonal antibody to detect the recombinant antigen, a single band at approximately 75 kD was observed. This corresponds to the expected size of the CKS-1.7 protein (SEQUENCE I.D. NO. 604). For the CKS-1.4 protein (SEQUENCE I.D. NO. 611), the anti-CKS monoclonal antibody detects a quadruplet banding pattern between 60 and 70 kD. These observed bands are smaller than the expected size of the full length protein and probably represent truncation products. When the CKS-4.1 protein (SEQUENCE I.D. NO. 52) was examined by Western blot, the anti-CKS monoclonal antibody detected the recombinant antigen as a single band at approximately 42 kD. This corresponds to the expected size of the CKS-4.1 protein (SEQUENCE I.D. NO. 606).

B. Polystyrene Bead Coating Procedure

The proteins were dialyzed and evaluated for their antigenicity on polystyrene coated beads as described below. Separate enzyme-linked immunosorbent assays (ELISA's) were developed for detecting antibodies to HGBV using each of the three purified HGBV recombinant proteins (CKS-1.7 (SEQUENCE I.D. NO. 604); CKS-1.4 (SEQUENCE I.D. NO. 605); and the CKS-4.1 protein (SEQUENCE I.D. NO. 606). The ELISA's developed with these proteins are referred to as the 1.7 ELISA (utilizing the CKS-1.7 (SEQUENCE I.D. NO. 604) recombinant protein), the 1.4 ELISA (utilizing the CKS-1.4 (SEQUENCE I.D. NO. 605) recombinant protein), the 4.1 ELISA (utilizing the CKS-4.1 [SEQUENCE I.D. NO. 606]) recombinant protein. In the first study, one-quarter inch polystyrene beads were coated with various concentrations with each of the purified proteins (approximately 60 beads per lot) and evaluated in an ELISA test (described below) using serum from an uninoculated tamarin as a negative control and convalescent sera from an inoculated tamarin as a positive control. Additional controls included the a pool of human serum from individuals testing negative for various hepatitis viruses. An additional positive control consisted of monoclonal antibodies to the CKS protein to monitor the efficiency of bead coating. The bead coating conditions providing the highest ratio of positive control signal to negative control signal were selected for scaling up the bead coating process. For each of the four ELISA's at least two lots of 1,000 beads were produced and utilized for serological studies.

Briefly, polystyrene beads were coated with the purified proteins by adding the washed beads to a scintillation vial and immersing the beads (approximately 0.233 ml per bead) in a buffered solution containing the recombinant antigen. Several different concentrations of each of the recombinant antigens were evaluated along with several different buffers prepared at pHs ranging from pH 5.0 to pH 9.5. The vials were then placed on a rotating device in a 40° C. incubator for 2 hours after which the fluids were aspirated and the beads were washed three times in phosphate buffered saline (PBS), pH 6.8. The beads were then treated with 0.1% Triton X-100 for 1 hour at 40° C. and washed three times in PBS. Next, the beads were overcoated with 5% bovine serum albumin and incubated at 40° C. for 1 hour with agitation. After additional washing steps with PBS, the beads were overcoated with 5% sucrose for 20 minutes at room temperature and the fluids were aspirated. Finally, the beads were air dried and then utilized for developing ELISA's for detection of antibodies to HGBV.

C. ELISA Protocol for Detection of Antibodies to HGBV

An indirect assay format was utilized for the ELISA's. Briefly, sera or plasma was diluted in specimen diluent and reacted with the antigen coated solid phase. After a washing step, the beads were reacted with horseradish-peroxidase (HRPO) labeled antibodies directed against human immunoglobulins to detect tamarin or human antibodies bound to the solid phase. Specimens which produced signals above a cutoff value were considered reactive. Additional details pertaining to the ELISA's are described below.

The format for the ELISA's entails contacting the antigen-coated solid phase with tamarin serum pre-diluted in specimen diluent (buffered solution containing animal sera and non-ionic detergents). This specimen diluent was formulated to reduce background signals obtained from non-specific binding of immunoglobulins to the solid phase while enhancing the binding of specific antibodies to the antigen-coated solid phase. Specifically, 10 µl of tamarin serum was diluted in 150 µl of specimen diluent and vortexed. Ten microliters of this pre-diluted specimen was then added to the well of a reaction tray, followed by the addition of 200 µl of specimen diluent and an antigen coated polystyrene bead. The reaction tray was then incubated in a Dynamic Incubator (Abbott Laboratories) set for constant agitation at room temperature. After a 1 hour incubation, the fluids were aspirated, and the wells containing the beads were washed three times in distilled water (5 ml per wash). Next, 200 µl of HRPO-labeled goat anti-human immunoglobulins diluted in a conjugate diluent (buffered solution containing animal sera and non-ionic detergents) was added to each well and the reaction tray was incubated again as above for 1 hour. The fluids were aspirated and the wells containing the beads were washed three times in distilled water as above. The beads containing antigen and bound immunoglobulins were removed from the wells, each was placed in a test tube and reacted with 300 µL of a solution of 0.3% o-phenylenediamine-2 HCl in 0.1 M citrate buffer (pH 5.5) with 0.02% $H_2O_2$. After 30 minutes at room temperature, the reaction was terminated by the addition of 1 N $H_2SO_4$. The absorbance at 492 nm was read on a spectrophotometer. The color produced was directly proportional to the amount of antibody present in the test sample.

For each group of specimens, a preliminary cutoff value was set to separate those specimens which presumably contain antibodies to the HGBV epitope from those which did not.

D. Detection of HGBV Derived RNA in Serum From Infected Individuals

In order to correlate serological data obtained for 1.7 and 1.4 ELISA's with the presence of HGBV RNA in tamarin serum or in human serum/plasma, RT-PCR was performed as described in Example 7 of U.S. Ser. No. 08/283,314, previously incorporated herein by reference utilizing oligonucleotides derived from HGBV cloned sequences, at a final concentration of 0.5 µM for clone 4 (as described in Example 7) derived from the HGBV-B genome and for clone 16, derived from the HGBV-A genome.

E. Tamarin Serological Profiles

Serum was obtained from tamarins housed at LEMSIP on a weekly basis and tested for liver enzyme levels; the remaining volume from these specimens was sent to Abbott Laboratories for further studies.

1. ELISA Results on Tamarins (Initial Infectivity Studies)

Figure 2:
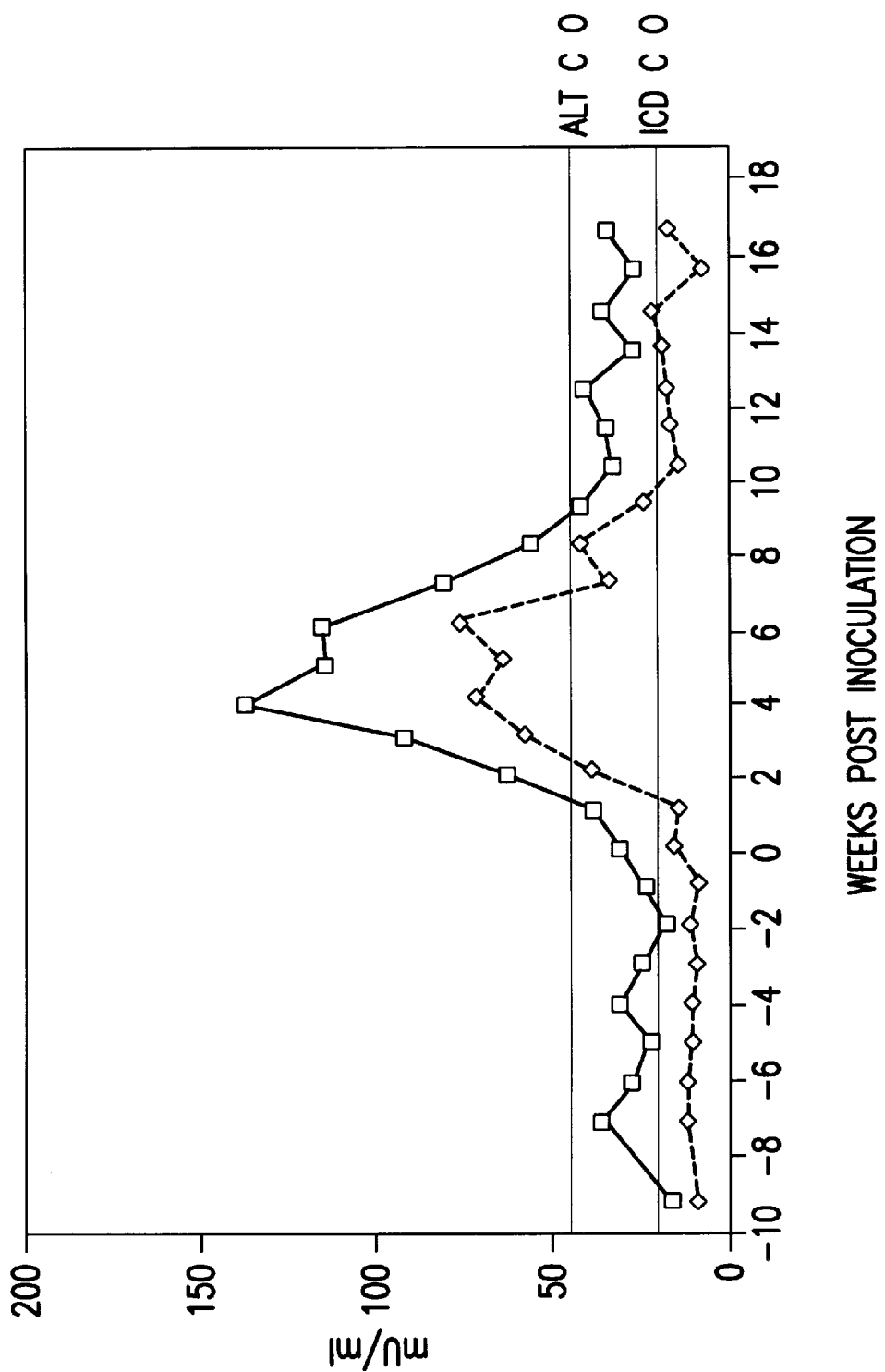

Four tamarins (T-1053, T-1048, T-1057 and T-1061) were inoculated with GB serum (designated as H205 GB passage 11). Elevated liver enzymes were noted in Tamarin T-1053 during the first week post-inoculation (PI): this tamarin was euthanized on day 12 PI. Tamarins T-1048, T-1057 and T-1061 exhibited elevated liver enzyme values within two weeks following their inoculation; these elevated values persisted until 8–9 weeks PI (FIGS. 2–4) before returning to pre-inoculation levels. On week 14 PI, these three tamarins were re-challenged with 0.10 ml of neat serum obtained from tamarin T-1053 (which was shown to be infectious— Example 2).

Sera from three convalescing tamarins (T-1048, T-1057 and T-1061) were tested for antibodies to the CKS-1.7

Figure 3:
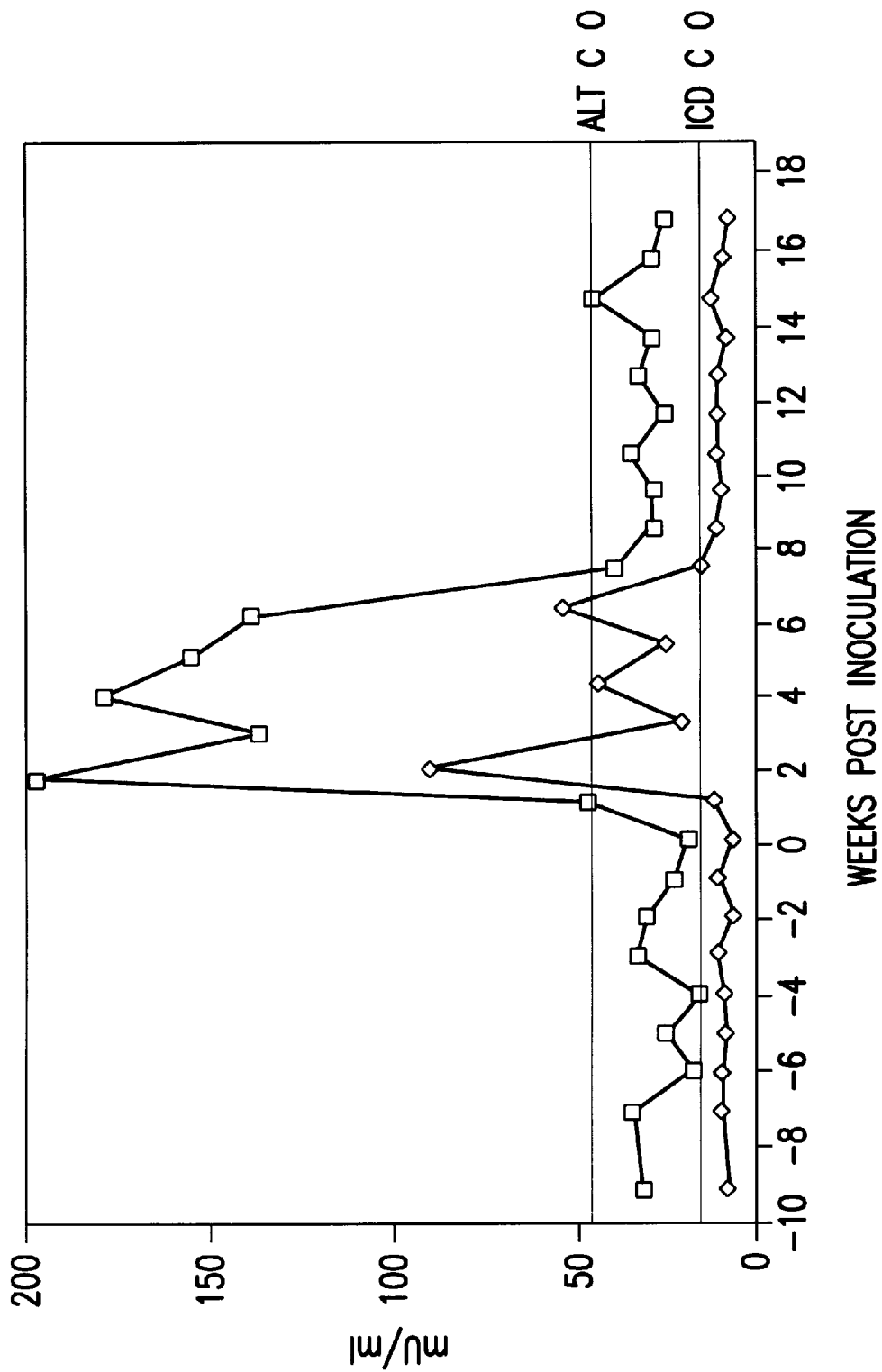
Figure 4:
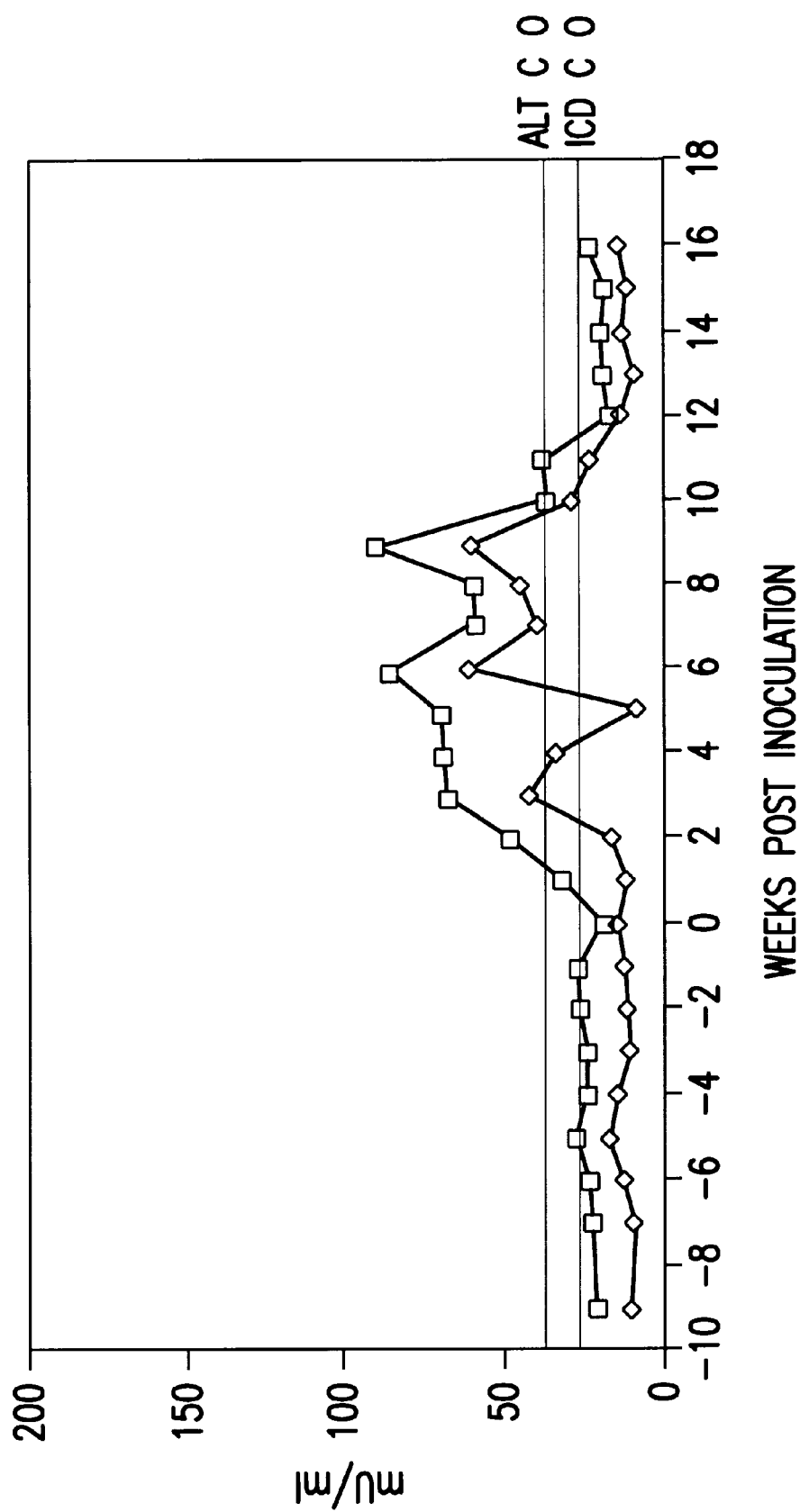
Figure 5:
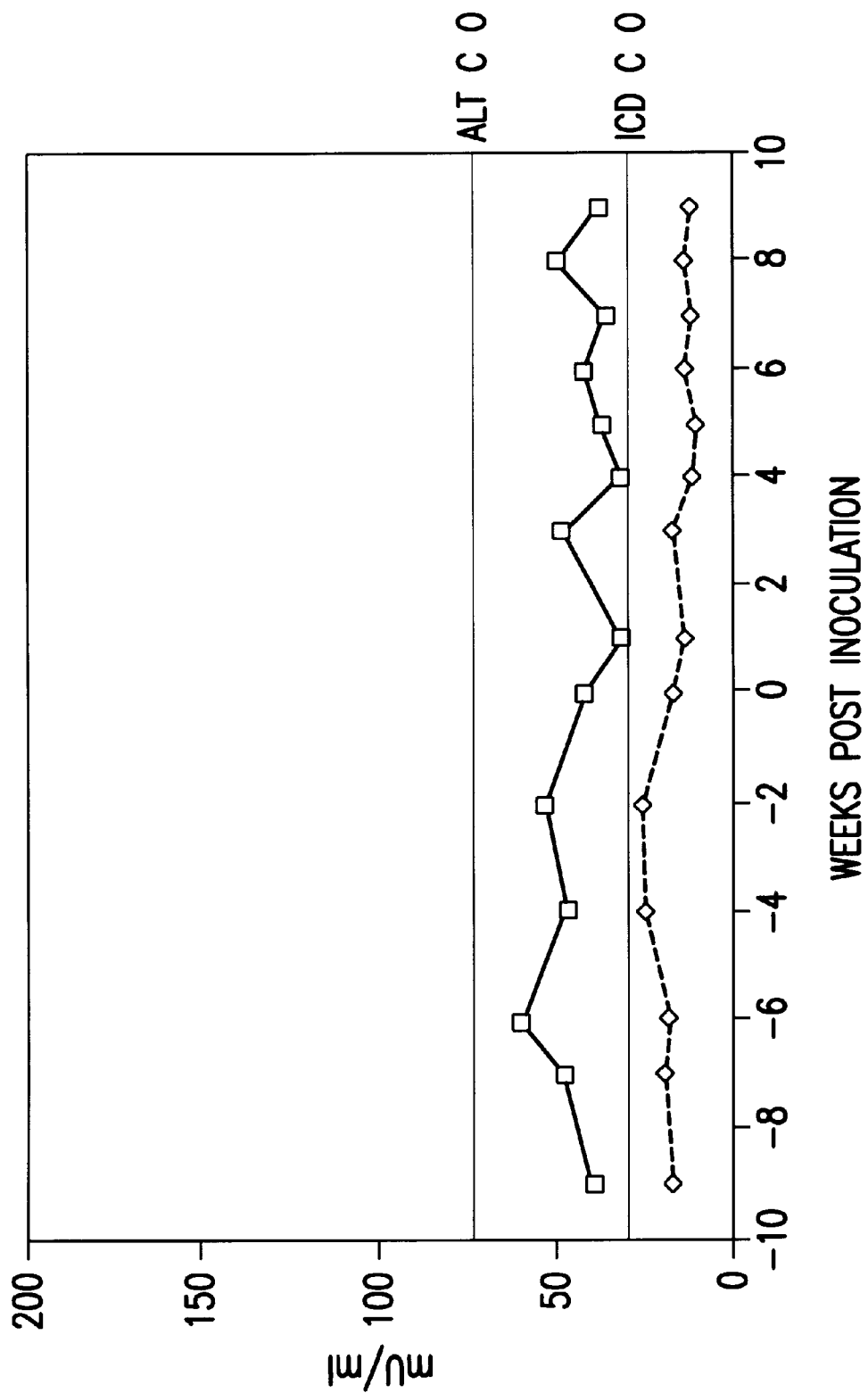
Figure 6:
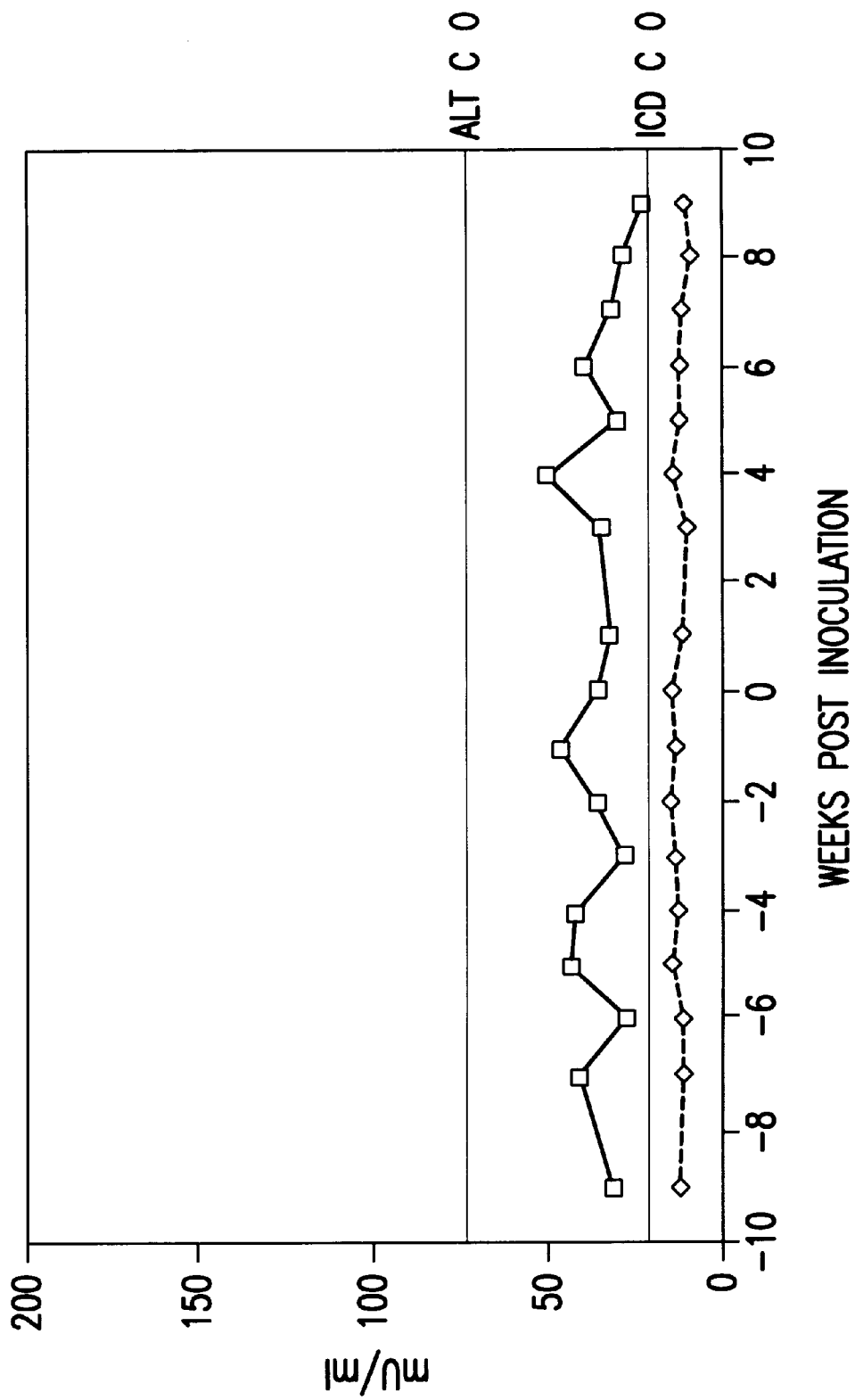

(SEQUENCE I.D. NO. 604) recombinant protein, the CKS-1.4 (SEQUENCE I.D. NO. 605) recombinant protein; and the CKS 4.1 (SEQUENCE I.D. NO. 606) recombinant protein, using separate ELISA's (FIGS. 3, 4 and 5). Specific antibodies to 1.7 (SEQUENCE I.D. NO. 604), 1.4 (SEQUENCE I.D. NO. 605), 4.1 (SEQUENCE I.D. NO. 606, or 1.5 (SEQUENCE I.D. NO. 608) recombinant proteins were not detected in any of the pre-inoculation specimens.

Figure 26:
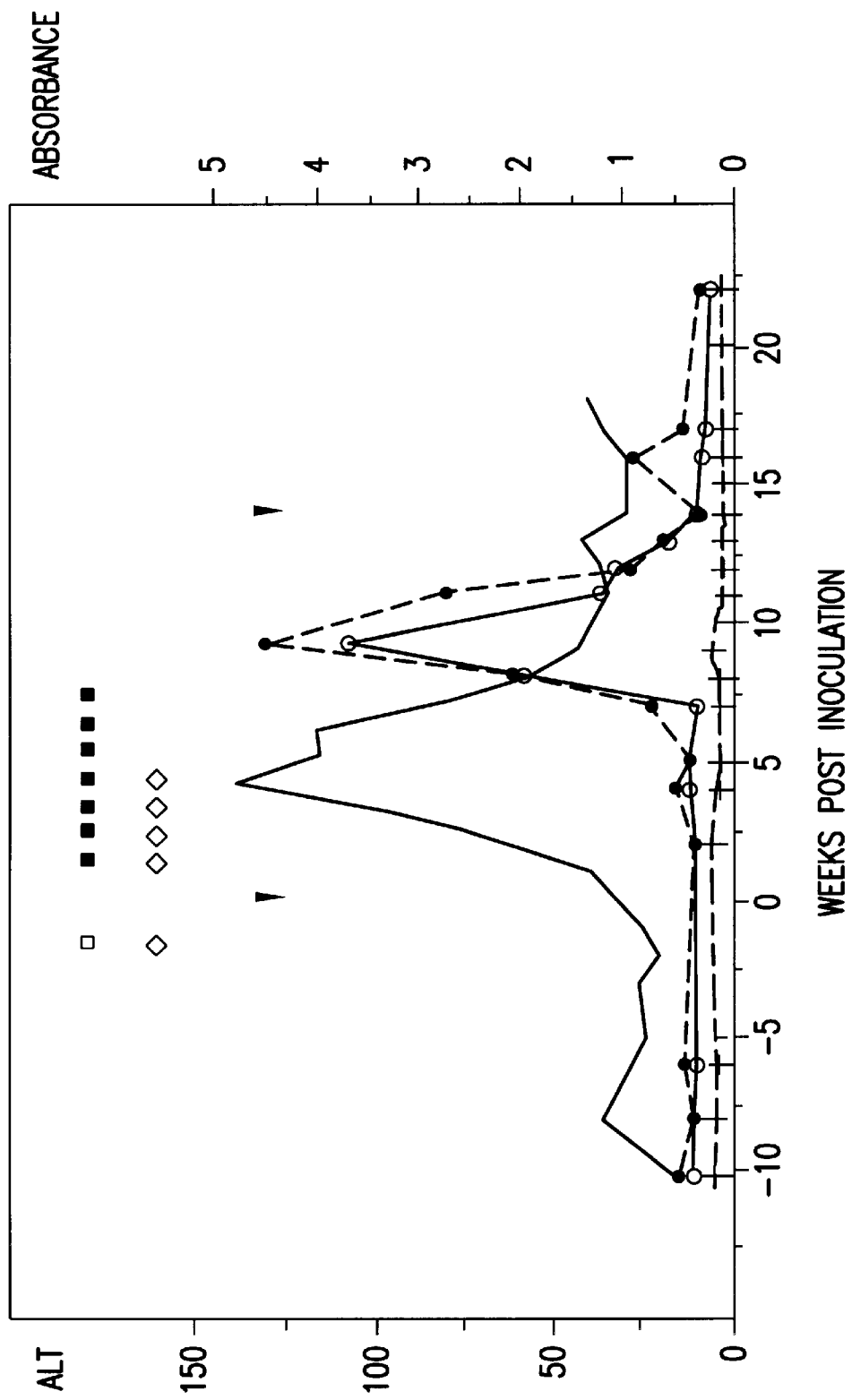
Figure 27:
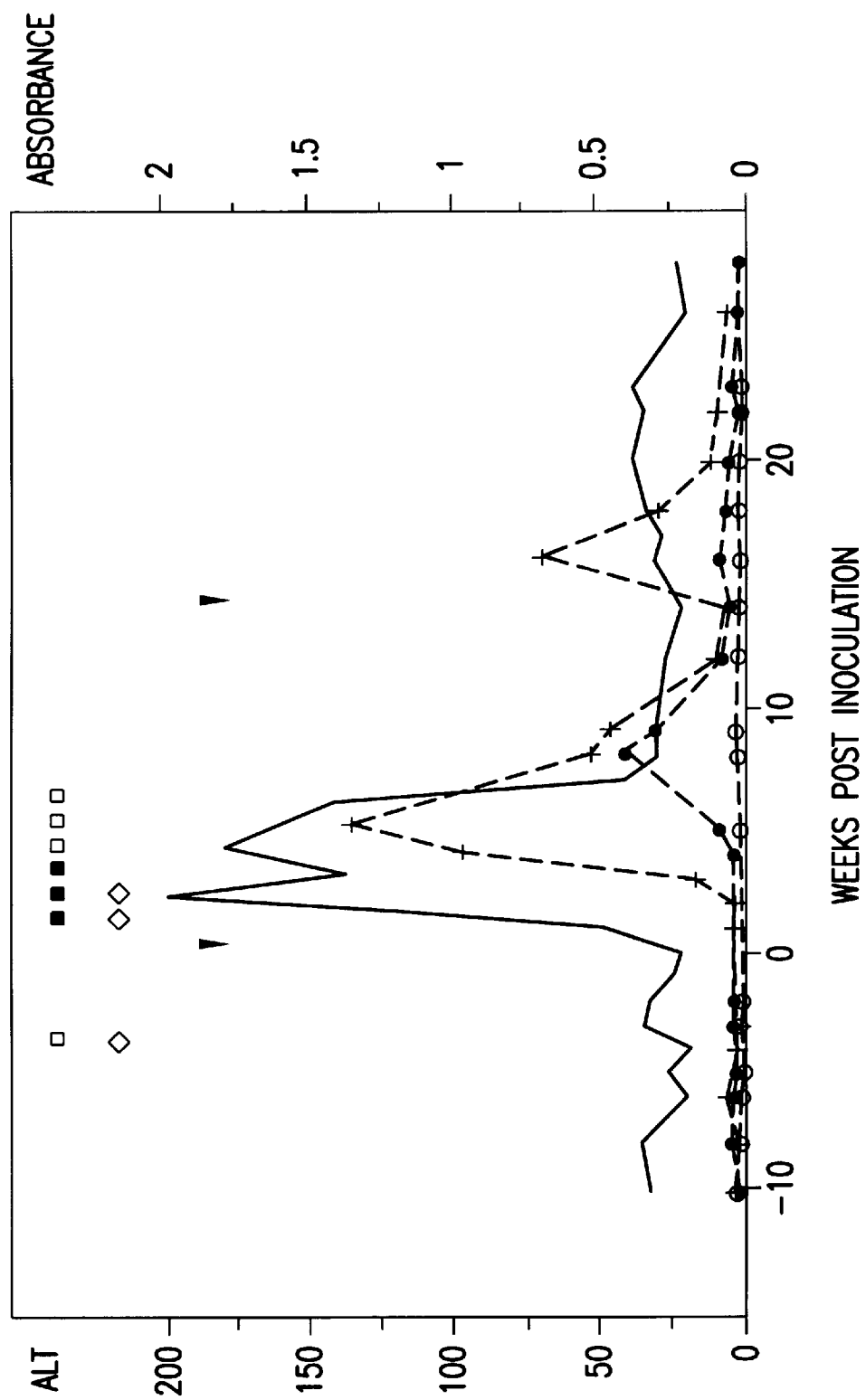

As shown in FIG. 26, specific antibodies were detected in T-1048 sera with the 1.7 and 1.4 ELISA's on days 56–84 but not on days 97 and 137 PI. Specific antibodies were not detected in T-1048 sera tested with the 4.1 ELISA. As shown in FIG. 27, antibodies to the 1.7 protein (SEQUENCE I.D. NO. 604) were detected in T-1057 serum at 56 and 63 days PI, but not after 63 days PI. Antibodies to the 4.1 protein (SEQUENCE I.D. NO. 606) were detected on days 28–63 PI but not on days 84–97 PI. As noted above, tamarins were challenged with a second dose of the H205 inoculum on day 97 PI. Specific antibodies to the 4.1 protein (SEQUENCE I.D. NO. 612) were detected on days 112 and 126 PI, suggesting an anamnestic response to the inoculum. No antibody reactivity was noted for the 1.4 recombinant protein (SEQUENCE I.D. NO. 605).

Figure 28:
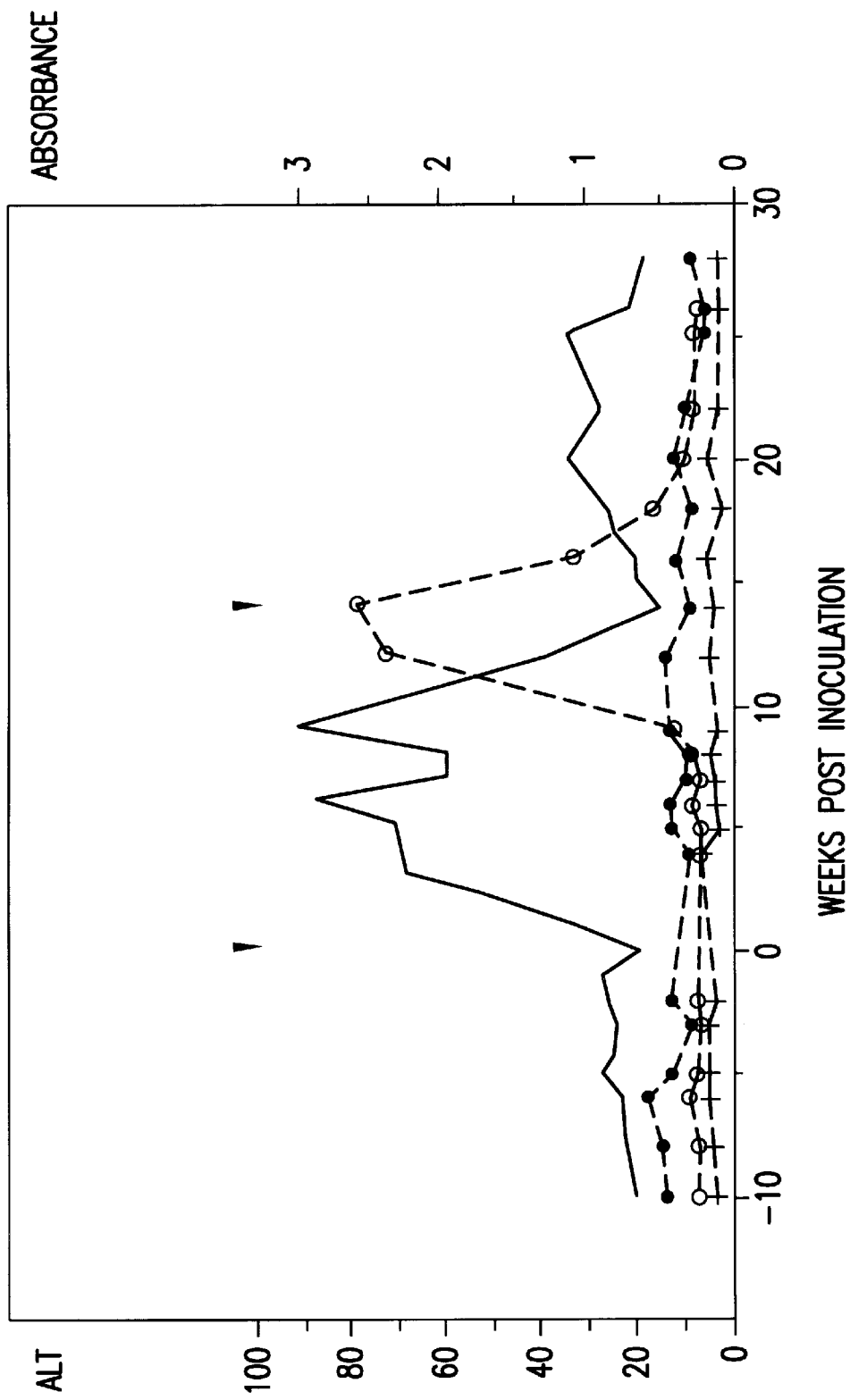

Specific antibodies to the recombinant 1.4 protein (SEQUENCE I.D. NO. 605) were detected in the serum of tamarin T-1061 between 84 and 112 days PI, but were not detected after 126 days PI. As shown in FIG. 28, Tamarin T-1061 sera were negative for antibodies to the 1.7 protein (SEQUENCE I.D. NO. 604) and to the 4.1 protein (SEQUENCE I.D. NO. 606) for 350 days PI.

2. PCR Results on Tamarins (Initial Infectivity Studies)

Selected sera obtained from tamarins T-1048 and T-1057 were tested for HGBV RNA via RT-PCR using primers from clone 4 as described in Example 7) and from clone 16 as described in Example 7.

HGBV RNA was not detected via RT-PCR with either set of primers in the serum obtained 10 and 17 days prior to inoculation (T-1048) as shown in FIG. 26, or 17, 37 and 59 days prior to inoculation (T-1057), as shown in FIG. 27. For T-1048, HGBV RNA was detected via RT-PCR using primers from clone 4 on fifteen of seventeen different sera obtained between 7–137 days PI. HGBV RNA was not detected via RT-PCR using primers from clone 16 in any of the 10 sera obtained on days 7–97 PI. After the challenge with T-1053 plasma, four of five sera obtained between 8 and 40 days after the challenge were positive for clone 16. For T-1057, positive RT-PCR results were obtained on four sera obtained on days 7–28 PI, using primers from clone 4, as shown in FIG. 27. RT-PCR performed on specimens drawn beyond day 28 PI were negative for clone 4, except for day 287 which showed a weak hybridization signal. Neither of the six specimens obtained from T-1057 on day 7–97 PI were positive via RT-PCR using primers from clone 16. However, sera obtained between 8–85 days after the T-1053 challenge were positive using primers from clone 16.

3. ELISA Results on Tamarins (Titration/Transmissibilty Studies)

Figure 29:
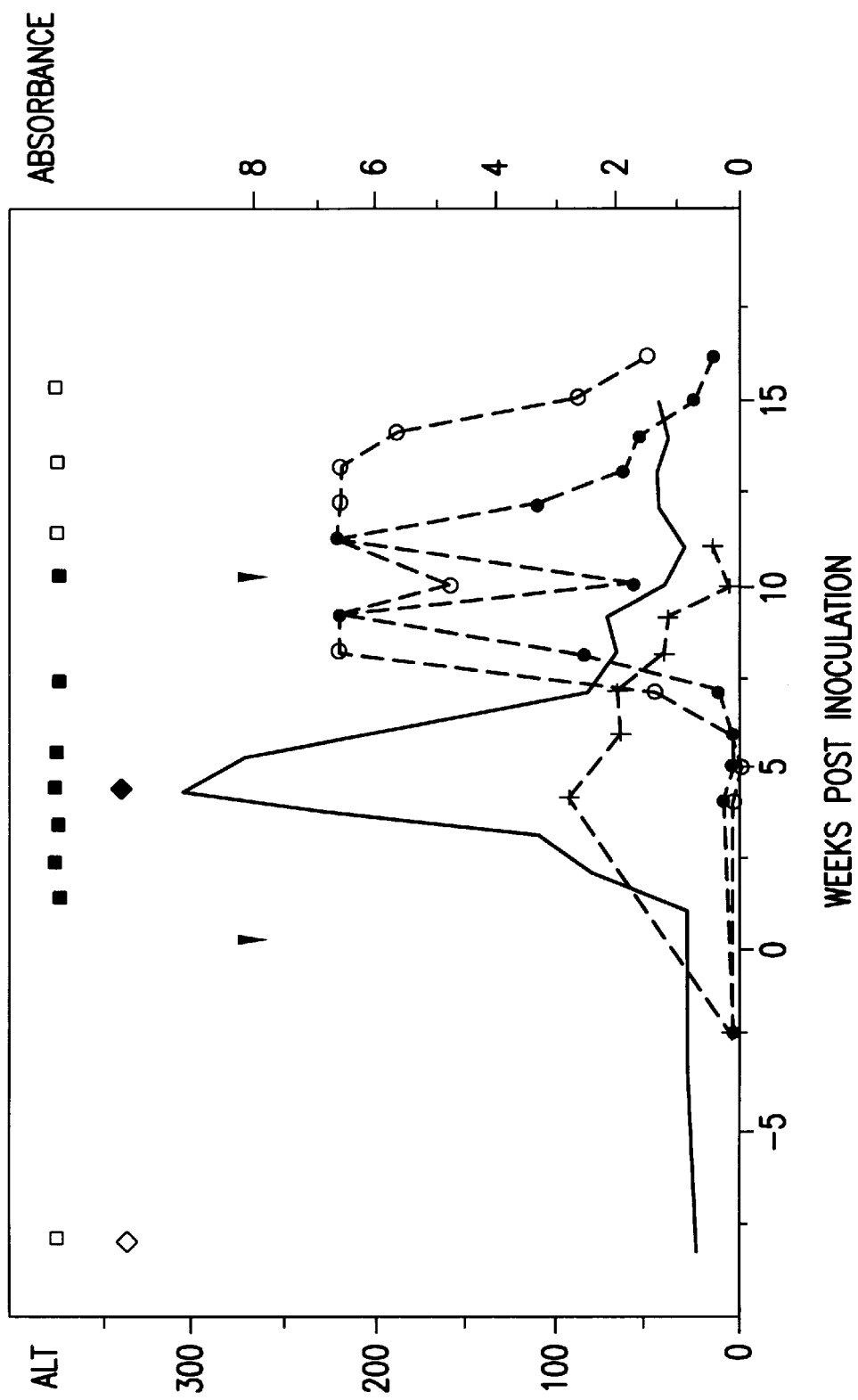

As described in Example 2, serum from tamarin T-1053 was inoculated into four tamarins. Three of these four tamarins were euthanized during the acute stage of the disease (between days 12 and 14 PI). The RT-PCR results obtained on these three tamarins are described below. The surviving tamarin (T-1051) first developed elevated liver enzyme values by day 14 PI and these values persisted for at least 8 weeks PI. Specimens from tamarin T-1051 were tested in the 1.7 and 1.4 ELISA's; the results are shown in FIG. 29. Specific antibodies were not detected in the pre-inoculation serum nor in serum drawn in the first 41 days PI. However, an antibody response was noted against the 1.4 protein (SEQUENCE I.D. NO. 605), and the 1.7 protein (SEQUENCE I.D. NO. 604) between 49 and 113 days PI and the 4.1 protein (SEQUENCE I.D. NO. 606) between 28 and 105 days PI. The tamarin was euthanized during the 113th day PI.

Tamarin (T-1034) was previously inoculated with 0.1 ml of potentially infectious serum obtained from a patient (original GB source) who was recovering from a recent hepatitis infection as described in Example 1 and in TABLE 4. No elevations in liver enzyme values were noted in T-1034 for nearly 10 weeks after inoculation. For this reason, it was decided that tamarin T-1034 could be used in an additional study. Tamarin T-1034 was inoculated with a preparation of HGBV prepared as described in Example 4?? from a pool of serum obtained from three tamarins (T-1055, T-1038 and T-1049) previously inoculated with serum from tamarin T-1053.

These three tamarins (T-1055, T-1038 and T-1049) were inoculated with serum prepared from tamarin T-1053 as described in Example 2. Elevated liver enzyme values were noted in all 3 tamarins by day 11 PI. Tamarin T-1055 was sacrificed on day 12 PI: tamarins T-1038 and T-1049 were sacrificed on day 14 PI. Serum from these tamarins was pooled, clarified and filtered. Tamarin T-1034 was inoculated with 0.25 ml of a $10^{-6}$ dilution (prepared in normal tamarin serum) of this filtered material.

Elevated ALT liver enzyme values were first noted in T-1034 at 2 weeks PI, and remained elevated for the next 7 weeks, finally normalizing by week 10 PI. As demonstrated in FIG. 30, a specific antibody response to the 1.4 (SEQUENCE I.D. NO. 22) recombinant protein was first detected on day 49 PI and continued to be detected on days 56–118 PI. The antibody response to the 4.1 (SEQUENCE I.D. NO. 52) recombinant protein was first detected on day 49 PI and continued to be detected between days 56–77 PI, but was not detected on between days 84–118 PI. The antibody response to the 1.7 (SEQUENCE I.D. NO. 604) recombinant protein was first detected on day 56 PI and continued to be detected between days 63–118 PI. The tamarin was sacrificed on day 118 PI.

As described in Example 2, tamarin T-1044 was inoculated with serum obtained from T-1057 that had been obtained 7 days after the H205 inoculation. This inoculum was positive only for sequences detected with clone 4 primers. The inoculum was negative by RT-PCR with clone 16 primers. Mild elevations in ALT levels above the cutoff were observed from days 14–63 PI. As demonstrated previously, a specific antibody response to the 1.7 (SEQUENCE I.D. NO. 604) recombinant protein was detected between 63–84 days PI. No antibody response to the 4.1 (SEQUENCE I.D. NO. 606) recombinant protein or to the 1.4 (SEQUENCE I.D. NO. 605) recombinant protein was detected. The tamarin was sacrificed on 161 days PI.

4. PCR Results on Tamarins (Titration/Transmissibilty Studies)

Sera obtained from T-1049 and T-1055 during the 8th week prior to inoculation and T-1038 on the day of inoculation, were negative by RT-PCR for sequences to clone 16 (SEQUENCE I.D. NO. 26) and clone 4 (SEQUENCE I.D. NO. 21). Tamarins T-1049 and T-1055 were positive for clone 4 sequences (SEQUENCE I.D. NO. 21) by RT-PCR 1 week after inoculation (clone 16 PCR was not done). Prior to the day of sacrifice, T-1049 (14 days PI) as well as T-1055 (11 days PI) were positive by RT-PCR for both clone 4 (SEQUENCE I.D. NO. 21) and clone 16 sequences (SEQUENCE I.D. NO. 26). Tamarin T-1038 was positive with both sets of primers on the day of sacrifice (14 days PI).

Figure 30:
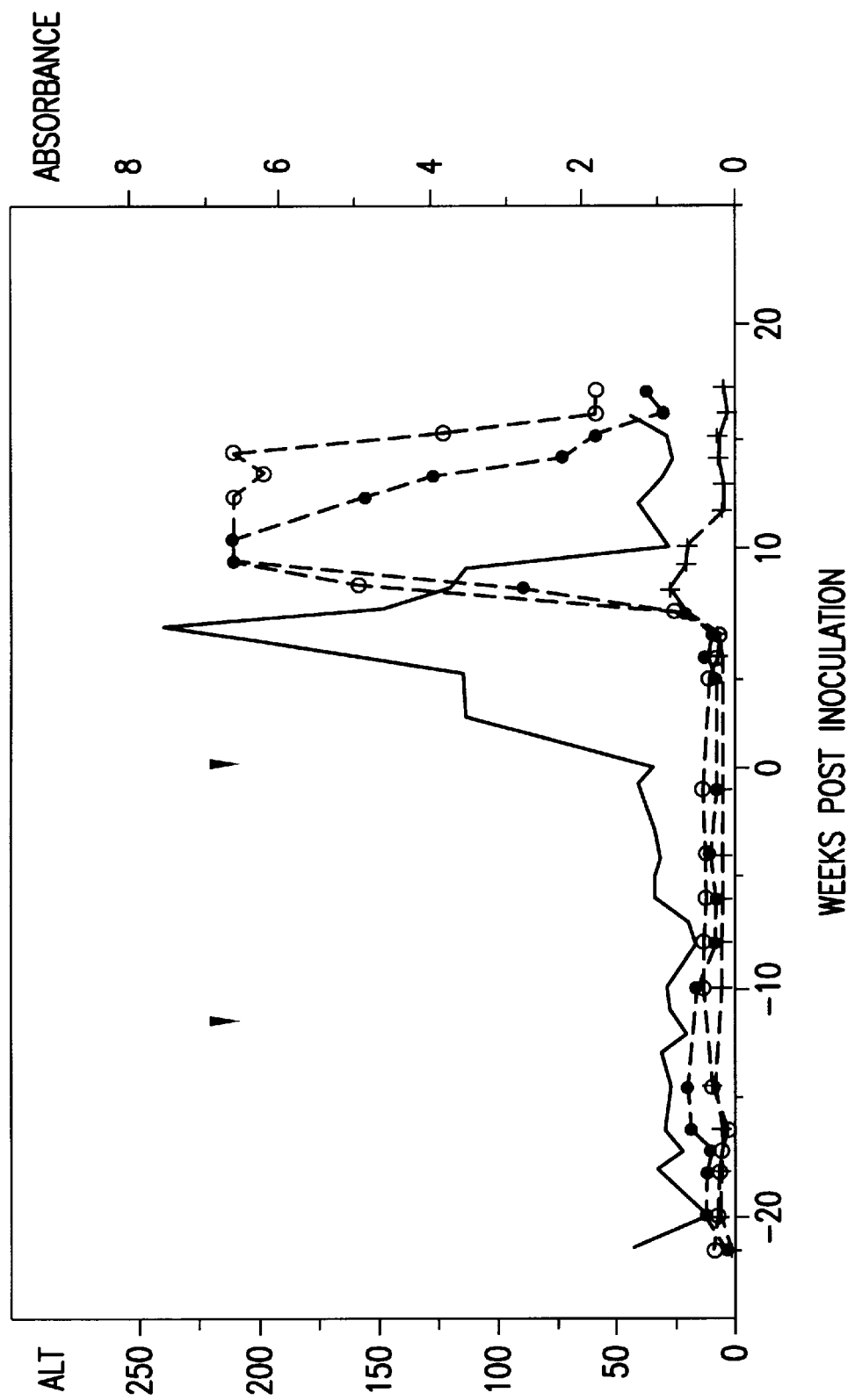

As seen in FIG. 30, T-1034 was positive by RT-PCR for sequences detected with clone 4 primers on the first serum sample obtained after inoculation (7 days PI) and remained positive to day 70 PI. A sample obtained on day 112 PI was negative. All of these samples were negative by RT-PCR with clone 16 primers. Samples obtained 70 and 101 days prior to inoculation were negative with both sets of primers.

As can be seen in FIG. 29 for tamarin T-1051, HGBV RNA was not detected with either set of primers (from clones 4 and 16 as described above) in the serum specimen obtained 8 weeks prior to inoculation. HGBV RNA was detected by RT-PCR using primers from clone 4 on six sera obtained between days 7–69 PI, but not on days 77, 84, 91, or 105 PI. HGBV RNA was detected by RT-PCR using primers from clone 16 on nine samples obtained after inoculation.

Figure 7:
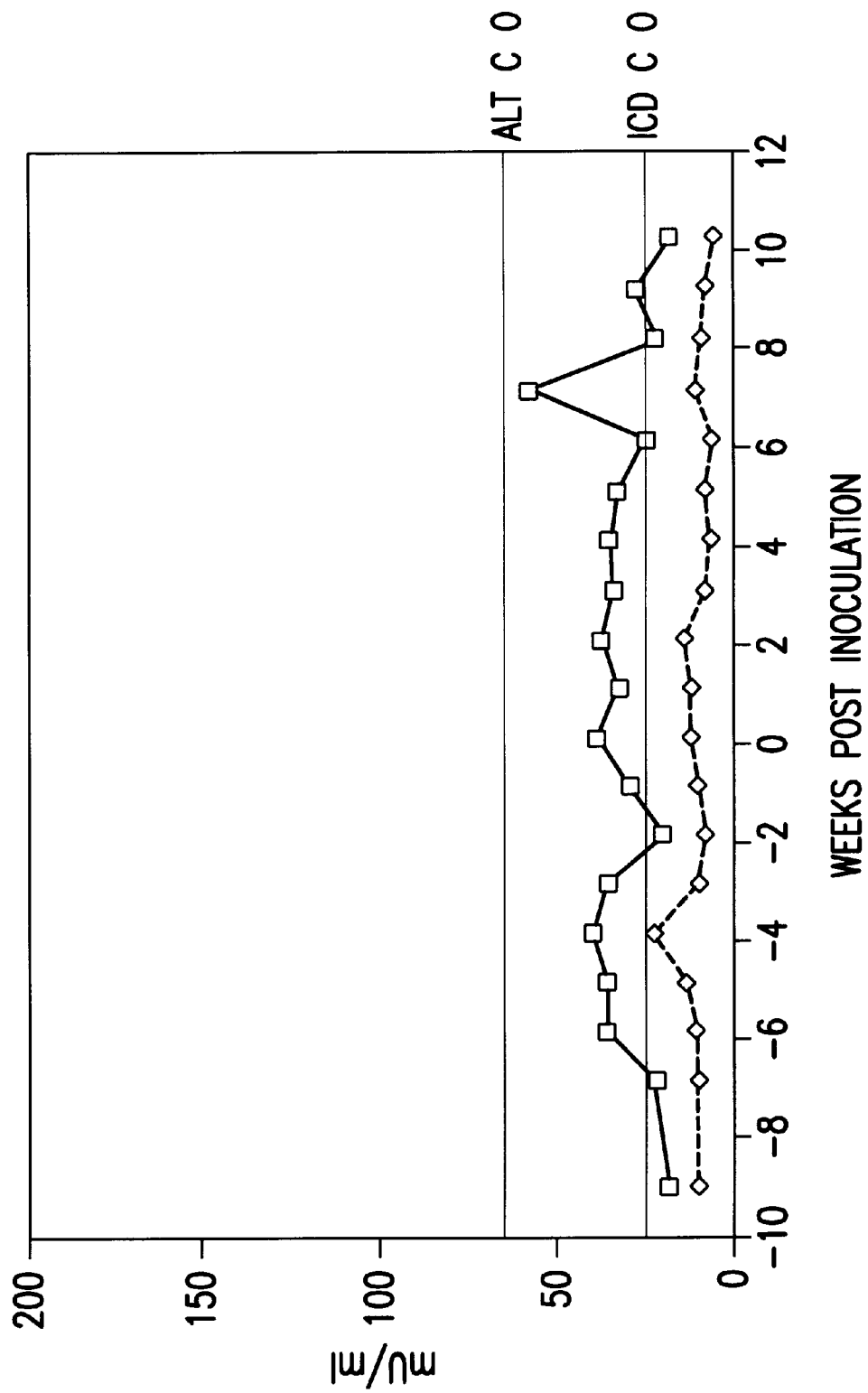
Figure 8:
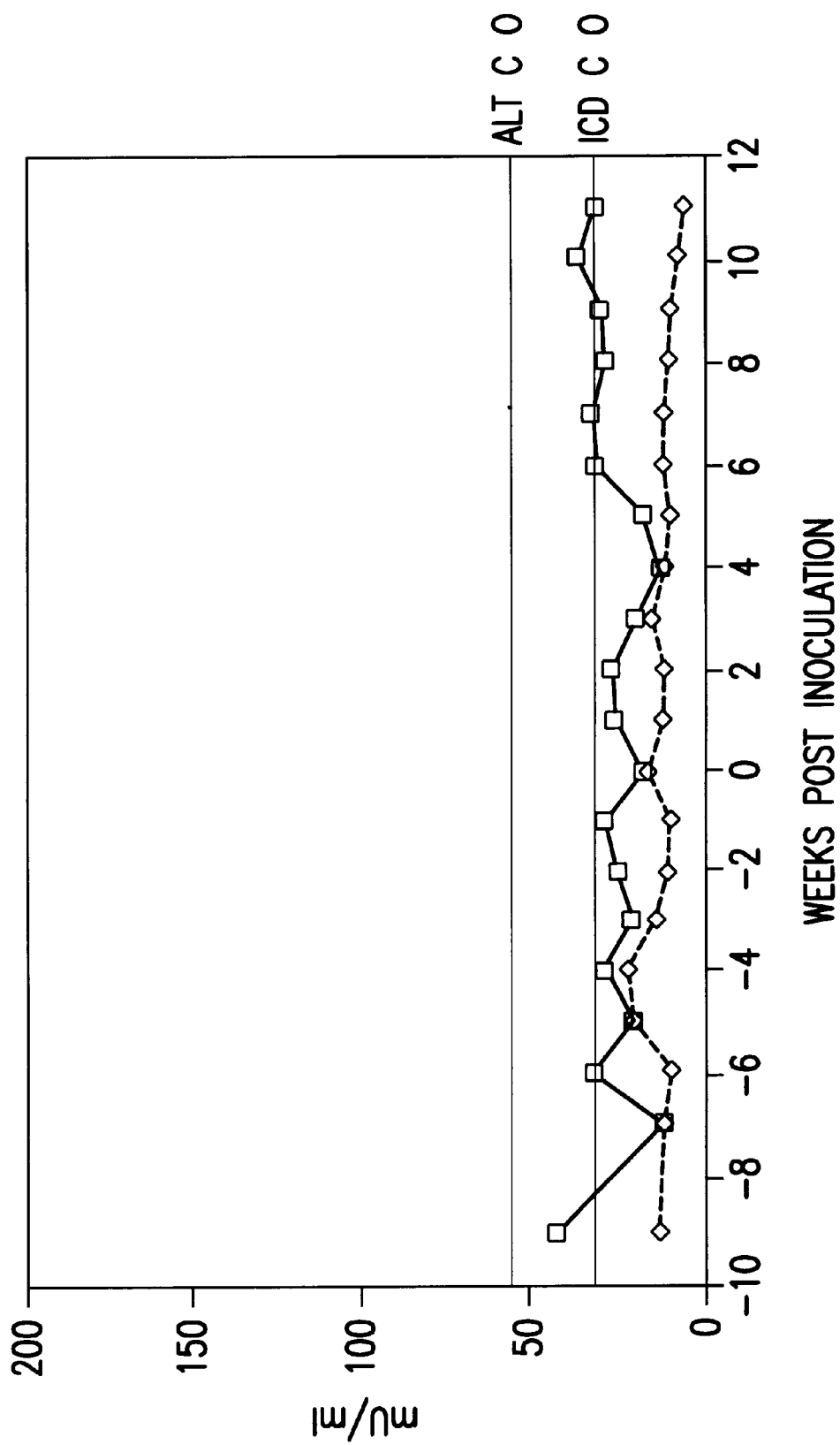

As seen in FIG. 7, T-1044 was positive by RT-PCR for sequences detected with clone 4 primers on the first serum sample obtained after inoculation (7 days PI) and remained positive to day 63 PI. Samples obtained between days 77–119 were negative. All of these samples were negative by RT-PCR with clone 16 primers. A sample obtained 42 days prior to inoculation was negative for both sets of primers.

Tamarins T-1047 and T-1056 were inoculated with T-1044 serum obtained 14 days PI. Nine samples obtained between 7–64 days PI from both of these animals were positive by RT-PCR with clone 4 primers (SEQUENCE I.D. NOS. 8 and 9) but negative with clone 16 primers.

Tamarin T-1058 was inoculated with neat T-1057 serum obtained 22 days after the challenge with T-1053 serum. This inoculum was positive for sequences detected with clone 16 primers but negative with clone 4 primers. Serum samples obtained from this animal were tested with primers derived from GBV-sequences [clone 16, clone 2 clone 10 and clone 18)] and GB-B sequences [clone 4 and clone 50]. A sample obtained 9 days prior to inoculation was negative with all primer sets. A sample obtained 14 days PI was positive only with clone 10 and 18 primers. A sample obtained 21 days PI was positive only with clone 16, 10 and 18 primers. A sample obtained 28 days PI was positive only with clone 18 primers. A sample obtained 35 days PI was positive only with clone 2, 16 (and 18 primers. A sample obtained 41 days PI was positive only with clone 16 and 18 primers. All samples tested were negative with primers from clone 4 and clone 50.

5. Summary of Serological Studies in Tamarins

Five tamarins were inoculated with various preparations of HGBV and developed elevated liver enzyme values by two weeks PI. These elevations persisted for the next six to eight weeks. A specific antibody response to one or more HGBV recombinant antigens, 1.7, 1.4, and 4.1 was noted in all five tamarins. In all cases, the antibodies were first detected by six to ten weeks PI, and persisted for two to seven or more weeks. In general, the antibody levels peaked and then declined rapidly over the next several weeks. It is observed that the antibodies become detectable shortly after the liver enzyme values returned to normal levels, suggesting that the generation of antibodies may play a role in clearing the viral infection.

6. Summary of PCR Studies on Tamarins

The results of the genomic walking experiments suggest that clone 4 (SEQUENCE I.D. NO. 21) and clone 16 (SEQUENCE I.D. NO. 26) reside on separate RNA molecules. We previously provided arguments that supported the idea that there are two distinct viral genomes, one comprised partly of clone 4 (SEQUENCE I.D. NO. 21) and one comprised partly of clone 16 (SEQUENCE I.D. NO. 26). The observation that some animals are positive with primers from clone 4 and not with primers from clone 16 supported the existence of two distinct viral genomes. However, it can also be argued that the inability to detect clone 16 (SEQUENCE I.D. NO. 26) sequence in some of the infected tamarins may reflect a lower limit of sensitivity of the clone 16 primer set relative to the clone 4 primer set. If this latter possibility was the case, then a tamarin positive for both primer sets should exhibit a difference in sensitivity with these two primer sets. In order to support the explanation that these results are explained by the existence of two separate viruses, and not differences in sensitivities of these two primer sets, PCR was performed on a dilution series of cDNA from tamarins T-1057 and T1053. T-1057 serum was positive at $5 \times 10^{-3}$ but negative at $5 \times 10^{-4}$ $\mu$l serum equivalents with clone 4 primers. As much as 20 $\mu$l of T-1057 serum was used for RT-PCR with clone 16 primers with negative results. If this difference was due to the relative sensitivity of the two primer sets (clone 4 vs. clone 16), one would expect that other specimens would also show a 4000 fold higher endpoint dilution when tested by PCR. However, cDNA derived from T-1053 serum was found to be positive at $2.5 \times 10^{-4}$ but negative at $2.5 \times 10^{-5}$ ul serum equivalents for both clone 4 (SEQUENCE I.D. NO. 21) and clone 16 (SEQUENCE I.D. NO. 26) sequences. These observations are therefore not consistent with a difference in sensitivity of primer sets but are consistent with the existence of contig B-clone 4 (SEQUENCE I.D. NO. 21) and contig A-clone 16 (SEQUENCE I.D. NO. 26) sequences on separate viral genomes of roughly equal titer in T-1053 but differing in titer by at least 4000 fold in T-1057. This data is therefore consistent with the existence of two separate viruses which may have different relative endpoint titers in different specimens.

The observation that HGBV-B viremia alone was sufficient to cause elevations in liver enzyme levels and that no elevations were observed during a GBV-A-only viremic stage, indicated that HGBV-B was the probable causative agent for hepatitis in these tamarins. The immune response to the HGBV-B antigens appeared to be for a short duration, at most 150 days PI. One explanation could be that the selection of epitopes used in these ELISAs was not from the dominant epitopes to which the immune response is generated. Another explanation could be that in tamarins the hepatic challenge may not be significant enough to necessitate a long-lived response. This is consistent with histological evidence from animals that were sacrificed during the acute phase of the disease or had died of natural causes some time after the acute phase which showed that hepatic inflammation ranged from mild to not significant (results not shown).

Five of six animals described in this study resolved viremia of HGBV-B by 112 days PI. In contrast, Tamarin T-1048 remained viremic for 136 days and was found to be viremic at the time of death (137 days PI). Of the four animals that were positive for GBV-A sequence, three showed resolution by 77 days after the first appearance of GBV-A sequence. In contrast, tamarin T-1061 was viremic for 245 days up to the time the animal was sacrificed. In addition, tamarin T-1051 was viremic up to the time of sacrifice (day 113 PI), however, it is unclear if this persistent viremia is due to the initial inoculation with T-1053 plasma or a result of the subsequent challenge with additional T-1053 plasma 69 days later.

The average peak ALT value for the six animals positive for both HGBV-A and HGBV-B was higher than the average value for the four HGBV-B-only animals. In addition, the peak value occurred, on average, earlier in animals positive for GBV-A and GBV-B than for animals positive only for GBV-B. These results suggest that the intensity of the hepatitis may be related to the presence of both agents at significant levels. The observation from the additional passage of GBV-B into tamarins T-1047 and T-1056 that minimal elevation in liver enzymes occurred with GBV-B viremia supports this assumption that both agents may be necessary for major elevations in ALT levels to occur in tamarins. In addition to the passage of HGBV-B alone, initial results from the inoculation of T-1058 with HGBV-A inoculum suggest that HGBV-A can be transmitted independent of any detectable HGBV-B as indicated by the absence of any detectable GB-B sequences with clone 4 and clone 50 primers.

F. Experimental Protocol for Demonstrating Exposure to HGBV in Human Populations Specimens were obtained from various human populations and tested for antibodies to HGBV utilizing three separate ELISA's utilizing recombinant proteins derived from HGBV-B. The 1.7 ELISA utilized the CKS-1.7 recombinant protein (SEQUENCE I.D. NO. 604) coated onto the solid phase; the 1.4 ELISA utilized the CKS-1.4 recombinant proteins (SEQUENCE I.D. NO. 605) coated on the solid phase and the 4.1 ELISA utilized the 4.1 recombinant protein (SEQUENCE I.D. NO. 606) coated on the solid phase as described in Example 15.B. As also noted in Example 15.E, tamarins inoculated with HGBV produce a specific, but short-lived antibody response to these proteins. In view of the transient nature of this detectable immune response, a negative result in human populations would not necessarily exclude previous exposure to HGBV.

The objective of the serological studies conducted with human specimens was two-fold. First, the seroprevalence of antibodies to the current HGBV recombinant antigens in various human populations was to be determined. These studies included testing (1) populations considered at low risk for exposure to HGBV (e.g. healthy volunteer blood donors in U.S.); (2) populations considered to be "at risk" for exposure to HGBV (e.g. specimens obtained from intravenous drug users and hemophiliacs are frequently seropositive for parenterally transmitted hepatitis viruses (HBV and HCV); specimens obtained from individuals residing in developing nations are frequently seropositive for enterically transmitted viruses (HAV and HEV); (3) panels of specimens obtained from individuals with "non-A–E hepatitis" that is not associated with exposure to known hepatitis viruses (HAV, HBV, HCV, HDV or HEV) or to other viruses associated with hepatitis such as cytomegalovirus (CMV) or Epstein-Barr Virus (EBV). In some cases, members of the panels under the general heading of non A–E hepatitis were not tested for antibodies to HEV. Therefore, all specimens in the non A–E group which were reactive with the 1.7, 1.4 or 4.1 ELISA's were retested with an HEV ELISA assay (available from Abbott Laboratories, Abbott Park, Ill.). Positive anti-HEV results were noted with samples from three sites (Pakistan, U.S. and New Zealand), as explained hereinbelow.

One would expect to observe higher seroprevalence rates among populations "at risk" for exposure to HGBV and among individuals with non-A–E hepatitis, than among populations considered to be at "low risk" for exposure to HGBV.

The second objective of the serological studies was to examine specimens found to be positive for antibodies to one or more HGBV epitopes by RT-PCR to determine if the virus is present in serum. It is well known that HBV and HCV can establish a viremic state which persists for months or years, and in general, that HAV and HEV establish a short-lived viremia persisting in general for several weeks. In cases of HBV and HCV infection which are acute, resolving hepatitis, the viremic stage may also be short-lived persisting for several weeks. Thus, RT-PCR can be used to provide evidence that the virus is present in an infected individual. However, because the viremic state can be short-lived, a negative RT-PCR result for a given agent can be observed in individuals who are infected with that agent.

G. Cutoff Determination

Previous experience with other ELISA's utilizing the indirect assay format indicated that a preliminary cutoff value can be calculated based on the absorbance values obtained on a population presumably negative for antibodies to the protein being studied. A preliminary cutoff value was calculated as the sum of the mean absorbance value of the population plus 10 standard deviations from the population mean. Since the cutoff value was to be used every time a panel was run, a more convenient method to express the cutoff was as a factor of the negative control (pool of normal human plasma—NHP) which was run in replicates of five for each assay run. For the 1.7, 1.4 and 4.1 ELISA's, the negative control typically had an absorbance value of between 0.030 and 0.060. As described below, the cutoff values were calculated to be at an absorbance value of approximately 0.300 to 0.600, which was equivalent to an absorbance signal of ten times the negative control value. Thus, in order for a specimen to be considered reactive, the ratio of the sample (S) absorbance value to the negative (N) control absorbance value (S/N ratio) had to be equal to or greater than 10.0.

H. Supplemental Testing

Specimens which were initially reactive were typically retested in duplicate. If one or both of the retest absorbance values were above the cutoff value, the specimen was considered repeatably reactive. Specimens which were repeatably reactive were then tested with supplemental assays which may further support the ELISA data. Repeatably reactive specimens which had sufficient volume may be tested by Western blot to determine that the antibody response was directed against the CKS-1.7 (SEQUENCE I.D. NO. 604), a CKS-1.4 (SEQUENCE I.D. NO. 605) or CKS 4.1 (SEQUENCE I.D. NO. 606) antigens and not to *E. coli* proteins which may have been co-coated on the solid phase with the major protein of interest. For a Western blot result to be considered positive, a visible band had to be detected at 80 kD for the 1.7 protein (SEQUENCE I.D. NO. 604), 60–70 kD for the 1.4 protein (SEQUENCE I.D. NO. 605) or at 42 kD for the 4.1 protein (SEQUENCE I.D. NO. 606). Since the Western blot has not been optimized to match or exceed the sensitivity of the ELISA's, a negative result was not used to discard the ELISA data. However, a positive result reinforced the reactivity detected by the ELISA's.

Repeatably reactive specimens which had sufficient volume may be tested by RT-PCR (performed as described in Example 15.D using clone 4 primers to identify HGBV specific nucleotide sequences in serum. A positive result would indicate a viremic specimen and would ultimately help in establishing the role of HGBV in human hepatitis. A negative result, however, was not to be construed to indicate that the ELISA results was incorrect. As noted in the tamarin study in Example 15.E, RT-PCR results were positive in the first several weeks after infection and then became negative at about the time when antibodies were just beginning to be detected with the current ELISA's. These later specimens may be RT-PCR negative but positive in one or both of the ELISA's.

1. Serological Data Obtained with Low-Risk Specimens

A population consisting of 100 sera and 100 plasma was obtained from healthy, volunteer blood donors in Southeastern Wisconsin and tested for antibodies to the 1.7 (SEQUENCE I.D. NO. 604) and 1.4 (SEQUENCE I.D. NO. 605) and 4.1 (SEQUENCE I.D. NO. 606) recombinant proteins utilizing the ELISA's described above. The absorbance values obtained with the 1.7, 1.4 and 4.1 ELISA's for serum and plasma were plotted separately (FIGS. 9–14).

For the 1.7 ELISA, the mean absorbance values for the serum and plasma specimens were 0.072 [with a standard deviation (SD) of 0.061] and 0.083 (SD=0.055), respectively. Thus, for the 1.7 ELISA's, the tentative cutoff values for serum and plasma were 0.499 and 0.468, respectively. As discussed above, the cutoff also was expressed as a factor of the negative control absorbance value: specimens having S/N values above 10.0 were considered reactive. Using this cutoff value, 0 of 200 specimens tested for antibodies to 1.7 (SEQUENCE I.D. NO. 604).

For the 1.4 ELISA, several specimens (three from the serum population and six from the plasma population) had absorbance values greater than 0.300 (S/N's of 6–12, near or above the expected cutoff value). When retested, all nine of these specimens produced S/N values of less than 10.0. The mean absorbance value for the serum and plasma specimens were 0.072 (SD=0.052) and 0.108 (SD=0.062), respectively. The cutoff for the 1.4 ELISA was calculated using the formula described above; the cutoff values for serum and plasma populations were 0.436 and 0.542, respectively. One specimen from the serum population was initially reactive and when re-tested in duplicate was negative. Two specimens from the plasma population were initially reactive but were negative upon re-test. A second population of 200 normals was tested including 100 plasma and 100 serum. Using the proposed cutoff, two plasma and two sera were repeatably reactive.

For the 4.1 ELISA, the mean absorbance values for the serum and plasma specimens were 0.070 [with a standard deviation (SD) of 0.037] and 0.063 (SD=0.040), respectively. Thus, for the 4.1 ELISA, the tentative cutoff values for serum and plasma were 0.329 and 0.511, respectively. As discussed above, the cutoff also was expressed as a factor of the negative control absorbance value; specimens having S/N values above 10.0 were considered reactive. Using this cutoff value, 0 of 100 plasma specimens and 0 of 100 serum specimens were initially reactive for antibodies to 4.1 (SEQUENCE I.D. NO. 606).

An additional 760 plasma donors from the Interstate Blood Bank (Ohio) were tested with the 1.7 and 1.4 ELISAs. A total of 9 specimens were repeatably reactive. None of the specimens were reactive in both ELISAs. All 9 specimens were repeatably reactive with the 1.4 ELISA.

In total, 960 specimens from plasma or blood donors residing in the U.S. were tested for antibodies to the 1.7 and 1.4 proteins. A total of 13 specimens were repeatebly reactive by the 1.4 ELISA. None of the specimens were repeatably reactive with the 1.7 ELISA.

In summary, these data indicate that, with the existing ELISA's, a total of 13 of 960 specimens obtained from U.S. blood donors were reactive for antibodies in one or more of the ELISA's employing recombinant antigens from HGBV-B. These data suggest that HGBV may be endemic in the U.S.

These data are summarized in TABLE 16.

J. Specimens Considered "At Risk" for Hepatitis

The data for these studies is summarized in TABLE 16.

(i) Specimens from West Africa

A total of 181 of 1300 specimens obtained from West Africa were repeatably reactive in one or more of the ELISA's. One specimen was repeatably reactive in all 3 ELISA's. A total of 43 specimens were repeatably reactive with the 1.7 ELISA, 91 specimens were repeatably reactive with the 1.4 ELISA and 51 specimens were repeatably reactive in the 4.1 ELISA.

One of six specimens repeatably reactive in the 1.7 ELISA was reactive by Western blot for the 1.7 protein (SEQUENCE I.D. NO. 604). Nine of 9 specimens (100%) which were repeatably reactive in the 1.4 ELISA were positive by Western blot for antibodies to the 1.4 protein (SEQUENCE I.D. NO. 605). One specimen was positive by Western blot for both proteins. Twelve of 12 specimens (100%) repeatably reactive in the 4.1 ELISA were positive by Western blot for the 4.1 protein (SEQUENCE I.D. NO. 606).

Three repeatably reactive specimens (including one specimen positive in the 1.4 ELISA and one specimen positive in both ELISA's and both Western blots) were tested for HGBV RNA by RT-PCR using primers from clone 4 as described above. All three specimens were negative by RT-PCR.

These data suggest that HGBV may be endemic in West Africa.

(ii) Specimens from Intravenous Drug Users (IVDU's)

Set 1: Three of 112 specimens were positive with the 1.4 ELISA. Five specimens were reactive on 4.1 ELISA and three on 1.7 ELISA. Two samples were positive on more than one ELISA.

Set 2: A total of 99 specimens were obtained from a population of intravenous drug users, as part of a study being conducted at Hines Veteran's Administration Hospital, in Chicago, Ill. None of these specimens were reactive in the 1.7 or 4.1 ELISA. One specimen was repeatably reactive in the 1.4 ELISA. This repeatedly reactive specimen was tested for HGBV RNA by RT-PCR using primers from clone 4 as described above. This specimen was RT-PCR negative.

K. Specimens Obtained from Individuals With non A–E Hepatitis

The data for these studies is summarized in TABLE 16.

Various populations of specimens were obtained from individuals diagnosed as having non-A–E hepatitis and tested with the 1.7, 1.4, and 4.1 ELISA's described in Example 15.C. These specimens included: 180 specimens obtained from a Japanese clinic; 56 specimens from a clinic in New Zealand; 73 specimens obtained from a clinic in Greece; 132 specimens from a clinic in Egypt; 64 specimens from a U.S. clinic in Texas (set T), 72 specimens from a research center in Minnesota (set M); 62 specimens from U.S. (set #1); 82 specimens obtained from a clinic in Pakistan; 10 specimens from a clinic in Italy. (Due to insufficient volumes of some sera, certain specimens from these groups were not tested on all of the available ELISAs).

(i) Specimens from Japan

These 180 specimens were obtained from 85 different patients. These two reactive specimens came from 2 individuals. A total of 2 of 180 specimens were repeatably reactive in the 1.7 ELISA. These 2 specimens were tested by RT-PCR using primers from clone 4 as described above. None of the specimens were positive.

None of the specimens were positive in the 1.4 ELISA.

For the 4.1 ELISA, seven of 89 specimens were repeatably reactive in the 4.1 assay. (Note: these 89 specimens were obtained from 29 different patients). Five of the reactive specimens were obtained from one patient. The remaining two were from a different patient.

(ii) Specimens from New Zealand

A total four of 56 specimens were repeatably reactive in one or more of the ELISA's 1.7, 1.4, and 4.1. None of these specimens were reactive in two or more ELISA's. One specimen was repeatably reactive in the 1.7 ELISA and two specimens were repeatably reactive in the 1.4 ELISA. One specimen was repeatably reactive with the 4.1 ELISA. PCR was performed on two repeatably reactive specimens; both specimens were negative. One specimen which was repeatably reactive in the 1.4 ELISA was also reactive for antibodies to HEV.

(iii) Specimens from Greece

A total of 5 of 73 specimens were found to be reactive for antibodies in the 1.7 and/or 1.4 ELISA's. These 73 specimens were obtained from a total of 11 patients. Two of the five repeatably reactive specimens were repeatably reactive for both ELISA's and were obtained from one individual on different dates. Two repeatably reactive specimens were tested by RT-PCR and were negative. None of these specimens were reactive for antibodies with the 4.1 ELISA.

(iv) Specimens from Egypt

Figure 31:
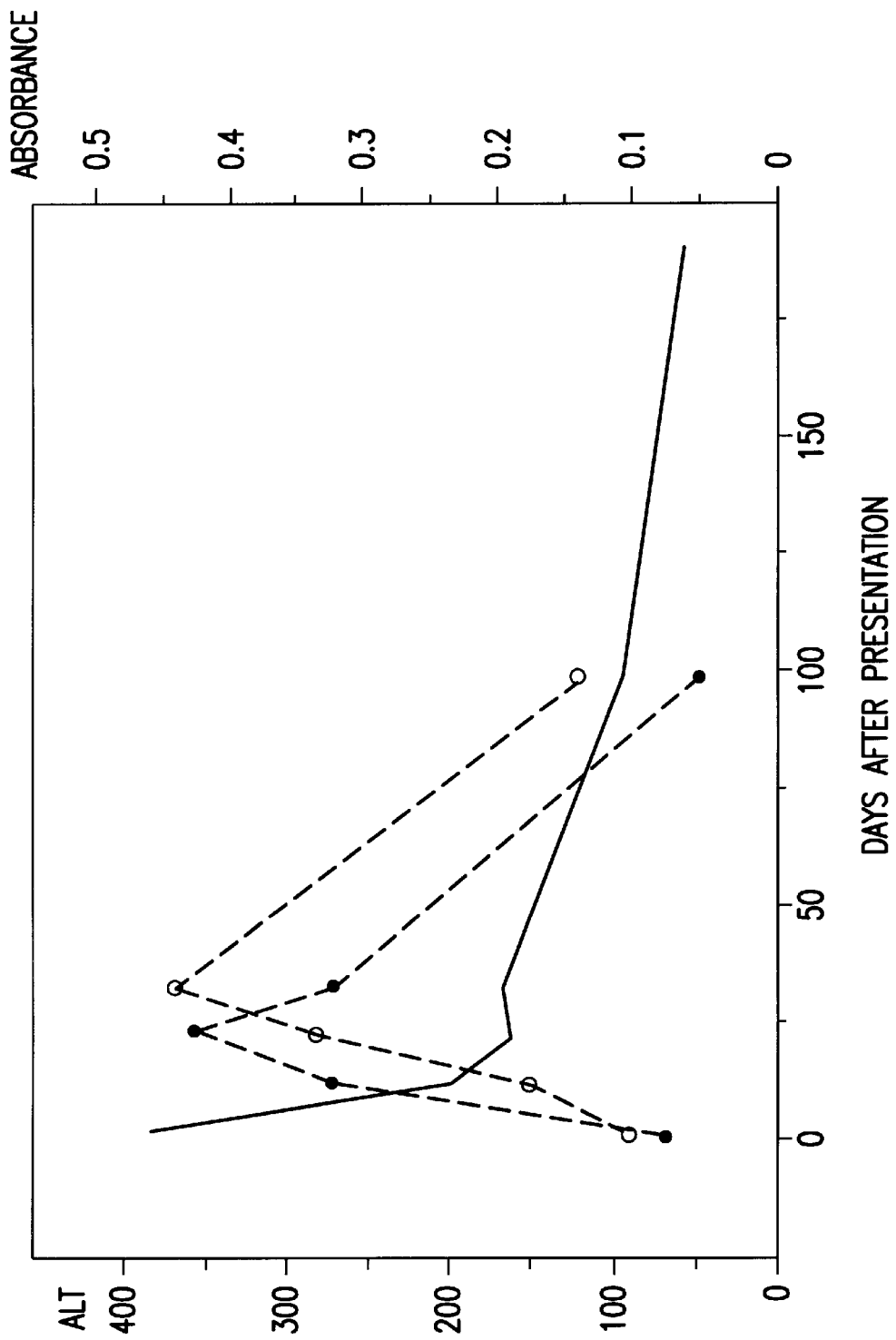
Figure 32:
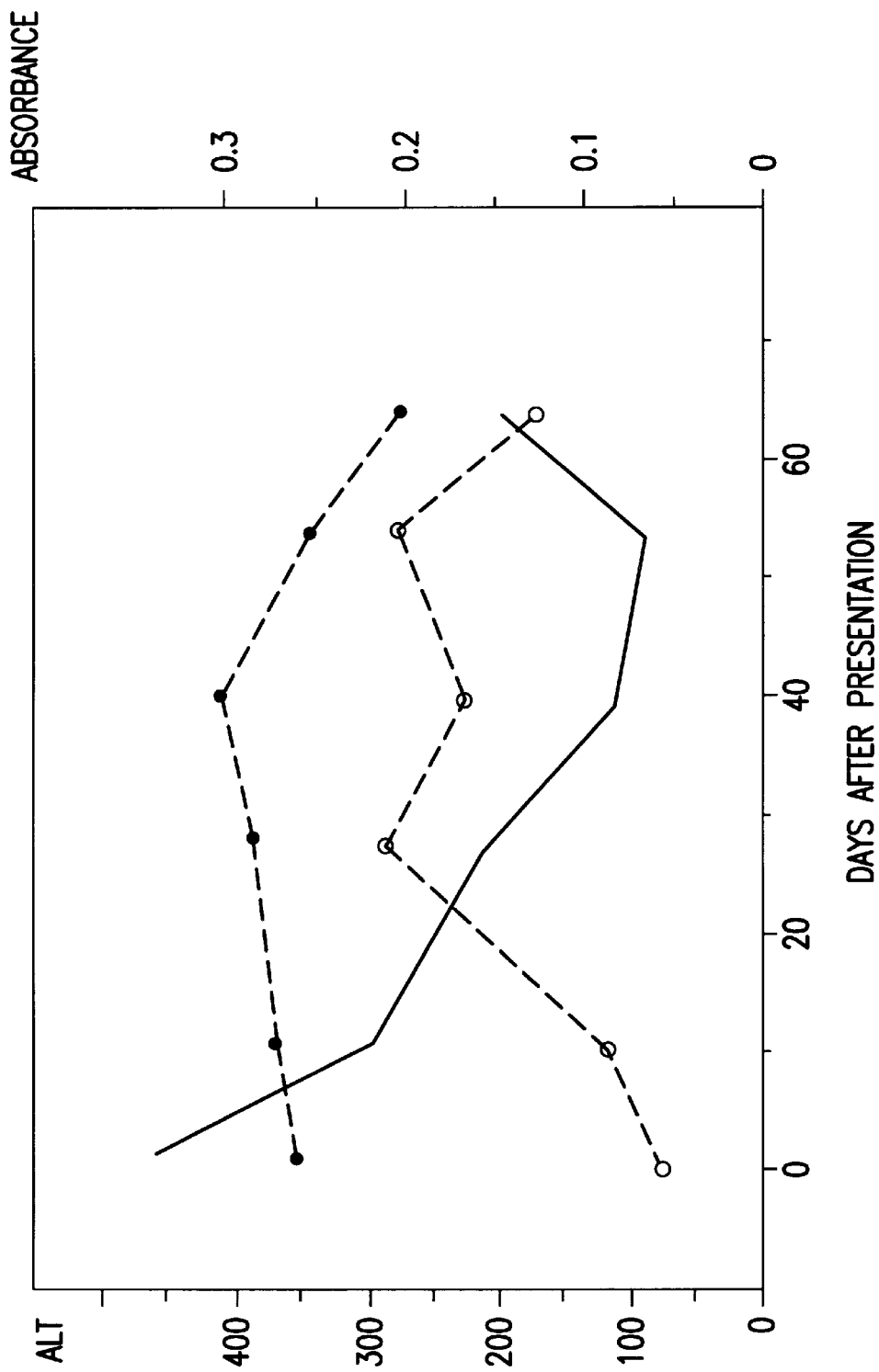
Figure 33:
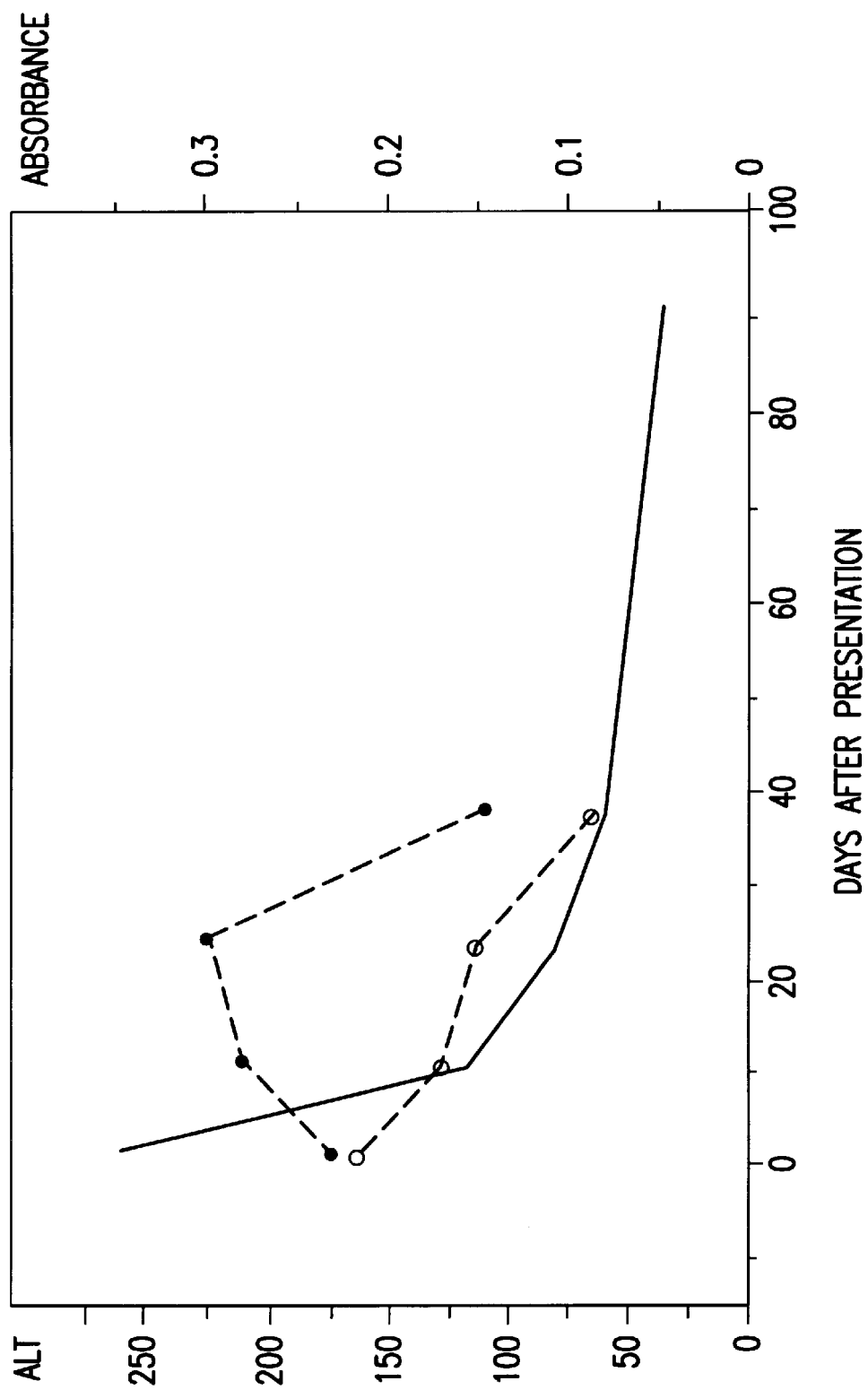
Figure 34:
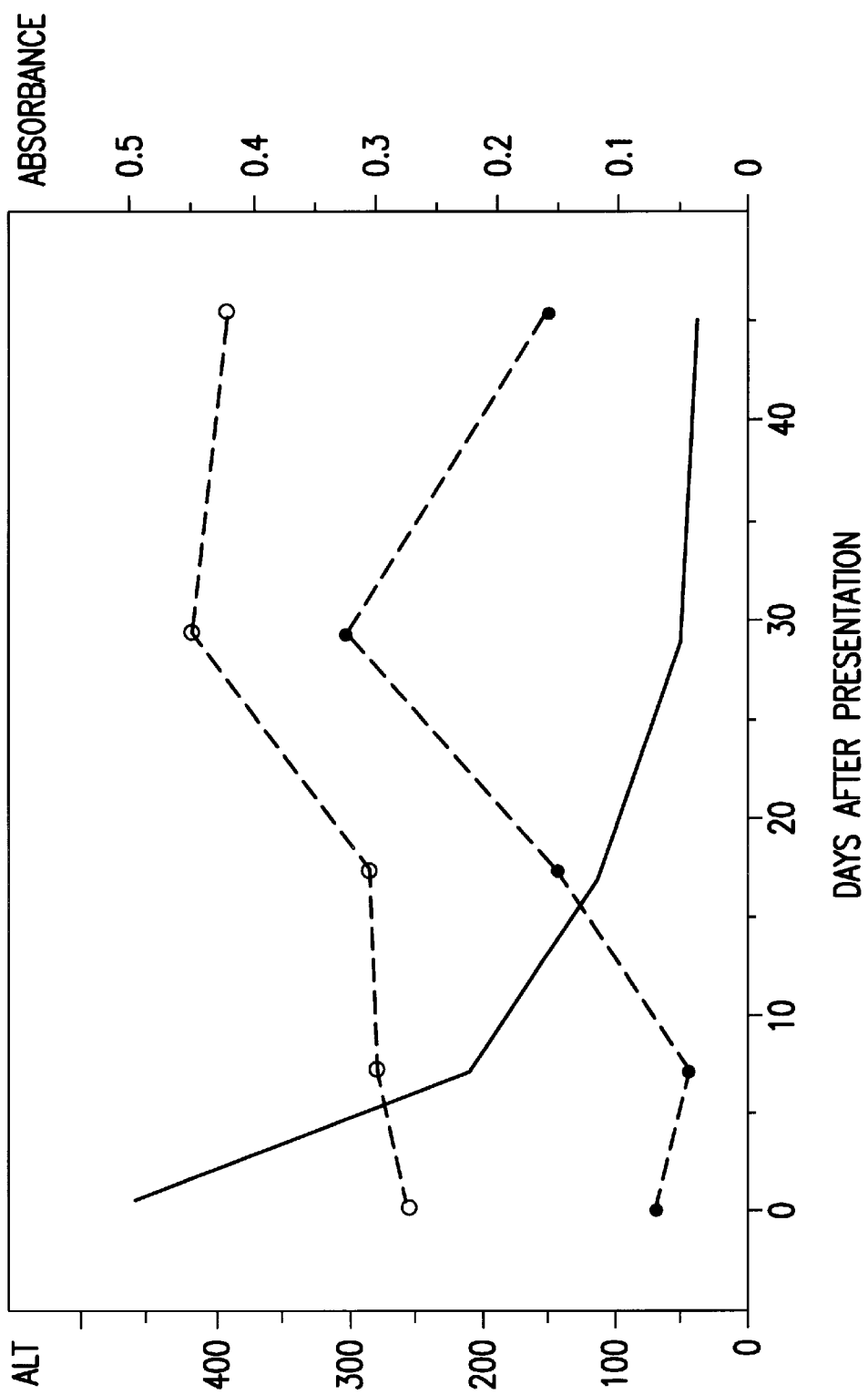

A total of 11 of 132 specimens were reactive in the 1.7, 1.4, or 4.1 ELISA's. Eight specimens were positive in both the 1.7 and 1.4 ELISA's. Nine specimens were reactive for antibodies in the 1.7 ELISA and 9 specimens were reactive in the 1.4 ELISA. One specimen repeatably reactive in the 4.1 ELISA but negative in the 1.7 and 1.4 ELISAs. One specimen repeatably reactive in the 1.7 ELISA was tested by Western blot and was negative for antibodies to the 1.7 recombinant protein (SEQUENCE I.D. NO. 604). Six of nine specimens repeatably reactive in the 1.4 ELISA tested positive by Western blot for antibodies to the 1.4 recombinant protein (SEQUENCE I.D. NO. 605). Seven of the repeatably reactive specimens were tested by RT-PCR; none of the specimens were reactive. These 132 specimens were obtained on different dates from 25 different individuals. The 11 repeatably reactive specimens were obtained from five different individuals. For one of these individuals (patient #101), the immune response clearly mimics that observed with the tamarins (FIG. 31). Note that in FIG. 31, the ALT levels were elevated at the time of presentation of symptoms to the physician. In subsequent specimens, the ALT levels declined and antibodies were detected utilizing the 1.4 and 1.7 ELISA's. The antibody response declined over the next several weeks as was noted with the serologic profiles observed in the tamarins. Three additional patients (257, 260, and 340) exhibited serologic patterns similar to patient #101 (as shown in FIGS. 32–34. These data provide supportive evidence that HGBV may be the etiologic agent in these cases of hepatitis.

None of the seven specimens obtained from these four patients were positive for HGBV RNA by RT-PCR. There are several potential reasons for these results. First, the viremic phase may have been very short-lived: the virus may have been cleared from the serum by the time of the first bleed date. Secondly, these specimens were shipped from Egypt and may potentially have been frozen and thawed or otherwise compromised during the storage and shipping process, thus reducing the potential to detect HGBV RNA.

(v) Specimens from U.S. (Set T)

None of 64 specimens from the U.S. (set T) were repeatably reactive in the 1.7, 1.4 or 4.1 ELISA.

(vi) Specimens from U.S. (Set M)

A total of 4 of 72 specimens from U.S. specimens (set M) were repeatably reactive in one or more of the ELISA's. Two specimens were reactive with the 1.7 and 4.1 ELISA's. One specimen was reactive only with 1.7 and one specimen was reactive only with the 4.1 ELISA.

vii) Specimens from the United States (set 1)

A total of three of 51 specimens from non A–E hepatitis U.S. set 1 were repeatably reactive in one or both of the ELISA's. One specimen was repeatably reactive in both ELISA's. One specimen was reactive in the 1.7 ELISA and three specimens were repeatably reactive in the 1.4 ELISA. The specimen positive in both ELISA's was positive by Western blot for the 1.4 recombinant protein (SEQUENCE I.D. NO. 22) but negative for the 1.7 recombinant protein (SEQUENCE I.D. NO. 23). One additional specimen was positive in the 1.4 ELISA and Western blot positive for the 1.4 recombinant protein (SEQUENCE I.D. NO. 605). One specimen which was repeatably reactive in the 1.4 ELISA was reactive for antibodies to HEV.

(viii) Specimens from Pakistan

A total of four of 82 specimens were repeatably reactive for antibodies in 1.4 and/or 1.7 ELISAs. None of the specimens were reactive in both ELISA's. Two specimens were repeatably reactive in the 1.7 ELISA and two specimens were repeatably reactive in the 1.4 ELISA. Two specimens repeatably reactive in the 1.4 ELISA were also reactive for antibodies to HEV. None of these 82 specimens were positive with the 4.1 ELISA.

(ix) Specimens from Italy

None of the ten specimens were repeatably reactive in the 1.7, 1.4, or 4.1 ELISA.

L. Statistical Significance of Serological Results

These data indicate that specific antibodies to HGBV proteins (i.e. specimens repeatably reactive for antibodies in 1.7, 1.4, or 4.1 ELISA's can be detected in all three categories of populations studied. Serological results obtained with the various categories of specimens ("low risk", "at risk" and non A–E hepatitis patients) were grouped together and analyzed for statistical significance using the Chi square test. The data indicated that there is a significant difference in comparing the seroprevalence of anti-HGBV in volunteer blood donors with either the individuals considered "at risk" for exposure to HGBV or to individuals diagnosed with hepatitis of an unknown etiology.

Among West Africans, the seroprevalence rate is 13.9% and is significantly higher than the baseline group (TABLE 17) with a p value of 0.000. Similarly, for the IVDU's, there was a statistically significant difference (p value of 0.000) when the results from IVDU's were compared with volunteer donors. In countries (including Japan, New Zealand, U.S., Egypt, and Pakistan), there were significant differences in antibody prevalence in patients with non A–E hepatitis when compared to the volunteer blood donors from the U.S.

H. Summary

These data suggest that the ELISA's described herein may be useful in diagnosing cases of hepatitis in humans in various geographical regions including Japan, New Zealand, U.S., Egypt, and Pakistan. It is likely that these data underestimate the seroprevalence of antibodies to HGBV among all categories of specimens tested. It is expected that as additional HGBV epitopes are discovered and evaluated, the utility of tests derived from the HGBV genome(s) will become more important in diagnosing hepatitis among patients whose diagnosis cannot currently be made. NOTE: Although the results of RT-PCR were negative in these initial studies, subsequent data revealed flavi-like vial sequences in serum of seropositive individuals (see Example 17).

As we have discussed supra, more than one strain of the HGBV is present. These are considered to be within the scope of the present invention and are termed "hepatitis GB Virus ("HGBV")".

Example 16

Serological Studies With HGBV-A

A. Recombinant Protein Purification Protocol

Bacterial cells expressing the CKS fusion proteins were frozen and stored at −70° C. The bacterial cells from each of the GBV-A constructs were thawed and disrupted as described in Example 15 for GBV-B constructs. Further, the recombinant proteins were purified as described for GBV-B recombinant proteins in example 15.

The fractions which were collected during the purification protocol were electrophoretically separated and stained with Coomassie Brilliant Blue R250 and examined for the presence of a protein having a molecular weight of approximately 60 kD (CKS 1.5/SEQUENCE NO. 608), 65 kD (CKS 2.17/SEQUENCE NO. 607), 55 kD (CKS 1.18/SEQUENCE NO. 387) and 66 kD (CKS 1.22/SEQUENCE NO. 387). Fractions containing the protein of interest were pooled and re-examined by SDS-PAGE.

The immunogenicity and structural integrity of the pooled fractions containing the purified antigen were determined by immunoblot following electrotransfer to nitrocellulose as described in Example 13. In the absence of a qualified positive control, the recombinant proteins were identified by their reactivity with a monoclonal antibody directed against the CKS portion of each fusion protein. When the CKS-1.5 protein (SEQUENCE I.D. NO. 608) was examined by Western blot, using the anti-CKS monoclonal antibody to detect the recombinant antigen, a single band at approximately 60 kD was observed. This corresponds to the expected size of the CKS-1.5 protein (SEQUENCE I.D. NO. 608). Similarly, bands of the expected sizes were noted for the CKS-2.17 protein (SEQUENCE I.D. NO. 607), the CKS 1.18 protein (SEQUENCE NO. 387) and the CKS-1.22 protein (SEQUENCE I.D. NO. 387) when examined by immunoblot.

B. Polystyrene Bead Coating Procedure

The proteins were dialyzed and evaluated for their antigenicity on polystyrene beads described in Example 15.

C. ELISA Protocol for Detection of Antibodies to HGBV

The ELISA's were performed as described in Example 15.

D. Detection of HGBV RNA in Serum of Infected Individuals

Specimens which were repeatably reactive in the ELISAs were tested for HGBV RNA as described in section D. of Example 15.

E. Tamarin Serological Profiles

None of the sera from the tamarins produced a specific immune response when tested in the ELISA utilizing the CKS 1.5 protein, the CKS 2.17 protein, the CKS 1.18 protein or the CKS 1.22 protein, all derived from the HGBV-A genome. However, HGBV-A RNA was detected in several of the infected tamarins as described in the previous example. (See Example 15 for a summary of the tamarin serological profiles).

F. Experimental Protocol for Serologic Studies on Human Populations

In Example 15, ELISA's employing recombinant antigens from HGBV-B were utilized to evaluate the presence of antibodies to HGBV-B in various human populations. Many of the same specimens were then tested for antibodies to HGBV-A utilizing the 1.5 ELISA employing the CKS-1.5 recombinant protein (SEQUENCE I.D. NO. 614), the 2.17 ELISA employing the CKS-2.17 recombinant protein (SEQUENCE I.D. NO. 607), the 1.18 ELISA employing the CKS-1.18 recombinant protein (SEQUENCE I.D. NO. 387), and the ELISA employing the CKS-1.22 recombinant protein (SEQUENCE I.D. NO. 387), coated on the solid phase (as described in Example 15). As noted in Example 15, all five of the convalescing tamarins inoculated with HGBV produced a specific but short-lived antibody response to the HGBV-B recombinant proteins (as detected with the 1.7, 1.4 and 4.1 ELISA's). Although none of the tamarins produced a detectable antibody response in the 1.5, 2.17, 1.18 or 1.22 ELISAs, some human specimens from West Africa produced a specific antibody response to one or more of these recombinant proteins when tested via Western blot and one of the specimens obtained from the surgeon (who was the source of the GB agent) at 22 days after onset of hepatitis produced a specific antibody response to the 2.17 recombinant protein when tested by Western blot (see Example 3). In the current example, we evaluated the utility of the 1.5, 2.17, 1.18 and 1.22 ELISA's in detecting antibodies in various human populations.

G. Cutoff Determination

The cutoff for the 1.5, 2.17, 1.18, and 1.22 ELISAs were determined as described in Example 15.

H. Supplemental Testing

As noted in Example 15, specimens which were initially reactive were typically retested; if the specimen was repeatably reactive, additional tests (e.g. Western blot) may be performed to further support the ELISA data. For a Western blot result to be considered positive, a visible band should be observed at 60 kD for the 1.5 protein (SEQUENCE I.D. NO. 608) at 65 kD for the 2.17 protein (SEQUENCE I.D. NO. 607), at 55 kD for the 1.18 protein (SEQUENCE I.D. NO. 389) at 66 kD for the 1.22 protein (SEQUENCE I.D. NO. 387). Since the Western blot had not been optimized to match or exceed the sensitivity of the ELISA's, a negative result was not used to discard the ELISA data. However, a positive result reinforced the reactivity detected by the ELISA's.

As also noted in Example 15, repeatably reactive specimens which have sufficient volume may be tested by RT-PCR (performed as described in Example 15) using primers to identify HGBV specific nucleotide sequences in serum.

I. Serological Data Obtained With Low-Risk Specimens

A total of 252 plasma specimens were obtained from the Interstate Blood Bank in Ohio and tested for antibodies with the 1.5 ELISA which utilizes the 1.5 recombinant protein (SEQUENCE I.D. NO. 608). The mean absorbance value for the population was 0.036 (SD=0.022). The cutoff was calculated to be 0.168, corresponding to an S/N value of 10.0. A total of 760 plasma specimens (including the 252 specimens utilized to determine the cutoff) were tested for antibodies with the 1.5 ELISA. None of the specimens were repeatably reactive. In addition, 100 plasma specimens were obtained from Southeastern Wisconsin and tested for antibodies with the 1.5 ELISA. None of the specimens were repeatably reactive.

Thus, there is no evidence that antibodies to the 1.5 protein were present in U.S. blood donors.

A total of 200 specimens were obtained from Wisconsin blood donors and tested for antibodies with the 2.17 ELISA which utilizes the 2.17 recombinant protein (SEQUENCE I.D. NO. 60). The mean absorbance value for the population was 0.058 (SD=0.025). The cutoff was calculated to be 0.208, corresponding to an S/N value of approximately 10.0. One of the specimens was repeatably reactive. Thus, the seroprevalence in U.S. blood donors (N=200) is relatively low.

The same 200 specimens described in the above paragraph were tested for antibodies with the 1.18 and 1.22 ELISAs. None of the specimens were repeatably reactive. Thus, there is no evidence that specimens from volunteer blood donors are antibody positive for HGBV-A proteins as determine by the 1.5, 2.17, 1.18 and 1.22 ELISAs.

J. Specimens Considered "At Risk" for Hepatitis

The data for these studies is summarized in TABLE 18.

(i) Specimens from West Africa

A total of 58 of 1300 specimens were reactive with the 1.5 ELISA. Twelve of 18 repeatably reactive specimens were positive by Western blot for antibodies to the 1.5 protein (SEQUENCE I.D. NO. 608). A total of 43 of 817 specimens were reactive in the 2.17 ELISA. These repeatably reactive specimens were not tested by Western blot for antibodies to the 2.17 protein (SEQUENCE I.D. NO. 607).

Six of the 817 specimens were reactive with the 1.22 ELISA. Nine of the 353 specimens were reactive for 1.18 ELISA. Twenty-one specimens reactive with the 2.17 ELISA were tested by Western blot and 13 were reactive. All eight specimens that were repeatably reactive with the 1.18 ELISA was positive by Western blot.

These data suggest that HGBV may be endemic in West Africa.

(ii) Specimens from Intravenous Drug Users

A total of 112 specimens were obtained from a population of intravenous drug users, as part of a study being conducted at Hines Veteran's Administration Hospital, in Chicago, Ill. One specimen was repeatably reactive in the 2.17 ELISA and an additional specimen was reactive in the 1.18 ELISA. None of these specimens were positive in the 1.5 or 1.22 ELISA.

K. Specimens Obtained From Individuals With Non A–E Hepatitis

The data for these studies is summarized in TABLE 18.

Various populations of specimens (described in Example 15.K) were obtained from individuals with non-A–E hepatitis and tested with the 1.5, 2.17, 1.18 and 1.22 ELISAs (described in Example 15.C). Due to insufficient sample volume, not all specimens were tested in all of the ELISAs.

(i) Specimens from Japan

A total of four of 89 specimens were repeatably reactive in the 1.5 ELISA, with three of the specimens being from one individual and one of the specimens from a second individual. One specimen which had tested negative for the 1.5 ELISA, the 1.18 ELISA and the 1.22 ELISA was reactive in the 2.17 ELISA.

None of the specimens were reactive in the 1.18 ELISA. These specimens were not tested with the 1.22 ELISA.

(ii) Specimens from New Zealand

None of these 56 specimens were reactive in the 1.5 ELISA. These specimens were not tested in the 2.17 ELISA, the 1.18 ELISA or the 1.22 ELISA.

(iii) Specimens from Greece

None of the 67 specimens (obtained from a total of 10 patients) were reactive for antibodies with the 1.5, 2.17 or 1.22 ELISA.

(iv) Specimens from Egypt

None of 132 specimens were reactive in the 1.5 ELISA. A total of 7 of 132 specimens available for testing were reactive in the 2.17 ELISA. These specimens were obtained from 25 individuals with acute non A–E hepatitis. Three of the 25 patients were seropositive in the 2.17 ELISA on one or more separate dates following the onset of hepatitis. None were reactive in the 1.18 or 1.22 ELISA.

(v) Specimen from the U.S. (Set M)

None of the 72 specimens were reactive with the 1.5 ELISA. Three of the 72 specimens were reactive for the 1.18 ELISA. Two of the specimens were reactive in the 2.17 ELISA and four specimens were reactive with the 1.22 ELISA. Two of the samples were reactive in one of more of the ELISAs.

(vi) Specimens from U.S. (Set T)

None of the 64 specimens were reactive with the 1.5, 1.22 or 2.17 ELISAs. One specimen was reactive for the 1.18 ELISA.

(vii) Specimens from U.S. (Set 1)

A total of 3 of 62 specimens were reactive in one or more of the GBV-A ELISAs. One specimen was repeatedly reactive in both the 2.17 and 1.22 ELISA. One specimen was reactive only in the 2.17 ELISA and an additional specimen was reactive only in the 1.22 ELISA. None of the specimens were reactive in the or 1.18 ELISA.

As we have discussed supra, it is possible that more than one strain of the HGBV may be present, or that more than one distinct virus may be represented by the sequences disclosed herein. These are considered to be within the scope of the present invention and are termed "hepatitis GB Virus ("HGBV").

L. Statistical Significance of Serological Results

These data indicated that specific antibodies to HGBV-A proteins (i.e. specimens repeatably reactive for antibodies in 1.5, 2.17, 1,18 and 1.22 ELISA's) were detected among individuals considered "at risk" for exposure to HGBV and among individuals diagnosed with non A–E hepatitis, but were not frequently detected either among volunteer or paid blood donors from the U.S. In TABLE 19, the serological results obtained with the various categories of specimens ("low risk", "at risk" and non A–E hepatitis patients as shown in TABLE 18) were grouped together and analyzed for statistical significance using the Chi square test. Unlike the data in TABLE 18, which compiled the seroprevalence of antibodies to HGBV proteins in the total number of specimens tested, the data in TABLE 19 reflect the results obtained with different individuals (persons). For the GBV-A ELISAs, the data indicate that there is a significant difference (with a p value of 0.000) in comparing the seroprevalence of anti-HGBV in volunteer blood donors with the individuals considered "at risk" for exposure to HGBV (West Africa) but not in the IVDUs. In addition, there was a statistically significant difference between the seroprevalence of antibodies to HGBV-A in individuals with non A–E hepatitis in Egypt and the U.S. when compared to volunteer donors These data suggest that exposure to HGBV-A was associated with non-A through E hepatitis. NOTE: although the results of RT-PCR were negative in these initial studies, subsequent data revealed flavi-like vial sequences in serum of seropositive individuals (see Example 19).

M. Summary

These data suggest that the ELISA described herein may be useful in detecting antibodies among individuals residing in West Africa and among individuals with non-A through E hepatitis. The risk for hepatitis among the West Africans is relatively high; nearly 85% of these individuals are seropositive for antibodies to Hepatitis B virus, and approximately 5% are positive for antibodies to hepatitis C virus. It is likely that these data underestimate the seroprevalence of antibodies to HGBV among all categories of specimens tested. It is expected that as additional HGBV epitopes are discovered and evaluated, the utility of tests derived from the HGBV genome(s) will become more important in diagnosing hepatitis among patients whose diagnosis cannot currently be made.

Example 18

Identification of a GB-Related Virus in Humans

A. Theory

Epitopes from both HGBV-A and HGBV-B have been identified (Example 3). These have been used as serologic markers to screen human serum and plasma samples (Examples 5 and 6). A significant correlation between seroreactivity with some of these markers and the incidence of non A–E hepatitis has suggested that HGBV-B is the causative agent of non A–E hepatitis in humans (Example 5.G). However, Western blot analysis of GB human sera gave no indication of reactivity to HGBV-B epitopes (Example 3). Instead, at least one HGBV-A epitope was identified with the GB human sera suggesting that HGBV-A was the causative agent of hepatitis in GB. Neither HGBV-A nor HGBV-B sequences have been identified in patients with non A–E hepatitis by RT-PCR (Example 5.E). Therefore, proof of HGBV-A and/or HGBV-B infection in humans with non A–E hepatitis remains to be determined.

The failure to identify HGBV-A and/or HGBV-B sequences in human sera or plasma sources may be due to several factors. First, we have looked at only a limited number of HGBV-A and/or HGBV-B-seropositive samples by RT-PCR, and the complete storage history of many of these samples is unknown. Thus, it is possible that viral RNA present in these samples was compromised by incorrect storage. Second, GB infection appears to be resolving in nature. As such, the window of time in which GB sequences are present in an infected individual's serum may be very narrow. Thus, the chances of obtaining serum samples containing GB sequences may be extremely low. Finally, a limited number of PCR primer sets were used to look for HGBV-A and/or HGBV-B sequences. HGBV-A and/or HGBV-B are RNA viruses and, therefore, are likely to have high rates of mutation (Holland, et al. (1982) *Science* 215:1577–1585). Thus, the sequence of HGBV-A and/or HGBV-B present in the examined human sera may be different enough from the sequence of our PCR primers such that HGBV-A and/or HGBV-B may be not be detected.

To address the possibility that the genomic variability of HGBV-A and/or HGBV-B prevented these viruses in our PCR studies, degenerate PCR primers were designed to the highly conserved NS3-like regions of HGBV-A and HGBV-B (see FIG. 17). It was reasoned that these highly conserved regions serve a necessary function in the viral replicative cycle. Therefore, these sequences should be maintained HGBV-A and HGBV-B variants. PCR primers designed within this region should be able to detect HGBV-A and/or HGBV-B genomic RNA by RT-PCR. In addition, by designing degenerate PCR primers that can specifically amplify HGBV-A, HGBV-B and HCV sequences, we reasoned that we might be able to amplify sequences from viruses related to HGBV-A, HGBV-B and HCV. Thus, if the limited seroreactivity detected in human serum and plasma samples (Examples 5 and 6) is the result of cross-reactive antibodies to antigens from distinct HGBV-A- or HGBV-B-related viruses, we may be able to obtain sequences from these GB-related viruses. [This is similar to the experimental approach that Nichol and colleagues took to identify the unique Hantavirus associated with the recent outbreak of acute respiratory illness in the Southwest United States. Nichol, et al. *Science* 262:914–917 (1993)].

B. Cloning the NS3-Like Region of Hepatitis GB Virus C (HGBV-C).

In several models of virus infections, viremia occurs during the early stages of infection and is often associated with the detection of IgM class antibodies to viral proteins. As noted in examples 5 and 6, several specimens were immunoreactive in ELISA's which detected IgG class antibodies to recombinant proteins derived from HGBV-A and HGBV-B. Additional ELISA's were performed to determine if IgM class antibodies could be detected to these proteins. Several seropositive specimens obtained from West African individuals (Example 5.E.i) were reactive for IgM class antibodies to the recombinant proteins (data not shown). These specimens were thought to have a high probability of containing virus. In addition, specimens obtained from HGBV-A- and HGBV-B-seropositive Egyptian individuals (Example 5.F.vii) suffering from acute hepatitis in the absence of detectable IgM class antibodies to HGBV-A or HGBV-B recombinant proteins were also examined due to the likelihood that acute liver disease is most likely linked to viral presence. A "hemi-nested" RT-PCR was performed on the nucleic acids from these samples with degenerate oligonucleotide primers which will amplify HGBV-A, HGBV-B and HCV-1 sequences using the GeneAmp® RNA PCR kit (Perkin Elmer) as directed by the manufacturer. Briefly, the first set of amplifications were performed on the cDNA products of random-primed reverse transcription reactions of the extracted nucleic acids with 2 mM MgCl$_2$ and 1 μM primers ns3.1-s and ns3.1-a (SEQUENCE ID. NOS. 665 and 666, respectively). Reactions were subjected to 40 cycles of denaturation-annealing-extension [three cycles of (94° C., 30 sec; 37° C., 30 sec; 2 min ramp to 72° C.; 72° C., 30 sec) followed by 37 cycles of (94° C., 30 sec; 55° C., 3 sec; 72° C., 30 sec)] followed by a 10 min extension at 72° C. Completed reactions were held at 4° C. The second set of amplifications were as described above except that 4% of the first PCR products were used as the template, and ns3.1-s and ns3-a (SEQUENCE ID. NOS. 665 and 667, respectively) were used as the "heminested" primer set. Products from the first and second sets of PCRs were analyzed by gel electrophoresis.

One sample from West Africa had a PCR product from the hemi-nested reaction that migrated at approximately 386 bp (the expected size of a HGBV-A, HGBV-B or HCV product). This product was cloned into pT7 Blue T-vector plasmid (Novagen) as described in the art. The sequence obtained from this clone (GB contig C [GB-C], SEQUENCE ID. NO. 667, residues 2274–2640) was compared with GB contig A (GB-A, SEQUENCE ID. NO. 163, residues 4438–4804), GB contig B (GB-B, SEQUENCE ID. NO. 390, residues 4218–4587) and HCV-1 (SEQUENCE ID. NO. 395). FIG. 36 shows a nucleotide alignment of these sequences, while TABLE 20 shows the percent identity between these sequences.

TABLE 20

|       | GB-A  | GB-B  | GB-C  | HCV-1 |
|-------|-------|-------|-------|-------|
| GB-A  | 100.0 | 47.99 | 61.66 | 52.55 |
| GB-B  |       | 100.0 | 52.55 | 54.96 |
| GB-C  |       |       | 100.0 | 57.37 |
| HCV-1 |       |       |       | 100.0 |

As demonstrated in FIG. 36 and TABLE 20, nucleotide comparisons of GB-A, GB-B and HCV-1 show that these sequences are 47.99 to 61.66% identical to one another. This is not surprising when one considers the conserved amino acid residues present in the NTP-binding helicase of these viruses (Example 2.B.3, FIG. 17A). The nucleotide comparison of the NS3 PCR product obtained from the West African sample (GB-C, SEQUENCE ID. NO. 667, residues 2274–2640) with the other viruses suggests that the West African NS3 product (GB-C, SEQUENCE ID. NO. 667, residues 2274–2640) is related to, but distinct from the NS3 sequences from GB-A (SEQUENCE ID. NO. 163, residues 4438–4804), GB-B (SEQUENCE. ID. NO. 390, residues 4218–4587) and HCV-1 (SEQUENCE ID. NO. 395). This sequence comparison suggests that GB-C may be from a GB-like virus more closely related to GB-A than GB-B or HCV. BLASTN and BLASTX searches of nucleic acid and protein databases in the Wisconsin Sequence Analysis Package (Version 8) with GB-C (SEQUENCE ID. NO. 667, residues 2274–2640) finds limited sequence identity with several strains of HCV. The highest P values (i.e. adds of alignment being made by chance) for nucleotide and amino acid searches were $1.9 \times 10^{-20}$ and $5.3 \times 10^{-31}$, respectively (data not shown). Together, these data suggest that GB-C (SEQUENCE ID. NO. 667, residues 2274–2640) may be from a unique GB-like virus related to HGBV-A, HGBV-B and HCV which we now designate, HGBV-C.

C. GB-C is Exogenous

Figure 37:
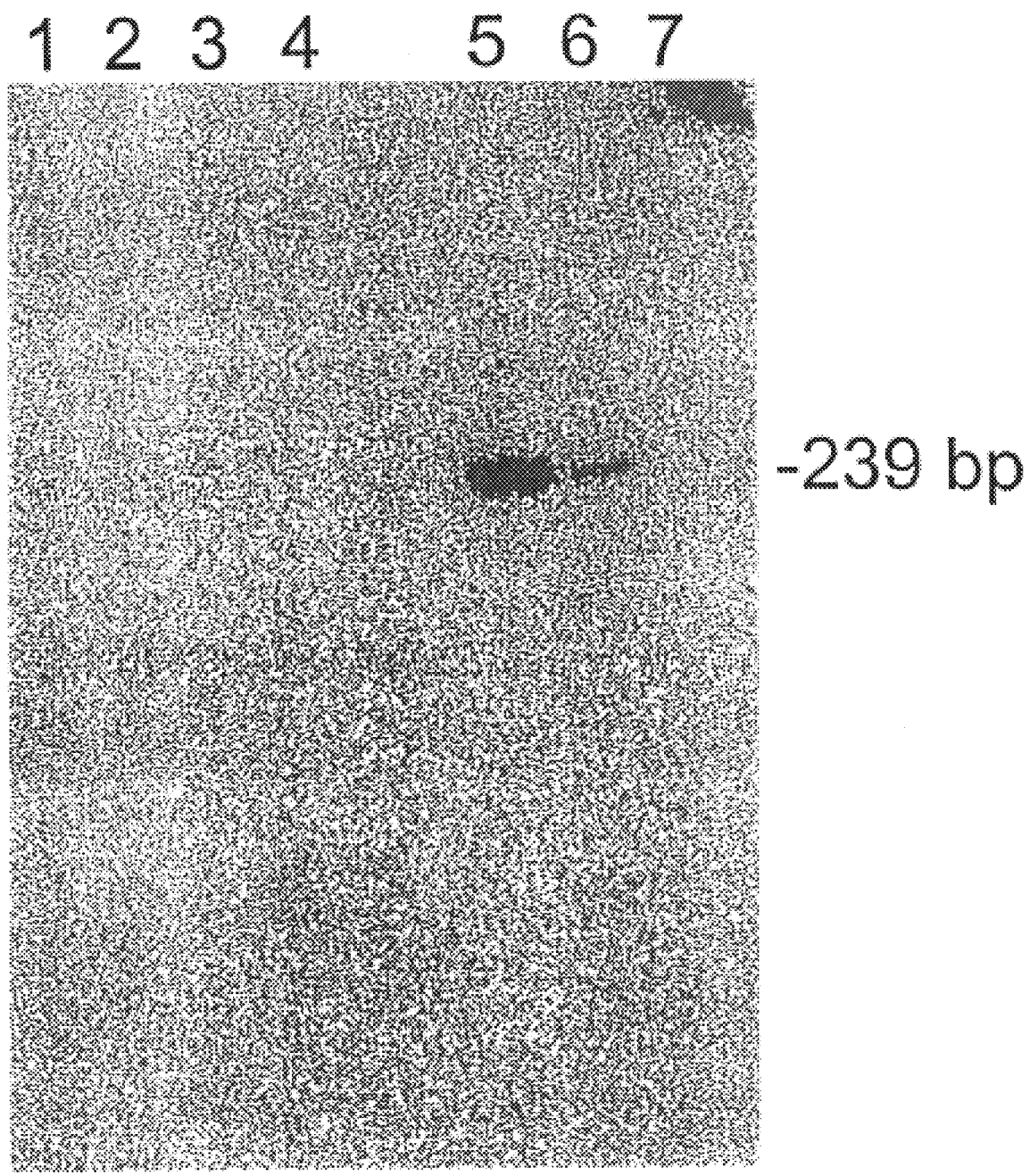
FIG. 37 shows a PhosphoImage (Molecular Dynamics, Sunnyvale, Calif.) from a Southern blot of the PCR products after hybridization with the radiolabeled probe from GB-C.

PCR primers to GB-C sequence were utilized to determine whether this sequence could be detected in the genomes of humans, Rhesus monkeys, *S. cerevisiae* and *E. coli* as described, for example, in Example 6.B. PCR was performed using GeneAmp® reagents from Perkin-Elmer-Cetus essentially as directed by the supplier's instructions. Briefly, 300 ng of genomic DNA was used for each 100 µl reaction. PCR primers (SEQUENCE I.D. NOS. 669 and 670) were used at a final concentration of 1.0 µM. PCR was performed for 40 cycles (94° C., 30 sec; 55° C., 30 sec; 72° C., 30 sec) followed by an extension at 72° C. for 10 min. PCR products were separated by agarose gel electrophoresis and visualized by UV irradiation after direct staining of the nucleic acid with ethidium bromide, followed by hybridization to a radiolabeled probe after Southern transfer to a Hybond-N+ nylon filter. FIG. 37 shows a PhosphoImage (Molecular Dynamics, Sunnyvale, Calif.) from a Southern blot of the PCR products after hybridization with the radiolabeled probe from GB-C (SEQUENCE I.D. NO. 667, residues 2274–2640). GB-C (SEQUENCE I.D. NO. 667) sequences were not detected in human (FIG. 19, lane 1), Rhesus monkey (lane 2), *S. cerevisiae* (lane 3) or *E. coli* (lane 4) genomic DNAs despite the detection of 350 fg (one genome copy equivalent, lane 5) and ~35 fg (0.1 genome copy equivalents, lane 6) of GB-C plasmid template in 300 ng human genomic DNA. (Lane 7 contains the PCR products from ~3.5 fg [0.01 genome copy equivalents] GB-C plasmid template in 300 ng human genomic DNA.) Thus, using genomic PCR that can detect 0.1 genome copy equivalents, GB-C (SEQUENCE I.D. NO. 667) cannot be detected in the genomes of human, Rhesus monkey, *S. cerevisiae*, and *E. coli*. These data are consistent with the purported exogenous (i.e. viral) origin of GB-C (SEQUENCE I.D. NO. 667).

D. GB-C Can be Detected in Additional Human Serum Samples

Additional HGBV-A and HGBV-B immunoreactive human serum samples were tested for the presence of GB-C sequences using RT-PCR. As in Example 7, nucleic acids extracted from serum samples were reverse transcribed using random hexamers, and cDNAs were subjected to 35–40 cycles of amplification (94° C., 30 sec; 55° C., 30 sec; 72° C., 30–90 sec) followed by an extension at 72° C. for 10 min. GB-C-specific PCR primers (g131-s1 and g131-a1, SEQUENCE ID. NOS. 666 AND 670) were used at 1.0 µM concentration. The PCR products were separated by agarose gel electrophoresis and visualized by UV irradiation after direct staining of the nucleic acid with ethidium bromide and hybridization to a radiolabeled probe after Southern transfer to a Hybond-N+ nylon filter. A total of 48 HGBV-immunopositive samples were tested from West Africa. Including the original sample from which GB-C was identified, eight samples from West Africa were positive for GB-C sequences by RT-PCR. A total of ten GB seronegative West African serum samples were tested, none of which had detectable GB-C sequences. PCR products from four of the positive samples were cloned and sequenced as described above. Over the 156 nucleotides examined, two of four clones examined were identical to GB-C sequence (SEQUENCE I.D. NO. 667, residues 2274–2640), and two clones (SEQUENCE I.D. NOS. 671 and 672) contained sequences that were 88.4% and 83.6% identical to GB-C (SEQUENCE I.D. NO. 667, residues 2274–2640) (FIG. 38). However, despite the divergence at the nucleotide level, the predicted translation product of each clone is remarkably similar with only one amino acid change occurring in the predicted translation of SEQUENCE ID NO. 672.

Additional serum samples from individuals with non A–E hepatitis from Greece, Egypt and the United States were tested for GB-C sequences as described above. None of these samples contained detectable GB-C sequences. The lack of detection of GB-C sequences in these samples may be due to several reasons (see above, Theory). However, the sequence variation noted above between GB-C (SEQUENCE I.D. NO. 667, residues 2274–2640) and the two GB-C variants (SEQUENCE I.D. NOS. 672 and 671) suggest that if the closely related HGBV-C's from West Africa can differ by 15.1% at the nucleotide level, it is likely that the GB-C-specific PCR primers (g131-s1, g131-a1, SEQUENCE ID. NOS. 669 and 670) may not hybridize sufficiently to geographically distinct isolates of GB-C virus to generate a detectable PCR product. In this case, PCR primers designed to a more conserved region (5' UTR) of the genome may allow the detection of GB-C sequences in non-West African serum samples.

E. Extension of the HGBV-C Sequences

The PCR walking technique described in Example 2.A hereinabove was utilized to obtain additional GB-C sequences. Briefly, total nucleic acid were extracted from the West African human serum originally used to identify GB-C (SEQUENCE I.D. NO. 667, residues 2274–2640). This nucleic acid was reverse transcribed as described supra. The resultant cDNAs were amplified in 50 µl PCR reactions (PCR 1) as described by Sorensen et al. except that 2 mM MgCl$_2$ was used. Reactions were subjected to 35 cycles of denaturation-annealing-extension (94° C., 30 sec; 55° C., 30 sec; 72° C., 90 sec) followed by a 10 min extension at 72° C. Biotinylated products were isolated using streptavidin-coated paramagnetic beads (Promega) as described by Sorensen et al. Nested PCRs (PCR 2) were performed on the streptavidin-purified products as described by Sorensen et al. for a total of 35 cycles of denaturation-annealing-extension as described above. The resultant products and the PCR primers used to generate them are listed in TABLE 21.

TABLE 21

| Reaction | Primer set PCR 1 | Primer set PCR 2 | Size of PCR product |
|---|---|---|---|
| C.1 | SEQ ID #673/SEQ ID #135 | SEQ ID #674/SEQ ID #126 | 1250 bp |
| C.2 | SEQ ID #675/SEQ ID #688 | SEQ ID #680/SEQ ID #126 | 220 bp |
| C.3 | SEQ ID #676/SEQ ID #688 | SEQ ID #677/SEQ ID #126 | 250 bp |
| C.4 | SEQ ID #678/SEQ ID #689 | SEQ ID #679/SEQ ID #126 | 800 bp |

TABLE 21-continued

| Reaction | Primer set PCR 1 | Primer set PCR 2 | Size of PCR product |
| --- | --- | --- | --- |
| C.5 | comp. of SEQ ID #673/ SEQ ID #689 | SEQ ID #90/SEQ ID #126 | 750 bp |
| C.6 | SEQ ID #682/SEQ ID #666 | SEQ ID #92/SEQ ID #126 | 1150 bp |
| C.7 | SEQ ID #684/SEQ ID #689 | SEQ ID #94/SEQ ID #126 | 550 bp |
| C.8 | SEQ ID #686/SEQ ID #689 | SEQ ID #96/SEQ ID #126 | 250 bp |
| C.9 | 647/SEQ ID #135 | 648/SEQ ID #126 | 625 bp |
| C.10 | 649/SEQ ID #688 | 650/SEQ ID #126 | 350 bp |
| C.11 | 651/SEQ ID #688 | 652/SEQ ID #126 | 550 bp |
| C.12 | 653/SEQ ID #689 | 654/SEQ ID #126 | 450 bp |
| C.13 | 655/659 | 656/SEQ ID #126 | 750 bp |
| C.14 | 657/FP3 (SEQ ID #13) | 658/SEQ ID #126 | 550 bp |
| C.15 | 660/125 | 661/SEQ ID #126 | 600 bp |

In addition, a 1.3 kb product (C.16) was generated with oligonucleotide primers SEQ I.D. NO. 663 AND SEQ I.D. NO. 664 using PCR 1 conditions described above. This product, together with those described in TABLE 21 were isolated from agarose gels and cloned into pT7 Blue T-vector plasmid (Novagen) as described in the art.

The cloned products were sequenced as described in Example 5. The sequences were assembled using the GCG Package (version 7) of programs. A schematic of the assembled contig is presented in FIG. 39. GB-C is 9034 bp in length, all of which has been sequenced and is presented in SEQUENCE I.D. NO. 397–600. These SEQUENCE I.D.'s correspond to the three forward translation frames.

Example 19

CKS-Based Expression and Detection of Immunogenic

HGBV-C Polypeptides

Figure 39:
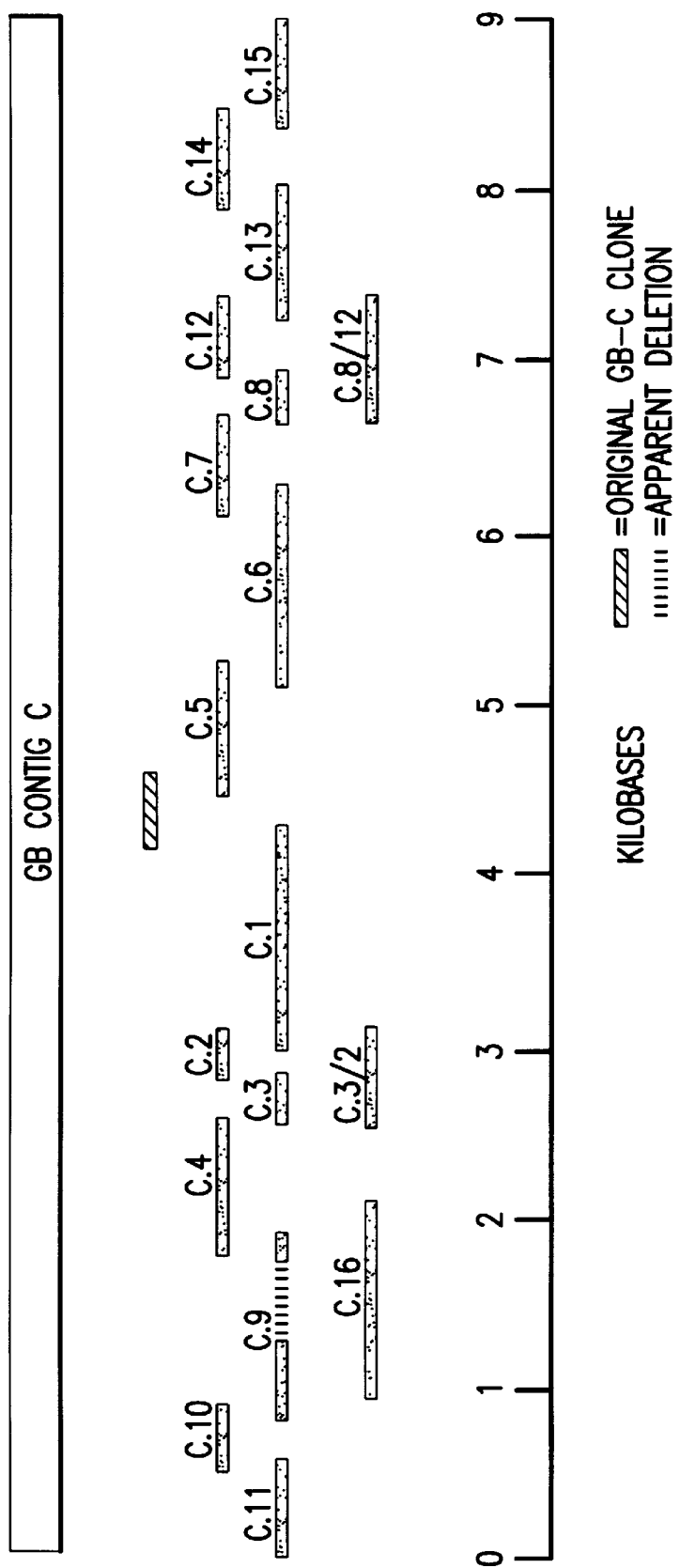
FIG. 39 presents a schematic of the assembled contig of HGBV-C.

The HGBV-C sequences obtained from the walking experiments described in Example 17 (TABLE 13) were cloned into the CKS expression vectors pJO200, pJO201, and pJO202 using the restriction enzymes listed in TABLE 22 (10 units, NEB) as described in Example 13. Two additional PCR clones, designated C.3/2 and C.8/12, were also expressed (FIG. 39). PCR product C.3/2 was generated using primers SEQUENCE I.D. NO. 676 and the complement of SEQUENCE I.D. NO. 679 and PCR product C.8/12 was generated using primers (SEQUENCE I.D. NO. 687 and its complement) as described in Example 9. The PCR products were cloned into pT7Blue as described previously, then liberated with the restriction enzymes listed in TABLE 22 and cloned into pJO200, pJO201 and pJO202 as above.

Two human sera which had indicated the presence of antibodies to one or more of the CKS/HGBV-A or CKS/HGBV-B fusion proteins by the 1.7, 4.1 or 2.17 ELISAS (see Examples 15 and 16) were chosen for Western blot analysis. One of these sera (240D) was from an individual with non A–E hepatitis (Egypt) and the other (G8-81) was from a West African individual "at risk" for exposure to HGBV (see Example 15). The CKS/HGBV-C fusion proteins were expressed and transferred to nitrocellulose sheets as described above. The blots were preblocked as described and incubated overnight with one of the human serum sample diluted 1:100 in blocking buffer containing 10% E. coli lysate and 6 mg/ml XL1-Blue/CKS lysate. The blots were washed two times in TBS, reacted with HRPO-conjugated goat anti-human IgG and developed as indicated above. The results are shown in TABLE 22.

Several of the HGBV-C proteins showed reactivity with one or the other of the two sera, and three (C.1, C.6 and C.7) were chosen for use in ELISA assays (see Example 20). Thus, samples previously identified as reactive with HGBV-A and/or HGBV-B proteins additionally show reactivity with HGBV-C proteins. The reactivity with multiple proteins from the 3 HGBV viruses may be due to cross-reactivity resulting from shared epitopes between the viruses. Alternatively, this may be a result of infection with multiple viruses, or to other unidentified factors.

TABLE 22

HGBV-C Samples

| PCR product[a] | Restriction digest[b] | Reactivity with human G8-81 serum | Reactivity with human 240D serum |
| --- | --- | --- | --- |
| GB-C | KpnI, XbaI | + | − |
| C.1 | EcoRI, XbaI | + | − |
| C.3/2 | EcoRI, XbaI | − | − |
| C.4 | KpnI, XbaI | − | − |
| C.9 | KpnI, PstI | ND | − |
| C.10 | EcoRI, XbaI | ND | − |
| C.5 | KpnI, XbaI | +/− | − |
| C.6 | KpnI, PstI | + | − |
| C.7 | NdeI-fill, BamHI | − | + |
| C.8/12 | KpnI, XbaI | + | − |

[a]PCR product is as indicated in previous TABLES or Examples.
[b]Restriction digests used to liberate the PCR fragment from pT7Blue T-vector.
ND = not done.

Example 20

Serological Studies With GBV-C

A. Recombinant Protein Purification Protocol

Bacterial cells expressing the CKS fusion proteins were frozen and stored at −70 C. The bacterial cells from each of the GBV-C constructs were thawed and disrupted as described in Example 15 for GBV-B constructs. Further, the recombinant proteins were purified as described for GBV-B recombinant proteins in example 15.

The fractions which were collected during the purification protocol were electrophoretically separated and stained with Coomassie Brilliant Blue R250 and examined for the presence of a protein having a molecular weight of approximately 75 kD (CKS C.1/SEQUENCE I.D. NO. 401), 71 kD (CKS C.6/SEQUENCE I.D. NO. 401), and 49 kD (CKS C.7/SEQUENCE I.D. NO. 401). Proteins bands of the expected molecular weight were observed for the CKS-C.6 and CKS-C.7 recombinant proteins. For the CKS-C.1 protein, a band was observed which corresponded to a molecular weight of 62 kD rather than at the expected molecular weight of 75 kD. It is unclear why there are differences between the expected and observed protein band. Fractions containing the protein of interest were pooled and re-examined by SDS-PAGE.

The immunogenicity and structural integrity of the pooled fractions containing the purified antigen were determined by immunoblot following electrotransfer to nitrocellulose as described in Example 13. In the absence of a qualified positive control, the recombinant proteins were identified by their reactivity with a monoclonal antibody directed against the CKS portion of each fusion protein. When the CKS-C.1 protein (SEQUENCE I.D. NO. 401) was examined by Western blot, using the anti-CKS monoclonal antibody to detect the recombinant antigen, a single band at approximately 65 kD was observed. This differs from the expected size of 75 kD for the CKS-C.1 protein (SEQUENCE I.D. NO. 401). Bands of the expected sizes were noted for the CKS-C.6 protein (SEQUENCE I.D. NO. 401), and the CKS C.7 protein (SEQUENCE I.D. NO. 401) were observed when examined by immunoblot.

B. Polystyrene Bead Coating Procedure

The proteins were dialyzed and evaluated for their antigenicity on polystyrene beads described in Example 15.

C. ELISA Protocol for Detection of Antibodies to HGBV

The ELISA's were performed as described in the previous Example 15.

D. Detection of HGBV RNA in Serum of Infected Individuals

Specimens which were repeatably reactive in the ELISAs were tested for HGBV RNA as described in section D. of the previous example 15.

E. Tamarin Serological Profiles

None of the sera from the tamarins produced a specific immune response when tested in the ELISA utilizing the CKS-C.1 protein, the CKS-C.6 protein, or the CKS C.7 protein, all derived from the HGBV-C genome. See Example 15 for a description of the tamarin serological profiles.

F. Supplemental Testing

As noted in Example 15, specimens which were initially reactive were typically retested; if the specimen was repeatably reactive, additional tests (e.g. Western blot) may be performed to further support the ELISA data. For a Western blot result to be considered positive, a visible band should be observed at 65 kD for the C.1 protein (SEQUENCE I.D. NO. 401), at 71 kD for the C.6 protein (SEQUENCE I.D. NO. 401), or at 49 kD for the C.7 protein (SEQUENCE I.D. NO. 401). Since the Western blot had not been optimized to match or exceed the sensitivity of the ELISA's, a negative result was not used to discard the ELISA data. However, a positive result reinforced the reactivity detected by the ELISA's.

As also noted in Example 15, repeatably reactive specimens which have sufficient volume may be tested by RT-PCR (performed as described in Example 10 using primers corresponding to SEQUENCE I.D. NOS. 8 and 9) to identify HGBV-C specific nucleotide sequences in serum.

G. Experimental Protocol

In example 15, ELISA's employing recombinant antigens from HGBV-B were utilized to evaluate the presence of antibodies to HGBV-B AND HGBV-A in various human populations. Many of the same specimens were then tested for antibodies to HGBV-C utilizing the C.1 ELISA employing the CKS-C.1 recombinant protein (SEQUENCE I.D. NO. 401), the C.6 ELISA employing the CKS-C.6 recombinant protein (SEQUENCE I.D. NO. 401), the C.7 ELISA employing the CKS-C.7 recombinant protein (SEQUENCE I.D. NO. 401) coated on the solid phase (as described in Example 14). As noted in Example 15, all five of the convalescing tamarins inoculated with HGBV produced a specific but short-lived antibody response to the HGVB-B recombinant proteins (as detected with the 1.7, 1.4 and 4.1 ELISA's). Although none of the tamarins produced a detectable antibody response in the C.1, C.6, C.7 ELISAS, some of the human specimens produced a specific antibody response to the C.1, C.6, and C.7 recombinant protein when tested via Western blot (see Example 13) In the current example, we evaluated the utility of the C.1, C.6, and C.7 ELISA's in detecting antibodies in various human populations.

H. Cutoff Determination

The cutoff for the C.1, C.6, and C.7 ELISAs were determined as described in Example 15.

I. Serological Data Obtained With Low-Risk Specimens

A population consisting of 100 sera and 100 plasma was obtained from healthy, volunteer donors in Southeastern Wisconsin and tested for antibodies to three recombinant proteins from GBV-C including the CKS-C.1 (SEQUENCE I.D. NO. 401) protein in the C.1 ELISA, the CKS-C.6 (SEQUENCE I.D. NO. 401) protein in the C.6 ELISA, and the CKS-C.7 (SEQUENCE I.D. NO. 401) protein in the C.7 ELISA.

For the C.1 ELISA, the mean absorbance values for the serum and plasma specimens were 0.049 {with a standard deviation (SD) of 0.040} and 0.038 (SD=0.029), respectively The cutoff for serum and plasma were calculated to be 0.214 and 0.286, respectively. As discussed above, the cutoff value was also expressed as a factor of the negative control absorbance value; specimens having S/N values above 10.0 were considered reactive. Using this cutoff, 0 of 100 plasma specimens and 1 of 100 serum specimens were initially reactive and repeatably reactive for antibodies to the C.1 protein (SEQUENCE I.D. NO. 401). For the C.6 ELISA, the mean absorbance values for the serum and plasma specimens were 0.102 {with a standard deviation (SD) of 0.046} and 0.105 (SD=0.047), respectively. Cutoff values were set such that specimens having an S/N value of 10 or greater were considered reactive. Using this cutoff, three specimens (two from the serum population and one from the plasma population) were repeatably reactive (having S/N values of 10 or greater) for antibodies to the C.6 protein (SEQUENCE I.D. NO. 401).

For the C.7 ELISA, the mean absorbance values for the serum and plasma specimens were 0.061 {with a standard deviation (SD) of 0.040} and 0.050 (SD=0.055), respectively. Cutoff values were set such that specimens having an S/N value of 10 or greater were considered reactive. Using this cutoff, none of the specimens were repeatably reactive for antibodies to the C.7 protein (SEQUENCE I.D. NO. 401).

Thus, there is evidence that antibodies to the C.1, C.6, or C.7 proteins are present in approximately 1% of U.S. blood donors (N=200).

J. Specimens Considered "At Risk" for Hepatitis

The data for these studies is summarized in TABLE 23.

(i) Specimens from West Africa

A total of 20 of 137 specimens were reactive in one or more of the ELISAs utilizing GBV-C proteins. A total of 12 of 97 were repeatably reactive in the C.1 ELISA , 3 of 52 were repeatably reactive in the C.6 ELISA, 5 of 137 specimens were reactive in the C.7 ELISA. Three of the C.1 reactive specimens were tested on Western blot and found to be reactive.

These data suggest that HGBV may be endemic in West Africa.

(ii) Specimens from Intravenous Drug Users

A total of 112 specimens were obtained from a population of intravenous drug users, as part of a study being conducted at Hines Veteran's Administration Hospital, in Chicago, Ill.. A total of 2 of 112 specimens were repeatably reactive for one or more proteins. One specimen was repeatably reactive in the C.1 ELISA, one specimen was repeatably reactive in the C.7 ELISA. None of these specimens were positive in the C.6 ELISA.

K. Specimens Obtained from Individuals With Non A–E Hepatitis

The data for these studies is summarized in TABLE 23.

Various populations of specimens (described in Example 15.K) were obtained from individuals with non-A–E hepatitis and tested with the 1.5, 2.17, 1.18 and 1.22 ELISAs (described in Example 15.C). Due to insufficient sample volume, not all specimens were tested in all of the ELISAs.

(i) Specimens from Japan

None of a total of 89 specimens were repeatably reactive in the C.1 ELISA. Due to lack of specimen volume, the specimens were not tested for antibodies in the C.6 or C.7 ELISAs.

(ii) Specimens from Greece

A total of 67 specimens were tested with the C.1 and C.7 ELISAs. None of the specimens were reactive.

(iii) Specimens from Egypt

A total of 18 specimens of 132 specimens were reactive in one or more ELISA. None of the specimens were reactive in the C.1 ELISA. A total of 15 specimens were reactive in the C.6 ELISA and three were reactive in the C.7 ELISA.

(iv) Specimens from U.S. (M Set)

A total of 6 specimens were reactive in one or more ELISA. Two specimens were repeatably reactive in the C.1 ELISA. Four specimens were repeatably reactive in the C.6 ELISA. None of the specimens were reactive in the C.7 ELISA.

(v) Specimens from U.S. (T Set)

None of the 64 specimens were reactive in either the C.1 or the C.6 ELISAs. One specimen was repeatably reactive in the C.7 ELISA.

(vi) Specimens from Various U.S. Clinical Sites (Set 1)

In total, three of 62 specimens were reactive in one or more ELISA's. One specimen was repeatably reactive in both the C.1 and C.6 ELISA's. Two specimens were repeatably reactive in the C.7 ELISA.

As we have discussed supra, it is possible that more than one strain of the HGBV may be present, or that more than one distinct virus may be represented by the sequences disclosed herein. These are considered to be within the scope of the present invention and are termed "hepatitis GB Virus ("HGBV")".

L. Statistical Significance of Serological Results

These data indicated that specific antibodies to HGBV-C proteins (i.e. specimens repeatably reactive for antibodies in C.1, C.6 and C.7 ELISA's) were detected among individuals considered "at risk" for exposure to HGBV and among individuals diagnosed with non A–E hepatitis, and at low rate among volunteer or paid blood donors from the U.S. In TABLE 24, the serological results obtained with the various categories of specimens ("low risk", "at risk" and non A–E hepatitis patients as shown in TABLE 23) were grouped together and analyzed for statistical significance using the Chi square test. Unlike the data in TABLE 23, which compiled the seroprevalence of antibodies to HGBV proteins in the total number of specimens tested, the data in TABLE 24 reflect the results obtained with different individuals (persons). For the GBV-C ELISAs, the data indicate that there is a significant difference (with a p value of 0.000) in comparing the seroprevalence of anti-HGBV in volunteer blood donors with the individuals considered "at risk" for exposure to HGBV (West Africa) but not for the IVDUs. In addition, there was a statistically significant difference between the seroprevalence of antibodies to HGBV-C in individuals with non A–E hepatitis in Egypt and the U.S. when compared to volunteer donors. These data suggest that exposure to HGBV-C was associated with non-A through E hepatitis. NOTE: although the results of RT-PCR were negative in these initial studies, subsequent data revealed flavi-like vial sequences in serum of seropositive individuals (see Example 19).

Example 21

Presence of HGBV-C in Humans With non-A–E Hepatitis

The generation of HGBV-C-specific ELISAs allowed the identification of immunopositive sera from patients with non-A–E hepatitis (Example for HGBV-C serology). These sera, together with several HGBV-A and/or HGBV-B-immunopositive sera from individuals with documented cases of non-A–E hepatitis (TABLE 25) were examined by RT-PCR for HGBV-C sequences. To increase the likelihood of detecting HGBV-C variants, RT-PCR was performed using degenerate NS3 oligonucleotide primers in a first round of amplification followed by a second round of amplification with nested GB-C-specific primers. Briefly, the first round amplification was performed on serum cDNA products generated as described in Example 6, using 2 mM $MgCl_2$ and 1 $\mu M$ primers ns3.2-s1 and ns3.2-a1 (SEQ. ID. NOS. 711 and 712, respectively). Reactions were subjected to 40 cycles of denaturation-annealing-extension [three cycles of (94° C., 30 sec; 37° C., 30 sec; 2 min ramp to 72° C.; 72° C., 30 sec) followed by 37 cycles of (94° C., 30 sec; 50° C., 30 sec; 72° C., 30 sec)] followed by a 10 min extension at 72° C. Completed reactions were held at 4° C. A second round of amplification was performed utilizing 2 mM $MgCl_2$, 1 $\mu M$ GB-C-specific primers (SEQUENCE I.D. NOS. 669 and 670), and 4% of the first PCR products as template. The second round of amplification employed a thermocycling protocol designed to amplify specific products with oligonucleotide primers that may contain base pair mismatches with the template to be amplified [Roux, Bio/Techniques 16:812–814 (1994)]. Specifically, reactions were thermocycled 43 times (94° C., 20 sec; 55° C. decreasing 0.3° C./cycle, 30 sec; 72° C., 1 min) followed by 10 cycles (94° C., 20 sec; 40° C., 30 sec; 72° C., 1 min) with a final extension at 72° C. for 10 minutes. PCR products were separated by agarose gel electrophoresis, visualized by UV irradiation after direct staining of the nucleic acid with ethidium bromide, then hybridized to a radiolabeled probe for GB-C after Southern transfer to Hybond-N+ nylon filter. PCR products were cloned and sequenced as described in the art.

Using the above methodology, GB-C.4, GB-C.5, GB-C.6 and GB-C.7 were obtained. These sequences are 82.1–86.6% identical to GB-C (SEQUENCE I.D. NO. 397, bases 4167–4365). FIG. 40 displays the sequence differences of GB-C.4, GB-C.5, GB-C.6 and GB-C.7 aligned to the homologous region of GB-C in the predicted codon triplicates. As demonstrated, a majority of the nucleotide differences do not result in amino acid changes from GB-C. This overall sequence conservation at the amino acid level suggests that GB-C.4, GB-C.5, GB-C.6 and GB-C.7 were derived from different strains of the same virus, HGBV-C.1. In addition, the level of sequence divergence at the nucleotide level demonstrates that these PCR products are not a result of contamination with any of the previously identified GB-C sequences.

Three of these individuals (the sources of GB-C.4, GB-C.5 and GB-C.7) had no evidence of infection with hepatitis A, hepatitis B or hepatitis C viruses. The presence of GB-C sequences in these individuals with hepatitis of unknown etiology suggests that HGBV-C is one of the causative agents of human hepatitis. Serial samples were available for two of the individuals (containing GB-C.4 and GB-C.5). To follow the HGBV-C sequence in these samples, clone specific RT-PCRs were developed. Briefly, nucleic acids extracted from serum were reverse transcribed using random hexamers as in Example 7. The resultant cDNAs were subjected to 40 cycles of amplification (94° C., 30 sec; 55° C., 30 sec; 72° C., 30 sec) followed by an extension at 72° C. for 10 min. GB-C.4- or GB-C.5-specific PCR primers (GB-C.4-s1 and GB-C.4-a1, or GB-C.5-s1 and GB-C.5-a1, respectively) were used at 1.0 μM concentration. PCR products were separated by agarose gel electrophoresis, visualized by UV irradiation after direct staining of the nucleic acid with ethidium bromide, then hybridized to a radiolabeled probe after Southern transfer to Hybond-N+ nylon filter.

GB-C.4 was found in sera from an Egyptian patient with acute non-A–E hepatitis. This patient was seropositive for a HGBV-A protein (see HGBV-A ELISA Example). RT-PCR of five serial samples from the Egyptian patient demonstrated a viremia that persisted for at least 20 days after normalization of the serum ALT values (TABLE 26). The presence of GB-C sequence after serum ALT normalization suggested that HGBV-C may establish chronic infections in some individuals. However, the absence of additional samples from this patient prevents a conclusion as to the chronic nature of HGBV-C. Additional samples are being pursued to resolve this question.

Figure 41:
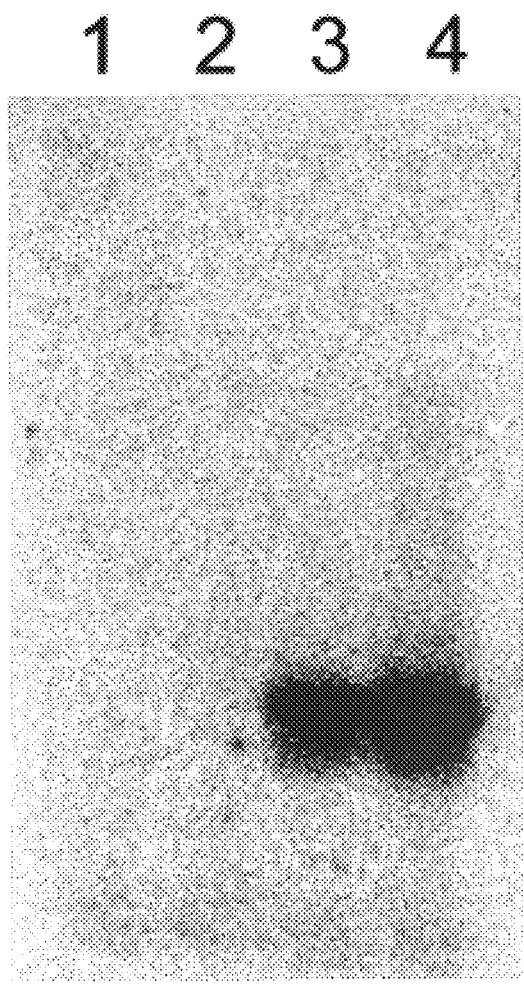
FIG. 41 shows a PhospholImage (Molecular Dynamics, Sunnyvale, Calif.) of a Southern blot of PCR products generated from a Canadian hepatitis patient after hybridization with radiolabeled from Canadian patient GB-C.5.

GB-C.5 was obtained from a Canadian patient with hepatitis associated aplastic anemia. Each sample from this patient was seropositive in the C.7 ELISA (Example 20). GB-C.5 was detected in the samples obtained from the Canadian patient during aplastic anemia (day 13 post-presentation) and at the time of death (day 14, FIG. 41) using GB-C.5-specific primers (GB-C.5-s1 and GB-C.5-a1). However, GB-C.5-specific PCR failed to detect GB-C.5 sequence at the time of presentation (day 0, acute hepatitis) and on day 3 (liver failure). Thus, it is unclear whether GB-C.5 was present below the limit of detection in the first samples. If so, HGBV-C may have been the causative agent of this patient's aplastic anemia. However, because GB-C.5 was detected by RT-PCR only during aplastic crisis, GB-C.5 may have been acquired from a blood product administered to combat the anemia. In this case, HGBV-C's association with aplastic anemia would be similar to HCV's [Hibbs, et al. *JAMA* 267:2051–2054 (1992)].

Due to the distant relation of HGBV-C and HCV, it was of interest to determine whether current methods for detecting HCV infection would recognize human samples containing HGBV-C. Routine detection of individuals exposed to or infected with HCV relies upon antibody tests which utilize antigens derived from three or more regions of HCV-1. These tests allow detection of antibodies to all of the known genotypes of HCV in most individuals[Sakamoto, et al. *J. Gen. Virol.* 75:1761–1768 (1994); Stuyver, et al. *J. Gen. Virol.* 74:1093–1102 (1993)]. Second generation ELISAs for HCV were performed on the samples that contain HGBV-C as described in Example 10 (TABLE 25). One of the 4 samples that contain HGBV-C was seropositive for HCV antigens. A limited number of human sera which are seronegative for HCV have been shown to be positive for HCV genomic RNA by a highly sensitive RT-PCR assay [Sugitani, 1992 #65]. A similar RT-PCR assay (as described in Example 9) confirmed the presence of an HCV viremia in the seropositive sample. However, none of the HCV seronegative samples were HCV viremic. Therefore, although 1 of the 4 individuals containing HGBV-C sequences have evidence of HCV infection, the current assays for the presence of HCV did not accurately predict the presence of HGBV-C. The one HCV-positive patient appears to be co-infected with HGBV-C. It is unclear whether the hepatitis noted in this patient was due to HCV, HGBV-C or the presence of both viruses. That HGBV-C and HCV are found in the same patient may suggest that common risk factors exist for acquiring these infections.

Using the PCR protocol described above, GB-C sequences (~85% identical to the previous GB-C isolates shown in FIG. 41, data not shown) were identified in "normal" units of blood from two volunteer U.S. donor obtained in 1994. These units tested negative for HBV, HCV, and had normal serum ALT values. However, these units tested positive in the 1.4 ELISA. Finding HGBV-C in at least two units of "normal" blood out of ~1000 units immunoscreened suggests that this virus is currently in the U.S. blood supply. However, using ELISAs developed from HGBV proteins and nucleotide probes from HGBV sequences, we demonstrate that these units of blood can be identified.

The large amount of sequence variation in the various GB-C sequences (FIG. 41) should be noted. Although highly sensitive, PCR based assays for viral nucleic acids are dependent on the sequence match between oligonucleotide primers and the viral template. Therefore, because the PCR primers utilized in this study were located in a region of the HGBV-C genome that is not well conserved in various isolates, not all HGBV-C viremic samples tested may have been detected by the RT-PCR assays employed here. Utilization of PCR primers from a highly conserved region of the HGBV-C genome, as have been found in the HCV 5' untranslated region [Cha, et al. *J. Clin. Microbiol.* 29:2528–2534 (1991)], should allow more accurate detection of HGBV-C viremic samples.

TABLE 25

GB-C containing sera

| Sequence | Origin | Clinical | GB reactivity[1] | HCV ELISA[2] | HCV RNA |
|---|---|---|---|---|---|
| GB-C.4 | Egyptian | Acute Hepatitis | A | 0.25 | 0 |
| GB-C.5 | Canada | HA-AA[3] | C | 0.15 | 0 |
| GB-C.6 | U.S. | history of hepatitis | C | <u>11.51</u> | + |
| GB-C.7 | U.S. | hepatitis | A | 0.26 | 0 |

[1]Immunoreactivity detected to recombinant HGBV protein(s) from virus A, B or C.
[2]Sample to cutoff values reported. Values ≧1 (underlined) are considered positive.
[3]hepatitis associated aplastic anemia

TABLE 26

Egyptian Serial Samples

| Days post-presentation | ALT (U/l)[1] | 2.17 ELISA Reactivity[2] | GB-C.4 RT-PCR |
|---|---|---|---|
| 0 | 128 | 61.0 | + |
| 10 | 78 | 62.9 | + |
| 20 | 49 | 69.4 | + |
| 30 | 33 | 39.1 | + |
| 40 | 30 | 55.9 | + |

[1]Upper limit of normal: 45 U/l.
[2]Sample to normal reported. Values ≧10 are considered positive.

Example 21

Sequence Comparisons and Phylogenetic Analysis

Information about the degree of relatedness of viruses can be obtained by performing comparisons, i.e. alignments, of nucleotide and predicted amino acid sequences. Performing alignments of the HGBV sequences with sequences of other viruses can provide a quantitative assessment of the degree of similarity and identity between the sequences. This information can then be used to develop a rationale for the taxonomic classification of the HGBV viruses. In general, the calculation of similarity between two amino acid sequences is based upon the degree of likeness exhibited between the side chains of an amino acid pair in an alignment. The degree of likeness is based upon the physical-chemical characteristics of the amino acid side chains, i.e. size, shape, charge, hydrogen-bonding capacity, and chemical reactivity, thus, similar amino acids possess side chains that have similar physical-chemical characteristics. For example, phenylalanine and tyrosine are amino acids containing aromatic side chains and are, therefore, regarded as chemically similar. A discussion of the chemistry of amino acids can be found in any basic biochemistry textbook, for example, *Biochemistry*, Third Edition, Lubert Stryer, Editor, W. H. Freeman and Company, New York 1988. The calculation of identity between two aligned amino acid sequences is, in general, an arithmetic calculation which counts the number of identical pairs of amino acids in the alignment and divides this number by the length of the sequence(s) in the alignment. Analogous to the method used for amino acid sequence alignments, the determination of the degree of identity between two aligned nucleotide sequences is an arithmetic calculation which counts the number of identical pairs of nucleotide bases in the alignment and divides this number by the length of the sequence(s) in the alignment. The calculation of similarity between two aligned nucleotide sequences sometimes uses different values for transitions and transversions between paired (i.e. matched) nucleotides at various positions in the alignment; however, the magnitude of the similarity and identity scores between pairs of nucleotide sequences are usually very close, i.e. within one to two percent.

As has been stated earlier, limited identity exists between amino acid sequences of the HGBV agents and hepatitis C genotypes. In order to more accurately determine the degree of relatedness between the HGBV agents and HCV, amino acid sequence alignments were performed using the sequence of the entire large open reading frame (ORF) of HGBV-A, B, and C, and the amino acid sequence of the large ORF of several representative HCV isolates. In addition, the degree of relatedness between the HGBV agents and HCV at the nucleotide level was determined using the entire genomic nucleotide sequence of HGBV-A, B, and C, and that of several representative HCV isolates. Alignment of the amino acid and nucleotide sequences was performed using the program GAP of the Wisconsin Sequence Analysis Package (Version 8) which is available from the Genetics Computer Group, Inc., 575 Science Drive, Madison, Wis., 53711. The gap creation and gap extension penalties were 5.0 and 0.3, respectively, for nucleic acid sequence alignments, and 3.0 and 0.1, respectively, for amino acid sequence comparisons. The GAP program uses the algorithm of Needleman and Wunsch (*J. Mol. Biol.* 48:443–453, 1970) to calculate the degree of similarity and identity, expressed as percentages, between the two sequences being aligned.

The nucleotide and amino acid sequences of selected members of the major hepatitis C virus (HCV) genotypes were obtained from GenBank and are shown below with their respective accession numbers:

TABLE 27

| HCV Isolate | Genotype designation | GenBank Accession Number |
|---|---|---|
| HCV-1 | 1a | M62321 |
| HCV-JK1 | 1b | X61596 |
| HCV-J6 | 2a | D00944 |
| HCV-J8 | 2b | D10988 |
| HCV-K3a | 3a | D28917 |
| HCV-Tr | 3b | D26556 |

Results of pairwise comparisons of the predicted amino acid sequences of the large open reading frame (i.e. putative precursor polyprotein) and the nucleotide sequences between each of the above HCV genotypes and each of the HGBV isolates are shown in Tables 28 and 29, respectively. The genotype designation, which is based on the system of nomenclature for HCV isolates described by Simmonds P. et al (1994) *Hepatology,* 19:1321–1324, of each of the HCV isolates are shown in the top row.

The data shown in TABLE 28 demonstrate that the lower limit of amino acid sequence identity between the HCV genotypes is 69%. This value is very close to that shown by Simmonds et al. [Simmonds, P. et al. *Hepatology,* 19:1321–1324, 1994] who reported that comparisons of the coding region (i.e. large open reading frame) of eight complete HCV genomes from two major groups showed amino acid sequence similarities of 67.1% to 68.6%; however, these authors did not describe the method by which the similarities were calculated. This value (69%) is also very close to the value of 71–84% identity reported by Okomoto et al., [*Virology,* 188:331–341, 1992] for comparisons of HCV-J8 with other major HCV isolates; however, these investigators did not describe the method by which the identities were calculated. Comparisons of the HGBV polyprotein sequences with each of the HCV genotypes reveals that the HGBV-encoded polyprotein sequences exhibit no more than 33% identity to any of the HCV polyproteins (TABLE 28). A comparison of the nucleotide sequences (TABLE 29) demonstrates a maximum sequence identity of 44.2% between any HGBV virus and any HCV isolate, whereas, the minimum nucleotide sequence identity between HCV isolates is 64.9%. Therefore, since HGBV-A, B, and C possess nucleotide and predicted amino acid sequence identity with HCV that is well outside the range of identities established for the known HCV genotypes, the HGBV viruses cannot be considered genotypes of the hepatitis C viruses.

The relationship between the hepatitis C viruses and the hepatitis GB viruses can be examined by performing phylogenetic analysis on their aligned nucleotide or deduced amino acid sequences (i.e. large open reading frames) or on a portion of these sequences. This approach has been applied to the hepatitis C viruses and showed that the variability of HCV isolates delineated six equally divergent main groups of sequences [Simmonds, P. et al., *J. Gen. Virol.* (1993) 74:2391–2399 and Simmonds, P. et al., *J. Gen. Virol.* (1994) 75:1053–1061]. This analysis resulted in the establishment of a system of nomenclature for the hepatitis C viruses [Simmonds, P. et al. *Hepatology,* 19:1321–1324, 1994] where the isolates are classified into genotypes based upon the evolutionary distance between sequences.

In order to determine the phylogenetic relationship between the hepatitis GB viruses and the hepatitis C viruses, alignments of amino acid sequences within the putative helicase gene of NS3 and the putative RNA-dependent RNA-polymerase (RdRp) of NS5B were performed. Also included in the alignments were related sequences from other viruses in the Flaviviridae and viruses that have been shown to possess evolutionary relatedness within their helicase or polymerase genes to members of the Flaviviridae [Koonin, E. V. & Dolja, V. V. (1993) *Crit. Rev. Biochem. Mol. Biol.* 28, 375–430 and Koonin, E. V. (1991) *J. Gen. Virol.* 72, 2179–2206].

Figure 42:
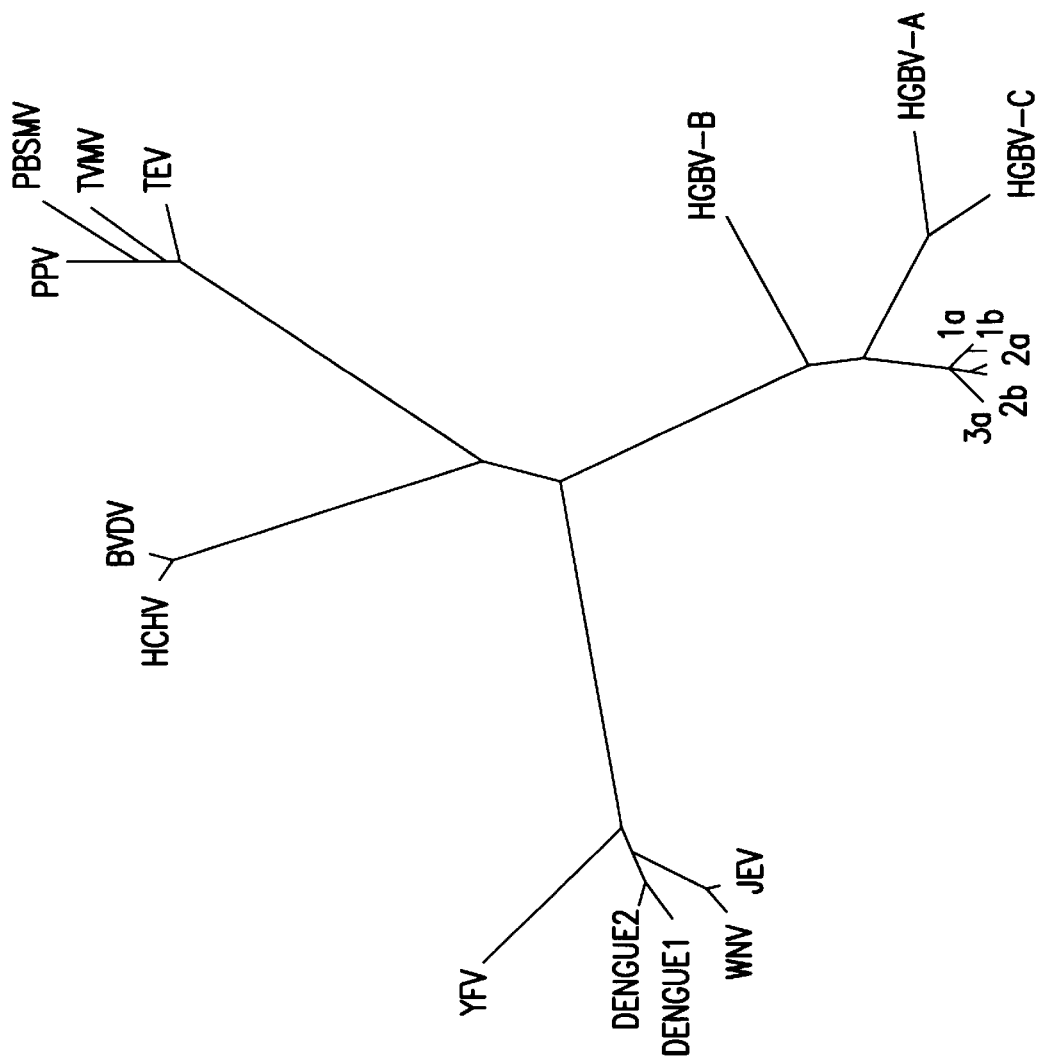
FIG. 42 depicts a phylogenetic tree produced from alignment of the helicase domains of the viruses indicated.
Figure 43:
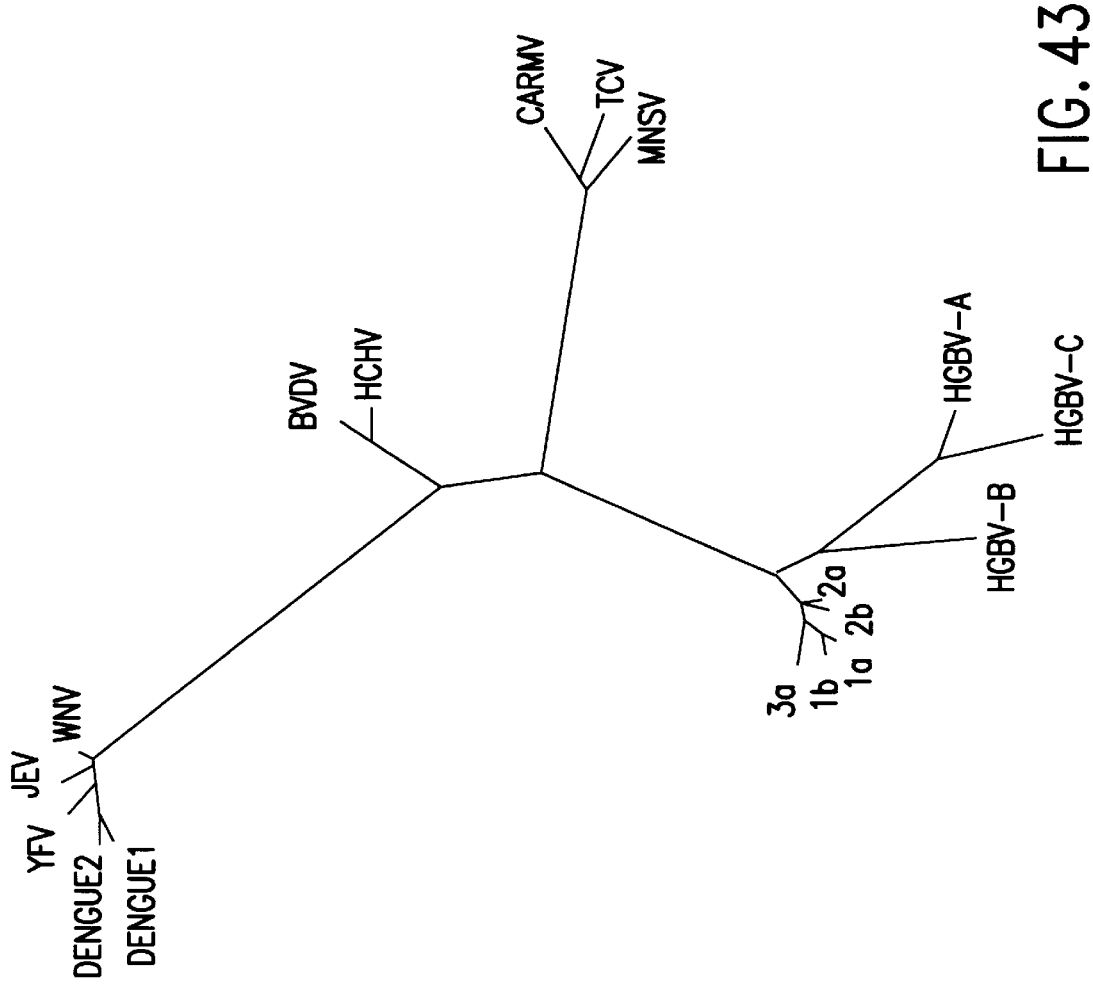
FIG. 43 SCOTT depicts a phylogenetic tree produced from alignment of the RNA-dependent RNA polymerase domains of the viruses indicated.
Figure 44:
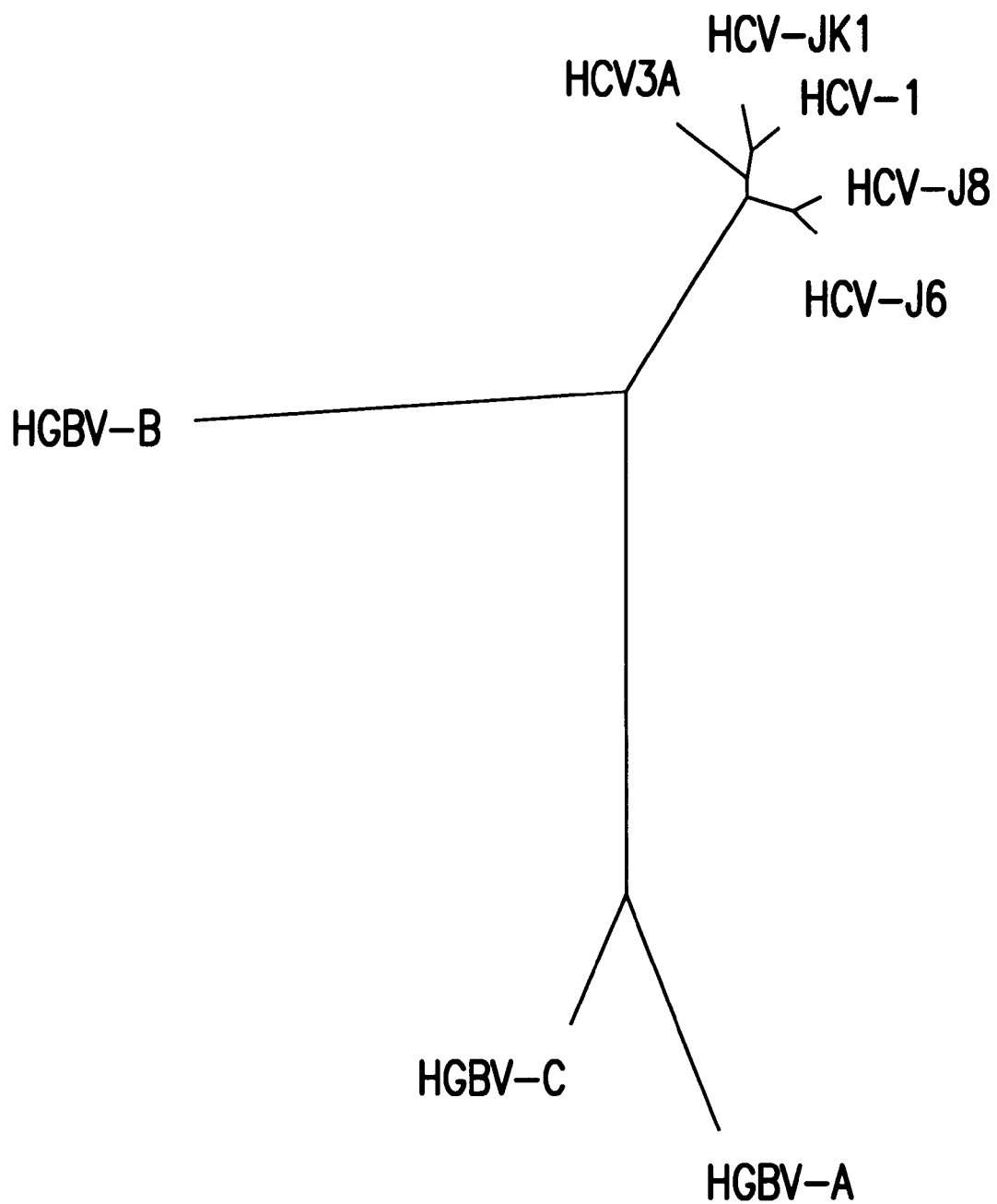
FIG. 44 presents a phylogenetic tree produced from alignment of the large open reading frames (putative precursor polyproteins) of the viruses indicated.

The amino acid sequence alignments were made using the program PILEUP of the Wisconsin Sequence Analysis Package (version 8). Phylogenetic distances between pairs of aligned sequences were determined using the PROTDIST program of the PHYLIP package (version 3.5c, 1993) kindly provided by J. Felsenstein [Felsenstein, J. (1989) *Cladistics* 5:164–166]. These computed distances were used for the construction of phylogenetic trees using the program NEIGHBOR (neighbor-joining setting). The trees were plotted using the program DRAWTREE. The trees shown are not rooted. The viral sequences used and their corresponding GenBank accession numbers are shown in TABLES 30. The evolutionary distance between each HCV genotype and each of the HGBV viruses for alignments made within the helicase, RdRp, or complete large open reading frame are presented below in TABLES 31, 32, and 33 respectively. The distances calculated between the HCV genotypes or the HGBV viruses and the other viruses listed in TABLE 30 are not shown. The phylogenetic trees produced for amino acids alignments of the viral helicases, RdRps, or complete large open reading frames sequences are shown in FIGS. 42, 43 and 44, respectively.

Amino acid sequence alignments of the putative RdRps, encoded within the NS5B region, of HGBV-A, B and C with the RdRp of several HCV genotypes, two of the pestiviruses, several representative flaviviruses, and several positive-strand RNA plant viruses, show that they possess conserved sequence motifs associated with the RdRps of positive-strand RNA viruses (data not shown). Based on similar analyses, the HGBV-A and HGBV-B encoded helicases show significant identity with the helicases of these positive-strand RNA viruses (data not shown), with the exception of CARMV, TCV, and MNSV which presumably do not possess helicase genes [Guilley, H et al. (1985) *Nucleic Acids Res.* 13:6663–6671]. These results were not unexpected in view of the association of the helicase and RdRp genes of these viruses into Supergroups demonstrated by previous phylogenetic analyses [Koonin, E. V. & Dolja, V. V. (1993) *Crit. Rev. Biochem. Mol. Biol.* 28, 375–430]. However, examination of the phylogenetic distances between the HGBV isolates and the HCV isolates based upon alignment of the helicase or RdRp sequences (TABLES 31 and 33) demonstrates that there is considerable distance between the members of these two groups. The distances calculated demonstrate the close relationship among the HCV genotypes, where the maximum distance between any two genotypes is 0.3696 (RdRp distance). However, the distances calculated from the RdRp alignment between HGBV-A, -B, or -C and any member of the HCV group is 0.96042–1.46261. Similarly, the distances calculated from the helicase alignments for any two HCV genotype ranges from 0.044555–0.19706, while distances between any member of the HCV group and HGBV-A, -B, or -C ranges from 0.69130–0.87120. In addition, alignment of the predicted amino acid sequence of the entire large open reading frames of the HCV genotype and the GB viruses demonstrates a narrow range of evolutionary distance for the HCV isolates (0.17918–0.39646) while the minimum distance between any GB virus and any HCV isolate is 1.68650. Thus, the hepatitis GB viruses exhibit evolutionary distances that are clearly outside the range demonstrated for the hepatitis C virus genotypes.

The phylogenetic analysis of the HGBV and HCV sequences is attempting to answer the question, "How does the divergence of the HGBV sequences from the HCV sequences compare with the divergence among the HCV sequences? In particular, might it be that the HGBV sequences are no more diverged from HCV sequences than the HCV sequences are from one another?" A reasonable condition to be met, if the HGBV sequences were no more diverged from HCV sequences than HCV sequences are from one another, would be that the HGBV-A, HGBV-B, and/or HGBV-C sequences would be at least as close to one of the HCV sequences as the most distantly related pair of HCV sequences (i.e., the minimum distance from any HGBV sequence to any HCV sequence is less than or equal to the maximum observed distance among HCV sequences). This condition is not met by the present sequence data; in Table 31 (RdRp alignment), the minimum HCV-HGBV distance is 2.83 times the maximum HCV-HCV distance; and in Table 32 (helicase alignment), the minimum HCV-HGBV distance is 3.51 times the maximum HCV-HCV distance. Thus, the data do not support the idea that the HGBV sequences are members of a group whose diversity is delimited by previously characterized members of the HCV group.

The distribution of these relative distances can be examined with a test based on the bootstrap [Efron, B. (1982) "The jackknife, the bootstrap, and other resampling plans", *Society Industrial and Applied Mathematics*: Philadelphia; Efron, B. and Gong, G. (1983) "A leisurely look at the bootstrap, the jackknife, and cross-validation." *Am. Stat.* 37: 36–48]. The results obtained from the bootstrap sampling are shown in Table 32; which shows the comparison of the HCV-HGBV divergence (minimum of all HCV-HGBV distances) to the HCV diversity (maximum of all HCV-HCV distances) based on PAM distances as calculated using the PROTDIST program. In 1000 bootstrap resamplings of the columns in the sequence alignments, the greatest divergence among HCV sequences was never as large as the smallest of the divergences of the HGBV sequences from the HCV sequences (Table 34). Thus, in independent measurements based on alignments of coding regions from two separate genes, there was not a single instance in which the data were consistent with the HGBV sequences falling within the genetic sequence diversity of HCV genotypes. Leaning in the direction of a conservative estimate, there is less than one chance in 100,000 that the data for the HGBVs could be drawn from the same pool of sequences as the HCV sequences.

TABLE 34

(a) Distances Determined from RdRp AlignmentAlignment Out of bootstrap 1000 samples:

| | |
|---|---|
| Average min(HCV-HGBV distance)/max(HCV-HCV distance) = | 2.543645 +/− 0.367443 |
| Minimum min(HCV-HGBV distance)/max(HCV-HCV distance) = | 1.617575 |

(b) Distances Determined from Helicase Alignment Out of bootstrap 1000 samples:

| | |
|---|---|
| Average min(HCV-HGBV distance)/max(HCV-HCV distance) = | 3.346040 +/− 0.511875 |
| Minimum min(HCV-HGBV distance)/max(HCV-HCV distance) = | 2.092055 |

Assuming that the HCV sequences utilized in this study are representative of the most divergent of the HCV genotypes, these results indicate that HGBV-A, B and C are not genotypes of HCV. In addition, it appears that HGBV-A and HGBV-C are more closely related to each other than either is to HGBV-B, which suggests that HGBV-A and HGBV-C may be representatives of a separate viral lineage. Similarly, HGBV-B may be the sole representative of its own viral lineage. The relative evolutionary distances between the viral sequences analyzed are readily apparent upon inspection of the unrooted phylogenetic trees presented in FIGS. 45 and 46, where the branch lengths are proportional to the evolutionary distance. The close evolutionary relationship of the HCV viruses is apparent and is consistent whether the analysis is performed using a portion of the encoded genomic sequence or the entire genome (FIG. 44). The large degree of divergence between HGBV-A, HGBV-B, and HGBV-C and other Flaviviridae members demonstrate that, while being most closely related to the hepatitis C viruses, the GB-agents cannot be considered genotypes of HCV and may actually be representatives of a new virus group, or groups, within the Flaviviridae.

The present invention thus provides reagents and methods for determining the presence of HGBV-A, HGBV-B and HGBV-C in a test sample. It is contemplated and within the scope of the present invention that a polynucleotide or polypeptide (or fragment[s] thereof) specific for HGBV-A, HGBV-B and HGBV-C described herein, or antibodies produced from these polypeptides and polynucleotides, can be combined with commonly used assay reagents and incorporated into current assay procedures for the detection of antibody to these viruses. Alternatively, the polynucleotides or polypeptides specific for the HGBV-A, HGBV-B and HGBV-C (or fragment[s] thereof) described herein, or anti-bodies produced from such polypeptides and polynucleotides (or fragment[s] thereof), can be used separately for detection of the HGBV-A, HGBV-B and HGBV-C viruses.

Other uses or variations of the present invention will be apparent to those of ordinary skill of the art when considering this disclosure. Therefore, the present invention is intended to be limited only by the appended claims.

TABLE 2

| | T-1048 | | | T-1053 | | | T-1057 | | | T-1061 | | | |
|---|---|---|---|---|---|---|---|---|---|---|---|---|---|
| | ALT | GGT | ICD | ALT | GGT | ICD | ALT | GGT | ICD | ALT | GGT | ICD | |
| PRE INOCULATION DAYS PRE | | | | | | | | | | | | | |
| 87 | 16 | 7 | | 59 | 12 | | 107 | 4 | | 56 | 4 | | |
| 72 | 16 | 8 | 9 | 47 | 10 | 17 | 32 | 19 | 9 | 20 | 7 | 9 | |
| 59 | 36 | 8 | 12 | 37 | 10 | 18 | 35 | 7 | 11 | 22 | 5 | 9 | |
| 45 | 28 | 5 | 12 | 37 | 8 | 17 | 19 | 4 | 11 | 23 | 5 | 12 | |
| 37 | 23 | 5 | 11 | 32 | 8 | 17 | 26 | 8 | 10 | 27 | 6 | 17 | |
| 30 | 31 | 5 | 11 | 44 | 10 | 18 | 18 | 7 | 10 | 24 | 6 | 14 | |
| 24 | 25 | 5 | 10 | 39 | 9 | 18 | 34 | 3 | 12 | 24 | 7 | 10 | |
| 17 | 19 | 4 | 11 | 49 | 10 | 18 | 32 | 7 | 8 | 26 | 7 | 11 | |
| 9 | 24 | 6 | 9 | 30 | 7 | 15 | 24 | 12 | 12 | 27 | 8 | 12 | |
| 0 | 31 | 6 | 16 | 48 | 4 | 17 | 21 | 9 | 8 | 19 | 2 | 15 | |
| POST INOCULATION DAYS POST | | | | | | | | | | | | | |
| 7 | 38 | 9 | 15 | 67 | 11 | 29 | 47 | 10 | 13 | 32 | 8 | 12 | |
| 11 | | | | 172 | 15 | 53 | | | | | | | |
| 14 | 63 | | 39 | Sacrificed | | | 198 | 34 | 90 | 48 | 7 | 16 | |
| 21 | 93 | 28 | 57 | | | | 137 | 180 | 22 | 68 | 11 | 42 | |
| 28 | 138 | 42 | 71 | | | | 179 | 197 | 45 | 69 | 19 | 34 | |
| 35 | 115 | 37 | 64 | | | | 156 | 112 | 26 | 70 | 21 | 8 | |
| 42 | 116 | 42 | 76 | | | | 139 | 177 | 54 | 87 | 23 | 61 | |
| 49 | 81 | 56 | 34 | | | | 40 | 59 | 16 | 59 | 20 | 41 | |
| 56 | 56 | 34 | 42 | | | | 29 | 26 | 12 | 59 | 30 | 45 | |
| 63 | 42 | 18 | 25 | | | | 29 | 13 | 11 | 91 | 34 | 60 | |
| 77 | 33 | 7 | 15 | | | | 35 | 9 | 12 | 37 | 22 | 29 | |
| 84 | 35 | 6 | 17 | | | | 26 | 10 | 12 | 38 | 15 | 23 | |
| 91 | 41 | 7 | 19 | | | | 33 | 7 | 12 | 17 | 11 | 14 | |
| 97 | 28 | 7 | 20 | | | | 20 | 8 | 10 | 15 | 10 | 9 | GB Challenge |
| 105 | 36 | 11 | 22 | | | | 46 | 23 | 14 | 20 | 8 | 13 | |
| 112 | 28 | 8 | 9 | | | | 30 | 13 | 11 | 19 | 10 | 12 | |
| 119 | 35 | 6 | 18 | | | | 27 | 7 | 10 | 24 | 11 | 15 | |
| CO | 48.1 | 10.1 | 18.7 | 65.1 | 15.5 | 20.7 | 50.3 | 25.2 | 15.5 | 33.7 | 12.1 | 21.9 | |

TABLE 3

| | T-1047 | | | T-1042 | | |
|---|---|---|---|---|---|---|
| | ALT | GGT | ICD | ALT | GGT | ICD |
| PRE INOCULATION DAYS PRE | | | | | | |
| 87 | 79 | 12 | | 99 | 6 | |
| 72 | 40 | 6 | 18 | 27 | 4 | 8 |
| 59 | 48 | 5 | 20 | 37 | 6 | 8 |
| 45 | 60 | 10 | 19 | 24 | 5 | 8 |
| 37 | | | | 40 | 7 | 11 |
| 30 | 47 | 8 | 26 | 39 | 4 | 10 |
| 24 | | | | 25 | 2 | 11 |
| 17 | 54 | 12 | 27 | 33 | 5 | 12 |
| 9 | | | | 44 | 5 | 11 |
| 0 | 43 | 12 | 18 | 33 | 5 | 12 |

TABLE 3-continued

|  | T-1047 | | | T-1042 | | |
|---|---|---|---|---|---|---|
|  | ALT | GGT | ICD | ALT | GGT | ICD |
| POST INOCULATION DAYS POST | | | | | | |
| 7 | 33 | 10 | 15 | 30 | 6 | 9 |
| 11 | | | | | | |
| 14 | 49 | 9 | 18 | 32 | 6 | 8 |
| 21 | 33 | 6 | 13 | 48 | 8 | 12 |
| 28 | 38 | 7 | 12 | 28 | 5 | 11 |
| 35 | 44 | 8 | 15 | 38 | 7 | 11 |
| 42 | 38 | 8 | 14 | 31 | 9 | 11 |
| 49 | 52 | 8 | 16 | 28 | 7 | 9 |
| 56 | 41 | 9 | 15 | 21 | 6 | 11 |
| CO | 73.7 | 19.1 | 35.3 | 58.6 | 9.7 | 16.1 |

TABLE 4

|  | T-1044 | | | T-1034 | | |
|---|---|---|---|---|---|---|
|  | ALT | GGT | ICD | ALT | GGT | ICD |
| PRE INOCULATION DAYS PRE | | | | | | |
| 87 | 102 | 6 | | 97 | | |
| 72 | 19 | 5 | 11 | 42 | 6 | 12 |
| 59 | 23 | 6 | 11 | 12 | 11 | 12 |
| 45 | 37 | 6 | 12 | 32 | 6 | 10 |
| 37 | 37 | 6 | 15 | 21 | 6 | 22 |
| 30 | 41 | 7 | 24 | 29 | 6 | 23 |
| 24 | 27 | 5 | 12 | 22 | 8 | 15 |
| 17 | 22 | 6 | 10 | 26 | 10 | 12 |
| 9 | 31 | 4 | 12 | 30 | 4 | 11 |
| 0 | 40 | 4 | 14 | 19 | 3 | 17 |
| POST INOCULATION DAYS POST | | | | | | |
| 7 | 34 | 6 | 14 | 27 | 8 | 13 |
| 11 | | | | | | |
| 14 | 39 | 8 | 16 | 28 | 12 | 13 |
| 21 | 36 | 6 | 10 | 21 | 8 | 16 |
| 28 | 37 | 6 | 9 | 14 | 9 | 13 |
| 35 | 35 | 5 | 10 | 19 | 9 | 12 |
| 42 | 27 | 4 | 9 | 32 | 8 | 13 |
| 49 | 59 | 7 | 13 | 33 | 7 | 14 |
| 56 | 24 | 4 | 12 | 30 | 9 | 12 |
| 63 | 30 | 5 | 11 | 31 | 9 | 12 |
| 67 | 21 | 7 | 9 | 39 | 11 | 10 |
| CO | 60.3 | 9.0 | 28.5 | 56.6 | 15.9 | 31.9 |

TABLE 5

|  | T-1038 | | | T-1049 | | | T-1051 | | | T-1055 | | |
|---|---|---|---|---|---|---|---|---|---|---|---|---|
|  | ALT | CGT | ICD | ALT | CGT | ICD | ALT | CGT | ICD | ALT | GGT | ICD |
| PRE INOCULATION DAYS PRE | | | | | | | | | | | | |
| 115 | 82 | 9 | | 102 | 13 | | 41 | 15 | | 97 | 34 | |
| 100 | 42 | 4 | 15 | 23 | 9 | 9 | 31 | 6 | 13 | 30 | 3 | 9 |
| 87 | 30 | 8 | 13 | 28 | 7 | 12 | | | | 41 | 6 | 11 |
| 73 | 45 | 5 | 16 | 68 | 10 | 27 | | | | 44 | 4 | 12 |
| 65 | | | | | | | | | | | | |
| 58 | 29 | 9 | 15 | 22 | 6 | 15 | 23 | 10 | 16 | 35 | 6 | 14 |
| 52 | | | | | | | | | | | | |
| 45 | 48 | 8 | 17 | 49 | 9 | 16 | 23 | 13 | 13 | 27 | 8 | 11 |
| 37 | | | | | | | | | | | | |
| 31 | 41 | 14 | 12 | 28 | 7 | 14 | 26 | 7 | 12 | 24 | 3 | 10 |
| 28 | | | | | | | | | | | | |
| 16 | | | | 30 | 9 | 14 | 29 | 9 | 13 | 15 | 5 | 8 |
| 0 | 32 | 16 | 10 | 24 | 6 | 15 | 27 | 9 | 11 | 23 | 7 | 10 |
| POST INOCULATION DAYS POST | | | | | | | | | | | | |
| 7 | 30 | 12 | 10 | 42 | 5 | 15 | 27 | 6 | 18 | 150 | 11 | 21 |
| 11 | 81 | 18 | 42 | 79 | 15 | 33 | 66 | 13 | 42 | 161 | 19 | 50 |
| 14 | 178 | 24 | 77 | 123 | 21 | 86 | 78 | 14 | 35 | | | |
| | | sacrificed | | | sacrificed | | | | | | sacrificed | |
| 21 | | | | | | | 108 | 18 | 60 | | | |
| 28 | | | | | | | 308 | 53 | 39 | | | |
| 35 | | | | | | | 273 | 108 | 56 | | | |
| 49 | | | | | | | 84 | 27 | 34 | | | |
| 56 | | | | | | | 66 | 28 | 34 | | | |
| 63 | | | | | | | 72 | 28 | 29 | | | |
| 69 | | | | | | | 41 | 18 | 19 | | | |
| 76 | | | | | | | 28 | 11 | 13 | | | |
| 83 | | | | | | | 44 | 12 | 15 | | | |
| 90 | | | | | | | 43 | 7 | 16 | | | |
| CO | 66.2 | 20.1 | 21.0 | 94.2 | 13.2 | 34.9 | 38.4 | 18.2 | 18.5 | 65.8 | 11.3 | 17.6 |

TABLE 8

HGBV CLONES

| Clone | size[a] | Southern[b] | Genomic PCR[c] | Tamarin Plasma[d] Pre-inoculation PCR | Tamarin Plasma[d] Pre-inoculation RT-PCR | Tamarin Plasma[d] Acute Phase PCR | Tamarin Plasma[d] Acute Phase RT-PCR | H205[e] | Northern[f] |
|---|---|---|---|---|---|---|---|---|---|
| 2 | 737 bp | neg. | ND | 0/1 | 0/1 | 0/1 | 1/1 | + | ND |
| 4 | 221 bp | ND[g] | neg. | ND | 0/1 | 0/1 | 1/1 | + | ≧7 kb |
| 10 | 307 bp | ND | neg. | ND | 0/1 | 0/1 | 1/1 | + | ND |
| 16 | 532 bp | neg. | neg. | 0/1 | 0/7 | 0/1 | 4/6 | + | ND |
| 18 | 306 bp | ND | neg. | ND | 0/1 | 0/1 | 1/1 | + | ND |
| 23 | 369 bp | ND | ND | ND | 0/1 | ND | 1/1 | + | ND |
| 50 | 337 bp | ND | neg. | ND | 0/1 | 0/1 | 1/1 | + | ≧7 kb |

[a]size of clone in base pairs (bp).
[b]Southern blot analysis of tamarin, human, yeast and *E. coli* genomic DNA using GB clone sequence as a probe. Negative (neg.) indicates that clone did not hybridize with any of the genomic DNAs tested.
[c]Genomic PCR was performed on tamarin, human yeast and *E. coli* DNAs with primers that amplify the cloned sequence. Neg. indicates that the clone was not amplified from the DNA sources tested.
[d]Tamarin plasmas, both pre-HGBV-inoculation (pre-inoc.) and acute phase (acute) were tested for the presence of cloned sequence by PCR (to detect DNA sequences) or RT-PCR (to detect RNA and DNA sequences). The results are reported as the number of PCR-positive samples per number of samples examined.
[e]H205 was tested for the presence of the clones by RT-PCR. All clones were RT-PCR positive (+) in H205 source.
[f]Northern blot analysis was performed on total liver RNA from normal tamarin liver and acute phase tamarin liver using radiolabel clone sequences. The estimated size of the specific band detected in the acute phase liver RNA is given.
[g]ND: not determined.

TABLE 12

| Sera | Days Pre (−) or Post (+) Inoculation | CORZYME A492 c/o = 0.582* | CORZYME Result | HAVAB A492 c/o = 0.662** | HAVAB Result | HCV 2.0 A492 c/o = 0.408*** | HCV 2.0 Result | HEV A492 c/o = >6**** | HEV S/N |
|---|---|---|---|---|---|---|---|---|---|
| Control Sera | | | | | | | | | |
| HuN/C | | 1.397 | − | 1.295 | − | 0.070 | − | 0.038 | − |
| HuP/C | | 0.036 | + | 0.030 | + | 1.352 | + | 1.932 | + |
| Tamarin Sera | | | | | | | | | |
| T1048 pre | −44 | N.D | N.D | N.D | N.D | N.D | N.D | 0.007 | 1.47 |
| T1048 pre | −23 | 0.912 | − | 1.834 | − | 0.023 | − | N.D | N.D |
| T1048 post | +112 | 1.148 | − | 1.387 | − | 0.025 | − | 0.026 | 0.68 |
| T1051 pre | −52 | N.D | N.D | N.D | N.D | N.D | N.D | 0.019 | 0.50 |
| T1051 pre | −8 | 0.548 | + | 1.465 | − | 0.035 | − | N.D | N.D |
| T1051 post | +76 | 0.700 | − | 1.559 | − | 0.043 | − | 0.029 | 0.76 |
| T1057 pre | −30 | N.D | N.D | N.D | N.D | N.D | N.D | 0.016 | 0.42 |
| T1057 pre | −23 | 0.369 | + | 1.411 | − | 0.029 | − | N.D | N.D |
| T1057 post | +49 | N.D | N.D | N.D | N.D | N.D | N.D | 0.017 | 0.45 |
| T1057 post | +77 | 0.580 | + | 1.444 | − | 0.028 | − | N.D | N.D |
| T1061 pre | −30 | N.D | N.D | N.D | N.D | N.D | N.D | 0.102 | 2.68 |
| T1061 pre | −23 | 0.248 | + | 0.029 | + | 0.040 | − | N.D | N.D |
| T1061 post | +112 | 0.240 | + | 0.048 | + | 0.030 | − | 0.077 | 2.03 |

*Cutoff was determined: 0.4 × N/Cx + 0.6 × P/Cx
**Cutoff was determined: N/Cx + P/Cx / 2
***Cutoff was determined: N/Cx + 25% P/C
****Cutoff was determined: S/N > 6

TABLE 14

HGBV-A Samples

| PCR product[a] | Restriction digest[b] | Reactivity with T1048 + T1051 sera | Reactivity with GB serum | Reactivity with G1-41 serum | Reactivity with G1-14 serum | Reactivity with G1-31 serum | Reactivity with 341C serum |
|---|---|---|---|---|---|---|---|
| 1.2 | EcoRI, PstI | − | − | − | − | − | − |
| 1.5 | EcoRI, HindIII | − | − | + | − | − | − |
| 1.8 | KpnI, PstI | − | − | − | − | − | − |
| 1.17 | KpnI, PstI | − | − | ND | ND | − | − |
| 1.18 | KpnI, PstI | − | − | ND | ND | + | + |
| 1.19 | KpnI, PstI | − | − | ND | ND | − | + |
| 1.20 | KpnI, PstI | − | − | ND | ND | − | − |
| 1.21 | XbaI, BamHI | − | − | ND | ND | − | − |
| 1.22 | KpnI, PstI | − | + | ND | ND | − | − |
| 1.23 | KpnI, PstI | − | − | ND | ND | − | − |
| 2.17 | BamHI, SphI | − | + | ND | ND | + | + |
| 2.18 | KpnI, PstI | − | − | ND | ND | − | − |
| 4.2 | EcoRI, blunt | − | − | ND | ND | − | − |

[a]PCR product is as indicated in Table 9, Table 10, or Example 13.
[b]Restriction digests used to liberate the PCR fragment from pT7Blue T-vector or for direct digestion of 4.2 PCR product.
ND = not done.

TABLE 16

SEROLOGIC RESULTS HGBV- B POS/TOTAL

| CATEGORY | SPECIMENS | 1.4 ELISA* | 4.1 ELISA* | 1.7 ELISA* | TOTAL |
|---|---|---|---|---|---|
| Individuals Assumed "Low Risk" for HGBV Exposure | Volunteer Blood Donors | | | | |
| | 1 | 0/200 | 0/200 | 0/200 | 0/200 |
| | 2 | 4/200 | | | 4/200 |
| | Interstate Blood Bank | 9/760 | ND** | 0/760 | 9/760 |
| Individuals Assumed "At Risk" for HCBV Exposure | Intravenous Drug Users | | | | |
| | 1 | 3/112 | 5/112 | 3/112 | 9/112 |
| | 2 | 1/99 | 0/99 | 0/99 | 1/99 |
| | Western Africa | 91/1300 | 51/1300 | 43/1300 | 181/1300 |
| | Hemophiliacs | 2/100 | ND | 1/100 | 2/100 |
| Individuals with "Non A-E Hepatitis" | Clinics in Japan | 0/180 | 7/89 | 2/180 | 9/180 |
| | Clinics in Greece | 4/73 | 0/67 | 3/73 | 5/73 |
| | Clinics in U.S. (SET M) | 1/72 | 2/72 | 3/72 | 4/72 |
| | Clinics in U.S. (SET T) | 0/64 | 0/64 | 0/64 | 0/64 |
| | Clinics in U.S. | 0/62 | 2/62 | 2/62 | 3/62 |
| | Clinics in Egypt | 9/132 | 1/132 | 9/132 | 11/132 |
| | Clinics in New Zealand | 2/56 | 1/56 | 1/56 | 4/56 |
| | Clinics in Costa Rica | 2/100 | ND | 1/100 | 2/100 |
| | Clinics in Pakistan | 2/82 | ND | 2/82 | 4/82 |
| | Clinics in Italy | 0/10 | 0/10 | 0/10 | 0/10 |
| | Clinics in U.S. | | | | |
| | SET 1 | 0/56 | ND** | 0/56 | 0/56 |
| | SET 2 | 0/20 | ND** | 0/20 | 0/20 |
| | SET 3 | 3/51 | ND** | 1/51 | 3/51 |

TABLE 17

HGBV-B Serological Results

| | Repeatably Reactive 1.4, 1.7 or 4.1 ELISA | Negative In 1.4, 1.7 or 4.1 ELISA | $X^{2*}$ | SIG** |
|---|---|---|---|---|
| Volunteer Blood Donors | 0 | 200 | — | — |
| IBB Ohio | 9 | 751 | — | ???* |
| Intravenous Drug Users | 1 | 99 | — | NS* |
| (US) | 9 | 103 | | ??? |
| West Africa | 181 | 1119 | | ???● |
| Clinics in Japan | 4 | 81 | — | ???* |
| Clinics in New Zealand | 4 | 52 | — | ???* |
| Clinics in Greece | 1 | 10 | — | ???* |
| Clinics in Egypt in U.S. | 5 | 20 | — | ???* |
| Set 1 | 0 | 56 | | NS* |
| Set 2 | 0 | 20 | | NS* |
| Set 3 | 3 | 51 | | ??? |
| Set M | 4 | 68 | | ???? |
| Set T | 0 | 64 | | NS* |
| Assumed Low Risk | 0 | 200 | — | — |
| Paid Blood Donors | 9 | 751 | | ??? |
| Assumed High Risk | 191 | 1321 | | ●?? |
| Non A-E Hepatitis | 21 | 431 | — | NS* |

*Chi square value obtained by applying the Chi square test.
**Determination of statistical significance based upon the Chi square analysis.
†Not statistically significant by the Chi square test.
●Statistically significant by the Chi square test, with p < 0.050.

TABLE 18

SEROLOGIC RESULTS - TABLE A

| | | POS/TOTAL | | | | |
|---|---|---|---|---|---|---|
| CATEGORY | SPECIMENS | 1.18 ELISA | 2.17 ELISA | 1.22 ELISA | 1.5 ELISA | TOTAL REACTIVE |
| Individuals Assumed "Low Risk" for HGBV Exposure | Volunteer Blood Donors 1 2 | 0/209 | 1/200 | 0/200 | 0/200 | 1/200 |
| | Interstate Blood Bank | ND* | ND | ND | 0/760 | 0/760 |
| Individuals Assumed "At Risk" for HGBV Exposure | Intravenous Drug Users | 1/112 | 1/112 | 0/112 | 0/112 | 2/112 |
| | Western Africa | 9/353 | 43/817 | 6/817 | 58/1300 | 91/1300 |
| Individuals with "Non A-E Hepatitis" | Clinics in Japan | 0/89 | 1/89 | ND | 4/89 | 3/89 |
| | Clinica in Greece | 0/67 | 0/67 | 0/67 | 0/67 | 0/67 |
| | Clinics in (Mayo) | 3/72 | 2/72 | 4/72 | 0/72 | 7/72 |
| | Clinics in U.S. (Thiele) | 0/64 | 0/64 | 0/64 | 0/64 | 1/64 |
| | Clinics in U.S. (1/3) | 1/62 | 2/62 | 2/62 | 0/62 | 3/62 |
| | Clinics in Egypt | 0/132 | 7/132 | 0/132 | 0/132 | 7/132 |
| | Clinica in New Zealand | ND | ND | ND | 0/56 | ND |

*Separate ELISA's were developed and cutoffs determined
**Not Done

TABLE 19

HGBV-A Serological Results

| | Repeatably Reactive in 1.18, 2.17, 1.22, or 1.5 ELISA | Negative In 1.18, 2.17, 1.22, or 1.5 ELISA | $X^2$* | SIG** |
|---|---|---|---|---|
| Volunteer Blood Donors | 1 | 199 | — | — |
| IBB Ohio | 0 | 760 | — | NS* |
| Intravenous Drug Users (US) | 2 | 110 | — | NS* |
| West Africa | 91 | 1209 | — | ???• |
| Clinics in Japan | 2 | 83 | — | ???* |
| Clinics in New Zealand | 0 | 56 | — | NS* |
| Clinics in Greece | 0 | 11 | — | NS* |
| Clinics in Egypt | 3 | 22 | — | ???* |
| in U.S. | | | | |
| Set 1 | ND | ND | — | |
| Set 2 | ND | ND | — | |
| Set 3 | ND | ND | — | |
| Set M | 7 | 65 | | ??? |
| Set T | 1 | 63 | | ??? |
| Assumed Low Risk | 1 | 200 | — | — |
| Paid Blood Donors | 0 | 760 | | NS* |
| Assumed High Risk | 93 | 1319 | | ???• |
| Non A-E Hepatitis | 13 | 300 | — | ?????* |

*Chi square value obtained by applying the Chi square test.
**Determination of statistical significance based upon the Chi square analysis.
†Not statistically significant by the Chi square test.
•Statistically significant by the Chi square test, with $p < 0.050$.

TABLE 24

HGBV-C Serological Results

| | Repeatably Reactive in C.1, C.6, or C.7 ELISA | Negative In C.1, C.6, or C.7 ELISA | $X^2$* | SIG** |
|---|---|---|---|---|
| Volunteer Blood Donors | 4 | 196 | — | — |
| IBB Ohio | ND | ND | — | NS* |
| Intravenous Drug Users (US) | 2 | 110 | — | NS* |
| West Africa | 20 | 117 | — | ???? |
| Clinics in Japan | 0 | 85 | — | NS* |
| Clinics in New Zealand | ND | ND | — | NS* |
| Clinics in Greece | 0 | 11 | — | NS* |
| Clinics in Egypt | 6 | 19 | — | ???? |
| in U.S. | | | | |
| Set 1/3 | 3 | 59 | | ???? |
| Set M | 6 | 66 | | ??? |
| Set T | 1 | 63 | | NS* |
| Assumed Low Risk | 0 | 200 | — | — |
| Paid Blood Donors | 9 | 751 | | ??? |
| Assumed High Risk | 191 | 1330 | | ???• |
| Non A-E Hepatitis | 21 | 303 | — | ???* |

*Chi square value obtained by applying the Chi square test.
**Determination of statistical significance based upon the Chi square analysis.
†Not statistically significant by the Chi square test.
•Statistically significant by the Chi square test, with $p < 0.050$.

TABLE 23

SEROLOGIC RESULTS HGBV-C

| CATEGORY | SPECIMENS | POS/TOTAL C.7 ELISA* | C.1 ELISA* | C.6 ELISA* | TOTAL |
|---|---|---|---|---|---|
| Individuals Assumed "Low Risk" for HGBV Exposure | Volunteer Blood Donors 1 2 | 0/200 | 1/200 | 3/200 | 4/200 |
| | Interstate Blood Bank | ND** | ND** | ND** | ND** |
| Individuals Assumes "At Risk" for HGBV Exposure | Intravenous Drug Users | 1/112 | 1/112 | 0/112 | 2/112 |
| | Western Africa | 5/137 | 12/97 | 3/52 | 20/137 |
| Individuals with "Non A-E Hepatitis" | Clinics in Japan | ND** | 0/89 | ND** | 0/89 |
| | Clinics in Greece | 0/67 | 0/67 | ND** | 0/67 |
| | Clinics in U.S. (SET M) | 0/72 | 2/72 | 4/72 | 6/72 |
| | Clinics in U.S. (SET T) | 1/64 | 0/64 | 0/64 | 1/64 |
| | Clinics in U.S. (SET 1/3) | 2/62 | 1/62 | 1/62 | 3/62 |
| | Clinics in Egypt | 3/132 | 0/132 | 15/132 | 18/132 |
| | Clinics in New Zealand | ND** | ND** | ND** | ND** |

TABLE 28

Amino Acid sequence similarity (identity) across large ORF's (%)

| genotype<br>isolate | 1a<br>HCV-1 | 1b<br>JK1 | 2a<br>J6 | 2b<br>J8 | 3a<br>K3A | 3b<br>Tr | HGBV-A | HGBV-B |
|---|---|---|---|---|---|---|---|---|
| HCV-JK1 | 91 (85) | | | | | | | |
| HCV-J6 | 84 (72) | 83 (71) | | | | | | |
| JCV-J8 | 84 (72) | 83 (71) | 92 (84) | | | | | |
| HCV-K3A | 85 (74) | 84 (75) | 91 (84) | 82 (70) | | | | |
| HCV-Tr | 84 (74) | 84 (73) | 82 (69) | 81 (69) | 91 (84) | | | |
| HGBV-A | 49 (26) | 52 (31) | 49 (28) | 50 (28) | 48 (26) | 47 (27) | | |
| HGBV-B | 52 (32) | 49 (27) | 52 (33) | 52 (33) | 50 (31) | 50 (31) | 29 (27) | |
| HGBV-C | 51 (29) | 49 (27) | 51 (28) | 50 (28) | 51 (29) | 50 (28) | 66 (48) | 51 (28) |

TABLE 29

Nucleotide sequence identity across entire genomes (%)

| genotype<br>isolate | 1a<br>HCV-1 | 1b<br>JK1 | 2a<br>J6 | 2b<br>J8 | 3a<br>K3A | 3b<br>Tr | HGBV-A | HGBV-B |
|---|---|---|---|---|---|---|---|---|
| HCV-JK1 | 78.8 | | | | | | | |
| HCV-J6 | 67.8 | 68.0 | | | | | | |
| JCV-J8 | 67.3 | 67.2 | 77.0 | | | | | |
| HCV-K3A | 68.6 | 69.1 | 65.9 | 65.2 | | | | |
| HCV-Tr | 68.3 | 68.4 | 65.1 | 64.9 | 77.5 | | | |
| HGBV-A | 41.6 | 41.8 | 41.5 | 41.0 | 41.6 | 41.6 | | |
| HGBV-B | 43.8 | 43.4 | 44.2 | 43.3 | 43.5 | 43.1 | 42.6 | |
| HGBV-C | 42.9 | 42.3 | 42.1 | 42.1 | 41.1 | 41.5 | 53.3 | |

TABLE 30

GenBank Accession numbers

| VIRUS | GenBank Accession Number |
|---|---|
| HCV-1 | M62321 |
| HCV-JK1 | X61596 |
| HCV-J6 | D00944 |
| HCV-J8 | D10988 |
| HCV-Tr | D26556 |
| Dengue 1 | M87512 |
| Dengue 2 | M29095 |
| BVDV, Bovine viral diarrhea virus | M31182 |
| HCHV, Hog cholera virus | J04358 |
| WNV, West nile virus | M12294 |
| YFV, Yellow fever virus | X15062 |
| JEV, Japanese encephalitis virus | M18370 |
| CARMV, Carnation mottle virus | X02986 |
| TCV, Turnip crinkle virus | M22445 |
| MNSV, Melon necrotic spot virus | D12536 |
| PMBSV, Pea seed-borne mosaic virus | D10930 |
| PPV, Plum pox virus | X16415 |
| TVMV Tobacco vien mottling virus | X04083 |
| TEV, Tobacco etch virus | M15239 |

TABLE 31

Phylogenetic distances: RdRp sequences

| | HGBV-A | HGBV-C | HCV-J6 | HCV-J8 | HCV-1 | HCV-JK1 | HCV-3A |
|---|---|---|---|---|---|---|---|
| HGBV-C | 0.54878 | | | | | | |
| HCV-J6 | 1.14632 | 1.43972 | | | | | |
| HCV-J8 | 1.16398 | 1.43043 | 0.11550 | | | | |
| HCV-1 | 1.25705 | 1.36554 | 0.26824 | 0.26864 | | | |
| HCV-JK1 | 1.23506 | 1.46261 | 0.29041 | 0.29207 | 0.11347 | | |
| HCV-3A | 1.26876 | 1.40316 | 0.34880 | 0.36960 | 0.30535 | 0.35182 | |
| HGBV-B | 1.14880 | 1.31596 | 1.00961 | 0.96402 | 1.07379 | 1.04486 | 1.01997 |

TABLE 32

Evolutionary distances: helicase sequences

|        | HGBV-A  | HGBV-C  | HCV-J6  | HCV-J8  | HCV-1   | HCV-JK1 | HCV-3A  |
|--------|---------|---------|---------|---------|---------|---------|---------|
| HGBV-C | 0.42074 |         |         |         |         |         |         |
| HCV-J6 | 0.86162 | 0.71571 |         |         |         |         |         |
| HCV-J8 | 0.87120 | 0.71731 | 0.04455 |         |         |         |         |
| HCV-1  | 0.85757 | 0.73261 | 0.14090 | 0.14079 |         |         |         |
| HCV-JK1| 0.83480 | 0.72594 | 0.14200 | 0.14779 | 0.07495 |         |         |
| HCV-3A | 0.86537 | 0.77858 | 0.18703 | 0.19706 | 0.16267 | 0.17985 |         |
| HGBV-B | 1.02224 | 0.92174 | 0.72260 | 0.71806 | 0.72050 | 0.69130 | 0.73171 |

TABLE 33

Phylogenetic distances: complete large open reading frames

|        | HGBV-A  | HGBV-C  | HCV-J6  | HCV-J8  | HCV-1   | HCV-JK1 | HCV-3A  |
|--------|---------|---------|---------|---------|---------|---------|---------|
| HGBV-C | 0.92796 |         |         |         |         |         |         |
| HCV-J6 | 2.41182 | 2.14894 |         |         |         |         |         |
| HCV-J8 | 2.41162 | 2.16319 | 0.17918 |         |         |         |         |
| HCV-1  | 2.38813 | 2.11644 | 0.35897 | 0.36481 |         |         |         |
| HCV-JK1| 2.40833 | 2.12664 | 0.36577 | 0.37948 | 0.17411 |         |         |
| HCV-3A | 2.44255 | 2.15842 | 0.38848 | 0.39646 | 0.32500 | 0.32271 |         |
| HGBV-B | 2.68767 | 2.47039 | 1.69983 | 1.68650 | 1.71216 | 1.71657 | 1.73779 |

---

SEQUENCE LISTING (1) GENERAL INFORMATION:

(iii) NUMBER OF SEQUENCES: 716

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AGCACTCTCC AGCCTCTCAC CGCA                                           24

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GATCTGCGGT GA                                                                 12

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

AGGCAACTGT GCTATCCGAG GGAA                                                              24

(2) INFORMATION FOR SEQ ID NO:4:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

GATCTTCCCT CG                                                                           12

(2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

ACCGACGTCG ACTATCCATG AACA                                                              24

(2) INFORMATION FOR SEQ ID NO:6:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GATCTGTTCA TG                                                                           12

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GGAATTCGCG GCCGCTCG                                                                     18

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

```
CGAGCGGCCG CGAATTCCTT                                                    20

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTGACACCAG ACCAACTGGT AATG                                               24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGTGGCGACG ACTCCTGGAG CCCG                                               24

(2) INFORMATION FOR SEQ ID NO:11:

(i) SEQUENCE CHARACTERISTICS:
        (A) LENGTH: 8912 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TGAATTCGTG TGGGTTCGGT GGTGGTGGCG CTTTAGGCAG CCTCCACGCC CACCACCTCC          60

CAGATAGAGC GGCGGCACTG TAGGGAAGAC CGGGGACCGG TCACTACCAA GGACGCAGAC         120

CTCTTTTTGA GTATCACGCC TCCGGAAGTA GTTGGGCAAG CCCACCTAYA TGTGTTGGGA         180

TGGTTGGGGT TAGCCATCCA TACCGTACTG CCTGATAGGG TCCTTGCGAG GGGATCTGGG         240

AGTCTCGTAG ACCGTAGCAC ATGCCTGTTA TTTCTACTCA AACAAGTCCT GTACCTGCRC         300

CCAGAACGCG CAAGAACAAG CAGACGCAGG CTTCATATCC TGTGTCCATT AAAACATCTG         360

TTGAAAGGGG ACAACGAGCA ARGCGCAAAG TCCAGCGCGA TGCTCGGCCT CGTAATTACA         420

AAATTGCTGG TATCCATGAT GGCTTGCAGA CATTGGCTCA GGCTGCTTTR CCAGCTCATG         480

GTTGGGGACG CCAAGACCCT CGCCATAAGT CTCGCAATCT TGGAATCCTT CTGGATTACC         540

CTTTGGGGTG GATTGGTGAT GTTACAACTC ACACACCTCT AGTAGGCCCG CTGGTGGCAG         600

GAGCGGTCGT TCGACCAGTC TGCCAGATAG TACGCTTGCT GGAGGATGGA GTCAACTGGG         660

CTACTGGTTG GTTCGGTGTC CACCTTTTTG TGGTATGTCT GCTATYTTTG GCCTGTCCCT         720

GTAGTGGGGC GCGGGTCACT GACCCAGACA CAAATACCAC AATCCTGACC AATTGCTGCC         780

AGCGTAATCA GGTTATCTAY TGTTCTCCTT CCACTTGCCT ACACGAGCCT GGTTGTGTGA         840

TCTGTGYGGA CGAGTGCTGG GTTCCCGCCA ATCCRTACAT CTCACACCCT TCCAATTGGA         900

CTGGCACGGA CTCCTTCTTG GCTGACCACA TTGATTTTGT TATGGGCGCT CTTGTGACCT         960

GTGACGCCCT TGACATTGGT GAGTTGTGTG GTGCGTGTGT ATTAGTCGGT GACTGGCTTG        1020
```

```
TCAGGCACTG GCTTATTCAC ATAGACCTCA ATGAAACTGG TACTTGTTAC CTGGAAKTGC    1080

CTACTGGAAT AGATCCTGGG TTCCTAGGGT TTATCGGGTG GATGGCCGGC AAGGTCGAGG    1140

CTGTCATCTT CTTGACCAAA CTGGCTTCAC AAGTACCATA CGCTATTGCG ACTATGTTTA    1200

GCAGTGTACA CTACCTGGCG GTTGGCGCTC TGATCTACTA YGCCTCTCGG GGCAAGTGGT    1260

ATCAGTTGCT CCTAGCGCTT AYGCTTTACA TAGAAGCGAC CTCTGGAAAC CCYATCAGGG    1320

TGCCCACTGG ATGCTCAATA GCTGAGTTTT GCTCGCCTTT GATGATACCA TGTCCTTGCC    1380

ACTCTTATTT GAGTGAGAAT GTGTCAGAAG TCATTTGTTA CAGTCCAAAG TGGACCAGGC    1440

CTGTCACTCT AGAGTATAAB AACTCCATAT CTTGGTACCC CTATACAATC CCTGGTGCGA    1500

GGGGATGTAT GGTTAAATTC AAAAATAACA CATGGGGTTG CTGCCGWWTC GCAATGTGCC    1560

ATCGTACTGC ACTATGGGCA CTGATGCAGT GTGGAASSAC AGTCGCAACA CTTACGAAGC    1620

ATGCGGTGTA ACACCATGGC TAACAACCGC ATGGCACAAC GGCTCAGCCC TGAAATTGGC    1680

TATATTACAA TACCCTGGGT CTAAAGAAAT GTTTAAACCT CATAATTGGA TGTCAGGCCA    1740

CTTGTATTTT GAGGGATCAG ATACCCCTAT AGTTTACTTT TATGACCCTG TGAATTCCAC    1800

TCTCCTACCA CCGGAGAGGT GGGCTAGGTT GCCCGGTACC CCACCTGTGG TACGTGGTTC    1860

TTGGTTACAG GTTCCGCAAG GTTTTACAGT GATGTGAAAG ACCTAGCCAC AGGATTGATC    1920

ACCAAAGACA AAGCCTGGAA AAATTATCAG YTCTTATATT CCGCCACGGG TGCTTTGTCT    1980

CTTACGGGAG TTACCACCAA GGCCGTGGTG CTAATTCTGT TGGGGTTGTG TGGCAGCAAG    2040

TATCTTATTT TAGCCTACCT CTGTTACTTG TCCCTTTGTT TTGGGCGCGC TTCTGGTTAC    2100

MCTTTGCGTC CTGTGCTCCC ATCCCAGTCG TATCTCCAAG CTGGCTGGGA TGTTTTGTCT    2160

AAAGCTCAAG TAGCTCMTTT TGCTTTGATT TTCTTCATCT GTTGCTATCT CCGCTGCAGG    2220

CTACGTTATG CTGCCCTTTT AGGGTTTGTG CCCATGGCTG CGGGCTTGCC CCTAACTTTC    2280

TTTGTTGCAG CAGCTGCTGC CCAACCAGAT TATGACTGGT GGGTGCGACT GCTAGTGGCA    2340

GGGTTAGTTT TGTGGGCCGG CCGTGACCGT GGTCACGCAT AGCTCTGCTT GTAGGTCCTT    2400

GGCCTCTGGT AGCGCTTTYT AACCCTCTTG CATTTSSTKA CGCCTGCTTA GCTTTTGACA    2460

CCGAGATAAT TGGAGGGCTG ACAATACCAC CTGTAGTAGC ATTAGTTGTC ATGTCTCGTT    2520

TTGGCTTCTT TGCTCACTTG TTACCTCGCT GTGCTTTAGT TAACTCCTAT CTTTGGCAAC    2580

GTTGGGAGAA TTGGTTTTGG AACGTTACAC TAAGACCGGA GAGGTTTCTC CTTGYGCTGG    2640

TTTGTTTCCC CGGTGCGACA TATGACGTGC TGGTGACWTT CTGTGTGTGT CACGTAGCTC    2700

TTCTATGTTT AACATCCAGT GCAGCAYMGT TCTTTGGGAC TGACTCTAGG GTTAGGGCCC    2760

ATAGAATGTT GGTGCGTCTC GGAAAGTGTC ATGCTTGGTA TTCTCATTAT GTTCTTAAGT    2820

TTTTCCTCTT AGTGTTTGGT GAGAATGGTG TGTTTTTCTA KAAGCACTTG CATGGTGATG    2880

TCTTGCCTAA TGATTTTGCC TCGAAACTAC CATTGCAAGA GCCATTTTTC CCTTTTGAAG    2940

GCAAGGCAAG GGTCTATAGG AATGAAGGAA GACGCTTGGS KKGTGGGGAC ACGGTTGATG    3000

GTTTGSSCGT TGTBGCGCGT CTCGGCGACC TTGTTTTCGC AGGGTTAGCT ATGCCGCCAG    3060

ATGGGTGGGC CATTACCGCA CCTTTTACGC TGCAGTGTCT CTCTGAACGT GGCACGCTGT    3120

CAGCGATGGC AGTGGTCATG ACTGGTATAG ACCCCCGAAC TTGGACTGGA ACTATCTTCA    3180

GATTAGGATC TCTGGCCACT AGCTACATGG GATTTGTTTG TGACAACGTG TTGAATACTG    3240

CTCACCATGG CAGCAACGGG GGCCGGTTGG CTCATCCCAC AGGCTCCATA CACCCAATAA    3300

CCGTTGACGC GGCTAATGAC CAGGACATCT ATCAACCACC ATGTGGAGCT GGGTCCCTTA    3360

CTCGGTGCTC TTGCGGGGAG ACCAAGGGGT ATCTGGTAAC ACGACTGGGG TCATTGGTTG    3420
```

```
AGGTCAACAA ATCCGATGAC CCTTATTGGT GTGTGTGCGG GGCCCTTCCC ATGGCTGTTG    3480
CCAAGGGTTC TTCAGGTGCC CCGATTCTGT GCTCCTCCGG GCATGTTATT GGGATGTTCA    3540
CCGCTGCTAG AAATTCTGGC GGTTCAGTCG GCCAGATTAG GGTTAGGCCG TTGGTGTGTG    3600
CTGGATACCA TCCCCAGTAC ACAGCACATG CCACTCTTGA TACAAAACCT ACTGTGCCTA    3660
ACGAGTATTC AGTGCAAATT TTAATTGCCC CCACTGGCAG CGGCAAGTCA ACCAAATTAC    3720
CACTTTCTTA CATGCAGGRG AAGYATGAGG TCTTGGTCCT AAATCCCAGT GTGGCTACAA    3780
CAGCATCAAT GCCAAAGTAC ATGCACGCGA CGTACGGCGT GAATCCAAAT TGCTATTTTA    3840
ATGGCAAATG TACCAACACA GGGGCTTCAC TTACGTACAG CACATATGGC ATGTACCTGA    3900
CCGGACGATG TTCCCGGAAC TATGATGTAA TCATTTGTGA CGAATGCCAT GCTACCGATC    3960
GAACCACCGT GTTGGGCATT GGAAAGGTCC TAACCGAAGC TCCATCCAAA AATGTTAGGC    4020
TAGTGGTTCT TGCCACGGCT ACCCCCCCTG GAGTAATCCC TACACCACAT GCCAACATAA    4080
CTGAGATTCA ATTAACYGAT GAAGGCACTA TCCCCTTTCA TGGAAAAAAG ATTAAGGAGG    4140
AAAATCTGAA GAAAGGGAGA CACCTTATCT TTGAGGCTAC CAAAAAACAC TGTGATGAGC    4200
TTGCTAACGA GTTAGCTCGA AAGGGAATAA CAGCTGTCTC TTACTATAGG GGATGTGACA    4260
TCTCAAAAAT GCCTGAGGGC GACTGTGTAG TAGTTGCCAC TGATGCCTTG TGTACAGGGT    4320
ACACTGGTGA CTTTGATTCC GTGTATGACT GCAGCCTCAT GGTAGAAGGC ACATGCCATG    4380
TTGACCTTGA CCCTACTTTC ACCATGGGTG TTCGTGTGTG CGGGGTTTCA GCAATAGTTA    4440
AAGGCCAGCG TAGGGGCCGC ACAGGCCGTG GGAGAGCTGG CATATACTAC TATGTAGACG    4500
GGAGTTGTAC CCCTTCGGGT ATGGTTCCTG AATGCAACAT TGTTGAAGCC TTCGACGCAG    4560
CCAAGGCATG GTATGGTTTG TCATCAACAG AAGCTCAAAC TATTCTGGAC ACCTATCGCA    4620
CCCAACCTGG GTTACCTGCG ATAGGAGCAA ATTTGGACGA GTGGGCTGAT CTCTTTTCTA    4680
TGGTCAACCC CGAACCTTCA TTTGTCAATA CTGCAAAAAG AACTGCTGAC AATTATGTTT    4740
TGTTGACTGC AGCCCAACTA CAACTGTGTC ATCAGTATGG CTATGCTGCT CCCAATGACG    4800
CACCACGGTG GCAGGGAGCC CGGCTTGGGA AAAAACCTTG TGGGGTTCTG TGGCGCTTGG    4860
ACGGCTGTGA CGCCTGTCCT GGCCCAGAGC CCAGCGAGGT GACCAGATAC CAAATGTGCT    4920
TCACTGAAGT CAATACTTCT GGGACAGCCG CACTCGCTGT TGGCGTTGGA GTGGCTATGG    4980
CTTATCTAGC CATTGACACT TTTGGCGCCA CTTGTGTGCG GCGTTGCTGG TCTATTACAT    5040
CAGTCCCTAC CGGTGCTACT GTCGCCCCAG TGGTTGACGA AGAGGAAATC GTGGAGGAGT    5100
GTGCATCATT CATTCCCTTG GAGGCCATGG TTGCTGCAAT TGACAAGCTG AAGAGTACAA    5160
TCACCACAAC TAGTCCTTTC ACATTGGAAA CCGCCCTTGA AAAACTTAAC ACCTTTCTTG    5220
GGCCTCATGC AGCTACAATC CTTGCTATCA TAGAGTATTG CTGTGGCTTA GTCACTTTAC    5280
CTGACAATCC CTTTGCATCA TGCGTGTTTG CTTTCATTGC GGGTATTACT ACCCCACTAC    5340
CTCACAAGAT CAAAATGTTC CTGTCATTAT TTGGAGGCGC AATTGCGTCC AAGCTTACAG    5400
ACGCTAGAGR CGCACTGGCG TTCATGATGG CCGGGGCTGY GGGAACAGCT CTTGGTACAT    5460
GGACATCGGT GGGTTTTGTC TTTGACATGC TAGGCGGCTA TGCTGGCGCC TCATCCACTG    5520
CTTGCTTGAC ATTTAAATGC TTGATGGGTG AGTGGCYCAC TATGGATCAG TTGCTGGTT    5580
TAGTCTACTC CGCGTTCAAT CCGGCCGCAG GAGTTGTGGG CGTCTTGTCA GCTTGTGCAA    5640
TGTTTGCTTT GACAACAGCA GGGCCAGATC ACTGGCCCAA CAGACTTCTT ACTATGCTTG    5700
CTAGGAGCAA CACTGTATGT ARTGAGTACT TTATTGCCAC TCGTGACATC CGCAGGAAGA    5760
```

-continued

```
TACTGGGCAT TCTGGAGGCA TCTACCCCCT GGAGTRTCAT ATCAGCTTGC ATCCGTTGGC      5820
TYCACACCCC GACGGAGGAT GATTGCGGCC TCATTGCTTG GGGTCTARAG ATTTGGCAGT      5880
ATGTGTGCAA TTTCTTTGTG ATTTGCTTTA ATGTCCTTAA AGCTGGAGTT CAGAGCATGG      5940
TTAACATTCC TGGTTGTCCT TTCTACAGCT GCCAGAAGGG GTACAAGGGC CCCTGGATTG      6000
GATCAGGTAT GCTCCAAGCA CGCTGTCCAT GCGGTGCTGA ACTCATCTTT TCTGTTGAGA      6060
ATGGTTTTGC AAAACTTTAC AAAGGACCCA GAACTTGTTC AAATTACTGG AGAGGGCTG       6120
TTCCAGTCAA CGCTAGGCTG TGTGGGTCGG CTAGACCGGA CCCAACTGAT GGACTAGTC       6180
TTGTCGTCAA TTATGGCGTT AGGGACTACT GTAAATATGA GAAATTGGGA GATCACATTT      6240
TTGTTACAGC AGTATCCTCT CCAAATGTCT GTTTCACCCA GGTGCCCCCA ACCTTGAGAG      6300
CTGCAGTGGC CGTGGACCGC GTACAGGTTC AGYGTTATCT AGGTGAGCCC AAAACTCCTT      6360
GGACGACATC TGCTTGCTGT TACGGTCCTG ACGGTAAGGG TAAAACTGTT AAGCTTCCCT      6420
TCCGCGTTGA CGGACACACA CCTGGTGGTC GCATGCAACT TAATTTGCGT GATCGACTTG      6480
AGGCAAATGA CTGTAATTCC ATAAACAACA CTCCTAGTGA TGAAGCCGCA GTGTCCGCTC      6540
TTGTTTTCAA ACAGGAGTTG CGGCGTACAA ACCAATTGCT TGAGGCAATT TCAGCTGGCG      6600
TTGACACCAC CAAACTGCCA GCCCCCTCCC AGATCGAAGA GGTAGTGGTA AGAAAGCGCC      6660
AGTTCCGGGC AAGAACTGGT TCGCTTACCT TGCCTCCCCC TCCGAGATCC GTCCCAGGAG      6720
TGTCATGTCC TGAAAGCCTG CAACGAAGTG ACCCGTTAGA AGGTCCTTCA AMCCTCCCTT      6780
CTTCACCACC TGTTCTRCAG TTGGCCATGC CGATGCCCCT GTTGGGAGCA GGTGAGTGTA      6840
ACCCTTTCAC TGCAATTGGA TGTGCAATGA CCGAAACARG YGGAGKCCCW MAKRATTTAC      6900
CCAGTTACCC TCCCAAAAAG GAGGTCTCTG AATGGTCAGA CGAAAGTTGG TCAACGACTA      6960
CAACCGCTTC CAGCTACGTT ACTGGCCCCC CGTACCCTAA GATACGGGGC AAGGATTCCA      7020
CTCAATCAGC CACCGCCAAA CGGCCTACAA AAAAGAAGTT GGGAAAGAGT GAGTTTTCGT      7080
GCAGCATGAG CTACACTTGG ACCGACGTGA TTAGCTTCAA AACTGCTTCT AAAGTTCTGT      7140
CTGCAACTCG GGCCATCACT AGTGGTTTCC TCAAACAAAG ATCATTGGTG TATGTGACTG      7200
AGCCGCGGGA TGCGGAGCTT AGAAAACAAA AAGTCACTAT TAATAGACAA CCTCTGTTCC      7260
CCCCATCATA CCACAAGCAA GTGAGATTGG CTAAGGAAAA AGCTTCAAAA GTTGTCGGTG      7320
TCATGTGGGA CTATGATGAA GTAGCAGCTC ACACGCCCTC TAAGTCTGCT AAGTCCCACA      7380
TCACTGGCCT TCGGGCACT GATGTTCGTT CTGGAGCGGC CCGCAAGGCT GTTCTGGACT       7440
TGCAGAAGTG TGTCGAGGCA GGTGAGATAC CGAGTCATTA TCGGCAAACT GTGATAGTTC      7500
CAAAGGAGGA GGTCTTCGTG AAGACCCCCC AGAAACCAAC AAAGAAACCC CCAAGGCTTA      7560
TCTCGTACCC CCACCTTGAA ATGAGATGTG TTGAGAAGAT GTACTACGGT CAGGTTGCTC      7620
CTGACGTAGT TAAAGCTGTC ATGGGAGATG CGTACGGGTT TGTAGATCCA CGTACCCGTG      7680
TCAAGCGTCT GTTGTCGATG TGGTCACCCG ATGCAGTCGG AGCCACATGC GATACAGTGT      7740
GTTTTGACAG TACCATCACA CCCGAGGATA TCATGGTGGA GACAGACATC TACTCAGCAG      7800
CTAAACTCAG TGACCAACAC CGAGCTGGCA TTCACACCAT TGCGAGGCAG TATCACGCTG      7860
GAGGACCGAT GATCGCTTAT GATGGCCGAG AGATCGGATA TCGTAGGTGT AGGTCTTCCG      7920
GCGTCTATAC TACCTCAAGT TCCAACAGTT TGACCTGCTG GCTGAAGGTA AATGCTGCAG      7980
CCGAACAGGC TGGCATGAAG AACCCTCGCT TCCTTATTTG CGGCGATGAT TGCACCGTAA      8040
TTTGGAAGAG CGCCGGAGCA GATGCAGACA AACAAGCAAT GCGTGTCTTT GCTAGCTGGA      8100
TGAAGGTGAT GGGTGCACCA CAAGATTGTG TGCCTCAACC CAAATACAGT TTGGAAGAAT      8160
```

```
TAACATCATG CTCATCAAAT GTTACCTCTG GAATTACCAA AAGTGGCAAG CCTTACTACT      8220

TTCTTACAAG AGATCCTCGT ATCCCCCTTG GCAGGTGCTC TGCCGAGGGT CTGGGATACA      8280

ACCCCAGKGC KGCGTGGATT GGGTATCTAA TACATCACTA CCCATGTTTG TGGGTTAGCC      8340

GTGTGTTGGC TGTCCATTTC ATGGAGCAGA TGCTCTTTGA GGACAAACTT CCCGAGACTG      8400

TGACCTTTGA CTGGTATGGG AAAAATTATA CGGTGCCTGT AGAAGATCTG CCCAGCATCA      8460

TTGCTGGTGT GCACGGTATT GAGGCTTTCT CGGTGGTGCG CTACACCAAC GCTGAGATCC      8520

TCAGAGTTTC CCAATCACTA ACAGACATGA CCATGCCCCC CCTGCGAGCC TGGCGAAAGA      8580

AAGCCAGGGC GGTCCTCGCC AGCGCCAAGA GGCGTGGCGG AGCACACGAA AATTGGCTCG      8640

CTTCCTTCTC TGGCATGCTA CATCTAGACC TCTACCAGAT TTGGATAAGA CGAGCGTGGC      8700

TCGGTACACC ACTTTCAATT ATTGTGATGT TTACTCCCSG AGRGGGATGT GTTTATTACA      8760

CCACAGAGAA GATTGCAGAA GTTTCTTGTG AAGTATTTGG CTGTCATTGT TTGTGCCCTA      8820

GGGCTCATTG CTGTTGGACT AGCCATCAGC TGAACCCCCA AATTCAAAAT TAATTAACAG      8880

TTTTTTTTTT TTTTTTTTTT TTTTTTTAGG GC                                    8912

(2) INFORMATION FOR SEQ ID NO:12:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGTGTAACC CTTTCACTGC AATTGGATGT GCAATGACCG AAACAGGCGG AGGCCCTGAT       60

GATTTACCCA GTTACCCTCC CAAAAAGGAG GTCTCTGAAT GGTCAGACGA AAGTTGGTCA      120

ACGACTACAA CCGCTTCCAG CTACGTTACT GGCCCCGTA CCCTAAGATA CGGGAAGGA       180

TTCCACTCAA TTAGCCC                                                     197

(2) INFORMATION FOR SEQ ID NO:13:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CCTCGACACA CTTCTGCAAG TCCAGAACAG CCTTGCGGGC TGCTCCAGAA CGAACATCAG       60

TGCCCCGAAG CCAGTGATGT GGGACTTAGC AGACTTAGAG GGCGTGTGAG CTGCTACTTC      120

ATCATAGTCC CACATGACAC CGACAACTTT TGAAGCTTTT TCCTTAGCCA ATCTCACTTG      180

CTTGTGGTAT GATGGGGGA ACAGAGG                                           207

(2) INFORMATION FOR SEQ ID NO:14:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:14:

Glu Cys Asn Pro Phe Thr Ala Ile Gly Cys Ala Met Thr Glu Thr Xaa
1               5                   10                  15

Gly Xaa Xaa Xaa Xaa Leu Pro Ser Tyr Pro Pro Lys Lys Glu Val Ser
                20                  25                  30

Glu Trp Ser Asp Glu Ser Trp Ser Thr Thr Thr Ala Ser Ser Tyr
        35                  40                  45

Val Thr Gly Pro Pro Tyr Pro Lys Ile Arg Gly Lys Asp Ser Thr Gln
    50                  55                  60

Ser Ala Thr Ala Lys Arg Pro Thr Lys Lys Leu Gly Lys Ser Glu
65              70                  75                  80

Phe Ser Cys Ser Met Ser Tyr Thr Trp Thr Asp Val Ile Ser Phe Lys
                85                  90                  95

Thr Ala Ser Lys Val Leu Ser Ala Thr Arg Ala Ile Thr Ser Gly Phe
                100                 105                 110

Leu Lys Gln Arg Ser Leu Val Tyr Val Thr Glu Pro Arg Asp Ala Glu
        115                 120                 125

Leu Arg Lys Gln Lys Val Thr Ile Asn Arg Gln Pro Leu Phe Pro Pro
130                 135                 140

Ser Tyr His Lys Gln Val Arg Leu Ala Lys Glu Lys Ala Ser Lys Val
145                 150                 155                 160

Val Gly Val Met Trp Asp Tyr Asp Glu Val Ala Ala His Thr Pro Ser
                165                 170                 175

Lys Ser Ala Lys Ser His Ile Thr Gly Leu Arg Gly Thr Asp Val Arg
                180                 185                 190

Ser Gly Ala Ala Arg Lys Ala Val Leu Asp Leu Gln Lys Cys Val Glu
                195                 200                 205

(2) INFORMATION FOR SEQ ID NO:15:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGTTCCTGAA TGCAACATTG TTGAAGCCTT CGACGCAGCC AAGGCATGGT ATGGTTTGTC     60

ATCAACAGAA GCTCAAACTA TTCTGGACAC CTATCGCACC CAACCTGGGT TACCTGCGAT    120

AGGAGCAAAT TTGGACGAGT GGGCTGATCT CTTTTCTATG GTCAACCCCG AACCTTCATT    180

TGTCAATACT GCAAAAAGAA CTGCTGACAA TTATGTTTTG TTGACTGCAG               230

(2) INFORMATION FOR SEQ ID NO:16:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Val Pro Glu Cys Asn Ile Val Glu Ala Phe Asp Ala Ala Lys Ala Trp
            5                   10                  15

```
Tyr Gly Leu Ser Ser Thr Glu Ala Gln Thr Ile Leu Asp Thr Tyr Arg
            20                  25                  30

Thr Gln Pro Gly Leu Pro Ala Ile Gly Ala Asn Leu Asp Glu Trp Ala
            35                  40                  45

Asp Leu Phe Ser Met Val Asn Pro Glu Pro Ser Phe Val Asn Thr Ala
        50                  55                  60

Lys Arg Thr Ala Asp Asn Tyr Val Leu Leu Thr Ala
65                  70                  75
```

(2) INFORMATION FOR SEQ ID NO:17:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GTATGGTTCC TGAATGCAAC ATTGTTGAAG CCTTCGACGC AGCCAAGGCA TGGTATGGTT      60

TGTCATCAAC AGAAGCTCAA ACTATTCTGG ACACCTATCG CACCCAACCT GGGTTACCTG     120

CGATAGGAGC AAATTTGGAC GAGTGGGCTG ATCTCTTTTC TATGGTCAAC CCCGAACCTT     180

CATTTGTCAA TACTGCAAAA AGAACTGCTG ACAATTATGT TTTGTTGACT GCAGCCCTGC     240

CACCGTGGTG CGTCATTGGG AGCAGCATAG CCATACTGAT GACACAGTTG T              291
```

(2) INFORMATION FOR SEQ ID NO:18:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GCGCATGCAA CTTAATTTGC GTGATGCACT TGAGACAAAT GACTGTAATT CCATAAACAA      60

CACTCCTAGT GATGAAGCCG CAGTGTCCGC TCTTGTTTTC AAACAGGAGT TGCGGCGTAC     120

AAACCAATTG CTTGAGGCAA TTTCAGCTGG CGTTGACACC ACCAAACTGC CAGCCCCCTC     180

CATCGAAGAG GTAGTGGTAA GAAAGCGCCA GTTCCGGGCA AGAACTGGTT CGCTTACCTT     240

GCCTCCCCCT CCGAGATCCG TCCCAGGAGT GTCATGTCCT G                        281
```

(2) INFORMATION FOR SEQ ID NO:19:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Arg Met Gln Leu Asn Leu Arg Asp Ala Leu Glu Thr Asn Asp Cys Asn
1               5                   10                  15

Ser Ile Asn Asn Thr Pro Ser Asp Glu Ala Ala Val Ser Ala Leu Val
            20                  25                  30

Phe Lys Gln Glu Leu Arg Arg Thr Asn Gln Leu Leu Glu Ala Ile Ser
            35                  40                  45
```

```
Ala Gly Val Asp Thr Thr Lys Leu Pro Ala Pro Ser Ile Glu Glu Val
    50                  55                  60

Val Val Arg Lys Arg Gln Phe Arg Ala Arg Thr Gly Ser Leu Thr Leu
65                  70                  75                  80

Pro Pro Pro Pro Arg Ser Val Pro Gly Val Ser Cys Pro
                85                  90
```

(2) INFORMATION FOR SEQ ID NO:20:

(i) SEQUENCE CHARACTERISTICS:
        (A) LENGTH: 281 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GCGCATGCAA CTTAATTTGC GTGATGCACT TGAGACAAAT GACTGTAATT CCATAAACAA      60

CACTCCTAGT GATGAAGCCG CAGTGTCCGC TCTTGTTTTC AAACAGGAGT TGCGGCGTAC     120

AAACCAATTG CTTGAGGCAA TTTCAGCTGG CGTTGACACC ACCAAACTGC CAGCCCCCTC     180

CATCGAAGAG GTAGTGGTAA GAAAGCGCCA GTTCCGGGCA AGAACTGGTT CGCTTACCTT     240

GCCTCCCCCT CCGAGATCCG TCCCAGGAGT GTCATGTCCT G                        281
```

(2) INFORMATION FOR SEQ ID NO:21:

(i) SEQUENCE CHARACTERISTICS:
        (A) LENGTH: 221 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GATCCATAGT GAGCCACTCA CCCATCAAGC ATTTAAATGT CAAGCAAGCA GTGGATGAGG      60

CGGCAGCATA GCCGCCTAGC ATGTCAAAGA CAAAACCCAC CGATGTCCAT GTACCAAGAG     120

CTGTTCCCAC AGCCCCGGCC ATCATGAACG CCAGTGCGTC TCTAGCGTCT GTAAGCTTGG     180

ACGCAATTGC GCCTCCAAAT AATGACAGGA ACATTTTGAT C                        221
```

(2) INFORMATION FOR SEQ ID NO:22:

(i) SEQUENCE CHARACTERISTICS:
        (A) LENGTH: 737 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GATCGAAGCA CACCTCAAGC CCTAAGACGC TGTGTCGCTC CCGGGTTACC CCGCAGCTAC      60

CACCAATACC AGCGGCAGAC GACCCCTTGC GAAGTGCATC GCCACAAGCA CGGCAGCCCT     120

CACAGAGCCC AGGACATTCA GGTACGCCAC GACACACATC ACACCCAGAC AACCAGTGAA     180

CCACCACTCC TGGGCTGCCC AGCCGACCAC CGGGGCGCAC ACCAGCTCGG GAGCCAGCGC     240

GCCTCGACGA CCGGCAAGTA AGCCCCAACA TTTGACAACC AGGCCAGACC GGCAGCGAAC     300

GTTCGCAGCT TGAGCCACGC GGGCCAGATG TCACCAACGA CGGCCTGAGC ACCATCATTG     360
```

```
GCAGCACCCC AGACCGCCTG AGCCCCGGCC GTCAGGCCTG CCACCATGTA GCAACCAGCA      420

TTGTAGGTAG AGTCCGCGAC TCCGGTGGTA GAATTCGGAC AAGATGGAGT TGGAACAGTG      480

GGCGGAGTCC ACAATGGAAC ACTTTCAGTG GACTTCGTGA CAGAAGGGTG TATGATAACA      540

ATAGTGGCGG CAGATGCTCC ATTCAACCAC CACCACATTG CCAGCATAAA CAGGGGGCA      600

ACTCTAGCCT CAGCCAACTT CATCACTACC AACAGGGCCA GGACCATGTC AGTAAGCAAC      660

CAAGCCGCGG AAGACCTTCG CTGACCACTG TAAACCTGCT GTCTGTTGCC TTTAACATGG      720

ATGAAGCCGT TGTGATC                                                     737

(2) INFORMATION FOR SEQ ID NO:23:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GATCACTGTG GACGCCACTT GTTTCGACTC ATCGATTGAT GAGCACGATA TGCAGGTGGA       60

GGCCTCGGTG TTTGCGGCGG CTAGTGACAA CCCCTCAATG GTACATGCTT TGTGCAAGTA      120

CTACTCTGGT GGCCCTATGG TTTCCCCAGA TGGGGTTCCC TTGGGGTACC GCCAGTGTAG      180

GTCGTCGGGC GTGTTGACAA CTAGCTCGGC GAACAGCATC ACTTGTTACA TTAAGGTCAG      240

CGCGGCCTGC AGGCGGGTGG GGATTAAGGC ACCATCATTC TTTATAGCTG GAGATGATTG      300

CTTGATC                                                                307

(2) INFORMATION FOR SEQ ID NO:24:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GATCAGGCCG CTGAGCGGCC GAGAAGGTTA CAATCTGGAG GGGTGATAGG AAGTATGACA       60

AGCATTATGA GGCTGTCGTT GAGGCTGTCC TGAAAAAGGC AGCCGCGACG AAGTCTCATG      120

GCTGGACCTA TTCCCAGGCT ATAGCTAAAG TTAGGCGCCG AGCAGCCGCT GGATACGGCA      180

GCAAGGTGAC CGCCTCCACA TTGGCCACTG GTTGGCCTCA CGTGGAGGAG ATGCTGGACA      240

AAATAGCCAG GGGACAGGAA GTTCCTTTCA CTTTTGTGAC CAAGCGAGAG GTTTTCTTCT      300

CCAAAACTAC CCGTAAGCCC CCAAGATTCA TAGTTTTCCC ACCTTTGGAC TTCAGGATAG      360

CTGAAAAGAT GATTCTGGGT GACCCCGGCA TCGTTGCAAA GTCAATTCTG GGTGACGCTT      420

ATCTGTTCCA GTACACGCCC AATCAGAGGG TCAAAGCTCT GGTTAAGGCG TGGGAGGGGA      480

AGTTGCATCC CGCTGCGATC                                                  500

(2) INFORMATION FOR SEQ ID NO:25:

(i) SEQUENCE CHARACTERISTICS:
        (A) LENGTH: 479 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:25:

| | | | | | |
|---|---|---|---|---|---|
| GATCACATTT | TTGTTACAGC | AGTATCCTCT | CCAAATGTCT | GTTTCACCCA | GGTGCCCCCA | 60 |
| ACCTTGAGAG | CTGCAGTGGC | CGTGGACCGC | GTACAGGTTC | AGYGTTATCT | AGGTGAGCCC | 120 |
| AAAACTCCTT | GGACGACATC | TGCTTGCTGT | TACGGTCCTG | ACGGTAAGGG | TAAAACTGTT | 180 |
| AAGCTTCCCT | TCCGCGTTGA | CGGACACACA | CCTGGTGGTC | GCATGCAACT | TAATTTGCGT | 240 |
| GATCGACTTG | AGGCAAATGA | CTGTAATTCC | ATAAACAACA | CTCCTAGTGA | TGAAGCCGCA | 300 |
| GTGTCCGCTC | TTGTTTTCAA | ACAGGAGTTG | CGGCGTACAA | ACCAATTGCT | TGAGGCAATT | 360 |
| TCAGCTGGCG | TTGACACCAC | CAAACTGCCA | GCCCCCTCCC | AGATCGAAGA | GGTAGTGGTA | 420 |
| AGAAAGCGCC | AGTTCCGGGC | AAGAACTGGT | TCGCTTACCT | TGCCTCCCCC | TCCGAGATC | 479 |

(2) INFORMATION FOR SEQ ID NO:26:

(i) SEQUENCE CHARACTERISTICS:
        (A) LENGTH: 532 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

| | | | | | |
|---|---|---|---|---|---|
| GATCAACACC | TCGTCACCCC | GTCTCGCAAC | CACAGGTTTC | CCGTGGACCA | ACTGTCCACA | 60 |
| GCCTAACACA | CGAGCAGAGT | CCCGAACAAT | AGCACAATCT | TCCTTGGTTA | TGCTAACAGG | 120 |
| CTCAAGCGCA | AAACCCCACT | CTCGCAAGCG | GGCAGCACCG | CGCCTGCTAG | TGTGACCGGC | 180 |
| GTGCTCGTAG | AGGAGGACGC | CCTGCTTGCG | CAGGACGCCC | ACCAGCCAAG | AGCAGGCCAG | 240 |
| CCGCTCCTCA | GCAAGAGCTA | AGGAGTCCAG | CACCCGCGCC | AAGCGCGCGA | GATTTGGTGA | 300 |
| GTTAACCAAG | AGTACTTCCA | AGATGAAATC | AATGACATCT | AAACTGCTCA | AACAGAGTAT | 360 |
| GAAGATGACG | GAAACTGTGG | CAACTGTTTG | GGGGAAGAAC | CAAGCCACAA | CCAACCAAGC | 420 |
| TTTCCAGCAC | GCCTCCAACG | GCCAAAAGCT | CCAACCGGCG | AGTTGTTCAC | CCACCGGCGA | 480 |
| ACCCTCTGGT | AATTGACGGC | CCACCTGGCA | TACCAAGTCA | ATCTGGCTGA | TC | 532 |

(2) INFORMATION FOR SEQ ID NO:27:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

| | | | | | |
|---|---|---|---|---|---|
| GATCCATCTT | GACAATGACA | ACTTTCGCAG | GACAGTAGAC | ACCTTGGTGACGAACTCATC | | 60 |
| TTTGAGGAAG | AAATCGTCAG | GCATCACCGA | ACTGCGTGGC | ATCATCGTCAACAATCTGTT | | 120 |
| AACCCAATCT | TGACCCACAC | CCTTTTTGAC | AGACCAGAGC | AACAAGCCCAGAACCACACC | | 180 |
| GGCCACCGAA | GCCCCGGAG | AGGCCAGGCA | ACTGACCAGG | CACCAAGCGTCACTCGCTTG | | 240 |
| TAACTTCCCC | GCCAGGAGGT | CGAAGGTGAG | TGAGCGCGGT | TCACCGCCCCCTCCCAGCCT | | 300 |
| CTGATC | | | | | | 306 |

(2) INFORMATION FOR SEQ ID NO:28:

(i) SEQUENCE CHARACTERISTICS:
            (A) LENGTH: 369 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:28:

GATCACCCAC ACCCCGGTTG GTTGGCACTT GCATGCCTGA AGGCAAGAAGCACCATTAGG     60

GAGCGGGTAG ACCGTGACGT CGTCACTCGC TAACCACCAC CGAGCATTGACAGGACCGAA    120

AGCCCCACCA TAGGCCGGAC GTTGGTACCA CGGTATGTCG TGTACATCACTCCGTTCACG    180

CAGCAGCCCA TGGAACGAGT TGTTGAAGTC CCAAGGACCA CCACGTTCCCGTGATGTTCG    240

GACGAGTCCT TGCCTGTCAT GGAGGTCCTC ACAACCCCGA AGAATCCCTTGCCAGCTTGA    300

TGAAGCACCA CGGGAGCAGT GGGAACAAAG CCAGGCGGAA GGTCGAACCGACTGTTCACA    360

CAACTGATC                                                          369

(2) INFORMATION FOR SEQ ID NO:29:

(i) SEQUENCE CHARACTERISTICS:
            (A) LENGTH: 337 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:29:

GATCCAATCC AGGGGCCCTC GTACCCCTCC TGGCAGCTGT AGAAAGGACAACCAGGAATG     60

TTAACCATGC TCTGAACTCC AGCTTTAAGG ACATTAAAGC AAATCACAAAGAAATTGCAC    120

ACATACTGCC AAATCTCTAG ACCCCAAGCA ATGAGGCCGC AATCATCCTCCGTCGGGGTG    180

TGGAGCCAAC GGATGCAAGC TGATATGATA CTCCAGGGGG TAGATGCCTCCAGAATGCCC    240

AGTATCTTCT GCGGATGTCA CGAGTGGCAA TAAAGTACTC ACTACATACAGTGTTGCTCC    300

TAGCAAGCAT AGTAAGAAGT CTGTTGGGCC AGTGATC                           337

(2) INFORMATION FOR SEQ ID NO:30:

(i) SEQUENCE CHARACTERISTICS:
            (A) LENGTH: 234 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:30:

GATCAGGTAT GCTCCAAGCA CGCTGTCCAT GCGGTGCTGA ACTCATCTTTTCTGTTGAGA     60

ATGGTTTTGC AAAACTTTAC AAAGGACCCA GAACTTGTTC AAATTACTGGAGAGGGCTG    120

TTCCAGTCAA CGCTAGGCTG TGTGGGTCGG CTAGACCGGA CCCAACTGATTGGACTAGTC    180

TTGTCGTCAA TTATGGCGTT AGGGACTACT GTAAATATGA GAAATTGGGA GATC        234

(2) INFORMATION FOR SEQ ID NO:31:

(i) SEQUENCE CHARACTERISTICS:
            (A) LENGTH: 73 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:31:

```
Asp Pro Xaa Xaa Ala Thr His Pro Ser Ser Ile Xaa Met Ser Ser Lys
1               5                   10                  15

Gln Trp Met Arg Arg Gln His Ser Arg Leu Ala Cys Gln Arg Gln Asn
            20                  25                  30

Pro Pro Met Ser Met Tyr Gln Glu Leu Phe Pro Gln Pro Arg Pro Ser
            35                  40                  45

Xaa Thr Pro Val Arg Leu Xaa Arg Leu Xaa Ala Trp Thr Gln Leu Arg
        50                  55                  60

Leu Gln Ile Met Thr Gly Thr Phe Xaa
65                  70
```

(2) INFORMATION FOR SEQ ID NO:32:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Ile His Ser Glu Pro Leu Thr His Gln Ala Phe Lys Cys Gln Ala Ser
1               5                   10                  15

Ser Gly Xaa Gly Gly Ser Ile Ala Ala Xaa His Val Lys Asp Lys Thr
            20                  25                  30

His Arg Cys Pro Cys Thr Lys Ser Cys Ser His Ser Pro Gly His His
            35                  40                  45

Glu Arg Gln Cys Val Ser Ser Val Cys Lys Leu Gly Arg Asn Cys Ala
        50                  55                  60

Ser Lys Xaa Xaa Gln Glu His Phe Asp
65                  70
```

(2) INFORMATION FOR SEQ ID NO:33:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Ser Ile Val Ser His Ser Pro Ile Lys His Leu Asn Val Lys Gln Ala
1               5                   10                  15

Val Asp Glu Ala Ala Ala Xaa Pro Pro Ser Met Ser Lys Thr Lys Pro
            20                  25                  30

Thr Asp Val His Val Pro Arg Ala Val Pro Thr Ala Pro Ala Ile Met
            35                  40                  45

Asn Ala Ser Ala Ser Leu Ala Ser Val Ser Leu Asp Ala Ile Ala Pro
        50                  55                  60

Pro Asn Asn Asp Arg Asn Ile Leu Ile
65                  70
```

(2) INFORMATION FOR SEQ ID NO:34:

(i) SEQUENCE CHARACTERISTICS:

(A) LENGTH: 73 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:34:

Asp Gln Asn Val Pro Val Ile Ile Trp Arg Arg Asn Cys Val Gln Ala
1               5                   10                  15

Tyr Arg Arg Xaa Arg Arg Thr Gly Val His Asp Gly Arg Gly Cys Gly
                20                  25                  30

Asn Ser Ser Trp Tyr Met Asp Ile Gly Gly Phe Cys Leu Xaa His Ala
            35                  40                  45

Arg Arg Leu Cys Cys Arg Leu Ile His Cys Leu Leu Asp Ile Xaa Met
50                  55                  60

Leu Asp Gly Xaa Val Ala His Tyr Gly
65                  70

(2) INFORMATION FOR SEQ ID NO:35:

(i) SEQUENCE CHARACTERISTICS:
           (A) LENGTH: 73 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:35:

Ile Lys Met Phe Leu Ser Leu Phe Gly Gly Ala Ile Ala Ser Lys Leu
1               5                   10                  15

Thr Asp Ala Arg Asp Ala Leu Ala Phe Met Met Ala Gly Ala Val Gly
                20                  25                  30

Thr Ala Leu Gly Thr Trp Thr Ser Val Gly Phe Val Phe Asp Met Leu
            35                  40                  45

Gly Gly Tyr Ala Ala Ala Ser Ser Thr Ala Cys Leu Thr Phe Lys Cys
50                  55                  60

Leu Met Gly Glu Trp Leu Thr Met Asp
65                  70

(2) INFORMATION FOR SEQ ID NO:36:

(i) SEQUENCE CHARACTERISTICS:
           (A) LENGTH: 73 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:36:

Ser Lys Cys Ser Cys His Tyr Leu Glu Ala Gln Leu Arg Pro Ser Leu
1               5                   10                  15

Gln Thr Leu Glu Thr His Trp Arg Ser Xaa Trp Pro Gly Leu Trp Glu
                20                  25                  30

Gln Leu Leu Val His Gly His Arg Trp Val Leu Ser Leu Thr Cys Xaa
            35                  40                  45

Ala Ala Met Leu Pro Pro His Pro Leu Leu Ala Xaa His Leu Asn Ala
50                  55                  60

Xaa Trp Val Ser Gly Ser Leu Trp Ile
65                  70

(2) INFORMATION FOR SEQ ID NO:37:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Asp Arg Ser Thr Pro Gln Ala Leu Arg Arg Cys Val Ala Pro Gly Leu
 1               5                  10                  15
Pro Arg Ser Tyr His Gln Tyr Gln Arg Gln Thr Thr Pro Cys Glu Val
             20                  25                  30
His Arg His Lys His Gly Ser Pro His Arg Ala Gln Asp Ile Gln Val
         35                  40                  45
Arg His Asp Thr His His Thr Gln Thr Thr Ser Glu Pro Pro Leu Leu
     50                  55                  60
Gly Cys Pro Ala Asp His Arg Gly Ala His Gln Leu Gly Ser Gln Arg
 65                  70                  75                  80
Ala Ser Thr Thr Gly Lys Xaa Ala Pro Thr Phe Asp Asn Gln Ala Arg
                 85                  90                  95
Pro Ala Ala Asn Val Arg Ser Leu Ser His Ala Gly Gln Met Ser Pro
            100                 105                 110
Thr Thr Ala Xaa Ala Pro Ser Leu Ala Ala Pro Gln Thr Ala Xaa Ala
        115                 120                 125
Pro Ala Val Arg Pro Ala Thr Met Xaa Gln Pro Ala Leu Xaa Val Glu
    130                 135                 140
Ser Ala Thr Pro Val Val Glu Phe Gly Gln Asp Gly Val Gly Thr Val
145                 150                 155                 160
Gly Gly Val His Asn Gly Thr Leu Ser Val Asp Phe Val Thr Glu Gly
                165                 170                 175
Cys Met Ile Thr Ile Val Ala Ala Asp Ala Pro Phe Asn His His His
            180                 185                 190
Ile Ala Ser Ile Asn Arg Gly Ala Thr Leu Ala Ser Ala Asn Phe Ile
        195                 200                 205
Thr Thr Asn Arg Ala Arg Thr Met Ser Val Ser Asn Gln Ala Ala Glu
    210                 215                 220
Asp Leu Arg Xaa Pro Leu Xaa Thr Cys Cys Leu Leu Pro Leu Thr Trp
225                 230                 235                 240
Met Lys Pro Leu Xaa
                245
```

(2) INFORMATION FOR SEQ ID NO:38:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Ile Glu Ala His Leu Lys Pro Xaa Asp Ala Val Ser Leu Pro Gly Tyr
 1               5                  10                  15
Pro Ala Ala Thr Thr Asn Thr Ser Gly Arg Arg Pro Leu Ala Lys Cys
```

```
                    20                  25                  30
Ile Ala Thr Ser Thr Ala Ala Leu Thr Glu Pro Arg Thr Phe Arg Tyr
                35                  40                  45
Ala Thr Thr His Ile Thr Pro Arg Gln Pro Val Asn His His Ser Trp
 50                  55                  60
Ala Ala Gln Pro Thr Thr Gly Ala His Thr Ser Ser Gly Ala Ser Ala
 65                  70                  75                  80
Pro Arg Arg Pro Ala Ser Lys Pro Gln His Leu Thr Arg Pro Asp
                 85                  90                  95
Arg Gln Arg Thr Phe Ala Ala Xaa Ala Thr Arg Ala Arg Cys His Gln
                100                 105                 110
Arg Arg Pro Glu His His His Trp Gln His Pro Arg Pro Glu Pro
                115                 120                 125
Arg Pro Ser Gly Leu Pro Pro Cys Ser Asn Gln His Cys Arg Xaa Ser
130                 135                 140
Pro Arg Leu Arg Trp Xaa Asn Ser Asp Lys Met Glu Leu Glu Gln Trp
145                 150                 155                 160
Ala Glu Ser Thr Met Glu His Phe Gln Trp Thr Ser Xaa Gln Lys Gly
                165                 170                 175
Val Xaa Xaa Gln Xaa Trp Arg Gln Met Leu His Ser Thr Thr Thr Thr
                180                 185                 190
Leu Pro Ala Xaa Thr Gly Gly Gln Leu Xaa Pro Gln Pro Thr Ser Ser
                195                 200                 205
Leu Pro Thr Gly Pro Gly Pro Cys Gln Xaa Ala Thr Lys Pro Arg Lys
                210                 215                 220
Thr Phe Ala Asp His Cys Lys Pro Ala Val Cys Cys Leu Xaa His Gly
225                 230                 235                 240
Xaa Ser Arg Cys Asp
                245

(2) INFORMATION FOR SEQ ID NO:39:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

Ser Lys His Thr Ser Ser Pro Lys Thr Leu Cys Arg Ser Arg Val Thr
 1                   5                  10                  15
Pro Gln Leu Pro Pro Ile Pro Ala Ala Asp Asp Pro Leu Arg Ser Ala
                20                  25                  30
Ser Pro Gln Ala Arg Gln Pro Ser Gln Ser Pro Gly His Ser Gly Thr
                35                  40                  45
Pro Arg His Thr Ser His Pro Asp Asn Gln Xaa Thr Thr Pro Gly
                 50                  55                  60
Leu Pro Ser Arg Pro Pro Gly Arg Thr Pro Ala Arg Glu Pro Ala Arg
 65                  70                  75                  80
Leu Asp Asp Arg Gln Val Ser Pro Asn Ile Xaa Gln Pro Gly Gln Thr
                85                  90                  95
Gly Ser Glu Arg Ser Gln Leu Glu Pro Arg Gly Pro Asp Val Thr Asn
                100                 105                 110
Asp Gly Leu Ser Thr Ile Ile Gly Ser Thr Pro Asp Arg Leu Ser Pro
```

```
            115                 120                 125
Gly Arg Gln Ala Cys His His Val Ala Thr Ser Ile Val Gly Arg Val
        130                 135                 140

Arg Asp Ser Gly Gly Arg Ile Arg Thr Arg Trp Ser Trp Asn Ser Gly
145                 150                 155                 160

Arg Ser Pro Gln Trp Asn Thr Phe Ser Gly Leu Arg Asp Arg Arg Val
                165                 170                 175

Tyr Asp Asn Asn Ser Gly Gly Arg Cys Ser Ile Gln Pro Pro Pro His
            180                 185                 190

Cys Gln His Lys Gln Gly Gly Asn Ser Ser Leu Ser Gln Leu His His
        195                 200                 205

Tyr Gln Gln Gly Gln Asp His Val Ser Lys Gln Pro Ser Arg Gly Arg
    210                 215                 220

Pro Ser Leu Thr Thr Val Asn Leu Leu Ser Val Ala Phe Asn Met Asp
225                 230                 235                 240

Glu Ala Val Val Ile
                245

(2) INFORMATION FOR SEQ ID NO:40:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Asp His Asn Gly Phe Ile His Val Lys Gly Asn Arg Gln Gln Val Tyr
1               5                   10                  15

Ser Gly Gln Arg Arg Ser Ser Ala Ala Trp Leu Leu Thr Asp Met Val
                20                  25                  30

Leu Ala Leu Leu Val Val Met Lys Leu Ala Glu Ala Arg Val Ala Pro
            35                  40                  45

Leu Phe Met Leu Ala Met Trp Trp Trp Leu Asn Gly Ala Ser Ala Ala
        50                  55                  60

Thr Ile Val Ile Ile His Pro Ser Val Thr Lys Ser Thr Glu Ser Val
65                  70                  75                  80

Pro Leu Trp Thr Pro Pro Thr Val Pro Thr Pro Ser Cys Pro Asn Ser
                85                  90                  95

Thr Thr Gly Val Ala Asp Ser Thr Tyr Asn Ala Gly Cys Tyr Met Val
                100                 105                 110

Ala Gly Leu Thr Ala Gly Ala Gln Ala Val Trp Gly Ala Ala Asn Asp
            115                 120                 125

Gly Ala Gln Ala Val Val Gly Asp Ile Trp Pro Ala Trp Leu Lys Leu
        130                 135                 140

Arg Thr Phe Ala Ala Gly Leu Ala Trp Leu Ser Asn Val Gly Ala Tyr
145                 150                 155                 160

Leu Pro Val Val Glu Ala Arg Trp Leu Pro Ser Trp Cys Ala Pro Arg
                165                 170                 175

Trp Ser Ala Gly Gln Pro Arg Ser Gly Gly Ser Leu Val Trp Val
            180                 185                 190

Xaa Cys Val Ser Trp Arg Thr Xaa Met Ser Trp Ala Leu Xaa Gly Leu
        195                 200                 205

Pro Cys Leu Trp Arg Cys Thr Ser Gln Gly Val Val Cys Arg Trp Tyr
```

-continued

```
            210                 215                 220
Trp Trp Xaa Leu Arg Gly Asn Pro Gly Ala Thr Gln Arg Leu Arg Ala
225                 230                 235                 240

Xaa Gly Val Leu Arg
            245
```

(2) INFORMATION FOR SEQ ID NO:41:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Ile Thr Thr Ala Ser Ser Met Leu Lys Ala Thr Asp Ser Arg Phe Thr
1               5                   10                  15

Val Val Ser Glu Gly Leu Pro Arg Leu Gly Cys Leu Leu Thr Trp Ser
                20                  25                  30

Trp Pro Cys Trp Xaa Xaa Xaa Ser Trp Leu Arg Leu Glu Leu Pro Pro
            35                  40                  45

Cys Leu Cys Trp Gln Cys Gly Gly Gly Xaa Met Glu His Leu Pro Pro
50                  55                  60

Leu Leu Leu Ser Tyr Thr Leu Leu Ser Arg Ser Pro Leu Lys Val Phe
65                  70                  75                  80

His Cys Gly Leu Arg Pro Leu Phe Gln Leu His Leu Val Arg Ile Leu
                85                  90                  95

Pro Pro Glu Ser Arg Thr Leu Pro Thr Met Leu Val Ala Thr Trp Trp
                100                 105                 110

Gln Ala Xaa Arg Pro Gly Leu Arg Arg Ser Gly Val Leu Pro Met Met
            115                 120                 125

Val Leu Arg Pro Ser Leu Val Thr Ser Gly Pro Arg Gly Ser Ser Cys
130                 135                 140

Glu Arg Ser Leu Pro Val Trp Pro Gly Cys Gln Met Leu Gly Leu Thr
145                 150                 155                 160

Cys Arg Ser Ser Arg Arg Ala Gly Ser Arg Ala Gly Val Arg Pro Gly
                165                 170                 175

Gly Arg Leu Gly Ser Pro Gly Val Val Val His Trp Leu Ser Gly Cys
            180                 185                 190

Asp Val Cys Arg Gly Val Pro Glu Cys Pro Gly Leu Cys Glu Gly Cys
            195                 200                 205

Arg Ala Cys Gly Asp Ala Leu Arg Lys Gly Ser Ser Ala Ala Gly Ile
210                 215                 220

Gly Gly Ser Cys Gly Val Thr Arg Glu Arg His Ser Val Leu Gly Leu
225                 230                 235                 240

Glu Val Cys Phe Asp
            245
```

(2) INFORMATION FOR SEQ ID NO:42:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

```
Ser Gln Arg Leu His Pro Cys Xaa Arg Gln Gln Thr Ala Gly Leu Gln
1               5                  10                 15

Trp Ser Ala Lys Val Phe Arg Gly Leu Val Ala Tyr Xaa His Gly Pro
            20                  25                 30

Gly Pro Val Gly Ser Asp Glu Val Gly Xaa Gly Xaa Ser Cys Pro Pro
            35                  40                 45

Val Tyr Ala Gly Asn Val Val Val Glu Trp Ser Ile Cys Arg His
    50                  55                  60

Tyr Cys Tyr His Thr Pro Phe Cys His Glu Val His Xaa Lys Cys Ser
65                  70                  75                  80

Ile Val Asp Ser Ala His Cys Ser Asn Ser Ile Leu Ser Glu Phe Tyr
                85                  90                  95

His Arg Ser Arg Gly Leu Tyr Leu Gln Cys Trp Leu Leu His Gly Gly
            100                 105                110

Arg Pro Asp Gly Arg Gly Ser Gly Gly Leu Gly Cys Cys Gln Xaa Trp
            115                 120                125

Cys Ser Gly Arg Arg Trp Xaa His Leu Ala Arg Val Ala Gln Ala Ala
130                 135                 140

Asn Val Arg Cys Arg Ser Gly Leu Val Val Lys Cys Trp Gly Leu Leu
145                 150                 155                160

Ala Gly Arg Arg Gly Ala Leu Ala Pro Glu Leu Val Cys Ala Pro Val
            165                 170                 175

Val Gly Trp Ala Ala Gln Glu Trp Trp Phe Thr Gly Cys Leu Gly Val
            180                 185                 190

Met Cys Val Val Ala Tyr Leu Asn Val Leu Gly Ser Val Arg Ala Ala
            195                 200                 205

Val Leu Val Ala Met His Phe Ala Arg Gly Arg Leu Pro Leu Val Leu
            210                 215                 220

Val Val Ala Ala Gly Xaa Pro Gly Ser Asp Thr Ala Ser Xaa Gly Leu
225                 230                 235                 240

Arg Cys Ala Ser Ile
                245
```

(2) INFORMATION FOR SEQ ID NO:43:

(i) SEQUENCE CHARACTERISTICS:
       (A) LENGTH: 102 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:43:

```
Asp His Cys Gly Arg His Leu Phe Arg Leu Ile Asp Xaa Xaa Ala Arg
1               5                  10                 15

Tyr Ala Gly Gly Gly Leu Gly Val Cys Gly Gly Xaa Xaa Gln Pro Leu
            20                  25                 30

Asn Gly Thr Cys Phe Val Gln Val Leu Leu Trp Trp Pro Tyr Gly Phe
            35                  40                 45

Pro Arg Trp Gly Ser Leu Gly Val Pro Pro Val Xaa Val Val Gly Arg
    50                  55                  60

Val Asp Asn Xaa Leu Gly Glu Gln His Leu Leu His Xaa Gly Gln
65                  70                  75                  80
```

-continued

```
Arg Gly Leu Gln Ala Gly Gly Asp Xaa Gly Thr Ile Ile Leu Tyr Ser
                85                  90                  95

Trp Arg Xaa Leu Leu Asp
            100
```

(2) INFORMATION FOR SEQ ID NO:44:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Ile Thr Val Asp Ala Thr Cys Phe Asp Ser Ser Ile Asp Glu His Asp
1               5                   10                  15

Met Gln Val Glu Ala Ser Val Phe Ala Ala Ser Asp Asn Pro Ser
                20                  25                  30

Met Val His Ala Leu Cys Lys Tyr Tyr Ser Gly Gly Pro Met Val Ser
                35                  40                  45

Pro Asp Gly Val Pro Leu Gly Tyr Arg Gln Cys Arg Ser Ser Gly Val
                50                  55                  60

Leu Thr Thr Ser Ser Ala Asn Ser Ile Thr Cys Tyr Ile Lys Val Ser
65                  70                  75                  80

Ala Ala Cys Arg Arg Val Gly Ile Lys Ala Pro Ser Phe Phe Ile Ala
                85                  90                  95

Gly Asp Asp Cys Leu Ile
                100
```

(2) INFORMATION FOR SEQ ID NO:45:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Ser Leu Trp Thr Pro Leu Val Ser Thr His Arg Leu Met Ser Thr Ile
1               5                   10                  15

Cys Arg Trp Arg Pro Arg Cys Leu Arg Arg Leu Val Thr Thr Pro Gln
                20                  25                  30

Trp Tyr Met Leu Cys Ala Ser Thr Thr Leu Val Ala Leu Trp Phe Pro
                35                  40                  45

Gln Met Gly Phe Pro Trp Gly Thr Ala Ser Val Gly Arg Arg Ala Cys
                50                  55                  60

Xaa Gln Leu Ala Arg Arg Thr Ala Ser Leu Val Thr Leu Arg Ser Ala
65                  70                  75                  80

Arg Pro Ala Gly Gly Trp Gly Leu Arg His His His Ser Leu Xaa Leu
                85                  90                  95

Glu Met Ile Ala Xaa
                100
```

(2) INFORMATION FOR SEQ ID NO:46:

(i) SEQUENCE CHARACTERISTICS:
        (A) LENGTH: 102 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

Asp Gln Ala Ile Ile Ser Ser Tyr Lys Glu Xaa Trp Cys Leu Asn Pro
1               5                  10                  15

His Pro Pro Ala Gly Arg Ala Asp Leu Asn Val Thr Ser Asp Ala Val
            20                  25                  30

Arg Arg Ala Ser Cys Gln His Ala Arg Arg Pro Thr Leu Ala Val Pro
        35                  40                  45

Gln Gly Asn Pro Ile Trp Gly Asn His Arg Ala Thr Arg Val Val Leu
    50                  55                  60

Ala Gln Ser Met Tyr His Xaa Gly Val Val Thr Ser Arg Arg Lys His
65                  70                  75                  80

Arg Gly Leu His Leu His Ile Val Leu Ile Asn Arg Xaa Val Glu Thr
                85                  90                  95

Ser Gly Val His Ser Asp
            100

(2) INFORMATION FOR SEQ ID NO:47:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Ile Lys Gln Ser Ser Pro Ala Ile Lys Asn Asp Gly Ala Leu Ile Pro
1               5                  10                  15

Thr Arg Leu Gln Ala Ala Leu Thr Leu Met Xaa Gln Val Met Leu Phe
            20                  25                  30

Ala Glu Leu Val Val Asn Thr Pro Asp Asp Leu His Trp Arg Tyr Pro
        35                  40                  45

Lys Gly Thr Pro Ser Gly Glu Thr Ile Gly Pro Pro Glu Xaa Tyr Leu
    50                  55                  60

His Lys Ala Cys Thr Ile Glu Gly Leu Ser Leu Ala Ala Ala Asn Thr
65                  70                  75                  80

Glu Ala Ser Thr Cys Ile Ser Cys Ser Ser Ile Asp Glu Ser Lys Gln
                85                  90                  95

Val Ala Ser Thr Val Ile
            100

(2) INFORMATION FOR SEQ ID NO:48:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Ser Ser Asn His Leu Gln Leu Xaa Arg Met Met Val Pro Xaa Ser Pro
1               5                  10                  15

```
Pro Ala Cys Arg Pro Arg Xaa Pro Xaa Cys Asn Lys Xaa Cys Cys Ser
                20                  25                  30

Pro Ser Xaa Leu Ser Thr Arg Pro Thr Thr Tyr Thr Gly Gly Thr Pro
            35                  40                  45

Arg Glu Pro His Leu Gly Lys Pro Xaa Gly His Gln Ser Ser Thr Cys
        50                  55                  60

Thr Lys His Val Pro Leu Arg Gly Cys His Xaa Pro Pro Gln Thr Pro
65                  70                  75                  80

Arg Pro Pro Pro Ala Tyr Arg Ala His Gln Ser Met Ser Arg Asn Lys
                85                  90                  95

Trp Arg Pro Gln Xaa
            100
```

(2) INFORMATION FOR SEQ ID NO:49:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

```
Asp Gln His Leu Val Thr Pro Ser Arg Asn His Arg Phe Pro Val Asp
1               5                   10                  15

Gln Leu Ser Thr Ala Xaa His Thr Ser Arg Val Pro Asn Asn Ser Thr
                20                  25                  30

Ile Phe Leu Gly Tyr Ala Asn Arg Leu Lys Arg Lys Thr Pro Leu Ser
            35                  40                  45

Gln Ala Gly Ser Thr Ala Pro Ala Ser Val Thr Gly Val Leu Val Glu
        50                  55                  60

Glu Asp Ala Leu Leu Ala Gln Asp Ala His Gln Pro Arg Ala Gly Gln
65                  70                  75                  80

Pro Leu Leu Ser Lys Ser Xaa Gly Val Gln His Pro Arg Gln Ala Arg
                85                  90                  95

Glu Ile Trp Xaa Val Asn Gln Glu Tyr Phe Gln Asp Glu Ile Asn Asp
                100                 105                 110

Ile Xaa Thr Ala Gln Thr Glu Tyr Glu Asp Asp Gly Asn Cys Gly Asn
        115                 120                 125

Cys Leu Gly Glu Glu Pro Ser His Asn Gln Pro Ser Phe Pro Ala Arg
130                 135                 140

Leu Gln Arg Pro Lys Ala Pro Thr Gly Glu Leu Phe Thr His Arg Arg
145                 150                 155                 160

Thr Leu Trp Xaa Leu Thr Ala His Leu Ala Tyr Gln Val Asn Leu Ala
                165                 170                 175

Asp
```

(2) INFORMATION FOR SEQ ID NO:50:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

-continued

```
Ile Asn Thr Ser Ser Pro Arg Leu Ala Thr Thr Gly Phe Pro Trp Thr
1               5                   10                  15

Asn Cys Pro Gln Pro Asn Thr Arg Ala Glu Ser Arg Thr Ile Ala Gln
            20                  25                  30

Ser Ser Leu Val Met Leu Thr Gly Ser Ser Ala Lys Pro His Ser Arg
        35                  40                  45

Lys Arg Ala Ala Pro Arg Leu Leu Val Xaa Pro Ala Cys Ser Xaa Arg
    50                  55                  60

Arg Thr Pro Cys Leu Arg Arg Thr Pro Thr Ser Gln Glu Gln Ala Ser
65                  70                  75                  80

Arg Ser Ser Ala Arg Ala Lys Glu Ser Ser Thr Arg Ala Lys Arg Ala
                85                  90                  95

Arg Phe Gly Glu Leu Thr Lys Ser Thr Ser Lys Met Lys Ser Met Thr
                100                 105                 110

Ser Lys Leu Leu Lys Gln Ser Met Lys Met Thr Glu Thr Val Ala Thr
        115                 120                 125

Val Trp Gly Lys Asn Gln Ala Thr Thr Asn Gln Ala Phe Gln His Ala
    130                 135                 140

Ser Asn Gly Gln Lys Leu Gln Pro Ala Ser Cys Ser Pro Thr Gly Glu
145                 150                 155                 160

Pro Ser Gly Asn Xaa Arg Pro Thr Trp His Thr Lys Ser Ile Trp Leu
                165                 170                 175

Ile
```

(2) INFORMATION FOR SEQ ID NO:51:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Ser Thr Pro Arg His Pro Val Ser Gln Pro Gln Val Ser Arg Gly Pro
1               5                   10                  15

Thr Val His Ser Leu Thr His Glu Gln Ser Pro Glu Gln Xaa His Asn
            20                  25                  30

Leu Pro Trp Leu Cys Xaa Gln Ala Gln Ala Gln Asn Pro Thr Leu Ala
        35                  40                  45

Ser Gly Gln His Arg Ala Cys Xaa Cys Asp Arg Arg Ala Arg Arg Gly
    50                  55                  60

Gly Arg Pro Ala Cys Ala Gly Arg Pro Pro Ala Lys Ser Arg Pro Ala
65                  70                  75                  80

Ala Pro Gln Gln Glu Leu Arg Ser Pro Ala Pro Ala Pro Ser Ala Arg
                85                  90                  95

Asp Leu Val Ser Xaa Pro Arg Val Leu Pro Arg Xaa Asn Gln Xaa His
                100                 105                 110

Leu Asn Cys Ser Asn Arg Val Xaa Arg Xaa Arg Lys Leu Trp Gln Leu
        115                 120                 125

Phe Gly Gly Arg Thr Lys Pro Gln Pro Thr Lys Leu Ser Ser Thr Pro
    130                 135                 140

Pro Thr Ala Lys Ser Ser Asn Arg Arg Val Val His Pro Pro Ala Asn
145                 150                 155                 160

Pro Leu Val Ile Asp Gly Pro Pro Gly Ile Pro Ser Gln Ser Gly Xaa
```

165    170    175

(2) INFORMATION FOR SEQ ID NO:52:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

```
Asp Gln Pro Asp Xaa Leu Gly Met Pro Gly Gly Pro Ser Ile Thr Arg
1               5                   10                  15

Gly Phe Ala Gly Gly Xaa Thr Thr Arg Arg Leu Glu Leu Leu Ala Val
            20                  25                  30

Gly Gly Val Leu Glu Ser Leu Val Gly Cys Gly Leu Val Leu Pro Pro
            35                  40                  45

Asn Ser Cys His Ser Phe Arg His Leu His Thr Leu Phe Glu Gln Phe
        50                  55                  60

Arg Cys His Xaa Phe His Leu Gly Ser Thr Leu Gly Xaa Leu Thr Lys
65                  70                  75                  80

Ser Arg Ala Leu Gly Ala Gly Ala Gly Leu Leu Ser Ser Cys Xaa Gly
                85                  90                  95

Ala Ala Gly Leu Leu Leu Ala Gly Gly Arg Pro Ala Gln Ala Gly Arg
                100                 105                 110

Pro Pro Leu Arg Ala Arg Arg Ser His Xaa Gln Ala Arg Cys Cys Pro
            115                 120                 125

Leu Ala Arg Val Gly Phe Cys Ala Xaa Ala Cys Xaa His Asn Gln Gly
        130                 135                 140

Arg Leu Cys Tyr Cys Ser Gly Leu Cys Ser Cys Val Arg Leu Trp Thr
145                 150                 155                 160

Val Gly Pro Arg Glu Thr Cys Gly Cys Glu Thr Gly Xaa Arg Gly Val
                165                 170                 175

Asp
```

(2) INFORMATION FOR SEQ ID NO:53:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

```
Ile Ser Gln Ile Asp Leu Val Cys Gln Val Gly Arg Gln Leu Pro Glu
1               5                   10                  15

Gly Ser Pro Val Gly Glu Gln Leu Ala Gly Trp Ser Phe Trp Pro Leu
            20                  25                  30

Glu Ala Cys Trp Lys Ala Trp Leu Val Val Ala Trp Phe Phe Pro Gln
        35                  40                  45

Thr Val Ala Thr Val Ser Val Ile Phe Ile Leu Cys Leu Ser Ser Leu
    50                  55                  60

Asp Val Ile Asp Phe Ile Leu Glu Val Leu Leu Val Asn Ser Pro Asn
65                  70                  75                  80

Leu Ala Arg Leu Ala Arg Val Leu Asp Ser Leu Ala Leu Ala Glu Glu
```

-continued

```
                    85                  90                  95
Arg Leu Ala Cys Ser Trp Leu Val Gly Val Leu Arg Lys Gln Gly Val
                100                 105                 110

Leu Leu Tyr Glu His Ala Gly His Thr Ser Arg Arg Gly Ala Ala Arg
            115                 120                 125

Leu Arg Glu Trp Gly Phe Ala Leu Glu Pro Val Ser Ile Thr Lys Glu
130                 135                 140

Asp Cys Ala Ile Val Arg Asp Ser Ala Arg Val Leu Gly Cys Gly Gln
145                 150                 155                 160

Leu Val His Gly Lys Pro Val Val Ala Arg Gly Asp Glu Val Leu
                165                 170                 175

Ile
```

(2) INFORMATION FOR SEQ ID NO:54:

(i) SEQUENCE CHARACTERISTICS:
        (A) LENGTH: 176 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Ser Ala Arg Leu Thr Trp Tyr Ala Arg Trp Ala Val Asn Tyr Gln Arg
1               5                   10                  15

Val Arg Arg Trp Val Asn Asn Ser Pro Val Gly Ala Phe Gly Arg Trp
                20                  25                  30

Arg Arg Ala Gly Lys Leu Gly Trp Leu Trp Leu Gly Ser Ser Pro Lys
            35                  40                  45

Gln Leu Pro Gln Phe Pro Ser Ser Ser Tyr Ser Val Xaa Ala Val Xaa
        50                  55                  60

Met Ser Leu Ile Ser Ser Trp Lys Tyr Ser Trp Leu Thr His Gln Ile
65                  70                  75                  80

Ser Arg Ala Trp Arg Gly Cys Trp Thr Pro Xaa Leu Leu Leu Arg Ser
                85                  90                  95

Gly Trp Pro Ala Leu Gly Trp Trp Ala Ser Cys Ala Ser Arg Ala Ser
                100                 105                 110

Ser Ser Thr Ser Thr Pro Val Thr Leu Ala Gly Ala Val Leu Pro Ala
            115                 120                 125

Cys Glu Ser Gly Val Leu Arg Leu Ser Leu Leu Ala Xaa Pro Arg Lys
130                 135                 140

Ile Val Leu Leu Phe Gly Thr Leu Leu Val Cys Xaa Ala Val Asp Ser
145                 150                 155                 160

Trp Ser Thr Gly Asn Leu Trp Leu Arg Asp Gly Val Thr Arg Cys Xaa
                165                 170                 175
```

(2) INFORMATION FOR SEQ ID NO:55:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

Asp Pro Ser Xaa Gln Xaa Gln Leu Ser Gln Asp Ser Arg His Leu Gly

-continued

```
                1               5                   10                  15
Asp Glu Leu Ile Phe Glu Glu Glu Ile Val Arg His His Arg Thr Ala
                20                      25                  30
Trp His His Arg Gln Gln Ser Val Asn Pro Ile Leu Thr His Thr Leu
            35                      40                  45
Phe Asp Arg Pro Glu Gln Ala Gln Asn His Thr Gly His Arg Ser
        50                      55                  60
Pro Arg Arg Gly Gln Ala Thr Asp Gln Ala Pro Ser Val Thr Arg Leu
 65                     70                      75                  80
Xaa Leu Pro Arg Gln Glu Val Glu Gly Glu Xaa Ala Arg Phe Thr Ala
                    85                      90                      95
Pro Ser Gln Pro Leu Ile
                100
```

(2) INFORMATION FOR SEQ ID NO:56:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

```
Ile His Leu Asp Asn Asp Asn Phe Arg Arg Thr Val Asp Thr Leu Val
 1               5                   10                  15
Thr Asn Ser Ser Leu Arg Lys Lys Ser Ser Gly Ile Thr Glu Leu Arg
                20                      25                  30
Gly Ile Ile Val Asn Asn Leu Leu Thr Gln Ser Xaa Pro Thr Pro Phe
            35                      40                  45
Leu Thr Asp Gln Ser Asn Lys Pro Arg Thr Thr Pro Ala Thr Glu Ala
        50                      55                  60
Pro Gly Glu Ala Arg Gln Leu Thr Arg His Gln Ala Ser Leu Ala Cys
 65                     70                      75                  80
Asn Phe Pro Ala Arg Arg Ser Lys Val Ser Glu Arg Gly Ser Pro Pro
                    85                      90                      95
Pro Pro Ser Leu Xaa
                100
```

(2) INFORMATION FOR SEQ ID NO:57:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

```
Ser Ile Leu Thr Met Thr Thr Phe Ala Gly Gln Xaa Thr Pro Trp Xaa
 1               5                   10                  15
Arg Thr His Leu Xaa Gly Arg Asn Arg Gln Ala Ser Pro Asn Cys Val
                20                      25                  30
Ala Ser Ser Ser Thr Ile Cys Xaa Pro Asn Leu Asp Pro His Pro Phe
            35                      40                  45
Xaa Gln Thr Arg Ala Thr Ser Pro Glu Pro His Arg Pro Pro Lys Pro
        50                      55                  60
```

-continued

```
Pro Glu Arg Pro Gly Asn Xaa Pro Gly Thr Lys Arg His Ser Leu Val
65                  70                  75                  80

Thr Ser Pro Pro Gly Gly Arg Arg Xaa Val Ser Ala Val His Arg Pro
                85                  90                  95

Leu Pro Ala Ser Asp
            100
```

(2) INFORMATION FOR SEQ ID NO:58:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

```
Asp Gln Arg Leu Gly Gly Gly Glu Pro Arg Ser Leu Thr Phe Asp
1               5                   10                  15

Leu Leu Ala Gly Lys Leu Gln Ala Ser Asp Ala Trp Cys Leu Val Ser
                20                  25                  30

Cys Leu Ala Ser Pro Gly Ala Ser Val Ala Gly Val Val Leu Gly Leu
                35                  40                  45

Leu Leu Trp Ser Val Lys Lys Gly Val Gly Gln Asp Trp Val Asn Arg
            50                  55                  60

Leu Leu Thr Met Met Pro Arg Ser Ser Val Met Pro Asp Asp Phe Phe
65                  70                  75                  80

Leu Lys Asp Glu Phe Val Thr Lys Val Ser Thr Val Leu Arg Lys Leu
                85                  90                  95

Ser Leu Ser Arg Trp Ile
            100
```

(2) INFORMATION FOR SEQ ID NO:59:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

```
Ile Arg Gly Trp Glu Gly Ala Val Asn Arg Ala His Ser Pro Ser Thr
1               5                   10                  15

Ser Trp Arg Gly Ser Tyr Lys Arg Val Thr Leu Gly Ala Trp Ser Val
                20                  25                  30

Ala Trp Pro Leu Arg Gly Leu Arg Trp Pro Val Trp Phe Trp Ala Cys
                35                  40                  45

Cys Ser Gly Leu Ser Lys Arg Val Trp Val Lys Ile Gly Leu Thr Asp
            50                  55                  60

Cys Xaa Arg Xaa Cys His Ala Val Arg Xaa Cys Leu Thr Ile Ser Ser
65                  70                  75                  80

Ser Lys Met Ser Ser Ser Pro Arg Cys Leu Leu Ser Cys Glu Ser Cys
                85                  90                  95

His Cys Gln Asp Gly
            100
```

(2) INFORMATION FOR SEQ ID NO:60:

(i) SEQUENCE CHARACTERISTICS:
    (A) LENGTH: 101 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:60:

```
Ser Glu Ala Gly Arg Gly Arg Xaa Thr Ala Leu Thr His Leu Arg Pro
1               5                   10                  15

Pro Gly Gly Glu Val Thr Ser Glu Xaa Arg Leu Val Pro Gly Gln Leu
            20                  25                  30

Pro Gly Leu Ser Gly Gly Phe Gly Gly Arg Cys Gly Ser Gly Leu Val
            35                  40                  45

Ala Leu Val Cys Gln Lys Gly Cys Gly Ser Arg Leu Gly Xaa Gln Ile
        50                  55                  60

Val Asp Asp Ala Thr Gln Phe Gly Asp Ala Xaa Arg Phe Leu Pro
65                  70                  75                  80

Gln Arg Xaa Val Arg His Gln Gly Val Tyr Cys Pro Ala Lys Val Val
                85                  90                  95

Ile Val Lys Met Asp
            100
```

(2) INFORMATION FOR SEQ ID NO:61:

(i) SEQUENCE CHARACTERISTICS:
       (A) LENGTH: 123 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:61:

```
Asp His Pro His Pro Gly Trp Leu Ala Leu Ala Cys Leu Lys Ala Arg
1               5                   10                  15

Ser Thr Ile Arg Glu Arg Val Asp Arg Asp Val Val Thr Arg Xaa Pro
            20                  25                  30

Pro Pro Ser Ile Asp Arg Thr Glu Ser Pro Thr Ile Gly Arg Thr Leu
            35                  40                  45

Val Pro Arg Tyr Val Val Tyr Ile Thr Pro Phe Thr Gln Gln Pro Met
        50                  55                  60

Glu Arg Val Val Glu Val Pro Arg Thr Thr Thr Phe Pro Xaa Cys Ser
65                  70                  75                  80

Asp Glu Ser Leu Pro Val Met Glu Val Leu Thr Thr Pro Lys Asn Pro
                85                  90                  95

Leu Pro Ala Xaa Xaa Ser Thr Thr Gly Ala Val Gly Thr Lys Pro Gly
            100                 105                 110

Gly Arg Ser Asn Arg Leu Phe Thr Gln Leu Ile
            115                 120
```

(2) INFORMATION FOR SEQ ID NO:62:

(i) SEQUENCE CHARACTERISTICS:
       (A) LENGTH: 122 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:62:

Ile Thr His Thr Pro Val Gly Trp His Leu His Ala Xaa Arg Gln Glu
1               5                   10                  15

Ala Pro Leu Gly Ser Gly Xaa Thr Val Thr Ser Ser Leu Ala Asn His
                20                  25                  30

His Arg Ala Leu Thr Gly Pro Lys Ala Pro Xaa Ala Gly Arg Trp
            35                  40                  45

Tyr His Gly Met Ser Cys Thr Ser Leu Arg Ser Arg Ser Ser Pro Trp
        50                  55                  60

Asn Glu Leu Leu Lys Ser Gln Gly Pro Pro Arg Ser Arg Asp Val Arg
65                  70                  75                  80

Thr Ser Pro Cys Leu Ser Trp Arg Ser Ser Gln Pro Arg Arg Ile Pro
                85                  90                  95

Cys Gln Leu Asp Glu Ala Pro Arg Glu Gln Trp Glu Gln Ser Gln Ala
            100                 105                 110

Glu Gly Arg Thr Asp Cys Ser His Asn Xaa
        115                 120

(2) INFORMATION FOR SEQ ID NO:63:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 63:

Ser Pro Thr Pro Arg Leu Val Gly Thr Cys Met Pro Glu Gly Lys Lys
1               5                   10                  15

His His Xaa Gly Ala Gly Arg Pro Xaa Arg Arg His Ser Leu Thr Thr
                20                  25                  30

Thr Glu His Xaa Gln Asp Arg Lys Pro His His Arg Pro Asp Val Gly
            35                  40                  45

Thr Thr Val Cys Arg Val His His Ser Val His Ala Ala Ala His Gly
        50                  55                  60

Thr Ser Cys Xaa Ser Pro Lys Asp His His Val Pro Val Met Phe Gly
65                  70                  75                  80

Arg Val Leu Ala Cys His Gly Gly Pro His Asn Pro Glu Glu Ser Leu
                85                  90                  95

Ala Ser Leu Met Lys His His Gly Ser Ser Gly Asn Lys Ala Arg Arg
            100                 105                 110

Lys Val Glu Pro Thr Val His Thr Thr Asp
        115                 120

(2) INFORMATION FOR SEQ ID NO:64:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

Asp Gln Leu Cys Glu Gln Ser Val Arg Pro Ser Ala Trp Leu Cys Ser
1               5                   10                  15

```
His Cys Ser Arg Gly Ala Ser Ser Trp Gln Gly Ile Leu Arg Gly
            20                  25                  30

Cys Glu Asp Leu His Asp Arg Gln Gly Leu Val Arg Thr Ser Arg Glu
        35                  40                  45

Arg Gly Gly Pro Trp Asp Phe Asn Asn Ser Phe His Gly Leu Leu Arg
    50                  55                  60

Glu Arg Ser Asp Val His Asp Ile Pro Trp Tyr Gln Arg Pro Ala Tyr
65                  70                  75                  80

Gly Gly Ala Phe Gly Pro Val Asn Ala Arg Trp Trp Leu Ala Ser Asp
            85                  90                  95

Asp Val Thr Val Tyr Pro Leu Pro Asn Gly Ala Ser Cys Leu Gln Ala
            100                 105                 110

Cys Lys Cys Gln Pro Thr Gly Val Trp Val Ile
            115                 120
```

(2) INFORMATION FOR SEQ ID NO:65:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

```
Ile Ser Cys Val Asn Ser Arg Phe Asp Leu Pro Pro Gly Phe Val Pro
1               5                   10                  15

Thr Ala Pro Val Val Leu His Gln Ala Gly Lys Gly Phe Phe Gly Val
            20                  25                  30

Val Arg Thr Ser Met Thr Gly Lys Asp Ser Ser Glu His His Gly Asn
        35                  40                  45

Val Val Val Leu Gly Thr Ser Thr Thr Arg Ser Met Gly Cys Cys Val
    50                  55                  60

Asn Gly Val Met Tyr Thr Thr Tyr Arg Gly Thr Asn Val Arg Pro Met
65                  70                  75                  80

Val Gly Leu Ser Val Leu Ser Met Leu Gly Gly Gly Xaa Arg Val Thr
            85                  90                  95

Thr Ser Arg Ser Thr Arg Ser Leu Met Val Leu Leu Ala Phe Arg His
            100                 105                 110

Ala Ser Ala Asn Gln Pro Gly Cys Gly Xaa
            115                 120
```

(2) INFORMATION FOR SEQ ID NO:66:

(i) SEQUENCE CHARACTERISTICS:
        (A) LENGTH: 122 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:66:

```
Ser Val Val Xaa Thr Val Gly Ser Thr Phe Arg Leu Ala Leu Phe Pro
1               5                   10                  15

Leu Leu Pro Trp Cys Phe Ile Lys Leu Ala Arg Asp Ser Ser Gly Leu
            20                  25                  30

Xaa Gly Pro Pro Xaa Gln Ala Arg Thr Arg Pro Asn Ile Thr Gly Thr
```

```
                   35                  40                  45
Trp Trp Ser Leu Gly Leu Gln Gln Leu Val Pro Trp Ala Ala Ala Xaa
    50                  55                  60

Thr Glu Xaa Cys Thr Arg His Thr Val Val Pro Thr Ser Gly Leu Trp
65                  70                  75                  80

Trp Gly Phe Arg Ser Cys Gln Cys Ser Val Val Ser Glu Xaa Arg
                85                  90                  95

Arg His Gly Leu Pro Ala Pro Xaa Trp Cys Phe Leu Pro Ser Gly Met
                100                 105                 110

Gln Val Pro Thr Asn Arg Gly Val Gly Asp
                115                 120

(2) INFORMATION FOR SEQ ID NO:67:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:67:

Asp Pro Ile Gln Gly Pro Ser Tyr Pro Ser Trp Gln Leu Xaa Lys Gly
1               5                   10                  15

Gln Pro Gly Met Leu Thr Met Leu Xaa Thr Pro Ala Leu Arg Thr Leu
                20                  25                  30

Lys Gln Ile Thr Lys Lys Leu His Thr Tyr Cys Gln Ile Ser Arg Pro
                35                  40                  45

Gln Ala Met Arg Pro Gln Ser Ser Val Gly Val Trp Ser Gln Arg
    50                  55                  60

Met Gln Ala Asp Met Ile Leu Gln Gly Val Asp Ala Ser Arg Met Pro
65                  70                  75                  80

Ser Ile Phe Cys Gly Cys His Glu Trp Gln Xaa Ser Thr His Tyr Ile
                85                  90                  95

Gln Cys Cys Ser Xaa Gln Ala Xaa Xaa Glu Val Cys Trp Ala Ser Asp
                100                 105                 110

(2) INFORMATION FOR SEQ ID NO:68:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:68:

Ile Gln Ser Arg Gly Pro Arg Thr Pro Pro Gly Ser Cys Arg Lys Asp
1               5                   10                  15

Asn Gln Glu Cys Xaa Pro Cys Ser Glu Leu Gln Leu Xaa Gly His Xaa
                20                  25                  30

Ser Lys Ser Gln Arg Asn Cys Thr His Thr Ala Lys Ser Leu Asp Pro
                35                  40                  45

Lys Gln Xaa Gly Arg Asn His Pro Pro Ser Gly Cys Gly Ala Asn Gly
    50                  55                  60

Cys Lys Leu Ile Xaa Tyr Ser Arg Gly Xaa Met Pro Pro Glu Cys Pro
65                  70                  75                  80
```

―continued

```
Val Ser Ser Ala Asp Val Thr Ser Gly Asn Lys Val Leu Thr Thr Tyr
                85                  90                  95
Ser Val Ala Pro Ser Lys His Ser Lys Lys Ser Val Gly Pro Val Ile
            100                 105                 110
```

(2) INFORMATION FOR SEQ ID NO:69:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:69:

```
Ser Asn Pro Gly Ala Leu Val Pro Leu Leu Ala Ala Val Glu Arg Thr
  1               5                  10                  15
Thr Arg Asn Val Asn His Ala Leu Asn Ser Ser Phe Lys Asp Ile Lys
                20                  25                  30
Ala Asn His Lys Glu Ile Ala His Ile Leu Pro Asn Leu Xaa Thr Pro
            35                  40                  45
Ser Asn Glu Ala Ala Ile Ile Leu Arg Arg Gly Val Glu Pro Thr Asp
        50                  55                  60
Ala Ser Xaa Tyr Asp Thr Pro Gly Gly Arg Cys Leu Gln Asn Ala Gln
 65                 70                  75                  80
Tyr Leu Leu Arg Met Ser Arg Val Ala Ile Lys Tyr Ser Leu His Thr
                85                  90                  95
Val Leu Leu Leu Ala Ser Ile Val Arg Ser Leu Leu Gly Gln Xaa
            100                 105                 110
```

(2) INFORMATION FOR SEQ ID NO:70:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:70:

```
Asp His Trp Pro Asn Arg Leu Leu Thr Met Leu Ala Arg Ser Asn Thr
  1               5                  10                  15
Val Cys Ser Glu Tyr Phe Ile Ala Thr Arg Asp Ile Arg Arg Arg Tyr
                20                  25                  30
Trp Ala Phe Trp Arg His Leu Pro Pro Gly Val Ser Tyr Gln Leu Ala
            35                  40                  45
Ser Val Gly Ser Thr Pro Arg Arg Arg Met Ile Ala Ala Ser Leu Leu
        50                  55                  60
Gly Val Xaa Arg Phe Gly Ser Met Cys Ala Ile Ser Leu Xaa Phe Ala
 65                 70                  75                  80
Leu Met Ser Leu Lys Leu Glu Phe Arg Ala Trp Leu Thr Phe Leu Val
                85                  90                  95
Val Leu Ser Thr Ala Ala Arg Arg Gly Thr Arg Ala Pro Gly Leu Asp
            100                 105                 110
```

(2) INFORMATION FOR SEQ ID NO:71:

(i) SEQUENCE CHARACTERISTICS:
        (A) LENGTH: 112 amino acids (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:71:

Ile Thr Gly Pro Thr Asp Phe Leu Leu Cys Leu Leu Gly Ala Thr Leu
1               5                   10                  15

Tyr Val Val Ser Thr Leu Leu Pro Leu Val Thr Ser Ala Glu Asp Thr
                20                  25                  30

Gly His Ser Gly Gly Ile Tyr Pro Leu Glu Tyr His Ile Ser Leu His
            35                  40                  45

Pro Leu Ala Pro His Pro Asp Gly Gly Xaa Leu Arg Pro His Cys Leu
        50                  55                  60

Gly Ser Arg Asp Leu Ala Val Cys Val Gln Phe Leu Cys Asp Leu Leu
65                  70                  75                  80

Xaa Cys Pro Xaa Ser Trp Ser Ser Glu His Gly Xaa His Ser Trp Leu
                85                  90                  95

Ser Phe Leu Gln Leu Pro Gly Gly Val Arg Gly Pro Leu Asp Trp Ile
                100                 105                 110

(2) INFORMATION FOR SEQ ID NO:72:

(i) SEQUENCE CHARACTERISTICS:
           (A) LENGTH: 111 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:72:

Ser Leu Ala Gln Gln Thr Ser Tyr Tyr Ala Cys Xaa Glu Gln His Cys
1               5                   10                  15

Met Xaa Xaa Val Leu Tyr Cys His Ser Xaa His Pro Gln Lys Ile Leu
                20                  25                  30

Gly Ile Leu Glu Ala Ser Thr Pro Trp Ser Ile Ile Ser Ala Cys Ile
            35                  40                  45

Arg Trp Leu His Thr Pro Thr Glu Asp Asp Cys Gly Leu Ile Ala Trp
        50                  55                  60

Gly Leu Glu Ile Trp Gln Tyr Val Cys Asn Phe Phe Val Ile Cys Phe
65                  70                  75                  80

Asn Val Leu Lys Ala Gly Val Gln Ser Met Val Asn Ile Pro Gly Cys
                85                  90                  95

Pro Phe Tyr Ser Cys Gln Glu Gly Tyr Glu Gly Pro Trp Ile Gly
                100                 105                 110

(2) INFORMATION FOR SEQ ID NO:73:

(i) SEQUENCE CHARACTERISTICS:
           (A) LENGTH: 795 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:73:

GATCAGGCCG CTGAGCGGCC GAGAAGGTTA CAATCTGGAG GGGTGATAGG AAGTATGACA        60

AGCATTATGA GGCTGTCGTT GAGGCTGTCC TGAAAAAGGC AGCCGCGACG AAGTCTCATG       120

```
GCTGGACCTA TTCCCAGGCT ATAGCTAAAG TTAGGCGCCG AGCAGCCGCT GGATACGGCA      180

GCAAGGTGAC CGCCTCCACA TTGGCCACTG GTTGGCCTCA CGTGGAGGAG ATGCTGGACA      240

AAATAGCCAG GGGACAGGAA GTTCCTTTCA CTTTTGTGAC CAAGCGAGAG GTTTTCTTCT      300

CCAAAACTAC CCGTAAGCCC CCAAGATTCA TAGTTTTCCC ACCTTTGGAC TTCAGGATAG      360

CTGAAAAGAT GATTCTGGGT GACCCCGGCA TCGTTGCAAA GTCAATTCTG GGTGACGCTT      420

ATCTGTTCCA GTACACGCCC AATCAGAGGG TCAAAGCTCT GGTTAAGGCG TGGGAGGGGA      480

AGTTGCATCC CGCTGCGATC ACCGTGKACG CCACTTGTTT CGACTCATCG ATTGATGAGC      540

ACGACATGCA GGTGGAGGCT TCGGTGTTTG CGGCGGCTAG TGACAACCCC TCAATGGTAC      600

ATGCTTTGTG CAAGTACTAC TCTGGTGGCC CTATGGTTTC CCCAGATGGG GTTCCCTTGG      660

GGTACCGCCA GTGTAGGTCG TCGGGCGTGT TGACAACTAG CTCGGCGAAC AGCATCACTT      720

GTTACATTAA GGTCAGCGCG GCCTGCAGGC GGGTGGGGAT TAAGGCACCA TCATTCTTTA      780

TAGCTGGAGA TGATT                                                       795
```

(2) INFORMATION FOR SEQ ID NO:74:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:74:

```
Asp Gln Ala Ala Glu Arg Pro Arg Arg Leu Gln Ser Gly Gly Val Ile
1               5                   10                  15

Gly Ser Met Thr Ser Ile Met Arg Leu Ser Leu Arg Leu Ser Xaa Lys
            20                  25                  30

Arg Gln Pro Arg Arg Ser Leu Met Ala Gly Pro Ile Pro Arg Leu Xaa
        35                  40                  45

Leu Lys Leu Gly Ala Glu Gln Pro Leu Asp Thr Ala Ala Arg Xaa Pro
    50                  55                  60

Pro Pro His Trp Pro Leu Val Gly Leu Thr Trp Arg Arg Cys Trp Thr
65                  70                  75                  80

Lys Xaa Pro Gly Asp Arg Lys Phe Leu Ser Leu Xaa Pro Ser Glu
            85                  90                  95

Arg Phe Ser Ser Pro Lys Leu Pro Val Ser Pro Gln Asp Ser Xaa Phe
            100                 105                 110

Ser His Leu Trp Thr Ser Gly Xaa Leu Lys Arg Xaa Phe Trp Val Thr
            115                 120                 125

Pro Ala Ser Leu Gln Ser Gln Phe Trp Val Thr Leu Ile Cys Ser Ser
    130                 135                 140

Thr Arg Pro Ile Arg Gly Ser Lys Leu Trp Leu Arg Gly Arg Gly
145                 150                 155                 160

Ser Cys Ile Pro Leu Arg Ser Pro Xaa Thr Pro Leu Val Ser Thr His
            165                 170                 175

Arg Leu Met Ser Thr Thr Cys Arg Trp Arg Leu Arg Cys Leu Arg Arg
            180                 185                 190

Leu Val Thr Thr Pro Gln Trp Tyr Met Leu Cys Ala Ser Thr Thr Leu
        195                 200                 205

Val Ala Leu Trp Phe Pro Gln Met Gly Phe Pro Trp Gly Thr Ala Ser
    210                 215                 220
```

Val Gly Arg Arg Ala Cys Xaa Gln Leu Ala Arg Arg Thr Ala Ser Leu
225                 230                 235                 240

Val Thr Leu Arg Ser Ala Arg Pro Ala Gly Gly Trp Gly Leu Arg His
            245                 250                 255

His His Ser Leu Xaa Leu Glu Met Ile
            260                 265

(2) INFORMATION FOR SEQ ID NO:75:

(i) SEQUENCE CHARACTERISTICS:
        (A) LENGTH: 264 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

Ile Arg Pro Leu Ser Gly Arg Glu Gly Tyr Asn Leu Glu Gly Xaa Xaa
1               5                   10                  15

Glu Val Xaa Gln Ala Leu Xaa Gly Cys Arg Xaa Gly Cys Pro Glu Lys
            20                  25                  30

Gly Ser Arg Asp Glu Val Ser Trp Leu Asp Leu Phe Pro Gly Tyr Ser
            35                  40                  45

Xaa Ser Xaa Ala Pro Ser Ser Arg Trp Ile Arg Gln Gln Gly Asp Arg
50                  55                  60

Leu His Ile Gly His Trp Leu Ala Ser Arg Gly Gly Asp Ala Gly Gln
65                  70                  75                  80

Asn Ser Gln Gly Thr Gly Ser Ser Phe His Phe Cys Asp Gln Ala Arg
            85                  90                  95

Gly Phe Leu Leu Gln Asn Tyr Pro Xaa Ala Pro Lys Ile His Ser Phe
            100                 105                 110

Pro Thr Phe Gly Leu Gln Asp Ser Xaa Lys Asp Asp Ser Gly Xaa Pro
            115                 120                 125

Arg His Arg Cys Lys Val Asn Ser Gly Xaa Arg Leu Ser Val Pro Val
            130                 135                 140

His Ala Gln Ser Glu Gly Gln Ser Ser Gly Xaa Gly Val Gly Gly Glu
145                 150                 155                 160

Val Ala Ser Arg Cys Asp His Arg Xaa Arg His Leu Phe Arg Leu Ile
            165                 170                 175

Asp Xaa Xaa Ala Arg His Ala Gly Gly Gly Phe Gly Val Cys Gly Gly
            180                 185                 190

Xaa Xaa Gln Pro Leu Asn Gly Thr Cys Phe Val Gln Val Leu Leu Trp
            195                 200                 205

Trp Pro Tyr Gly Phe Pro Arg Trp Gly Ser Leu Gly Val Pro Pro Val
            210                 215                 220

Xaa Val Val Gly Arg Val Asp Asn Xaa Leu Gly Glu Gln His His Leu
225                 230                 235                 240

Leu His Xaa Gly Gln Arg Gly Leu Gln Ala Gly Gly Asp Xaa Gly Thr
            245                 250                 255

Ile Ile Leu Tyr Ser Trp Arg Xaa
            260

(2) INFORMATION FOR SEQ ID NO:76:

(i) SEQUENCE CHARACTERISTICS:
        (A) LENGTH: 264 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Ser Gly Arg Xaa Ala Ala Glu Lys Val Thr Ile Trp Arg Gly Asp Arg
1               5                   10                  15

Lys Tyr Asp Lys His Tyr Glu Ala Val Val Glu Ala Val Leu Lys Lys
                20                  25                  30

Ala Ala Ala Thr Lys Ser His Gly Trp Thr Tyr Ser Gln Ala Ile Ala
            35                  40                  45

Lys Val Arg Arg Arg Ala Ala Ala Gly Tyr Gly Ser Lys Val Thr Ala
50                  55                  60

Ser Thr Leu Ala Thr Gly Trp Pro His Val Glu Glu Met Leu Asp Lys
65                  70                  75                  80

Ile Ala Arg Gly Gln Glu Val Pro Phe Thr Phe Val Thr Lys Arg Glu
                85                  90                  95

Val Phe Phe Ser Lys Thr Thr Arg Lys Pro Pro Arg Phe Ile Val Phe
                100                 105                 110

Pro Pro Leu Asp Phe Arg Ile Ala Glu Lys Met Ile Leu Gly Asp Pro
            115                 120                 125

Gly Ile Val Ala Lys Ser Ile Leu Gly Asp Ala Tyr Leu Phe Gln Tyr
130                 135                 140

Thr Pro Asn Gln Arg Val Lys Ala Leu Val Lys Ala Trp Glu Gly Lys
145                 150                 155                 160

Leu His Pro Ala Ala Ile Thr Val Xaa Ala Thr Cys Phe Asp Ser Ser
                165                 170                 175

Ile Asp Glu His Asp Met Gln Val Glu Ala Ser Val Phe Ala Ala Ala
                180                 185                 190

Ser Asp Asn Pro Ser Met Val His Ala Leu Cys Lys Tyr Tyr Ser Gly
            195                 200                 205

Gly Pro Met Val Ser Pro Asp Gly Val Pro Leu Gly Tyr Arg Gln Cys
            210                 215                 220

Arg Ser Ser Gly Val Leu Thr Thr Ser Ser Ala Asn Ser Ile Thr Cys
225                 230                 235                 240

Tyr Ile Lys Val Ser Ala Ala Cys Arg Arg Val Gly Ile Lys Ala Pro
                245                 250                 255

Ser Phe Phe Ile Ala Gly Asp Asp
            260

(2) INFORMATION FOR SEQ ID NO:77:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:77:

Asn His Leu Gln Leu Xaa Arg Met Met Val Pro Xaa Ser Pro Pro Ala
1               5                   10                  15

Cys Arg Pro Arg Xaa Pro Xaa Cys Asn Lys Xaa Cys Cys Ser Pro Ser
                20                  25                  30

Xaa Leu Ser Thr Arg Pro Thr Thr Tyr Thr Gly Gly Thr Pro Arg Glu

-continued

```
              35                  40                  45
Pro His Leu Gly Lys Pro Xaa Gly His Gln Ser Ser Thr Cys Thr Lys
             50                  55                  60
His Val Pro Leu Arg Gly Cys His Xaa Pro Pro Gln Thr Pro Lys Pro
 65                  70                  75                  80
Pro Pro Ala Cys Arg Ala His Gln Ser Met Ser Arg Asn Lys Trp Arg
                 85                  90                  95
Xaa Arg Xaa Ser Gln Arg Asp Ala Thr Ser Pro Pro Thr Pro Xaa Pro
                100                 105                 110
Glu Leu Xaa Pro Ser Asp Trp Ala Cys Thr Gly Thr Asp Lys Arg His
            115                 120                 125
Pro Glu Leu Thr Leu Gln Arg Cys Arg Gly His Pro Glu Ser Ser Phe
            130                 135                 140
Gln Leu Ser Xaa Ser Pro Lys Val Gly Lys Leu Xaa Ile Leu Gly Ala
145                 150                 155                 160
Tyr Gly Xaa Phe Trp Arg Arg Lys Pro Leu Ala Trp Ser Gln Lys Xaa
                165                 170                 175
Lys Glu Leu Pro Val Pro Trp Leu Phe Cys Pro Ala Ser Pro Pro Arg
            180                 185                 190
Glu Ala Asn Gln Trp Pro Met Trp Arg Arg Ser Pro Cys Cys Arg Ile
            195                 200                 205
Gln Arg Leu Leu Gly Ala Xaa Leu Xaa Leu Xaa Pro Gly Asn Arg Ser
            210                 215                 220
Ser His Glu Thr Ser Ser Arg Leu Pro Phe Ser Gly Gln Pro Gln Arg
225                 230                 235                 240
Gln Pro His Asn Ala Cys His Thr Ser Tyr His Pro Ser Arg Leu Xaa
                245                 250                 255
Pro Ser Arg Pro Leu Ser Gly Leu Ile
            260                 265

(2) INFORMATION FOR SEQ ID NO:78:

(i) SEQUENCE CHARACTERISTICS:
        (A) LENGTH: 264 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

Ile Ile Ser Ser Tyr Lys Glu Xaa Trp Cys Leu Asn Pro His Pro Pro
 1               5                  10                  15
Ala Gly Arg Ala Asp Leu Asn Val Thr Ser Asp Ala Val Arg Arg Ala
                 20                  25                  30
Ser Cys Gln His Ala Arg Arg Pro Thr Leu Ala Val Pro Gln Gly Asn
             35                  40                  45
Pro Ile Trp Gly Asn His Arg Ala Thr Arg Val Val Leu Ala Gln Ser
             50                  55                  60
Met Tyr His Xaa Gly Val Val Thr Ser Arg Arg Lys His Arg Ser Leu
 65                  70                  75                  80
His Leu His Val Val Leu Ile Asn Arg Xaa Val Glu Thr Ser Gly Val
                 85                  90                  95
His Gly Asp Arg Ser Gly Met Gln Leu Pro Leu Pro Arg Leu Asn Gln
                100                 105                 110
Ser Phe Asp Pro Leu Ile Gly Arg Val Leu Glu Gln Ile Ser Val Thr
```

```
                 115                 120                 125
Gln Asn Xaa Leu Cys Asn Asp Ala Gly Val Thr Gln Asn His Leu Phe
        130                 135                 140

Ser Tyr Pro Glu Val Gln Arg Trp Glu Asn Tyr Glu Ser Trp Gly Leu
145                 150                 155                 160

Thr Gly Ser Phe Gly Glu Glu Asn Leu Ser Leu Gly His Lys Ser Glu
                165                 170                 175

Arg Asn Phe Leu Ser Pro Gly Tyr Phe Val Gln His Leu Leu His Val
        180                 185                 190

Arg Pro Thr Ser Gly Gln Cys Gly Gly His Leu Ala Ala Val Ser
        195                 200                 205

Ser Gly Cys Ser Ala Pro Asn Phe Ser Tyr Ser Leu Gly Ile Gly Pro
        210                 215                 220

Ala Met Arg Leu Arg Arg Gly Cys Leu Phe Gln Asp Ser Leu Asn Asp
225                 230                 235                 240

Ser Leu Ile Met Leu Val Ile Leu Pro Ile Thr Pro Pro Asp Cys Asn
                245                 250                 255

Leu Leu Gly Arg Ser Ala Ala Xaa
                260
```

(2) INFORMATION FOR SEQ ID NO:79:

(i) SEQUENCE CHARACTERISTICS:
        (A) LENGTH: 264 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:79:

```
Ser Ser Pro Ala Ile Lys Asn Asp Gly Ala Leu Ile Pro Thr Arg Leu
1               5                  10                  15

Gln Ala Ala Leu Thr Leu Met Xaa Gln Val Met Leu Phe Ala Glu Leu
                20                  25                  30

Val Val Asn Thr Pro Asp Asp Leu His Trp Arg Tyr Pro Lys Gly Thr
                35                  40                  45

Pro Ser Gly Glu Thr Ile Gly Pro Pro Glu Xaa Tyr Leu His Lys Ala
    50                  55                  60

Cys Thr Ile Glu Gly Leu Ser Leu Ala Ala Asn Thr Glu Ala Ser
65                  70                  75                  80

Thr Cys Met Ser Cys Ser Ser Ile Asp Glu Ser Lys Gln Val Ala Xaa
                85                  90                  95

Thr Val Ile Ala Ala Gly Cys Asn Phe Pro Ser His Ala Leu Thr Arg
                100                 105                 110

Ala Leu Thr Leu Xaa Leu Gly Val Tyr Trp Asn Arg Xaa Ala Ser Pro
                115                 120                 125

Arg Ile Asp Phe Ala Thr Met Pro Gly Ser Pro Arg Ile Ile Phe Ser
        130                 135                 140

Ala Ile Leu Lys Ser Lys Gly Gly Lys Thr Met Asn Leu Gly Gly Leu
145                 150                 155                 160

Arg Val Val Leu Glu Lys Lys Thr Ser Arg Leu Val Thr Lys Val Lys
                165                 170                 175

Gly Thr Ser Cys Pro Leu Ala Ile Leu Ser Ser Ile Ser Ser Thr Xaa
                180                 185                 190

Gly Gln Pro Val Ala Asn Val Glu Ala Val Thr Leu Leu Pro Tyr Pro
```

```
            195                 200                 205
Ala Ala Ala Arg Arg Leu Thr Leu Ala Ile Ala Trp Glu Xaa Val Gln
    210                 215                 220

Pro Xaa Asp Phe Val Ala Ala Ala Phe Phe Arg Thr Ala Ser Thr Thr
225                 230                 235                 240

Ala Ser Xaa Cys Leu Ser Tyr Phe Leu Ser Pro Leu Gln Ile Val Thr
                245                 250                 255

Phe Ser Ala Ala Gln Arg Pro Asp
                260
```

(2) INFORMATION FOR SEQ ID NO:80:

(i) SEQUENCE CHARACTERISTICS:
        (A) LENGTH: 4268 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:80:

```
TGGCTCATCC CACAGGCTCC ATACACCCAA TAACCGTTGA CGCGGCTAAT GACCAGGACA      60

TCTATCAACC ACCATGTGGA GCTGGGTCCC TTACTCGGTG CTCTTGCGGG GAGACCAAGG     120

GGTATCTGGT AACACGACTG GGTCATTGG TTGAGGTCAA CAAATCCGAT GACCCTTATT     180

GGTGTGTGTG CGGGGCCCTT CCCATGGCTG TTGCCAAGGG TTCTTCAGGT GCCCCGATTC     240

TGTGCTCCTC CGGGCATGTT ATTGGGATGT TCACCGCTGC TAGAAATTCT GGCGGTTCAG     300

TCGGCCAGAT TAGGGTTAGG CCGTTGGTGT GTGCTGGATA CCATCCCCAG TACACAGCAC     360

ATGCCACTCT TGATACAAAA CCTACTGTGC CTAACGAGTA TTCAGTGCAA ATTTTAATTG     420

CCCCCACTGG CAGCGGCAAG TCAACCAAAT TACCACTTTC TTACATGCAG GRGAAGYATG     480

AGGTCTTGGT CCTAAATCCC AGTGTGGCTA CAACAGCATC AATGCCAAAG TACATGCACG     540

CGACGTACGG CGTGAATCCA AATTGCTATT TTAATGGCAA ATGTACCAAC ACAGGGGCTT     600

CACTTACGTA CAGCACATAT GGCATGTACC TGACCGGACG ATGTTCCCGG AACTATGATG     660

TAATCATTTG TGACGAATGC CATGCTACCG ATCGAACCAC CGTGTGGGC ATTGAAAGG     720

TCCTAACCGA AGCTCCATCC AAAAATGTTA GGCTAGTGGT TCTTGCCACG GCTACCCCCC     780

CTGGAGTAAT CCCTACACCA CATGCCAACA TAACTGAGAT TCAATTAACY GATGAAGGCA     840

CTATCCCCTT TCATGGAAAA AAGATTAAGG AGGAAAATCT GAAGAAAGGG AGACACCTTA     900

TCTTTGAGGC TACCAAAAAA CACTGTGATG AGCTTGCTAA CGAGTTAGCT CGAAAGGGAA     960

TAACAGCTGT CTCTTACTAT AGGGGATGTG ACATCTCAAA AATGCCTGAG GGCGACTGTG    1020

TAGTAGTTGC CACTGATGCC TTGTGTACAG GGTACACTGG TGACTTTGAT TCCGTGTATG    1080

ACTGCAGCCT CATGGTAGAA GGCACATGCC ATGTTGACCT TGACCCTACT TTCACCATGG    1140

GTGTTCGTGT GTGCGGGGTT TCAGCAATAG TTAAAGGCCA GCGTAGGGGC CGCACAGGCC    1200

GTGGGAGAGC TGGCATATAC TACTATGTAG ACGGGAGTTG TACCCCTTCG GGTATGGTTC    1260

CTGAATGCAA CATTGTTGAA GCCTTCGACG CAGCCAAGGC ATGGTATGGT TTGTCATCAA    1320

CAGAAGCTCA AACTATTCTG GACACCTATC GCACCCAACC TGGGTTACCT GCGATAGGAG    1380

CAAATTTGGA CGAGTGGGCT GATCTCTTTT CTATGGTCAA CCCCGAACCT TCATTTGTCA    1440

ATACTGCAAA AAGAACTGCT GACAATTATG TTTTGTTGAC TGCAGCCCAA CTACAACTGT    1500

GTCATCAGTA TGGCTATGCT GCTCCCAATG ACGCACCACG GTGGCAGGGA GCCCGGCTTG    1560
```

```
GGAAAAAACC TTGTGGGGTT CTGTGGCGCT TGGACGGCTG TGACGCCTGT CCTGGCCCAG    1620

AGCCCAGCGA GGTGACCAGA TACCAAATGT GCTTCACTGA AGTCAATACT TCTGGGACAG    1680

CCGCACTCGC TGTTGGCGTT GGAGTGGCTA TGGCTTATCT AGCCATTGAC ACTTTTGGCG    1740

CCACTTGTGT GCGGCGTTGC TGGTCTATTA CATCAGTCCC TACCGGTGCT ACTGTCGCCC    1800

CAGTGGTTGA CGAAGAGGAA ATCGTGGAGG AGTGTGCATC ATTCATTCCC TTGGAGGCCA    1860

TGGTTGCTGC AATTGACAAG CTGAAGAGTA CAATCACCAC AACTAGTCCT TTCACATTGG    1920

AAACCGCCCT TGAAAAACTT AACACCTTTC TTGGGCCTCA TGCAGCTACA ATCCTTGCTA    1980

TCATAGAGTA TTGCTGTGGC TTAGTCACTT TACCTGACAA TCCCTTTGCA TCATGCGTGT    2040

TTGCTTTCAT TGCGGGTATT ACTACCCCAC TACCTCACAA GATCAAAATG TTCCTGTCAT    2100

TATTTGGAGG CGCAATTGCG TCCAAGCTTA CAGACGCTAG AGRCGCACTG GCGTTCATGA    2160

TGGCCGGGGC TGYGGGAACA GCTCTTGGTA CATGGACATC GGTGGGTTTT GTCTTTGACA    2220

TGCTAGGCGG CTATGCTGGC GCCTCATCCA CTGCTTGCTT GACATTTAAA TGCTTGATGG    2280

GTGAGTGGCY CACTATGGAT CAGCTTGCTG GTTTAGTCTA CTCCGCGTTC AATCCGGCCG    2340

CAGGAGTTGT GGGCGTCTTG TCAGCTTGTG CAATGTTTGC TTTGACAACA GCAGGGCCAG    2400

ATCACTGGCC CAACAGACTT CTTACTATGC TTGCTAGGAG CAACACTGTA TGTARTGAGT    2460

ACTTTATTGC CACTCGTGAC ATCCGCAGGA AGATACTGGG CATTCTGGAG GCATCTACCC    2520

CCTGGAGTRT CATATCAGCT TGCATCCGTT GGCTYCACAC CCCGACGGAG GATGATTGCG    2580

GCCTCATTGC TTGGGGTCTA RAGATTTGGC AGTATGTGTG CAATTTCTTT GTGATTTGCT    2640

TTAATGTCCT TAAAGCTGGA GTTCAGAGCA TGGTTAACAT TCCTGGTTGT CCTTTCTACA    2700

GCTGCCAGAA GGGGTACAAG GGCCCCTGGA TTGGATCAGG TATGCTCCAA GCACGCTGTC    2760

CATGCGGTGC TGAACTCATC TTTTCTGTTG AGAATGGTTT TGCAAAACTT TACAAAGGAC    2820

CCAGAACTTG TTCAAATTAC TGGAGAGGGG CTGTTCCAGT CAACGCTAGG CTGTGTGGGT    2880

CGGCTAGACC GGACCCAACT GATTGGACTA GTCTTGTCGT CAATTATGGC GTTAGGGACT    2940

ACTGTAAATA TGAGAAATTG GGAGATCACA TTTTTGTTAC AGCAGTATCC TCTCCAAATG    3000

TCTGTTTCAC CCAGGTGCCC CCAACCTTGA GAGCTGCAGT GGCCGTGGAC CGCGTACAGG    3060

TTCAGYGTTA TCTAGGTGAG CCCAAAACTC CTTGGACGAC ATCTGCTTGC TGTTACGGTC    3120

CTGACGGTAA GGGTAAAACT GTTAAGCTTC CCTTCCGCGT TGACGGACAC ACACCTGGTG    3180

GTCGCATGCA ACTTAATTTG CGTGATCGAC TTGAGGCAAA TGACTGTAAT TCCATAAACA    3240

ACACTCCTAG TGATGAAGCC GCAGTGTCCG CTCTTGTTTT CAAACAGGAG TTGCGGCGTA    3300

CAAACCAATT GCTTGAGGCA ATTTCAGCTG GCGTTGACAC CACCAAACTG CCAGCCCCCT    3360

CCCAGATCGA AGAGGTAGTG GTAAGAAAGC GCCAGTTCCG GGCAAGAACT GGTTCGCTTA    3420

CCTTGCCTCC CCCTCCGAGA TCCGTCCCAG GAGTGTCATG TCCTGAAAGC CTGCAACGAA    3480

GTGACCCGTT AGAAGGTCCT TCAAMCCTCC CTTCTTCACC ACCTGTTCTR CAGTTGGCCA    3540

TGCCGATGCC CCTGTTGGGA GCAGGTGAGT GTAACCCTTT CACTGCAATT GGATGTGCAA    3600

TGACCGAAAC ARGYGGAGKC CCWSAKRATT TACCCAGTTA CCCTCCCAAA AAGGAGGTCT    3660

CTGAATGGTC AGACGAAAGT TGGTCAACGA CTACAACCGC TTCCAGCTAC GTTACTGGCC    3720

CCCCGTACCC TAAGATACGG GGCAAGGATT CCACTCAATC AGCCACCGCC AAACGGCCTA    3780

CAAAAAAGAA GTTGGGAAAG AGTGAGTTTT CGTGCAGCAT GAGCTACACT TGGACCGACG    3840

TGATTAGCTT CAAAACTGCT TCTAAAGTTC TGTCTGCAAC TCGGGCCATC ACTAGTGGTT    3900

TCCTCAAACA AAGATCATTG GTGTATGTGA CTGAGCCGCG GGATGCGGAG CTTAGAAAAC    3960
```

```
AAAAAGTCAC TATTAATAGA CAACCTCTGT TCCCCCCATC ATACCACAAG CAAGTGAGAT    4020

TGGCTAAGGA AAAAGCTTCA AAAGTTGTCG GTGTCATGTG GGACTATGAT GAAGTAGCAG    4080

CTCACACGCC CTCTAAGTCT GCTAAGTCCC ACATCACTGG CCTTCGGGGC ACTGATGTTC    4140

TGGACTTGCA GAAGTGTGTC GAGGCAGGTG AGATACCGAG TCATTATCGG CAAACTGTGA    4200

TAGTTCCAAA GGAGGAGGTC TTCGTGAAGA CCCCCCAGAA ACCAACAAAG AAACCCCCAA    4260

GGCTTATC                                                            4268
```

(2) INFORMATION FOR SEQ ID NO:81:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:81:

```
Trp Leu Ile Pro Gln Ala Pro Tyr Thr Gln Xaa Pro Leu Thr Arg Leu
  1               5                  10                  15

Met Thr Arg Thr Ser Ile Asn His His Val Glu Leu Gly Pro Leu Leu
             20                  25                  30

Gly Ala Leu Ala Gly Arg Pro Arg Gly Ile Trp Xaa His Asp Trp Gly
         35                  40                  45

His Trp Leu Arg Ser Thr Asn Pro Met Thr Leu Ile Gly Val Cys Ala
     50                  55                  60

Gly Pro Phe Pro Trp Leu Leu Pro Arg Val Leu Gln Val Pro Arg Phe
 65                  70                  75                  80

Cys Ala Pro Pro Gly Met Leu Leu Gly Cys Ser Pro Leu Leu Glu Ile
             85                  90                  95

Leu Ala Val Gln Ser Ala Arg Leu Gly Leu Gly Arg Trp Cys Val Leu
            100                 105                 110

Asp Thr Ile Pro Ser Thr Gln His Met Pro Leu Leu Ile Gln Asn Leu
        115                 120                 125

Leu Cys Leu Thr Ser Ile Gln Cys Lys Phe Xaa Leu Pro Pro Leu Ala
    130                 135                 140

Ala Ala Ser Gln Pro Asn Tyr His Phe Leu Thr Cys Arg Xaa Ser Met
145                 150                 155                 160

Arg Ser Trp Ser Xaa Ile Pro Val Trp Leu Gln Gln His Gln Cys Gln
                165                 170                 175

Ser Thr Cys Thr Arg Arg Thr Ala Xaa Ile Gln Ile Ala Ile Leu Met
            180                 185                 190

Ala Asn Val Pro Thr Gln Gly Leu His Leu Arg Thr Ala His Met Ala
        195                 200                 205

Cys Thr Xaa Pro Asp Asp Val Pro Gly Thr Met Met Xaa Ser Phe Val
    210                 215                 220

Thr Asn Ala Met Leu Pro Ile Glu Pro Pro Cys Trp Ala Leu Glu Arg
225                 230                 235                 240

Ser Xaa Pro Lys Leu His Pro Lys Met Leu Gly Xaa Trp Phe Leu Pro
                245                 250                 255

Arg Leu Pro Pro Leu Glu Xaa Ser Leu His His Met Pro Thr Xaa Leu
            260                 265                 270

Arg Phe Asn Xaa Xaa Met Lys Ala Leu Ser Pro Phe Met Glu Lys Arg
        275                 280                 285
```

-continued

```
Leu Arg Arg Lys Ile Xaa Arg Lys Gly Asp Thr Leu Ser Leu Arg Leu
    290                 295                 300

Pro Lys Asn Thr Val Met Ser Leu Leu Thr Ser Xaa Leu Glu Arg Glu
305                 310                 315                 320

Xaa Gln Leu Ser Leu Thr Ile Gly Asp Val Thr Ser Gln Lys Cys Leu
                325                 330                 335

Arg Ala Thr Val Xaa Xaa Leu Pro Leu Met Pro Cys Val Gln Gly Thr
                340                 345                 350

Leu Val Thr Leu Ile Pro Cys Met Thr Ala Ala Ser Trp Xaa Lys Ala
            355                 360                 365

His Ala Met Leu Thr Leu Thr Leu Leu Ser Pro Trp Val Phe Val Cys
370                 375                 380

Ala Gly Phe Gln Gln Xaa Leu Lys Ala Ser Val Gly Ala Ala Gln Ala
385                 390                 395                 400

Val Gly Glu Leu Ala Tyr Thr Thr Met Xaa Thr Gly Val Val Pro Leu
                405                 410                 415

Arg Val Trp Phe Leu Asn Ala Thr Leu Leu Lys Pro Ser Thr Gln Pro
                420                 425                 430

Arg His Gly Met Val Cys His Gln Gln Lys Leu Lys Leu Phe Trp Thr
                435                 440                 445

Pro Ile Ala Pro Asn Leu Gly Tyr Leu Arg Xaa Glu Gln Ile Trp Thr
450                 455                 460

Ser Gly Leu Ile Ser Phe Leu Trp Ser Thr Pro Asn Leu His Leu Ser
465                 470                 475                 480

Ile Leu Gln Lys Glu Leu Leu Thr Ile Met Phe Cys Xaa Leu Gln Pro
                485                 490                 495

Asn Tyr Asn Cys Val Ile Ser Met Ala Met Leu Leu Pro Met Thr His
                500                 505                 510

His Gly Gly Arg Glu Pro Gly Leu Gly Lys Asn Leu Val Gly Phe Cys
            515                 520                 525

Gly Ala Trp Thr Ala Val Thr Pro Val Leu Ala Gln Ser Pro Ala Arg
530                 535                 540

Xaa Pro Asp Thr Lys Cys Ala Ser Leu Lys Ser Ile Leu Leu Gly Gln
545                 550                 555                 560

Pro His Ser Leu Leu Ala Leu Glu Trp Leu Trp Leu Ile Xaa Pro Leu
                565                 570                 575

Thr Leu Leu Ala Pro Leu Val Cys Gly Val Ala Gly Leu Leu His Gln
                580                 585                 590

Ser Leu Pro Val Leu Leu Ser Pro Gln Trp Leu Thr Lys Arg Lys Ser
            595                 600                 605

Trp Arg Ser Val His His Ser Phe Pro Trp Arg Pro Trp Leu Leu Gln
610                 615                 620

Leu Thr Ser Xaa Arg Val Gln Ser Pro Gln Leu Val Leu Ser His Trp
625                 630                 635                 640

Lys Pro Pro Leu Lys Asn Leu Thr Pro Phe Leu Gly Leu Met Gln Leu
                645                 650                 655

Gln Ser Leu Leu Ser Xaa Ser Ile Ala Val Ala Xaa Ser Leu Tyr Leu
                660                 665                 670

Thr Ile Pro Leu His His Ala Cys Leu Leu Ser Leu Arg Val Leu Leu
            675                 680                 685

Pro His Tyr Leu Thr Arg Ser Lys Cys Ser Cys His Tyr Leu Glu Ala
690                 695                 700
```

-continued

```
Gln Leu Arg Pro Ser Leu Gln Thr Leu Glu Xaa His Trp Arg Ser Xaa
705                 710                 715                 720

Trp Pro Gly Leu Xaa Glu Gln Leu Leu Val His Gly His Arg Trp Val
                725                 730                 735

Leu Ser Leu Thr Cys Xaa Ala Ala Met Leu Ala Pro His Pro Leu Leu
                740                 745                 750

Ala Xaa His Leu Asn Ala Xaa Trp Val Ser Gly Xaa Leu Trp Ile Ser
            755                 760                 765

Leu Leu Val Xaa Ser Thr Pro Arg Ser Ile Arg Pro Gln Glu Leu Trp
770                 775                 780

Ala Ser Cys Gln Leu Val Gln Cys Leu Leu Xaa Gln Gln Gly Gln
785                 790                 795                 800

Ile Thr Gly Pro Thr Asp Phe Leu Leu Cys Leu Leu Gly Ala Thr Leu
                805                 810                 815

Tyr Val Xaa Ser Thr Leu Leu Pro Leu Val Thr Ser Ala Gly Arg Tyr
            820                 825                 830

Trp Ala Phe Trp Arg His Leu Pro Pro Gly Val Ser Tyr Gln Leu Ala
                835                 840                 845

Ser Val Gly Xaa Thr Pro Arg Arg Met Ile Ala Ala Ser Leu Leu
850                 855                 860

Gly Val Xaa Arg Phe Gly Ser Met Cys Ala Ile Ser Leu Xaa Phe Ala
865                 870                 875                 880

Leu Met Ser Leu Lys Leu Glu Phe Arg Ala Trp Leu Thr Phe Leu Val
                885                 890                 895

Val Leu Ser Thr Ala Ala Arg Arg Gly Thr Arg Ala Pro Gly Leu Asp
                900                 905                 910

Gln Val Cys Ser Lys His Ala Val His Ala Val Leu Asn Ser Ser Phe
            915                 920                 925

Leu Leu Arg Met Val Leu Gln Asn Phe Thr Lys Asp Pro Glu Leu Val
            930                 935                 940

Gln Ile Thr Gly Glu Gly Leu Phe Gln Ser Thr Leu Gly Cys Val Gly
945                 950                 955                 960

Arg Leu Asp Arg Thr Gln Leu Ile Gly Leu Val Leu Ser Ser Ile Met
                965                 970                 975

Ala Leu Gly Thr Thr Val Asn Met Arg Asn Trp Glu Ile Thr Phe Leu
            980                 985                 990

Leu Gln Gln Tyr Pro Leu Gln Met Ser Val Ser Pro Arg Cys Pro Gln
            995                 1000                1005

Pro Xaa Glu Leu Gln Trp Pro Trp Thr Ala Tyr Arg Phe Ser Val Ile
    1010                1015                1020

Xaa Val Ser Pro Lys Leu Leu Gly Arg His Leu Leu Ala Val Thr Val
1025                1030                1035                1040

Leu Thr Val Arg Val Lys Leu Leu Ser Phe Pro Ser Ala Leu Thr Asp
                    1045                1050                1055

Thr His Leu Val Val Ala Cys Asn Leu Ile Cys Val Ile Asp Leu Arg
                1060                1065                1070

Gln Met Thr Val Ile Pro Xaa Thr Thr Leu Leu Val Met Lys Pro Gln
            1075                1080                1085

Cys Pro Leu Leu Phe Ser Asn Arg Ser Cys Gly Val Gln Thr Asn Cys
            1090                1095                1100

Leu Arg Gln Phe Gln Leu Ala Leu Thr Pro Pro Asn Cys Gln Pro Pro
1105                1110                1115                1120

Pro Arg Ser Lys Arg Xaa Trp Xaa Glu Ser Ala Ser Ser Gly Gln Glu
```

-continued

```
                    1125                1130                1135
Leu Val Arg Leu Pro Cys Leu Pro Leu Arg Asp Pro Ser Gln Glu Cys
            1140                1145                1150
His Val Leu Lys Ala Cys Asn Glu Val Thr Arg Xaa Lys Val Leu Gln
        1155                1160                1165
Xaa Ser Leu Leu His His Leu Phe Xaa Ser Trp Pro Cys Arg Cys Pro
    1170                1175                1180
Cys Trp Glu Gln Val Ser Val Thr Leu Ser Leu Gln Leu Asp Val Gln
1185                1190                1195                1200
Xaa Pro Lys Gln Xaa Glu Xaa Xaa Ile Tyr Pro Val Thr Leu Pro
                1205                1210                1215
Lys Arg Arg Ser Leu Asn Gly Gln Thr Lys Val Gly Gln Arg Leu Gln
            1220                1225                1230
Pro Leu Pro Ala Thr Leu Leu Ala Pro Arg Thr Leu Arg Tyr Gly Ala
        1235                1240                1245
Arg Ile Pro Leu Asn Gln Pro Pro Asn Gly Leu Gln Lys Arg Ser
    1250                1255                1260
Trp Glu Arg Val Ser Phe Arg Ala Ala Xaa Ala Thr Leu Gly Pro Thr
1265                1270                1275                1280
Xaa Leu Ala Ser Lys Leu Leu Lys Phe Cys Leu Gln Leu Gly Pro
            1285                1290                1295
Ser Leu Val Val Ser Ser Asn Lys Asp His Trp Cys Met Xaa Leu Ser
        1300                1305                1310
Arg Gly Met Arg Ser Leu Glu Asn Lys Lys Ser Leu Leu Ile Asp Asn
    1315                1320                1325
Leu Cys Ser Pro His His Thr Thr Ser Lys Xaa Asp Trp Leu Arg Lys
    1330                1335                1340
Lys Leu Gln Lys Leu Ser Val Ser Cys Gly Thr Met Met Lys Xaa Gln
1345                1350                1355                1360
Leu Thr Arg Pro Leu Ser Leu Leu Ser Pro Thr Ser Leu Ala Phe Gly
            1365                1370                1375
Ala Leu Met Phe Trp Thr Cys Arg Ser Val Ser Arg Gln Val Arg Tyr
        1380                1385                1390
Arg Val Ile Ile Gly Lys Leu Xaa Xaa Phe Gln Arg Arg Ser Ser
    1395                1400                1405
Xaa Arg Pro Pro Arg Asn Gln Gln Arg Asn Pro Gln Gly Leu
    1410                1415                1420

(2) INFORMATION FOR SEQ ID NO:82:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:82:

Gly Ser Ser His Arg Leu His Thr Pro Asn Asn Arg Xaa Arg Gly Xaa
1               5                   10                  15
Xaa Pro Gly His Leu Ser Thr Thr Met Trp Ser Trp Val Pro Tyr Ser
            20                  25                  30
Val Leu Leu Arg Gly Asp Gln Gly Val Ser Gly Asn Thr Thr Gly Val
        35                  40                  45
Ile Gly Xaa Gly Gln Gln Ile Arg Xaa Pro Leu Leu Val Cys Val Arg
```

-continued

```
        50                  55                  60
Gly Pro Ser His Gly Cys Cys Gln Gly Phe Phe Arg Cys Pro Asp Ser
 65                  70                  75                  80

Val Leu Leu Arg Ala Cys Tyr Trp Asp Val His Arg Cys Xaa Lys Phe
                 85                  90                  95

Trp Arg Phe Ser Arg Pro Asp Xaa Gly Xaa Ala Val Gly Val Cys Trp
                100                 105                 110

Ile Pro Ser Pro Val His Ser Thr Cys His Ser Xaa Tyr Lys Thr Tyr
                115                 120                 125

Cys Ala Xaa Arg Val Phe Ser Ala Asn Phe Asn Cys Pro His Trp Gln
            130                 135                 140

Arg Gln Val Asn Gln Ile Thr Thr Phe Leu His Ala Gly Glu Xaa Xaa
145                 150                 155                 160

Gly Leu Gly Pro Lys Ser Gln Cys Gly Tyr Asn Ser Ile Asn Ala Lys
                165                 170                 175

Val His Ala Arg Asp Val Arg Arg Glu Ser Lys Leu Leu Phe Xaa Trp
                180                 185                 190

Gln Met Tyr Gln His Arg Gly Phe Thr Tyr Val Gln His Ile Trp His
            195                 200                 205

Val Pro Asp Arg Thr Met Phe Pro Glu Leu Xaa Cys Asn His Leu Xaa
210                 215                 220

Arg Met Pro Cys Tyr Arg Ser Asn His Arg Val Gly His Trp Lys Gly
225                 230                 235                 240

Pro Asn Arg Ser Ser Ile Gln Lys Cys Xaa Ala Ser Gly Ser Cys His
                245                 250                 255

Gly Tyr Pro Pro Trp Ser Asn Pro Tyr Thr Thr Cys Gln His Asn Xaa
                260                 265                 270

Asp Ser Ile Asn Xaa Xaa Arg His Tyr Pro Leu Ser Trp Lys Lys Asp
            275                 280                 285

Xaa Gly Gly Lys Ser Glu Glu Arg Glu Thr Pro Tyr Leu Xaa Gly Tyr
290                 295                 300

Gln Lys Thr Leu Xaa Xaa Ala Cys Xaa Arg Val Ser Ser Lys Gly Asn
305                 310                 315                 320

Asn Ser Cys Leu Leu Leu Xaa Gly Met Xaa His Leu Lys Asn Ala Xaa
                325                 330                 335

Gly Arg Leu Cys Ser Ser Cys His Xaa Cys Leu Val Tyr Arg Val His
            340                 345                 350

Trp Xaa Leu Xaa Phe Arg Val Xaa Leu Gln Pro His Gly Arg Arg His
            355                 360                 365

Met Pro Cys Xaa Pro Xaa Pro Tyr Phe His His Gly Cys Ser Cys Val
            370                 375                 380

Arg Gly Phe Ser Asn Ser Xaa Arg Pro Ala Xaa Gly Pro His Arg Pro
385                 390                 395                 400

Trp Glu Ser Trp His Ile Leu Leu Cys Arg Arg Glu Leu Tyr Pro Phe
                405                 410                 415

Gly Tyr Gly Ser Xaa Met Gln His Cys Xaa Ser Leu Arg Arg Ser Gln
                420                 425                 430

Gly Met Val Trp Phe Val Ile Asn Arg Ser Ser Asn Tyr Ser Gly His
            435                 440                 445

Leu Ser His Pro Thr Trp Val Thr Cys Asp Arg Ser Lys Phe Gly Arg
            450                 455                 460

Val Gly Xaa Ser Leu Phe Tyr Gly Gln Pro Arg Thr Phe Ile Cys Gln
465                 470                 475                 480
```

```
Tyr Cys Lys Lys Asn Cys Xaa Gln Leu Cys Phe Val Asp Cys Ser Pro
                485                 490                 495

Thr Thr Thr Val Ser Ser Val Trp Leu Cys Cys Ser Gln Xaa Arg Thr
            500                 505                 510

Thr Val Ala Gly Ser Pro Ala Trp Glu Lys Thr Leu Trp Gly Ser Val
            515                 520                 525

Ala Leu Gly Arg Leu Xaa Arg Leu Ser Trp Pro Arg Ala Gln Arg Gly
            530                 535                 540

Asp Gln Ile Pro Asn Val Leu His Xaa Ser Gln Tyr Phe Trp Asp Ser
545                 550                 555                 560

Arg Thr Arg Cys Trp Arg Trp Ser Gly Tyr Gly Leu Ser Ser His Xaa
                565                 570                 575

His Phe Trp Arg His Leu Cys Ala Ala Leu Leu Val Tyr Tyr Ile Ser
            580                 585                 590

Pro Tyr Arg Cys Tyr Cys Arg Pro Ser Gly Xaa Arg Arg Gly Asn Arg
                595                 600                 605

Gly Gly Val Cys Ile Ile His Ser Leu Gly Gly His Gly Cys Cys Asn
            610                 615                 620

Xaa Gln Ala Glu Glu Tyr Asn His His Asn Xaa Ser Phe His Ile Gly
625                 630                 635                 640

Asn Arg Pro Xaa Lys Thr Xaa His Leu Ser Trp Ala Ser Cys Ser Tyr
                645                 650                 655

Asn Pro Cys Tyr His Arg Val Leu Leu Trp Leu Ser His Phe Thr Xaa
                660                 665                 670

Gln Ser Leu Cys Ile Met Arg Val Cys Phe His Cys Gly Tyr Tyr Tyr
            675                 680                 685

Pro Thr Thr Ser Gln Asp Gln Asn Val Pro Val Ile Ile Trp Arg Arg
            690                 695                 700

Asn Cys Val Gln Ala Tyr Arg Arg Xaa Arg Arg Thr Gly Val His Asp
705                 710                 715                 720

Gly Arg Gly Cys Gly Asn Ser Ser Trp Tyr Met Asp Ile Gly Gly Phe
                725                 730                 735

Cys Leu Xaa His Ala Arg Arg Leu Cys Trp Arg Leu Ile His Cys Leu
            740                 745                 750

Leu Asp Ile Xaa Met Leu Asp Gly Xaa Val Ala His Tyr Gly Ser Ala
            755                 760                 765

Cys Trp Phe Ser Leu Leu Arg Val Gln Ser Gly Arg Arg Ser Cys Gly
            770                 775                 780

Arg Leu Val Ser Leu Cys Asn Val Cys Phe Asp Asn Ser Arg Ala Arg
785                 790                 795                 800

Ser Leu Ala Gln Gln Thr Ser Tyr Tyr Ala Cys Xaa Glu Gln His Cys
            805                 810                 815

Met Xaa Xaa Val Leu Tyr Cys His Ser Xaa His Pro Gln Glu Asp Thr
            820                 825                 830

Gly His Ser Gly Gly Ile Tyr Pro Leu Glu Xaa His Ile Ser Leu His
            835                 840                 845

Pro Leu Ala Xaa His Pro Asp Gly Gly Xaa Leu Arg Pro His Cys Leu
            850                 855                 860

Gly Ser Xaa Asp Leu Ala Val Cys Val Gln Phe Leu Cys Asp Leu Leu
865                 870                 875                 880

Xaa Cys Pro Xaa Ser Trp Ser Ser Glu His Gly Xaa His Ser Trp Leu
                885                 890                 895
```

-continued

```
Ser Phe Leu Gln Leu Pro Glu Gly Val Gln Gly Pro Leu Asp Trp Ile
            900                 905                 910
Arg Tyr Ala Pro Ser Thr Leu Ser Met Arg Cys Xaa Thr His Leu Phe
        915                 920                 925
Cys Xaa Glu Trp Phe Cys Lys Thr Leu Gln Arg Thr Gln Asn Leu Phe
930                 935                 940
Lys Leu Leu Glu Arg Gly Cys Ser Ser Gln Arg Xaa Ala Val Trp Val
945                 950                 955                 960
Gly Xaa Thr Gly Pro Asn Xaa Leu Asp Xaa Ser Cys Arg Gln Leu Trp
                965                 970                 975
Arg Xaa Gly Leu Leu Xaa Ile Xaa Glu Ile Gly Arg Ser His Phe Cys
        980                 985                 990
Tyr Ser Ser Ile Leu Ser Lys Cys Leu Phe His Pro Gly Ala Pro Asn
            995                 1000                1005
Leu Glu Ser Cys Ser Gly Arg Gly Pro Arg Thr Gly Ser Xaa Leu Ser
        1010                1015                1020
Arg Xaa Ala Gln Asn Ser Leu Asp Asp Ile Cys Leu Leu Arg Ser
1025                1030                1035                1040
Xaa Arg Xaa Gly Xaa Asn Cys Xaa Ala Ser Leu Pro Arg Xaa Arg Thr
                1045                1050                1055
His Thr Trp Trp Ser His Ala Thr Xaa Phe Ala Xaa Ser Thr Xaa Gly
            1060                1065                1070
Lys Xaa Leu Xaa Phe His Lys Gln His Ser Xaa Xaa Ser Arg Ser
            1075                1080                1085
Val Arg Ser Cys Phe Gln Thr Gly Val Ala Ala Tyr Lys Pro Ile Ala
        1090                1095                1100
Xaa Gly Asn Phe Ser Trp Arg Xaa His His Gln Thr Ala Ser Pro Leu
1105                1110                1115                1120
Pro Asp Arg Arg Gly Ser Gly Lys Lys Ala Pro Val Pro Gly Lys Asn
                1125                1130                1135
Trp Phe Ala Tyr Leu Ala Ser Pro Ser Glu Ile Arg Pro Arg Ser Val
            1140                1145                1150
Met Ser Xaa Lys Pro Ala Thr Lys Xaa Pro Val Arg Arg Ser Phe Xaa
            1155                1160                1165
Pro Pro Phe Phe Thr Thr Cys Ser Xaa Val Gly His Ala Asp Ala Pro
        1170                1175                1180
Val Gly Ser Arg Xaa Val Xaa Pro Phe His Cys Asn Trp Met Cys Asn
1185                1190                1195                1200
Asp Arg Asn Xaa Xaa Xaa Pro Xaa Xaa Phe Thr Gln Leu Pro Ser Gln
                1205                1210                1215
Lys Gly Gly Leu Xaa Met Val Arg Arg Lys Leu Val Asn Asp Tyr Asn
            1220                1225                1230
Arg Phe Gln Leu Arg Tyr Trp Pro Pro Val Pro Xaa Asp Thr Gly Gln
            1235                1240                1245
Gly Phe His Ser Ile Ser His Arg Gln Thr Ala Tyr Lys Lys Glu Val
        1250                1255                1260
Gly Lys Glu Xaa Val Phe Val Gln His Glu Leu His Leu Asp Arg Arg
1265                1270                1275                1280
Asp Xaa Leu Gln Asn Cys Phe Xaa Ser Ser Val Cys Asn Ser Gly His
                1285                1290                1295
His Xaa Trp Phe Pro Gln Thr Lys Ile Ile Gly Val Cys Asp Xaa Ala
            1300                1305                1310
Ala Gly Cys Gly Ala Xaa Lys Thr Lys Ser His Tyr Xaa Xaa Thr Thr
```

-continued

```
                1315                1320                    1325
Ser Val Pro Pro Ile Ile Pro Gln Ala Ser Glu Ile Gly Xaa Gly Lys
        1330                1335                1340

Ser Phe Lys Ser Cys Arg Cys His Val Gly Leu Xaa Xaa Ser Ser Ser
1345                1350                1355                1360

Ser His Ala Leu Xaa Val Cys Xaa Val Pro His His Trp Pro Ser Gly
            1365                1370                1375

His Xaa Cys Ser Gly Leu Ala Glu Val Cys Arg Gly Arg Xaa Asp Thr
        1380                1385                1390

Glu Ser Leu Ser Ala Asn Cys Asp Ser Ser Lys Gly Gly Gly Leu Arg
        1395                1400                1405

Glu Asp Pro Pro Glu Thr Asn Lys Glu Thr Pro Lys Ala Tyr
        1410                1415                1420

(2) INFORMATION FOR SEQ ID NO:83:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:83:

Ala His Pro Thr Gly Ser Ile His Pro Ile Thr Val Asp Ala Ala Asn
1               5                   10                  15

Asp Gln Asp Ile Tyr Gln Pro Pro Cys Gly Ala Gly Ser Leu Thr Arg
            20                  25                  30

Cys Ser Cys Gly Glu Thr Lys Gly Tyr Leu Val Thr Arg Leu Gly Ser
        35                  40                  45

Leu Val Glu Val Asn Lys Ser Asp Asp Pro Tyr Trp Cys Val Cys Gly
    50                  55                  60

Ala Leu Pro Met Ala Val Ala Lys Gly Ser Ser Gly Ala Pro Ile Leu
65                  70                  75                  80

Cys Ser Ser Gly His Val Ile Gly Met Phe Thr Ala Ala Arg Asn Ser
                85                  90                  95

Gly Gly Ser Val Gly Gln Ile Arg Val Arg Pro Leu Val Cys Ala Gly
            100                 105                 110

Tyr His Pro Gln Tyr Thr Ala His Ala Thr Leu Asp Thr Lys Pro Thr
        115                 120                 125

Val Pro Asn Glu Tyr Ser Val Gln Ile Leu Ile Ala Pro Thr Gly Ser
    130                 135                 140

Gly Lys Ser Thr Lys Leu Pro Leu Ser Tyr Met Gln Xaa Lys Xaa Glu
145                 150                 155                 160

Val Leu Val Leu Asn Pro Ser Val Ala Thr Thr Ala Ser Met Pro Lys
                165                 170                 175

Tyr Met His Ala Thr Tyr Gly Val Asn Pro Asn Cys Tyr Phe Asn Gly
            180                 185                 190

Lys Cys Thr Asn Thr Gly Ala Ser Leu Thr Tyr Ser Thr Tyr Gly Met
        195                 200                 205

Tyr Leu Thr Gly Arg Cys Ser Arg Asn Tyr Asp Val Ile Ile Cys Asp
    210                 215                 220

Glu Cys His Ala Thr Asp Arg Thr Thr Val Leu Gly Ile Gly Lys Val
225                 230                 235                 240

Leu Thr Glu Ala Pro Ser Lys Asn Val Arg Leu Val Val Leu Ala Thr
```

-continued

```
                245                 250                 255
Ala Thr Pro Pro Gly Val Ile Pro Thr Pro His Ala Asn Ile Thr Glu
                260                 265                 270

Ile Gln Leu Thr Asp Glu Gly Thr Ile Pro Phe His Gly Lys Lys Ile
            275                 280                 285

Lys Glu Glu Asn Leu Lys Lys Gly Arg His Leu Ile Phe Glu Ala Thr
        290                 295                 300

Lys Lys His Cys Asp Glu Leu Ala Asn Glu Leu Ala Arg Lys Gly Ile
305                 310                 315                 320

Thr Ala Val Ser Tyr Tyr Arg Gly Cys Asp Ile Ser Lys Met Pro Glu
                325                 330                 335

Gly Asp Cys Val Val Ala Thr Asp Ala Leu Cys Thr Gly Tyr Thr
                340                 345                 350

Gly Asp Phe Asp Ser Val Tyr Asp Cys Ser Leu Met Val Glu Gly Thr
            355                 360                 365

Cys His Val Asp Leu Asp Pro Thr Phe Thr Met Gly Val Arg Val Cys
        370                 375                 380

Gly Val Ser Ala Ile Val Lys Gly Gln Arg Arg Gly Arg Thr Gly Arg
385                 390                 395                 400

Gly Arg Ala Gly Ile Tyr Tyr Tyr Val Asp Gly Ser Cys Thr Pro Ser
                405                 410                 415

Gly Met Val Pro Glu Cys Asn Ile Val Glu Ala Phe Asp Ala Ala Lys
            420                 425                 430

Ala Trp Tyr Gly Leu Ser Ser Thr Glu Ala Gln Thr Ile Leu Asp Thr
        435                 440                 445

Tyr Arg Thr Gln Pro Gly Leu Pro Ala Ile Gly Ala Asn Leu Asp Glu
    450                 455                 460

Trp Ala Asp Leu Phe Ser Met Val Asn Pro Glu Pro Ser Phe Val Asn
465                 470                 475                 480

Thr Ala Lys Arg Thr Ala Asp Asn Tyr Val Leu Leu Thr Ala Ala Gln
                485                 490                 495

Leu Gln Leu Cys His Gln Tyr Gly Tyr Ala Ala Pro Asn Asp Ala Pro
            500                 505                 510

Arg Trp Gln Gly Ala Arg Leu Gly Lys Lys Pro Cys Gly Val Leu Trp
        515                 520                 525

Arg Leu Asp Gly Cys Asp Ala Cys Pro Gly Pro Glu Pro Ser Glu Val
    530                 535                 540

Thr Arg Tyr Gln Met Cys Phe Thr Glu Val Asn Thr Ser Gly Thr Ala
545                 550                 555                 560

Ala Leu Ala Val Gly Val Gly Val Ala Met Ala Tyr Leu Ala Ile Asp
                565                 570                 575

Thr Phe Gly Ala Thr Cys Val Arg Arg Cys Trp Ser Ile Thr Ser Val
            580                 585                 590

Pro Thr Gly Ala Thr Val Ala Pro Val Val Asp Glu Glu Ile Val
        595                 600                 605

Glu Glu Cys Ala Ser Phe Ile Pro Leu Glu Ala Met Val Ala Ala Ile
    610                 615                 620

Asp Lys Leu Lys Ser Thr Ile Thr Thr Ser Pro Phe Thr Leu Glu
625                 630                 635                 640

Thr Ala Leu Glu Lys Leu Asn Thr Phe Leu Gly Pro His Ala Ala Thr
                645                 650                 655

Ile Leu Ala Ile Ile Glu Tyr Cys Cys Gly Leu Val Thr Leu Pro Asp
            660                 665                 670
```

-continued

```
Asn Pro Phe Ala Ser Cys Val Phe Ala Phe Ile Ala Gly Ile Thr Thr
        675                 680                 685

Pro Leu Pro His Lys Ile Lys Met Phe Leu Ser Leu Phe Gly Gly Ala
    690                 695                 700

Ile Ala Ser Lys Leu Thr Asp Ala Arg Xaa Ala Leu Ala Phe Met Met
705                 710                 715                 720

Ala Gly Ala Xaa Gly Thr Ala Leu Gly Thr Trp Thr Ser Val Gly Phe
            725                 730                 735

Val Phe Asp Met Leu Gly Gly Tyr Ala Gly Ala Ser Ser Thr Ala Cys
                740                 745                 750

Leu Thr Phe Lys Cys Leu Met Gly Glu Trp Xaa Thr Met Asp Gln Leu
        755                 760                 765

Ala Gly Leu Val Tyr Ser Ala Phe Asn Pro Ala Ala Gly Val Val Gly
    770                 775                 780

Val Leu Ser Ala Cys Ala Met Phe Ala Leu Thr Thr Ala Gly Pro Asp
785                 790                 795                 800

His Trp Pro Asn Arg Leu Leu Thr Met Leu Ala Arg Ser Asn Thr Val
            805                 810                 815

Cys Xaa Glu Tyr Phe Ile Ala Thr Arg Asp Ile Arg Arg Lys Ile Leu
                820                 825                 830

Gly Ile Leu Glu Ala Ser Thr Pro Trp Ser Xaa Ile Ser Ala Cys Ile
        835                 840                 845

Arg Trp Leu His Thr Pro Thr Glu Asp Asp Cys Gly Leu Ile Ala Trp
    850                 855                 860

Gly Leu Xaa Ile Trp Gln Tyr Val Cys Asn Phe Phe Val Ile Cys Phe
865                 870                 875                 880

Asn Val Leu Lys Ala Gly Val Gln Ser Met Val Asn Ile Pro Gly Cys
            885                 890                 895

Pro Phe Tyr Ser Cys Gln Lys Gly Tyr Lys Gly Pro Trp Ile Gly Ser
                900                 905                 910

Gly Met Leu Gln Ala Arg Cys Pro Cys Gly Ala Glu Leu Ile Phe Ser
        915                 920                 925

Val Glu Asn Gly Phe Ala Lys Leu Tyr Lys Gly Pro Arg Thr Cys Ser
    930                 935                 940

Asn Tyr Trp Arg Gly Ala Val Pro Val Asn Ala Arg Leu Cys Gly Ser
945                 950                 955                 960

Ala Arg Pro Asp Pro Thr Asp Trp Thr Ser Leu Val Val Asn Tyr Gly
            965                 970                 975

Val Arg Asp Tyr Cys Lys Tyr Glu Lys Leu Gly Asp His Ile Phe Val
                980                 985                 990

Thr Ala Val Ser Ser Pro Asn Val Cys Phe Thr Gln Val Pro Pro Thr
        995                 1000                1005

Leu Arg Ala Ala Val Ala Val Asp Arg Val Gln Val Gln Xaa Tyr Leu
    1010                1015                1020

Gly Glu Pro Lys Thr Pro Trp Thr Thr Ser Ala Cys Cys Tyr Gly Pro
1025                1030                1035                1040

Asp Gly Lys Gly Lys Thr Val Lys Leu Pro Phe Arg Val Asp Gly His
            1045                1050                1055

Thr Pro Gly Gly Arg Met Gln Leu Asn Leu Arg Asp Arg Leu Glu Ala
                1060                1065                1070

Asn Asp Cys Asn Ser Ile Asn Asn Thr Pro Ser Asp Glu Ala Ala Val
        1075                1080                1085
```

```
Ser Ala Leu Val Phe Lys Gln Glu Leu Arg Arg Thr Asn Gln Leu Leu
    1090                1095                1100

Glu Ala Ile Ser Ala Gly Val Asp Thr Thr Lys Leu Pro Ala Pro Ser
1105                1110                1115                1120

Gln Ile Glu Glu Val Val Arg Lys Arg Gln Phe Arg Ala Arg Thr
            1125                1130                1135

Gly Ser Leu Thr Leu Pro Pro Pro Arg Ser Val Pro Gly Val Ser
        1140                1145                1150

Cys Pro Glu Ser Leu Gln Arg Ser Asp Pro Leu Glu Gly Pro Ser Xaa
        1155                1160                1165

Leu Pro Ser Ser Pro Pro Val Leu Gln Leu Ala Met Pro Met Pro Leu
    1170                1175                1180

Leu Gly Ala Gly Glu Cys Asn Pro Phe Thr Ala Ile Gly Cys Ala Met
1185                1190                1195                1200

Thr Glu Thr Xaa Gly Xaa Pro Xaa Xaa Leu Pro Ser Tyr Pro Pro Lys
            1205                1210                1215

Lys Glu Val Ser Glu Trp Ser Asp Glu Ser Trp Ser Thr Thr Thr Thr
        1220                1225                1230

Ala Ser Ser Tyr Val Thr Gly Pro Pro Tyr Pro Lys Ile Arg Gly Lys
        1235                1240                1245

Asp Ser Thr Gln Ser Ala Thr Ala Lys Arg Pro Thr Lys Lys Leu
        1250                1255                1260

Gly Lys Ser Glu Phe Ser Cys Ser Met Ser Tyr Thr Trp Thr Asp Val
1265                1270                1275                1280

Ile Ser Phe Lys Thr Ala Ser Lys Val Leu Ser Ala Thr Arg Ala Ile
            1285                1290                1295

Thr Ser Gly Phe Leu Lys Gln Arg Ser Leu Val Tyr Val Thr Glu Pro
        1300                1305                1310

Arg Asp Ala Glu Leu Arg Lys Gln Lys Val Thr Ile Asn Arg Gln Pro
        1315                1320                1325

Leu Phe Pro Pro Ser Tyr His Lys Gln Val Arg Leu Ala Lys Glu Lys
    1330                1335                1340

Ala Ser Lys Val Val Gly Val Met Trp Asp Tyr Asp Glu Val Ala Ala
1345                1350                1355                1360

His Thr Pro Ser Lys Ser Ala Lys Ser His Ile Thr Gly Leu Arg Gly
            1365                1370                1375

Thr Asp Val Leu Asp Leu Gln Lys Cys Val Glu Ala Gly Glu Ile Pro
        1380                1385                1390

Ser His Tyr Arg Gln Thr Val Ile Val Pro Lys Glu Glu Val Phe Val
        1395                1400                1405

Lys Thr Pro Gln Lys Pro Thr Lys Lys Pro Pro Arg Leu Ile
    1410                1415                1420
```

(2) INFORMATION FOR SEQ ID NO:84:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:84:

```
Asp Lys Pro Trp Gly Phe Leu Cys Trp Phe Leu Gly Gly Leu His Glu
1               5                   10                  15
```

-continued

```
Asp Leu Leu Leu Trp Asn Tyr His Ser Leu Pro Ile Met Thr Arg Tyr
        20                  25                  30

Leu Thr Cys Leu Asp Thr Leu Leu Gln Val Gln Asn Ile Ser Ala Pro
        35                  40                  45

Lys Ala Ser Asp Val Gly Leu Ser Arg Leu Arg Gly Arg Val Ser Cys
    50                  55                  60

Tyr Phe Ile Ile Val Pro His Asp Thr Asp Asn Phe Xaa Ser Phe Phe
65                  70                  75                  80

Leu Ser Gln Ser His Leu Leu Val Val Xaa Trp Gly Glu Gln Arg Leu
                85                  90                  95

Ser Ile Asn Ser Asp Phe Leu Phe Ser Lys Leu Arg Ile Pro Arg Leu
            100                 105                 110

Ser His Ile His Gln Xaa Ser Leu Phe Glu Glu Thr Thr Ser Asp Gly
        115                 120                 125

Pro Ser Cys Arg Gln Asn Phe Arg Ser Ser Phe Glu Ala Asn His Val
    130                 135                 140

Gly Pro Ser Val Ala His Ala Ala Arg Lys Leu Thr Leu Ser Gln Leu
145                 150                 155                 160

Leu Phe Cys Arg Pro Phe Gly Gly Gly Xaa Leu Ser Gly Ile Leu Ala
                165                 170                 175

Pro Tyr Leu Arg Val Arg Gly Ala Ser Asn Val Ala Gly Ser Gly Cys
            180                 185                 190

Ser Arg Xaa Pro Thr Phe Val Xaa Pro Phe Arg Asp Leu Leu Phe Gly
        195                 200                 205

Arg Val Thr Gly Xaa Ile Xaa Xaa Xaa Ser Xaa Cys Phe Gly His Cys
    210                 215                 220

Thr Ser Asn Cys Ser Glu Arg Val Thr Leu Thr Cys Ser Gln Gln Gly
225                 230                 235                 240

His Arg His Gly Gln Leu Xaa Asn Arg Trp Xaa Arg Arg Glu Xaa Xaa
                245                 250                 255

Arg Thr Phe Xaa Arg Val Thr Ser Leu Gln Ala Phe Arg Thr Xaa His
            260                 265                 270

Ser Trp Asp Gly Ser Arg Arg Gly Arg Gln Gly Lys Arg Thr Ser Ser
       275                  280                 285

Cys Pro Glu Leu Ala Leu Ser Tyr His Tyr Leu Phe Asp Leu Gly Gly
    290                 295                 300

Gly Trp Gln Phe Gly Gly Val Asn Ala Ser Xaa Asn Cys Leu Lys Gln
305                 310                 315                 320

Leu Val Cys Thr Pro Gln Leu Leu Phe Glu Asn Lys Ser Gly His Cys
                325                 330                 335

Gly Phe Ile Thr Arg Ser Val Val Tyr Gly Ile Thr Val Ile Cys Leu
            340                 345                 350

Lys Ser Ile Thr Gln Ile Lys Leu His Ala Thr Thr Arg Cys Val Ser
        355                 360                 365

Val Asn Ala Glu Gly Lys Leu Asn Ser Phe Thr Leu Thr Val Arg Thr
    370                 375                 380

Val Thr Ala Ser Arg Cys Arg Pro Arg Ser Phe Gly Leu Thr Xaa Ile
385                 390                 395                 400

Thr Leu Asn Leu Tyr Ala Val His Gly His Cys Ser Ser Gln Gly Trp
                405                 410                 415

Gly His Leu Gly Glu Thr Asp Ile Trp Arg Gly Tyr Cys Cys Asn Lys
            420                 425                 430

Asn Val Ile Ser Gln Phe Leu Ile Phe Thr Val Val Pro Asn Ala Ile
```

-continued

```
              435                 440                 445
Ile Asp Asp Lys Thr Ser Pro Ile Ser Trp Val Arg Ser Ser Arg Pro
450                 455                 460
Thr Gln Pro Ser Val Asp Trp Asn Ser Pro Ser Pro Val Ile Xaa Thr
465                 470                 475                 480
Ser Ser Gly Ser Phe Val Lys Phe Cys Lys Thr Ile Leu Asn Arg Lys
                485                 490                 495
Asp Glu Phe Ser Thr Ala Trp Thr Ala Cys Leu Glu His Thr Xaa Ser
                500                 505                 510
Asn Pro Gly Ala Leu Val Pro Leu Leu Ala Ala Val Glu Arg Thr Thr
                515                 520                 525
Arg Asn Val Asn His Ala Leu Asn Ser Ser Phe Lys Asp Ile Lys Ala
530                 535                 540
Asn His Lys Glu Ile Ala His Ile Leu Pro Asn Leu Xaa Thr Pro Ser
545                 550                 555                 560
Asn Glu Ala Ala Ile Ile Leu Arg Arg Gly Val Xaa Pro Thr Asp Ala
                565                 570                 575
Ser Xaa Tyr Asp Thr Pro Gly Gly Arg Cys Leu Gln Asn Ala Gln Tyr
                580                 585                 590
Leu Pro Ala Asp Val Thr Ser Gly Asn Lys Val Leu Xaa Thr Tyr Ser
                595                 600                 605
Val Ala Pro Ser Lys His Ser Lys Lys Ser Val Gly Pro Val Ile Trp
610                 615                 620
Pro Cys Cys Cys Gln Ser Lys His Cys Thr Ser Xaa Gln Asp Ala His
625                 630                 635                 640
Asn Ser Cys Gly Arg Ile Glu Arg Gly Val Asp Xaa Thr Ser Lys Leu
                645                 650                 655
Ile His Ser Xaa Pro Leu Thr His Gln Ala Phe Lys Cys Gln Ala Ser
                660                 665                 670
Ser Gly Xaa Gly Ala Ser Ile Ala Ala Xaa His Val Lys Asp Lys Thr
                675                 680                 685
His Arg Cys Pro Cys Thr Lys Ser Cys Ser Xaa Ser Pro Gly His His
                690                 695                 700
Glu Arg Gln Cys Xaa Ser Ser Val Cys Lys Leu Gly Arg Asn Cys Ala
705                 710                 715                 720
Ser Lys Xaa Xaa Gln Glu His Phe Asp Leu Val Arg Xaa Trp Gly Ser
                725                 730                 735
Asn Thr Arg Asn Glu Ser Lys His Ala Xaa Cys Lys Gly Ile Val Arg
                740                 745                 750
Xaa Ser Asp Xaa Ala Thr Ala Ile Leu Tyr Asp Ser Lys Asp Cys Ser
                755                 760                 765
Cys Met Arg Pro Lys Lys Gly Val Lys Phe Lys Gly Gly Phe Gln
770                 775                 780
Cys Glu Arg Thr Ser Cys Gly Asp Cys Thr Leu Gln Leu Val Asn Cys
785                 790                 795                 800
Ser Asn His Gly Leu Gln Gly Asn Glu Xaa Cys Thr Leu Leu His Asp
                805                 810                 815
Phe Leu Phe Val Asn His Trp Gly Asp Ser Ser Thr Gly Arg Asp Xaa
                820                 825                 830
Cys Asn Arg Pro Ala Thr Pro His Thr Ser Gly Ala Lys Ser Val Asn
                835                 840                 845
Gly Xaa Ile Ser His Ser His Ser Asn Ala Asn Ser Glu Cys Gly Cys
                850                 855                 860
```

-continued

```
Pro Arg Ser Ile Asp Phe Ser Glu Ala His Leu Val Ser Gly His Leu
865                 870                 875                 880

Ala Gly Leu Trp Ala Arg Thr Gly Val Thr Ala Val Gln Ala Pro Gln
            885                 890                 895

Asn Pro Thr Arg Phe Phe Pro Lys Pro Gly Ser Leu Pro Pro Trp Cys
        900                 905                 910

Val Ile Gly Ser Ser Ile Ala Ile Leu Met Thr Gln Leu Xaa Leu Gly
    915                 920                 925

Cys Ser Gln Gln Asn Ile Ile Val Ser Ser Phe Cys Ser Ile Asp
930                 935                 940

Lys Xaa Arg Phe Gly Val Asp His Arg Lys Glu Ile Ser Pro Leu Val
945                 950                 955                 960

Gln Ile Cys Ser Tyr Arg Arg Xaa Pro Arg Leu Gly Ala Ile Gly Val
                965                 970                 975

Gln Asn Ser Leu Ser Phe Cys Xaa Xaa Gln Thr Ile Pro Cys Leu Gly
            980                 985                 990

Cys Val Glu Gly Phe Asn Asn Val Ala Phe Arg Asn His Thr Arg Arg
        995                 1000                1005

Gly Thr Thr Pro Val Tyr Ile Val Val Tyr Ala Ser Ser Pro Thr Ala
    1010                1015                1020

Cys Ala Ala Pro Thr Leu Ala Phe Asn Tyr Cys Xaa Asn Pro Ala His
1025                1030                1035                1040

Thr Asn Thr His Gly Glu Ser Arg Val Lys Val Asn Met Ala Cys Ala
                1045                1050                1055

Phe Tyr His Glu Ala Ala Val Ile His Gly Ile Lys Val Thr Ser Val
            1060                1065                1070

Pro Cys Thr Gln Gly Ile Ser Gly Asn Tyr Tyr Thr Val Ala Leu Arg
        1075                1080                1085

His Phe Xaa Asp Val Thr Ser Pro Ile Val Arg Asp Ser Cys Tyr Ser
    1090                1095                1100

Leu Ser Ser Xaa Leu Val Ser Lys Leu Ile Thr Val Phe Phe Gly Ser
1105                1110                1115                1120

Leu Lys Asp Lys Val Ser Pro Phe Leu Gln Ile Phe Leu Leu Asn Leu
                1125                1130                1135

Phe Ser Met Lys Gly Asp Ser Ala Phe Ile Xaa Xaa Leu Asn Leu Ser
            1140                1145                1150

Tyr Val Gly Met Trp Cys Arg Asp Tyr Ser Arg Gly Gly Ser Arg Gly
        1155                1160                1165

Lys Asn His Xaa Pro Asn Ile Phe Gly Trp Ser Phe Gly Xaa Asp Leu
    1170                1175                1180

Ser Asn Ala Gln His Gly Gly Ser Ile Gly Ser Met Ala Phe Val Thr
1185                1190                1195                1200

Asn Asp Tyr Ile Ile Val Pro Gly Thr Ser Ser Gly Gln Val His Ala
                1205                1210                1215

Ile Cys Ala Val Arg Lys Xaa Ser Pro Cys Val Gly Thr Phe Ala Ile
            1220                1225                1230

Lys Ile Ala Ile Trp Ile His Ala Val Arg Arg Val His Val Leu Trp
        1235                1240                1245

His Xaa Cys Cys Cys Ser His Thr Gly Ile Xaa Asp Gln Asp Leu Xaa
    1250                1255                1260

Leu Xaa Leu His Val Arg Lys Trp Xaa Phe Gly Xaa Leu Ala Ala Ala
1265                1270                1275                1280
```

```
Ser Gly Gly Asn Xaa Asn Leu His Xaa Ile Leu Val Arg His Ser Arg
            1285                1290                1295

Phe Cys Ile Lys Ser Gly Met Cys Cys Val Leu Gly Met Val Ser Ser
        1300                1305                1310

Thr His Gln Arg Pro Asn Pro Asn Leu Ala Asp Xaa Thr Ala Arg Ile
        1315                1320                1325

Ser Ser Ser Gly Glu His Pro Asn Asn Met Pro Gly Gly Ala Gln Asn
        1330                1335                1340

Arg Gly Thr Xaa Arg Thr Leu Gly Asn Ser His Gly Lys Gly Pro Ala
1345                1350                1355                1360

His Thr Pro Ile Arg Val Ile Gly Phe Val Asp Leu Asn Gln Xaa Pro
                1365                1370                1375

Gln Ser Cys Tyr Gln Ile Pro Leu Gly Leu Pro Ala Arg Ala Pro Ser
        1380                1385                1390

Lys Gly Pro Ser Ser Thr Trp Trp Leu Ile Asp Val Leu Val Ile Ser
        1395                1400                1405

Arg Val Asn Gly Tyr Trp Val Tyr Gly Ala Cys Gly Met Ser
        1410                1415                1420

(2) INFORMATION FOR SEQ ID NO:85:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:85:

Ile Ser Leu Gly Gly Phe Phe Val Gly Phe Trp Gly Val Phe Thr Lys
1               5                   10                  15

Thr Ser Ser Phe Gly Thr Ile Thr Val Cys Arg Xaa Xaa Leu Gly Ile
            20                  25                  30

Ser Pro Ala Ser Thr His Phe Cys Lys Ser Arg Thr Ser Val Pro Arg
        35                  40                  45

Arg Pro Val Met Trp Asp Leu Ala Asp Leu Glu Gly Val Xaa Ala Ala
50                  55                  60

Thr Ser Ser Xaa Ser His Met Thr Pro Thr Thr Phe Glu Ala Phe Ser
65                  70                  75                  80

Leu Ala Asn Leu Thr Cys Leu Trp Tyr Asp Gly Gly Asn Arg Gly Cys
                85                  90                  95

Leu Leu Ile Val Thr Phe Cys Phe Leu Ser Ser Ala Ser Arg Gly Ser
            100                 105                 110

Val Thr Tyr Thr Asn Asp Leu Cys Leu Arg Lys Pro Leu Val Met Ala
        115                 120                 125

Arg Val Ala Asp Arg Thr Leu Glu Ala Val Leu Lys Leu Ile Thr Ser
    130                 135                 140

Val Gln Val Xaa Leu Met Leu His Glu Asn Ser Leu Phe Pro Asn Phe
145                 150                 155                 160

Phe Phe Val Gly Arg Leu Ala Val Ala Asp Xaa Val Glu Ser Leu Pro
                165                 170                 175

Arg Ile Leu Gly Tyr Gly Gly Pro Val Thr Xaa Leu Glu Ala Val Val
            180                 185                 190

Val Val Asp Gln Leu Ser Ser Asp His Ser Glu Thr Ser Phe Leu Gly
        195                 200                 205
```

-continued

```
Gly Xaa Leu Gly Lys Xaa Xaa Gly Xaa Pro Xaa Val Ser Val Ile Ala
    210                 215                 220

His Pro Ile Ala Val Lys Gly Leu His Ser Pro Ala Pro Asn Arg Gly
225                 230                 235                 240

Ile Gly Met Ala Asn Cys Arg Thr Gly Gly Glu Gly Arg Xaa Glu
                245                 250                 255

Gly Pro Ser Asn Gly Ser Leu Arg Cys Arg Leu Ser Gly His Asp Thr
                260                 265                 270

Pro Gly Thr Asp Leu Gly Gly Gly Lys Val Ser Glu Pro Val Leu
            275                 280                 285

Ala Arg Asn Trp Arg Phe Leu Thr Thr Thr Ser Ser Ile Trp Glu Gly
    290                 295                 300

Ala Gly Ser Leu Val Val Ser Thr Pro Ala Glu Ile Ala Ser Ser Asn
305                 310                 315                 320

Trp Phe Val Arg Arg Asn Ser Cys Leu Lys Thr Arg Ala Asp Thr Ala
                325                 330                 335

Ala Ser Ser Leu Gly Val Leu Phe Met Glu Leu Gln Ser Phe Ala Ser
                340                 345                 350

Ser Arg Ser Arg Lys Leu Ser Cys Met Arg Pro Pro Gly Val Cys Pro
    355                 360                 365

Ser Thr Arg Lys Gly Ser Leu Thr Val Leu Pro Leu Pro Ser Gly Pro
370                 375                 380

Xaa Gln Gln Ala Asp Val Val Gln Gly Val Leu Gly Ser Pro Arg Xaa
385                 390                 395                 400

Xaa Xaa Thr Cys Thr Arg Ser Thr Ala Thr Ala Leu Lys Val Gly
                405                 410                 415

Gly Thr Trp Val Lys Gln Thr Phe Gly Glu Asp Thr Ala Val Thr Lys
                420                 425                 430

Met Xaa Ser Pro Asn Phe Ser Tyr Leu Gln Xaa Ser Leu Thr Pro Xaa
    435                 440                 445

Leu Thr Thr Arg Leu Val Gln Ser Val Gly Ser Gly Leu Ala Asp Pro
    450                 455                 460

His Ser Leu Ala Leu Thr Gly Thr Ala Pro Leu Gln Xaa Phe Glu Gln
465                 470                 475                 480

Val Leu Gly Pro Leu Xaa Ser Phe Ala Lys Pro Phe Ser Thr Glu Lys
                485                 490                 495

Met Ser Ser Ala Pro His Gly Gln Arg Ala Trp Ser Ile Pro Asp Pro
            500                 505                 510

Ile Gln Gly Pro Leu Tyr Pro Phe Trp Gln Leu Xaa Lys Gly Gln Pro
        515                 520                 525

Gly Met Leu Thr Met Leu Xaa Thr Pro Ala Leu Arg Thr Leu Lys Gln
    530                 535                 540

Ile Thr Lys Lys Leu His Thr Tyr Cys Gln Ile Xaa Arg Pro Gln Ala
545                 550                 555                 560

Met Arg Pro Gln Ser Ser Ser Val Gly Val Xaa Ser Gln Arg Met Gln
                565                 570                 575

Ala Asp Met Xaa Leu Gln Gly Val Asp Ala Ser Arg Met Pro Ser Ile
                580                 585                 590

Phe Leu Arg Met Ser Arg Val Ala Ile Lys Tyr Ser Xaa His Thr Val
            595                 600                 605

Leu Leu Leu Ala Ser Ile Val Arg Ser Leu Leu Gly Gln Xaa Ser Gly
610                 615                 620

Pro Ala Val Val Lys Ala Asn Ile Ala Gln Ala Asp Lys Thr Pro Thr
```

-continued

```
                625                 630                 635                 640
Thr Pro Ala Ala Gly Leu Asn Ala Glu Xaa Thr Lys Pro Ala Ser Xaa
                        645                 650                 655
Ser Ile Val Xaa His Ser Pro Ile Lys His Leu Asn Val Lys Gln Ala
                660                 665                 670
Val Asp Glu Ala Pro Ala Xaa Pro Pro Ser Met Ser Lys Thr Lys Pro
                675                 680                 685
Thr Asp Val His Val Pro Arg Ala Val Pro Xaa Ala Pro Ala Ile Met
            690                 695                 700
Asn Ala Ser Ala Xaa Leu Ala Ser Val Ser Leu Asp Ala Ile Ala Pro
705                 710                 715                 720
Pro Asn Asn Asp Arg Asn Ile Leu Ile Leu Xaa Gly Ser Gly Val Val
                        725                 730                 735
Ile Pro Ala Met Lys Ala Asn Thr His Asp Ala Lys Gly Leu Ser Gly
                740                 745                 750
Lys Val Thr Lys Pro Gln Gln Tyr Ser Met Ile Ala Arg Ile Val Ala
                755                 760                 765
Ala Xaa Gly Pro Arg Lys Val Leu Ser Phe Ser Arg Ala Val Ser Asn
        770                 775                 780
Val Lys Gly Leu Val Val Ile Val Leu Phe Ser Leu Ser Ile Ala
785                 790                 795                 800
Ala Thr Met Ala Ser Lys Gly Met Asn Asp Ala His Ser Ser Thr Ile
                        805                 810                 815
Ser Ser Ser Ser Thr Thr Gly Ala Thr Val Ala Pro Val Gly Thr Asp
                820                 825                 830
Val Ile Asp Gln Gln Arg Arg Thr Gln Val Ala Pro Lys Val Ser Met
            835                 840                 845
Ala Arg Xaa Ala Ile Ala Thr Pro Thr Pro Thr Ala Ser Ala Ala Val
850                 855                 860
Pro Glu Val Leu Thr Ser Val Lys His Ile Trp Tyr Leu Val Thr Ser
865                 870                 875                 880
Leu Gly Ser Gly Pro Gly Gln Ala Ser Gln Pro Ser Lys Arg His Arg
                        885                 890                 895
Thr Pro Gln Gly Phe Phe Pro Ser Arg Ala Pro Cys His Arg Gly Ala
                900                 905                 910
Ser Leu Gly Ala Ala Xaa Pro Tyr Xaa Xaa His Ser Cys Ser Trp Ala
                915                 920                 925
Ala Val Asn Lys Thr Xaa Leu Ser Ala Val Leu Phe Ala Val Leu Thr
        930                 935                 940
Asn Glu Gly Ser Gly Leu Thr Ile Glu Lys Arg Ser Ala His Ser Ser
945                 950                 955                 960
Lys Phe Ala Pro Ile Ala Gly Asn Pro Gly Trp Val Arg Xaa Val Ser
                        965                 970                 975
Arg Ile Val Xaa Ala Ser Val Asp Asp Lys Pro Tyr His Ala Leu Ala
                980                 985                 990
Ala Ser Lys Ala Ser Thr Met Leu His Ser Gly Thr Ile Pro Glu Gly
            995                 1000                1005
Val Gln Leu Pro Ser Thr Xaa Xaa Tyr Met Pro Ala Leu Pro Arg Pro
        1010                1015                1020
Val Arg Pro Leu Arg Trp Pro Leu Thr Ile Ala Glu Thr Pro His Thr
1025                1030                1035                1040
Arg Thr Pro Met Val Lys Val Gly Ser Arg Ser Thr Trp His Val Pro
                        1045                1050                1055
```

Ser Thr Met Arg Leu Gln Ser Tyr Thr Glu Ser Lys Ser Pro Val Tyr
            1060                1065                1070

Pro Val His Lys Ala Ser Val Ala Thr Thr Gln Ser Pro Ser Gly
        1075                1080                1085

Ile Phe Glu Met Ser His Pro Leu Xaa Xaa Glu Thr Ala Val Ile Pro
            1090                1095                1100

Phe Arg Ala Asn Ser Leu Ala Ser Ser Ser Gln Cys Phe Leu Val Ala
1105                1110                1115                1120

Ser Lys Ile Arg Cys Leu Pro Phe Phe Arg Phe Ser Ser Leu Ile Phe
                1125                1130                1135

Phe Pro Xaa Lys Gly Ile Val Pro Ser Ser Val Asn Xaa Ile Ser Val
            1140                1145                1150

Met Leu Ala Cys Gly Val Gly Ile Thr Pro Gly Gly Val Ala Val Ala
            1155                1160                1165

Arg Thr Thr Ser Leu Thr Phe Leu Asp Gly Ala Ser Val Arg Thr Phe
            1170                1175                1180

Pro Met Pro Asn Thr Val Val Arg Ser Val Ala Trp His Ser Ser Gln
1185                1190                1195                1200

Met Ile Thr Ser Xaa Phe Arg Glu His Arg Pro Val Arg Tyr Met Pro
            1205                1210                1215

Tyr Val Leu Tyr Val Ser Glu Ala Pro Val Leu Val His Leu Pro Leu
            1220                1225                1230

Lys Xaa Gln Phe Gly Phe Thr Pro Tyr Val Ala Cys Met Tyr Phe Gly
            1235                1240                1245

Ile Asp Ala Val Val Ala Thr Leu Gly Phe Arg Thr Lys Thr Ser Xaa
            1250                1255                1260

Phe Xaa Cys Met Xaa Glu Ser Gly Asn Leu Val Asp Leu Pro Leu Pro
1265                1270                1275                1280

Val Gly Ala Ile Lys Ile Cys Thr Glu Tyr Ser Leu Gly Thr Val Gly
            1285                1290                1295

Phe Val Ser Arg Val Ala Cys Ala Val Tyr Trp Gly Trp Tyr Pro Ala
            1300                1305                1310

His Thr Asn Gly Leu Thr Leu Ile Trp Pro Thr Glu Pro Pro Glu Phe
            1315                1320                1325

Leu Ala Ala Val Asn Ile Pro Ile Thr Cys Pro Glu Glu His Arg Ile
            1330                1335                1340

Gly Ala Pro Glu Glu Pro Leu Thr Ala Met Gly Arg Ala Pro His
1345                1350                1355                1360

Thr His Gln Xaa Gly Ser Ser Asp Leu Leu Thr Ser Thr Asn Asp Pro
            1365                1370                1375

Ser Arg Val Thr Arg Tyr Pro Leu Val Ser Pro Gln Glu His Arg Val
            1380                1385                1390

Arg Asp Pro Ala Pro His Gly Gly Xaa Xaa Met Ser Trp Ser Leu Ala
            1395                1400                1405

Ala Ser Thr Val Ile Gly Cys Met Glu Pro Val Gly Xaa Ala
            1410                1415                1420

(2) INFORMATION FOR SEQ ID NO:86:

(i) SEQUENCE CHARACTERISTICS:
        (A) LENGTH: 1422 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:86:

```
Xaa Ala Leu Gly Val Ser Leu Leu Val Ser Gly Gly Ser Ser Arg Arg
1               5                  10                  15

Pro Pro Pro Leu Glu Leu Ser Gln Phe Ala Asp Asn Asp Ser Val Ser
             20                  25                  30

His Leu Pro Arg His Thr Ser Ala Ser Pro Glu His Gln Cys Pro Glu
         35                  40                  45

Gly Gln Xaa Cys Gly Thr Xaa Gln Thr Xaa Arg Ala Cys Glu Leu Leu
     50                  55                  60

Leu His His Ser Pro Thr Xaa His Arg Gln Leu Leu Lys Leu Phe Pro
65                  70                  75                  80

Xaa Pro Ile Ser Leu Ala Cys Gly Met Met Gly Gly Thr Glu Val Val
             85                  90                  95

Tyr Xaa Xaa Xaa Leu Phe Val Phe Xaa Ala Pro His Pro Ala Ala Gln
            100                 105                 110

Ser His Thr Pro Met Ile Phe Val Xaa Gly Asn His Xaa Xaa Trp Pro
            115                 120                 125

Glu Leu Gln Thr Glu Leu Xaa Lys Gln Phe Xaa Ser Xaa Ser Arg Arg
            130                 135                 140

Ser Lys Cys Ser Ser Cys Cys Thr Lys Thr His Ser Phe Pro Thr Ser
145                 150                 155                 160

Phe Leu Xaa Ala Val Trp Arg Trp Leu Ile Glu Trp Asn Pro Cys Pro
            165                 170                 175

Val Ser Xaa Gly Thr Gly Gly Gln Xaa Arg Ser Trp Lys Arg Leu Xaa
            180                 185                 190

Ser Leu Thr Asn Phe Arg Leu Thr Ile Gln Arg Pro Pro Phe Trp Glu
            195                 200                 205

Gly Asn Trp Val Asn Xaa Xaa Gly Leu Xaa Xaa Phe Arg Ser Leu His
            210                 215                 220

Ile Gln Leu Gln Xaa Lys Gly Tyr Thr His Leu Leu Pro Thr Gly Ala
225                 230                 235                 240

Ser Ala Trp Pro Thr Xaa Glu Gln Val Val Lys Lys Gly Gly Leu Lys
            245                 250                 255

Asp Leu Leu Thr Gly His Phe Val Ala Gly Phe Gln Asp Met Thr Leu
            260                 265                 270

Leu Gly Arg Ile Ser Glu Gly Glu Ala Arg Xaa Ala Asn Gln Phe Leu
            275                 280                 285

Pro Gly Thr Gly Ala Phe Leu Pro Leu Pro Leu Arg Ser Gly Arg Gly
            290                 295                 300

Leu Ala Val Trp Trp Cys Gln Arg Gln Leu Lys Leu Pro Gln Ala Ile
305                 310                 315                 320

Gly Leu Tyr Ala Ala Thr Pro Val Xaa Lys Gln Glu Arg Thr Leu Arg
            325                 330                 335

Leu His His Xaa Glu Cys Cys Leu Trp Asn Tyr Ser His Leu Pro Gln
            340                 345                 350

Val Asp His Ala Asn Xaa Val Ala Cys Asp His Gln Val Cys Val Arg
            355                 360                 365

Gln Arg Gly Arg Glu Ala Xaa Gln Phe Tyr Pro Tyr Arg Gln Asp Arg
            370                 375                 380

Asn Ser Lys Gln Met Ser Ser Lys Glu Phe Trp Ala His Leu Asp Asn
385                 390                 395                 400
```

-continued

```
Xaa Glu Pro Val Arg Gly Pro Arg Pro Leu Gln Leu Ser Arg Leu Gly
            405                 410                 415

Ala Pro Gly Xaa Asn Arg His Leu Glu Arg Ile Leu Leu Xaa Gln Lys
            420                 425                 430

Cys Asp Leu Pro Ile Ser His Ile Tyr Ser Ser Pro Xaa Arg His Asn
            435                 440                 445

Xaa Arg Gln Asp Xaa Ser Asn Gln Leu Gly Pro Val Xaa Pro Thr His
            450                 455                 460

Thr Ala Xaa Arg Xaa Leu Glu Gln Pro Leu Ser Ser Asn Leu Asn Lys
465                 470                 475                 480

Phe Trp Val Leu Cys Lys Val Leu Gln Asn His Ser Gln Gln Lys Arg
            485                 490                 495

Xaa Val Gln His Arg Met Asp Ser Val Leu Gly Ala Tyr Leu Ile Gln
            500                 505                 510

Ser Arg Gly Pro Cys Thr Pro Ser Gly Ser Cys Arg Lys Asp Asn Gln
            515                 520                 525

Glu Cys Xaa Pro Cys Ser Glu Leu Gln Leu Xaa Gly His Xaa Ser Lys
            530                 535                 540

Ser Gln Arg Asn Cys Thr His Thr Ala Lys Ser Xaa Asp Pro Lys Gln
545                 550                 555                 560

Xaa Gly Arg Asn His Pro Pro Ser Gly Cys Xaa Ala Asn Gly Cys Lys
            565                 570                 575

Leu Ile Xaa Xaa Ser Arg Gly Xaa Met Pro Pro Glu Cys Pro Val Ser
            580                 585                 590

Ser Cys Gly Cys His Glu Trp Gln Xaa Ser Thr His Tyr Ile Gln Cys
            595                 600                 605

Cys Ser Xaa Gln Ala Xaa Xaa Glu Val Cys Trp Ala Ser Asp Leu Ala
            610                 615                 620

Leu Leu Leu Ser Lys Gln Thr Leu His Lys Leu Thr Arg Arg Pro Gln
625                 630                 635                 640

Leu Leu Arg Pro Asp Xaa Thr Arg Ser Arg Leu Asn Gln Gln Ala Asp
            645                 650                 655

Pro Xaa Xaa Ala Thr His Pro Ser Ser Ile Xaa Met Ser Ser Lys Gln
            660                 665                 670

Trp Met Arg Arg Gln His Ser Arg Leu Ala Cys Gln Arg Gln Asn Pro
            675                 680                 685

Pro Met Ser Met Tyr Gln Glu Leu Phe Pro Gln Pro Arg Pro Ser Xaa
            690                 695                 700

Thr Pro Val Arg Leu Xaa Arg Leu Xaa Ala Trp Thr Gln Leu Arg Leu
705                 710                 715                 720

Gln Ile Met Thr Gly Thr Phe Xaa Ser Cys Glu Val Val Gly Xaa Xaa
            725                 730                 735

Tyr Pro Gln Xaa Lys Gln Thr Arg Met Met Gln Arg Asp Cys Gln Val
            740                 745                 750

Lys Xaa Leu Ser His Ser Asn Thr Leu Xaa Xaa Gln Gly Leu Xaa Leu
            755                 760                 765

His Glu Ala Gln Glu Arg Cys Xaa Val Phe Gln Gly Arg Phe Pro Met
            770                 775                 780

Xaa Lys Asp Xaa Leu Trp Xaa Leu Tyr Ser Ser Ala Cys Gln Leu Gln
785                 790                 795                 800

Gln Pro Trp Pro Pro Arg Glu Xaa Met Met His Thr Pro Pro Arg Phe
            805                 810                 815

Pro Leu Arg Gln Pro Leu Gly Arg Gln Xaa His Arg Xaa Gly Leu Met
```

-continued

```
              820                 825                 830
Xaa Xaa Thr Ser Asn Ala Ala His Lys Trp Arg Gln Lys Cys Gln Trp
        835                 840                 845
Leu Asp Lys Pro Xaa Pro Leu Gln Arg Gln Gln Arg Val Arg Leu Ser
850                 855                 860
Gln Lys Tyr Xaa Leu Gln Xaa Ser Thr Phe Gly Ile Trp Ser Pro Arg
865                 870                 875                 880
Trp Ala Leu Gly Gln Asp Arg Arg His Ser Arg Pro Ser Ala Thr Glu
                885                 890                 895
Pro His Lys Val Phe Ser Gln Ala Gly Leu Pro Ala Thr Val Val Arg
                900                 905                 910
His Trp Glu Gln His Ser His Thr Asp Asp Thr Val Val Val Gly Leu
        915                 920                 925
Gln Ser Thr Lys His Asn Cys Gln Gln Phe Phe Leu Gln Tyr Xaa Gln
930                 935                 940
Met Lys Val Arg Gly Xaa Pro Xaa Lys Arg Asp Gln Pro Thr Arg Pro
945                 950                 955                 960
Asn Leu Leu Leu Ser Gln Val Thr Gln Val Gly Cys Asp Arg Cys Pro
                965                 970                 975
Glu Xaa Phe Glu Leu Leu Leu Met Thr Asn His Thr Met Pro Trp Leu
        980                 985                 990
Arg Arg Arg Leu Gln Gln Cys Cys Ile Gln Glu Pro Tyr Pro Lys Gly
        995                1000                1005
Tyr Asn Ser Arg Leu His Ser Ser Ile Cys Gln Leu Ser His Gly Leu
        1010                1015                1020
Cys Gly Pro Tyr Ala Gly Leu Xaa Leu Leu Lys Pro Arg Thr His
1025                1030                1035                1040
Glu His Pro Trp Xaa Lys Xaa Gly Gln Gly Gln His Gly Met Cys Leu
                1045                1050                1055
Leu Pro Xaa Gly Cys Ser His Thr Arg Asn Gln Ser His Gln Cys Thr
        1060                1065                1070
Leu Tyr Thr Arg His Gln Trp Gln Leu Leu His Ser Arg Pro Gln Ala
        1075                1080                1085
Phe Leu Arg Cys His Ile Pro Tyr Ser Lys Arg Gln Leu Leu Phe Pro
        1090                1095                1100
Phe Glu Leu Thr Arg Xaa Gln Ala His His Ser Val Phe Trp Xaa Pro
1105                1110                1115                1120
Gln Arg Xaa Gly Val Ser Leu Ser Ser Asp Phe Pro Pro Xaa Ser Phe
                1125                1130                1135
Phe His Glu Arg Gly Xaa Cys Leu His Xaa Leu Ile Glu Ser Gln Leu
                1140                1145                1150
Cys Trp His Val Val Xaa Gly Leu Leu Gln Gly Gly Xaa Pro Trp Gln
        1155                1160                1165
Glu Pro Leu Ala Xaa His Phe Trp Met Glu Leu Arg Leu Gly Pro Phe
        1170                1175                1180
Gln Cys Pro Thr Arg Trp Phe Asp Arg Xaa His Gly Ile Arg His Lys
1185                1190                1195                1200
Xaa Leu His His Ser Ser Gly Asn Ile Val Arg Ser Gly Thr Cys His
                1205                1210                1215
Met Cys Cys Thr Xaa Val Lys Pro Leu Cys Trp Tyr Ile Cys His Xaa
                1220                1225                1230
Asn Ser Asn Leu Asp Ser Arg Arg Thr Ser Arg Ala Cys Thr Leu Ala
                1235                1240                1245
```

```
Leu Met Leu Leu Xaa Pro His Trp Asp Leu Gly Pro Arg Pro His Xaa
    1250            1255                1260

Ser Pro Ala Cys Lys Lys Val Val Ile Trp Leu Thr Cys Arg Cys Gln
1265            1270            1275                1280

Trp Gly Gln Leu Lys Phe Ala Leu Asn Thr Arg Xaa Ala Gln Xaa Val
                1285            1290            1295

Leu Tyr Gln Glu Trp His Val Leu Cys Thr Gly Asp Gly Ile Gln His
            1300            1305            1310

Thr Pro Thr Ala Xaa Pro Xaa Ser Gly Arg Leu Asn Arg Gln Asn Phe
        1315            1320            1325

Xaa Gln Arg Xaa Thr Ser Gln Xaa His Ala Arg Ser Thr Glu Ser
    1330            1335            1340

Gly His Leu Lys Asn Pro Trp Gln Gln Pro Trp Glu Gly Pro Arg Thr
1345            1350            1355                1360

His Thr Asn Lys Gly His Arg Ile Cys Xaa Pro Gln Pro Met Thr Pro
                1365            1370            1375

Val Val Leu Pro Asp Thr Pro Trp Ser Pro Arg Lys Ser Thr Glu Xaa
            1380            1385            1390

Gly Thr Gln Leu His Met Val Val Asp Arg Cys Pro Gly His Xaa Pro
            1395            1400            1405

Arg Gln Arg Leu Leu Gly Val Trp Ser Leu Trp Asp Glu Pro
    1410            1415            1420

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

CTACCACCAA TACCAGCGGC                                              20

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

GACATGGTCC TGGCCCTGTT GG                                           22

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:89:

GATCCATAGT GAGCCACTCA C                                            21
```

(2) INFORMATION FOR SEQ ID NO:90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:90:

CAAAATGTTC CTGTCATTAT TTG                                                  23

(2) INFORMATION FOR SEQ ID NO:91:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

CAATCATCTC CAGCTATAAA G                                                    21

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

CTGTGGACGC CACTTGTTTC                                                      20

(2) INFORMATION FOR SEQ ID NO:93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:93:

CAATAGCACA ATCTTCCTTG G                                                    21

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:94:

GAAAGCTTGG TTGGTTGTGG                                                      20

(2) INFORMATION FOR SEQ ID NO:95:

(i) SEQUENCE CHARACTERISTICS:

(A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:95:

CATCTTGACA ATGACAACTT TC                                              22

(2) INFORMATION FOR SEQ ID NO:96:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:96:

CCTCACTCAC CTTCGACCTC                                                 20

(2) INFORMATION FOR SEQ ID NO:97:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:97:

GGTTGGCACT TGCATGCCTG                                                 20

(2) INFORMATION FOR SEQ ID NO:98:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:98:

CCTGGCTTTG TTCCCACTGC                                                 20

(2) INFORMATION FOR SEQ ID NO:99:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:99:

CTCGTACCCC TCCTGGCAGC                                                 20

(2) INFORMATION FOR SEQ ID NO:100:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:100:

GCTAGGAGCA ACACTGTATG                                                      20

(2) INFORMATION FOR SEQ ID NO:101:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:101:

CGCCATAATT GACGACAAGA CTAGTCC                                              27

(2) INFORMATION FOR SEQ ID NO:102:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:102:

CTATTCCCAG GCTATAGCTA AAG                                                  23

(2) INFORMATION FOR SEQ ID NO:103:

(i) SEQUENCE CHARACTERISTICS:
              (A) LENGTH: 26 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:103:

CAGGTACATG CCATATGTGC TGTACG                                               26

(2) INFORMATION FOR SEQ ID NO:104:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:104:

CTTGGACGCA ATTGCGCCTC                                                      20

(2) INFORMATION FOR SEQ ID NO:105:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:105:

```
GTCACTAGGT AACTGATGTT G                                              21

(2) INFORMATION FOR SEQ ID NO:106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

CATGGTGGTT GATAGATGTC C                                              21

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:107:

GTGTCAAAAG CTAAGCAGGC                                                20

(2) INFORMATION FOR SEQ ID NO:108:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:108:

AGATACCCCT TGGTCTCCC                                                 19

(2) INFORMATION FOR SEQ ID NO:109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:109:

CAGGATCTAT TCCAGTAGGC                                                20

(2) INFORMATION FOR SEQ ID NO:110:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:110:

GTATAGGGGT ACCAAGATAT GG                                             22
```

(2) INFORMATION FOR SEQ ID NO:111:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

GTCTGCTAAG TCCCACATCA CTGGC                                      25

(2) INFORMATION FOR SEQ ID NO:112:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:112:

CATGAAGAAC CCTCGCTTCC                                            20

(2) INFORMATION FOR SEQ ID NO:113:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:113:

CACCCAACCC GAGGACTCCA G                                          21

(2) INFORMATION FOR SEQ ID NO:114:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

CACTTCAGCG CATGCCAATA GC                                       22

(2) INFORMATION FOR SEQ ID NO:115:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

GTACTAAACC CATCCATTGC CAC                                    23

(2) INFORMATION FOR SEQ ID NO:116:

(i) SEQUENCE CHARACTERISTICS:
        (A) LENGTH: 20 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:116:

GCCGAATGAG TACGTCAAGG                                                    20

(2) INFORMATION FOR SEQ ID NO:117:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:117:

GTAGGTGTGG CCGTGGGAAA G                                                  21

(2) INFORMATION FOR SEQ ID NO:118:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:118:

CTGCCGAACT GAGGGCTCAG                                                    20

(2) INFORMATION FOR SEQ ID NO:119:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:119:

GGTTACCGTT CCCATTGACA ACCC                                               24

(2) INFORMATION FOR SEQ ID NO:120:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:120:

GGACGGGGTC TCTGGTTGTA GTG                                                23

(2) INFORMATION FOR SEQ ID NO:121:

(i) SEQUENCE CHARACTERISTICS:
            (A) LENGTH: 24 base pairs
            (B) TYPE: nucleic acid
            (C) STRANDEDNESS: single
            (D) TOPOLOGY: linear

```
         (ii) MOLECULE TYPE: DNA (genomic)

(xi) SEQUENCE DESCRIPTION: SEQ ID NO:121:

GTGAACCGCG CTCACTCACC TTCG                                             24

(2) INFORMATION FOR SEQ ID NO:122:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:122:

CCTCTAGAGC GGCCTGAGCA G                                                21

(2) INFORMATION FOR SEQ ID NO:123:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:123:

GGATTAAGGC ACCATCATTC                                                  20

(2) INFORMATION FOR SEQ ID NO:124:

(i) SEQUENCE CHARACTERISTICS:
              (A) LENGTH: 23 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:124:

GCACGATTGG ATGCCGGGGA TAC                                              23

(2) INFORMATION FOR SEQ ID NO:125:

(i) SEQUENCE CHARACTERISTICS:
              (A) LENGTH: 34 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:125:

CAGTTCAAGC TTGTCCAGGA ATTCNNNNNC CGGT                                  34

(2) INFORMATION FOR SEQ ID NO:126:

(i) SEQUENCE CHARACTERISTICS:
              (A) LENGTH: 24 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:126:
```

```
CAGTTCAAGC TTGTCCAGGA ATTC                                              24

(2) INFORMATION FOR SEQ ID NO:127:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

GCCTCAGCCA ACTTCATCAC                                                   20

(2) INFORMATION FOR SEQ ID NO:128:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

CAGTTCAAGC TTGTCCAGGA ATTCNNNNNG CGCT                                   34

(2) INFORMATION FOR SEQ ID NO:129:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

GCGCTGAGCC TGTTAGCATA AC                                                22

(2) INFORMATION FOR SEQ ID NO:130:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

CAGGCGGTGG TATTGTCAGC                                                   20

(2) INFORMATION FOR SEQ ID NO:131:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:131:

CACTTTGGAC TGTAACAAAT GAC                                               23

(2) INFORMATION FOR SEQ ID NO:132:
```

```
        (i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:132:

CATCCACCCG ATAAACCCTA G                                          21

(2) INFORMATION FOR SEQ ID NO:133:

(i) SEQUENCE CHARACTERISTICS:
             (A) LENGTH: 24 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:133:

CTTGCAGAAG TGTGTCGAGG CAGG                                       24

(2) INFORMATION FOR SEQ ID NO:134:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:134:

TAATGCTGCA GCCGACAGCT G                                          21

(2) INFORMATION FOR SEQ ID NO:135:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:135:

CAGTTCAAGC TTGTCCAGGA ATTCNNNNNG GCCT                            34

(2) INFORMATION FOR SEQ ID NO:136:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:136:

CTTTCTCGGT GGTGCGCTAC                                            20

(2) INFORMATION FOR SEQ ID NO:137:

(i) SEQUENCE CHARACTERISTICS:
             (A) LENGTH: 20 base pairs
             (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:137:

CAACGCTGAG ATCCTCAGAG                                                    20

(2) INFORMATION FOR SEQ ID NO:138:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:138:

CCGTGAGAGG CGACTGGTGA G                                                  21

(2) INFORMATION FOR SEQ ID NO:139:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:139:

CGCAGGACAG TAGACACCTT GGTG                                               24

(2) INFORMATION FOR SEQ ID NO:140:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:140:

CAGGCATCAC CGAACTGCGT GGC                                                23

(2) INFORMATION FOR SEQ ID NO:141:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:141:

CGAGTGACGC TTGGTGCCTG GTC                                                23

(2) INFORMATION FOR SEQ ID NO:142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:142:

CACCTTGCTG CCGTATCCAG                                            20

(2) INFORMATION FOR SEQ ID NO:143:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:143:

CCAATCGGCA GTGCTTTAGG GACC                                       24

(2) INFORMATION FOR SEQ ID NO:144:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:144:

GTATCCCCGG CATCCAATCG TGC                                        23

(2) INFORMATION FOR SEQ ID NO:145:

(i) SEQUENCE CHARACTERISTICS:
          (A) LENGTH: 22 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:145:

CAACCATCCC AACACATGTA GG                                         22

(2) INFORMATION FOR SEQ ID NO:146:

(i) SEQUENCE CHARACTERISTICS:
          (A) LENGTH: 20 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:146:

GGGCTTGCCC AACTACTTCC                                            20

(2) INFORMATION FOR SEQ ID NO:147:

(i) SEQUENCE CHARACTERISTICS:
          (A) LENGTH: 21 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:147:

GGAGGCGTGA TACTCAAAAA G                                          21

(2) INFORMATION FOR SEQ ID NO:148:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:148:

CCGTGAGAGG CGACTGGTGA G                              21

(2) INFORMATION FOR SEQ ID NO:149:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:149:

CACCCAACCC GAGGACTCCA G                              21

(2) INFORMATION FOR SEQ ID NO:150:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:150:

CAGCAACCAC ACAGCCAAGC C                              21

(2) INFORMATION FOR SEQ ID NO:151:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:151:

GGGCTTGCCC AACTACTTCC                                20

(2) INFORMATION FOR SEQ ID NO:152:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:152:

TAATGCTGCA GCCGACAGCT G                              21

(2) INFORMATION FOR SEQ ID NO:153:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:153:

GGAGGCGTGA TACTCAAAAA G                                               21

(2) INFORMATION FOR SEQ ID NO:154:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:154:

CATGAAGAAC CCTCGCTTCC                                                 20

(2) INFORMATION FOR SEQ ID NO:155:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:155:

CCAAGTCAAG CTTGGCGCTT GTCATCAC                                        28

(2) INFORMATION FOR SEQ ID NO:156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:156:

CAACGCTGAG ATCCTCAGAG                                                 20

(2) INFORMATION FOR SEQ ID NO:157:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:157:

GATCCATAGT GAGCCACTCA C                                               21

(2) INFORMATION FOR SEQ ID NO:158:

(i) SEQUENCE CHARACTERISTICS:
        (A) LENGTH: 221 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:158:

```
GATCCATAGT GAGCCACTCA CCCATCAAGC ATTTAAATGT CAAGCAAGCA GTGGATGAGG      60

CGGCAGCATA GCCGCCTAGC ATGTCAAAGA CAAAACCCAC CGATGTCCAT GTACCAAGAG     120

CTGTTCCCAC AGCCCCGGCC ATCATGAACG CCAGTGCGTC TCTAGCGTCT GTAAGCTTGG     180

ACGCAATTGC GCCTCCAAAT AATGACAGGA ACATTTTGAT C                        221
```

(2) INFORMATION FOR SEQ ID NO:159:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:159:

```
GATCCAATCC AGGGGCCCTC GTACCCCTCC TGGCAGCTGT AGAAAGGACA ACCAGGAATG      60

TTAACCATGC TCTGAACTCC AGCTTTAAGG ACATTAAAGC AAATCACAAA GAAATTGCAC     120

ACATACTGCC AAATCTCTAG ACCCCAAGCA ATGAGGCCGC AATCATCCTC CGTCGGGGTG     180

TGGAGCCAAC GGATGCAAGC TGATATGATA CTCCAGGGGG TAGATGCCTC CAGAATGCCC     240

AGTATCTTCT GCGGATGTCA CGAGTGGCAA TAAAGTACTC ACTACATACA GTGTTGCTCC     300

TAGCAAGCAT AGTAAGAAGT CTGTTGGGCC AGTGATC                             337
```

(2) INFORMATION FOR SEQ ID NO:160:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:160:

```
CCTCACTCAC CTTCGACCTC                                                 20
```

(2) INFORMATION FOR SEQ ID NO:161:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:161:

```
GATCCATCTT GACAATGACA ACTTTCGCAG GACAGTAGAC ACCTTGGTGA CGAACTCATC      60

TTTGAGGAAG AAATCGTCAG GCATCACCGA ACTGCGTGGC ATCATCGTCA ACAATCTGTT     120

AACCCAATCT TGACCCACAC CCTTTTTGAC AGACCAGAGC AACAAGCCCA GAACCACACC     180

GGCCACCGAA GCCCCCGGAG AGGCCAGGCA ACTGACCAGG CACCAAGCGT CACTCGCTTG     240

TAACTTCCCC GCCAGGAGGT CGAAGGTGAG TGAGCGCGGT TCACCGCCCC CTCCCAGCCT     300

CTGATC                                                               306
```

(2) INFORMATION FOR SEQ ID NO:162:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:162:

```
GTGTCAAAAG CTAAGCAGGC                                            20
```

(2) INFORMATION FOR SEQ ID NO:163:

(i) SEQUENCE CHARACTERISTICS:
    (A) LENGTH: 9493 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:163:

```
CGTGGGAGTC CGGGGCCCCG GACCTCCCAC CGAGGTGGGG GGAAAGGGGC CCTGGACCGG      60
CCGGGTGGAA GGCCCGGAAC CGGTCCATCT TCCTCAAGGT TGAGGAAGGG GTACGTCTAT     120
CGGTCCGGTC GGTCCGAAAG GCGTCTGGAT GCCTAGTGTT AGGGTTCGTA GGTGGTAAAT     180
CCCAGCTAGG CGTGAAAGCG CTATAGGATA GGCTTATCCC GGTGACCGCT GCCCCGGAAC     240
CAGCCCCGCG GKTCTTTGGA CACGGTCCAC AGGTTGGGGG TACCGGTGTG AATAACCCCC     300
CGACTGAAGC GTCAGTCGTT AAACGGAGAC GGTCTCCTGA GATCGCAACG ACGCCCCACG     360
TACGGGAACG CCGCCAAAAC CTTCGGGACA GCTATGCGGG TTGACAATCC CAGTGGGGGG     420
CCGGGGACCA GCTGATTACT TGTCCTGCGA GTTCCTCTTG AGACTGGCCG AAAGGCAGCC     480
ACGGGGCCAC CAAGGCGGCG CAGCGCTGCA TGCGGCAAGG GGAAAAATCC TTCGGGTGAC     540
CCCTGGTGGC AATCCCTTCC CTTAGGAGCA TGAGTGTGGT CGACACATTC ACCATGGCTT     600
GGCTGTGGTT GCTGGTTTGC TTCCCCCTCG CGGGGGGGGT GCTCTTCAAC TCGCGGCACC     660
AGTGCTTCAA TGGGACCAT TATGTGCTTT CCAATTGTTG TTCCCGAGAC GAGGTTTACT     720
TCTGTTTCGG GGACGGATGT CTGGTGGCTT ATGGCTGTAC TGTTTGCACA CAGTCTTGCT     780
GGAAGCTCTA CCGCCTGGG GTGGCTACTC GGCCCGGGTC CGAACCAGGT GAGCTGCTGG     840
GGAGATTTGG GAGTGTAATT GGTCCGGTGT CGGCTTCGGC TTACACCGCT GGAGTCCTCG     900
GGTTGGGTGA ACCTTACAGT TTGGCCTTCT TGGGGACGTT CCTCACCAGT CGCCTCTCAC     960
GGATTCCCAA CGTCACCTGC GTGAAGGCTT GTGACCTTGA GTTTACCTAC CCAGGCTTGT    1020
CCATCGATTT TGACTGGGCG TTTACCAAGA TCTTGCAGTT GCCGGCCAAG CTGTGGCGAG    1080
GCCTAACGGC RGCWCCGGTC TTGAGCCTCC TCGTGATCCT CATGCTGGTC CTCGAGCAGC    1140
GCCTCCTGAT AGCCTTCCTA CTGCTTTTGG TAGTGGGCGA GGCTCAGAGG GGGATGTTCG    1200
ACAACTGCGT GTGTGGTTAC TGGGGGGGCA AGAGGCCCCC GTCGGTGACC CCGCTGTACC    1260
GTGGCAACGG TACTGTGGTG TGTGACTGTG ATTTTGGAAA AATGCATTGG GCCCCCCCCT    1320
TGTGTTCCGG YCTGGTGTGG CGGGACGGTC ATAGGAGGGG CACCGTGCGC GACCTCCCCC    1380
CGGTTTGCCC CCGGGAGGTT CTCGGCACGG TGACAGTCAT GTGTCAGTGG GGTTCTGCCT    1440
ACTGGATTTG GAGATTTGGG GACTGGGTTG CATTGTACGA CGAGCTACCA CGATCAGCTC    1500
TCTGTACTTT CTTCTCAGGT CATGGTCCAC AACCTAAAGA TCTCTCAGTC TTGAATCCAT    1560
```

```
CCGGGGCACC TTGTGCTTCT TGCGTCGTTG ACCAGAGGCC GCTGAAATGT GGTTCCTGCG    1620

TCCGCGACTG CTGGGAGACG GGGGGTCCTG GGTTCGATGA GTGCGGTGTC GGTACTCGGA    1680

TGACGAAGCA CCTCGAGGCC GTCCTGGTTG ATGGAGGTGT GGAGTCCAAG GTGACAACGC    1740

CCAAGGGTGA GCGCCCCAAA TACATAGGTC AGCACGGTGT GGGAACCTAC TACGGCGCTG    1800

TCCGTAGCCT CAACATCAGT TACCTAGTGA CTGAGGTGGG GGGCTATTGG CATGCGCTGA    1860

AGTGCCCGTG CGACTTTGTG CCCCGAGTGC TCCCAGAAAG AATTCCAGGT AGGCCTGTGA    1920

ATGCATGTCT AGCTGGGAAG TCTCCGCACC CGTTCGCAAG TTGGGCTCCC GGTGGGTTTT    1980

ACGCCCCCGT GTTCACCAAG TGCAACTGGC CGAAGACCTC CGGAGTGGAT GTGTGTCCTG    2040

GGTTTGCTTT CGATTTCCCT GGTGATCACA ACGGCTTCAT CCATGTTAAA GGCAACAGAC    2100

AGCAGGTTTA CAGTGGTCAG CGAAGGTCTT CGCCGGCTTG GTTGCTTACT GACATGGTCC    2160

TGGCCCTGTT GGTGGTGATG AAGTTGGCTG AGGCTAGAGT TGTCCCCCTG TTTATGCTGG    2220

CAATGTGGTG GTGGTTGAAT GGAGCATCTG CTGCCACTAT TGTCATCATA CACCCTACTG    2280

TCACGAAGTC CACTGAAAGT GTTCCATTGT GGACTCCGCC CACTGTTCCA ACTCCATCTT    2340

GCCCGAATTC TACCACCGGA GTCGCGGACT CTACCTACAA TGCTGGTTGC TACATGGTGG    2400

CAGGCCTGGC GGCCGGGGCT CAGGCGGTCT GGGGTGCTGC CAATGATGGT GCTCAGGCCG    2460

TCGTTGGTGG CATCTGGCCC GCGTGGCTCA AGCTGCGAAG CTTCGCTGCC GGTCTGGCCT    2520

GGTTGTCAAA TGTTGGGGCT TACTTGCCGG TCGTCGAGGC CGCVCTGGCT CCCGAGCTGG    2580

TGTGCACCCC GGTGGTCGGC TGGGCAGCCC AGGAGTGGTG GTTCACTGGT TGTCTGGGTG    2640

TGATGTGTGT CGTGGCGTAC CTGAATGTCC TGGGCTCTGT RAGGGCTGCC GTGCTTGTGG    2700

CGATGCACTT CGCAAGGGGT GCTCTGCCGC TGGTATTGGT GGTAGCTGCC GGGGTRACCC    2760

GGGAGCGGCA CAGCGTCTTA GGGCTTGAGG TGTGCTTCGA TCTGGATGGT GGAGACTGGC    2820

CRGACGCCAG TTGGTCTTGG GGTTTAGCAG GCGTGGTGAG CTGGGCCCTC CTGGTGGGGG    2880

GTCTGATGAC CCACGGTGGC CGATCAGCCA GAYTGACTTG GTAYGCCAGG TGGGCCGTCA    2940

ATTAYCAGAG GGTTCGYCGG TGGGTGAACA ACTCACCGGT TGGAGCYTTT GGYCGTTGGM    3000

GGCGYGCCTG GAAAGCYTGG TTRGTKGTGG CTTGGTTCTT CCCCCAGACA GTTGCCACAG    3060

TYTCCGTCAT CTTCATACTC TGTTTGAGCA GTTTAGATGT CATTGATTTC ATCTTGGARG    3120

TACTCTTGGT TAACTCACCA AATCTCGCGC GCTTGGCGCG RGTGCTGGAC TCCTTAGCTC    3180

THGCTGAGGA GCGGCTGGCC TGCTCTTGGC TGGTGGGCGT CCTGCGCAAG CGGGGCGTCC    3240

TCCTCTACGA GCACGCYGGT CACACTAGCA GGCGCGGTGC TGCCCGCTTG CGAGAGTGGG    3300

GYTTTGCGCT YGAGCCKGTT AGYATAACCA AGGAAGATTG YGCYATTGTT CGGGACTCTG    3360

CTCGTGTGTT GGGCTGTGGA CAATTGGTCC ATGGGAAACC AGTGGTCGCG AGGCGAGGCG    3420

ACGAGGTGTT GATCGGCTGT GTGAACAGTC GGTTCGACCT TCCGCCTGGC TTTGTTCCCA    3480

CTGCTCCCGT GGTSCTTCAT CARGCWGGCA ARGGRTTYTT YGGGGTTGTG AAGACMTCCA    3540

TGACAGGCAA GGACCCGTCC GAACACCACG GRAACGTGGT GGTCCTWGGG ACTTCAACAA    3600

CKCGTTCCAT GGGCTGCTGC GTGAACGGAG TAGTGTACAC RACATACCAT GGYACCAACG    3660

CCCGRCCKAT GGCGGGGCCK TTTGGKCCYG TCAAYGCTCG GTGGTGGTCW GCGAGYGACG    3720

ACGTCACGGT YTACCCGCTC CCWAATGGYG CTTCTTGCCT YCARGCWTGY AAGTGCCAAC    3780

CAACTGGGGT GTGGGTGATC CGGAATGACG GAGCTCTTTG CCATGGAACT CTCGGCAAGG    3840

TGGTGGATTT AGATATGCCC GCTGAGTTGT CAGACTTTCG CGGGTCTTCT GGATCACCAA    3900
```

```
TCTTGTGCGA TGAGGGTCAT GCTGTTGGCA TGCTGATTTC GGTGCTTCAT AGGGGGAGTA    3960

GGGTTTCCTC GGTGCGGTAT ACCAAACCTT GGGAAACTCT CCCTCGGGAG ATTGAGGCTC    4020

GATCGGAGGC CCCCCCTGTG CCAGGAACCA CTGGATACAG GGAGGCGCCA CTGTTCCTGC    4080

CCACCGGAGC TGGCAAGTCG ACGCGCGTGC CGAATGAGTA CGTCAAGGCT GGACACAARG    4140

TGCTTGTACT AAACCCATCC ATTGCCACAG TGAGGGCCAT GGGCCCTTAC ATGGAAAAGT    4200

TAACCGGCAA ACATCCGTCG GTGTACTGTG GCCATGACAC TACTGCATAT TCCAGGACTA    4260

CTGACTCATC TTTGACCTAC TGTACATACG GCAGGTTTAT GGCCAATCCC AGGAAATACT    4320

TGCGGGGAA CGACGTCGTA ATTTGCGACG AGTTGCACGT CACCGACCCG ACCTCAATTT    4380

TGGGGATGGG TCGGGCGAGG TTACTCGCTC GCGAGTGCGG CGTACGCCTC CTGCTTTTCG    4440

CTACGGCGAC CCCACCGGTC TCTCCGATGG CGAAGCATGA ATCTATTCAT GAGGAGATGT    4500

TGGGCAGTGA GGGGGAGGTC CCCTTCTATT GCCAATTCCT CCCACTGAGT AGGTATGCTA    4560

CTGGGAGACA CCTGCTGTTT TGTCATTCCA AGGTAGARTG CACTAGGTTA TCCTCAGCTT    4620

TGGCCAGCTT TGGTGTCAAC ACCGTTGTGT ACTTCAGAGG CAAAGAAACT GACATTCCAA    4680

CTGGTGACGT GTGCGTTTGC GCCACAGACG CACTTTCCAC TGGTTACACT GGCAATTTTG    4740

ACACCGTAAC AGACTGTGGT TTAATGGTTG AGGAGGTAGT GGAAGTGACC CTGGACCCGA    4800

CCATCACTAT CGGTGTGAAG ACCGTCCCGG CCCCTGCCGA ACTGAGGGCT CAGAGGCGTG    4860

GTAGGTGTGG CCGTGGGAAA GCGGGCACTT ACTATCAGGC ATTGATGTCT TCGGCGCCGG    4920

CGGGAACSGT TCGGTCTGGG GCTCTCTGGG CAGCTGTTGA GGCTGGHGTC TCGTGGTATG    4980

GCCTAGAGCC CGATGCTATT GGAGACCTGC TTAGGGCCTA CGACTCGTGT CCTTATACTG    5040

CTGCCATCAG TGCGTCCATC GGAGAGGCCA TTGCCTTTTT TACTGGYCTA GTGCCAATGA    5100

GGAATTATCC TCAGGTGGTT TGGGCCAAGC AGAAGGGRCA CAACTGGCCA CTCTTGGTGG    5160

GTGTGCAGAG GCACATGTGT GAGGACGCGG GCTGTGGTCC KCCCGCTAAT GGTCCCGAAT    5220

GGAGCGGCAT CAGGGGAAAA GGGCCTGTTC CCCTGTTGTG CCGATGGGGT GGTGACTTGC    5280

CTGAGTCGGT GGCTCCGCAT CACTGGGTTG ATGACCTACA GGCCCGGCTC GGTGTGGCCG    5340

AGGGTTACAC TCCCTGCATT GCTGGACCGG TGCTTTTGGT CGGTTTGGCG ATGGCGGGGG    5400

GGGCTATCCT GGCACACTGG ACGGGTCTC TGGTTGTAGT GACCAGTTGG GTTGTCAATG    5460

GGAACGGTAA CCCGCTGATA CAAAGCGCCT CTAGGGGCGT GGCKACYAGC GGTCCATACC    5520

CAGTACCCCC AGATGGTGGT GAACGGTACC CATCAGACAT CAAGCCAATY ACTGAGGCTG    5580

TGACCACCCT TGAGACTGCG TGCGGYTGGG GCCCAGCCGC GGCBAGTCTG GCTTATGTGA    5640

AGGCCTGTGA AACTGGAACC ATGTTGGCTG ACAARGCGAG TGCTGCGTGG CAGGCTTGGG    5700

CTGCAAACAA CTTTGTGCCT CCACCAGCAT CACACTCAAC TTCCTTGTTR CAGAGCTTGG    5760

AYGCTGCGTT CACTTCAGCT TGGGATAGCG TGTTCACTCA CGGCCGTTCC TTGCTTGTTG    5820

GGTTCACAGC TGCTTACGGC GCTCGGCGGA ACCCACCGCT GGGCGTCGGA GCCTCTTTCT    5880

TGCTGGGCAT GTCATCGAGC CACYTRACTC ACGTCAGACT TGCTGCTGCG TTGCTCCTCG    5940

GCGTCGGGGG TACCGTCCTA GGCACGCCTG CTACTGGGCT TGCTATGGCG GGTGCCTACT    6000

TCGCKGGGGG CAGCGTTACC GCTAACTGGC TGAGTATCAT TGTGGCTCTA ATCGGAGGCT    6060

GGGAGGGGGC RGTKAACGCA GCCTCACTCA CCTTCGAYCT CCTGGCKGGG AAGTTACAAG    6120

CKAGYGAYGC TTGGTGCCTR GTCAGYTGCY TGGCCTCTCC GGGGGCTTCG GTGGCYGGTG    6180

TGGCDCTVGG YCTDYTGCTV TGGTCTGTCA ARAAGGGTGT GGGWCARGAY TGGGTTAACA    6240

GAYTGTTGAC GATGATGCCA CGCAGTTCGG TGATGCCTGA CGATTTCTTC CTCAAAGATG    6300
```

```
AGTTCGTCAC CAAGGTGTCT ACTGTCCTGC GAAAGTTGTC ATTGTCAAGA TGGATCATGA     6360

CTCTTGTGGA CAAGCGGGAG ATGGAGATGG AGACMCCCGC TTCTCAGATT GTTTGGGACT     6420

TGCTTGACTG GTGCATCCGG CTRGGTCGGT TCCTGTACAA TAAACTYATG TTTGCTCTCC     6480

CTAGGTTGCG CCTGCCGCTT ATCGGTTGCA GTACCGGTTG GGGTGGCCCG TGGGAGGGCA     6540

ATGGTCATTT GGAAACAAGG TGTACTTGTG GCTGTGTGAT TACCGGTGAT ATTCACGATG     6600

GTATATTGCA CGACCTACAT TATACCTCCC TACTGTGCAG ACATTACTAC AAGAGGACAG     6660

TGCCTGTTGG CGTCATGGGC AATGCTGAGG GAGCAGTCCC CCTTGTGCCT ACTGGCGGTG     6720

GAATCAGGAC TTACCAAATT GGGACTTCTG ACTGGTTTGA GGCTGTGGTC GTGCATGGGA     6780

CAATCACGGT GCACGCCACC AGTTGCTATG AGTTGAAAGC TGCTGACGTT CGGAGGGCGG     6840

TGCGAGCCGG CCCGACTTAC GTTGGTGGCG TACCTTGCAG CTGGAGCGCG CCGTGTACTG     6900

CGCCTGCGCT CGTTTACAGG CTAGGCCAGG GCATCAAAAT CGATGGAGCG CGCCGACTGT     6960

TGCCCTGTGA CTTAGCACAG GGAGCGCGCC ACCCCCGGT ATCTGGCAGT GTTGCCGGTA      7020

GTGGTTGGAC AGATGAGGAC GAGAGGGACT TGGTGGAAAC CAAGGCTGCC GCCATCGAGG     7080

CCATTGGGGC GGCCTTGCAC CTCCCTTCAC CGGAGGCTGC TCAGGCCGCT CTAGAGGCTT     7140

TGGAGGAGGC TGCCGTGTCC CTGTTGCCCC ATGTGCCCGT CATTATGGGG GATGACTGTT     7200

CATGCCGGGA TGAGGCGTTC CAAGGCCACT TCATCCCAGA ACCCAATGTG ACAGAGGTAC     7260

CCATTGAGCC CACGGTCGGA GACGTGGAGG CACTCAAGCT GCGGGCTGCA GACCTGACCG     7320

CCAGGTTGCA AGACTTGGAG GCCATGGCTC TCGCCCGCGC TGAGTCAATC GAGGATGCTC     7380

GCGCAGCTTC GATGCCTTCG CTCACCGAGG TGGACTCAAT GCCATCATTG GAGTCGAGCC     7440

CTTGCTCCTC CTTTGAACAA ATCTCTTTAA CTGAAAGTGA CCCTGAGACT GTCGTCGAGG     7500

CTGGCTTACC CTTGGAGTTC GTGAACTCCA ACACCGGGCC GTCTCCGGCT CGGAGGATTG     7560

TCAGAATCCG ACAGGCTTGC TGTTGTGACA GATCCACAAT GAAGGCCATG CCGTTGTCGT     7620

TCACTGTCGG GGAGTGCCTC TTCGTTACTC GCTATGACCC GGACGGTCAC CAACTGTTTG     7680

ACGAGCGAGG TCCGATAGAG GTATCTACTC CTATATGTGA AGTGATTGGG GACATCAGGC     7740

TTCAGTGTGA CCAAATTGAG GAAACTCCAA CATCTTACTC TTACATCTGG TCAGGGGCGC     7800

CCTTGGGTAC TGGGAGAAGT GTCCCCCAAC CCATGACGCG CCCTATAGGG ACCCATCTGA     7860

CTTGTGACAC TACCAAAGTT TATGTTACTG ACCCTGATCG GGCCGCTGAG CGGGCCGAGA     7920

AGGTTACAAT CTGGAGGGGT GATAGGAAGT ATGACAAGCA TTATGAGGCT GTCGTTGAGG     7980

CTGTCCTGAA AAAGGCAGCC GCGACGAAGT CTCATGGCTG GACCTATTCC CAGGCTATAG     8040

CTAAAGTTAG GCGCCGAGCA GCCGCTGGAT ACGGCAGCAA GGTGACCGCC TCCACATTGG     8100

CCACTGGTTG GCCTCACGTG GAGGAGATGC TGGACAAAAT AGCCAGGGGA CAGGAAGTTC     8160

CTTTCACTTT TGTGACCAAG CGAGAGGTTT TCTTCTCCAA AACTACCCGT AAGCCCCCAA     8220

GATTCATAGT TTTCCCACCT TTGGACTTCA GGATAGCTGA AAAGATGATT CTGGGTGACC     8280

CCGGCATCGT TGCAAAGTCA ATTCTGGGTG ACGCTTATCT GTTCCAGTAC ACGCCCAATC     8340

AGAGGGTCAA AGCTCTGGTT AAGGCGTGGG AGGGGAAGTT GCATCCCGCT GCGATCACTG     8400

TGGACGCCAC TTGTTTCGAC TCATCGATTG ATGAGCACGA CATGCAGGTG GAGGCTTCGG     8460

TGTTTGCGGC GGCTAGTGAC AACCCCTCAA TGGTACATGC TTTGTGCAAG TACTACTCTG     8520

GTGGCCCTAT GGTTTCCCCA GATGGGGTTC CCTTGGGGTA CCGCCAGTGT AGGTCGTCGG     8580

GCGTGTTAAC AACTAGCTCG GCGAACAGCA TCACTTGTTA CATTAAGGTC AGCGCGGCCT     8640
```

```
GCAGGCGGGT GGGGATTAAG GCACCATCAT TCTTTATAGC TGGAGATGAT TGCTTGATCA      8700

TCTATGAAAA TGATGGAACT GATCCCTGCC CTGCTCTTAA GGCTGCCCTG GCCAACTATG      8760

GATACAGGTG TGAACCAACA AAGCATGCTT CACTGGACAC AGCTGAGTGT TGCTCGGCCT      8820

ACTTGGCTGA GTGCGTAGCT GGGGGTGCCA AGCGCTGGTG GTTGAGCACG GACATGAGGA      8880

AGCCGCTCGC AAGGGCGTCT TCCGAATATT CGGACCCAAT CGGCAGTGCT TTAGGGACCA      8940

TCTTGATGTA TCCCCGGCAT CCAATCGTGC GGTATGTTCT AATACCACAC GTACTAATAA      9000

TGGCTTACAG GAGTGGCAGC ACACCGGATG AGTTGGTTAT GTGTCAGGTT CAGGGAAATC      9060

ATTACTCTTT CCCGCTGCGG CTGCTGCCTC GCGTCTTGGT CTCTCTACAT GGTCCGTGGT      9120

GCCTACAAGT CACCACGGAC AGTACGAAGA CTAGGATGGA GGCAGGCTCA GCSTTGCGGG      9180

ATTTAGGAAT GAAATCCCTA GCCTGGCACC GCCGACGTGC CGGAAATGTG CGCACTCGCC      9240

TCCTGAGGGG AGGCAAGGAG TGGGGGCACC TGGCCAGAGC CCTCCTCTGG CAYCCAGGKT      9300

TGAAGGAGCA YCCCCCRCCC ATAAATTCAC TTCCAGGTTT TCAGCTGGCG ACGCCTTACG      9360

AACACCATGA AGAGGTCTTG ATCTCGATCA AGAGTCGACC ACCTTGGATA AGGTGGATTC      9420

TTGGTGCTTG TCTCTCGTTG CTGGCCGCCT TGCTGTGAAT TCGCTCCAGG CAGTAGGACC      9480

TTCGGGTCGG GGG                                                        9493

(2) INFORMATION FOR SEQ ID NO:164:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:164:

Arg Gly Ser Pro Gly Pro Arg Thr Ser His Arg Gly Gly Gly Lys Gly
 1               5                  10                  15

Ala Leu Asp Arg Pro Gly Gly Arg Pro Gly Thr Gly Pro Ser Ser Ser
            20                  25                  30

Arg Leu Arg Lys Gly Tyr Val Tyr Arg Ser Gly Arg Ser Glu Arg Arg
        35                  40                  45

Leu Asp Ala
    50

(2) INFORMATION FOR SEQ ID NO:165:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:165:

Val Val Asn Pro Ser
 1               5

(2) INFORMATION FOR SEQ ID NO:166:

(i) SEQUENCE CHARACTERISTICS:
        (A) LENGTH: 9 amino acids
        (B) TYPE: amino acid
        (D) TOPOLOGY: linear (ii) MOLECULE TYPE: protein
```

(xi) SEQUENCE DESCRIPTION: SEQ ID NO:166:

Lys Arg Tyr Arg Ile Gly Leu Ser Arg
 1               5

(2) INFORMATION FOR SEQ ID NO:167:

(i) SEQUENCE CHARACTERISTICS:
       (A) LENGTH: 21 amino acids
       (B) TYPE: amino acid
       (D) TOPOLOGY: linear (ii) MOLECULE TYPE: protein (xi) SEQUENCE DESCRIPTION: SEQ ID NO:167:

Pro Leu Pro Arg Asn Gln Pro Arg Xaa Ser Leu Asp Thr Val His Arg
 1               5                  10                  15

Leu Gly Val Pro Val
            20

(2) INFORMATION FOR SEQ ID NO:168:

(i) SEQUENCE CHARACTERISTICS:
       (A) LENGTH: 47 amino acids
       (B) TYPE: amino acid
       (D) TOPOLOGY: linear (ii) MOLECULE TYPE: protein (xi) SEQUENCE DESCRIPTION: SEQ ID NO:168:

Ile Thr Pro Arg Leu Lys Arg Gln Ser Leu Asn Gly Asp Gly Leu Leu
 1               5                  10                  15

Arg Ser Gln Arg Arg Pro Thr Tyr Gly Asn Ala Ala Lys Thr Phe Gly
            20                  25                  30

Thr Ala Met Arg Val Asp Asn Pro Ser Gly Gly Pro Gly Thr Ser
            35                  40                  45

(2) INFORMATION FOR SEQ ID NO:169:

(i) SEQUENCE CHARACTERISTICS:
       (A) LENGTH: 45 amino acids
       (B) TYPE: amino acid
       (D) TOPOLOGY: linear (ii) MOLECULE TYPE: protein (xi) SEQUENCE DESCRIPTION: SEQ ID NO:169:

Leu Leu Val Leu Arg Val Pro Leu Glu Thr Gly Arg Lys Ala Ala Thr
 1               5                  10                  15

Gly Pro Pro Arg Arg Arg Ser Ala Ala Cys Gly Lys Gly Lys Asn Pro
            20                  25                  30

Ser Gly Asp Pro Trp Trp Gln Ser Leu Pro Leu Gly Ala
            35                  40                  45

(2) INFORMATION FOR SEQ ID NO:170:

(i) SEQUENCE CHARACTERISTICS:
       (A) LENGTH: 94 amino acids
       (B) TYPE: amino acid
       (D) TOPOLOGY: linear (ii) MOLECULE TYPE: protein (xi) SEQUENCE DESCRIPTION: SEQ ID NO:170:

Val Trp Ser Thr His Ser Pro Trp Leu Gly Cys Gly Cys Trp Phe Ala
 1               5                  10                  15

```
Ser Pro Ser Arg Gly Gly Cys Ser Ser Thr Arg Thr Ser Ala Ser
            20                  25                  30

Met Gly Thr Ile Met Cys Phe Pro Ile Val Pro Glu Thr Arg Phe
            35                  40                  45

Thr Ser Val Ser Gly Thr Asp Val Trp Trp Leu Met Ala Val Leu Phe
            50                  55                  60

Ala His Ser Leu Ala Gly Ser Ser Thr Gly Leu Gly Trp Leu Leu Gly
 65             70                  75                      80

Pro Gly Pro Asn Gln Val Ser Cys Trp Gly Asp Leu Gly Val
                85                  90
```

(2) INFORMATION FOR SEQ ID NO:171:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO:171:

```
Leu Val Arg Cys Arg Leu Arg Leu Thr Pro Leu Glu Ser Ser Gly Trp
 1               5                  10                      15

Val Asn Leu Thr Val Trp Pro Ser Trp Gly Arg Ser Ser Pro Val Ala
            20                  25                  30

Ser His Gly Phe Pro Thr Ser Pro Ala
            35                  40
```

(2) INFORMATION FOR SEQ ID NO:172:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:172:

```
Arg Leu Val Thr Leu Ser Leu Pro Thr Gln Ala Cys Pro Ser Ile Leu
 1               5                  10                      15

Thr Gly Arg Leu Pro Arg Ser Cys Ser Cys Arg Pro Ser Cys Gly Glu
            20                  25                  30

Ala
```

(2) INFORMATION FOR SEQ ID NO:173:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:173:

```
Arg Xaa Xaa Arg Ser
 1               5
```

(2) INFORMATION FOR SEQ ID NO:174:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:174:

Ser Ser Cys Trp Ser Ser Ser Ser Ala Ser
1               5                   10

(2) INFORMATION FOR SEQ ID NO:175:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO:175:

Pro Ser Tyr Cys Phe Trp
1               5

(2) INFORMATION FOR SEQ ID NO:176:

(i) SEQUENCE CHARACTERISTICS:
            (A) LENGTH: 24 amino acids
            (B) TYPE: amino acid
            (D) TOPOLOGY: linear (ii) MOLECULE TYPE: protein (xi) SEQUENCE DESCRIPTION: SEQ ID NO:176:

Trp Ala Arg Leu Arg Gly Gly Cys Ser Thr Thr Ala Cys Val Val Thr
1               5                   10                  15

Gly Gly Ala Arg Gly Pro Arg Arg
            20

(2) INFORMATION FOR SEQ ID NO:177:

(i) SEQUENCE CHARACTERISTICS:
            (A) LENGTH: 54 amino acids
            (B) TYPE: amino acid
            (D) TOPOLOGY: linear (ii) MOLECULE TYPE: protein (xi) SEQUENCE DESCRIPTION: SEQ ID NO:177:

Pro Arg Cys Thr Val Ala Thr Val Leu Trp Cys Val Thr Val Ile Leu
1               5                   10                  15

Glu Lys Cys Ile Gly Pro Pro Cys Val Pro Xaa Trp Cys Gly Gly
            20                  25                  30

Thr Val Ile Gly Gly Ala Pro Cys Ala Thr Ser Pro Arg Phe Ala Pro
            35                  40                  45

Gly Arg Phe Ser Ala Arg
        50

(2) INFORMATION FOR SEQ ID NO:178:

(i) SEQUENCE CHARACTERISTICS:
            (A) LENGTH: 46 amino acids
            (B) TYPE: amino acid
            (D) TOPOLOGY: linear (ii) MOLECULE TYPE: protein (xi) SEQUENCE DESCRIPTION: SEQ ID NO:178:

Gln Ser Cys Val Ser Gly Val Leu Pro Thr Gly Phe Gly Asp Leu Gly
1               5                   10                  15

```
Thr Gly Leu His Cys Thr Thr Ser Tyr His Asp Gln Leu Ser Val Leu
        20                  25                  30

Ser Ser Gln Val Met Val His Asn Leu Lys Ile Ser Gln Ser
        35                  40                  45
```

(2) INFORMATION FOR SEQ ID NO:179:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:179:

```
Ile His Pro Gly His Leu Val Leu Leu Ala Ser Leu Thr Arg Gly Arg
 1               5                  10                  15
```

(2) INFORMATION FOR SEQ ID NO:180:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:180:

```
Asn Val Val Pro Ala Ser Ala Thr Ala Gly Arg Arg Gly Val Leu Gly
 1               5                  10                  15

Ser Met Ser Ala Val Ser Val Leu Gly
        20                  25
```

(2) INFORMATION FOR SEQ ID NO:181:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:181:

```
Arg Ser Thr Ser Arg Pro Ser Trp Leu Met Glu Val Trp Ser Pro Arg
 1               5                  10                  15
```

(2) INFORMATION FOR SEQ ID NO:182:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:182:

```
Gln Arg Pro Arg Val Ser Ala Pro Asn Thr
 1               5                  10
```

(2) INFORMATION FOR SEQ ID NO:183:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:183:

Val Ser Thr Val Trp Glu Pro Thr Thr Ala Leu Ser Val Ala Ser Thr
 1               5                  10                  15

Ser Val Thr (2) INFORMATION FOR SEQ ID NO:184:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:184:

Leu Arg Trp Gly Ala Ile Gly Met Arg
 1               5

(2) INFORMATION FOR SEQ ID NO:185:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:185:

Ser Ala Arg Ala Thr Leu Cys Pro Glu Cys Ser Gln Lys Glu Phe Gln
 1               5                  10                  15

Val Gly Leu (2) INFORMATION FOR SEQ ID NO:186:

(i) SEQUENCE CHARACTERISTICS:
        (A) LENGTH: 3 amino acids
        (B) TYPE: amino acid
        (D) TOPOLOGY: linear (ii) MOLECULE TYPE: protein (xi) SEQUENCE DESCRIPTION: SEQ ID NO:186:

Met His Val
 1

(2) INFORMATION FOR SEQ ID NO:187:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:187:

Leu Gly Ser Leu Arg Thr Arg Ser Gln Val Gly Leu Pro Val Gly Phe
 1               5                  10                  15

Thr Pro Pro Cys Ser Pro Ser Ala Thr Gly Arg Arg Pro Pro Glu Trp
                20                  25                  30

Met Cys Val Leu Gly Leu Leu Ser Ile Ser Leu Val Ile Thr Thr Ala
                35                  40                  45

Ser Ser Met Leu Lys Ala Thr Asp Ser Arg Phe Thr Val Val Ser Glu
                50                  55                  60

```
Gly Leu Arg Arg Leu Gly Cys Leu Leu Thr Trp Ser Trp Pro Cys Trp
65                  70                  75                  80

Trp
```

(2) INFORMATION FOR SEQ ID NO:188:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:188:

```
Ser Trp Leu Arg Leu Glu Leu Ser Pro Cys Leu Cys Trp Gln Cys Gly
1                5                  10                  15

Gly Gly
```

(2) INFORMATION FOR SEQ ID NO:189:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:189:

```
Met Glu His Leu Leu Pro Leu Ser Ser Tyr Thr Leu Leu Ser Arg
1                5                  10                  15

Ser Pro Leu Lys Val Phe His Cys Gly Leu Arg Pro Leu Phe Gln Leu
                 20                  25                  30

His Leu Ala Arg Ile Leu Pro Pro Glu Ser Arg Thr Leu Pro Thr Met
                 35                  40                  45

Leu Val Ala Thr Trp Trp Gln Ala Trp Arg Pro Gly Leu Arg Arg Ser
            50                  55                  60

Gly Val Leu Pro Met Met Val Leu Arg Pro Ser Leu Val Ala Ser Gly
65                  70                  75                  80

Pro Arg Gly Ser Ser Cys Glu Ala Ser Leu Pro Val Trp Pro Gly Cys
                 85                  90                  95

Gln Met Leu Gly Leu Thr Cys Arg Ser Ser Arg Pro Xaa Trp Leu Pro
                 100                 105                 110

Ser Trp Cys Ala Pro Arg Trp Ser Ala Gly Gln Pro Arg Ser Gly Gly
            115                 120                 125

Ser Leu Val Val Trp Val
            130
```

(2) INFORMATION FOR SEQ ID NO:190:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:190:

```
Cys Val Ser Trp Arg Thr
1                5
```

(2) INFORMATION FOR SEQ ID NO:191:

```
    (i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:191:

Met Ser Trp Ala Leu Xaa Gly Leu Pro Cys Leu Trp Arg Cys Thr Ser
 1               5                  10                  15

Gln Gly Val Leu Cys Arg Trp Tyr Trp Trp
            20                  25

(2) INFORMATION FOR SEQ ID NO:192:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:192:

Leu Pro Gly Xaa Pro Gly Ser Gly Thr Ala Ser
 1               5                  10

(2) INFORMATION FOR SEQ ID NO:193:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:193:

Gly Leu Arg Cys Ala Ser Ile Trp Met Val Glu Thr Gly Xaa Thr Pro
 1               5                  10                  15

Val Gly Leu Gly Val
            20

(2) INFORMATION FOR SEQ ID NO:194:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:194:

Ala Gly Pro Ser Trp Trp Gly Val
 1               5

(2) INFORMATION FOR SEQ ID NO:195:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:195:

Pro Thr Val Ala Asp Gln Pro Xaa
 1               5
```

```
(2) INFORMATION FOR SEQ ID NO:196:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:196:

Leu Gly Xaa Pro Gly Gly Pro Ser Ile Xaa Arg Gly Phe Xaa Gly Gly
 1               5                  10                  15

(2) INFORMATION FOR SEQ ID NO:197:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:197:

Thr Thr His Arg Leu Glu Xaa Leu Xaa Val Xaa Gly Xaa Pro Gly Lys
 1               5                  10                  15

Xaa Gly Xaa Xaa Trp Leu Gly Ser Ser Pro Arg Gln Leu Pro Gln Xaa
            20                  25                  30

Pro Ser Ser Ser Tyr Ser Val
        35

(2) INFORMATION FOR SEQ ID NO:198:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:198:

Met Ser Leu Ile Ser Ser Trp Xaa Tyr Ser Trp Leu Thr His Gln Ile
 1               5                  10                  15

Ser Arg Ala Trp Arg Xaa Cys Trp Thr Pro
            20                  25

(2) INFORMATION FOR SEQ ID NO:199:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:199:

Leu Xaa Leu Arg Ser Gly Trp Pro Ala Leu Gly Trp Trp Ala Ser Cys
 1               5                  10                  15

Ala Ser Gly Ala Ser Ser Ser Thr Ser Thr Xaa Val Thr Leu Ala Gly
            20                  25                  30

Ala Val Leu Pro Ala Cys Glu Ser Gly Xaa Leu Arg Xaa
        35                  40                  45

(2) INFORMATION FOR SEQ ID NO:200:

(i) SEQUENCE CHARACTERISTICS:
        (A) LENGTH: 4 amino acids
```

(B) TYPE: amino acid
        (D) TOPOLOGY: linear (ii) MOLECULE TYPE: protein (xi) SEQUENCE DESCRIPTION: SEQ ID NO:200:

Ser Xaa Leu Xaa
1

(2) INFORMATION FOR SEQ ID NO:201:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:201:

Pro Arg Lys Ile Xaa Xaa Leu Phe Gly Thr Leu Leu Val Cys Trp Ala
1               5                  10                  15

Val Asp Asn Trp Ser Met Gly Asn Gln Trp Ser Arg Gly Glu Ala Thr
            20                  25                  30

Arg Cys (2) INFORMATION FOR SEQ ID NO:202:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:202:

Thr Val Gly Ser Thr Phe Arg Leu Ala Leu Phe Pro Leu Leu Pro Trp
1               5                  10                  15

Xaa Phe Ile Xaa Xaa Ala Xaa Xaa Xaa Xaa Gly Leu
            20                  25

(2) INFORMATION FOR SEQ ID NO:203:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:203:

Gln Ala Arg Thr Arg Pro Asn Thr Thr Xaa Thr Trp Trp Ser Xaa Gly
1               5                  10                  15

Leu Gln Gln Xaa Val Pro Trp Ala Ala Ala
            20                  25

(2) INFORMATION FOR SEQ ID NO:204:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:204:

Cys Thr Xaa His Thr Met Xaa Pro Thr Pro Xaa Xaa Trp Arg Gly Xaa

-continued

```
                1               5              10              15
Leu Xaa Xaa Ser Xaa Leu Gly Gly Gly Xaa Arg Xaa Thr Thr Ser Arg
                    20                  25                  30

Xaa Thr Arg Ser Xaa Met Xaa Leu Leu Ala Xaa Xaa Xaa Xaa Ser Ala
        35                  40                  45

Asn Gln Leu Gly Cys Gly
    50
```

(2) INFORMATION FOR SEQ ID NO:205:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:205:

```
Ser Gly Met Thr Glu Leu Phe Ala Met Glu Leu Ser Ala Arg Trp Trp
1               5                  10                  15

Ile
```

(2) INFORMATION FOR SEQ ID NO:206:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:206:

```
Ile Cys Pro Leu Ser Cys Gln Thr Phe Ala Gly Leu Leu Asp His Gln
1               5                  10                  15

Ser Cys Ala Met Arg Val Met Leu Leu Ala Cys
            20                  25
```

(2) INFORMATION FOR SEQ ID NO:207:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:207:

```
Phe Arg Cys Phe Ile Gly Gly Val Gly Phe Pro Arg Cys Gly Ile Pro
1               5                  10                  15

Asn Leu Gly Lys Leu Ser Leu Gly Arg Leu Arg Leu Asp Arg Arg Pro
                20                  25                  30

Pro Leu Cys Gln Glu Pro Leu Asp Thr Gly Arg Arg His Cys Ser Cys
            35                  40                  45

Pro Pro Glu Leu Ala Ser Arg Arg Ala Cys Arg Met Ser Thr Ser Arg
        50                  55                  60

Leu Asp Thr Xaa Cys Leu Tyr
65                  70
```

(2) INFORMATION FOR SEQ ID NO:208:

(i) SEQUENCE CHARACTERISTICS:
        (A) LENGTH: 6 amino acids
        (B) TYPE: amino acid (D) TOPOLOGY: linear (ii) MOLECULE TYPE: protein (xi) SEQUENCE DESCRIPTION: SEQ ID NO:208:

Thr His Pro Leu Pro Gln
 1               5

(2) INFORMATION FOR SEQ ID NO:209:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:209:

Gly Pro Trp Ala Leu Thr Trp Lys Ser
 1               5

(2) INFORMATION FOR SEQ ID NO:210:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:210:

Pro Ala Asn Ile Arg Arg Cys Thr Val Ala Met Thr Leu Leu His Ile
 1               5                  10                  15

Pro Gly Leu Leu Thr His Leu
            20

(2) INFORMATION FOR SEQ ID NO:211:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:211:

Pro Thr Val His Thr Ala Gly Leu Trp Pro Ile Pro Gly Asn Thr Cys
 1               5                  10                  15

Gly Gly Thr Thr Ser
            20

(2) INFORMATION FOR SEQ ID NO:212:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:212:

Phe Ala Thr Ser Cys Thr Ser Pro Thr Arg Pro Gln Phe Trp Gly Trp
 1               5                  10                  15

Val Gly Arg Gly Tyr Ser Leu Ala Ser Ala Tyr Ala Ser Cys Phe
            20                  25                  30

Ser Leu Arg Arg Pro His Arg Ser Leu Arg Trp Arg Ser Met Asn Leu

```
              35                  40                  45
Phe Met Arg Arg Cys Trp Ala Val Arg Gly Arg Ser Pro Ser Ile Ala
            50                  55                  60
Asn Ser Ser His
 65
```

(2) INFORMATION FOR SEQ ID NO:213:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:213:

```
Val Gly Met Leu Leu Gly Asp Thr Cys Cys Phe Val Ile Pro Arg
 1               5                  10                  15
```

(2) INFORMATION FOR SEQ ID NO:214:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:214:

```
Xaa Ala Leu Gly Tyr Pro Gln Leu Trp Pro Ala Leu Val Ser Thr Pro
 1               5                  10                  15
Leu Cys Thr Ser Glu Ala Lys Lys Leu Thr Phe Gln Leu Val Thr Cys
                20                  25                  30
Ala Phe Ala Pro Gln Thr His Phe Pro Leu Val Thr Leu Ala Ile Leu
            35                  40                  45
Thr Pro
    50
```

(2) INFORMATION FOR SEQ ID NO:215:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:215:

```
Gln Thr Val Val
 1
```

(2) INFORMATION FOR SEQ ID NO:216:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:216:

```
Trp Leu Arg Arg
 1
```

(2) INFORMATION FOR SEQ ID NO:217:

```
    (i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:217:

Pro Trp Thr Arg Pro Ser Leu Ser Val
 1               5

(2) INFORMATION FOR SEQ ID NO:218:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:218:

Arg Pro Ser Arg Pro Leu Pro Asn
 1               5

(2) INFORMATION FOR SEQ ID NO:219:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:219:

Gly Leu Arg Gly Val Val Gly Val Ala Val Gly Lys Arg Ala Leu Thr
 1               5                  10                  15

Ile Arg His (2) INFORMATION FOR SEQ ID NO:220:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:220:

Cys Leu Arg Arg Arg Arg Glu Xaa Phe Gly Leu Gly Leu Ser Gly Gln
 1               5                  10                  15

Leu Leu Arg Leu Xaa Ser Arg Gly Met Ala
                20                  25

(2) INFORMATION FOR SEQ ID NO:221:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:221:

Ser Pro Met Leu Leu Glu Thr Cys Leu Gly Pro Thr Thr Arg Val Leu
 1               5                  10                  15

Ile Leu Leu Pro Ser Val Arg Pro Ser Glu Arg Pro Leu Pro Phe Leu
```

```
                    20                  25                  30

Leu Xaa (2) INFORMATION FOR SEQ ID NO:222:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:222:

Gly Ile Ile Leu Arg Trp Phe Gly Pro Ser Arg Arg Xaa Thr Thr Gly
 1               5                  10                  15

His Ser Trp Trp Val Cys Arg Gly Thr Cys Val Arg Thr Arg Ala Val
                20                  25                  30

Val Xaa Pro Leu Met Val Pro Asn Gly Ala Ala Ser Gly Glu Lys Gly
            35                  40                  45

Leu Phe Pro Cys Cys Ala Asp Gly Val Val Thr Cys Leu Ser Arg Trp
        50                  55                  60

Leu Arg Ile Thr Gly Leu Met Thr Tyr Arg Pro Gly Ser Val Trp Pro
65                  70                  75                  80

Arg Val Thr Leu Pro Ala Leu Leu Asp Arg Cys Phe Trp Ser Val Trp
                85                  90                  95

Arg Trp Arg Gly Gly Leu Ser Trp His Thr Gly Arg Gly Leu Trp Leu
            100                 105                 110

(2) INFORMATION FOR SEQ ID NO:223:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:223:

Pro Val Gly Leu Ser Met Gly Thr Val Thr Arg
 1               5                  10

(2) INFORMATION FOR SEQ ID NO:224:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:224:

Tyr Lys Ala Pro Leu Gly Ala Trp Xaa Xaa Ala Val His Thr Gln Tyr
 1               5                  10                  15

Pro Gln Met Val Val Asn Gly Thr His Gln Thr Ser Ser Gln Xaa Leu
                20                  25                  30

Arg Leu (2) INFORMATION FOR SEQ ID NO:225:

(i) SEQUENCE CHARACTERISTICS:
        (A) LENGTH: 18 amino acids
        (B) TYPE: amino acid
        (D) TOPOLOGY: linear
```

(ii) MOLECULE TYPE: protein (xi) SEQUENCE DESCRIPTION: SEQ ID NO:225:

Pro Pro Leu Arg Leu Arg Ala Xaa Gly Ala Gln Pro Arg Xaa Val Trp
1               5                   10                  15

Leu Met (2) INFORMATION FOR SEQ ID NO:226:

(i) SEQUENCE CHARACTERISTICS:
            (A) LENGTH: 106 amino acids
            (B) TYPE: amino acid
            (D) TOPOLOGY: linear (ii) MOLECULE TYPE: protein (xi) SEQUENCE DESCRIPTION: SEQ ID NO:226:

Arg Pro Val Lys Leu Glu Pro Cys Trp Leu Thr Xaa Arg Val Leu Arg
1               5                   10                  15

Gly Arg Leu Gly Leu Gln Thr Thr Leu Cys Leu His Gln His His Thr
            20                  25                  30

Gln Leu Pro Cys Xaa Arg Ala Trp Xaa Leu Arg Ser Leu Gln Leu Gly
        35                  40                  45

Ile Ala Cys Ser Leu Thr Ala Val Pro Cys Leu Leu Gly Ser Gln Leu
    50                  55                  60

Leu Thr Ala Leu Gly Gly Thr His Arg Trp Ala Ser Glu Pro Leu Ser
65                  70                  75                  80

Cys Trp Ala Cys His Arg Ala Xaa Xaa Leu Thr Ser Asp Leu Leu Leu
                85                  90                  95

Arg Cys Ser Ser Ala Ser Gly Val Pro Ser
            100                 105

(2) INFORMATION FOR SEQ ID NO:227:

(i) SEQUENCE CHARACTERISTICS:
            (A) LENGTH: 23 amino acids
            (B) TYPE: amino acid
            (D) TOPOLOGY: linear (ii) MOLECULE TYPE: protein (xi) SEQUENCE DESCRIPTION: SEQ ID NO:227:

Ala Arg Leu Leu Leu Gly Leu Leu Trp Arg Val Pro Thr Ser Xaa Gly
1               5                   10                  15

Ala Ala Leu Pro Leu Thr Gly
            20

(2) INFORMATION FOR SEQ ID NO:228:

(i) SEQUENCE CHARACTERISTICS:
            (A) LENGTH: 5 amino acids
            (B) TYPE: amino acid
            (D) TOPOLOGY: linear (ii) MOLECULE TYPE: protein (xi) SEQUENCE DESCRIPTION: SEQ ID NO:228:

Val Ser Leu Trp Leu
1               5

(2) INFORMATION FOR SEQ ID NO:229:

(i) SEQUENCE CHARACTERISTICS:
    (A) LENGTH: 65 amino acids
    (B) TYPE: amino acid
    (D) TOPOLOGY: linear (ii) MOLECULE TYPE: protein (xi) SEQUENCE DESCRIPTION: SEQ ID NO:229:

Ser Glu Ala Gly Arg Gly Xaa Xaa Thr Gln Pro His Ser Pro Ser Xaa
 1               5                  10                  15

Ser Trp Xaa Gly Ser Tyr Lys Xaa Xaa Xaa Leu Gly Ala Xaa Ser Xaa
            20                  25                  30

Xaa Trp Pro Leu Arg Gly Leu Arg Trp Xaa Val Trp Xaa Xaa Xaa Xaa
            35                  40                  45

Cys Xaa Gly Leu Ser Xaa Arg Val Trp Xaa Xaa Xaa Gly Leu Thr Xaa
        50                  55                  60

Cys
 65

(2) INFORMATION FOR SEQ ID NO:230:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:230:

Cys His Ala Val Arg
 1               5

(2) INFORMATION FOR SEQ ID NO:231:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:231:

Cys Leu Thr Ile Ser Ser Ser Lys Met Ser Ser Ser Pro Arg Cys Leu
 1               5                  10                  15

Leu Ser Cys Glu Ser
            20

(2) INFORMATION FOR SEQ ID NO:232:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:232:

Cys His Cys Gln Asp Gly Ser
 1               5

(2) INFORMATION FOR SEQ ID NO:233:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:233:

Leu Leu Trp Thr Ser Gly Arg Trp Arg Trp Arg Xaa Pro Leu Leu Arg
 1               5                  10                  15

Leu Phe Gly Thr Cys Leu Thr Gly Ala Ser Gly Xaa Val Gly Ser Cys
                20                  25                  30

Thr Ile Asn Xaa Cys Leu Leu Ser Leu Gly Cys Ala Cys Arg Leu Ser
            35                  40                  45

Val Ala Val Pro Val Gly Val Ala Arg Gly Arg Ala Met Val Ile Trp
        50                  55                  60

Lys Gln Gly Val Leu Val Ala Val
 65                  70

(2) INFORMATION FOR SEQ ID NO:234:

(i) SEQUENCE CHARACTERISTICS:
            (A) LENGTH: 78 amino acids
            (B) TYPE: amino acid
            (D) TOPOLOGY: linear (ii) MOLECULE TYPE: protein (xi) SEQUENCE DESCRIPTION: SEQ ID NO:234:

Leu Pro Val Ile Phe Thr Met Val Tyr Cys Thr Thr Tyr Ile Ile Pro
 1               5                  10                  15

Pro Tyr Cys Ala Asp Ile Thr Thr Arg Gly Gln Cys Leu Leu Ala Ser
                20                  25                  30

Trp Ala Met Leu Arg Glu Gln Ser Pro Leu Cys Leu Leu Ala Val Glu
            35                  40                  45

Ser Gly Leu Thr Lys Leu Gly Leu Leu Thr Gly Leu Arg Leu Trp Ser
        50                  55                  60

Cys Met Gly Gln Ser Arg Cys Thr Pro Pro Val Ala Met Ser
 65                  70                  75

(2) INFORMATION FOR SEQ ID NO:235:

(i) SEQUENCE CHARACTERISTICS:
            (A) LENGTH: 35 amino acids
            (B) TYPE: amino acid
            (D) TOPOLOGY: linear (ii) MOLECULE TYPE: protein (xi) SEQUENCE DESCRIPTION: SEQ ID NO:235:

Lys Leu Leu Thr Phe Gly Gly Arg Cys Glu Pro Ala Arg Leu Thr Leu
 1               5                  10                  15

Val Ala Tyr Leu Ala Ala Gly Ala Arg Arg Val Leu Arg Leu Arg Ser
                20                  25                  30

Phe Thr Gly
        35

(2) INFORMATION FOR SEQ ID NO:236:

(i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO:236:

```
Ala Arg Ala Ser Lys Ser Met Glu Arg Ala Asp Cys Cys Pro Val Thr
 1               5                  10                  15
```

(2) INFORMATION FOR SEQ ID NO:237:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:237:

```
His Arg Glu Arg Ala Thr Pro Arg Tyr Leu Ala Val Leu Pro Val Val
 1               5                  10                  15

Val Gly Gln Met Arg Thr Arg Gly Thr Trp Trp Lys Pro Arg Leu Pro
                20                  25                  30

Pro Ser Arg Pro Leu Gly Arg Pro Cys Thr Ser Leu His Arg Arg Leu
            35                  40                  45

Leu Arg Pro Leu
        50
```

(2) INFORMATION FOR SEQ ID NO:238:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:238:

```
Arg Leu Trp Arg Arg Leu Pro Cys Pro Cys Cys Pro Met Cys Pro Ser
 1               5                  10                  15

Leu Trp Val Met Thr Val His Ala Gly Met Arg Arg Ser Lys Ala Thr
                20                  25                  30

Ser Ser Gln Asn Pro Met
            35
```

(2) INFORMATION FOR SEQ ID NO:239:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:239:

```
Gln Arg Tyr Pro Leu Ser Pro Arg Ser Glu Thr Trp Arg His Ser Ser
 1               5                  10                  15

Cys Gly Leu Gln Thr
            20
```

(2) INFORMATION FOR SEQ ID NO:240:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:240:

-continued

```
Pro Pro Gly Cys Lys Thr Trp Arg Pro Trp Leu Ser Pro Ala Leu Ser
 1               5                  10                  15

Gln Ser Arg Met Leu Ala Gln Leu Arg Cys Leu Arg Ser Pro Arg Trp
                20                  25                  30

Thr Gln Cys His His Trp Ser Arg Ala Leu Ala Pro Pro Leu Asn Lys
                35                  40                  45

Ser Leu
    50
```

(2) INFORMATION FOR SEQ ID NO:241:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:241:

```
Leu Lys Val Thr Leu Arg Leu Ser Ser Arg Leu Ala Tyr Pro Trp Ser
 1               5                  10                  15

Ser
```

(2) INFORMATION FOR SEQ ID NO:242:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:242:

```
Thr Pro Thr Pro Gly Arg Leu Arg Leu Gly Gly Leu Ser Glu Ser Asp
 1               5                  10                  15

Arg Leu Ala Val Val Thr Asp Pro Gln
                20                  25
```

(2) INFORMATION FOR SEQ ID NO:243:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:243:

```
Arg Pro Cys Arg Cys Arg Ser Leu Ser Gly Ser Ala Ser Ser Leu Leu
 1               5                  10                  15

Ala Met Thr Arg Thr Val Thr Asn Cys Leu Thr Ser Glu Val Arg
                20                  25                  30
```

(2) INFORMATION FOR SEQ ID NO:244:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:244:

```
Arg Tyr Leu Leu Leu Tyr Val Lys
 1               5
```

(2) INFORMATION FOR SEQ ID NO:245:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:245:

```
Leu Gly Thr Ser Gly Phe Ser Val Thr Lys Leu Arg Lys Leu Gln His
 1               5                  10                  15
Leu Thr Leu Thr Ser Gly Gln Gly Arg Pro Trp Val Leu Gly Glu Val
                20                  25                  30
Ser Pro Asn Pro
            35
```

(2) INFORMATION FOR SEQ ID NO:246:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:246:

```
Leu Val Thr Leu Pro Lys Phe Met Leu Leu Thr Leu Ile Gly Pro Leu
 1               5                  10                  15
Ser Gly Pro Arg Arg Leu Gln Ser Gly Gly Val Ile Gly Ser Met Thr
                20                  25                  30
Ser Ile Met Arg Leu Ser Leu Arg Leu Ser
            35                  40
```

(2) INFORMATION FOR SEQ ID NO:247:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:247:

```
Lys Arg Gln Pro Arg Arg Ser Leu Met Ala Gly Pro Ile Pro Arg Leu
 1               5                  10                  15
```

(2) INFORMATION FOR SEQ ID NO:248:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:248:

```
Leu Lys Leu Gly Ala Glu Gln Pro Leu Asp Thr Ala Ala Arg
 1               5                  10
```

(2) INFORMATION FOR SEQ ID NO:249:

(i) SEQUENCE CHARACTERISTICS:
        (A) LENGTH: 18 amino acids
        (B) TYPE: amino acid (D) TOPOLOGY: linear (ii) MOLECULE TYPE: protein (xi) SEQUENCE DESCRIPTION: SEQ ID NO:249:

Pro Pro Pro His Trp Pro Leu Val Gly Leu Thr Trp Arg Arg Cys Trp
 1               5                  10                  15
Thr Lys (2) INFORMATION FOR SEQ ID NO:250:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:250:

Pro Gly Asp Arg Lys Phe Leu Ser Leu Leu
 1               5                  10

(2) INFORMATION FOR SEQ ID NO:251:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:251:

Pro Ser Glu Arg Phe Ser Ser Pro Lys Leu Pro Val Ser Pro Gln Asp
 1               5                  10                  15
Ser (2) INFORMATION FOR SEQ ID NO:252:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:252:

Phe Ser His Leu Trp Thr Ser Gly
 1               5

(2) INFORMATION FOR SEQ ID NO:253:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:253:

Phe Trp Val Thr Pro Ala Ser Leu Gln Ser Gln Phe Trp Val Thr Leu
 1               5                  10                  15
Ile Cys Ser Ser Thr Arg Pro Ile Arg Gly Ser Lys Leu Trp Leu Arg
                20                  25                  30
Arg Gly Arg Gly Ser Cys Ile Pro Leu Arg Ser Leu Trp Thr Pro Leu
                35                  40                  45

```
Val Ser Thr His Arg Leu Met Ser Thr Thr Cys Arg Trp Arg Leu Arg
    50                  55                  60
Cys Leu Arg Arg Leu Val Thr Thr Pro Gln Trp Tyr Met Leu Cys Ala
 65                  70                  75                  80
Ser Thr Thr Leu Val Ala Leu Trp Phe Pro Gln Met Gly Phe Pro Trp
                 85                  90                  95
Gly Thr Ala Ser Val Gly Arg Arg Ala Cys
                100                 105
```

(2) INFORMATION FOR SEQ ID NO:254:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:254:

```
Gln Leu Ala Arg Arg Thr Ala Ser Leu Val Thr Leu Arg Ser Ala Arg
 1               5                  10                  15
Pro Ala Gly Gly Trp Gly Leu Arg His His Ser Leu
                 20                  25
```

(2) INFORMATION FOR SEQ ID NO:255:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:255:

```
Leu Glu Met Ile Ala
 1               5
```

(2) INFORMATION FOR SEQ ID NO:256:

(i) SEQUENCE CHARACTERISTICS:
        (A) LENGTH: 46 amino acids
        (B) TYPE: amino acid
        (D) TOPOLOGY: linear (ii) MOLECULE TYPE: protein (xi) SEQUENCE DESCRIPTION: SEQ ID NO:256:

```
Ser Ser Met Lys Met Met Glu Leu Ile Pro Ala Leu Leu Arg Leu
 1               5                  10                  15
Pro Trp Pro Thr Met Asp Thr Gly Val Asn Gln Gln Ser Met Leu His
                 20                  25                  30
Trp Thr Gln Leu Ser Val Ala Arg Pro Thr Trp Leu Ser Ala
                 35                  40                  45
```

(2) INFORMATION FOR SEQ ID NO:257:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:257:

```
Leu Gly Val Pro Ser Ala Gly Gly
```

(2) INFORMATION FOR SEQ ID NO:258:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:258:

Gly Ser Arg Ser Gln Gly Arg Leu Pro Asn Ile Arg Thr Gln Ser Ala
1               5                   10                15

Val Leu (2) INFORMATION FOR SEQ ID NO:259:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:259:

Cys Ile Pro Gly Ile Gln Ser Cys Gly Met Phe
1               5                   10

(2) INFORMATION FOR SEQ ID NO:260:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:260:

Tyr His Thr Tyr
1

(2) INFORMATION FOR SEQ ID NO:261:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:261:

Trp Leu Thr Gly Val Ala Ala His Arg Met Ser Trp Leu Cys Val Arg
1               5                   10                15

Phe Arg Glu Ile Ile Thr Leu Ser Arg Cys Gly Cys Leu Ala Ser
        20                   25                 30

Trp Ser Leu Tyr Met Val Arg Gly Ala Tyr Lys Ser Pro Arg Thr Val
        35                   40                 45

Arg Arg Leu Gly Trp Arg Gln Ala Gln Xaa Cys Gly Ile
    50                   55                 60

(2) INFORMATION FOR SEQ ID NO:262:

(i) SEQUENCE CHARACTERISTICS:
        (A) LENGTH: 14 amino acids
        (B) TYPE: amino acid (D) TOPOLOGY: linear (ii) MOLECULE TYPE: protein (xi) SEQUENCE DESCRIPTION: SEQ ID NO:262:

Pro Gly Thr Ala Asp Val Pro Glu Met Cys Ala Leu Ala Ser
  1               5                  10

(2) INFORMATION FOR SEQ ID NO:263:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:263:

Gly Glu Ala Arg Ser Gly Gly Thr Trp Pro Glu Pro Ser Ser Gly Xaa
  1               5                  10                  15

Gln Xaa (2) INFORMATION FOR SEQ ID NO:264:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:264:

Arg Ser Xaa Pro Xaa Pro
  1               5

(2) INFORMATION FOR SEQ ID NO:265:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:265:

Ile His Phe Gln Val Phe Ser Trp Arg Arg Leu Thr Asn Thr Met Lys
  1               5                  10                  15

Arg Ser (2) INFORMATION FOR SEQ ID NO:266:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:266:

Ser Arg Ser Arg Val Asp His Leu Gly
  1               5

(2) INFORMATION FOR SEQ ID NO:267:

(i) SEQUENCE CHARACTERISTICS:
        (A) LENGTH: 27 amino acids
        (B) TYPE: amino acid (D) TOPOLOGY: linear (ii) MOLECULE TYPE: protein (xi) SEQUENCE DESCRIPTION: SEQ ID NO:267:

Gly Gly Phe Leu Val Leu Val Ser Arg Cys Trp Pro Pro Cys Cys Glu
 1               5                  10                  15

Phe Ala Pro Gly Ser Arg Thr Phe Gly Ser Gly
             20                  25

(2) INFORMATION FOR SEQ ID NO:268:

(i) SEQUENCE CHARACTERISTICS:
          (A) LENGTH:  33 amino acids
          (B) TYPE: amino acid
          (D) TOPOLOGY: linear (ii) MOLECULE TYPE: protein (xi) SEQUENCE DESCRIPTION: SEQ ID NO:268:

Val Gly Val Arg Gly Pro Gly Pro Thr Glu Val Gly Gly Lys Gly
 1               5                  10                  15

Pro Trp Thr Gly Arg Val Glu Gly Pro Glu Pro Val His Leu Pro Gln
             20                  25                  30

Gly (2) INFORMATION FOR SEQ ID NO:269:

(i) SEQUENCE CHARACTERISTICS:
          (A) LENGTH: 24 amino acids
          (B) TYPE: amino acid
          (D) TOPOLOGY: linear (ii) MOLECULE TYPE: protein (xi) SEQUENCE DESCRIPTION: SEQ ID NO:269:

Gly Arg Gly Thr Ser Ile Gly Pro Val Gly Pro Lys Gly Val Trp Met
 1               5                  10                  15

Pro Ser Val Arg Val Arg Arg Trp
             20

(2) INFORMATION FOR SEQ ID NO:270:

(i) SEQUENCE CHARACTERISTICS:
          (A) LENGTH:  10 amino acids
          (B) TYPE: amino acid
          (D) TOPOLOGY: linear (ii) MOLECULE TYPE: protein (xi) SEQUENCE DESCRIPTION: SEQ ID NO:270:

Ile Pro Ala Arg Arg Glu Ser Ala Ile Gly
 1               5                  10

(2) INFORMATION FOR SEQ ID NO:271:

(i) SEQUENCE CHARACTERISTICS:
          (A) LENGTH:  27 amino acids
          (B) TYPE: amino acid
          (D) TOPOLOGY: linear (ii) MOLECULE TYPE: protein (xi) SEQUENCE DESCRIPTION: SEQ ID NO:271:

Ala Tyr Pro Gly Asp Arg Cys Pro Gly Thr Ser Pro Ala Xaa Leu Trp
 1               5                  10                  15

```
Thr Arg Ser Thr Gly Trp Gly Tyr Arg Cys Glu
            20                  25
```

(2) INFORMATION FOR SEQ ID NO:272:

(i) SEQUENCE CHARACTERISTICS:
        (A) LENGTH:  4 amino acids
        (B) TYPE: amino acid
        (D) TOPOLOGY: linear (ii) MOLECULE TYPE: protein (xi) SEQUENCE DESCRIPTION: SEQ ID NO:272:

```
Ser Val Ser Arg
 1
```

(2) INFORMATION FOR SEQ ID NO:273:

(i) SEQUENCE CHARACTERISTICS:
        (A) LENGTH:  5 amino acids
        (B) TYPE: amino acid
        (D) TOPOLOGY: linear (ii) MOLECULE TYPE: protein (xi) SEQUENCE DESCRIPTION: SEQ ID NO:273:

```
Thr Glu Thr Val Ser
 1               5
```

(2) INFORMATION FOR SEQ ID NO:274:

(i) SEQUENCE CHARACTERISTICS:
        (A) LENGTH:  74 amino acids
        (B) TYPE: amino acid
        (D) TOPOLOGY: linear (ii) MOLECULE TYPE: protein (xi) SEQUENCE DESCRIPTION: SEQ ID NO:274:

```
Asp Arg Asn Asp Ala Pro Arg Thr Gly Thr Pro Pro Lys Pro Ser Gly
 1               5                  10                  15

Gln Leu Cys Gly Leu Thr Ile Pro Val Gly Gly Arg Gly Pro Ala Asp
            20                  25                  30

Tyr Leu Ser Cys Glu Phe Leu Leu Arg Leu Ala Glu Arg Gln Pro Arg
        35                  40                  45

Gly His Gln Gly Gly Ala Ala Leu His Ala Ala Arg Gly Lys Ile Leu
    50                  55                  60

Arg Val Thr Pro Gly Gly Asn Pro Phe Pro
65                  70
```

(2) INFORMATION FOR SEQ ID NO:275:

(i) SEQUENCE CHARACTERISTICS:
        (A) LENGTH:  88 amino acids
        (B) TYPE: amino acid
        (D) TOPOLOGY: linear (ii) MOLECULE TYPE: protein (xi) SEQUENCE DESCRIPTION: SEQ ID NO:275:

```
Glu His Glu Cys Gly Arg His Ile His His Gly Leu Ala Val Val Ala
 1               5                  10                  15

Gly Leu Leu Pro Pro Arg Gly Gly Gly Ala Leu Gln Leu Ala Ala Pro
            20                  25                  30
```

-continued

```
Val Leu Gln Trp Gly Pro Leu Cys Ala Phe Gln Leu Leu Phe Pro Arg
            35                  40                  45

Arg Gly Leu Leu Leu Phe Arg Gly Arg Met Ser Gly Gly Leu Trp Leu
        50                  55                  60

Tyr Cys Leu His Thr Val Leu Leu Glu Ala Leu Pro Ala Trp Gly Gly
 65                  70                  75                  80

Tyr Ser Ala Arg Val Arg Thr Arg
                85
```

(2) INFORMATION FOR SEQ ID NO:276:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:276:

```
Ala Ala Gly Glu Ile Trp Glu Cys Asn Trp Ser Gly Val Gly Phe Gly
 1               5                  10                  15

Leu His Arg Trp Ser Pro Arg Val Gly
                20                  25
```

(2) INFORMATION FOR SEQ ID NO:277:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:277:

```
Thr Leu Gln Phe Gly Leu Leu Gly Asp Val Pro His Gln Ser Pro Leu
 1               5                  10                  15

Thr Asp Ser Gln Arg His Leu Arg Glu Gly Leu
                20                  25
```

(2) INFORMATION FOR SEQ ID NO:278:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:278:

```
Val Tyr Leu Pro Arg Leu Val His Arg Phe
 1               5                  10
```

(2) INFORMATION FOR SEQ ID NO:279:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:279:

```
Leu Gly Val Tyr Gln Asp Leu Ala Val Ala Gly Gln Ala Val Ala Arg
 1               5                  10                  16

Pro Asn Gly Xaa Xaa Gly Leu Glu Pro Pro Arg Asp Pro His Ala Gly
```

```
                    20                  25                  30
Pro Arg Ala Ala Pro Pro Asp Ser Leu Pro Thr Ala Phe Gly Ser Gly
            35                  40                  45
Arg Gly Ser Glu Gly Asp Val Arg Gln Leu Arg Val Trp Leu Leu Gly
        50                  55                  60
Gly Gln Glu Ala Pro Val Gly Asp Pro Ala Val Pro Trp Gln Arg Tyr
65                  70                  75                  80
Cys Gly Val
```

(2) INFORMATION FOR SEQ ID NO:280:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:280:

```
Phe Trp Lys Asn Ala Leu Gly Pro Pro Leu Val Phe Arg Xaa Gly Val
1               5                   10                  15
Ala Gly Arg Ser
            20
```

(2) INFORMATION FOR SEQ ID NO:281:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:281:

```
Glu Gly His Arg Ala Arg Pro Pro Pro Gly Leu Pro Pro Gly Gly Ser
1               5                   10                  15
Arg His Gly Asp Ser His Val Ser Val Gly Phe Cys Leu Leu Asp Leu
            20                  25                  30
Glu Ile Trp Gly Leu Gly Cys Ile Val Arg Arg Ala Thr Thr Ile Ser
        35                  40                  45
Ser Leu Tyr Phe Leu Leu Arg Ser Trp Ser Thr Thr
    50                  55                  60
```

(2) INFORMATION FOR SEQ ID NO:282:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:282:

```
Arg Ser Leu Ser Leu Glu Ser Ile Arg Gly Thr Leu Cys Phe Leu Arg
1               5                   10                  15
Arg
```

(2) INFORMATION FOR SEQ ID NO:283:

(i) SEQUENCE CHARACTERISTICS:
        (A) LENGTH: 22 amino acids
        (B) TYPE: amino acid
        (D) TOPOLOGY: linear -continued (ii) MOLECULE TYPE: protein (xi) SEQUENCE DESCRIPTION: SEQ ID NO:283:

Pro Glu Ala Ala Glu Met Trp Phe Leu Arg Pro Arg Leu Leu Gly Asp
1               5                   10                  15
Gly Gly Ser Trp Val Arg
            20

(2) INFORMATION FOR SEQ ID NO:284:

(i) SEQUENCE CHARACTERISTICS:
            (A) LENGTH: 16 amino acids
            (B) TYPE: amino acid
            (D) TOPOLOGY: linear (ii) MOLECULE TYPE: protein (xi) SEQUENCE DESCRIPTION: SEQ ID NO:284:

Val Arg Cys Arg Tyr Ser Asp Asp Glu Ala Pro Arg Gly Arg Pro Gly
1               5                   10                  15

(2) INFORMATION FOR SEQ ID NO:285:

(i) SEQUENCE CHARACTERISTICS:
            (A) LENGTH: 12 amino acids
            (B) TYPE: amino acid
            (D) TOPOLOGY: linear (ii) MOLECULE TYPE: protein (xi) SEQUENCE DESCRIPTION: SEQ ID NO:285:

Trp Arg Cys Gly Val Gln Gly Asp Asn Ala Gln Gly
1               5                   10

(2) INFORMATION FOR SEQ ID NO:286:

(i) SEQUENCE CHARACTERISTICS:
            (A) LENGTH: 18 amino acids
            (B) TYPE: amino acid
            (D) TOPOLOGY: linear (ii) MOLECULE TYPE: protein (xi) SEQUENCE DESCRIPTION: SEQ ID NO:286:

Ala Pro Gln Ile His Arg Ser Ala Arg Cys Gly Asn Leu Leu Arg Arg
1               5                   10                  15
Cys Pro (2) INFORMATION FOR SEQ ID NO:287:

(i) SEQUENCE CHARACTERISTICS:
            (A) LENGTH: 8 amino acids
            (B) TYPE: amino acid
            (D) TOPOLOGY: linear (ii) MOLECULE TYPE: protein (xi) SEQUENCE DESCRIPTION: SEQ ID NO:287:

Pro Gln His Gln Leu Pro Ser Asp
1               5

(2) INFORMATION FOR SEQ ID NO:288:

(i) SEQUENCE CHARACTERISTICS:
            (A) LENGTH: 25 amino acids
            (B) TYPE: amino acid (D) TOPOLOGY: linear (ii) MOLECULE TYPE: protein (xi) SEQUENCE DESCRIPTION: SEQ ID NO:288:

Gly Gly Gly Leu Leu Ala Cys Ala Glu Val Pro Val Arg Leu Cys Ala
1               5                  10                  15

Pro Ser Ala Pro Arg Lys Asn Ser Arg
            20                  25

(2) INFORMATION FOR SEQ ID NO:289:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:289:

Ala Cys Glu Cys Met Ser Ser Trp Glu Val Ser Ala Pro Val Arg Lys
1               5                  10                  15

Leu Gly Ser Arg Trp Val Leu Arg Pro Arg Val His Gln Val Gln Leu
            20                  25                  30

Ala Glu Asp Leu Arg Ser Gly Cys Val Ser Trp Val Cys Phe Arg Phe
        35                  40                  45

Pro Trp
    50

(2) INFORMATION FOR SEQ ID NO:290:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:290:

Ser Gln Arg Leu His Pro Cys
1               5

(2) INFORMATION FOR SEQ ID NO:291:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:291:

Arg Gln Gln Thr Ala Gly Leu Gln Trp Ser Ala Lys Val Phe Ala Gly
1               5                  10                  15

Leu Val Ala Tyr
            20

(2) INFORMATION FOR SEQ ID NO:292:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:292:

His Gly Pro Gly Pro Val Gly Gly Asp Glu Val Gly
 1               5                  10

(2) INFORMATION FOR SEQ ID NO:293:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:293:

Ser Cys Pro Pro Val Tyr Ala Gly Asn Val Val Val Glu Trp Ser
 1               5                  10                  15

Ile Cys Cys His Tyr Cys His His Thr Pro Tyr Cys His Glu Val His
                20                  25                  30

(2) INFORMATION FOR SEQ ID NO:294:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:294:

Lys Cys Ser Ile Val Asp Ser Ala His Cys Ser Asn Ser Ile Leu Pro
 1               5                  10                  15

Glu Phe Tyr His Arg Ser Arg Gly Leu Tyr Leu Gln Cys Trp Leu Leu
                20                  25                  30

His Gly Gly Arg Pro Gly Gly Arg Gly Ser Gly Gly Leu Gly Cys Cys
            35                  40                  45

Gln (2) INFORMATION FOR SEQ ID NO:295:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:295:

Trp Cys Ser Gly Arg Arg Trp Trp His Leu Ala Arg Val Ala Gln Ala
 1               5                  10                  15

Ala Lys Leu Arg Cys Arg Ser Gly Leu Val Val Lys Cys Trp Gly Leu
                20                  25                  30

Leu Ala Gly Arg Arg Gly Arg Xaa Gly Ser Arg Ala Gly Val His Pro
            35                  40                  45

Gly Gly Arg Leu Gly Ser Pro Gly Val Val Val His Trp Leu Ser Gly
        50                  55                  60

Cys Asp Val Cys Arg Gly Val Pro Glu Cys Pro Gly Leu Cys Xaa Gly
 65                 70                  75                  80

Cys Arg Ala Cys Gly Asp Ala Leu Arg Lys Gly Cys Ser Ala Ala Gly
                85                  90                  95

Ile Gly Gly Ser Cys Arg Gly Xaa Pro Gly Ala Ala Gln Arg Leu Arg
            100                 105                 110

Ala (2) INFORMATION FOR SEQ ID NO:296:

(i) SEQUENCE CHARACTERISTICS:
　　　　(A) LENGTH: 104 amino acids
　　　　(B) TYPE: amino acid
　　　　(D) TOPOLOGY: linear (ii) MOLECULE TYPE: protein (xi) SEQUENCE DESCRIPTION: SEQ ID NO:296:

```
Gly Val Leu Arg Ser Gly Trp Trp Arg Leu Ala Xaa Arg Gln Leu Val
 1               5                  10                  15

Leu Gly Phe Ser Arg Arg Gly Glu Leu Gly Pro Pro Gly Gly Gly Ser
             20                  25                  30

Asp Asp Pro Arg Trp Pro Ile Ser Gln Xaa Asp Leu Val Xaa Gln Val
         35                  40                  45

Gly Arg Gln Leu Xaa Glu Gly Ser Xaa Val Gly Glu Gln Leu Thr Gly
     50                  55                  60

Trp Ser Xaa Trp Xaa Leu Xaa Ala Xaa Leu Glu Ser Xaa Val Xaa Xaa
 65                  70                  75                  80

Gly Leu Val Leu Pro Pro Asp Ser Cys His Ser Xaa Arg His Leu His
                 85                  90                  95

Thr Leu Phe Glu Gln Phe Arg Cys
                100
```

(2) INFORMATION FOR SEQ ID NO:297:

(i) SEQUENCE CHARACTERISTICS:
　　　　(A) LENGTH: 8 amino acids
　　　　(B) TYPE: amino acid
　　　　(D) TOPOLOGY: linear (ii) MOLECULE TYPE: protein (xi) SEQUENCE DESCRIPTION: SEQ ID NO:297:

```
Phe His Leu Gly Xaa Thr Leu Gly
 1               5
```

(2) INFORMATION FOR SEQ ID NO:298:

(i) SEQUENCE CHARACTERISTICS:
　　　　(A) LENGTH: 17 amino acids
　　　　(B) TYPE: amino acid
　　　　(D) TOPOLOGY: linear (ii) MOLECULE TYPE: protein (xi) SEQUENCE DESCRIPTION: SEQ ID NO:298:

```
Leu Thr Lys Ser Arg Ala Leu Gly Ala Xaa Ala Gly Leu Leu Ser Ser
 1               5                  10                  15

Xaa
```

(2) INFORMATION FOR SEQ ID NO:299:

(i) SEQUENCE CHARACTERISTICS:
　　　　(A) LENGTH: 26 amino acids
　　　　(B) TYPE: amino acid
　　　　(D) TOPOLOGY: linear (ii) MOLECULE TYPE: protein (xi) SEQUENCE DESCRIPTION: SEQ ID NO:299:

```
Gly Ala Ala Gly Leu Leu Leu Ala Gly Gly Arg Pro Ala Gln Ala Gly
 1               5                  10                  15

Arg Pro Pro Leu Arg Ala Arg Xaa Ser His
             20                  25
```

(2) INFORMATION FOR SEQ ID NO:300:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:300:

```
Gln Ala Arg Cys Cys Pro Leu Ala Arg Val Gly Xaa Cys Ala Xaa Ala
 1               5                  10                  15

Xaa
```

(2) INFORMATION FOR SEQ ID NO:301:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:301:

```
Xaa Asn Gln Gly Arg Leu Xaa Xaa Cys Ser Gly Leu Cys Ser Cys Val
 1               5                  10                  15

Gly Leu Trp Thr Ile Gly Pro Trp Glu Thr Ser Gly Arg Glu Ala Arg
                 20                  25                  30

Arg Arg Gly Val Asp Arg Leu Cys Glu Gln Ser Val Arg Pro Ser Ala
             35                  40                  45

Trp Leu Cys Ser His Cys Ser Arg Gly Xaa Ser Ser Xaa Xaa Gln Xaa
         50                  55                  60

Xaa Xaa Xaa Gly Cys Glu Asp Xaa His Asp Arg Gln Gly Pro Val Arg
65                  70                  75                  80

Thr Pro Arg Xaa Arg Gly Gly Pro Xaa Asp Phe Asn Asn Xaa Phe His
                 85                  90                  95

Gly Leu Leu Arg Glu Arg Ser Ser Val His Xaa Ile Pro Trp Xaa Gln
            100                 105                 110

Arg Pro Xaa Xaa Gly Gly Ala Xaa Trp Xaa Xaa Gln Xaa Ser Val Val
        115                 120                 125

Val Xaa Glu Xaa Arg Arg His Gly Xaa Pro Ala Pro Xaa Trp Xaa Phe
    130                 135                 140

Leu Pro Xaa Xaa Xaa Xaa Val Pro Thr Asn Trp Gly Val Gly Asp Pro
145                 150                 155                 160

Glu
```

(2) INFORMATION FOR SEQ ID NO:302:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:302:

-continued

```
Arg Ser Ser Leu Pro Trp Asn Ser Arg Gln Gly Gly Gly Phe Arg Tyr
 1               5                  10                  15
Ala Arg
```

(2) INFORMATION FOR SEQ ID NO:303:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:303:

```
Val Val Arg Leu Ser Arg Val Phe Trp Ile Thr Asn Leu Val Arg
 1               5                  10                  15
```

(2) INFORMATION FOR SEQ ID NO:304:

(i) SEQUENCE CHARACTERISTICS:
        (A) LENGTH:12 amino acids
        (B) TYPE: amino acid
        (D) TOPOLOGY: linear (ii) MOLECULE TYPE: protein (xi) SEQUENCE DESCRIPTION: SEQ ID NO:304:

```
Gly Ser Cys Cys Trp His Ala Asp Phe Gly Ala Ser
 1               5                  10
```

(2) INFORMATION FOR SEQ ID NO:305:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:305:

```
Gly Phe Leu Gly Ala Val Tyr Gln Thr Leu Gly Asn Ser Pro Ser Gly
 1               5                  10                  15
Asp
```

(2) INFORMATION FOR SEQ ID NO:306:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:306:

```
Gly Ser Ile Gly Gly Pro Pro Cys Ala Arg Asn His Trp Ile Gln Gly
 1               5                  10                  15
Gly Ala Thr Val Pro Ala His Arg Ser Trp Gln Val Asp Ala Arg Ala
                20                  25                  30
Glu
```

(2) INFORMATION FOR SEQ ID NO:307:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:307:

Val Arg Gln Gly Trp Thr Gln Xaa Ala Cys Thr Lys Pro Ile His Cys
 1               5                  10                  15

His Ser Glu Gly His Gly Pro Leu His Gly Lys Val Asn Arg Gln Thr
            20                  25                  30

Ser Val Gly Val Leu Trp Pro
            35

(2) INFORMATION FOR SEQ ID NO:308:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:308:

His Tyr Cys Ile Phe Gln Asp Tyr
 1               5

(2) INFORMATION FOR SEQ ID NO:309:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:309:

Leu Ile Phe Asp Leu Leu Tyr Ile Arg Gln Val Tyr Gly Gln Ser Gln
 1               5                  10                  15

Glu Ile Leu Ala Gly Glu Arg Arg Asn Leu Arg Arg Val Ala Arg
            20                  25                  30

His Arg Pro Asp Leu Asn Phe Gly Asp Gly Ser Gly Glu Val Thr Arg
            35                  40                  45

Ser Arg Val Arg Arg Thr Pro Pro Ala Phe Arg Tyr Gly Asp Pro Thr
        50                  55                  60

Gly Leu Ser Asp Gly Glu Ala
65                  70

(2) INFORMATION FOR SEQ ID NO:310:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:310:

Gly Asp Val Gly Gln
 1               5

(2) INFORMATION FOR SEQ ID NO:311:

(i) SEQUENCE CHARACTERISTICS:
        (A) LENGTH: 13 amino acids
        (B) TYPE: amino acid
        (D) TOPOLOGY: linear

```
    (ii) MOLECULE TYPE: protein (xi) SEQUENCE DESCRIPTION: SEQ ID NO:311:

Gly Gly Gly Pro Leu Leu Leu Pro Ile Pro Pro Thr Glu
 1               5                  10

(2) INFORMATION FOR SEQ ID NO:312:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:312:

Val Cys Tyr Trp Glu Thr Pro Ala Val Leu Ser Phe Gln Gly Arg Xaa
 1               5                  10                  15
His (2) INFORMATION FOR SEQ ID NO:313:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:313:

Val Ile Leu Ser Phe Gly Gln Leu Trp Cys Gln His Arg Cys Val Leu
 1               5                  10                  15
Gln Arg Gln Arg Asn
            20

(2) INFORMATION FOR SEQ ID NO:314:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:314:

His Ser Asn Trp
 1

(2) INFORMATION FOR SEQ ID NO:315:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:315:

Arg Val Arg Leu Arg His Arg Arg Thr Phe His Trp Leu His Trp Gln Phe
 1               5                  10                  15

(2) INFORMATION FOR SEQ ID NO:316:

(i) SEQUENCE CHARACTERISTICS:
        (A) LENGTH:9 amino acids
        (B) TYPE: amino acid
        (D) TOPOLOGY: linear
```

(ii) MOLECULE TYPE: protein (xi) SEQUENCE DESCRIPTION: SEQ ID NO:316:

His Arg Asn Arg Leu Trp Phe Asn Gly
 1               5

(2) INFORMATION FOR SEQ ID NO:317:

(i) SEQUENCE CHARACTERISTICS:
            (A) LENGTH: 30 amino acids
            (B) TYPE: amino acid
            (D) TOPOLOGY: linear (ii) MOLECULE TYPE: protein (xi) SEQUENCE DESCRIPTION: SEQ ID NO:317:

Gly Gly Ser Gly Ser Asp Pro Gly Pro Asp His His Tyr Arg Cys Glu
 1               5                  10                  15

Asp Arg Pro Gly Pro Cys Arg Thr Glu Gly Ser Glu Ala Trp
             20                  25                  30

(2) INFORMATION FOR SEQ ID NO:318:

(i) SEQUENCE CHARACTERISTICS:
            (A) LENGTH: 31 amino acids
            (B) TYPE: amino acid
            (D) TOPOLOGY: linear (ii) MOLECULE TYPE: protein (xi) SEQUENCE DESCRIPTION: SEQ ID NO:318:

Val Trp Pro Trp Glu Ser Gly His Leu Leu Ser Gly Ile Asp Val Phe
 1               5                  10                  15

Gly Ala Gly Gly Asn Xaa Ser Val Trp Gly Ser Leu Gly Ser Cys
             20                  25                  30

(2) INFORMATION FOR SEQ ID NO:319:

(i) SEQUENCE CHARACTERISTICS:
            (A) LENGTH: 17 amino acids
            (B) TYPE: amino acid
            (D) TOPOLOGY: linear (ii) MOLECULE TYPE: protein (xi) SEQUENCE DESCRIPTION: SEQ ID NO:319:

Gly Trp Xaa Leu Val Val Trp Pro Arg Ala Arg Cys Tyr Trp Arg Pro
 1               5                  10                  15

Ala (2) INFORMATION FOR SEQ ID NO:320:

(i) SEQUENCE CHARACTERISTICS:
            (A) LENGTH: 55 amino acids
            (B) TYPE: amino acid
            (D) TOPOLOGY: linear (ii) MOLECULE TYPE: protein (xi) SEQUENCE DESCRIPTION: SEQ ID NO:320:

Gly Leu Arg Leu Val Ser Leu Tyr Cys Cys His Gln Cys Val His Arg
 1               5                  10                  15

Arg Gly His Cys Leu Phe Tyr Trp Xaa Ser Ala Asn Glu Glu Leu Ser
             20                  25                  30

```
Ser Gly Gly Leu Gly Gln Ala Glu Gly Xaa Gln Leu Ala Thr Leu Gly
        35                  40                  45

Gly Cys Ala Glu Ala His Val
        50                  55
```

(2) INFORMATION FOR SEQ ID NO:321:

(i) SEQUENCE CHARACTERISTICS:
        (A) LENGTH:8 amino acids
        (B) TYPE: amino acid
        (D) TOPOLOGY: linear (ii) MOLECULE TYPE: protein (xi) SEQUENCE DESCRIPTION: SEQ ID NO:321:

```
Gly Arg Gly Leu Trp Ser Xaa Arg
 1                   5
```

(2) INFORMATION FOR SEQ ID NO:322:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:322:

```
Trp Ser Arg Met Glu Arg His Gln  Gly Lys Arg Ala Cys Ser Pro Val
 1                   5                   10                  15

Val Pro Met Gly Trp
                20
```

(2) INFORMATION FOR SEQ ID NO:323:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:323:

```
Val Gly Gly Ser Ala Ser Leu Gly
 1                   5
```

(2) INFORMATION FOR SEQ ID NO:324:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:324:

```
Pro Thr Gly Pro Ala Arg Cys Gly Arg Gly Leu His Ser Leu His Cys
 1                   5                  10                  15

Trp Thr Gly Ala Phe Gly Arg Phe Gly Asp Gly Gly Gly Tyr Pro
                20                  25                  30

Gly Thr Leu Asp Gly Val Ser Gly Cys Ser Asp Gln Leu Gly Cys Gln
        35                  40                  45

Trp Glu Arg
        50
```

(2) INFORMATION FOR SEQ ID NO:325:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:325:

```
Pro Ala Asp Thr Lys Arg Leu
 1               5
```

(2) INFORMATION FOR SEQ ID NO:326:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:326:

```
Gly Arg Gly Xaa Xaa Arg Ser Ile Pro Ser Thr Pro Arg Trp Trp
 1               5                  10                  15
```

(2) INFORMATION FOR SEQ ID NO:327:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:327:

```
Thr Val Pro Ile Arg His Gln Ala Asn Xaa
 1               5                  10
```

(2) INFORMATION FOR SEQ ID NO:328:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:328:

```
Gly Cys Asp His Pro
 1               5
```

(2) INFORMATION FOR SEQ ID NO:329:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:329:

```
Asp Cys Val Arg Xaa Gly Pro Ser Arg Gly Xaa Ser Gly Leu Cys Glu
 1               5                  10                  15
Gly Leu
```

(2) INFORMATION FOR SEQ ID NO:330:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:330:

Asn Trp Asn His Val Gly
 1               5

(2) INFORMATION FOR SEQ ID NO:331:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:331:

Gln Xaa Glu Cys Cys Val Ala Gly Leu Gly Cys Lys Gln Leu Cys Ala
 1               5                  10                  15

Ser Thr Ser Ile Thr Leu Asn Phe Leu Val Xaa Glu Leu Gly Xaa Cys
                20                  25                  30

Val His Phe Ser Leu Gly
            35

(2) INFORMATION FOR SEQ ID NO:332:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO:332:

Arg Val His Ser Arg Pro Phe Leu Ala Cys Trp Val His Ser Cys Leu
 1               5                  10                  15

Arg Arg Ser Ala Glu Pro Thr Ala Gly Arg Arg Ser Leu Phe Leu Ala
                20                  25                  30

Gly His Val Ile Glu Pro Xaa Xaa Ser Arg Gln Thr Cys Cys Cys Val
            35                  40                  45

Ala Pro Arg Arg Arg Gly Tyr Arg Pro Arg His Ala Cys Tyr Trp Ala
        50                  55                  60

Cys Tyr Gly Gly Cys Leu Leu Arg Xaa Gly Gln Arg Tyr Arg
 65                  70                  75

(2) INFORMATION FOR SEQ ID NO:333:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:333:

Leu Ala Glu Tyr His Cys Gly Ser Asn Arg Arg Leu Gly Gly Gly Xaa
 1               5                  10                  15

Xaa Arg Ser Leu Thr His Leu Arg Xaa Pro Gly Xaa Glu Val Thr Ser
                20                  25                  30

Xaa Xaa Xaa Leu Val Pro Xaa Gln Xaa Xaa Gly Leu Ser Gly Gly Phe

```
                35                  40                  45
Gly Gly Xaa Cys Gly Xaa Xaa Xaa Xaa Ala Xaa Val Cys Gln Xaa Gly
    50                  55                  60
Cys Gly Xaa Xaa Xaa Gly
65                  70
```

(2) INFORMATION FOR SEQ ID NO:334:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:334:

```
Gln Xaa Val Asp Asp Asp Ala Thr Gln Phe Gly Asp Ala
1               5                  10
```

(2) INFORMATION FOR SEQ ID NO:335:

(i) SEQUENCE CHARACTERISTICS:
        (A) LENGTH:6 amino acids
        (B) TYPE: amino acid
        (D) TOPOLOGY: linear (ii) MOLECULE TYPE: protein (xi) SEQUENCE DESCRIPTION: SEQ ID NO:335:

```
Arg Phe Leu Pro Gln Arg
1               5
```

(2) INFORMATION FOR SEQ ID NO:336:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO:336:

```
Val Arg His Gln Gly Val Tyr Cys Pro Ala Lys Val Val Ile Val Lys
1               5                  10                  15
Met Asp His Asp Ser Cys Gly Gln Ala Gly Asp Gly Asp Gly Asp Xaa
                20                  25                  30
Arg Phe Ser Asp Cys Leu Gly Leu Ala
            35                  40
```

(2) INFORMATION FOR SEQ ID NO:337:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:337:

```
Leu Val His Pro Ala Xaa Ser Val Pro Val Gln
1               5                  10
```

(2) INFORMATION FOR SEQ ID NO:338:

(i) SEQUENCE CHARACTERISTICS:
        (A) LENGTH: 6 amino acids (B) TYPE: amino acid
          (D) TOPOLOGY: linear (ii) MOLECULE TYPE: protein (xi) SEQUENCE DESCRIPTION: SEQ ID NO:338:

Thr Xaa Val Cys Ser Pro
 1               5

(2) INFORMATION FOR SEQ ID NO:339:

(i) SEQUENCE CHARACTERISTICS:
          (A) LENGTH: 34 amino acids
          (B) TYPE: amino acid
          (D) TOPOLOGY: linear (ii) MOLECULE TYPE: protein (xi) SEQUENCE DESCRIPTION: SEQ ID NO:339:

Val Ala Pro Ala Ala Tyr Arg Leu Gln Tyr Arg Leu Gly Trp Pro Val
 1               5                  10                  15

Gly Gly Gln Trp Ser Phe Gly Asn Lys Val Tyr Leu Trp Leu Cys Asp
                20                  25                  30

Tyr Arg (2) INFORMATION FOR SEQ ID NO:340:

(i) SEQUENCE CHARACTERISTICS:
          (A) LENGTH: 32 amino acids
          (B) TYPE: amino acid
          (D) TOPOLOGY: linear (ii) MOLECULE TYPE: protein (xi) SEQUENCE DESCRIPTION: SEQ ID NO:340:

Tyr Ser Arg Trp Tyr Ile Ala Arg Pro Thr Leu Tyr Leu Pro Thr Val
 1               5                  10                  15

Gln Thr Leu Leu Gln Glu Asp Ser Ala Cys Trp Arg His Gly Gln Cys
                20                  25                  30

(2) INFORMATION FOR SEQ ID NO:341:

(i) SEQUENCE CHARACTERISTICS:
          (A) LENGTH: 20 amino acids
          (B) TYPE: amino acid
          (D) TOPOLOGY: linear (ii) MOLECULE TYPE: protein (xi) SEQUENCE DESCRIPTION: SEQ ID NO:341:

Gly Ser Ser Pro Pro Cys Ala Tyr Trp Arg Trp Asn Gln Asp Leu Pro
 1               5                  10                  15

Asn Trp Asp Phe
                20

(2) INFORMATION FOR SEQ ID NO:342:

(i) SEQUENCE CHARACTERISTICS:
          (A) LENGTH: 16 amino acids
          (B) TYPE: amino acid
          (D) TOPOLOGY: linear (ii) MOLECULE TYPE: protein (xi) SEQUENCE DESCRIPTION: SEQ ID NO:342:

Gly Cys Gly Arg Ala Trp Asp Asn His Gly Ala Arg His Gln Leu Leu

```
                    1               5              10              15
```

(2) INFORMATION FOR SEQ ID NO:343:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:343:

```
Val Glu Ser Cys
  1
```

(2) INFORMATION FOR SEQ ID NO:344:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:344:

```
Arg Ser Glu Gly Gly Ala Ser Arg Pro Asp Leu Arg Trp Trp Arg Thr
  1               5                  10                  15

Leu Gln Leu Glu Arg Ala Val Tyr Cys Ala Cys Ala Arg Leu Gln Ala
             20                  25                  30

Arg Pro Gly His Gln Asn Arg Trp Ser Ala Pro Thr Val Ala Leu
         35                  40                  45
```

(2) INFORMATION FOR SEQ ID NO:345:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:345:

```
Leu Ser Thr Gly Ser Ala Pro Pro Gly Ile Trp Gln Cys Cys Arg
  1               5                  10                  15
```

(2) INFORMATION FOR SEQ ID NO:346:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:346:

```
Trp Leu Asp Arg
  1
```

(2) INFORMATION FOR SEQ ID NO:347:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:347:

```
Gly Arg Glu Gly Leu Gly Gly Asn Gln Gly Cys Arg His Arg Gly His
  1               5                  10                 15

Trp Gly Gly Leu Ala Pro Pro Phe Thr Gly Gly Cys Ser Gly Arg Ser
               20                  25                  30

Arg Gly Phe Gly Gly Gly Cys Arg Val Pro Val Ala Pro Cys Ala Arg
               35                  40                  45

His Tyr Gly
   50
```

(2) INFORMATION FOR SEQ ID NO:348:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:348:

```
Leu Phe Met Pro Gly
  1               5
```

(2) INFORMATION FOR SEQ ID NO:349:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:349:

```
Gly Val Pro Arg Pro Leu His Pro Arg Thr Gln Cys Asp Arg Gly Thr
  1               5                  10                 15

His
```

(2) INFORMATION FOR SEQ ID NO:350:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:350:

```
Ala His Gly Arg Arg Arg Gly Gly Thr Gln Ala Ala Gly Cys Arg Pro
  1               5                  10                 15

Asp Arg Gln Val Ala Arg Leu Gly Gly His Gly Ser Arg Pro Arg
               20                  25                  30
```

(2) INFORMATION FOR SEQ ID NO:351:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:351:

```
Val Asn Arg Gly Cys Ser Arg Ser Phe Asp Ala Phe Ala His Arg Gly
  1               5                  10                 15

Gly Leu Asn Ala Ile Ile Gly Val Glu Pro Leu Leu Leu Leu
```

```
                    20                  25                  30
```

(2) INFORMATION FOR SEQ ID NO:352:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:352:

```
Thr Asn Leu Phe Asn
 1               5
```

(2) INFORMATION FOR SEQ ID NO:353:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:353:

```
Asp Cys Arg Arg Gly Trp Leu Thr Leu Gly Val Arg Glu Leu Gln His
 1               5                  10                  15
Arg Ala Val Ser Gly Ser Glu Asp Cys Gln Asn Pro Thr Gly Leu Leu
                20                  25                  30
Leu
```

(2) INFORMATION FOR SEQ ID NO:354:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:354:

```
Gln Ile His Asn Glu Gly His Ala Val Val Val His Cys Arg Gly Val
 1               5                  10                  15
Pro Leu Arg Tyr Ser Leu
                20
```

(2) INFORMATION FOR SEQ ID NO:355:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:355:

```
Pro Gly Arg Ser Pro Thr Val
 1               5
```

(2) INFORMATION FOR SEQ ID NO:356:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:356:

Arg Ala Arg Ser Asp Arg Gly Ile Tyr Ser Tyr Met
 1               5                  10

(2) INFORMATION FOR SEQ ID NO:357:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:357:

Ser Asp Trp Gly His Gln Ala Ser Val
 1               5

(2) INFORMATION FOR SEQ ID NO:358:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:358:

Gly Asn Ser Asn Ile Leu Leu Leu His Leu Val Arg Gly Ala Leu Gly
 1               5                  10                  15

Tyr Trp Glu Lys Cys Pro Pro Thr His Asp Ala Pro Tyr Arg Asp Pro
            20                  25                  30

Ser Asp Leu
        35

(2) INFORMATION FOR SEQ ID NO:359:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:359:

His Tyr Gln Ser Leu Cys Tyr
 1               5

(2) INFORMATION FOR SEQ ID NO:360:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:360:

Ala Gly Arg Glu Gly Tyr Asn Leu Glu Gly
 1               5                  10

(2) INFORMATION FOR SEQ ID NO:361:

(i) SEQUENCE CHARACTERISTICS:
        (A) LENGTH: 21 amino acids
        (B) TYPE: amino acid
        (D) TOPOLOGY: linear

```
        (ii) MOLECULE TYPE: protein (xi) SEQUENCE DESCRIPTION: SEQ ID NO:361:

Gly Cys Pro Glu Lys Gly Ser Arg Asp Glu Val Ser Trp Leu Asp Leu
 1               5                  10                  15

Phe Pro Gly Tyr Ser
             20

(2) INFORMATION FOR SEQ ID NO:362:

(i) SEQUENCE CHARACTERISTICS:
            (A) LENGTH: 53 amino acids
            (B) TYPE: amino acid
            (D) TOPOLOGY: linear (ii) MOLECULE TYPE: protein (xi) SEQUENCE DESCRIPTION: SEQ ID NO:362:

Ala Pro Ser Ser Arg Trp Ile Arg Gln Gln Gly Asp Arg Leu His Ile
 1               5                  10                  15

Gly His Trp Leu Ala Ser Arg Gly Gly Asp Ala Gly Gln Asn Ser Gln
             20                  25                  30

Gly Thr Gly Ser Ser Phe His Phe Cys Asp Gln Ala Arg Gly Phe Leu
         35                  40                  45

Leu Gln Asn Tyr Pro
         50

(2) INFORMATION FOR SEQ ID NO:363:

(i) SEQUENCE CHARACTERISTICS:
            (A) LENGTH: 15 amino acids
            (B) TYPE: amino acid
            (D) TOPOLOGY: linear (ii) MOLECULE TYPE: protein (xi) SEQUENCE DESCRIPTION: SEQ ID NO:363:

Ala Pro Lys Ile His Ser Phe Pro Thr Phe Gly Leu Gln Asp Ser
 1               5                  10                  15

(2) INFORMATION FOR SEQ ID NO:364:

(i) SEQUENCE CHARACTERISTICS:
            (A) LENGTH: 5 amino acids
            (B) TYPE: amino acid
            (D) TOPOLOGY: linear (ii) MOLECULE TYPE: protein (xi) SEQUENCE DESCRIPTION: SEQ ID NO:364:

Lys Asp Asp Ser Gly
 1               5

(2) INFORMATION FOR SEQ ID NO:365:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO:365:

Pro Arg His Arg Cys Lys Val Asn Ser Gly
 1               5                  10
```

(2) INFORMATION FOR SEQ ID NO:366:

(i) SEQUENCE CHARACTERISTICS:
       (A) LENGTH: 16 amino acids
       (B) TYPE: amino acid
       (D) TOPOLOGY: linear (ii) MOLECULE TYPE: protein (xi) SEQUENCE DESCRIPTION: SEQ ID NO:366:

Arg Leu Ser Val Pro Val His Ala Gln Ser Glu Gly Gln Ser Ser Gly
  1               5                  10                  15

(2) INFORMATION FOR SEQ ID NO:367:

(i) SEQUENCE CHARACTERISTICS:
       (A) LENGTH: 21 amino acids
       (B) TYPE: amino acid
       (D) TOPOLOGY: linear (ii) MOLECULE TYPE: protein (xi) SEQUENCE DESCRIPTION: SEQ ID NO:367:

Gly Val Gly Gly Glu Val Ala Ser Arg Cys Asp His Cys Gly Arg His
  1               5                  10                  15

Leu Phe Arg Leu Ile
            20

(2) INFORMATION FOR SEQ ID NO:368:

(i) SEQUENCE CHARACTERISTICS:
       (A) LENGTH:13 amino acids
       (B) TYPE: amino acid
       (D) TOPOLOGY: linear (ii) MOLECULE TYPE: protein (xi) SEQUENCE DESCRIPTION: SEQ ID NO:368:

Ala Arg His Ala Gly Gly Gly Phe Gly Val Cys Gly Gly
  1               5                  10

(2) INFORMATION FOR SEQ ID NO:369:

(i) SEQUENCE CHARACTERISTICS:
       (A) LENGTH: 30 amino acids
       (B) TYPE: amino acid
       (D) TOPOLOGY: linear (ii) MOLECULE TYPE: protein (xi) SEQUENCE DESCRIPTION: SEQ ID NO:369:

Gln Pro Leu Asn Gly Thr Cys Phe Val Gln Val Leu Leu Trp Trp Pro
  1               5                  10                  15

Tyr Gly Phe Pro Arg Trp Gly Ser Leu Gly Val Pro Pro Val
            20                  25                  30

(2) INFORMATION FOR SEQ ID NO:370:

(i) SEQUENCE CHARACTERISTICS:
       (A) LENGTH:7 amino acids
       (B) TYPE: amino acid
       (D) TOPOLOGY: linear (ii) MOLECULE TYPE: protein (xi) SEQUENCE DESCRIPTION: SEQ ID NO:370:

```
Val Val Gly Arg Val Asn Asn
1               5
```

(2) INFORMATION FOR SEQ ID NO:371:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:371:

```
Leu Gly Glu Gln His His Leu Leu His
1               5
```

(2) INFORMATION FOR SEQ ID NO:372:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:372:

```
Gly Gln Arg Gly Leu Gln Ala Gly Gly Asp
1               5                   10
```

(2) INFORMATION FOR SEQ ID NO:373:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:373:

```
Gly Thr Ile Ile Leu Tyr Ser Trp Arg
1               5
```

(2) INFORMATION FOR SEQ ID NO:374:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:374:

```
Leu Leu Asp His Leu
1               5
```

(2) INFORMATION FOR SEQ ID NO:375:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:375:

```
Ser Leu Pro Cys Ser
1               5
```

(2) INFORMATION FOR SEQ ID NO:376:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:376:

Gly Cys Pro Gly Gln Leu Trp Ile Gln Val
 1               5                  10

(2) INFORMATION FOR SEQ ID NO:377:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:377:

Thr Asn Lys Ala Cys Phe Thr Gly His Ser
 1               5                  10

(2) INFORMATION FOR SEQ ID NO:378:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:378:

Val Leu Leu Gly Leu Leu Gly
 1               5

(2) INFORMATION FOR SEQ ID NO:379:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO:379:

Val Arg Ser Trp Gly Cys Gln Ala Leu Val Val Glu His Gly His Glu
 1               5                  10                  15

Glu Ala Ala Arg Lys Gly Val Phe Arg Ile Phe Gly Pro Asn Arg Gln
                20                  25                  30

Cys Phe Arg Asp His Leu Asp Val Ser Pro Ala Ser Asn Arg Ala Val
            35                  40                  45

Cys Ser Asn Thr Thr Arg Thr Asn Asn Gly Leu Gln Glu Trp Gln His
        50                  55                  60

Thr Gly
 65

(2) INFORMATION FOR SEQ ID NO:380:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:380:

Val Gly Tyr Val Ser Gly Ser Gly Lys Ser Leu Leu Phe Pro Ala Ala
1               5                   10                  15

Ala Ala Ala Ser Arg Leu Gly Leu Ser Thr Trp Ser Val Val Pro Thr
                20                  25                  30

Ser His His Gly Gln Tyr Glu
            35

(2) INFORMATION FOR SEQ ID NO:381:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:381:

Asp Gly Gly Arg Leu Ser Xaa Ala Gly Phe Arg Asn Glu Ile Pro Ser
1               5                   10                  15

Leu Ala Pro Pro Thr Cys Arg Lys Cys Ala His Ser Pro Pro Glu Gly
                20                  25                  30

Arg Gln Gly Val Gly Ala Pro Gly Gln Ser Pro Pro Leu Ala Xaa Arg
            35                  40                  45

Xaa Glu Gly Ala Xaa Pro Xaa His Lys Phe Thr Ser Arg Phe Ser Ala
        50                  55                  60

Gly Asp Ala Leu Arg Thr Pro
65                      70

(2) INFORMATION FOR SEQ ID NO:382:

(i) SEQUENCE CHARACTERISTICS:
        (A) LENGTH:41  amino acids
        (B) TYPE: amino acid
        (D) TOPOLOGY: linear (ii) MOLECULE TYPE: protein (xi) SEQUENCE DESCRIPTION: SEQ ID NO:382:

Arg Gly Leu Asp Leu Asp Gln Glu Ser Thr Thr Leu Asp Lys Val Asp
1               5                   10                  15

Ser Trp Cys Leu Ser Leu Val Ala Gly Arg Leu Ala Val Asn Ser Leu
                20                  25                  30

Gln Ala Val Gly Pro Ser Gly Arg Gly
            355                 40

(2) INFORMATION FOR SEQ ID NO:383:

(i) SEQUENCE CHARACTERISTICS:
        (A) LENGTH: 67 amino acids
        (B) TYPE: amino acid
        (D) TOPOLOGY: linear (ii) MOLECULE TYPE: protein (xi) SEQUENCE DESCRIPTION: SEQ ID NO:383:

Trp Glu Ser Gly Ala Pro Asp Leu Pro Pro Arg Trp Gly Glu Arg Gly
1               5                   10                  15

Pro Gly Pro Ala Gly Trp Lys Ala Arg Asn Arg Ser Ile Phe Leu Lys
                20                  25                  30

-continued

Val Glu Glu Gly Val Arg Leu Ser Val Arg Ser Val Arg Lys Ala Ser
         35                  40                  45

Gly Cys Leu Val Leu Gly Phe Val Gly Gly Lys Ser Gln Leu Gly Val
     50                  55                  60

Lys Ala Leu
 65

(2) INFORMATION FOR SEQ ID NO:384:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO:384:

Asp Arg Leu Ile Pro Val Thr Ala Ala Pro Glu Pro Ala Pro Arg Xaa
 1               5                  10                  15

Phe Gly His Gly Pro Gln Val Gly Gly Thr Gly Val Asn Asn Pro Pro
             20                  25                  30

Thr Glu Ala Ser Val Val Lys Arg Arg Arg Ser Pro Glu Ile Ala Thr
         35                  40                  45

Thr Pro His Val Arg Glu Arg Arg Gln Asn Leu Arg Asp Ser Tyr Ala
     50                  55                  60

(2) INFORMATION FOR SEQ ID NO:385:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:385:

Gln Ser Gln Trp Gly Ala Gly Asp Gln Leu Ile Thr Cys Pro Ala Ser
 1               5                  10                  15

Ser Ser (2) INFORMATION FOR SEQ ID NO:386:

(i) SEQUENCE CHARACTERISTICS:
        (A) LENGTH: 25 amino acids
        (B) TYPE: amino acid
        (D) TOPOLOGY: linear (ii) MOLECULE TYPE: protein (xi) SEQUENCE DESCRIPTION: SEQ ID NO:386:

Asp Trp Pro Lys Gly Ser His Gly Ala Thr Lys Ala Ala Gln Arg Cys
 1               5                  10                  15

Met Arg Gln Gly Glu Lys Ser Phe Gly
             20                  25

(2) INFORMATION FOR SEQ ID NO:387:

(i) SEQUENCE CHARACTERISTICS:
        (A) LENGTH: 2972 amino acids
        (B) TYPE: amino acid
        (D) TOPOLOGY: linear (ii) MOLECULE TYPE: protein (xi) SEQUENCE DESCRIPTION: SEQ ID NO:387:

-continued

```
Pro Leu Val Ala Ile Pro Ser Leu Arg Ser Met Ser Val Val Asp Thr
 1               5                  10                  15

Phe Thr Met Ala Trp Leu Trp Leu Val Cys Phe Pro Leu Ala Gly
             20                  25                  30

Gly Val Leu Phe Asn Ser Arg His Gln Cys Phe Asn Gly Asp His Tyr
             35                  40                  45

Val Leu Ser Asn Cys Cys Ser Arg Asp Glu Val Tyr Phe Cys Phe Gly
         50                  55                  60

Asp Gly Cys Leu Val Ala Tyr Gly Cys Thr Val Cys Thr Gln Ser Cys
 65                  70                  75                  80

Trp Lys Leu Tyr Arg Pro Gly Val Ala Thr Arg Pro Gly Ser Glu Pro
                 85                  90                  95

Gly Glu Leu Leu Gly Arg Phe Gly Ser Val Ile Gly Pro Val Ser Ala
                100                 105                 110

Ser Ala Tyr Thr Ala Gly Val Leu Gly Leu Gly Glu Pro Tyr Ser Leu
            115                 120                 125

Ala Phe Leu Gly Thr Phe Leu Thr Ser Arg Leu Ser Arg Ile Pro Asn
        130                 135                 140

Val Thr Cys Val Lys Ala Cys Asp Leu Glu Phe Thr Tyr Pro Gly Leu
145                 150                 155                 160

Ser Ile Asp Phe Asp Trp Ala Phe Thr Lys Ile Leu Gln Leu Pro Ala
                165                 170                 175

Lys Leu Trp Arg Gly Leu Thr Xaa Xaa Pro Val Leu Ser Leu Leu Val
                180                 185                 190

Ile Leu Met Leu Val Leu Glu Gln Arg Leu Leu Ile Ala Phe Leu Leu
            195                 200                 205

Leu Leu Val Val Gly Glu Ala Gln Arg Gly Met Phe Asp Asn Cys Val
210                 215                 220

Cys Gly Tyr Trp Gly Gly Lys Arg Pro Pro Ser Val Thr Pro Leu Tyr
225                 230                 235                 240

Arg Gly Asn Gly Thr Val Val Cys Asp Cys Asp Phe Gly Lys Met His
                245                 250                 255

Trp Ala Pro Pro Leu Cys Ser Xaa Leu Val Trp Arg Asp Gly His Arg
                260                 265                 270

Arg Gly Thr Val Arg Asp Leu Pro Pro Val Cys Pro Arg Glu Val Leu
            275                 280                 285

Gly Thr Val Thr Val Met Cys Gln Trp Gly Ser Ala Tyr Trp Ile Trp
        290                 295                 300

Arg Phe Gly Asp Trp Val Ala Leu Tyr Asp Glu Leu Pro Arg Ser Ala
305                 310                 315                 320

Leu Cys Thr Phe Phe Ser Gly His Gly Pro Gln Pro Lys Asp Leu Ser
                325                 330                 335

Val Leu Asn Pro Ser Gly Ala Pro Cys Ala Ser Cys Val Val Asp Gln
            340                 345                 350

Arg Pro Leu Lys Cys Gly Ser Cys Val Arg Asp Cys Trp Glu Thr Gly
        355                 360                 365

Gly Pro Gly Phe Asp Glu Cys Gly Val Gly Thr Arg Met Thr Lys His
370                 375                 380

Leu Glu Ala Val Leu Val Asp Gly Gly Val Glu Ser Lys Val Thr Thr
385                 390                 395                 400

Pro Lys Gly Glu Arg Pro Lys Tyr Ile Gly Gln His Gly Val Gly Thr
                405                 410                 415
```

-continued

```
Tyr Tyr Gly Ala Val Arg Ser Leu Asn Ile Ser Tyr Leu Val Thr Glu
            420                 425                 430

Val Gly Gly Tyr Trp His Ala Leu Lys Cys Pro Cys Asp Phe Val Pro
            435                 440                 445

Arg Val Leu Pro Glu Arg Ile Pro Gly Arg Pro Val Asn Ala Cys Leu
            450                 455                 460

Ala Gly Lys Ser Pro His Pro Phe Ala Ser Trp Ala Pro Gly Gly Phe
465                 470                 475                 480

Tyr Ala Pro Val Phe Thr Lys Cys Asn Trp Pro Lys Thr Ser Gly Val
                485                 490                 495

Asp Val Cys Pro Gly Phe Ala Phe Asp Phe Pro Gly Asp His Asn Gly
                500                 505                 510

Phe Ile His Val Lys Gly Asn Arg Gln Gln Val Tyr Ser Gly Gln Arg
            515                 520                 525

Arg Ser Ser Pro Ala Trp Leu Leu Thr Asp Met Val Leu Ala Leu Leu
            530                 535                 540

Val Val Met Lys Leu Ala Glu Ala Arg Val Val Pro Leu Phe Met Leu
545                 550                 555                 560

Ala Met Trp Trp Trp Leu Asn Gly Ala Ser Ala Ala Thr Ile Val Ile
                565                 570                 575

Ile His Pro Thr Val Thr Lys Ser Thr Glu Ser Val Pro Leu Trp Thr
            580                 585                 590

Pro Pro Thr Val Pro Thr Pro Ser Cys Pro Asn Ser Thr Thr Gly Val
            595                 600                 605

Ala Asp Ser Thr Tyr Asn Ala Gly Cys Tyr Met Val Ala Gly Leu Ala
            610                 615                 620

Ala Gly Ala Gln Ala Val Trp Gly Ala Ala Asn Asp Gly Ala Gln Ala
625                 630                 635                 640

Val Val Gly Gly Ile Trp Pro Ala Trp Leu Lys Leu Arg Ser Phe Ala
                645                 650                 655

Ala Gly Leu Ala Trp Leu Ser Asn Val Gly Ala Tyr Leu Pro Val Val
            660                 665                 670

Glu Ala Xaa Leu Ala Pro Glu Leu Val Cys Thr Pro Val Val Gly Trp
            675                 680                 685

Ala Ala Gln Glu Trp Trp Phe Thr Gly Cys Leu Gly Val Met Cys Val
            690                 695                 700

Val Ala Tyr Leu Asn Val Leu Gly Ser Xaa Arg Ala Ala Val Leu Val
705                 710                 715                 720

Ala Met His Phe Ala Arg Gly Ala Leu Pro Leu Val Leu Val Val Ala
                725                 730                 735

Ala Gly Xaa Thr Arg Glu Arg His Ser Val Leu Gly Leu Glu Val Cys
            740                 745                 750

Phe Asp Leu Asp Gly Gly Asp Trp Xaa Asp Ala Ser Trp Ser Trp Gly
            755                 760                 765

Leu Ala Gly Val Val Ser Trp Ala Leu Leu Val Gly Gly Leu Met Thr
            770                 775                 780

His Gly Gly Arg Ser Ala Arg Xaa Thr Trp Xaa Ala Arg Trp Ala Val
785                 790                 795                 800

Asn Xaa Gln Arg Val Xaa Arg Trp Val Asn Asn Ser Pro Val Gly Xaa
                805                 810                 815

Phe Xaa Arg Trp Xaa Xaa Ala Trp Lys Xaa Trp Xaa Xaa Val Ala Trp
            820                 825                 830

Phe Phe Pro Gln Thr Val Ala Thr Xaa Ser Val Ile Phe Ile Leu Cys
```

```
                835                 840                 845
Leu Ser Ser Leu Asp Val Ile Asp Phe Ile Leu Xaa Val Leu Leu Val
850                 855                 860

Asn Ser Pro Asn Leu Ala Arg Leu Ala Xaa Val Leu Asp Ser Leu Ala
865                 870                 875                 880

Xaa Ala Glu Glu Arg Leu Ala Cys Ser Trp Leu Val Gly Val Leu Arg
                885                 890                 895

Lys Arg Gly Val Leu Leu Tyr Glu His Xaa Gly His Thr Ser Arg Arg
                900                 905                 910

Gly Ala Ala Arg Leu Arg Glu Trp Xaa Phe Ala Xaa Glu Xaa Val Xaa
                915                 920                 925

Ile Thr Lys Glu Asp Xaa Xaa Ile Val Arg Asp Ser Ala Arg Val Leu
                930                 935                 940

Gly Cys Gly Gln Leu Val His Gly Lys Pro Val Val Ala Arg Arg Gly
945                 950                 955                 960

Asp Glu Val Leu Ile Gly Cys Val Asn Ser Arg Phe Asp Leu Pro Pro
                965                 970                 975

Gly Phe Val Pro Thr Ala Pro Val Xaa Leu His Xaa Xaa Gly Xaa Xaa
                980                 985                 990

Xaa Xaa Gly Val Val Lys Xaa Ser Met Thr Gly Lys Asp Pro Ser Glu
                995                1000                1005

His His Xaa Asn Val Val Xaa Gly Thr Ser Thr Xaa Arg Ser Met
                1010                1015                1020

Gly Cys Cys Val Asn Gly Val Val Tyr Xaa Thr Tyr His Xaa Thr Asn
1025                1030                1035                1040

Ala Xaa Xaa Met Ala Gly Xaa Phe Xaa Xaa Val Xaa Ala Arg Trp Trp
                1045                1050                1055

Xaa Ala Xaa Asp Asp Val Thr Xaa Tyr Pro Leu Xaa Asn Xaa Ala Ser
                1060                1065                1070

Cys Xaa Xaa Xaa Xaa Lys Cys Gln Pro Thr Gly Val Trp Val Ile Arg
                1075                1080                1085

Asn Asp Gly Ala Leu Cys His Gly Thr Leu Gly Lys Val Val Asp Leu
                1090                1095                1100

Asp Met Pro Ala Glu Leu Ser Asp Phe Arg Gly Ser Ser Gly Ser Pro
1105                1110                1115                1120

Ile Leu Cys Asp Glu Gly His Ala Val Gly Met Leu Ile Ser Val Leu
                1125                1130                1135

His Arg Gly Ser Arg Val Ser Ser Val Arg Tyr Thr Lys Pro Trp Glu
                1140                1145                1150

Thr Leu Pro Arg Glu Ile Glu Ala Arg Ser Glu Ala Pro Pro Val Pro
                1155                1160                1165

Gly Thr Thr Gly Tyr Arg Glu Ala Pro Leu Phe Leu Pro Thr Gly Ala
                1170                1175                1180

Gly Lys Ser Thr Arg Val Pro Asn Glu Tyr Val Lys Ala Gly His Xaa
1185                1190                1195                1200

Val Leu Val Leu Asn Pro Ser Ile Ala Thr Val Arg Ala Met Gly Pro
                1205                1210                1215

Tyr Met Glu Lys Leu Thr Gly Lys His Pro Ser Val Tyr Cys Gly His
                1220                1225                1230

Asp Thr Thr Ala Tyr Ser Arg Thr Thr Asp Ser Ser Leu Thr Tyr Cys
                1235                1240                1245

Thr Tyr Gly Arg Phe Met Ala Asn Pro Arg Lys Tyr Leu Arg Gly Asn
                1250                1255                1260
```

```
Asp Val Val Ile Cys Asp Glu Leu His Val Thr Asp Pro Thr Ser Ile
1265                1270                1275                1280

Leu Gly Met Gly Arg Ala Arg Leu Leu Ala Arg Glu Cys Gly Val Arg
            1285                1290                1295

Leu Leu Leu Phe Ala Thr Ala Thr Pro Pro Val Ser Pro Met Ala Lys
            1300                1305                1310

His Glu Ser Ile His Glu Glu Met Leu Gly Ser Glu Gly Glu Val Pro
            1315                1320                1325

Phe Tyr Cys Gln Phe Leu Pro Leu Ser Arg Tyr Ala Thr Gly Arg His
            1330                1335                1340

Leu Leu Phe Cys His Ser Lys Val Xaa Cys Thr Arg Leu Ser Ser Ala
1345                1350                1355                1360

Leu Ala Ser Phe Gly Val Asn Thr Val Val Tyr Phe Arg Gly Lys Glu
            1365                1370                1375

Thr Asp Ile Pro Thr Gly Asp Val Cys Val Cys Ala Thr Asp Ala Leu
            1380                1385                1390

Ser Thr Gly Tyr Thr Gly Asn Phe Asp Thr Val Thr Asp Cys Gly Leu
            1395                1400                1405

Met Val Glu Glu Val Val Glu Val Thr Leu Asp Pro Thr Ile Thr Ile
            1410                1415                1420

Gly Val Lys Thr Val Pro Ala Pro Ala Glu Leu Arg Ala Gln Arg Arg
1425                1430                1435                1440

Gly Arg Cys Gly Arg Gly Lys Ala Gly Thr Tyr Tyr Gln Ala Leu Met
            1445                1450                1455

Ser Ser Ala Pro Ala Gly Xaa Val Arg Ser Gly Ala Leu Trp Ala Ala
            1460                1465                1470

Val Glu Ala Xaa Val Ser Trp Tyr Gly Leu Glu Pro Asp Ala Ile Gly
            1475                1480                1485

Asp Leu Leu Arg Ala Tyr Asp Ser Cys Pro Tyr Thr Ala Ala Ile Ser
            1490                1495                1500

Ala Ser Ile Gly Glu Ala Ile Ala Phe Phe Thr Xaa Leu Val Pro Met
1505                1510                1515                1520

Arg Asn Tyr Pro Gln Val Val Trp Ala Lys Gln Lys Xaa His Asn Trp
            1525                1530                1535

Pro Leu Leu Val Gly Val Gln Arg His Met Cys Glu Asp Ala Gly Cys
            1540                1545                1550

Gly Xaa Pro Ala Asn Gly Pro Glu Trp Ser Gly Ile Arg Gly Lys Gly
            1555                1560                1565

Pro Val Pro Leu Leu Cys Arg Trp Gly Gly Asp Leu Pro Glu Ser Val
            1570                1575                1580

Ala Pro His His Trp Val Asp Asp Leu Gln Ala Arg Leu Gly Val Ala
1585                1590                1595                1600

Glu Gly Tyr Thr Pro Cys Ile Ala Gly Pro Val Leu Leu Val Gly Leu
            1605                1610                1615

Ala Met Ala Gly Gly Ala Ile Leu Ala His Trp Thr Gly Ser Leu Val
            1620                1625                1630

Val Val Thr Ser Trp Val Val Asn Gly Asn Gly Asn Pro Leu Ile Gln
            1635                1640                1645

Ser Ala Ser Arg Gly Val Xaa Xaa Ser Gly Pro Tyr Pro Val Pro Pro
1650                1655                1660

Asp Gly Gly Glu Arg Tyr Pro Ser Asp Ile Lys Pro Xaa Thr Glu Ala
1665                1670                1675                1680
```

-continued

```
Val Thr Thr Leu Glu Thr Ala Cys Xaa Trp Gly Pro Ala Ala Xaa Ser
            1685                1690                1695

Leu Ala Tyr Val Lys Ala Cys Glu Thr Gly Thr Met Leu Ala Asp Xaa
            1700                1705                1710

Ala Ser Ala Ala Trp Gln Ala Trp Ala Ala Asn Asn Phe Val Pro Pro
            1715                1720                1725

Pro Ala Ser His Ser Thr Ser Leu Xaa Gln Ser Leu Xaa Ala Ala Phe
            1730                1735                1740

Thr Ser Ala Trp Asp Ser Val Phe Thr His Gly Arg Ser Leu Leu Val
1745                1750                1755                1760

Gly Phe Thr Ala Ala Tyr Gly Ala Arg Arg Asn Pro Pro Leu Gly Val
            1765                1770                1775

Gly Ala Ser Phe Leu Leu Gly Met Ser Ser Ser His Xaa Thr His Val
            1780                1785                1790

Arg Leu Ala Ala Ala Leu Leu Leu Gly Val Gly Gly Thr Val Leu Gly
            1795                1800                1805

Thr Pro Ala Thr Gly Leu Ala Met Ala Gly Ala Tyr Phe Xaa Gly Gly
            1810                1815                1820

Ser Val Thr Ala Asn Trp Leu Ser Ile Ile Val Ala Leu Ile Gly Gly
1825                1830                1835                1840

Trp Glu Gly Xaa Xaa Asn Ala Ala Ser Leu Thr Phe Xaa Leu Leu Xaa
            1845                1850                1855

Gly Lys Leu Gln Xaa Xaa Xaa Ala Trp Cys Xaa Val Xaa Cys Xaa Ala
            1860                1865                1870

Ser Pro Gly Ala Ser Val Xaa Gly Val Xaa Xaa Xaa Xaa Xaa Xaa Trp
            1875                1880                1885

Ser Val Xaa Lys Gly Val Xaa Xaa Xaa Trp Val Asn Arg Xaa Leu Thr
            1890                1895                1900

Met Met Pro Arg Ser Ser Val Met Pro Asp Asp Phe Phe Leu Lys Asp
1905                1910                1915                1920

Glu Phe Val Thr Lys Val Ser Thr Val Leu Arg Lys Leu Ser Leu Ser
            1925                1930                1935

Arg Trp Ile Met Thr Leu Val Asp Lys Arg Glu Met Glu Met Glu Xaa
            1940                1945                1950

Pro Ala Ser Gln Ile Val Trp Asp Leu Leu Asp Trp Cys Ile Arg Xaa
            1955                1960                1965

Gly Arg Phe Leu Tyr Asn Lys Xaa Met Phe Ala Leu Pro Arg Leu Arg
            1970                1975                1980

Leu Pro Leu Ile Gly Cys Ser Thr Gly Trp Gly Pro Trp Glu Gly
1985                1990                1995                2000

Asn Gly His Leu Glu Thr Arg Cys Thr Cys Gly Cys Val Ile Thr Gly
            2005                2010                2015

Asp Ile His Asp Gly Ile Leu His Asp Leu His Tyr Thr Ser Leu Leu
            2020                2025                2030

Cys Arg His Tyr Tyr Lys Arg Thr Val Pro Val Gly Val Met Gly Asn
            2035                2040                2045

Ala Glu Gly Ala Val Pro Leu Val Pro Thr Gly Gly Ile Arg Thr
2050                2055                2060

Tyr Gln Ile Gly Thr Ser Asp Trp Phe Glu Ala Val Val His Gly
2065                2070                2075                2080

Thr Ile Thr Val His Ala Thr Ser Cys Tyr Glu Leu Lys Ala Ala Asp
            2085                2090                2095

Val Arg Arg Ala Val Arg Ala Gly Pro Thr Tyr Val Gly Gly Val Pro
```

-continued

```
                2100                2105                2110
Cys Ser Trp Ser Ala Pro Cys Thr Ala Pro Ala Leu Val Tyr Arg Leu
            2115                2120            2125
Gly Gln Gly Ile Lys Ile Asp Gly Ala Arg Arg Leu Leu Pro Cys Asp
        2130                2135            2140
Leu Ala Gln Gly Ala Arg His Pro Pro Val Ser Gly Ser Val Ala Gly
2145                2150                2155                2160
Ser Gly Trp Thr Asp Glu Asp Glu Arg Asp Leu Val Glu Thr Lys Ala
            2165                2170            2175
Ala Ala Ile Glu Ala Ile Gly Ala Ala Leu His Leu Pro Ser Pro Glu
            2180                2185            2190
Ala Ala Gln Ala Ala Leu Glu Ala Leu Glu Glu Ala Ala Val Ser Leu
        2195                2200            2205
Leu Pro His Val Pro Val Ile Met Gly Asp Asp Cys Ser Cys Arg Asp
    2210                2215                2220
Glu Ala Phe Gln Gly His Phe Ile Pro Glu Pro Asn Val Thr Glu Val
2225                2230                2235                2240
Pro Ile Glu Pro Thr Val Gly Asp Val Glu Ala Leu Lys Leu Arg Ala
            2245                2250            2255
Ala Asp Leu Thr Ala Arg Leu Gln Asp Leu Glu Ala Met Ala Leu Ala
            2260                2265            2270
Arg Ala Glu Ser Ile Glu Asp Ala Arg Ala Ala Ser Met Pro Ser Leu
        2275                2280            2285
Thr Glu Val Asp Ser Met Pro Ser Leu Glu Ser Ser Pro Cys Ser Ser
        2290                2295            2300
Phe Glu Gln Ile Ser Leu Thr Glu Ser Asp Pro Glu Thr Val Val Glu
2305                2310                2315                2320
Ala Gly Leu Pro Leu Glu Phe Val Asn Ser Asn Thr Gly Pro Ser Pro
            2325                2330            2335
Ala Arg Arg Ile Val Arg Ile Arg Gln Ala Cys Cys Cys Asp Arg Ser
            2340                2345            2350
Thr Met Lys Ala Met Pro Leu Ser Phe Thr Val Gly Glu Cys Leu Phe
        2355                2360            2365
Val Thr Arg Tyr Asp Pro Asp Gly His Gln Leu Phe Asp Glu Arg Gly
        2370                2375            2380
Pro Ile Glu Val Ser Thr Pro Ile Cys Glu Val Ile Gly Asp Ile Arg
2385                2390                2395                2400
Leu Gln Cys Asp Gln Ile Glu Glu Thr Pro Thr Ser Tyr Ser Tyr Ile
            2405                2410            2415
Trp Ser Gly Ala Pro Leu Gly Thr Gly Arg Ser Val Pro Gln Pro Met
            2420                2425            2430
Thr Arg Pro Ile Gly Thr His Leu Thr Cys Asp Thr Thr Lys Val Tyr
        2435                2440            2445
Val Thr Asp Pro Asp Arg Ala Ala Glu Arg Ala Glu Lys Val Thr Ile
    2450                2455                2460
Trp Arg Gly Asp Arg Lys Tyr Asp Lys His Tyr Glu Ala Val Val Glu
2465                2470                2475                2480
Ala Val Leu Lys Lys Ala Ala Thr Lys Ser His Gly Trp Thr Tyr
            2485                2490            2495
Ser Gln Ala Ile Ala Lys Val Arg Arg Arg Ala Ala Ala Gly Tyr Gly
            2500                2505            2510
Ser Lys Val Thr Ala Ser Thr Leu Ala Thr Gly Trp Pro His Val Glu
        2515                2520            2525
```

-continued

```
Glu Met Leu Asp Lys Ile Ala Arg Gly Gln Val Pro Phe Thr Phe
    2530                2535                2540
Val Thr Lys Arg Glu Val Phe Phe Ser Lys Thr Thr Arg Lys Pro Pro
2545                2550                2555                2560
Arg Phe Ile Val Phe Pro Leu Asp Phe Arg Ile Ala Glu Lys Met
            2565                2570                2575
Ile Leu Gly Asp Pro Gly Ile Val Ala Lys Ser Ile Leu Gly Asp Ala
            2580                2585                2590
Tyr Leu Phe Gln Tyr Thr Pro Asn Gln Arg Val Lys Ala Leu Val Lys
            2595                2600                2605
Ala Trp Glu Gly Lys Leu His Pro Ala Ala Ile Thr Val Asp Ala Thr
            2610                2615                2620
Cys Phe Asp Ser Ser Ile Asp Glu His Asp Met Gln Val Glu Ala Ser
2625                2630                2635                2640
Val Phe Ala Ala Ala Ser Asp Asn Pro Ser Met Val His Ala Leu Cys
            2645                2650                2655
Lys Tyr Tyr Ser Gly Gly Pro Met Val Ser Pro Asp Gly Val Pro Leu
            2660                2665                2670
Gly Tyr Arg Gln Cys Arg Ser Ser Gly Val Leu Thr Thr Ser Ser Ala
            2675                2680                2685
Asn Ser Ile Thr Cys Tyr Ile Lys Val Ser Ala Ala Cys Arg Arg Val
            2690                2695                2700
Gly Ile Lys Ala Pro Ser Phe Phe Ile Ala Gly Asp Asp Cys Leu Ile
2705                2710                2715                2720
Ile Tyr Glu Asn Asp Gly Thr Asp Pro Cys Pro Ala Leu Lys Ala Ala
            2725                2730                2735
Leu Ala Asn Tyr Gly Tyr Arg Cys Glu Pro Thr Lys His Ala Ser Leu
            2740                2745                2750
Asp Thr Ala Glu Cys Cys Ser Ala Tyr Leu Ala Glu Cys Val Ala Gly
            2755                2760                2765
Gly Ala Lys Arg Trp Trp Leu Ser Thr Asp Met Arg Lys Pro Leu Ala
            2770                2775                2780
Arg Ala Ser Ser Glu Tyr Ser Asp Pro Ile Gly Ser Ala Leu Gly Thr
2785                2790                2795                2800
Ile Leu Met Tyr Pro Arg His Pro Ile Val Arg Tyr Val Leu Ile Pro
            2805                2810                2815
His Val Leu Ile Met Ala Tyr Arg Ser Gly Ser Thr Pro Asp Glu Leu
            2820                2825                2830
Val Met Cys Gln Val Gln Gly Asn His Tyr Ser Phe Pro Leu Arg Leu
            2835                2840                2845
Leu Pro Arg Val Leu Val Ser Leu His Gly Pro Trp Cys Leu Gln Val
            2850                2855                2860
Thr Thr Asp Ser Thr Lys Thr Arg Met Glu Ala Gly Ser Xaa Leu Arg
2865                2870                2875                2880
Asp Leu Gly Met Lys Ser Leu Ala Trp His Arg Arg Ala Gly Asn
            2885                2890                2895
Val Arg Thr Arg Leu Leu Arg Gly Gly Lys Glu Trp Gly His Leu Ala
            2900                2905                2910
Arg Ala Leu Leu Trp Xaa Pro Xaa Leu Lys Glu Xaa Pro Xaa Pro Ile
            2915                2920                2925
Asn Ser Leu Pro Gly Phe Gln Leu Ala Thr Pro Tyr Glu His His Glu
            2930                2935                2940
```

```
Glu Val Leu Ile Ser Ile Lys Ser Arg Pro Pro Trp Ile Arg Trp Ile
2945                2950                2955                2960

Leu Gly Ala Cys Leu Ser Leu Leu Ala Ala Leu Leu
            2965                2970
```

(2) INFORMATION FOR SEQ ID NO:388:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:388:

```
Ile Arg Ser Arg Gln
1               5
```

(2) INFORMATION FOR SEQ ID NO:389:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:389:

```
Asp Leu Arg Val Gly
1               5
```

(2) INFORMATION FOR SEQ ID NO:390:

(i) SEQUENCE CHARACTERISTICS:
        (A) LENGTH: 9143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:390:

```
ACCACAAACA CTCCAGTTTG TTACACTCCG CTAGGAATGC TCCTGGAGCA CCCCCCCTAG      60
CAGGGCGTGG GGGATTTCCC CTGCCCGTCT GCAGAAGGGT GGAGCCAACC ACCTTAGTAT     120
GTAGGCGGCG GGACTCATGA CGCTCGCGTG ATGACAAGCG CCAAGCTTGA CTTGGATGGC     180
CCTGATGGGC GTTCATGGGT TCGGTGGTGG TGGCGCTTTA GGCAGCCTCC ACGCCCACCA     240
CCTCCCAGAT AGAGCGGCGG CACTGTAGGG AAGACCGGGG ACCGGTCACT ACCAAGGACG     300
CAGACCTCTT TTTGAGTATC ACGCCTCCGG AAGTAGTTGG GCAAGCCCAC CTATATGTGT     360
TGGGATGGTT GGGGTTAGCC ATCCATACCG TACTGCCTGA TAGGGTCCTT GCGAGGGGAT     420
CTGGGAGTCT CGTAGACCGT AGCACATGCC TGTTATTTCT ACTCAAACAA GTCCTGTACC     480
TGCGCCCAGA ACGCGCAAGA ACAAGCAGAC GCAGGCTTCA TATCCTGTGT CCATTAAAAC     540
ATCTGTTGAA AGGGGACAAC GAGCAAAGCG CAAAGTCCAG CGCGATGCTC GGCCTCGTAA     600
TTACAAAATT GCTGGTATCC ATGATGGCTT GCAGACATTG GCTCAGGCTG CTTTGCCAGC     660
TCATGGTTGG GGACGCCAAG ACCCTCGCCA TAAGTCTCGC AATCTTGGAA TCCTTCTGGA     720
TTACCCTTTG GGGTGGATTG GTGATGTTAC AACTCACACA CCTCTAGTAG GCCCGCTGGT     780
GGCAGGAGCG GTCGTTCGAC CAGTCTGCCA GATAGTACGC TTGCTGGAGG ATGGAGTCAA     840
CTGGGCTACT GGTTGGTTCG GTGTCCACCT TTTTGTGGTA TGTCTGCTAT CTTTGGCCTG     900
```

```
TCCCTGTAGT GGGGCGCGGG TCACTGACCC AGACACAAAT ACCACAATCC TGACCAATTG    960

CTGCCAGCGT AATCAGGTTA TCTATTGTTC TCCTTCCACT TGCCTACACG AGCCTGGTTG   1020

TGTGATCTGC GCGGACGAGT GCTGGGTTCC CGCCAATCCG TACATCTCAC ACCCTTCCAA   1080

TTGGACTGGC ACGGACTCCT TCTTGGCTGA CCACATTGAT TTTGTTATGG GCGCTCTTGT   1140

GACCTGTGAC GCCCTTGACA TTGGTGAGTT GTGTGGTGCG TGTGTATTAG TCGGTGACTG   1200

GCTTGTCAGG CACTGGCTTA TTCACATAGA CCTCAATGAA ACTGGTACTT GTTACCTGGA   1260

AGTGCCCACT GGAATAGATC CTGGGTTCCT AGGGTTTATC GGGTGGATGG CCGGCAAGGT   1320

CGAGGCTGTC ATCTTCTTGA CCAAACTGGC TTCACAAGTA CCATACGCTA TTGCGACTAT   1380

GTTTAGCAGT GTACACTACC TGGCGGTTGG CGCTCTGATC TACTATGCCT CTCGGGGCAA   1440

GTGGTATCAG TTGCTCCTAG CGCTTATGCT TTACATAGAA GCGACCTCTG GAAACCCTAT   1500

CAGGGTGCCC ACTGGATGCT CAATAGCTGA GTTTTGCTCG CCTTTGATGA TACCATGTCC   1560

TTGCCACTCT TATTTGAGTG AGAATGTGTC AGAAGTCATT TGTTACAGTC CAAAGTGGAC   1620

CAGGCCTGTC ACTCTAGAGT ATAACAACTC CATATCTTGG TACCCCTATA CAATCCCTGG   1680

TGCGAGGGGA TGTATGGTTA AATTCAAAAA TAACACATGG GGTTGCTGCC GTATTCGCAA   1740

TGTGCCATCG TACTGCACTA TGGGCACTGA TGCAGTGTGG AACGACACTC GCAACACTTA   1800

CGAAGCATGC GGTGTAACAC CATGGCTAAC AACCGCATGG CACAACGGCT CAGCCCTGAA   1860

ATTGGCTATA TTACAATACC CTGGGTCTAA AGAAATGTTT AAACCTCATA ATTGGATGTC   1920

AGGCCATTTG TATTTTGAGG GATCAGATAC CCCTATAGTT TACTTTTATG ACCCTGTGAA   1980

TTCCACTCTC CTACCACCGG AGAGGTGGGC TAGGTTGCCC GGTACCCCAC CTGTGGTACG   2040

TGGTTCTTGG TTACAGGTTC CGCAAGGGTT TTACAGTGAT GTGAAAGACC TAGCCACAGG   2100

ATTGATCACC AAAGACAAAG CCTGGAAAAA TTATCAGGTC TTATATTCCG CCACGGGTGC   2160

TTTGTCTCTT ACGGGAGTTA CCACCAAGGC CGTGGTGCTA ATTCTGTTGG GGTTGTGTGG   2220

CAGCAAGTAT CTTATTTTAG CCTACCTCTG TTACTTGTCC CTTTGTTTTG GGCGCGCTTC   2280

TGGTTACCCT TTGCGTCCTG TGCTCCCATC CCAGTCGTAT CTCCAAGCTG GCTGGGATGT   2340

TTTGTCTAAA GCTCAAGTAG CTCCTTTTGC TTTGATTTTC TTCATCTGTT GCTATCTCCG   2400

CTGCAGGCTA CGTTATGCTG CCCTTTTAGG GTTTGTGCCC ATGGCTGCGG GCTTGCCCCT   2460

AACTTTCTTT GTTGCAGCAG CTGCTGCCCA ACCAGATTAT GACTGGTGGG TGCGACTGCT   2520

AGTGGCAGGG TTAGTTTTGT GGGCCGGCCG TGACCGTGGT CCACGTATAG CTCTGCTTGT   2580

AGGTCCTTGG CCTCTGGTAG CGCTTTTAAC CCTCTTGCAT TTGGCTACGC CTGCTTCAGC   2640

TTTTGACACC GAGATAATTG GAGGGCTGAC AATACCACCT GTAGTAGCAT TAGTTGTCAT   2700

GTCTCGTTTT GGCTTCTTTG CTCACTTGTT ACCTCGCTGT GCTTTAGTTA ACTCCTATCT   2760

TTGGCAACGT TGGGAGAATT GGTTTTGGAA CGTTACACTA AGACCGGAGA GGTTTCTCCT   2820

TGTGCTGGTT TGTTTCCCCG GTGCGACATA TGACACGCTG GTGACTTTCT GTGTGTGTCA   2880

CGTAGCTCTT CTATGTTTAA CATCCAGTGC AGCATCGTTC TTTGGGACTG ACTCTAGGGT   2940

TAGGGCCCAT AGAATGTTGG TGCGTCTCGG AAAGTGTCAT GCTTGGTATT CTCATTATGT   3000

TCTTAAGTTT TTCCTCTTAG TGTTTGGTGA GAATGGTGTG TTTTTCTATA AGCACTTGCA   3060

TGGTGATGTC TTGCCTAATG ATTTTGCCTC GAAACTACCA TTGCAAGAGC CATTTTTCCC   3120

TTTTGAAGGC AAGGCAAGGG TCTATAGGAA TGAAGGAAGA CGCTTGGCGT GTGGGGACAC   3180

GGTTGATGGT TTGCCCGTTG TTGCGCGTCT CGGCGACCTT GTTTTCGCAG GGTTAGCTAT   3240

GCCGCCAGAT GGGTGGGCCA TTACCGCACC TTTTACGCTG CAGTGTCTCT CTGAACGTGG   3300
```

-continued

```
CACGCTGTCA GCGATGGCAG TGGTCATGAC TGGTATAGAC CCCCGAACTT GGACTGGAAC    3360
TATCTTCAGA TTAGGATCTC TGGCCACTAG CTACATGGGA TTTGTTTGTG ACAACGTGTT    3420
GTATACTGCT CACCATGGCA GCAAGGGGCG CCGGTTGGCC CATCCCACAG GCTCCATACA    3480
CCCAATAACC GTTGACGCGG CTAATGACCA GGACATCTAT CAACCACCAT GTGGAGCTGG    3540
GTCCCTTACT CGGTGCTCTT GCGGGAGAC CAAGGGGTAT CTGGTAACAC GACTGGGGTC     3600
ATTGGTTGAG GTCAACAAAT CCGATGACCC TTATTGGTGT GTGTGCGGGG CCCTTCCCAT    3660
GGCTGTTGCC AAGGGTTCTT CAGGTGCCCC GATTCTGTGC TCCTCCGGGC ATGTTATTGG    3720
GATGTTCACC GCTGCTAGAA ATTCTGGCGG TTCAGTCAGC CAGATTAGGG TTAGGCCGTT    3780
GGTGTGTGCT GGATACCATC CCCAGTACAC AGCACATGCC ACTCTTGATA CAAAACCTAC    3840
TGTGCCTAAC GAGTATTCAG TGCAAATTTT AATTGCCCCC ACTGGCAGCG GCAAGTCAAC    3900
CAAATTACCA CTTTCTTACA TGCAGGAGAA GTATGAGGTC TTGGTCCTAA ATCCCAGTGT    3960
GGCTACAACA GCATCAATGC CAAAGTACAT GCACGCGACG TACGGCGTGA ATCCAAATTG    4020
CTATTTTAAT GGCAAATGTA CCAACACAGG GGCTTCACTT ACGTACAGCA CATATGGCAT    4080
GTACCTGACC GGAGCATGTT CCCGGAACTA TGACGTCATC ATTTGTGACG AATGCCATGC    4140
TACCGATCA ACCACCGTGT TGGGCATTGG AAAGGTTCTA ACCGAAGCTC CATCCAAAAA     4200
TGTTAGGCTA GTGGTTCTTG CCACGGCTAC CCCCCCTGGA GTAATCCCTA CACCACATGC    4260
CAACATAACT GAGATTCAAT TAACCGATGA AGGCACTATC CCCTTTCATG GAAAAAGAT    4320
TAAGGAGGAA AATCTGAAGA AAGGGAGACA CCTTATCTTT GAGGCTACCA AAAAACACTG    4380
TGATGAGCTT GCTAACGAGT TAGCTCGAAA GGGAATAACA GCTGTCTCTT ACTATAGGGG    4440
ATGTGACATC TCAAAAATCC CTGAGGGCGA CTGTGTAGTA GTTGCCACTG ATGCCTTGTG    4500
TACAGGGTAC ACTGGTGACT TTGATTCCGT GTATGACTGC AGCCTCATGG TAGAAGGCAC    4560
ATGCCATGTT GACCTTGACC CTACTTTCAC CATGGGTGTT CGTGTGTGCG GGTCTCAGC    4620
AATAGTTAAA GGCCAGCGTA GGGGCCGCAC AGGCCGTGGG AGAGCTGGCA TATACTACTA    4680
TGTAGACGGG AGTTGTACCC CTTCGGGTAT GGTTCCTGAA TGCAACATTG TTGAAGCCTT    4740
CGACGCAGCC AAGGCATGGT ATGGTTTGTC ATCAACAGAA GCTCAAACTA TTCTGGACAC    4800
CTATCGCACC CAACCTGGGT TACCTGCGAT AGGAGCAAAT TTGGACAGTG GGCTGATCT    4860
CTTTTCTATG GTCAACCCCG AACCTTCATT TGTCAATACT GCAAAAAGAA CTGCTGACAA    4920
TTATGTTTTG TTGACTGCAG CCCAACTACA ACTGTGTCAT CAGTATGGCT ATGCTGCTCC    4980
CAATGACGCA CCACGGTGGC AGGGAGCCCG GCTTGGGAAA AAACCTTGTG GGGTTCTGTG    5040
GCGCTTGGAC GGCGCTGACG CCTGTCCTGG CCCAGAGCCC AGCGAGGTGA CCAGATACCA    5100
AATGTGCTTC ACTGAAGTCA ATACTTCTGG GACAGCCGCA CTCGCTGTTG GCGTTGGAGT    5160
GGCTATGGCT TATCTAGCCA TTGACACTTT TGGCGCCACT TGTGTGCGGC GTTGCTGGTC    5220
TATTACATCA GTCCCTACCG GTGCTACTGT CGCCCCAGTG GTTGACGAAG AAGAAATCGT    5280
GGAGGAGTGT GCATCATTCA TTCCCTTGGA GGCCATGGTT GCTGCAATCG ATAAGCTGAA    5340
GAGTACAATA ACCACAACTA GTCCTTTCAC ATTGGAAACC GCCCTTGAAA AACTTAACAC    5400
CTTTCTTGGG CCTCATCAG CTACAATCCT TGCTATCATA GAGTATTGCT GTGGCTTAGT     5460
CACTTTACCT GACAATCCCT TTGCATCATG CGTGTTTGCT TTCATTGCGG GTATTACTAC    5520
CCCACTACCT CACAAGATCA AAATGTTCCT GTCATTATTT GGAGGCGCAA TTGCGTCCAA    5580
GCTTACAGAC GCTAGAGGCG CACTGGCGTT CATGATGGCC GGGGCTGCGG GAACAGCTCT    5640
```

-continued

```
TGGTACATGG ACATCGGTGG GTTTTGTCTT TGACATGCTA GGCGGCTATG CTGCCGCCTC    5700

ATCCACTGCT TGCTTGACAT TTAAATGCTT GATGGGTGAG TGGCCCACTA TGGATCAGCT    5760

TGCTGGTTTA GTCTACTCCG CGTTCAATCC GGCCGCAGGA GTTGTGGGCG TCTTGTCAGC    5820

TTGTGCAATG TTTGCTTTGA CAACAGCAGG GCCAGATCAC TGGCCCAACA GACTTCTTAC    5880

TATGCTTGCT AGGAGCAACA CTGTATGTAA TGAGTACTTT ATTGCCACTC GTGACATCCG    5940

CAGGAAGATA CTGGGCATTC TGGAGGCATC TACCCCCTGG AGTGTCATAT CAGCTTGCAT    6000

CCGTTGGCTC CACACCCCGA CGGAGGATGA TTGCGGCCTC ATTGCTTGGG GTCTAGAGAT    6060

TTGGCAGTAT GTGTGCAATT TCTTTGTGAT TTGCTTTAAT GTCCTTAAAG CTGGAGTTCA    6120

GAGCATGGTT AACATTCCTG GTTGTCCTTT CTACAGCTGC CAGAAGGGGT ACAAGGGCCC    6180

CTGGATTGGA TCAGGTATGC TCCAAGCACG CTGTCCATGC GGTGCTGAAC TCATCTTTTC    6240

TGTTGAGAAT GGTTTTGCAA AACTTTACAA AGGACCCAGA ACTTGTTCAA ATTACTGGAG    6300

AGGGGCTGTT CCAGTCAACG CTAGGCTGTG TGGGTCGGCT AGACCGGACC CAACTGATTG    6360

GACTAGTCTT GTCGTCAATT ATGGCGTTAG GGACTACTGT AAATATGAGA AATTGGGAGA    6420

TCACATTTTT GTTACAGCAG TATCCTCTCC AAATGTCTGT TTCACCCAGG TGCCCCCAAC    6480

CTTGAGAGCT GCAGTGGCCG TGGACGGCGT ACAGGTTCAG TGTTATCTAG GTGAGCCCAA    6540

AACTCCTTGG ACGACATCTG CTTGCTGTTA CGGTCCGGAC GGTAAGGGTA AAACTGTTAA    6600

GCTTCCCTTC CGCGTTGACG GTCACACACC TGGTGTGCGC ATGCAACTTA ATTTGCGTGA    6660

TGCACTTGAG ACAAATGACT GTAATTCCAT AAACAACACT CCTAGTGATG AAGCCGCAGT    6720

GTCCGCTCTT GTTTTCAAAC AGGAGTTGCG GCGTACAAAC CAATTGCTTG AGGCAATTTC    6780

AGCTGGCGTT GACACCACCA AACTGCCAGC CCCCTCCATC GAAGAGGTAG TGGTAAGAAA    6840

GCGCCAGTTC CGGGCAAGAA CTGGTTCGCT TACCTTGCCT CCCCCTCCGA GATCCGTCCC    6900

AGGAGTGTCA TGTCCTGAAA GCCTGCAACG AAGTGACCCG TTAGAAGGTC CTTCAAACCT    6960

CCCTTCTTCA CCACCTGTTC TACAGTTGGC CATGCCGATG CCCCTGTTGG GAGCAGGTGA    7020

GTGTAACCCT TTCACTGCAA TTGGATGTGC AATGACCGAA ACAGGCGGAG GCCCTGATGA    7080

TTTACCCAGT TACCCTCCCA AAAGGAGGT CTCTGAATGG TCAGACGGAA GTTGGTCAAC    7140

GACTACAACC GCTTCCAGCT ACGTTACTGG CCCCCCGTAC CCTAAGATAC GGGGAAAGGA    7200

TTCCACTCAG TCAGCCCCCG CCAAACGGCC TACAAAAAAG AAGTTGGGAA AGAGTGAGTT    7260

TTCGTGCAGC ATGAGCTACA CTTGGACCGA CGTGATTAGC TTCAAAACTG CTTCTAAAGT    7320

TCTGTCTGCA ACTCGGGCCA TCACTAGTGG TTTCCTCAAA CAAAGATCAT TGGTGTATGT    7380

GACTGAGCCG CGGGATGCGG AGCTTAGAAA ACAAAAAGTC ACTATTAATA GACAACCTCT    7440

GTTCCCCCCA TCATACCACA AGCAAGTGAG ATTGGCTAAG GAAAAAGCTT CAAAAGTTGT    7500

CGGTGTCATG TGGGACTATG ATGAAGTAGC AGCTCACACG CCCTCTAAGT CTGCTAAGTC    7560

CCACATCACT GGCCTTCGGG GCACTGATGT TCGTTCTGGA GCAGCCCGCA AGGCTGTTCT    7620

GGACTTGCAG AAGTGTGTCG AGGCAGGTGA GATACCGAGT CATTATCGGC AAACTGTGAT    7680

AGTTCCAAAG GAGGAGGTCT TCGTGAAGAC CCCCCAGAAA CCAACAAAGA AACCCCCAAG    7740

GCTTATCTCG TACCCCCACC TTGAAATGAG ATGTGTTGAG AAGATGTACT ACGGTCAGGT    7800

TGCTCCTGAC GTAGTTAAAG CTGTCATGGG AGATGCGTAC GGGTTTGTCG ACCCACGTAC    7860

CCGTGTCAAG CGTCTGTTGT CGATGTGGTC ACCCGATGCA GTCGGAGCCA CATGCGATAC    7920

AGTGTGTTTT GACAGTACCA TCACACCCGA GGATATCATG GTGGAGACAG ACATCTACTC    7980

AGCAGCTAAA CTCAGTGACC AACACCGAGC TGGCATTCAC ACCATTGCGA GGCAGTTATA    8040
```

```
CGCTGGAGGA CCGATGATCG CTTATGATGG CCGAGAGATC GGATATCGTA GGTGTAGGTC    8100

TTCCGGCGTC TATACTACCT CAAGTTCCAA CAGTTTGACC TGCTGGCTGA AGGTAAATGC    8160

TGCAGCCGAA CAGGCTGGCA TGAAGAACCC TCGCTTCCTT ATTTGCGGCG ATGATTGCAC    8220

CGTAATTTGG AAGAGCGCCG GAGCAGATGC AGACAAACAA GCAATGCGTG TCTTTGCTAG    8280

CTGGATGAAG GTGATGGGTG CACCACAAGA TTGTGTGCCT CAACCCAAAT ACAGTTTGGA    8340

AGAATTAACA TCATGCTCAT CAAATGTTAC CTCTGGAATT ACCAAAAGTG GCAAGCCTTA    8400

CTACTTTCTT ACAAGAGATC CTCGTATCCC CCTTGGCAGG TGCTCTGCCG AGGGTCTGGG    8460

ATACAACCCC AGTGCTGCGT GGATTGGGTA TCTAATACAT CACTACCCAT GTTTGTGGGT    8520

TAGCCGTGTG TTGGCTGTCC ATTTCATGGA GCAGATGCTC TTTGAGGACA AACTTCCCGA    8580

GACTGTGACC TTTGACTGGT ATGGGAAAAA TTATACGGTG CCTGTAGAAG ATCTGCCCAG    8640

CATCATTGCT GGTGTGCACG GTATTGAGGC TTTCTCGGTG GTGCGCTACA CCAACGCTGA    8700

GATCCTCAGA GTTTCCCAAT CACTAACAGA CATGACCATG CCCCCCCTGC GAGCCTGGCG    8760

AAAGAAAGCC AGGGCGGTCC TCGCCAGCGC CAAGAGGCGT GGCGGAGCAC ACGCAAAATT    8820

GGCTCGCTTC CTTCTCTGGC ATGCTACATC TAGACCTCTA CCAGATTTGG ATAAGACGAG    8880

CGTGGCTCGG TACACCACTT TCAATTATTG TGATGTTTAC TCCCCGGAGG GGGATGTGTT    8940

TGTTACACCA CAGAGAAGAT TGCAGAAGTT TCTTGTGAAG TATTTGGCTG TCATTGTTTT    9000

TGCCCTAGGG CTCATTGCTG TTGGACTAGC CATCAGCTGA ACCCCAAAT TCAAAATTAA    9060

TTAACAGTTT TTTTTTTTTT TTTTTTTTTT TTTTAGGGCA GCGGCAACAG GGGAGACCCC    9120

GGGCTTAACG ACCCCGCGAT GTG                                           9143

(2) INFORMATION FOR SEQ ID NO:391:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:391:

GATCAGGTAT GCTCCAAGCA CGCTGTCCAT GCGGTGCTGA ACTCATCTTT TCTGTTGAGA     60

ATGGTTTTGC AAAACTTTAC AAAGGACCCA GAACTTGTTC AAATTACTGG AGAGGGGCTG    120

TTCCAGTCAA CGCTAGGCTG TGTGGGTCGG CTAGACCGGA CCCAACTGAT TGGACTAGTC    180

TTGTCGTCAA TTATGGCGTT AGGGACTACT GTAAATATGA GAAATTGGGA GATC          234

(2) INFORMATION FOR SEQ ID NO:392:

(i) SEQUENCE CHARACTERISTICS:
        (A) LENGTH: 479 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:392:

GATCACATTT TTGTTACAGC AGTATCCTCT CCAAATGTCT GTTTCACCCA GGTGCCCCCA     60

ACCTTGAGAG CTGCAGTGGC CGTGGACCGC GTACAGGTTC AGYGTTATCT AGGTGAGCCC    120

AAAACTCCTT GGACGACATC TGCTTGCTGT TACGGTCCTG ACGGTAAGGG TAAAACTGTT    180
```

-continued

```
AAGCTTCCCT TCCGCGTTGA CGGACACACA CCTGGTGGTC GCATGCAACT TAATTTGCGT      240

GATCGACTTG AGGCAAATGA CTGTAATTCC ATAAACAACA CTCCTAGTGA TGAAGCCGCA      300

GTGTCCGCTC TTGTTTTCAA ACAGGAGTTG CGGCGTACAA ACCAATTGCT TGAGGCAATT      360

TCAGCTGGCG TTGACACCAC CAAACTGCCA GCCCCCTCCC AGATCGAAGA GGTAGTGGTA      420

AGAAAGCGCC AGTTCCGGGC AAGAACTGGT TCGCTTACCT TGCCTCCCCC TCCGAGATC      479
```

(2) INFORMATION FOR SEQ ID NO:393:

(i) SEQUENCE CHARACTERISTICS:
        (A) LENGTH: 9143 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: 5'UTR
        (B) LOCATION: 1..445

(ix) FEATURE:
        (A) NAME/KEY: CDS
        (B) LOCATION: 446..9037

(ix) FEATURE:
        (A) NAME/KEY: 3'UTR
        (B) LOCATION: 9038..9143

(xi) SEQUENCE DESCRIPTION: SEQ ID NO:393:

```
ACCACAAACA CTCCAGTTTG TTACACTCCG CTAGGAATGC TCCTGGAGCA CCCCCCCTAG       60

CAGGGCGTGG GGGATTTCCC CTGCCCGTCT GCAGAAGGGT GGAGCCAACC ACCTTAGTAT      120

GTAGGCGGCG GGACTCATGA CGCTCGCGTG ATGACAAGCG CCAAGCTTGA CTTGGATGGC      180

CCTGATGGGC GTTCATGGGT TCGGTGGTGG TGGCGCTTTA GGCAGCCTCC ACGCCCACCA      240

CCTCCCAGAT AGAGCGGCGG CACTGTAGGG AAGACCGGGG ACCGGTCACT ACCAAGGACG      300

CAGACCTCTT TTTGAGTATC ACGCCTCCGG AAGTAGTTGG GCAAGCCCAC CTATATGTGT      360

TGGGATGGTT GGGGTTAGCC ATCCATACCG TACTGCCTGA TAGGGTCCTT GCGAGGGGAT      420

CTGGGAGTCT CGTAGACCGT AGCAC ATG CCT GTT ATT TCT ACT CAA ACA AGT      472
                          Met Pro Val Ile Ser Thr Gln Thr Ser
                            1               5

CCT GTA CCT GCG CCC AGA ACG CGC AAG AAC AAG CAG ACG CAG GCT TCA       520
Pro Val Pro Ala Pro Arg Thr Arg Lys Asn Lys Gln Thr Gln Ala Ser
 10              15                  20                  25

TAT CCT GTG TCC ATT AAA ACA TCT GTT GAA AGG GGA CAA CGA GCA AAG       568
Tyr Pro Val Ser Ile Lys Thr Ser Val Glu Arg Gly Gln Arg Ala Lys
             30                  35                  40

CGC AAA GTC CAG CGC GAT GCT CGG CCT CGT AAT TAC AAA ATT GCT GGT       616
Arg Lys Val Gln Arg Asp Ala Arg Pro Arg Asn Tyr Lys Ile Ala Gly
         45                  50                  55

ATC CAT GAT GGC TTG CAG ACA TTG GCT CAG GCT GCT TTG CCA GCT CAT       664
Ile His Asp Gly Leu Gln Thr Leu Ala Gln Ala Ala Leu Pro Ala His
     60                  65                  70

GGT TGG GGA CGC CAA GAC CCT CGC CAT AAG TCT CGC AAT CTT GGA ATC       712
Gly Trp Gly Arg Gln Asp Pro Arg His Lys Ser Arg Asn Leu Gly Ile
 75                  80                  85

CTT CTG GAT TAC CCT TTG GGG TGG ATT GGT GAT GTT ACA ACT CAC ACA       760
Leu Leu Asp Tyr Pro Leu Gly Trp Ile Gly Asp Val Thr Thr His Thr
 90                  95                 100                 105

CCT CTA GTA GGC CCG CTG GTG GCA GGA GCG GTC GTT CGA CCA GTC TGC       808
Pro Leu Val Gly Pro Leu Val Ala Gly Ala Val Val Arg Pro Val Cys
```

```
                          110                     115                     120
CAG ATA GTA CGC TTG CTG GAG GAT GGA GTC AAC TGG GCT ACT GGT TGG              856
Gln Ile Val Arg Leu Leu Glu Asp Gly Val Asn Trp Ala Thr Gly Trp
            125                     130                     135

TTC GGT GTC CAC CTT TTT GTG GTA TGT CTG CTA TCT TTG GCC TGT CCC              904
Phe Gly Val His Leu Phe Val Val Cys Leu Leu Ser Leu Ala Cys Pro
            140                     145                     150

TGT AGT GGG GCG CGG GTC ACT GAC CCA GAC ACA AAT ACC ACA ATC CTG              952
Cys Ser Gly Ala Arg Val Thr Asp Pro Asp Thr Asn Thr Thr Ile Leu
155                     160                     165

ACC AAT TGC TGC CAG CGT AAT CAG GTT ATC TAT TGT TCT CCT TCC ACT             1000
Thr Asn Cys Cys Gln Arg Asn Gln Val Ile Tyr Cys Ser Pro Ser Thr
170                     175                     180                     185

TGC CTA CAC GAG CCT GGT TGT GTG ATC TGC GCG GAC GAG TGC TGG GTT             1048
Cys Leu His Glu Pro Gly Cys Val Ile Cys Ala Asp Glu Cys Trp Val
                        190                     195                     200

CCC GCC AAT CCG TAC ATC TCA CAC CCT TCC AAT TGG ACT GGC ACG GAC             1096
Pro Ala Asn Pro Tyr Ile Ser His Pro Ser Asn Trp Thr Gly Thr Asp
                        205                     210                     215

TCC TTC TTG GCT GAC CAC ATT GAT TTT GTT ATG GGC GCT CTT GTG ACC             1144
Ser Phe Leu Ala Asp His Ile Asp Phe Val Met Gly Ala Leu Val Thr
                        220                     225                     230

TGT GAC GCC CTT GAC ATT GGT GAG TTG TGT GGT GCG TGT GTA TTA GTC             1192
Cys Asp Ala Leu Asp Ile Gly Glu Leu Cys Gly Ala Cys Val Leu Val
235                     240                     245

GGT GAC TGG CTT GTC AGG CAC TGG CTT ATT CAC ATA GAC CTC AAT GAA             1240
Gly Asp Trp Leu Val Arg His Trp Leu Ile His Ile Asp Leu Asn Glu
250                     255                     260                     265

ACT GGT ACT TGT TAC CTG GAA GTG CCC ACT GGA ATA GAT CCT GGG TTC             1288
Thr Gly Thr Cys Tyr Leu Glu Val Pro Thr Gly Ile Asp Pro Gly Phe
                        270                     275                     280

CTA GGG TTT ATC GGG TGG ATG GCC GGC AAG GTC GAG GCT GTC ATC TTC             1336
Leu Gly Phe Ile Gly Trp Met Ala Gly Lys Val Glu Ala Val Ile Phe
                        285                     290                     295

TTG ACC AAA CTG GCT TCA CAA GTA CCA TAC GCT ATT GCG ACT ATG TTT             1384
Leu Thr Lys Leu Ala Ser Gln Val Pro Tyr Ala Ile Ala Thr Met Phe
            300                     305                     310

AGC AGT GTA CAC TAC CTG GCG GTT GGC GCT CTG ATC TAC TAT GCC TCT             1432
Ser Ser Val His Tyr Leu Ala Val Gly Ala Leu Ile Tyr Tyr Ala Ser
            315                     320                     325

CGG GGC AAG TGG TAT CAG TTG CTC CTA GCG CTT ATG CTT TAC ATA GAA             1480
Arg Gly Lys Trp Tyr Gln Leu Leu Leu Ala Leu Met Leu Tyr Ile Glu
330                     335                     340                     345

GCG ACC TCT GGA AAC CCT ATC AGG GTG CCC ACT GGA TGC TCA ATA GCT             1528
Ala Thr Ser Gly Asn Pro Ile Arg Val Pro Thr Gly Cys Ser Ile Ala
                        350                     355                     360

GAG TTT TGC TCG CCT TTG ATG ATA CCA TGT CCT TGC CAC TCT TAT TTG             1576
Glu Phe Cys Ser Pro Leu Met Ile Pro Cys Pro Cys His Ser Tyr Leu
                        365                     370                     375

AGT GAG AAT GTG TCA GAA GTC ATT TGT TAC AGT CCA AAG TGG ACC AGG             1624
Ser Glu Asn Val Ser Glu Val Ile Cys Tyr Ser Pro Lys Trp Thr Arg
            380                     385                     390

CCT GTC ACT CTA GAG TAT AAC AAC TCC ATA TCT TGG TAC CCC TAT ACA             1672
Pro Val Thr Leu Glu Tyr Asn Asn Ser Ile Ser Trp Tyr Pro Tyr Thr
395                     400                     405

ATC CCT GGT GCG AGG GGA TGT ATG GTT AAA TTC AAA AAT AAC ACA TGG             1720
Ile Pro Gly Ala Arg Gly Cys Met Val Lys Phe Lys Asn Asn Thr Trp
410                     415                     420                     425

GGT TGC TGC CGT ATT CGC AAT GTG CCA TCG TAC TGC ACT ATG GGC ACT             1768
```

-continued

```
         Gly Cys Cys Arg Ile Arg Asn Val Pro Ser Tyr Cys Thr Met Gly Thr
                         430                 435                 440

GAT GCA GTG TGG AAC GAC ACT CGC AAC ACT TAC GAA GCA TGC GGT GTA         1816
Asp Ala Val Trp Asn Asp Thr Arg Asn Thr Tyr Glu Ala Cys Gly Val
                445                 450                 455

ACA CCA TGG CTA ACA ACC GCA TGG CAC AAC GGC TCA GCC CTG AAA TTG         1864
Thr Pro Trp Leu Thr Thr Ala Trp His Asn Gly Ser Ala Leu Lys Leu
            460                 465                 470

GCT ATA TTA CAA TAC CCT GGG TCT AAA GAA ATG TTT AAA CCT CAT AAT         1912
Ala Ile Leu Gln Tyr Pro Gly Ser Lys Glu Met Phe Lys Pro His Asn
        475                 480                 485

TGG ATG TCA GGC CAT TTG TAT TTT GAG GGA TCA GAT ACC CCT ATA GTT         1960
Trp Met Ser Gly His Leu Tyr Phe Glu Gly Ser Asp Thr Pro Ile Val
490                 495                 500                 505

TAC TTT TAT GAC CCT GTG AAT TCC ACT CTC CTA CCA CCG GAG AGG TGG         2008
Tyr Phe Tyr Asp Pro Val Asn Ser Thr Leu Leu Pro Pro Glu Arg Trp
                510                 515                 520

GCT AGG TTG CCC GGT ACC CCA CCT GTG GTA CGT GGT TCT TGG TTA CAG         2056
Ala Arg Leu Pro Gly Thr Pro Pro Val Val Arg Gly Ser Trp Leu Gln
            525                 530                 535

GTT CCG CAA GGG TTT TAC AGT GAT GTG AAA GAC CTA GCC ACA GGA TTG         2104
Val Pro Gln Gly Phe Tyr Ser Asp Val Lys Asp Leu Ala Thr Gly Leu
        540                 545                 550

ATC ACC AAA GAC AAA GCC TGG AAA AAT TAT CAG GTC TTA TAT TCC GCC         2152
Ile Thr Lys Asp Lys Ala Trp Lys Asn Tyr Gln Val Leu Tyr Ser Ala
555                 560                 565

ACG GGT GCT TTG TCT CTT ACG GGA GTT ACC ACC AAG GCC GTG GTG CTA         2200
Thr Gly Ala Leu Ser Leu Thr Gly Val Thr Thr Lys Ala Val Val Leu
570                 575                 580                 585

ATT CTG TTG GGG TTG TGT GGC AGC AAG TAT CTT ATT TTA GCC TAC CTC         2248
Ile Leu Leu Gly Leu Cys Gly Ser Lys Tyr Leu Ile Leu Ala Tyr Leu
                590                 595                 600

TGT TAC TTG TCC CTT TGT TTT GGG CGC GCT TCT GGT TAC CCT TTG CGT         2296
Cys Tyr Leu Ser Leu Cys Phe Gly Arg Ala Ser Gly Tyr Pro Leu Arg
            605                 610                 615

CCT GTG CTC CCA TCC CAG TCG TAT CTC CAA GCT GGC TGG GAT GTT TTG         2344
Pro Val Leu Pro Ser Gln Ser Tyr Leu Gln Ala Gly Trp Asp Val Leu
        620                 625                 630

TCT AAA GCT CAA GTA GCT CCT TTT GCT TTG ATT TTC TTC ATC TGT TGC         2392
Ser Lys Ala Gln Val Ala Pro Phe Ala Leu Ile Phe Phe Ile Cys Cys
635                 640                 645

TAT CTC CGC TGC AGG CTA CGT TAT GCT GCC CTT TTA GGG TTT GTG CCC         2440
Tyr Leu Arg Cys Arg Leu Arg Tyr Ala Ala Leu Leu Gly Phe Val Pro
650                 655                 660                 665

ATG GCT GCG GGC TTG CCC CTA ACT TTC TTT GTT GCA GCA GCT GCT GCC         2488
Met Ala Ala Gly Leu Pro Leu Thr Phe Phe Val Ala Ala Ala Ala Ala
                670                 675                 680

CAA CCA GAT TAT GAC TGG TGG GTG CGA CTG CTA GTG GCA GGG TTA GTT         2536
Gln Pro Asp Tyr Asp Trp Trp Val Arg Leu Leu Val Ala Gly Leu Val
            685                 690                 695

TTG TGG GCC GGC CGT GAC CGT GGT CCA CGT ATA GCT CTG CTT GTA GGT         2584
Leu Trp Ala Gly Arg Asp Arg Gly Pro Arg Ile Ala Leu Leu Val Gly
        700                 705                 710

CCT TGG CCT CTG GTA GCG CTT TTA ACC CTC TTG CAT TTG GCT ACG CCT         2632
Pro Trp Pro Leu Val Ala Leu Leu Thr Leu Leu His Leu Ala Thr Pro
715                 720                 725

GCT TCA GCT TTT GAC ACC GAG ATA ATT GGA GGG CTG ACA ATA CCA CCT         2680
Ala Ser Ala Phe Asp Thr Glu Ile Ile Gly Gly Leu Thr Ile Pro Pro
730                 735                 740                 745
```

-continued

```
GTA GTA GCA TTA GTT GTC ATG TCT CGT TTT GGC TTC TTT GCT CAC TTG        2728
Val Val Ala Leu Val Val Met Ser Arg Phe Gly Phe Phe Ala His Leu
            750                 755                 760

TTA CCT CGC TGT GCT TTA GTT AAC TCC TAT CTT TGG CAA CGT TGG GAG        2776
Leu Pro Arg Cys Ala Leu Val Asn Ser Tyr Leu Trp Gln Arg Trp Glu
            765                 770                 775

AAT TGG TTT TGG AAC GTT ACA CTA AGA CCG GAG AGG TTT CTC CTT GTG        2824
Asn Trp Phe Trp Asn Val Thr Leu Arg Pro Glu Arg Phe Leu Leu Val
            780                 785                 790

CTG GTT TGT TTC CCC GGT GCG ACA TAT GAC ACG CTG GTG ACT TTC TGT        2872
Leu Val Cys Phe Pro Gly Ala Thr Tyr Asp Thr Leu Val Thr Phe Cys
            795                 800                 805

GTG TGT CAC GTA GCT CTT CTA TGT TTA ACA TCC AGT GCA GCA TCG TTC        2920
Val Cys His Val Ala Leu Leu Cys Leu Thr Ser Ser Ala Ala Ser Phe
810                 815                 820                 825

TTT GGG ACT GAC TCT AGG GTT AGG GCC CAT AGA ATG TTG GTG CGT CTC        2968
Phe Gly Thr Asp Ser Arg Val Arg Ala His Arg Met Leu Val Arg Leu
                830                 835                 840

GGA AAG TGT CAT GCT TGG TAT TCT CAT TAT GTT CTT AAG TTT TTC CTC        3016
Gly Lys Cys His Ala Trp Tyr Ser His Tyr Val Leu Lys Phe Phe Leu
            845                 850                 855

TTA GTG TTT GGT GAG AAT GGT GTG TTT TTC TAT AAG CAC TTG CAT GGT        3064
Leu Val Phe Gly Glu Asn Gly Val Phe Phe Tyr Lys His Leu His Gly
            860                 865                 870

GAT GTC TTG CCT AAT GAT TTT GCC TCG AAA CTA CCA TTG CAA GAG CCA        3112
Asp Val Leu Pro Asn Asp Phe Ala Ser Lys Leu Pro Leu Gln Glu Pro
875                 880                 885

TTT TTC CCT TTT GAA GGC AAG GCA AGG GTC TAT AGG AAT GAA GGA AGA        3160
Phe Phe Pro Phe Glu Gly Lys Ala Arg Val Tyr Arg Asn Glu Gly Arg
890                 895                 900                 905

CGC TTG GCG TGT GGG GAC ACG GTT GAT GGT TTG CCC GTT GTT GCG CGT        3208
Arg Leu Ala Cys Gly Asp Thr Val Asp Gly Leu Pro Val Val Ala Arg
                910                 915                 920

CTC GGC GAC CTT GTT TTC GCA GGG TTA GCT ATG CCG CCA GAT GGG TGG        3256
Leu Gly Asp Leu Val Phe Ala Gly Leu Ala Met Pro Pro Asp Gly Trp
            925                 930                 935

GCC ATT ACC GCA CCT TTT ACG CTG CAG TGT CTC TCT GAA CGT GGC ACG        3304
Ala Ile Thr Ala Pro Phe Thr Leu Gln Cys Leu Ser Glu Arg Gly Thr
            940                 945                 950

CTG TCA GCG ATG GCA GTG GTC ATG ACT GGT ATA GAC CCC CGA ACT TGG        3352
Leu Ser Ala Met Ala Val Val Met Thr Gly Ile Asp Pro Arg Thr Trp
955                 960                 965

ACT GGA ACT ATC TTC AGA TTA GGA TCT CTG GCC ACT AGC TAC ATG GGA        3400
Thr Gly Thr Ile Phe Arg Leu Gly Ser Leu Ala Thr Ser Tyr Met Gly
970                 975                 980                 985

TTT GTT TGT GAC AAC GTG TTG TAT ACT GCT CAC CAT GGC AGC AAG GGG        3448
Phe Val Cys Asp Asn Val Leu Tyr Thr Ala His His Gly Ser Lys Gly
                990                 995                 1000

CGC CGG TTG GCT CAT CCC ACA GGC TCC ATA CAC CCA ATA ACC GTT GAC        3496
Arg Arg Leu Ala His Pro Thr Gly Ser Ile His Pro Ile Thr Val Asp
            1005                1010                1015

GCG GCT AAT GAC CAG GAC ATC TAT CAA CCA CCA TGT GGA GCT GGG TCC        3544
Ala Ala Asn Asp Gln Asp Ile Tyr Gln Pro Pro Cys Gly Ala Gly Ser
            1020                1025                1030

CTT ACT CGG TGC TCT TGC GGG GAG ACC AAG GGG TAT CTG GTA ACA CGA        3592
Leu Thr Arg Cys Ser Cys Gly Glu Thr Lys Gly Tyr Leu Val Thr Arg
            1035                1040                1045

CTG GGG TCA TTG GTT GAG GTC AAC AAA TCC GAT GAC CCT TAT TGG TGT        3640
Leu Gly Ser Leu Val Glu Val Asn Lys Ser Asp Asp Pro Tyr Trp Cys
1050                1055                1060                1065
```

```
GTG TGC GGG GCC CTT CCC ATG GCT GTT GCC AAG GGT TCT TCA GGT GCC    3688
Val Cys Gly Ala Leu Pro Met Ala Val Ala Lys Gly Ser Ser Gly Ala
             1070                1075                1080

CCG ATT CTG TGC TCC TCC GGG CAT GTT ATT GGG ATG TTC ACC GCT GCT    3736
Pro Ile Leu Cys Ser Ser Gly His Val Ile Gly Met Phe Thr Ala Ala
             1085                1090                1095

AGA AAT TCT GGC GGT TCA GTC AGC CAG ATT AGG GTT AGG CCG TTG GTG    3784
Arg Asn Ser Gly Gly Ser Val Ser Gln Ile Arg Val Arg Pro Leu Val
             1100                1105                1110

TGT GCT GGA TAC CAT CCC CAG TAC ACA GCA CAT GCC ACT CTT GAT ACA    3832
Cys Ala Gly Tyr His Pro Gln Tyr Thr Ala His Ala Thr Leu Asp Thr
             1115                1120                1125

AAA CCT ACT GTG CCT AAC GAG TAT TCA GTG CAA ATT TTA ATT GCC CCC    3880
Lys Pro Thr Val Pro Asn Glu Tyr Ser Val Gln Ile Leu Ile Ala Pro
1130                1135                1140                1145

ACT GGC AGC GGC AAG TCA ACC AAA TTA CCA CTT TCT TAC ATG CAG GAG    3928
Thr Gly Ser Gly Lys Ser Thr Lys Leu Pro Leu Ser Tyr Met Gln Glu
             1150                1155                1160

AAG TAT GAG GTC TTG GTC CTA AAT CCC AGT GTG GCT ACA ACA GCA TCA    3976
Lys Tyr Glu Val Leu Val Leu Asn Pro Ser Val Ala Thr Thr Ala Ser
             1165                1170                1175

ATG CCA AAG TAC ATG CAC GCG ACG TAC GGC GTG AAT CCA AAT TGC TAT    4024
Met Pro Lys Tyr Met His Ala Thr Tyr Gly Val Asn Pro Asn Cys Tyr
             1180                1185                1190

TTT AAT GGC AAA TGT ACC AAC ACA GGG GCT TCA CTT ACG TAC AGC ACA    4072
Phe Asn Gly Lys Cys Thr Asn Thr Gly Ala Ser Leu Thr Tyr Ser Thr
             1195                1200                1205

TAT GGC ATG TAC CTG ACC GGA GCA TGT TCC CGG AAC TAT GAC GTC ATC    4120
Tyr Gly Met Tyr Leu Thr Gly Ala Cys Ser Arg Asn Tyr Asp Val Ile
1210                1215                1220                1225

ATT TGT GAC GAA TGC CAT GCT ACC GAT GCA ACC ACC GTG TTG GGC ATT    4168
Ile Cys Asp Glu Cys His Ala Thr Asp Ala Thr Thr Val Leu Gly Ile
             1230                1235                1240

GGA AAG GTT CTA ACC GAA GCT CCA TCC AAA AAT GTT AGG CTA GTG GTT    4216
Gly Lys Val Leu Thr Glu Ala Pro Ser Lys Asn Val Arg Leu Val Val
             1245                1250                1255

CTT GCC ACG GCT ACC CCC CCT GGA GTA ATC CCT ACA CCA CAT GCC AAC    4264
Leu Ala Thr Ala Thr Pro Pro Gly Val Ile Pro Thr Pro His Ala Asn
             1260                1265                1270

ATA ACT GAG ATT CAA TTA ACC GAT GAA GGC ACT ATC CCC TTT CAT GGA    4312
Ile Thr Glu Ile Gln Leu Thr Asp Glu Gly Thr Ile Pro Phe His Gly
             1275                1280                1285

AAA AAG ATT AAG GAG GAA AAT CTG AAG AAA GGG AGA CAC CTT ATC TTT    4360
Lys Lys Ile Lys Glu Glu Asn Leu Lys Lys Gly Arg His Leu Ile Phe
1290                1295                1300                1305

GAG GCT ACC AAA AAA CAC TGT GAT GAG CTT GCT AAC GAG TTA GCT CGA    4408
Glu Ala Thr Lys Lys His Cys Asp Glu Leu Ala Asn Glu Leu Ala Arg
             1310                1315                1320

AAG GGA ATA ACA GCT GTC TCT TAC TAT AGG GGA TGT GAC ATC TCA AAA    4456
Lys Gly Ile Thr Ala Val Ser Tyr Tyr Arg Gly Cys Asp Ile Ser Lys
             1325                1330                1335

ATC CCT GAG GGC GAC TGT GTA GTA GTT GCC ACT GAT GCC TTG TGT ACA    4504
Ile Pro Glu Gly Asp Cys Val Val Val Ala Thr Asp Ala Leu Cys Thr
             1340                1345                1350

GGG TAC ACT GGT GAC TTT GAT TCC GTG TAT GAC TGC AGC CTC ATG GTA    4552
Gly Tyr Thr Gly Asp Phe Asp Ser Val Tyr Asp Cys Ser Leu Met Val
             1355                1360                1365

GAA GGC ACA TGC CAT GTT GAC CTT GAC CCT ACT TTC ACC ATG GGT GTT    4600
Glu Gly Thr Cys His Val Asp Leu Asp Pro Thr Phe Thr Met Gly Val
```

```
                                                             -continued
1370                1375                1380                1385

CGT GTG TGC GGG GTC TCA GCA ATA GTT AAA GGC CAG CGT AGG GGC CGC      4648
Arg Val Cys Gly Val Ser Ala Ile Val Lys Gly Gln Arg Arg Gly Arg
            1390                1395                1400

ACA GGC CGT GGG AGA GCT GGC ATA TAC TAC TAT GTA GAC GGG AGT TGT      4696
Thr Gly Arg Gly Arg Ala Gly Ile Tyr Tyr Tyr Val Asp Gly Ser Cys
        1405                1410                1415

ACC CCT TCG GGT ATG GTT CCT GAA TGC AAC ATT GTT GAA GCC TTC GAC      4744
Thr Pro Ser Gly Met Val Pro Glu Cys Asn Ile Val Glu Ala Phe Asp
        1420                1425                1430

GCA GCC AAG GCA TGG TAT GGT TTG TCA TCA ACA GAA GCT CAA ACT ATT      4792
Ala Ala Lys Ala Trp Tyr Gly Leu Ser Ser Thr Glu Ala Gln Thr Ile
        1435                1440                1445

CTG GAC ACC TAT CGC ACC CAA CCT GGG TTA CCT GCG ATA GGA GCA AAT      4840
Leu Asp Thr Tyr Arg Thr Gln Pro Gly Leu Pro Ala Ile Gly Ala Asn
1450                1455                1460                1465

TTG GAC GAG TGG GCT GAT CTC TTT TCT ATG GTC AAC CCC GAA CCT TCA      4888
Leu Asp Glu Trp Ala Asp Leu Phe Ser Met Val Asn Pro Glu Pro Ser
            1470                1475                1480

TTT GTC AAT ACT GCA AAA AGA ACT GCT GAC AAT TAT GTT TTG TTG ACT      4936
Phe Val Asn Thr Ala Lys Arg Thr Ala Asp Asn Tyr Val Leu Leu Thr
            1485                1490                1495

GCA GCC CAA CTA CAA CTG TGT CAT CAG TAT GGC TAT GCT GCT CCC AAT      4984
Ala Ala Gln Leu Gln Leu Cys His Gln Tyr Gly Tyr Ala Ala Pro Asn
        1500                1505                1510

GAC GCA CCA CGG TGG CAG GGA GCC CGG CTT GGG AAA AAA CCT TGT GGG      5032
Asp Ala Pro Arg Trp Gln Gly Ala Arg Leu Gly Lys Lys Pro Cys Gly
        1515                1520                1525

GTT CTG TGG CGC TTG GAC GGC GCT GAC GCC TGT CCT GGC CCA GAG CCC      5080
Val Leu Trp Arg Leu Asp Gly Ala Asp Ala Cys Pro Gly Pro Glu Pro
1530                1535                1540                1545

AGC GAG GTG ACC AGA TAC CAA ATG TGC TTC ACT GAA GTC AAT ACT TCT      5128
Ser Glu Val Thr Arg Tyr Gln Met Cys Phe Thr Glu Val Asn Thr Ser
            1550                1555                1560

GGG ACA GCC GCA CTC GCT GTT GGC GTT GGA GTG GCT ATG GCT TAT CTA      5176
Gly Thr Ala Ala Leu Ala Val Gly Val Gly Val Ala Met Ala Tyr Leu
            1565                1570                1575

GCC ATT GAC ACT TTT GGC GCC ACT TGT GTG CGG CGT TGC TGG TCT ATT      5224
Ala Ile Asp Thr Phe Gly Ala Thr Cys Val Arg Arg Cys Trp Ser Ile
        1580                1585                1590

ACA TCA GTC CCT ACC GGT GCT ACT GTC GCC CCA GTG GTT GAC GAA GAA      5272
Thr Ser Val Pro Thr Gly Ala Thr Val Ala Pro Val Val Asp Glu Glu
        1595                1600                1605

GAA ATC GTG GAG GAG TGT GCA TCA TTC ATT CCC TTG GAG GCC ATG GTT      5320
Glu Ile Val Glu Glu Cys Ala Ser Phe Ile Pro Leu Glu Ala Met Val
1610                1615                1620                1625

GCT GCA ATC GAT AAG CTG AAG AGT ACA ATA ACC ACA ACT AGT CCT TTC      5368
Ala Ala Ile Asp Lys Leu Lys Ser Thr Ile Thr Thr Thr Ser Pro Phe
            1630                1635                1640

ACA TTG GAA ACC GCC CTT GAA AAA CTT AAC ACC TTT CTT GGG CCT CAT      5416
Thr Leu Glu Thr Ala Leu Glu Lys Leu Asn Thr Phe Leu Gly Pro His
            1645                1650                1655

GCA GCT ACA ATC CTT GCT ATC ATA GAG TAT TGC TGT GGC TTA GTC ACT      5464
Ala Ala Thr Ile Leu Ala Ile Ile Glu Tyr Cys Cys Gly Leu Val Thr
            1660                1665                1670

TTA CCT GAC AAT CCC TTT GCA TCA TGC GTG TTT GCT TTC ATT GCG GGT      5512
Leu Pro Asp Asn Pro Phe Ala Ser Cys Val Phe Ala Phe Ile Ala Gly
            1675                1680                1685

ATT ACT ACC CCA CTA CCT CAC AAG ATC AAA ATG TTC CTG TCA TTA TTT      5560
```

```
Ile Thr Thr Pro Leu Pro His Lys Ile Lys Met Phe Leu Ser Leu Phe
1690                1695                1700                1705

GGA GGC GCA ATT GCG TCC AAG CTT ACA GAC GCT AGA GGC GCA CTG GCG       5608
Gly Gly Ala Ile Ala Ser Lys Leu Thr Asp Ala Arg Gly Ala Leu Ala
            1710                1715                1720

TTC ATG ATG GCC GGG GCT GCG GGA ACA GCT CTT GGT ACA TGG ACA TCG       5656
Phe Met Met Ala Gly Ala Ala Gly Thr Ala Leu Gly Thr Trp Thr Ser
                1725                1730                1735

GTG GGT TTT GTC TTT GAC ATG CTA GGC GGC TAT GCT GCC GCC TCA TCC       5704
Val Gly Phe Val Phe Asp Met Leu Gly Gly Tyr Ala Ala Ala Ser Ser
            1740                1745                1750

ACT GCT TGC TTG ACA TTT AAA TGC TTG ATG GGT GAG TGG CCC ACT ATG       5752
Thr Ala Cys Leu Thr Phe Lys Cys Leu Met Gly Glu Trp Pro Thr Met
        1755                1760                1765

GAT CAG CTT GCT GGT TTA GTC TAC TCC GCG TTC AAT CCG GCC GCA GGA       5800
Asp Gln Leu Ala Gly Leu Val Tyr Ser Ala Phe Asn Pro Ala Ala Gly
1770                1775                1780                1785

GTT GTG GGC GTC TTG TCA GCT TGT GCA ATG TTT GCT TTG ACA ACA GCA       5848
Val Val Gly Val Leu Ser Ala Cys Ala Met Phe Ala Leu Thr Thr Ala
            1790                1795                1800

GGG CCA GAT CAC TGG CCC AAC AGA CTT CTT ACT ATG CTT GCT AGG AGC       5896
Gly Pro Asp His Trp Pro Asn Arg Leu Leu Thr Met Leu Ala Arg Ser
        1805                1810                1815

AAC ACT GTA TGT AAT GAG TAC TTT ATT GCC ACT CGT GAC ATC CGC AGG       5944
Asn Thr Val Cys Asn Glu Tyr Phe Ile Ala Thr Arg Asp Ile Arg Arg
        1820                1825                1830

AAG ATA CTG GGC ATT CTG GAG GCA TCT ACC CCC TGG AGT GTC ATA TCA       5992
Lys Ile Leu Gly Ile Leu Glu Ala Ser Thr Pro Trp Ser Val Ile Ser
        1835                1840                1845

GCT TGC ATC CGT TGG CTC CAC ACC CCG ACG GAG GAT GAT TGC GGC CTC       6040
Ala Cys Ile Arg Trp Leu His Thr Pro Thr Glu Asp Asp Cys Gly Leu
1850                1855                1860                1865

ATT GCT TGG GGT CTA GAG ATT TGG CAG TAT GTG TGC AAT TTC TTT GTG       6088
Ile Ala Trp Gly Leu Glu Ile Trp Gln Tyr Val Cys Asn Phe Phe Val
            1870                1875                1880

ATT TGC TTT AAT GTC CTT AAA GCT GGA GTT CAG AGC ATG GTT AAC ATT       6136
Ile Cys Phe Asn Val Leu Lys Ala Gly Val Gln Ser Met Val Asn Ile
        1885                1890                1895

CCT GGT TGT CCT TTC TAC AGC TGC CAG AAG GGG TAC AAG GGC CCC TGG       6184
Pro Gly Cys Pro Phe Tyr Ser Cys Gln Lys Gly Tyr Lys Gly Pro Trp
    1900                1905                1910

ATT GGA TCA GGT ATG CTC CAA GCA CGC TGT CCA TGC GGT GCT GAA CTC       6232
Ile Gly Ser Gly Met Leu Gln Ala Arg Cys Pro Cys Gly Ala Glu Leu
        1915                1920                1925

ATC TTT TCT GTT GAG AAT GGT TTT GCA AAA CTT TAC AAA GGA CCC AGA       6280
Ile Phe Ser Val Glu Asn Gly Phe Ala Lys Leu Tyr Lys Gly Pro Arg
1930                1935                1940                1945

ACT TGT TCA AAT TAC TGG AGA GGG GCT GTT CCA GTC AAC GCT AGG CTG       6328
Thr Cys Ser Asn Tyr Trp Arg Gly Ala Val Pro Val Asn Ala Arg Leu
            1950                1955                1960

TGT GGG TCG GCT AGA CCG GAC CCA ACT GAT TGG ACT AGT CTT GTC GTC       6376
Cys Gly Ser Ala Arg Pro Asp Pro Thr Asp Trp Thr Ser Leu Val Val
        1965                1970                1975

AAT TAT GGC GTT AGG GAC TAC TGT AAA TAT GAG AAA TTG GGA GAT CAC       6424
Asn Tyr Gly Val Arg Asp Tyr Cys Lys Tyr Glu Lys Leu Gly Asp His
        1980                1985                1990

ATT TTT GTT ACA GCA GTA TCC TCT CCA AAT GTC TGT TTC ACC CAG GTG       6472
Ile Phe Val Thr Ala Val Ser Ser Pro Asn Val Cys Phe Thr Gln Val
        1995                2000                2005
```

```
CCC CCA ACC TTG AGA GCT GCA GTG GCC GTG GAC GGC GTA CAG GTT CAG        6520
Pro Pro Thr Leu Arg Ala Ala Val Ala Val Asp Gly Val Gln Val Gln
2010                2015                2020                2025

TGT TAT CTA GGT GAG CCC AAA ACT CCT TGG ACG ACA TCT GCT TGC TGT        6568
Cys Tyr Leu Gly Glu Pro Lys Thr Pro Trp Thr Thr Ser Ala Cys Cys
            2030                2035                2040

TAC GGT CCG GAC GGT AAG GGT AAA ACT GTT AAG CTT CCC TTC CGC GTT        6616
Tyr Gly Pro Asp Gly Lys Gly Lys Thr Val Lys Leu Pro Phe Arg Val
                2045                2050                2055

GAC GGT CAC ACA CCT GGT GTG CGC ATG CAA CTT AAT TTG CGT GAT GCA        6664
Asp Gly His Thr Pro Gly Val Arg Met Gln Leu Asn Leu Arg Asp Ala
                    2060                2065                2070

CTT GAG ACA AAT GAC TGT AAT TCC ATA AAC AAC ACT CCT AGT GAT GAA        6712
Leu Glu Thr Asn Asp Cys Asn Ser Ile Asn Asn Thr Pro Ser Asp Glu
                        2075                2080                2085

GCC GCA GTG TCC GCT CTT GTT TTC AAA CAG GAG TTG CGG CGT ACA AAC        6760
Ala Ala Val Ser Ala Leu Val Phe Lys Gln Glu Leu Arg Arg Thr Asn
2090                2095                2100                2105

CAA TTG CTT GAG GCA ATT TCA GCT GGC GTT GAC ACC ACC AAA CTG CCA        6808
Gln Leu Leu Glu Ala Ile Ser Ala Gly Val Asp Thr Thr Lys Leu Pro
            2110                2115                2120

GCC CCC TCC ATC GAA GAG GTA GTG GTA AGA AAG CGC CAG TTC CGG GCA        6856
Ala Pro Ser Ile Glu Glu Val Val Val Arg Lys Arg Gln Phe Arg Ala
                2125                2130                2135

AGA ACT GGT TCG CTT ACC TTG CCT CCC CCT CCG AGA TCC GTC CCA GGA        6904
Arg Thr Gly Ser Leu Thr Leu Pro Pro Pro Pro Arg Ser Val Pro Gly
                    2140                2145                2150

GTG TCA TGT CCT GAA AGC CTG CAA CGA AGT GAC CCG TTA GAA GGT CCT        6952
Val Ser Cys Pro Glu Ser Leu Gln Arg Ser Asp Pro Leu Glu Gly Pro
                        2155                2160                2165

TCA AAC CTC CCT TCT TCA CCA CCT GTT CTA CAG TTG GCC ATG CCG ATG        7000
Ser Asn Leu Pro Ser Ser Pro Pro Val Leu Gln Leu Ala Met Pro Met
2170                2175                2180                2185

CCC CTG TTG GGA GCA GGT GAG TGT AAC CCT TTC ACT GCA ATT GGA TGT        7048
Pro Leu Leu Gly Ala Gly Glu Cys Asn Pro Phe Thr Ala Ile Gly Cys
            2190                2195                2200

GCA ATG ACC GAA ACA GGC GGA GGC CCT GAT GAT TTA CCC AGT TAC CCT    7096
Ala Met Thr Glu Thr Gly Gly Gly Pro Asp Asp Leu Pro Ser Tyr Pro
                2205                2210                2215

CCC AAA AAG GAG GTC TCT GAA TGG TCA GAC GGA AGT TGG TCA ACG ACT        7144
Pro Lys Lys Glu Val Ser Glu Trp Ser Asp Gly Ser Trp Ser Thr Thr
                    2220                2225                2230

ACA ACC GCT TCC AGC TAC GTT ACT GGC CCC CCG TAC CCT AAG ATA CGG        7192
Thr Thr Ala Ser Ser Tyr Val Thr Gly Pro Pro Tyr Pro Lys Ile Arg
                        2235                2240                2245

GGA AAG GAT TCC ACT CAG TCA GCC CCC GCC AAA CGG CCT ACA AAA AAG        7240
Gly Lys Asp Ser Thr Gln Ser Ala Pro Ala Lys Arg Pro Thr Lys Lys
2250                2255                2260                2265

AAG TTG GGA AAG AGT GAG TTT TCG TGC AGC ATG AGC TAC ACT TGG ACC        7288
Lys Leu Gly Lys Ser Glu Phe Ser Cys Ser Met Ser Tyr Thr Trp Thr
            2270                2275                2280

GAC GTG ATT AGC TTC AAA ACT GCT TCT AAA GTT CTG TCT GCA ACT CGG        7336
Asp Val Ile Ser Phe Lys Thr Ala Ser Lys Val Leu Ser Ala Thr Arg
                2285                2290                2295

GCC ATC ACT AGT GGT TTC CTC AAA CAA AGA TCA TTG GTG TAT GTG ACT        7384
Ala Ile Thr Ser Gly Phe Leu Lys Gln Arg Ser Leu Val Tyr Val Thr
                    2300                2305                2310

GAG CCG CGG GAT GCG GAG CTT AGA AAA CAA AAA GTC ACT ATT AAT AGA        7432
Glu Pro Arg Asp Ala Glu Leu Arg Lys Gln Lys Val Thr Ile Asn Arg
                        2315                2320                2325
```

```
CAA CCT CTG TTC CCC CCA TCA TAC CAC AAG CAA GTG AGA TTG GCT AAG         7480
Gln Pro Leu Phe Pro Pro Ser Tyr His Lys Gln Val Arg Leu Ala Lys
2330                2335                2340                2345

GAA AAA GCT TCA AAA GTT GTC GGT GTC ATG TGG GAC TAT GAT GAA GTA         7528
Glu Lys Ala Ser Lys Val Val Gly Val Met Trp Asp Tyr Asp Glu Val
                2350                2355                2360

GCA GCT CAC ACG CCC TCT AAG TCT GCT AAG TCC CAC ATC ACT GGC CTT         7576
Ala Ala His Thr Pro Ser Lys Ser Ala Lys Ser His Ile Thr Gly Leu
        2365                2370                2375

CGG GGC ACT GAT GTT CGT TCT GGA GCA GCC CGC AAG GCT GTT CTG GAC         7624
Arg Gly Thr Asp Val Arg Ser Gly Ala Ala Arg Lys Ala Val Leu Asp
            2380                2385                2390

TTG CAG AAG TGT GTC GAG GCA GGT GAG ATA CCG AGT CAT TAT CGG CAA         7672
Leu Gln Lys Cys Val Glu Ala Gly Glu Ile Pro Ser His Tyr Arg Gln
        2395                2400                2405

ACT GTG ATA GTT CCA AAG GAG GAG GTC TTC GTG AAG ACC CCC CAG AAA         7720
Thr Val Ile Val Pro Lys Glu Glu Val Phe Val Lys Thr Pro Gln Lys
2410                2415                2420                2425

CCA ACA AAG AAA CCC CCA AGG CTT ATC TCG TAC CCC CAC CTT GAA ATG         7768
Pro Thr Lys Lys Pro Pro Arg Leu Ile Ser Tyr Pro His Leu Glu Met
                2430                2435                2440

AGA TGT GTT GAG AAG ATG TAC TAC GGT CAG GTT GCT CCT GAC GTA GTT         7816
Arg Cys Val Glu Lys Met Tyr Tyr Gly Gln Val Ala Pro Asp Val Val
        2445                2450                2455

AAA GCT GTC ATG GGA GAT GCG TAC GGG TTT GTC GAC CCA CGT ACC CGT         7864
Lys Ala Val Met Gly Asp Ala Tyr Gly Phe Val Asp Pro Arg Thr Arg
            2460                2465                2470

GTC AAG CGT CTG TTG TCG ATG TGG TCA CCC GAT GCA GTC GGA GCC ACA         7912
Val Lys Arg Leu Leu Ser Met Trp Ser Pro Asp Ala Val Gly Ala Thr
        2475                2480                2485

TGC GAT ACA GTG TGT TTT GAC AGT ACC ATC ACA CCC GAG GAT ATC ATG         7960
Cys Asp Thr Val Cys Phe Asp Ser Thr Ile Thr Pro Glu Asp Ile Met
2490                2495                2500                2505

GTG GAG ACA GAC ATC TAC TCA GCA GCT AAA CTC AGT GAC CAA CAC CGA         8008
Val Glu Thr Asp Ile Tyr Ser Ala Ala Lys Leu Ser Asp Gln His Arg
                2510                2515                2520

GCT GGC ATT CAC ACC ATT GCG AGG CAG TTA TAC GCT GGA GGA CCG ATG         8056
Ala Gly Ile His Thr Ile Ala Arg Gln Leu Tyr Ala Gly Gly Pro Met
        2525                2530                2535

ATC GCT TAT GAT GGC CGA GAG ATC GGA TAT CGT AGG TGT AGG TCT TCC         8104
Ile Ala Tyr Asp Gly Arg Glu Ile Gly Tyr Arg Arg Cys Arg Ser Ser
            2540                2545                2550

GGC GTC TAT ACT ACC TCA AGT TCC AAC AGT TTG ACC TGC TGG CTG AAG         8152
Gly Val Tyr Thr Thr Ser Ser Ser Asn Ser Leu Thr Cys Trp Leu Lys
        2555                2560                2565

GTA AAT GCT GCA GCC GAA CAG GCT GGC ATG AAG AAC CCT CGC TTC CTT         8200
Val Asn Ala Ala Ala Glu Gln Ala Gly Met Lys Asn Pro Arg Phe Leu
2570                2575                2580                2585

ATT TGC GGC GAT GAT TGC ACC GTA ATT TGG AAG AGC GCC GGA GCA GAT         8248
Ile Cys Gly Asp Asp Cys Thr Val Ile Trp Lys Ser Ala Gly Ala Asp
                2590                2595                2600

GCA GAC AAA CAA GCA ATG CGT GTC TTT GCT AGC TGG ATG AAG GTG ATG         8296
Ala Asp Lys Gln Ala Met Arg Val Phe Ala Ser Trp Met Lys Val Met
        2605                2610                2615

GGT GCA CCA CAA GAT TGT GTG CCT CAA CCC AAA TAC AGT TTG GAA GAA         8344
Gly Ala Pro Gln Asp Cys Val Pro Gln Pro Lys Tyr Ser Leu Glu Glu
            2620                2625                2630

TTA ACA TCA TGC TCA TCA AAT GTT ACC TCT GGA ATT ACC AAA AGT GGC         8392
Leu Thr Ser Cys Ser Ser Asn Val Thr Ser Gly Ile Thr Lys Ser Gly
```

```
                    2635                2640                2645
AAG CCT TAC TAC TTT CTT ACA AGA GAT CCT CGT ATC CCC CTT GGC AGG       8440
Lys Pro Tyr Tyr Phe Leu Thr Arg Asp Pro Arg Ile Pro Leu Gly Arg
2650                2655                2660                2665

TGC TCT GCC GAG GGT CTG GGA TAC AAC CCC AGT GCT GCG TGG ATT GGG       8488
Cys Ser Ala Glu Gly Leu Gly Tyr Asn Pro Ser Ala Ala Trp Ile Gly
                2670                2675                2680

TAT CTA ATA CAT CAC TAC CCA TGT TTG TGG GTT AGC CGT GTG TTG GCT       8536
Tyr Leu Ile His His Tyr Pro Cys Leu Trp Val Ser Arg Val Leu Ala
                    2685                2690                2695

GTC CAT TTC ATG GAG CAG ATG CTC TTT GAG GAC AAA CTT CCC GAG ACT       8584
Val His Phe Met Glu Gln Met Leu Phe Glu Asp Lys Leu Pro Glu Thr
            2700                2705                2710

GTG ACC TTT GAC TGG TAT GGG AAA AAT TAT ACG GTG CCT GTA GAA GAT       8632
Val Thr Phe Asp Trp Tyr Gly Lys Asn Tyr Thr Val Pro Val Glu Asp
        2715                2720                2725

CTG CCC AGC ATC ATT GCT GGT GTG CAC GGT ATT GAG GCT TTC TCG GTG       8680
Leu Pro Ser Ile Ile Ala Gly Val His Gly Ile Glu Ala Phe Ser Val
2730                2735                2740                2745

GTG CGC TAC ACC AAC GCT GAG ATC CTC AGA GTT TCC CAA TCA CTA ACA       8728
Val Arg Tyr Thr Asn Ala Glu Ile Leu Arg Val Ser Gln Ser Leu Thr
                2750                2755                2760

GAC ATG ACC ATG CCC CCC CTG CGA GCC TGG CGA AAG AAA GCC AGG GCG       8776
Asp Met Thr Met Pro Pro Leu Arg Ala Trp Arg Lys Lys Ala Arg Ala
            2765                2770                2775

GTC CTC GCC AGC GCC AAG AGG CGT GGC GGA GCA CAC GCA AAA TTG GCT       8824
Val Leu Ala Ser Ala Lys Arg Arg Gly Gly Ala His Ala Lys Leu Ala
        2780                2785                2790

CGC TTC CTT CTC TGG CAT GCT ACA TCT AGA CCT CTA CCA GAT TTG GAT       8872
Arg Phe Leu Leu Trp His Ala Thr Ser Arg Pro Leu Pro Asp Leu Asp
2795                2800                2805

AAG ACG AGC GTG GCT CGG TAC ACC ACT TTC AAT TAT TGT GAT GTT TAC       8920
Lys Thr Ser Val Ala Arg Tyr Thr Thr Phe Asn Tyr Cys Asp Val Tyr
2810                2815                2820                2825

TCC CCG GAG GGG GAT GTG TTT GTT ACA CCA CAG AGA AGA TTG CAG AAG       8968
Ser Pro Glu Gly Asp Val Phe Val Thr Pro Gln Arg Arg Leu Gln Lys
                2830                2835                2840

TTT CTT GTG AAG TAT TTG GCT GTC ATT GTT TTT GCC CTA GGG CTC ATT       9016
Phe Leu Val Lys Tyr Leu Ala Val Ile Val Phe Ala Leu Gly Leu Ile
            2845                2850                2855

GCT GTT GGA CTA GCC ATC AGC TGAACCCCCA AATTCAAAAT TAATTAACAG          9067
Ala Val Gly Leu Ala Ile Ser
                2860

TTTTTTTTTT TTTTTTTTTT TTTTTTTAGG GCAGCGGCAA CAGGGGAGAC CCCGGGCTTA     9127

ACGACCCCGC GATGTG                                                     9143

(2) INFORMATION FOR SEQ ID NO:394:

(i) SEQUENCE CHARACTERISTICS:
        (A) LENGTH: 2864 amino acids
        (B) TYPE: amino acid
        (D) TOPOLOGY: linear (ii) MOLECULE TYPE: protein (xi) SEQUENCE DESCRIPTION: SEQ ID NO:394:

Met Pro Val Ile Ser Thr Gln Thr Ser Pro Val Pro Ala Pro Arg Thr
 1               5                  10                  15

Arg Lys Asn Lys Gln Thr Gln Ala Ser Tyr Pro Val Ser Ile Lys Thr
                20                  25                  30
```

-continued

```
Ser Val Glu Arg Gly Gln Arg Ala Lys Arg Lys Val Gln Arg Asp Ala
        35                  40                  45
Arg Pro Arg Asn Tyr Lys Ile Ala Gly Ile His Asp Gly Leu Gln Thr
 50                  55                  60
Leu Ala Gln Ala Ala Leu Pro Ala His Gly Trp Gly Arg Gln Asp Pro
 65                  70                  75                  80
Arg His Lys Ser Arg Asn Leu Gly Ile Leu Leu Asp Tyr Pro Leu Gly
                     85                  90                  95
Trp Ile Gly Asp Val Thr Thr His Thr Pro Leu Val Gly Pro Leu Val
                100                 105                 110
Ala Gly Ala Val Val Arg Pro Val Cys Gln Ile Val Arg Leu Leu Glu
                115                 120                 125
Asp Gly Val Asn Trp Ala Thr Gly Trp Phe Gly Val His Leu Phe Val
                130                 135                 140
Val Cys Leu Leu Ser Leu Ala Cys Pro Cys Ser Gly Ala Arg Val Thr
145                 150                 155                 160
Asp Pro Asp Thr Asn Thr Thr Ile Leu Thr Asn Cys Cys Gln Arg Asn
                    165                 170                 175
Gln Val Ile Tyr Cys Ser Pro Ser Thr Cys Leu His Glu Pro Gly Cys
                180                 185                 190
Val Ile Cys Ala Asp Glu Cys Trp Val Pro Ala Asn Pro Tyr Ile Ser
                195                 200                 205
His Pro Ser Asn Trp Thr Gly Thr Asp Ser Phe Leu Ala Asp His Ile
                210                 215                 220
Asp Phe Val Met Gly Ala Leu Val Thr Cys Asp Ala Leu Asp Ile Gly
225                 230                 235                 240
Glu Leu Cys Gly Ala Cys Val Leu Val Gly Asp Trp Leu Val Arg His
                245                 250                 255
Trp Leu Ile His Ile Asp Leu Asn Glu Thr Gly Thr Cys Tyr Leu Glu
                260                 265                 270
Val Pro Thr Gly Ile Asp Pro Gly Phe Leu Gly Phe Ile Gly Trp Met
                275                 280                 285
Ala Gly Lys Val Glu Ala Val Ile Phe Leu Thr Lys Leu Ala Ser Gln
                290                 295                 300
Val Pro Tyr Ala Ile Ala Thr Met Phe Ser Ser Val His Tyr Leu Ala
305                 310                 315                 320
Val Gly Ala Leu Ile Tyr Tyr Ala Ser Arg Gly Lys Trp Tyr Gln Leu
                325                 330                 335
Leu Leu Ala Leu Met Leu Tyr Ile Glu Ala Thr Ser Gly Asn Pro Ile
                340                 345                 350
Arg Val Pro Thr Gly Cys Ser Ile Ala Glu Phe Cys Ser Pro Leu Met
                355                 360                 365
Ile Pro Cys Pro Cys His Ser Tyr Leu Ser Glu Asn Val Ser Glu Val
                370                 375                 380
Ile Cys Tyr Ser Pro Lys Trp Thr Arg Pro Val Thr Leu Glu Tyr Asn
385                 390                 395                 400
Asn Ser Ile Ser Trp Tyr Pro Tyr Thr Ile Pro Gly Ala Arg Gly Cys
                405                 410                 415
Met Val Lys Phe Lys Asn Asn Thr Trp Gly Cys Cys Arg Ile Arg Asn
                420                 425                 430
Val Pro Ser Tyr Cys Thr Met Gly Thr Asp Ala Val Trp Asn Asp Thr
                435                 440                 445
```

-continued

```
Arg Asn Thr Tyr Glu Ala Cys Gly Val Thr Pro Trp Leu Thr Thr Ala
    450                 455                 460
Trp His Asn Gly Ser Ala Leu Lys Leu Ala Ile Leu Gln Tyr Pro Gly
465                 470                 475                 480
Ser Lys Glu Met Phe Lys Pro His Asn Trp Met Ser Gly His Leu Tyr
                485                 490                 495
Phe Glu Gly Ser Asp Thr Pro Ile Val Tyr Phe Tyr Asp Pro Val Asn
            500                 505                 510
Ser Thr Leu Leu Pro Pro Glu Arg Trp Ala Arg Leu Pro Gly Thr Pro
        515                 520                 525
Pro Val Val Arg Gly Ser Trp Leu Gln Val Pro Gln Gly Phe Tyr Ser
    530                 535                 540
Asp Val Lys Asp Leu Ala Thr Gly Leu Ile Thr Lys Asp Lys Ala Trp
545                 550                 555                 560
Lys Asn Tyr Gln Val Leu Tyr Ser Ala Thr Gly Ala Leu Ser Leu Thr
                565                 570                 575
Gly Val Thr Thr Lys Ala Val Val Leu Ile Leu Leu Gly Leu Cys Gly
            580                 585                 590
Ser Lys Tyr Leu Ile Leu Ala Tyr Leu Cys Tyr Leu Ser Leu Cys Phe
        595                 600                 605
Gly Arg Ala Ser Gly Tyr Pro Leu Arg Pro Val Leu Pro Ser Gln Ser
    610                 615                 620
Tyr Leu Gln Ala Gly Trp Asp Val Leu Ser Lys Ala Gln Val Ala Pro
625                 630                 635                 640
Phe Ala Leu Ile Phe Phe Ile Cys Cys Tyr Leu Arg Cys Arg Leu Arg
                645                 650                 655
Tyr Ala Ala Leu Leu Gly Phe Val Pro Met Ala Ala Gly Leu Pro Leu
            660                 665                 670
Thr Phe Phe Val Ala Ala Ala Ala Gln Pro Asp Tyr Asp Trp Trp
        675                 680                 685
Val Arg Leu Leu Val Ala Gly Leu Val Leu Trp Ala Gly Arg Asp Arg
    690                 695                 700
Gly Pro Arg Ile Ala Leu Leu Val Gly Pro Trp Pro Leu Val Ala Leu
705                 710                 715                 720
Leu Thr Leu Leu His Leu Ala Thr Pro Ala Ser Ala Phe Asp Thr Glu
                725                 730                 735
Ile Ile Gly Gly Leu Thr Ile Pro Pro Val Val Ala Leu Val Val Met
            740                 745                 750
Ser Arg Phe Gly Phe Phe Ala His Leu Leu Pro Arg Cys Ala Leu Val
        755                 760                 765
Asn Ser Tyr Leu Trp Gln Arg Trp Glu Asn Trp Phe Trp Asn Val Thr
    770                 775                 780
Leu Arg Pro Glu Arg Phe Leu Val Leu Val Cys Phe Pro Gly Ala
785                 790                 795                 800
Thr Tyr Asp Thr Leu Val Thr Phe Cys Val Cys His Val Ala Leu Leu
                805                 810                 815
Cys Leu Thr Ser Ser Ala Ala Ser Phe Phe Gly Thr Asp Ser Arg Val
            820                 825                 830
Arg Ala His Arg Met Leu Val Arg Leu Gly Lys Cys His Ala Trp Tyr
        835                 840                 845
Ser His Tyr Val Leu Lys Phe Phe Leu Leu Val Phe Gly Glu Asn Gly
    850                 855                 860
Val Phe Phe Tyr Lys His Leu His Gly Asp Val Leu Pro Asn Asp Phe
```

-continued

```
865                 870                 875                 880
Ala Ser Lys Leu Pro Leu Gln Glu Pro Phe Pro Phe Glu Gly Lys
                885                 890                 895
Ala Arg Val Tyr Arg Asn Glu Gly Arg Arg Leu Ala Cys Gly Asp Thr
            900                 905                 910
Val Asp Gly Leu Pro Val Val Ala Arg Leu Gly Asp Leu Val Phe Ala
            915                 920                 925
Gly Leu Ala Met Pro Pro Asp Gly Trp Ala Ile Thr Ala Pro Phe Thr
        930                 935                 940
Leu Gln Cys Leu Ser Glu Arg Gly Thr Leu Ser Ala Met Ala Val Val
945                 950                 955                 960
Met Thr Gly Ile Asp Pro Arg Thr Trp Thr Gly Thr Ile Phe Arg Leu
                965                 970                 975
Gly Ser Leu Ala Thr Ser Tyr Met Gly Phe Val Cys Asp Asn Val Leu
            980                 985                 990
Tyr Thr Ala His His Gly Ser Lys Gly Arg Arg Leu Ala His Pro Thr
        995                 1000                1005
Gly Ser Ile His Pro Ile Thr Val Asp Ala Ala Asn Asp Gln Asp Ile
    1010                1015                1020
Tyr Gln Pro Pro Cys Gly Ala Gly Ser Leu Thr Arg Cys Ser Cys Gly
1025                1030                1035                1040
Glu Thr Lys Gly Tyr Leu Val Thr Arg Leu Gly Ser Leu Val Glu Val
                1045                1050                1055
Asn Lys Ser Asp Asp Pro Tyr Trp Cys Val Cys Gly Ala Leu Pro Met
            1060                1065                1070
Ala Val Ala Lys Gly Ser Ser Gly Ala Pro Ile Leu Cys Ser Ser Gly
        1075                1080                1085
His Val Ile Gly Met Phe Thr Ala Ala Arg Asn Ser Gly Gly Ser Val
    1090                1095                1100
Ser Gln Ile Arg Val Arg Pro Leu Val Cys Ala Gly Tyr His Pro Gln
1105                1110                1115                1120
Tyr Thr Ala His Ala Thr Leu Asp Thr Lys Pro Thr Val Pro Asn Glu
                1125                1130                1135
Tyr Ser Val Gln Ile Leu Ile Ala Pro Thr Gly Ser Gly Lys Ser Thr
            1140                1145                1150
Lys Leu Pro Leu Ser Tyr Met Gln Glu Lys Tyr Glu Val Leu Val Leu
        1155                1160                1165
Asn Pro Ser Val Ala Thr Thr Ala Ser Met Pro Lys Tyr Met His Ala
    1170                1175                1180
Thr Tyr Gly Val Asn Pro Asn Cys Tyr Phe Asn Gly Lys Cys Thr Asn
1185                1190                1195                1200
Thr Gly Ala Ser Leu Thr Tyr Ser Thr Tyr Gly Met Tyr Leu Thr Gly
                1205                1210                1215
Ala Cys Ser Arg Asn Tyr Asp Val Ile Ile Cys Asp Glu Cys His Ala
            1220                1225                1230
Thr Asp Ala Thr Thr Val Leu Gly Ile Gly Lys Val Leu Thr Glu Ala
        1235                1240                1245
Pro Ser Lys Asn Val Arg Leu Val Val Leu Ala Thr Ala Thr Pro Pro
    1250                1255                1260
Gly Val Ile Pro Thr Pro His Ala Asn Ile Thr Glu Ile Gln Leu Thr
1265                1270                1275                1280
Asp Glu Gly Thr Ile Pro Phe His Gly Lys Lys Ile Lys Glu Glu Asn
                1285                1290                1295
```

-continued

```
Leu Lys Lys Gly Arg His Leu Ile Phe Glu Ala Thr Lys Lys His Cys
                1300                1305                1310

Asp Glu Leu Ala Asn Glu Leu Ala Arg Lys Gly Ile Thr Ala Val Ser
            1315                1320                1325

Tyr Tyr Arg Gly Cys Asp Ile Ser Lys Ile Pro Glu Gly Asp Cys Val
        1330                1335                1340

Val Val Ala Thr Asp Ala Leu Cys Thr Gly Tyr Thr Gly Asp Phe Asp
1345                1350                1355                1360

Ser Val Tyr Asp Cys Ser Leu Met Val Glu Gly Thr Cys His Val Asp
                1365                1370                1375

Leu Asp Pro Thr Phe Thr Met Gly Val Arg Val Cys Gly Val Ser Ala
            1380                1385                1390

Ile Val Lys Gly Gln Arg Arg Gly Arg Thr Gly Arg Gly Arg Ala Gly
        1395                1400                1405

Ile Tyr Tyr Tyr Val Asp Gly Ser Cys Thr Pro Ser Gly Met Val Pro
    1410                1415                1420

Glu Cys Asn Ile Val Glu Ala Phe Asp Ala Ala Lys Ala Trp Tyr Gly
1425                1430                1435                1440

Leu Ser Ser Thr Glu Ala Gln Thr Ile Leu Asp Thr Tyr Arg Thr Gln
                1445                1450                1455

Pro Gly Leu Pro Ala Ile Gly Ala Asn Leu Asp Glu Trp Ala Asp Leu
            1460                1465                1470

Phe Ser Met Val Asn Pro Glu Pro Ser Phe Val Asn Thr Ala Lys Arg
        1475                1480                1485

Thr Ala Asp Asn Tyr Val Leu Leu Thr Ala Ala Gln Leu Gln Leu Cys
    1490                1495                1500

His Gln Tyr Gly Tyr Ala Ala Pro Asn Asp Ala Pro Arg Trp Gln Gly
1505                1510                1515                1520

Ala Arg Leu Gly Lys Lys Pro Cys Gly Val Leu Trp Arg Leu Asp Gly
                1525                1530                1535

Ala Asp Ala Cys Pro Gly Pro Glu Pro Ser Glu Val Thr Arg Tyr Gln
            1540                1545                1550

Met Cys Phe Thr Glu Val Asn Thr Ser Gly Thr Ala Ala Leu Ala Val
        1555                1560                1565

Gly Val Gly Val Ala Met Ala Tyr Leu Ala Ile Asp Thr Phe Gly Ala
    1570                1575                1580

Thr Cys Val Arg Arg Cys Trp Ser Ile Thr Ser Val Pro Thr Gly Ala
1585                1590                1595                1600

Thr Val Ala Pro Val Val Asp Glu Glu Ile Val Glu Glu Cys Ala
            1605                1610                1615

Ser Phe Ile Pro Leu Glu Ala Met Val Ala Ala Ile Asp Lys Leu Lys
                1620                1625                1630

Ser Thr Ile Thr Thr Ser Pro Phe Thr Leu Glu Thr Ala Leu Glu
            1635                1640                1645

Lys Leu Asn Thr Phe Leu Gly Pro His Ala Ala Thr Ile Leu Ala Ile
        1650                1655                1660

Ile Glu Tyr Cys Cys Gly Leu Val Thr Leu Pro Asp Asn Pro Phe Ala
1665                1670                1675                1680

Ser Cys Val Phe Ala Phe Ile Ala Gly Ile Thr Thr Pro Leu Pro His
                1685                1690                1695

Lys Ile Lys Met Phe Leu Ser Leu Phe Gly Gly Ala Ile Ala Ser Lys
            1700                1705                1710
```

-continued

```
Leu Thr Asp Ala Arg Gly Ala Leu Ala Phe Met Met Ala Gly Ala Ala
        1715                1720                1725

Gly Thr Ala Leu Gly Thr Trp Thr Ser Val Gly Phe Val Phe Asp Met
    1730                1735                1740

Leu Gly Gly Tyr Ala Ala Ala Ser Ser Thr Ala Cys Leu Thr Phe Lys
1745                1750                1755                1760

Cys Leu Met Gly Glu Trp Pro Thr Met Asp Gln Leu Ala Gly Leu Val
            1765                1770                1775

Tyr Ser Ala Phe Asn Pro Ala Ala Gly Val Val Gly Val Leu Ser Ala
        1780                1785                1790

Cys Ala Met Phe Ala Leu Thr Thr Ala Gly Pro Asp His Trp Pro Asn
        1795                1800                1805

Arg Leu Leu Thr Met Leu Ala Arg Ser Asn Thr Val Cys Asn Glu Tyr
        1810                1815                1820

Phe Ile Ala Thr Arg Asp Ile Arg Arg Lys Ile Leu Gly Ile Leu Glu
1825                1830                1835                1840

Ala Ser Thr Pro Trp Ser Val Ile Ser Ala Cys Ile Arg Trp Leu His
            1845                1850                1855

Thr Pro Thr Glu Asp Asp Cys Gly Leu Ile Ala Trp Gly Leu Glu Ile
        1860                1865                1870

Trp Gln Tyr Val Cys Asn Phe Phe Val Ile Cys Phe Asn Val Leu Lys
        1875                1880                1885

Ala Gly Val Gln Ser Met Val Asn Ile Pro Gly Cys Pro Phe Tyr Ser
    1890                1895                1900

Cys Gln Lys Gly Tyr Lys Gly Pro Trp Ile Gly Ser Gly Met Leu Gln
1905                1910                1915                1920

Ala Arg Cys Pro Cys Gly Ala Glu Leu Ile Phe Ser Val Glu Asn Gly
            1925                1930                1935

Phe Ala Lys Leu Tyr Lys Gly Pro Arg Thr Cys Ser Asn Tyr Trp Arg
        1940                1945                1950

Gly Ala Val Pro Val Asn Ala Arg Leu Cys Gly Ser Ala Arg Pro Asp
        1955                1960                1965

Pro Thr Asp Trp Thr Ser Leu Val Val Asn Tyr Gly Val Arg Asp Tyr
    1970                1975                1980

Cys Lys Tyr Glu Lys Leu Gly Asp His Ile Phe Val Thr Ala Val Ser
1985                1990                1995                2000

Ser Pro Asn Val Cys Phe Thr Gln Val Pro Pro Thr Leu Arg Ala Ala
            2005                2010                2015

Val Ala Val Asp Gly Val Gln Val Gln Cys Tyr Leu Gly Glu Pro Lys
        2020                2025                2030

Thr Pro Trp Thr Thr Ser Ala Cys Cys Tyr Gly Pro Asp Gly Lys Gly
        2035                2040                2045

Lys Thr Val Lys Leu Pro Phe Arg Val Asp Gly His Thr Pro Gly Val
    2050                2055                2060

Arg Met Gln Leu Asn Leu Arg Asp Ala Leu Glu Thr Asn Asp Cys Asn
2065                2070                2075                2080

Ser Ile Asn Asn Thr Pro Ser Asp Glu Ala Ala Val Ser Ala Leu Val
            2085                2090                2095

Phe Lys Gln Glu Leu Arg Arg Thr Asn Gln Leu Leu Glu Ala Ile Ser
        2100                2105                2110

Ala Gly Val Asp Thr Thr Lys Leu Pro Ala Pro Ser Ile Glu Glu Val
        2115                2120                2125

Val Val Arg Lys Arg Gln Phe Arg Ala Arg Thr Gly Ser Leu Thr Leu
```

-continued

```
             2130                2135                2140
Pro Pro Pro Pro Arg Ser Val Pro Gly Val Ser Cys Pro Glu Ser Leu
2145                2150                2155                2160

Gln Arg Ser Asp Pro Leu Glu Gly Pro Ser Asn Leu Pro Ser Ser Pro
            2165                2170                2175

Pro Val Leu Gln Leu Ala Met Pro Met Pro Leu Leu Gly Ala Gly Glu
            2180                2185                2190

Cys Asn Pro Phe Thr Ala Ile Gly Cys Ala Met Thr Glu Thr Gly Gly
            2195                2200                2205

Gly Pro Asp Asp Leu Pro Ser Tyr Pro Pro Lys Lys Glu Val Ser Glu
            2210                2215                2220

Trp Ser Asp Gly Ser Trp Ser Thr Thr Thr Ala Ser Ser Tyr Val
2225                2230                2235                2240

Thr Gly Pro Pro Tyr Pro Lys Ile Arg Gly Lys Asp Ser Thr Gln Ser
            2245                2250                2255

Ala Pro Ala Lys Arg Pro Thr Lys Lys Leu Gly Lys Ser Glu Phe
            2260                2265                2270

Ser Cys Ser Met Ser Tyr Thr Trp Thr Asp Val Ile Ser Phe Lys Thr
            2275                2280                2285

Ala Ser Lys Val Leu Ser Ala Thr Arg Ala Ile Thr Ser Gly Phe Leu
            2290                2295                2300

Lys Gln Arg Ser Leu Val Tyr Val Thr Glu Pro Arg Asp Ala Glu Leu
2305                2310                2315                2320

Arg Lys Gln Lys Val Thr Ile Asn Arg Gln Pro Leu Phe Pro Pro Ser
            2325                2330                2335

Tyr His Lys Gln Val Arg Leu Ala Lys Glu Lys Ala Ser Lys Val Val
            2340                2345                2350

Gly Val Met Trp Asp Tyr Asp Glu Val Ala Ala His Thr Pro Ser Lys
            2355                2360                2365

Ser Ala Lys Ser His Ile Thr Gly Leu Arg Gly Thr Asp Val Arg Ser
            2370                2375                2380

Gly Ala Ala Arg Lys Ala Val Leu Asp Leu Gln Lys Cys Val Glu Ala
2385                2390                2395                2400

Gly Glu Ile Pro Ser His Tyr Arg Gln Thr Val Ile Pro Lys Glu
            2405                2410                2415

Glu Val Phe Val Lys Thr Pro Gln Lys Pro Thr Lys Lys Pro Pro Arg
            2420                2425                2430

Leu Ile Ser Tyr Pro His Leu Glu Met Arg Cys Val Glu Lys Met Tyr
            2435                2440                2445

Tyr Gly Gln Val Ala Pro Asp Val Val Lys Ala Val Met Gly Asp Ala
            2450                2455                2460

Tyr Gly Phe Val Asp Pro Arg Thr Arg Val Lys Arg Leu Leu Ser Met
2465                2470                2475                2480

Trp Ser Pro Asp Ala Val Gly Ala Thr Cys Asp Thr Val Cys Phe Asp
            2485                2490                2495

Ser Thr Ile Thr Pro Glu Asp Ile Met Val Glu Thr Asp Ile Tyr Ser
            2500                2505                2510

Ala Ala Lys Leu Ser Asp Gln His Arg Ala Gly Ile His Thr Ile Ala
            2515                2520                2525

Arg Gln Leu Tyr Ala Gly Gly Pro Met Ile Ala Tyr Asp Gly Arg Glu
            2530                2535                2540

Ile Gly Tyr Arg Arg Cys Arg Ser Ser Gly Val Tyr Thr Thr Ser Ser
2545                2550                2555                2560
```

-continued

```
Ser Asn Ser Leu Thr Cys Trp Leu Lys Val Asn Ala Ala Glu Gln
                2565                2570                2575

Ala Gly Met Lys Asn Pro Arg Phe Leu Ile Cys Gly Asp Asp Cys Thr
                2580                2585                2590

Val Ile Trp Lys Ser Ala Gly Ala Asp Ala Asp Lys Gln Ala Met Arg
                2595                2600                2605

Val Phe Ala Ser Trp Met Lys Val Met Gly Ala Pro Gln Asp Cys Val
                2610                2615                2620

Pro Gln Pro Lys Tyr Ser Leu Glu Glu Leu Thr Ser Cys Ser Ser Asn
2625                2630                2635                2640

Val Thr Ser Gly Ile Thr Lys Ser Gly Lys Pro Tyr Tyr Phe Leu Thr
                2645                2650                2655

Arg Asp Pro Arg Ile Pro Leu Gly Arg Cys Ser Ala Glu Gly Leu Gly
                2660                2665                2670

Tyr Asn Pro Ser Ala Ala Trp Ile Gly Tyr Leu Ile His His Tyr Pro
                2675                2680                2685

Cys Leu Trp Val Ser Arg Val Leu Ala Val His Phe Met Glu Gln Met
                2690                2695                2700

Leu Phe Glu Asp Lys Leu Pro Glu Thr Val Thr Phe Asp Trp Tyr Gly
2705                2710                2715                2720

Lys Asn Tyr Thr Val Pro Val Glu Asp Leu Pro Ser Ile Ile Ala Gly
                2725                2730                2735

Val His Gly Ile Glu Ala Phe Ser Val Val Arg Tyr Thr Asn Ala Glu
                2740                2745                2750

Ile Leu Arg Val Ser Gln Ser Leu Thr Asp Met Thr Met Pro Pro Leu
                2755                2760                2765

Arg Ala Trp Arg Lys Lys Ala Arg Ala Val Leu Ala Ser Ala Lys Arg
                2770                2775                2780

Arg Gly Gly Ala His Ala Lys Leu Ala Arg Phe Leu Leu Trp His Ala
2785                2790                2795                2800

Thr Ser Arg Pro Leu Pro Asp Leu Asp Lys Thr Ser Val Ala Arg Tyr
                2805                2810                2815

Thr Thr Phe Asn Tyr Cys Asp Val Tyr Ser Pro Glu Gly Asp Val Phe
                2820                2825                2830

Val Thr Pro Gln Arg Arg Leu Gln Lys Phe Leu Val Lys Tyr Leu Ala
                2835                2840                2845

Val Ile Val Phe Ala Leu Gly Leu Ile Ala Val Gly Leu Ala Ile Ser
                2850                2855                2860

(2) INFORMATION FOR SEQ ID NO:395:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:395:

Lys Phe Leu Ala Asp Gly Gly Cys Ser Gly Gly Ala Tyr Asp Ile Ile
1               5                   10                  15

Ile Cys Asp Glu Cys His Ser Thr Asp Ala Thr Ser Ile Leu Gly Ile
                20                  25                  30

Gly Thr Val Leu Asp Gln Ala Glu Thr Ala Gly Ala Arg Leu Val Val
                35                  40                  45
```

```
Leu Ala Thr Ala Thr Pro Pro Gly Ser Val Thr Val Pro His Pro Asn
    50                  55                  60

Ile Glu Glu Val Ala Leu Ser Thr Thr Gly Glu Ile Pro Phe Tyr Gly
65                  70                  75                  80

Lys Ala Ile Pro Leu Glu Val Ile Lys Gly Gly Arg His Leu Ile Phe
                85                  90                  95

Cys His Ser Lys Lys Lys Cys Asp Glu Leu Ala Ala Lys Leu Val Ala
            100                 105                 110

Leu Gly Ile Asn Ala Val Ala Tyr Tyr Arg Gly Leu Asp Val Ser Val
        115                 120                 125

Ile Pro Thr Ser Gly Asp Val Val Val Ala Thr Asp Ala Leu Met
130                 135                 140

Thr Gly Tyr Thr Gly Asp Phe Asp Ser Val Ile Asp Cys Asn Thr Cys
145                 150                 155                 160

Val Thr Gln Thr Val Asp Phe Ser Leu Asp Pro Thr Phe Thr Ile Glu
                165                 170                 175

Thr Ile Thr Leu Pro Gln Asp Ala Val Ser Arg Thr Gln Arg Arg Gly
            180                 185                 190

Arg Thr Gly Arg Gly Lys Pro Gly
        195                 200

(2) INFORMATION FOR SEQ ID NO:396:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:396:

Cys Cys Asp Leu Asp Pro Gln Ala Arg Val Ala Ile Lys Ser Leu Thr
1               5                   10                  15

Glu Arg Leu Tyr Val Gly Gly Pro Leu Thr Asn Ser Arg Gly Glu Asn
                20                  25                  30

Cys Gly Tyr Arg Arg Cys Arg Ala Ser Gly Val Leu Thr Thr Ser Cys
            35                  40                  45

Gly Asn Thr Leu Thr Cys Tyr Ile Lys Ala Arg Ala Ala Cys Arg Ala
        50                  55                  60

Ala Gly Leu Gln Asp Cys Thr Met Leu Val Cys Gly Asp Asp Leu Val
65                  70                  75                  80

Val Ile Cys Glu Ser Ala Gly Val Gln Glu Asp Ala Ala Ser Leu Arg
                85                  90                  95

Ala Phe Thr Glu
            100

(2) INFORMATION FOR SEQ ID NO:397:

(i) SEQUENCE CHARACTERISTICS:
        (A) LENGTH: 9034 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..9034
```

(xi) SEQUENCE DESCRIPTION: SEQ ID NO:397:

| | | | | | |
|---|---|---|---|---|---|
| AAAGGTGGTG | GATGGGTGAT | GACAGGGTTG | GTAGGTCGTA | AATCCCGGTC | ATCCTGGTAG | 60
| CCACTATAGG | TGGGTCTTAA | GGGGAGGCTA | CGGTCCCTCT | TGCGCATATG | GAGGAAAAGC | 120
| GCACGGTCCA | CAGGTGTTGG | TCCTACCGGT | GTAATAAGGA | CCCGGCGCTA | GGCACGCCGT | 180
| TAAACCGAGC | CCGTTACTCC | CCTGGGCAAA | CGACGCCCAC | GTACGGTCCA | CGTCGCCCTT | 240
| CAATGTCTCT | CTTGACCAAT | AGGCGTACGG | CGAGTTGACA | AGGACCAGTG | GGGGCCGGGC | 300
| GGGAGGGGGA | AGGACCCCCA | CCGCTGCCCT | TCCCGGGGAG | GCGGGAAATG | CATGGGGCCA | 360
| CCCAGCTCCG | CGGCGGCCTA | CAGCCGGGGT | AGCCCAAGAA | CTTCGGGTGA | GGGCGGGTGG | 420
| CATTTCTTTT | CCTATACCGA | TCATGGCAGT | CCTTCTGCTC | CTACTCGTGG | TGGAGCCGGG | 480
| GCTATTTTAG | CCCCGGCCAC | CCATGCTTGT | AGCGCGAAAG | GGCAATATTT | SCTCACAAAC | 540
| TGTTGCGCCC | TGGAGGACAT | AGGCTTCTGC | CTGGAGGGCG | GATGCCTGGT | GGCTCTGGGG | 600
| TGCACCATTT | GCACCGACCG | CTGCTGGCCA | CTGTATCAGG | CGGGTTTGGC | CGTGCGGCCC | 660
| GGCAAGTCCG | CCGCCCAGTT | GGTGGGGAA | CTCGGTAGTC | TCTACGGGCC | CTTGTCGGTC | 720
| TCGGCTTATG | TGGCCGGGAT | CCTGGGGCTT | GGGGAGGTCT | ACTCGGGGGT | CCTCACCGTC | 780
| GGGGTGGCGT | TGACGCGCAG | GGTCTACCCG | GTCCCGAACC | TGACGTGTGC | AGTAGAGTGT | 840
| GAGTTGAAGT | GGGAAAGTGA | GTTTTGGAGA | TGGACTGAAC | AGCTGGCCTC | AAACTACTGG | 900
| ATTCTGGAAT | ACCTCTGGAA | GGTGCCTTTC | GACTTTTGGC | GGGGAGTGAT | GAGCCTTACT | 960
| CCTCTCTTGG | TGTGCGTGGC | GGCCCTCCTC | CTGCTGGAGC | AGCGTATTGT | CATGGTCTTC | 1020
| CTCCTGGTCA | CTATGGCGGG | CATGTCGCAA | GGCGCGCCCG | CCTCAAGTGT | TGGGGTCACG | 1080
| GCCTTTCGAG | GCGGGTTTGA | CTTGGCAGTC | TTGTTCTTGC | AGGTCGAACG | GGTCCCGCGT | 1140
| GCCGACAGGG | AGAGGGTTTG | GGAACGTGGG | AACGTCACAC | TTTTGTGTGA | CTGCCCCAAC | 1200
| GGTCCTTGGG | TGTGGGTCCC | GGCCCTTTGC | CAGGCAATCG | GATGGGCGA | CCCTATCACT | 1260
| CATTGGAGCC | ACGACAAAA | TCAGTGGCCC | CTTTCTTGTC | CCCAATTTGT | CTACGGCGCC | 1320
| GTTTCAGTGA | CCTGCGTGTG | GGGTTCTGTG | TCTTGGTTTG | CTTCCACTGG | GGGTCGCGAC | 1380
| TCCAAGGTTG | ATGTGTGGAG | TTTGGTTCCA | GTTGGCTCTG | CCAGCTGCAC | CATAGCCGCA | 1440
| CTGGGATCTT | CGGATCGCGA | CACAGTGGTT | GAGCTCTCCG | AGTGGGGAAT | TCCCTGCGCC | 1500
| ACTTGTATCC | TGGACAGGCG | GCCTGCCTCG | TGTGGCACCT | GTGTGAGGGA | CTGCTGGCCC | 1560
| GAGACCGGGT | CGGTACGTTT | CCCATTCCAC | AGGTGTGGCG | CGGGACCGAG | GCTGACCAGA | 1620
| GACCTTGAGG | CTGTGCCCTT | CGTCAATAGG | ACAACTCCCT | TCACCATAAG | GGGGCCCCTG | 1680
| GGCAACCAGG | GGCGAGGCAA | CCCGGTGCGG | TCGCCCTTGG | GTTTTGGGTC | CTACACCATG | 1740
| ACCAAGATCC | GAGACTCCTT | ACACTTGGTG | AAATGTCCCA | CCCCAGCCAT | TGAGCCTCCC | 1800
| ACCGGAACGT | TTGGGTTCTT | CCCAGGAGTC | CCCCCCCTTA | ACAACTGCAT | GCTTCTCGGC | 1860
| ACTGAGGTGT | CAGAGGTATT | GGGTGGGGCG | GGCCTCACTG | GGGGGTTTTA | CGAACCTCTG | 1920
| GTGCGGCGGT | GTTCAGAGCT | GATGGGTCGG | CGGAATCCGG | TCTGCCCGGG | GTTTGCATGG | 1980
| CTCTCTTCGG | GACGGCCTGA | TGGGTTCATA | CATGTTCAGG | GCCACTTGCA | GGAGGTGGAT | 2040
| GCGGGCAACT | TCATTCCGCC | CCCACGCTGG | TTGCTCTTGG | ACTTTGTATT | TGTCCTGTTA | 2100
| TACCTGATGA | AGCTGGCAGA | GGCACGGTTG | GTCCCGCTGA | TCCTCCTCCT | GCTATGGTGG | 2160
| TGGGTGAACC | AGTTGGCGGT | CCTTGKTGTG | SCGGCTGCKC | RCGCCGCCGT | GGCTGGAGAG | 2220
| GTGTTTGCGG | GCCCTGCCTT | GTCCTGGTGT | CTGGGCCTAC | CCTTCGTGAG | TATGATCCTG | 2280

```
GGGCTAGCAA ACCTGGTGTT GTACTTCCGC TGGATGGGTC CTCAACGCCT GATGTTCCTC    2340

GTGTTGTGGA AGCTCGCTCG GGGGGCTTTC CCGCTGGCAT TACTGATGGG GATTTCCGCC    2400

ACTCGCGGCC GCACCTCTGT GCTTGGCGCC GAATTCTGCT TTGATGTCAC CTTTGAAGTG    2460

GACACGTCAG TCTTGGGTTG GGTGGTTGCT AGTGTGGTGG CTTGGGCCAT AGCGCTCCTG    2520

AGCTCTATGA GCGCGGGGGG GTGGAAGCAC AAAGCCATAA TCTATAGGAC GTGGTGTAAA    2580

GGGTACCAGG CYCTTCGCCA GCGCGTGGTG CGTAGCCCCC TCGGGAGGG GCGGCCCACC     2640

AAGCCGCTGA CGATAGCCTG GTGTCTGGCC TCTTACATCT GGCCGGACGC TGTGATGTTG    2700

GTGGTTGTGG CCATGGTCCT CCTCTTCGGC CTTTTCGACG CGCTCGATTG GGCCTTGGAG    2760

GAGCTCCTTG TGTCGCGGCC TTCGTTGCGT CGTTTGGCAA GGGTGGTGGA GTGTTGTGTG    2820

ATGGCGGGCG AGAAGGCCAC TACCGTCCGG CTTGTGTCCA AGATGTGCGC GAGAGGGCC     2880

TACCTGTTTG ACCACATGGG GTCGTTCTCG CGCGCGGTCA AGGAGCGCTT GCTGGAGTGG    2940

GACGCGGCTT TGGAGMCCCT GTCATTCACT AGGACGGACT GTCGCATCAT ACGAGACGCC    3000

GCCAGGACCC TGAGCTGCGG CCAATGCGTC ATGGGCTTGC CCGTGGTGGC TAGGCGCGGC    3060

GATGAGGTCC TGATTGGGGT CTTTCAGGAT GTGAACCACT TGCCTCCGGG GTTTGYTCCT    3120

ACAGCGCCTG TTGTCATCCG TCGGTGCGGA AAGGGCTTCC TCGGGGTCAC TAAGGCTGCC    3180

TTGACTGGTC GGGATCCTGA CTTACACCCA GGAAACGTCA TGGTTTTGGG GACGGCTACC    3240

TCGCGCAGCA TGGGAACGTG CTTAAACGGG TTGCTGTTCA CGACATTCCA TGGGGCTTCT    3300

TCCCGAACCA TTGCGACACC TGTGGGGGCC CTTAACCCAA GGTGGTGGTC GGCCAGTGAT    3360

GACGTCACGG TCTATCCCCT CCCCGATGGA GCTAACTCGT TGGTTCCCTG CTCGTGTCAG    3420

GCTGAGTCCT GTTGGGTCAT YCGATCCGAT GGGGCTCTTT GCCATGGCTT GAGCAAGGGG    3480

GACAAGGTAG AACTGGACGT GGCCATGGAG GTTGCTGACT TTCGTGGGTC GTCTGGGTCT    3540

CCTGTCCTAT GCGACGAGGG GCACGCTGTA GGAATGCTCG TGTCCGTCCT TCATTCGGGG    3600

GGGAGGGTGA CCGCGGCTCG ATTCACTCGG CCGTGGACCC AAGTCCCAAC AGACGCCAAG    3660

ACTACCACTG AGCCACCCCC GGTGCCAGCT AAAGGGGTTT TCAAAGAGGC TCCTCTTTTC    3720

ATGCCAACAG GGGCGGGGAA AAGCACACGC GTCCCTTTGG AGTATGGAAA CATGGGCAC    3780

AAGGTCCTGA TTCTCAACCC GTCGGTTGCC ACTGTGAGGG CCATGGGCCC TTACATGGAG    3840

AGGCTGGCGG GGAAACATCC TAGCATTTTC TGTGGACACG ACACAACAGC TTTCACACGG    3900

ATCACGGACT CTCCATTGAC GTACTCTACC TATGGGAGGT TTCTGGCCAA CCCGAGGCAG    3960

ATGCTGAGGG GAGTTTCCGT GGTCATCTGT GATGAGTGCC ACAGTCATGA CTCAACTGTG    4020

TTGCTGGGTA TAGGCAGGGT CAGGGACGTG GCGCGGGGGT GTGGAGTGCA ATTAGTGCTC    4080

TACGCTACTG CGACTCCCCC GGGCTCGCCT ATGACTCAGC ATCCATCCAT AATTGAGACA    4140

AAGCTGGACG TTGGTGAGAT CCCCTTTTAT GGGCATGGTA TCCCCCTCGA GCGTATGAGG    4200

ACTGGTCGCC ACCTTGTATT CTGCCATTCC AAGGCGGAGT GCGAGAGATT GGCCGGCCAG    4260

TTCTCCGCGC GGGGGGTTAA TGCCATCGCC TATTATAGGG GTAAGGACAG TTCCATCATC    4320

AAAGACGGAG ACCTGGTGGT TGTGCGACA GACGCGCTCT CTACCGGGTA CACAGGAAAC    4380

TTCGATTCTG TCACCGACTG TGGGTTGGTG GTGGAGGAGG TCGTTGAGGT GACCCTTGAT    4440

CCCACCATTA CCATTTCCTT GCGGACTGTC CCTGCTTCGG CTGAATTGTC GATGCAGCGG    4500

CGCGGACGCA CGGGGAGAGG TCGGTCGGGC CGCTACTACT ACGCTGGGGT CGGTAAGGCT    4560

CCCGCGGGGG TGGTGCGGTC TGGTCCGGTC TGGTCGGCAG TGGAAGCTGG AGTGACCTGG    4620

TATGGAATGG AACCTGACTT GACAGCAAAC CTTCTGAGAC TTTACGACGA CTGCCCTTAC    4680
```

```
ACCGCAGCCG TCGCAGCTGA CATTGGTGAA GCCGCGGTGT TCTTTGCGGG CCTCGCGCCC   4740

CTCAGGATGC ATCCCGATGT TAGCTGGGCA AAAGTTCGCG GCGTCAATTG GCCCCTCCTG   4800

GTGGGTGTTC AGCGGACGAT GTGTCGGGAA ACACTGTCTC CCGGCCCGTC GGACGACCCT   4860

CAGTGGGCAG GTCTGAAAGG CCCGAATCCT GTCCCACTAC TGCTGAGGTG GGGCAATGAT   4920

TTGCCATCAA AAGTGGCCGG CCACCACATA GTTGACGATC TGGTCCGTCG GCTCGGTGTG   4980

GCGGAGGGAT ACGTGCGCTG TGATGCTGGR CCCATCCTCA TGGTGGGCTT GGCCATAGCG   5040

GGCGGCATGA TCTACGCCTC TTACACTGGG TCGCTAGTGG TGGTAACAGA CTGGGATGTG   5100

AAGGGAGGTG GCAATCCCCT TTATAGGAGT GGTGACCAGG CCACCCCTCA ACCCGTGGTG   5160

CAGGTCCCCC CGGTAGACCA TCGGCCGGGG GGGGAGTCTG CGCCACGGGA TGCCAAGACA   5220

GTGACAGATG CGGTGGCAGC CATCCAGGTG AACTGCGATT GGTCTGTGAT GACCCTGTCG   5280

ATCGGGAAG TCCTCACCTT GGCTCAGGCT AAGACAGCCG AGGCCTACGC AGCTACTTCC    5340

AGGTGGCTCG CTGGCTGCTA CACGGGGACG CGGGCCGTCC CCACTGTATC AATTGTTGAC   5400

AAGCTCTTCG CCGGGGGTTG GGCCGCCGTG GTGGGTCACT GTCACAGCGT CATTGCTGCG   5460

GCGGTGGCTG CCTATGGAGC TTCTCGAAGT CCTCCACTGG CCGCGGCGGC GTCCTACCTC   5520

ATGGGGTTGG GCGTCGGAGG CAACGCACAG GCGCGCTTGG CTTCAGCTCT TCTACTGGGG   5580

GCTGCTGGTA CGGCTCTGGG ACCCCTGTC GTGGGACTCA CCATGGCGGG GGCCTTCATG    5640

GGCGGTGCCA GCGTGTCCCC CTCCCTCGTC ACTGTCCTAC TTGGGGCTGT GGGAGGTTGG   5700

GAGGGCGTTG TCAACGCTGC CAGTCTCGTC TTCGACTTCA TGGCTGGGAA ACTTTCAACA   5760

GAAGACCTTT GGTATGCCAT CCCGGTACTC ACTAGTCCTG GRGCGGGCCT CGCGGGGATT   5820

GCCCTTGGTC TGGTTTTGTA CTCAGCAAAC AACTCTGGCA CTACCACATG GCTGAACCGT   5880

CTGCTGACGA CGTTGCCACG GTCATCTTGC ATACCCGACA GCTACTTCCA ACAGGCTGAC   5940

TACTGCGACA AGGTCTCGGC AATCGTGCGC CGCCTGAGCC TTACTCGCAC CGTGGTGGCC   6000

CTGGTCAACA GGGAGCCTAA GGTGGATGAG GTCCAGGTGG GGTACGTCTG GGATCTGTGG   6060

GAGTGGGTGA TGCGCCAGGT GCGCATGGTG ATGTCTAGAC TCCGGGCCCT CTGCCCTGTG   6120

GTGTCACTCC CCTTGTGGCA CTGCGGGGAG GGGTGGTCCG GTGAATGGCT TCTCGATGGG   6180

CACGTGGAGA GTCGTTGTCT GTGCGGGTGT GTAATCACCG GCGACGTCCT CAATGGGCAA   6240

CTCAAAGATC CAGTTTACTC TACCAAGCTG TGCAGGCACT ACTGGATGGG AACTGTGCCG   6300

GTCAACATGC TGGGCTACGG GGAAACCTCA CCTCTTCTCG CCTCTGACAC CCCGAAGGTG   6360

GTACCCTTCG GGACGTCGGG GTGGGCTGAG GTGGTGGTGA CCCCTACCCA CGTGGTGATC   6420

AGGCGCACGT CCTGTTACAA ACTGCTTCGC CAGCAAATTC TTTCAGCAGC TGTAGCTGAG   6480

CCCTACTACG TTGATGGCAT TCCGGTCTCT TGGGAGGCTG ACGCGAGAGC GCCGGCCATG   6540

GTCTACGGTC CGGGCCAAAG TGTTACCATT GATGGGGAGC GCTACACCCT TCCGCACCAG   6600

TTGCGGATGC GGAATGTGGC GCCCTCTGAG GTTTCATCTG AGGTCAGCAT CGAGATCGGG   6660

ACGGAGACTG AAGACTCAGA ACTGACTGAG GCCGATTTGC CACCAGCGGC TGCTGCCCTC   6720

CAAGCGATAG AGAATGCTGC GAGAATTCTC GAACCGCACA TCGATGTCAY CATGGAGGAT   6780

TGCAGTACAC CCTCTCTCTG TGGTAGTAGC CGAGAGATGC CTGTGTGGGG AGAAGACATA   6840

CCCCGCACTC CATCGCCTGC ACTTATCTCG GTTACGGAGA GCAGCTCAGA TGAGAAGACC   6900

CTGTCGGTGA CCTCCTCGCA GGAGGACACC CCGTCCTCAG ACTCATTTGA AGTCATCCAA   6960

GAGTCTGATA CTGCTGAATC AGAGGAAAGC GTCTTCAACG TGGCTCTTTC CGTACTAAAA   7020
```

```
GCCTTATTTC CACAGAGCGA TGCCACACGA AAGCTAACGG TTAAGATGTC TTGCTGTGTT      7080

GAGAAGAGCG TAACACGCTT CTTTTCTTTA GGGTTGACCG TGGCTGACGT GGCTAGCCTG      7140

TGTGAGATGG AGATCCAGAA CCATACAGCC TATTGTGACA AGGTGCGCAC TCCGCTCGAA      7200

TTGCAAGTTG GGTGCTTGGT GGGCAATGAA CTTACCTTTG AATGTGACAA GTGTGAGGCA      7260

CGCCAAGAGA CCCTTGCCTC CTTCTCCTAC ATATGGTCCG GGGTCCCACT TACTCGGGCC      7320

ACTCCGGCCA AACCACCAGT GGTGAGGCCG GTGGGTCCT TGTTGGTGGC AGACACCACC       7380

AAGGTCTACG TGACCAATCC GGACAATGTT GGGAGGAGGG TTGACAAGGT GACTTTCTGG      7440

CGCGCTCCTC GGGTACACGA CAAGTTCCTC GTGGACTCGA TCGAGCGCGC TCGGAGAGCT      7500

GCTCAAGGCT GCCTAAGCAT GGGTTACACT TATGAGGAGG CAATAAGGAC TGTTAGGCCG      7560

CATGCTGCCA TGGGCTGGGG ATCTAAGGTG TCGGTCAAGG ACTTGGCCAC CCCTGCGGGG      7620

AAGATGGCTG TTCATGACCG GCTTCAGGAG ATACTTGAAG GGACTCCGGT CCCTTTTACC      7680

CTGACTGTCA AAAAGGAGGT GTTCTTCAAA GATCGTAAGG AGGAGAAGGC CCCCCGCCTC     7740

ATTGTGTTCC CCCCCCTGGA CTTCCGGATA GCTGAAAAGC TCATTCTGGG AGACCCGGGG     7800

CGGGTTGCAA AGGCCGGTGT TGGGGGGGCT TACGCCTTCC AGTACACCCC CAACCAGCGG     7860

GTTAAGGAGA TGCTAAAGCT GTGGGAATCA AAGAAGACCC CGTGCGCCAT CTGTGTGGAT     7920

GCCACTTGCT TCGACAGTAG CATTACTGAR GAGGACGTGG CACTAGAGAC AGAGCTTTAC     7980

GCCCTGGCCT CGGACCATCC AGAATGGGTG CGCGCCCTGG GGAAATACTR TGCCTCTGGC     8040

ACAATGGTGA CCCCGGAAGG GGTGCCAGTG GGCGAGAGGT ATTGTAGGTC CTCGGGTGTG     8100

TTGACCACAA GTGCTAGCAA CTGTTTGACC TGCTACATCA AAGTGAGAGC CGCCTGTGAG     8160

AGGATCGGAC TGAAAAATGT CTCGCTTCTC ATCGCGGGCG ATGACTGCTT AATTGTGTGC     8220

GAGAGGCCTG TATGCGACCC TTGCGAGGCC CTGGGCCGAA CCCTGGCTTC GTACGGGTAC     8280

GCGTGTGAGC CCTCGTATCA CGCTTCACTG GACACAGCCC CCTTCTGCTC CACTTGGCTC     8340

GCTGAGTGCA ATGCGGATGG GRAAAGGCAT TTCTTCCTGA CCACGGACTT TCGGAGACCA     8400

CTCGCTCGCA TGTCGAGCGA GTACAGTGAC CCTATGGCTT CGGCCATTGG TTACATTCTC     8460

CTCTACCCCT GGCRTCCCAT CACACGGTGG GTCATCATCC CGCATGTGCT AACATGCGCT     8520

TCTTCCCGGG GTGGTGGCAC ACSGTCTGAT CCGGTTTGGT GTCAGGTTCA TGGTAACTAC     8580

TACAAGTTTC CCCTGGACAA ACTGCCTAAC ATCATCGTGG CCCTCCACGG ACCAGCAGCG     8640

TTGAGGGTTA CCGCAGACAC AACCAAAACA AAGATGGAGG CTGGGAAGGT TCTGAGCGAC     8700

CTCAAGCTCC CTGGTCTAGC CGTCCACCGC AAGAAGGCCG GGGCATTGCG AACACGCATG     8760

CTCCGGTCGC GCGGTTGGGC GGAGTTGGCT AGGGGCCTGT TGTGGCATCC AGGACTCCGG     8820

CTTCCTCCCC CTGAGATTGC TGGTATCCCA GGGGGTTTCC CTCTGTCCCC CCCCTACATG     8880

GGGGTGGTTC ATCAATTGGA TTTCACAGCS CAGCGGAGTC GCTGGCGGTG GTTGGGGTTC     8940

TTAGCCCTGC TCATCGTAGC GCTCTTTGGG TGAACTAAAT TCATCTGTTG CGGCCGGAGT     9000

CAGACCTGAG CCCCGTTCAA AAGGGGATTG AGAC                                9034
```

(2) INFORMATION FOR SEQ ID NO:398:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:398:

```
Lys Gly Gly Gly Trp Val Met Thr Gly Leu Val Gly Arg Lys Ser Arg
  1               5                  10                  15

Ser Ser Trp
```

(2) INFORMATION FOR SEQ ID NO:399:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:399:

```
Val Gly Leu Lys Gly Arg Leu Arg Ser Leu Leu Arg Ile Trp Arg Lys
  1               5                  10                  15

Ser Ala Arg Ser Thr Gly Val Gly Pro Thr Gly Val Ile Arg Thr Arg
                 20                  25                  30

Arg
```

(2) INFORMATION FOR SEQ ID NO:400:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:400:

```
Thr Glu Pro Val Thr Pro Leu Gly Lys Arg Arg Pro Arg Thr Val His
  1               5                  10                  15

Val Ala Leu Gln Cys Leu Ser
                 20
```

(2) INFORMATION FOR SEQ ID NO:401:

(i) SEQUENCE CHARACTERISTICS:
        (A) LENGTH: 2905 amino acids
        (B) TYPE: amino acid
        (D) TOPOLOGY: linear (ii) MOLECULE TYPE: protein (xi) SEQUENCE DESCRIPTION: SEQ ID NO:401:

```
Pro Ile Gly Val Arg Arg Val Asp Lys Asp Gln Trp Gly Pro Gly Gly
  1               5                  10                  15

Arg Gly Lys Asp Pro His Arg Cys Pro Ser Arg Gly Gly Lys Cys
                 20                  25                  30

Met Gly Pro Pro Ser Ser Ala Ala Ala Tyr Ser Arg Gly Ser Pro Arg
                 35                  40                  45

Thr Ser Gly Glu Gly Gly Trp His Phe Phe Ser Tyr Thr Asp His Gly
         50                  55                  60

Ser Pro Ser Ala Pro Thr Arg Gly Gly Ala Gly Ala Ile Leu Ala Pro
 65                  70                  75                  80

Ala Thr His Ala Cys Ser Ala Lys Gly Gln Tyr Xaa Leu Thr Asn Cys
                 85                  90                  95

Cys Ala Leu Glu Asp Ile Gly Phe Cys Leu Glu Gly Cys Leu Val
                100                 105                 110

Ala Leu Gly Cys Thr Ile Cys Thr Asp Arg Cys Trp Pro Leu Tyr Gln
                115                 120                 125
```

```
Ala Gly Leu Ala Val Arg Pro Gly Lys Ser Ala Ala Gln Leu Val Gly
    130                 135                 140

Glu Leu Gly Ser Leu Tyr Gly Pro Leu Ser Val Ser Ala Tyr Val Ala
145                 150                 155                 160

Gly Ile Leu Gly Leu Gly Glu Val Tyr Ser Gly Val Leu Thr Val Gly
                165                 170                 175

Val Ala Leu Thr Arg Arg Val Tyr Pro Val Pro Asn Leu Thr Cys Ala
            180                 185                 190

Val Glu Cys Glu Leu Lys Trp Glu Ser Glu Phe Trp Arg Trp Thr Glu
        195                 200                 205

Gln Leu Ala Ser Asn Tyr Trp Ile Leu Glu Tyr Leu Trp Lys Val Pro
    210                 215                 220

Phe Asp Phe Trp Arg Gly Val Met Ser Leu Thr Pro Leu Leu Val Cys
225                 230                 235                 240

Val Ala Ala Leu Leu Leu Leu Glu Gln Arg Ile Val Met Val Phe Leu
                245                 250                 255

Leu Val Thr Met Ala Gly Met Ser Gln Gly Ala Pro Ala Ser Ser Val
            260                 265                 270

Gly Val Thr Ala Phe Arg Gly Gly Phe Asp Leu Ala Val Leu Phe Leu
        275                 280                 285

Gln Val Glu Arg Val Pro Arg Ala Asp Arg Glu Arg Val Trp Glu Arg
    290                 295                 300

Gly Asn Val Thr Leu Leu Cys Asp Cys Pro Asn Gly Pro Trp Val Trp
305                 310                 315                 320

Val Pro Ala Leu Cys Gln Ala Ile Gly Trp Gly Asp Pro Ile Thr His
                325                 330                 335

Trp Ser His Gly Gln Asn Gln Trp Pro Leu Ser Cys Pro Gln Phe Val
            340                 345                 350

Tyr Gly Ala Val Ser Val Thr Cys Val Trp Gly Ser Val Ser Trp Phe
        355                 360                 365

Ala Ser Thr Gly Gly Arg Asp Ser Lys Val Asp Val Trp Ser Leu Val
    370                 375                 380

Pro Val Gly Ser Ala Ser Cys Thr Ile Ala Ala Leu Gly Ser Ser Asp
385                 390                 395                 400

Arg Asp Thr Val Val Glu Leu Ser Glu Trp Gly Ile Pro Cys Ala Thr
                405                 410                 415

Cys Ile Leu Asp Arg Arg Pro Ala Ser Cys Gly Thr Cys Val Arg Asp
            420                 425                 430

Cys Trp Pro Glu Thr Gly Ser Val Arg Phe Pro Phe His Arg Cys Gly
        435                 440                 445

Ala Gly Pro Arg Leu Thr Arg Asp Leu Glu Ala Val Pro Phe Val Asn
    450                 455                 460

Arg Thr Thr Pro Phe Thr Ile Arg Gly Pro Leu Gly Asn Gln Gly Arg
465                 470                 475                 480

Gly Asn Pro Val Arg Ser Pro Leu Gly Phe Gly Ser Tyr Thr Met Thr
                485                 490                 495

Lys Ile Arg Asp Ser Leu His Leu Val Lys Cys Pro Thr Pro Ala Ile
            500                 505                 510

Glu Pro Pro Thr Gly Thr Phe Gly Phe Phe Pro Gly Val Pro Pro Leu
        515                 520                 525

Asn Asn Cys Met Leu Leu Gly Thr Glu Val Ser Glu Val Leu Gly Gly
    530                 535                 540
```

-continued

```
Ala Gly Leu Thr Gly Gly Phe Tyr Glu Pro Leu Val Arg Arg Cys Ser
545                 550                 555                 560

Glu Leu Met Gly Arg Arg Asn Pro Val Cys Pro Gly Phe Ala Trp Leu
                565                 570                 575

Ser Ser Gly Arg Pro Asp Gly Phe Ile His Val Gln Gly His Leu Gln
            580                 585                 590

Glu Val Asp Ala Gly Asn Phe Ile Pro Pro Arg Trp Leu Leu Leu
        595                 600                 605

Asp Phe Val Phe Val Leu Leu Tyr Leu Met Lys Leu Ala Glu Ala Arg
    610                 615                 620

Leu Val Pro Leu Ile Leu Leu Leu Trp Trp Val Asn Gln Leu
625                 630                 635                 640

Ala Val Leu Xaa Val Xaa Ala Xaa Xaa Ala Val Ala Gly Glu Val
                645                 650                 655

Phe Ala Gly Pro Ala Leu Ser Trp Cys Leu Gly Leu Pro Phe Val Ser
            660                 665                 670

Met Ile Leu Gly Leu Ala Asn Leu Val Leu Tyr Phe Arg Trp Met Gly
        675                 680                 685

Pro Gln Arg Leu Met Phe Leu Val Leu Trp Lys Leu Ala Arg Gly Ala
    690                 695                 700

Phe Pro Leu Ala Leu Leu Met Gly Ile Ser Ala Thr Arg Gly Arg Thr
705                 710                 715                 720

Ser Val Leu Gly Ala Glu Phe Cys Phe Asp Val Thr Phe Glu Val Asp
                725                 730                 735

Thr Ser Val Leu Gly Trp Val Ala Ser Val Ala Trp Ala Ile
            740                 745                 750

Ala Leu Leu Ser Ser Met Ser Ala Gly Gly Trp Lys His Lys Ala Ile
        755                 760                 765

Ile Tyr Arg Thr Trp Cys Lys Gly Tyr Gln Xaa Leu Arg Gln Arg Val
    770                 775                 780

Val Arg Ser Pro Leu Gly Glu Gly Arg Pro Thr Lys Pro Leu Thr Ile
785                 790                 795                 800

Ala Trp Cys Leu Ala Ser Tyr Ile Trp Pro Asp Ala Val Met Leu Val
                805                 810                 815

Val Val Ala Met Val Leu Leu Phe Gly Leu Phe Asp Ala Leu Asp Trp
            820                 825                 830

Ala Leu Glu Glu Leu Leu Val Ser Arg Pro Ser Leu Arg Arg Leu Ala
        835                 840                 845

Arg Val Val Glu Cys Cys Val Met Ala Gly Glu Lys Ala Thr Thr Val
850                 855                 860

Arg Leu Val Ser Lys Met Cys Ala Arg Gly Ala Tyr Leu Phe Asp His
865                 870                 875                 880

Met Gly Ser Phe Ser Arg Ala Val Lys Glu Arg Leu Leu Glu Trp Asp
            885                 890                 895

Ala Ala Leu Glu Xaa Leu Ser Phe Thr Arg Thr Asp Cys Arg Ile Ile
        900                 905                 910

Arg Asp Ala Ala Arg Thr Leu Ser Cys Gly Gln Cys Val Met Gly Leu
    915                 920                 925

Pro Val Val Ala Arg Arg Gly Asp Glu Val Leu Ile Gly Val Phe Gln
930                 935                 940

Asp Val Asn His Leu Pro Pro Gly Phe Xaa Pro Thr Ala Pro Val Val
945                 950                 955                 960

Ile Arg Arg Cys Gly Lys Gly Phe Leu Gly Val Thr Lys Ala Ala Leu
```

-continued

```
                965                 970                 975
Thr Gly Arg Asp Pro Asp Leu His Pro Gly Asn Val Met Val Leu Gly
                980                 985                 990
Thr Ala Thr Ser Arg Ser Met Gly Thr Cys Leu Asn Gly Leu Leu Phe
            995                1000                1005
Thr Thr Phe His Gly Ala Ser Ser Arg Thr Ile Ala Thr Pro Val Gly
       1010                1015                1020
Ala Leu Asn Pro Arg Trp Trp Ser Ala Ser Asp Asp Val Thr Val Tyr
1025                1030                1035                1040
Pro Leu Pro Asp Gly Ala Asn Ser Leu Val Pro Cys Ser Cys Gln Ala
                1045                1050                1055
Glu Ser Cys Trp Val Xaa Arg Ser Asp Gly Ala Leu Cys His Gly Leu
            1060                1065                1070
Ser Lys Gly Asp Lys Val Glu Leu Asp Val Ala Met Glu Val Ala Asp
       1075                1080                1085
Phe Arg Gly Ser Ser Gly Ser Pro Val Leu Cys Asp Glu Gly His Ala
1090                1095                1100
Val Gly Met Leu Val Ser Val Leu His Ser Gly Gly Arg Val Thr Ala
1105                1110                1115                1120
Ala Arg Phe Thr Arg Pro Trp Thr Gln Val Pro Thr Asp Ala Lys Thr
                1125                1130                1135
Thr Thr Glu Pro Pro Pro Val Pro Ala Lys Gly Val Phe Lys Glu Ala
            1140                1145                1150
Pro Leu Phe Met Pro Thr Gly Ala Gly Lys Ser Thr Arg Val Pro Leu
       1155                1160                1165
Glu Tyr Gly Asn Met Gly His Lys Val Leu Ile Leu Asn Pro Ser Val
       1170                1175                1180
Ala Thr Val Arg Ala Met Gly Pro Tyr Met Glu Arg Leu Ala Gly Lys
1185                1190                1195                1200
His Pro Ser Ile Phe Cys Gly His Asp Thr Thr Ala Phe Thr Arg Ile
                1205                1210                1215
Thr Asp Ser Pro Leu Thr Tyr Ser Thr Tyr Gly Arg Phe Leu Ala Asn
            1220                1225                1230
Pro Arg Gln Met Leu Arg Gly Val Ser Val Val Ile Cys Asp Glu Cys
       1235                1240                1245
His Ser His Asp Ser Thr Val Leu Leu Gly Ile Gly Arg Val Arg Asp
       1250                1255                1260
Val Ala Arg Gly Cys Gly Val Gln Leu Val Leu Tyr Ala Thr Ala Thr
1265                1270                1275                1280
Pro Pro Gly Ser Pro Met Thr Gln His Pro Ser Ile Ile Glu Thr Lys
                1285                1290                1295
Leu Asp Val Gly Glu Ile Pro Phe Tyr Gly His Gly Ile Pro Leu Glu
            1300                1305                1310
Arg Met Arg Thr Gly Arg His Leu Val Phe Cys His Ser Lys Ala Glu
       1315                1320                1325
Cys Glu Arg Leu Ala Gly Gln Phe Ser Ala Arg Gly Val Asn Ala Ile
       1330                1335                1340
Ala Tyr Tyr Arg Gly Lys Asp Ser Ser Ile Ile Lys Asp Gly Asp Leu
1345                1350                1355                1360
Val Val Cys Ala Thr Asp Ala Leu Ser Thr Gly Tyr Thr Gly Asn Phe
                1365                1370                1375
Asp Ser Val Thr Asp Cys Gly Leu Val Val Glu Val Val Glu Val
            1380                1385                1390
```

-continued

```
Thr Leu Asp Pro Thr Ile Thr Ile Ser Leu Arg Thr Val Pro Ala Ser
    1395                1400                1405

Ala Glu Leu Ser Met Gln Arg Arg Gly Arg Thr Gly Arg Gly Arg Ser
    1410                1415                1420

Gly Arg Tyr Tyr Tyr Ala Gly Val Gly Lys Ala Pro Ala Gly Val Val
1425                1430                1435                1440

Arg Ser Gly Pro Val Trp Ser Ala Val Glu Ala Gly Val Thr Trp Tyr
                1445                1450                1455

Gly Met Glu Pro Asp Leu Thr Ala Asn Leu Leu Arg Leu Tyr Asp Asp
                1460                1465                1470

Cys Pro Tyr Thr Ala Ala Val Ala Ala Asp Ile Gly Glu Ala Ala Val
                1475                1480                1485

Phe Phe Ala Gly Leu Ala Pro Leu Arg Met His Pro Asp Val Ser Trp
    1490                1495                1500

Ala Lys Val Arg Gly Val Asn Trp Pro Leu Leu Val Gly Val Gln Arg
1505                1510                1515                1520

Thr Met Cys Arg Glu Thr Leu Ser Pro Gly Pro Ser Asp Asp Pro Gln
                1525                1530                1535

Trp Ala Gly Leu Lys Gly Pro Asn Pro Val Pro Leu Leu Arg Trp
    1540                1545                1550

Gly Asn Asp Leu Pro Ser Lys Val Ala Gly His His Ile Val Asp Asp
                1555                1560                1565

Leu Val Arg Arg Leu Gly Val Ala Glu Gly Tyr Val Arg Cys Asp Ala
    1570                1575                1580

Xaa Pro Ile Leu Met Val Gly Leu Ala Ile Ala Gly Gly Met Ile Tyr
1585                1590                1595                1600

Ala Ser Tyr Thr Gly Ser Leu Val Val Val Thr Asp Trp Asp Val Lys
                1605                1610                1615

Gly Gly Gly Asn Pro Leu Tyr Arg Ser Gly Asp Gln Ala Thr Pro Gln
                1620                1625                1630

Pro Val Val Gln Val Pro Pro Val Asp His Arg Pro Gly Gly Glu Ser
                1635                1640                1645

Ala Pro Arg Asp Ala Lys Thr Val Thr Asp Ala Val Ala Ala Ile Gln
    1650                1655                1660

Val Asn Cys Asp Trp Ser Val Met Thr Leu Ser Ile Gly Glu Val Leu
1665                1670                1675                1680

Thr Leu Ala Gln Ala Lys Thr Ala Glu Ala Tyr Ala Ala Thr Ser Arg
                1685                1690                1695

Trp Leu Ala Gly Cys Tyr Thr Gly Thr Arg Ala Val Pro Thr Val Ser
                1700                1705                1710

Ile Val Asp Lys Leu Phe Ala Gly Gly Trp Ala Ala Val Val Gly His
                1715                1720                1725

Cys His Ser Val Ile Ala Ala Val Ala Ala Tyr Gly Ala Ser Arg
    1730                1735                1740

Ser Pro Pro Leu Ala Ala Ala Ser Tyr Leu Met Gly Leu Gly Val
1745                1750                1755                1760

Gly Gly Asn Ala Gln Ala Arg Leu Ala Ser Ala Leu Leu Gly Ala
                1765                1770                1775

Ala Gly Thr Ala Leu Gly Thr Pro Val Val Gly Leu Thr Met Ala Gly
                1780                1785                1790

Ala Phe Met Gly Gly Ala Ser Val Ser Pro Ser Leu Val Thr Val Leu
    1795                1800                1805
```

-continued

```
Leu Gly Ala Val Gly Gly Trp Glu Gly Val Val Asn Ala Ala Ser Leu
    1810                1815                1820

Val Phe Asp Phe Met Ala Gly Lys Leu Ser Thr Glu Asp Leu Trp Tyr
1825                1830                1835                1840

Ala Ile Pro Val Leu Thr Ser Pro Xaa Ala Gly Leu Ala Gly Ile Ala
                1845                1850                1855

Leu Gly Leu Val Leu Tyr Ser Ala Asn Asn Ser Gly Thr Thr Thr Trp
                1860                1865                1870

Leu Asn Arg Leu Leu Thr Thr Leu Pro Arg Ser Ser Cys Ile Pro Asp
            1875                1880                1885

Ser Tyr Phe Gln Gln Ala Asp Tyr Cys Asp Lys Val Ser Ala Ile Val
            1890                1895                1900

Arg Arg Leu Ser Leu Thr Arg Thr Val Val Ala Leu Val Asn Arg Glu
1905                1910                1915                1920

Pro Lys Val Asp Glu Val Gln Val Gly Tyr Val Trp Asp Leu Trp Glu
                1925                1930                1935

Trp Val Met Arg Gln Val Arg Met Val Met Ser Arg Leu Arg Ala Leu
                1940                1945                1950

Cys Pro Val Val Ser Leu Pro Leu Trp His Cys Gly Glu Gly Trp Ser
            1955                1960                1965

Gly Glu Trp Leu Leu Asp Gly His Val Glu Ser Arg Cys Leu Cys Gly
        1970                1975                1980

Cys Val Ile Thr Gly Asp Val Leu Asn Gly Gln Leu Lys Asp Pro Val
1985                1990                1995                2000

Tyr Ser Thr Lys Leu Cys Arg His Tyr Trp Met Gly Thr Val Pro Val
                2005                2010                2015

Asn Met Leu Gly Tyr Gly Glu Thr Ser Pro Leu Leu Ala Ser Asp Thr
                2020                2025                2030

Pro Lys Val Val Pro Phe Gly Thr Ser Gly Trp Ala Glu Val Val Val
            2035                2040                2045

Thr Pro Thr His Val Val Ile Arg Arg Thr Ser Cys Tyr Lys Leu Leu
        2050                2055                2060

Arg Gln Gln Ile Leu Ser Ala Ala Val Ala Glu Pro Tyr Tyr Val Asp
2065                2070                2075                2080

Gly Ile Pro Val Ser Trp Glu Ala Asp Ala Arg Ala Pro Ala Met Val
                2085                2090                2095

Tyr Gly Pro Gly Gln Ser Val Thr Ile Asp Gly Glu Arg Tyr Thr Leu
                2100                2105                2110

Pro His Gln Leu Arg Met Arg Asn Val Ala Pro Ser Glu Val Ser Ser
            2115                2120                2125

Glu Val Ser Ile Glu Ile Gly Thr Glu Thr Glu Asp Ser Glu Leu Thr
        2130                2135                2140

Glu Ala Asp Leu Pro Pro Ala Ala Ala Leu Gln Ala Ile Glu Asn
2145                2150                2155                2160

Ala Ala Arg Ile Leu Glu Pro His Ile Asp Val Xaa Met Glu Asp Cys
                2165                2170                2175

Ser Thr Pro Ser Leu Cys Gly Ser Ser Arg Glu Met Pro Val Trp Gly
            2180                2185                2190

Glu Asp Ile Pro Arg Thr Pro Ser Pro Ala Leu Ile Ser Val Thr Glu
            2195                2200                2205

Ser Ser Ser Asp Glu Lys Thr Leu Ser Val Thr Ser Ser Gln Glu Asp
            2210                2215                2220

Thr Pro Ser Ser Asp Ser Phe Glu Val Ile Gln Glu Ser Asp Thr Ala
```

-continued

```
              2225                2230                2235                2240

Glu Ser Glu Glu Ser Val Phe Asn Val Ala Leu Ser Val Leu Lys Ala
                2245                2250                2255

Leu Phe Pro Gln Ser Asp Ala Thr Arg Lys Leu Thr Val Lys Met Ser
                2260                2265                2270

Cys Cys Val Glu Lys Ser Val Thr Arg Phe Phe Ser Leu Gly Leu Thr
                2275                2280                2285

Val Ala Asp Val Ala Ser Leu Cys Glu Met Glu Ile Gln Asn His Thr
                2290                2295                2300

Ala Tyr Cys Asp Lys Val Arg Thr Pro Leu Glu Leu Gln Val Gly Cys
2305                2310                2315                2320

Leu Val Gly Asn Glu Leu Thr Phe Glu Cys Asp Lys Cys Glu Ala Arg
                2325                2330                2335

Gln Glu Thr Leu Ala Ser Phe Ser Tyr Ile Trp Ser Gly Val Pro Leu
                2340                2345                2350

Thr Arg Ala Thr Pro Ala Lys Pro Pro Val Val Arg Pro Val Gly Ser
                2355                2360                2365

Leu Leu Val Ala Asp Thr Thr Lys Val Tyr Val Thr Asn Pro Asp Asn
                2370                2375                2380

Val Gly Arg Arg Val Asp Lys Val Thr Phe Trp Arg Ala Pro Arg Val
2385                2390                2395                2400

His Asp Lys Phe Leu Val Asp Ser Ile Glu Arg Ala Arg Arg Ala Ala
                2405                2410                2415

Gln Gly Cys Leu Ser Met Gly Tyr Thr Tyr Glu Glu Ala Ile Arg Thr
                2420                2425                2430

Val Arg Pro His Ala Ala Met Gly Trp Gly Ser Lys Val Ser Val Lys
                2435                2440                2445

Asp Leu Ala Thr Pro Ala Gly Lys Met Ala Val His Asp Arg Leu Gln
                2450                2455                2460

Glu Ile Leu Glu Gly Thr Pro Val Pro Phe Thr Leu Thr Val Lys Lys
2465                2470                2475                2480

Glu Val Phe Phe Lys Asp Arg Lys Glu Glu Lys Ala Pro Arg Leu Ile
                2485                2490                2495

Val Phe Pro Pro Leu Asp Phe Arg Ile Ala Glu Lys Leu Ile Leu Gly
                2500                2505                2510

Asp Pro Gly Arg Val Ala Lys Ala Gly Val Gly Gly Ala Tyr Ala Phe
                2515                2520                2525

Gln Tyr Thr Pro Asn Gln Arg Val Lys Glu Met Leu Lys Leu Trp Glu
                2530                2535                2540

Ser Lys Lys Thr Pro Cys Ala Ile Cys Val Asp Ala Thr Cys Phe Asp
2545                2550                2555                2560

Ser Ser Ile Thr Xaa Glu Asp Val Ala Leu Glu Thr Glu Leu Tyr Ala
                2565                2570                2575

Leu Ala Ser Asp His Pro Glu Trp Val Arg Ala Leu Gly Lys Tyr Xaa
                2580                2585                2590

Ala Ser Gly Thr Met Val Thr Pro Glu Gly Val Pro Val Gly Glu Arg
                2595                2600                2605

Tyr Cys Arg Ser Ser Gly Val Leu Thr Thr Ser Ala Ser Asn Cys Leu
                2610                2615                2620

Thr Cys Tyr Ile Lys Val Arg Ala Ala Cys Glu Arg Ile Gly Leu Lys
2625                2630                2635                2640

Asn Val Ser Leu Leu Ile Ala Gly Asp Asp Cys Leu Ile Val Cys Glu
                2645                2650                2655
```

```
Arg Pro Val Cys Asp Pro Cys Glu Ala Leu Gly Arg Thr Leu Ala Ser
            2660                2665                2670

Tyr Gly Tyr Ala Cys Glu Pro Ser Tyr His Ala Ser Leu Asp Thr Ala
            2675                2680                2685

Pro Phe Cys Ser Thr Trp Leu Ala Glu Cys Asn Ala Asp Gly Xaa Arg
            2690                2695            2700

His Phe Phe Leu Thr Thr Asp Phe Arg Arg Pro Leu Ala Arg Met Ser
2705                2710                2715                2720

Ser Glu Tyr Ser Asp Pro Met Ala Ser Ala Ile Gly Tyr Ile Leu Leu
            2725                2730                2735

Tyr Pro Trp Xaa Pro Ile Thr Arg Trp Val Ile Ile Pro His Val Leu
            2740                2745                2750

Thr Cys Ala Ser Ser Arg Gly Gly Gly Thr Xaa Ser Asp Pro Val Trp
            2755                2760                2765

Cys Gln Val His Gly Asn Tyr Tyr Lys Phe Pro Leu Asp Lys Leu Pro
            2770                2775                2780

Asn Ile Ile Val Ala Leu His Gly Pro Ala Ala Leu Arg Val Thr Ala
2785                2790                2795                2800

Asp Thr Thr Lys Thr Lys Met Glu Ala Gly Lys Val Leu Ser Asp Leu
            2805                2810                2815

Lys Leu Pro Gly Leu Ala Val His Arg Lys Lys Ala Gly Ala Leu Arg
            2820                2825                2830

Thr Arg Met Leu Arg Ser Arg Gly Trp Ala Glu Leu Ala Arg Gly Leu
            2835                2840                2845

Leu Trp His Pro Gly Leu Arg Leu Pro Pro Glu Ile Ala Gly Ile
            2850                2855                2860

Pro Gly Gly Phe Pro Leu Ser Pro Pro Tyr Met Gly Val Val His Gln
2865                2870                2875                2880

Leu Asp Phe Thr Xaa Gln Arg Ser Arg Trp Arg Trp Leu Gly Phe Leu
            2885                2890                2895

Ala Leu Leu Ile Val Ala Leu Phe Gly
            2900                2905

(2) INFORMATION FOR SEQ ID NO:402:

(i) SEQUENCE CHARACTERISTICS:
        (A) LENGTH:  11 amino acids
        (B) TYPE: amino acid
        (D) TOPOLOGY: linear (ii) MOLECULE TYPE: protein (xi) SEQUENCE DESCRIPTION: SEQ ID NO:402:

Thr Lys Phe Ile Cys Cys Gly Arg Ser Gln Thr
 1               5                  10

(2) INFORMATION FOR SEQ ID NO:403:

(i) SEQUENCE CHARACTERISTICS:
        (A) LENGTH:  8 amino acids
        (B) TYPE: amino acid
        (D) TOPOLOGY: linear (ii) MOLECULE TYPE: protein (xi) SEQUENCE DESCRIPTION: SEQ ID NO:403:

Ala Pro Phe Lys Arg Gly Leu Arg
 1               5
```

(2) INFORMATION FOR SEQ ID NO:404:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:404:

```
Lys Val Val Asp Gly
 1               5
```

(2) INFORMATION FOR SEQ ID NO:405:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:405:

```
Val Val Asn Pro Gly His Pro Gly Ser His Tyr Arg Trp Val Leu Arg
 1               5                  10                  15

Gly Gly Tyr Gly Pro Ser Cys Ala Tyr Gly Gly Lys Ala His Gly Pro
                20                  25                  30

Gln Val Leu Val Leu Pro Val
            35
```

(2) INFORMATION FOR SEQ ID NO:406:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:406:

```
Gly Pro Gly Ala Arg His Ala Val Lys Pro Ser Pro Leu Leu Pro Trp
 1               5                  10                  15

Ala Asn Asp Ala His Val Arg Ser Thr Ser Pro Phe Asn Val Ser Leu
                20                  25                  30

Asp Gln
```

(2) INFORMATION FOR SEQ ID NO:407:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:407:

```
Ala Tyr Gly Glu Leu Thr Arg Thr Ser Gly Gly Arg Ala Gly Gly Gly
 1               5                  10                  15

Arg Thr Pro Thr Ala Ala Leu Pro Gly Glu Ala Gly Asn Ala Trp Gly
                20                  25                  30

His Pro Ala Pro Arg Arg Pro Thr Ala Gly Val Ala Gln Glu Leu Arg
            35                  40                  45

Val Arg Ala Gly Gly Ile Ser Phe Pro Ile Pro Ile Met Ala Val Leu
        50                  55                  60
```

```
Leu Leu Leu Leu Val Val Glu Pro Gly Leu Phe
 65              70              75

(2) INFORMATION FOR SEQ ID NO:408:

(i) SEQUENCE CHARACTERISTICS:
        (A) LENGTH:  23 amino acids
        (B) TYPE: amino acid
        (D) TOPOLOGY: linear (ii) MOLECULE TYPE: protein (xi) SEQUENCE DESCRIPTION: SEQ ID NO:408:

Pro Arg Pro Pro Met Leu Val Ala Arg Lys Gly Asn Ile Xaa Ser Gln
 1               5                  10                  15

Thr Val Ala Pro Trp Arg Thr
                20

(2) INFORMATION FOR SEQ ID NO:409:

(i) SEQUENCE CHARACTERISTICS:
        (A) LENGTH:  76 amino acids
        (B) TYPE: amino acid
        (D) TOPOLOGY: linear (ii) MOLECULE TYPE: protein (xi) SEQUENCE DESCRIPTION: SEQ ID NO:409:

Ala Ser Ala Trp Arg Ala Asp Ala Trp Trp Leu Trp Gly Ala Pro Phe
 1               5                  10                  15

Ala Pro Thr Ala Ala Gly His Cys Ile Arg Arg Val Trp Pro Cys Gly
                20                  25                  30

Pro Ala Ser Pro Pro Ser Trp Trp Gly Asn Ser Val Val Ser Thr
                35              40                  45

Gly Pro Cys Arg Ser Arg Leu Met Trp Pro Gly Ser Trp Gly Leu Gly
         50              55                  60

Arg Ser Thr Arg Gly Ser Ser Pro Ser Gly Trp Arg
 65              70                  75

(2) INFORMATION FOR SEQ ID NO:410:

(i) SEQUENCE CHARACTERISTICS:
        (A) LENGTH:  9 amino acids
        (B) TYPE: amino acid
        (D) TOPOLOGY: linear (ii) MOLECULE TYPE: protein (xi) SEQUENCE DESCRIPTION: SEQ ID NO:410:

Arg Ala Gly Ser Thr Arg Ser Arg Thr
 1               5

(2) INFORMATION FOR SEQ ID NO:411:

(i) SEQUENCE CHARACTERISTICS:
        (A) LENGTH:  33 amino acids
        (B) TYPE: amino acid
        (D) TOPOLOGY: linear (ii) MOLECULE TYPE: protein (xi) SEQUENCE DESCRIPTION: SEQ ID NO:411:

Ser Gly Lys Val Ser Phe Gly Asp Gly Leu Asn Ser Trp Pro Gln Thr
 1               5                  10                  15
```

```
Thr Gly Phe Trp Asn Thr Ser Gly Arg Cys Leu Ser Thr Phe Gly Gly
            20                  25                  30
Glu
```

(2) INFORMATION FOR SEQ ID NO:412:

(i) SEQUENCE CHARACTERISTICS:
        (A) LENGTH: 125 amino acids
    (B) TYPE: amino acid
        (D) TOPOLOGY: linear (ii) MOLECULE TYPE: protein (xi) SEQUENCE DESCRIPTION: SEQ ID NO:412:

```
Ala Leu Leu Ser Trp Cys Ala Trp Arg Pro Ser Cys Trp Ser
 1               5                  10                  15

Ser Val Leu Ser Trp Ser Ser Ser Trp Ser Leu Trp Arg Ala Cys Arg
            20                  25                  30

Lys Ala Arg Pro Pro Gln Val Leu Gly Ser Arg Pro Phe Glu Ala Gly
            35                  40                  45

Leu Thr Trp Gln Ser Cys Ser Cys Arg Ser Asn Gly Ser Arg Val Pro
 50                  55                  60

Thr Gly Arg Gly Phe Gly Asn Val Gly Thr Ser His Phe Cys Val Thr
 65                  70                  75                  80

Ala Pro Thr Val Leu Gly Cys Gly Ser Arg Pro Phe Ala Arg Gln Ser
             85                  90                  95

Asp Gly Ala Thr Leu Ser Leu Ile Gly Ala Thr Asp Lys Ile Ser Gly
             100                 105                 110

Pro Phe Leu Val Pro Asn Leu Ser Thr Ala Pro Phe Gln
         115                 120                 125
```

(2) INFORMATION FOR SEQ ID NO:413:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:413:

```
Pro Ala Cys Gly Val Leu Cys Leu Gly Leu Leu Pro Leu Gly Val Ala
 1               5                  10                  15

Thr Pro Arg Leu Met Cys Gly Val Trp Phe Gln Leu Ala Leu Pro Ala
             20                  25                  30

Ala Pro
```

(2) INFORMATION FOR SEQ ID NO:414:

(i) SEQUENCE CHARACTERISTICS:
        (A) LENGTH: 36 amino acids
        (B) TYPE: amino acid
        (D) TOPOLOGY: linear (ii) MOLECULE TYPE: protein (xi) SEQUENCE DESCRIPTION: SEQ ID NO:414:

```
Pro His Trp Asp Leu Arg Ile Ala Thr Gln Trp Leu Ser Ser Pro Ser
 1               5                  10                  15

Gly Glu Phe Pro Ala Pro Leu Val Ser Trp Thr Gly Gly Leu Pro Arg
             20                  25                  30
```

```
Val Ala Pro Val
        35

(2) INFORMATION FOR SEQ ID NO:415:

(i) SEQUENCE CHARACTERISTICS:
        (A) LENGTH:  22 amino acids
        (B) TYPE:  amino acid
        (D) TOPOLOGY:  linear (ii) MOLECULE TYPE:  protein (xi) SEQUENCE DESCRIPTION: SEQ ID NO:415:

Gly Thr Ala Gly Pro Arg Pro Gly Arg Tyr Val Ser His Ser Thr Gly
 1               5                  10                  15

Val Ala Arg Asp Arg Gly
            20

(2) INFORMATION FOR SEQ ID NO:416:

(i) SEQUENCE CHARACTERISTICS:
        (A) LENGTH:  17 amino acids
        (B) TYPE:  amino acid
        (D) TOPOLOGY:  linear (ii) MOLECULE TYPE:  protein (xi) SEQUENCE DESCRIPTION: SEQ ID NO:416:

Pro Glu Thr Leu Arg Leu Cys Pro Ser Ser Ile Gly Gln Leu Pro Ser
 1               5                  10                  15

Pro (2) INFORMATION FOR SEQ ID NO:417:

(i) SEQUENCE CHARACTERISTICS:
        (A) LENGTH:  23 amino acids
        (B) TYPE:  amino acid
        (D) TOPOLOGY:  linear (ii) MOLECULE TYPE:  protein (xi) SEQUENCE DESCRIPTION: SEQ ID NO:417:

Gly Gly Pro Trp Ala Thr Arg Gly Glu Ala Thr Arg Cys Gly Arg Pro
 1               5                  10                  15

Trp Val Leu Gly Pro Thr Pro
            20

(2) INFORMATION FOR SEQ ID NO:418:

(i) SEQUENCE CHARACTERISTICS:
        (A) LENGTH:  9 amino acids
        (B) TYPE:  amino acid
        (D) TOPOLOGY:  linear (ii) MOLECULE TYPE:  protein (xi) SEQUENCE DESCRIPTION: SEQ ID NO:418:

Pro Arg Ser Glu Thr Pro Tyr Thr Trp
  1               5

(2) INFORMATION FOR SEQ ID NO:419:

(i) SEQUENCE CHARACTERISTICS:
        (A) LENGTH:  56 amino acids
        (B) TYPE:  amino acid
        (D) TOPOLOGY:  linear
```

(ii) MOLECULE TYPE: protein (xi) SEQUENCE DESCRIPTION: SEQ ID NO:419:

Asn Val Pro Pro Gln Pro Leu Ser Leu Pro Pro Glu Arg Leu Gly Ser
1               5                   10                  15

Ser Gln Glu Ser Pro Pro Leu Thr Thr Ala Cys Phe Ser Ala Leu Arg
            20                  25                  30

Cys Gln Arg Tyr Trp Val Gly Arg Ala Ser Leu Gly Phe Thr Asn
        35                  40                  45

Leu Trp Cys Gly Gly Val Gln Ser
    50                  55

(2) INFORMATION FOR SEQ ID NO:420:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:420:

Trp Val Gly Gly Ile Arg Ser Ala Arg Gly Leu His Gly Ser Leu Arg
1               5                   10                  15

Asp Gly Leu Met Gly Ser Tyr Met Phe Arg Ala Thr Cys Arg Arg Trp
            20                  25                  30

Met Arg Ala Thr Ser Phe Arg Pro His Ala Gly Cys Ser Trp Thr Leu
        35                  40                  45

Tyr Leu Ser Cys Tyr Thr
    50

(2) INFORMATION FOR SEQ ID NO:421:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:421:

Ser Trp Gln Arg His Gly Trp Ser Arg
1               5

(2) INFORMATION FOR SEQ ID NO:422:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:422:

Ser Ser Ser Cys Tyr Gly Gly Gly
1               5

(2) INFORMATION FOR SEQ ID NO:423:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:423:

Thr Ser Trp Arg Ser Leu Xaa Xaa Arg Leu Xaa Xaa Pro Pro Trp Leu
 1               5                  10                  15

Glu Arg Cys Leu Arg Ala Leu Pro Cys Pro Gly Val Trp Ala Tyr Pro
                20                  25                  30

Ser (2) INFORMATION FOR SEQ ID NO:424:

(i) SEQUENCE CHARACTERISTICS:
        (A) LENGTH:   14 amino acids
        (B) TYPE: amino acid
        (D) TOPOLOGY: linear (ii) MOLECULE TYPE: protein (xi) SEQUENCE DESCRIPTION: SEQ ID NO:424:

Gln Thr Trp Cys Cys Thr Ser Ala Gly Trp Val Leu Asn Ala
 1               5                  10

(2) INFORMATION FOR SEQ ID NO:425:

(i) SEQUENCE CHARACTERISTICS:
        (A) LENGTH:   17 amino acids
        (B) TYPE: amino acid
        (D) TOPOLOGY: linear (ii) MOLECULE TYPE: protein (xi) SEQUENCE DESCRIPTION: SEQ ID NO:425:

Cys Ser Ser Cys Cys Gly Ser Ser Leu Gly Gly Leu Ser Arg Trp His
 1               5                  10                  15

Tyr (2) INFORMATION FOR SEQ ID NO:426:

(i) SEQUENCE CHARACTERISTICS:
        (A) LENGTH:   41 amino acids
        (B) TYPE: amino acid
        (D) TOPOLOGY: linear (ii) MOLECULE TYPE: protein (xi) SEQUENCE DESCRIPTION: SEQ ID NO:426:

Trp Gly Phe Pro Pro Leu Ala Ala Ala Pro Leu Cys Leu Ala Pro Asn
 1               5                  10                  15

Ser Ala Leu Met Ser Pro Leu Lys Trp Thr Arg Gln Ser Trp Val Gly
                20                  25                  30

Trp Leu Leu Val Trp Trp Leu Gly Pro
                35                  40

(2) INFORMATION FOR SEQ ID NO:427:

(i) SEQUENCE CHARACTERISTICS:
        (A) LENGTH:   9 amino acids
        (B) TYPE: amino acid
        (D) TOPOLOGY: linear (ii) MOLECULE TYPE: protein (xi) SEQUENCE DESCRIPTION: SEQ ID NO:427:

Ala Arg Gly Gly Gly Ser Thr Lys Pro
 1               5

(2) INFORMATION FOR SEQ ID NO:428:

(i) SEQUENCE CHARACTERISTICS:
        (A) LENGTH:  29 amino acids
        (B) TYPE: amino acid
        (D) TOPOLOGY: linear (ii) MOLECULE TYPE: protein (xi) SEQUENCE DESCRIPTION: SEQ ID NO:428:

Ser Ile Gly Arg Gly Val Lys Gly Thr Arg Xaa Phe Ala Ser Ala Trp
1               5                   10                  15

Cys Val Ala Pro Ser Gly Arg Gly Gly Pro Pro Ser Arg
            20                  25

(2) INFORMATION FOR SEQ ID NO:429:

(i) SEQUENCE CHARACTERISTICS:
        (A) LENGTH:  12 amino acids
        (B) TYPE: amino acid
        (D) TOPOLOGY: linear (ii) MOLECULE TYPE: protein (xi) SEQUENCE DESCRIPTION: SEQ ID NO:429:

Pro Gly Val Trp Pro Leu Thr Ser Gly Arg Thr Leu
1               5                   10

(2) INFORMATION FOR SEQ ID NO:430:

(i) SEQUENCE CHARACTERISTICS:
        (A) LENGTH:  41 amino acids
        (B) TYPE: amino acid
        (D) TOPOLOGY: linear (ii) MOLECULE TYPE: protein (xi) SEQUENCE DESCRIPTION: SEQ ID NO:430:

Cys Trp Trp Leu Trp Pro Trp Ser Ser Ser Ala Phe Ser Thr Arg
1               5                   10                  15

Ser Ile Gly Pro Trp Arg Ser Ser Leu Cys Arg Gly Leu Arg Cys Val
            20                  25                  30

Val Trp Gln Gly Trp Trp Ser Val Val
            35                  40

(2) INFORMATION FOR SEQ ID NO:431:

(i) SEQUENCE CHARACTERISTICS:
        (A) LENGTH:  63 amino acids
        (B) TYPE: amino acid
        (D) TOPOLOGY: linear (ii) MOLECULE TYPE: protein (xi) SEQUENCE DESCRIPTION: SEQ ID NO:431:

Trp Arg Ala Arg Arg Pro Leu Pro Ser Gly Leu Cys Pro Arg Cys Ala
1               5                   10                  15

Arg Glu Gly Pro Thr Cys Leu Thr Thr Trp Gly Arg Ser Arg Ala Arg
            20                  25                  30

Ser Arg Ser Ala Cys Trp Ser Gly Thr Arg Leu Trp Xaa Pro Cys His
            35                  40                  45

Ser Leu Gly Arg Thr Val Ala Ser Tyr Glu Thr Pro Pro Gly Pro
        50                  55                  60

(2) INFORMATION FOR SEQ ID NO:432:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:432:

```
Ala Ala Ala Asn Ala Ser Trp Ala Cys Pro Trp Trp Leu Gly Ala Ala
  1               5                  10                  15

Met Arg Ser
```

(2) INFORMATION FOR SEQ ID NO:433:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:433:

```
Leu Gly Ser Phe Arg Met
  1               5
```

(2) INFORMATION FOR SEQ ID NO:434:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:434:

```
Thr Thr Cys Leu Arg Gly Leu Xaa Leu Gln Arg Leu Leu Ser Ser Val
  1               5                  10                  15

Gly Ala Glu Arg Ala Ser Ser Gly Ser Leu Arg Leu Pro
                 20                  25
```

(2) INFORMATION FOR SEQ ID NO:435:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:435:

```
Leu Val Gly Ile Leu Thr Tyr Thr Gln Glu Thr Ser Trp Phe Trp Gly
  1               5                  10                  15

Arg Leu Pro Arg Ala Ala Trp Glu Arg Ala
                 20                  25
```

(2) INFORMATION FOR SEQ ID NO:436:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:436:

```
Thr Gly Cys Cys Ser Arg His Ser Met Gly Leu Leu Pro Glu Pro Leu
 1               5                  10                  15

Arg His Leu Trp Gly Pro Leu Thr Gln Gly Gly Gly Arg Pro Val Met
                20                  25                  30

Thr Ser Arg Ser Ile Pro Ser Pro Met Glu Leu Thr Arg Trp Phe Pro
            35                  40                  45

Ala Arg Val Arg Leu Ser Pro Val Gly Ser Xaa Asp Pro Met Gly Leu
        50                  55                  60

Phe Ala Met Ala
65
```

(2) INFORMATION FOR SEQ ID NO:437:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:437:

```
Ala Arg Gly Thr Arg
 1               5
```

(2) INFORMATION FOR SEQ ID NO:438:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:438:

```
Asn Trp Thr Trp Pro Trp Arg Leu Leu Thr Phe Val Gly Arg Leu Gly
 1               5                  10                  15

Leu Leu Ser Tyr Ala Thr Arg Gly Thr Leu
                20                  25
```

(2) INFORMATION FOR SEQ ID NO:439:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:439:

```
Glu Cys Ser Cys Pro Ser Phe Ile Arg Gly Gly Gly
 1               5                  10
```

(2) INFORMATION FOR SEQ ID NO:440:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:440:

```
Pro Arg Leu Asp Ser Leu Gly Arg Gly Pro Lys Ser Gln Gln Thr Pro
 1               5                  10                  15

Arg Leu Pro Leu Ser His Pro Arg Cys Gln Leu Lys Gly Phe Ser Lys
```

```
              20                  25                  30
Arg Leu Leu Phe Ser Cys Gln Gln Gly Arg Gly Lys Ala His Ala Ser
         35                  40                  45
Leu Trp Ser Met Glu Thr Trp Gly Thr Arg Ser
         50                  55
```

(2) INFORMATION FOR SEQ ID NO:441:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:441:

```
Phe Ser Thr Arg Arg Leu Pro Leu
 1               5
```

(2) INFORMATION FOR SEQ ID NO:442:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:442:

```
Gly Pro Trp Ala Leu Thr Trp Arg Gly Trp Arg Gly Asn Ile Leu Ala
 1               5                  10                  15
Phe Ser Val Asp Thr Thr Gln Gln Leu Ser His Gly Ser Arg Thr Leu
                 20                  25                  30
His
```

(2) INFORMATION FOR SEQ ID NO:443:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:443:

```
Arg Thr Leu Pro Met Gly Gly Phe Trp Pro Thr Arg Gly Arg Cys
 1               5                  10                  15
```

(2) INFORMATION FOR SEQ ID NO:444:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:444:

```
Gly Glu Phe Pro Trp Ser Ser Val Met Ser Ala Thr Val Met Thr Gln
 1               5                  10                  15
Leu Cys Cys Trp Val
                 20
```

(2) INFORMATION FOR SEQ ID NO:445:

(i) SEQUENCE CHARACTERISTICS:
       (A) LENGTH:  13 amino acids
       (B) TYPE: amino acid
       (D) TOPOLOGY: linear (ii) MOLECULE TYPE: protein (xi) SEQUENCE DESCRIPTION: SEQ ID NO:445:

Ala Gly Ser Gly Thr Trp Arg Gly Gly Val Glu Cys Asn
 1               5                  10

(2) INFORMATION FOR SEQ ID NO:446:

(i) SEQUENCE CHARACTERISTICS:
       (A) LENGTH:  12 amino acids
       (B) TYPE: amino acid
       (D) TOPOLOGY: linear (ii) MOLECULE TYPE: protein (xi) SEQUENCE DESCRIPTION: SEQ ID NO:446:

Cys Ser Thr Leu Leu Arg Leu Pro Arg Ala Arg Leu
 1               5                  10

(2) INFORMATION FOR SEQ ID NO:447:

(i) SEQUENCE CHARACTERISTICS:
       (A) LENGTH:  5 amino acids
       (B) TYPE: amino acid
       (D) TOPOLOGY: linear (ii) MOLECULE TYPE: protein (xi) SEQUENCE DESCRIPTION: SEQ ID NO:447:

Leu Ser Ile His Pro
 1               5

(2) INFORMATION FOR SEQ ID NO:448:

(i) SEQUENCE CHARACTERISTICS:
       (A) LENGTH:  21 amino acids
       (B) TYPE: amino acid
       (D) TOPOLOGY: linear (ii) MOLECULE TYPE: protein (xi) SEQUENCE DESCRIPTION: SEQ ID NO:448:

Leu Arg Gln Ser Trp Thr Leu Val Arg Ser Pro Phe Met Gly Met Val
 1               5                  10                  15

Ser Pro Ser Ser Val
            20

(2) INFORMATION FOR SEQ ID NO:449:

(i) SEQUENCE CHARACTERISTICS:
       (A) LENGTH:  77 amino acids
       (B) TYPE: amino acid
       (D) TOPOLOGY: linear (ii) MOLECULE TYPE: protein (xi) SEQUENCE DESCRIPTION: SEQ ID NO:449:

Gly Leu Val Ala Thr Leu Tyr Ser Ala Ile Pro Arg Arg Ser Ala Arg
 1               5                  10                  15

Asp Trp Pro Ala Ser Ser Pro Arg Gly Gly Leu Met Pro Ser Pro Ile
            20                  25                  30

Ile Gly Val Arg Thr Val Pro Ser Ser Lys Thr Glu Thr Trp Trp Phe

-continued

```
                 35                  40                  45
Val Arg Gln Thr Arg Ser Leu Pro Gly Thr Gln Glu Thr Ser Ile Leu
     50                  55                  60
Ser Pro Thr Val Gly Trp Trp Trp Arg Arg Ser Leu Arg
 65                  70                  75
```

(2) INFORMATION FOR SEQ ID NO:450:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:450:

```
Pro Leu Ile Pro Pro Leu Pro Phe Pro Cys Gly Leu Ser Leu Leu Arg
 1               5                  10                  15
Leu Asn Cys Arg Cys Ser Gly Ala Asp Ala Arg Gly Glu Val Gly Arg
                 20                  25                  30
Ala Ala Thr Thr Thr Leu Gly Ser Val Arg Leu Pro Arg Gly Trp Cys
                 35                  40                  45
Gly Leu Val Arg Ser Gly Arg Gln Trp Lys Leu Glu
     50                  55                  60
```

(2) INFORMATION FOR SEQ ID NO:451:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:451:

```
Pro Gly Met Glu Trp Asn Leu Thr
 1               5
```

(2) INFORMATION FOR SEQ ID NO:452:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:452:

```
Gln Gln Thr Phe
 1
```

(2) INFORMATION FOR SEQ ID NO:453:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:453:

```
Asp Phe Thr Thr Thr Ala Leu Thr Pro Gln Pro Ser Gln Leu Thr Leu
 1               5                  10                  15
Val Lys Pro Arg Cys Ser Leu Arg Ala Ser Arg Pro Ser Gly Cys Ile
                 20                  25                  30
```

```
Pro Met Leu Ala Gly Gln Lys Phe Ala Ala Ser Ile Gly Pro Ser Trp
         35                  40                  45

Trp Val Phe Ser Gly Arg Cys Val Gly Lys His Cys Leu Pro Ala Arg
     50                  55                  60

Arg Thr Thr Leu Ser Gly Gln Val
 65                  70
```

(2) INFORMATION FOR SEQ ID NO:454:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:454:

```
Lys Ala Arg Ile Leu Ser His Tyr Cys
 1               5
```

(2) INFORMATION FOR SEQ ID NO:455:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:455:

```
Gly Gly Ala Met Ile Cys His Gln Lys Trp Pro Ala Thr Thr
 1               5                  10
```

(2) INFORMATION FOR SEQ ID NO:456:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:456:

```
Leu Thr Ile Trp Ser Val Gly Ser Val Trp Arg Arg Asp Thr Cys Ala
 1               5                  10                  15

Val Met Leu Xaa Pro Ser Ser Trp Trp Ala Trp Pro
             20                  25
```

(2) INFORMATION FOR SEQ ID NO:457:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:457:

```
Ser Thr Pro Leu Thr Leu Gly Arg
 1               5
```

(2) INFORMATION FOR SEQ ID NO:458:

(i) SEQUENCE CHARACTERISTICS:
        (A) LENGTH: 4 amino acids
        (B) TYPE: amino acid (D) TOPOLOGY: linear (ii) MOLECULE TYPE: protein (xi) SEQUENCE DESCRIPTION: SEQ ID NO:458:

Gln Thr Gly Met
 1

(2) INFORMATION FOR SEQ ID NO:459:

(i) SEQUENCE CHARACTERISTICS:
        (A) LENGTH:  24 amino acids
        (B) TYPE: amino acid
        (D) TOPOLOGY: linear (ii) MOLECULE TYPE: protein (xi) SEQUENCE DESCRIPTION: SEQ ID NO:459:

Arg Glu Val Ala Ile Pro Phe Ile Gly Val Val Thr Arg Pro Pro Leu
 1               5                  10                  15

Asn Pro Trp Cys Arg Ser Pro Arg
            20

(2) INFORMATION FOR SEQ ID NO:460:

(i) SEQUENCE CHARACTERISTICS:
        (A) LENGTH:  15 amino acids
        (B) TYPE: amino acid
        (D) TOPOLOGY: linear (ii) MOLECULE TYPE: protein (xi) SEQUENCE DESCRIPTION: SEQ ID NO:460:

Thr Ile Gly Arg Gly Gly Ser Leu Arg His Gly Met Pro Arg Gln
 1               5                  10                  15

(2) INFORMATION FOR SEQ ID NO:461:

(i) SEQUENCE CHARACTERISTICS:
        (A) LENGTH:  8 amino acids
        (B) TYPE: amino acid
        (D) TOPOLOGY: linear (ii) MOLECULE TYPE: protein (xi) SEQUENCE DESCRIPTION: SEQ ID NO:461:

Gln Met Arg Trp Gln Pro Ser Arg
 1               5

(2) INFORMATION FOR SEQ ID NO:462:

(i) SEQUENCE CHARACTERISTICS:
        (A) LENGTH:  5 amino acids
        (B) TYPE: amino acid
        (D) TOPOLOGY: linear (ii) MOLECULE TYPE: protein (xi) SEQUENCE DESCRIPTION: SEQ ID NO:462:

Thr Ala Ile Gly Leu
 1               5

(2) INFORMATION FOR SEQ ID NO:463:

(i) SEQUENCE CHARACTERISTICS:
        (A) LENGTH:  200 amino acids
        (B) TYPE: amino acid
        (D) TOPOLOGY: linear (ii) MOLECULE TYPE: protein (xi) SEQUENCE DESCRIPTION: SEQ ID NO:463:

```
Pro Cys Arg Ser Gly Lys Ser Ser Pro Trp Leu Arg Leu Arg Gln Pro
1               5                   10                  15

Arg Pro Thr Gln Leu Leu Pro Gly Gly Ser Leu Ala Ala Thr Arg Gly
            20                  25                  30

Arg Gly Pro Ser Pro Leu Tyr Gln Leu Leu Thr Ser Ser Ser Pro Gly
        35                  40                  45

Val Gly Pro Pro Trp Trp Val Thr Val Thr Ala Ser Leu Leu Arg Arg
    50                  55                  60

Trp Leu Pro Met Glu Leu Leu Glu Val Leu His Trp Pro Arg Arg Arg
65                  70                  75                  80

Pro Thr Ser Trp Gly Trp Ala Ser Glu Ala Thr His Arg Arg Ala Trp
                85                  90                  95

Leu Gln Leu Phe Tyr Trp Gly Leu Leu Val Arg Leu Trp Gly Pro Leu
                100                 105                 110

Ser Trp Asp Ser Pro Trp Arg Gly Pro Ser Trp Ala Val Pro Ala Cys
                115                 120                 125

Pro Pro Pro Ser Ser Leu Ser Tyr Leu Gly Leu Trp Glu Val Gly Arg
130                 135                 140

Ala Leu Ser Thr Leu Pro Val Ser Ser Ser Thr Ser Trp Leu Gly Asn
145                 150                 155                 160

Phe Gln Gln Lys Thr Phe Gly Met Pro Ser Arg Tyr Ser Leu Val Leu
                165                 170                 175

Xaa Arg Ala Ser Arg Gly Leu Pro Leu Val Trp Phe Cys Thr Gln Gln
                180                 185                 190

Thr Thr Leu Ala Leu Pro His Gly
            195                 200
```

(2) INFORMATION FOR SEQ ID NO:464:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:464:

```
Arg Arg Cys His Gly His Leu Ala Tyr Pro Thr Ala Thr Ser Asn Arg
1               5                   10                  15

Leu Thr Thr Ala Thr Arg Ser Arg Gln Ser Cys Ala Ala
            20                  25
```

(2) INFORMATION FOR SEQ ID NO:465:

(i) SEQUENCE CHARACTERISTICS:
        (A) LENGTH: 30 amino acids
        (B) TYPE: amino acid
        (D) TOPOLOGY: linear (ii) MOLECULE TYPE: protein (xi) SEQUENCE DESCRIPTION: SEQ ID NO:465:

```
Ala Leu Leu Ala Pro Trp Trp Pro Trp Ser Thr Gly Ser Leu Arg Trp
1               5                   10                  15

Met Arg Ser Arg Trp Gly Thr Ser Gly Ile Cys Gly Ser Gly
            20                  25                  30
```

(2) INFORMATION FOR SEQ ID NO:466:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:466:

Cys Ala Arg Cys Ala Trp
1            5

(2) INFORMATION FOR SEQ ID NO:467:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:467:

Cys Leu Asp Ser Gly Pro Ser Ala Leu Trp Cys His Ser Pro Cys Gly
1            5                    10                15

Thr Ala Gly Arg Gly Gly Pro Val Asn Gly Phe Ser Met Gly Thr Trp
         20                   25                  30

Arg Val Val Val Cys Ala Gly Val
        35                    40

(2) INFORMATION FOR SEQ ID NO:468:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:468:

Ser Pro Ala Thr Ser Ser Met Gly Asn Ser Lys Ile Gln Phe Thr Leu
1            5                    10                15

Pro Ser Cys Ala Gly Thr Thr Gly Trp Glu Leu Cys Arg Ser Thr Cys
         20                   25                  30

Trp Ala Thr Gly Lys Pro His Leu Phe Ser Pro Leu Thr Pro Arg Arg
        35                    40                45

Trp Tyr Pro Ser Gly Arg Arg Gly Gly Leu Arg Trp Trp
        50                    55                  60

(2) INFORMATION FOR SEQ ID NO:469:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:469:

Pro Leu Pro Thr Trp
1            5

(2) INFORMATION FOR SEQ ID NO:470:

(i) SEQUENCE CHARACTERISTICS:
            (A) LENGTH: 18 amino acids
            (B) TYPE: amino acid
            (D) TOPOLOGY: linear (ii) MOLECULE TYPE: protein (xi) SEQUENCE DESCRIPTION: SEQ ID NO:470:

Ser Gly Ala Arg Pro Val Thr Asn Cys Phe Ala Ser Lys Phe Phe Gln
 1               5                  10                  15

Gln Leu (2) INFORMATION FOR SEQ ID NO:471:

(i) SEQUENCE CHARACTERISTICS:
            (A) LENGTH: 69 amino acids
            (B) TYPE: amino acid
            (D) TOPOLOGY: linear (ii) MOLECULE TYPE: protein (xi) SEQUENCE DESCRIPTION: SEQ ID NO:471:

Leu Ser Pro Thr Thr Leu Met Ala Phe Arg Ser Leu Gly Arg Leu Thr
 1               5                  10                  15

Arg Glu Arg Arg Pro Trp Ser Thr Val Arg Ala Lys Val Leu Pro Leu
                20                  25                  30

Met Gly Ser Ala Thr Pro Phe Arg Thr Ser Cys Gly Cys Gly Met Trp
            35                  40                  45

Arg Pro Leu Arg Phe His Leu Arg Ser Ala Ser Arg Ser Gly Arg Arg
        50                  55                  60

Leu Lys Thr Gln Asn
65

(2) INFORMATION FOR SEQ ID NO:472:

(i) SEQUENCE CHARACTERISTICS:
            (A) LENGTH: 14 amino acids
            (B) TYPE: amino acid
            (D) TOPOLOGY: linear (ii) MOLECULE TYPE: protein (xi) SEQUENCE DESCRIPTION: SEQ ID NO:472:

Leu Arg Pro Ile Cys His Gln Arg Leu Leu Pro Ser Lys Arg
 1               5                  10

(2) INFORMATION FOR SEQ ID NO:473:

(i) SEQUENCE CHARACTERISTICS:
            (A) LENGTH: 59 amino acids
            (B) TYPE: amino acid
            (D) TOPOLOGY: linear (ii) MOLECULE TYPE: protein (xi) SEQUENCE DESCRIPTION: SEQ ID NO:473:

Arg Met Leu Arg Glu Phe Ser Asn Arg Thr Ser Met Ser Xaa Trp Arg
 1               5                  10                  15

Ile Ala Val His Pro Leu Ser Val Val Val Ala Glu Arg Cys Leu Cys
                20                  25                  30

Gly Glu Lys Thr Tyr Pro Ala Leu His Arg Leu His Leu Ser Arg Leu
            35                  40                  45

Arg Arg Ala Ala Gln Met Arg Arg Pro Cys Arg
        50                  55

(2) INFORMATION FOR SEQ ID NO:474:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:474:

```
Pro Pro Arg Arg Arg Thr Pro Arg Pro Gln Thr His Leu Lys Ser Ser
 1               5                  10                  15
Lys Ser Leu Ile Leu Leu Asn Gln Arg Lys Ala Ser Ser Thr Trp Leu
            20                  25                  30
Phe Pro Tyr
        35
```

(2) INFORMATION FOR SEQ ID NO:475:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:475:

```
Lys Pro Tyr Phe His Arg Ala Met Pro His Glu Ser
 1               5                  10
```

(2) INFORMATION FOR SEQ ID NO:476:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:476:

```
Arg Leu Arg Cys Leu Ala Val Leu Arg Arg Ala
 1               5                  10
```

(2) INFORMATION FOR SEQ ID NO:477:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:477:

```
His Ala Ser Phe Leu
 1               5
```

(2) INFORMATION FOR SEQ ID NO:478:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO:478:

```
Pro Trp Leu Thr Trp Leu Ala Cys Val Arg Trp Arg Ser Arg Thr Ile
 1               5                  10                  15

Gln Pro Ile Val Thr Arg Cys Ala Leu Arg Ser Asn Cys Lys Leu Gly
                20                  25                  30

Ala Trp Ala Met Asn Leu Pro Leu Asn Val Thr Ser Val Arg His
            35                  40                  45

Ala Lys Arg Pro Leu Pro Ser Pro Thr Tyr Gly Pro Gly Ser His
        50                  55                  60

Leu Leu Gly Pro Leu Arg Pro Asn His Gln Trp
65                  70                  75
```

(2) INFORMATION FOR SEQ ID NO:479:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:479:

```
Gly Arg Trp Gly Pro Cys Trp Trp Gln Thr Pro Pro Arg Ser Thr
 1               5                  10                  15
```

(2) INFORMATION FOR SEQ ID NO:480:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:480:

```
Pro Ile Arg Thr Met Leu Gly Gly Gly Leu Thr Arg
 1               5                  10
```

(2) INFORMATION FOR SEQ ID NO:481:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:481:

```
Leu Ser Gly Ala Leu Leu Gly Tyr Thr Thr Ser Ser Ser Trp Thr Arg
 1               5                  10                  15

Ser Ser Ala Leu Gly Glu Leu Leu Lys Ala Ala
                20                  25
```

(2) INFORMATION FOR SEQ ID NO:482:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:482:

```
Ala Trp Val Thr Leu Met Arg Arg Gln
 1               5
```

(2) INFORMATION FOR SEQ ID NO:483:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:483:

```
Gly Leu Leu Gly Arg Met Leu Pro Trp Ala Gly Asp Leu Arg Cys Arg
 1               5                  10                  15
Ser Arg Thr Trp Pro Pro Leu Arg Gly Arg Trp Leu Phe Met Thr Gly
                20                  25                  30
Phe Arg Arg Tyr Leu Lys Gly Leu Arg Ser Leu Leu Pro
            35                  40                  45
```

(2) INFORMATION FOR SEQ ID NO:484:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:484:

```
Leu Ser Lys Arg Arg Cys Ser Ser Lys Ile Val Arg Arg Arg Pro
 1               5                  10                  15
Pro Ala Ser Leu Cys Ser Pro Pro Trp Thr Ser Gly
                20                  25
```

(2) INFORMATION FOR SEQ ID NO:485:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:485:

```
Leu Lys Ser Ser Phe Trp Glu Thr Arg Gly Gly Leu Gln Arg Pro Val
 1               5                  10                  15
Leu Gly Gly Leu Thr Pro Ser Ser Thr Pro Pro Thr Ser Gly Leu Arg
                20                  25                  30
Arg Cys
```

(2) INFORMATION FOR SEQ ID NO:486:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:486:

```
Ser Cys Gly Asn Gln Arg Arg Pro Arg Ala Pro Ser Val Trp Met Pro
 1               5                  10                  15
Leu Ala Ser Thr Val Ala Leu Leu Xaa Arg Thr Trp His
                20                  25
```

(2) INFORMATION FOR SEQ ID NO:487:

(i) SEQUENCE CHARACTERISTICS:
        (A) LENGTH:  27 amino acids
        (B) TYPE:  amino acid
        (D) TOPOLOGY:  linear (ii) MOLECULE TYPE: protein (xi) SEQUENCE DESCRIPTION: SEQ ID NO:487:

Arg Gln Ser Phe Thr Pro Trp Pro Arg Thr Ile Gln Asn Gly Cys Ala
1               5                  10                  15

Pro Trp Gly Asn Thr Xaa Pro Leu Ala Gln Trp
            20                  25

(2) INFORMATION FOR SEQ ID NO:488:

(i) SEQUENCE CHARACTERISTICS:
        (A) LENGTH:  17 amino acids
        (B) TYPE:  amino acid
        (D) TOPOLOGY:  linear (ii) MOLECULE TYPE: protein (xi) SEQUENCE DESCRIPTION: SEQ ID NO:488:

Pro Arg Lys Gly Cys Gln Trp Ala Arg Gly Ile Val Gly Pro Arg Val
1               5                  10                  15

Cys (2) INFORMATION FOR SEQ ID NO:489:

(i) SEQUENCE CHARACTERISTICS:
        (A) LENGTH:  7 amino acids
        (B) TYPE:  amino acid
        (D) TOPOLOGY:  linear (ii) MOLECULE TYPE: protein (xi) SEQUENCE DESCRIPTION: SEQ ID NO:489:

Pro Gln Val Leu Ala Thr Val
1               5

(2) INFORMATION FOR SEQ ID NO:490:

(i) SEQUENCE CHARACTERISTICS:
        (A) LENGTH:  5 amino acids
        (B) TYPE:  amino acid
        (D) TOPOLOGY:  linear (ii) MOLECULE TYPE: protein (xi) SEQUENCE DESCRIPTION: SEQ ID NO:490:

Pro Ala Thr Ser Lys
1               5

(2) INFORMATION FOR SEQ ID NO:491:

(i) SEQUENCE CHARACTERISTICS:
        (A) LENGTH:  8 amino acids
        (B) TYPE:  amino acid
        (D) TOPOLOGY:  linear (ii) MOLECULE TYPE: protein (xi) SEQUENCE DESCRIPTION: SEQ ID NO:491:

Glu Pro Pro Val Arg Gly Ser Asp
1               5

(2) INFORMATION FOR SEQ ID NO:492:

(i) SEQUENCE CHARACTERISTICS:
            (A) LENGTH:  12 amino acids
            (B) TYPE: amino acid
            (D) TOPOLOGY: linear (ii) MOLECULE TYPE: protein (xi) SEQUENCE DESCRIPTION: SEQ ID NO:492:

Lys Met Ser Arg Phe Ser Ser Arg Ala Met Thr Ala
  1               5                  10

(2) INFORMATION FOR SEQ ID NO:493:

(i) SEQUENCE CHARACTERISTICS:
            (A) LENGTH:  55 amino acids
            (B) TYPE: amino acid
            (D) TOPOLOGY: linear (ii) MOLECULE TYPE: protein (xi) SEQUENCE DESCRIPTION: SEQ ID NO:493:

Leu Cys Ala Arg Gly Leu Tyr Ala Thr Leu Ala Arg Pro Trp Ala Glu
  1               5                  10                  15

Pro Trp Leu Arg Thr Gly Thr Arg Val Ser Pro Arg Ile Thr Leu His
                 20                  25                  30

Trp Thr Gln Pro Pro Ser Ala Pro Leu Gly Ser Leu Ser Ala Met Arg
             35                  40                  45

Met Xaa Lys Gly Ile Ser Ser
         50                  55

(2) INFORMATION FOR SEQ ID NO:494:

(i) SEQUENCE CHARACTERISTICS:
            (A) LENGTH:  43 amino acids
            (B) TYPE: amino acid
            (D) TOPOLOGY: linear (ii) MOLECULE TYPE: protein (xi) SEQUENCE DESCRIPTION: SEQ ID NO:494:

Pro Arg Thr Phe Gly Asp His Ser Leu Ala Cys Arg Ala Ser Thr Val
  1               5                  10                  15

Thr Leu Trp Leu Arg Pro Leu Val Thr Phe Ser Ser Thr Pro Gly Xaa
                 20                  25                  30

Pro Ser His Gly Gly Ser Ser Arg Met Cys
             35                  40

(2) INFORMATION FOR SEQ ID NO:495:

(i) SEQUENCE CHARACTERISTICS:
            (A) LENGTH:  43 amino acids
            (B) TYPE: amino acid
            (D) TOPOLOGY: linear (ii) MOLECULE TYPE: protein (xi) SEQUENCE DESCRIPTION: SEQ ID NO:495:

His Ala Leu Leu Pro Gly Val Val Ala His Xaa Leu Ile Arg Phe Gly
  1               5                  10                  15

Val Arg Phe Met Val Thr Thr Thr Ser Phe Pro Trp Thr Asn Cys Leu
                 20                  25                  30

Thr Ser Ser Trp Pro Ser Thr Asp Gln Gln Arg
             35                  40

(2) INFORMATION FOR SEQ ID NO:496:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:496:

```
Gly Leu Pro Gln Thr Gln Pro Lys Gln Arg Trp Arg Leu Gly Arg Phe
 1               5                  10                  15
```

(2) INFORMATION FOR SEQ ID NO:497:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:497:

```
Ala Thr Ser Ser Ser Leu Val
 1               5
```

(2) INFORMATION FOR SEQ ID NO:498:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO:498:

```
Pro Ser Thr Ala Arg Arg Pro Gly His Cys Glu His Ala Cys Ser Gly
 1               5                  10                  15

Arg Ala Val Gly Arg Ser Trp Leu Gly Ala Cys Cys Gly Ile Gln Asp
                20                  25                  30

Ser Gly Phe Leu Pro Leu Arg Leu Leu Val Ser Gln Gly Val Ser Leu
                35                  40                  45

Cys Pro Pro Pro Thr Trp Gly Trp Phe Ile Asn Trp Ile Ser Gln Xaa
        50                  55                  60

Ser Gly Val Ala Gly Gly Gly Trp Gly Ser
65                  70
```

(2) INFORMATION FOR SEQ ID NO:499:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:499:

```
Pro Cys Ser Ser
 1
```

(2) INFORMATION FOR SEQ ID NO:500:

(i) SEQUENCE CHARACTERISTICS:
        (A) LENGTH: 23 amino acids
        (B) TYPE: amino acid
        (D) TOPOLOGY: linear -continued (ii) MOLECULE TYPE: protein (xi) SEQUENCE DESCRIPTION: SEQ ID NO:500:

Arg Ser Leu Gly Glu Leu Asn Ser Ser Val Ala Ala Gly Val Arg Pro
 1               5                  10                  15

Glu Pro Arg Ser Lys Gly Asp
             20

(2) INFORMATION FOR SEQ ID NO:501:

(i) SEQUENCE CHARACTERISTICS:
       (A) LENGTH:  12 amino acids
       (B) TYPE: amino acid
       (D) TOPOLOGY: linear (ii) MOLECULE TYPE: protein (xi) SEQUENCE DESCRIPTION: SEQ ID NO:501:

Arg Trp Trp Met Gly Asp Asp Arg Val Gly Arg Ser
 1               5                  10

(2) INFORMATION FOR SEQ ID NO:502:

(i) SEQUENCE CHARACTERISTICS:
       (A) LENGTH:  12 amino acids
       (B) TYPE: amino acid
       (D) TOPOLOGY: linear (ii) MOLECULE TYPE: protein (xi) SEQUENCE DESCRIPTION: SEQ ID NO:502:

Ile Pro Val Ile Leu Val Ala Thr Ile Gly Gly Ser
 1               5                  10

(2) INFORMATION FOR SEQ ID NO:503:

(i) SEQUENCE CHARACTERISTICS:
       (A) LENGTH:  65 amino acids
       (B) TYPE: amino acid
       (D) TOPOLOGY: linear (ii) MOLECULE TYPE: protein (xi) SEQUENCE DESCRIPTION: SEQ ID NO:503:

Gly Glu Ala Thr Val Pro Leu Ala His Met Glu Glu Lys Arg Thr Val
 1               5                  10                  15

His Arg Cys Trp Ser Tyr Arg Cys Asn Lys Asp Pro Ala Leu Gly Thr
                20                  25                  30

Pro Leu Asn Arg Ala Arg Tyr Ser Pro Gly Gln Thr Thr Pro Thr Tyr
             35                  40                  45

Gly Pro Arg Arg Pro Ser Met Ser Leu Leu Thr Asn Arg Arg Thr Ala
         50                  55                  60

Ser
65

(2) INFORMATION FOR SEQ ID NO:504:

(i) SEQUENCE CHARACTERISTICS:
       (A) LENGTH:  37 amino acids
       (B) TYPE: amino acid
       (D) TOPOLOGY: linear (ii) MOLECULE TYPE: protein (xi) SEQUENCE DESCRIPTION: SEQ ID NO:504:

```
Gln Gly Pro Val Gly Ala Gly Arg Glu Gly Glu Gly Pro Pro Leu
  1               5                  10                  15

Pro Phe Pro Gly Arg Arg Glu Met His Gly Ala Thr Gln Leu Arg Gly
                20                  25                  30

Gly Leu Gln Pro Gly
                35
```

(2) INFORMATION FOR SEQ ID NO:505:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:505:

```
Pro Lys Asn Phe Gly
  1               5
```

(2) INFORMATION FOR SEQ ID NO:506:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO:506:

```
Gly Arg Val Ala Phe Leu Phe Leu Tyr Arg Ser Trp Gln Ser Phe Cys
  1               5                  10                  15

Ser Tyr Ser Trp Trp Ser Arg Gly Tyr Phe Ser Pro Gly His Pro Cys
                20                  25                  30

Leu
```

(2) INFORMATION FOR SEQ ID NO:507:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:507:

```
Arg Glu Arg Ala Ile Phe Xaa His Lys Leu Leu Arg Pro Gly Gly His
  1               5                  10                  15

Arg Leu Leu Pro Gly Gly Arg Met Pro Gly Gly Ser Gly Val His His
                20                  25                  30

Leu His Arg Pro Leu Leu Ala Thr Val Ser Gly Gly Phe Gly Arg Ala
                35                  40                  45

Ala Arg Gln Val Arg Arg Pro Val Gly Gly Gly Thr Arg
       50                  55                  60
```

(2) INFORMATION FOR SEQ ID NO:508:

(i) SEQUENCE CHARACTERISTICS:
        (A) LENGTH: 47 amino acids
        (B) TYPE: amino acid
        (D) TOPOLOGY: linear (ii) MOLECULE TYPE: protein -continued (xi) SEQUENCE DESCRIPTION: SEQ ID NO:508:

Ser Leu Arg Ala Leu Val Gly Leu Gly Leu Cys Gly Arg Asp Pro Gly
1               5                   10                  15

Ala Trp Gly Gly Leu Leu Gly Gly Pro His Arg Arg Gly Gly Val Asp
            20                  25                  30

Ala Gln Gly Leu Pro Gly Pro Glu Pro Asp Val Cys Ser Arg Val
        35                  40                  45

(2) INFORMATION FOR SEQ ID NO:509:

(i) SEQUENCE CHARACTERISTICS:
        (A) LENGTH:  5 amino acids
        (B) TYPE: amino acid
        (D) TOPOLOGY: linear (ii) MOLECULE TYPE: protein (xi) SEQUENCE DESCRIPTION: SEQ ID NO:509:

Val Glu Val Gly Lys
1               5

(2) INFORMATION FOR SEQ ID NO:510:

(i) SEQUENCE CHARACTERISTICS:
        (A) LENGTH:  73 amino acids
        (B) TYPE: amino acid
        (D) TOPOLOGY: linear (ii) MOLECULE TYPE: protein (xi) SEQUENCE DESCRIPTION: SEQ ID NO:510:

Thr Ala Gly Leu Lys Leu Leu Asp Ser Gly Ile Pro Leu Glu Gly Ala
1               5                   10                  15

Phe Arg Leu Leu Ala Gly Ser Asp Glu Pro Tyr Ser Ser Leu Gly Val
            20                  25                  30

Arg Gly Gly Pro Pro Pro Ala Gly Ala Ala Tyr Cys His Gly Leu Pro
        35                  40                  45

Pro Gly His Tyr Gly Gly His Val Ala Arg Arg Ala Arg Leu Lys Cys
    50                  55                  60

Trp Gly His Gly Leu Ser Arg Arg Val
65                  70

(2) INFORMATION FOR SEQ ID NO:511:

(i) SEQUENCE CHARACTERISTICS:
        (A) LENGTH:  29 amino acids
        (B) TYPE: amino acid
        (D) TOPOLOGY: linear (ii) MOLECULE TYPE: protein (xi) SEQUENCE DESCRIPTION: SEQ ID NO:511:

Leu Gly Ser Leu Val Leu Ala Gly Arg Thr Gly Pro Ala Cys Arg Gln
1               5                   10                  15

Gly Glu Gly Leu Gly Thr Trp Glu Arg His Thr Phe Val
            20                  25

(2) INFORMATION FOR SEQ ID NO:512:

(i) SEQUENCE CHARACTERISTICS:
        (A) LENGTH:  66 amino acids
        (B) TYPE: amino acid
        (D) TOPOLOGY: linear (ii) MOLECULE TYPE: protein (xi) SEQUENCE DESCRIPTION: SEQ ID NO:512:

```
Leu Pro Gln Arg Ser Leu Gly Val Gly Pro Gly Pro Leu Pro Gly Asn
 1               5                  10                  15

Arg Met Gly Arg Pro Tyr His Ser Leu Glu Pro Arg Thr Lys Ser Val
            20                  25                  30

Ala Pro Phe Leu Ser Pro Ile Cys Leu Arg Arg Arg Phe Ser Asp Leu
        35                  40                  45

Arg Val Gly Phe Cys Val Leu Val Cys Phe His Trp Gly Ser Arg Leu
    50                  55                  60

Gln Gly
65
```

(2) INFORMATION FOR SEQ ID NO:513:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:513:

```
Cys Val Glu Phe Gly Ser Ser Trp Leu Cys Gln Leu His His Ser Arg
 1               5                  10                  15

Thr Gly Ile Phe Gly Ser Arg His Ser Gly
            20                  25
```

(2) INFORMATION FOR SEQ ID NO:514:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:514:

```
Ala Leu Arg Val Gly Asn Ser Leu Arg His Leu Tyr Pro Gly Gln Ala
 1               5                  10                  15

Ala Cys Leu Val Trp His Leu Cys Glu Gly Leu Leu Ala Arg Asp Arg
            20                  25                  30

Val Gly Thr Phe Pro Ile Pro Gln Val Trp Arg Gly Thr Glu Ala Asp
        35                  40                  45

Gln Arg Pro
    50
```

(2) INFORMATION FOR SEQ ID NO:515:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:515:

```
Gly Cys Ala Leu Arg Gln
 1               5
```

(2) INFORMATION FOR SEQ ID NO:516:

```
    (i) SEQUENCE CHARACTERISTICS:
         (A) LENGTH:  47 amino acids
         (B) TYPE:  amino acid
         (D) TOPOLOGY:  linear (ii) MOLECULE TYPE:  protein (xi) SEQUENCE DESCRIPTION: SEQ ID NO:516:

Asp Asn Ser Leu His His Lys Gly Ala Pro Gly Gln Pro Gly Ala Arg
 1               5                  10                  15

Gln Pro Gly Ala Val Ala Leu Gly Phe Trp Val Leu His His Asp Gln
                20                  25                  30

Asp Pro Arg Leu Leu Thr Leu Gly Glu Met Ser His Pro Ser His
            35                  40                  45

(2) INFORMATION FOR SEQ ID NO:517:

(i) SEQUENCE CHARACTERISTICS:
         (A) LENGTH:  15 amino acids
         (B) TYPE:  amino acid
         (D) TOPOLOGY:  linear (ii) MOLECULE TYPE:  protein (xi) SEQUENCE DESCRIPTION: SEQ ID NO:517:

Ala Ser His Arg Asn Val Trp Val Leu Pro Arg Ser Pro Pro Pro
 1               5                  10                  15

(2) INFORMATION FOR SEQ ID NO:518:

(i) SEQUENCE CHARACTERISTICS:
         (A) LENGTH:  7 amino acids
         (B) TYPE:  amino acid
         (D) TOPOLOGY:  linear (ii) MOLECULE TYPE:  protein (xi) SEQUENCE DESCRIPTION: SEQ ID NO:518:

Gln Leu His Ala Ser Arg His
 1               5

(2) INFORMATION FOR SEQ ID NO:519:

(i) SEQUENCE CHARACTERISTICS:
         (A) LENGTH:  44 amino acids
         (B) TYPE:  amino acid
         (D) TOPOLOGY:  linear (ii) MOLECULE TYPE:  protein (xi) SEQUENCE DESCRIPTION: SEQ ID NO:519:

Gly Val Arg Gly Ile Gly Trp Gly Gly Pro His Trp Gly Val Leu Arg
 1               5                  10                  15

Thr Ser Gly Ala Ala Val Phe Arg Ala Asp Gly Ser Ala Glu Ser Gly
                20                  25                  30

Leu Pro Gly Val Cys Met Ala Leu Phe Gly Thr Ala
            35                  40

(2) INFORMATION FOR SEQ ID NO:520:

(i) SEQUENCE CHARACTERISTICS:
         (A) LENGTH:  147 amino acids
         (B) TYPE:  amino acid
         (D) TOPOLOGY:  linear (ii) MOLECULE TYPE:  protein
```

(xi) SEQUENCE DESCRIPTION: SEQ ID NO:520:

Trp Val His Thr Cys Ser Gly Pro Leu Ala Gly Gly Cys Gly Gln
1               5                   10                  15

Leu His Ser Ala Pro Thr Leu Val Ala Leu Gly Leu Cys Ile Cys Pro
            20                  25                  30

Val Ile Pro Asp Glu Ala Gly Arg Gly Thr Val Gly Pro Ala Asp Pro
        35                  40                  45

Pro Pro Ala Met Val Val Gly Glu Pro Val Gly Gly Pro Xaa Cys Xaa
    50                  55                  60

Gly Cys Xaa Arg Arg Arg Gly Trp Arg Gly Val Cys Gly Pro Cys Leu
65                  70                  75                  80

Val Leu Val Ser Gly Pro Thr Leu Arg Glu Tyr Asp Pro Gly Ala Ser
                85                  90                  95

Lys Pro Gly Val Val Leu Pro Leu Asp Gly Ser Ser Thr Pro Asp Val
            100                 105                 110

Pro Arg Val Val Glu Ala Arg Ser Gly Gly Phe Pro Ala Gly Ile Thr
        115                 120                 125

Asp Gly Asp Phe Arg His Ser Arg Pro His Leu Cys Ala Trp Arg Arg
    130                 135                 140

Ile Leu Leu
145

(2) INFORMATION FOR SEQ ID NO:521:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:521:

Ser Gly His Val Ser Leu Gly Leu Gly Gly Cys
1               5                   10

(2) INFORMATION FOR SEQ ID NO:522:

(i) SEQUENCE CHARACTERISTICS:
        (A) LENGTH: 24 amino acids
        (B) TYPE: amino acid
        (D) TOPOLOGY: linear (ii) MOLECULE TYPE: protein (xi) SEQUENCE DESCRIPTION: SEQ ID NO:522:

Cys Gly Gly Leu Gly His Ser Ala Pro Glu Leu Tyr Glu Arg Gly Gly
1               5                   10                  15

Val Glu Ala Gln Ser His Asn Leu
            20

(2) INFORMATION FOR SEQ ID NO:523:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:523:

Arg Val Pro Gly Xaa Ser Pro Ala Arg Gly Ala
1               5                   10

(2) INFORMATION FOR SEQ ID NO:524:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:524:

Pro Pro Arg Gly Gly Ala Ala His Gln Ala Ala Asp Asp Ser Leu Val
  1               5                  10                  15

Ser Gly Leu Leu His Leu Ala Gly Arg Cys Asp Val Gly Gly Cys Gly
             20                  25                  30

His Gly Pro Pro Leu Arg Pro Phe Arg Arg Ala Arg Leu Gly Leu Gly
         35                  40                  45

Gly Ala Pro Cys Val Ala Ala Phe Val Ala Ser Phe Gly Lys Gly Gly
     50                  55                  60

Gly Val Leu Cys Asp Gly Gly Arg Glu Gly His Tyr Arg Pro Ala Cys
 65                  70                  75                  80

Val Gln Asp Val Arg Glu Arg Gly Leu Pro Val
                 85                  90

(2) INFORMATION FOR SEQ ID NO:525:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:525:

Pro His Gly Val Val Leu Ala Arg Gly Gln Gly Ala Leu Ala Gly Val
  1               5                  10                  15

Gly Arg Gly Phe Gly Xaa Pro Val Ile His
             20                  25

(2) INFORMATION FOR SEQ ID NO:526:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:526:

Asp Gly Leu Ser His His Thr Arg Arg Arg Gln Asp Pro Glu Leu Arg
  1               5                  10                  15

Pro Met Arg His Gly Leu Ala Arg Gly Gly
             20                  25

(2) INFORMATION FOR SEQ ID NO:527:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:527:

```
Gly Pro Asp Trp Gly Leu Ser Gly Cys Glu Pro Leu Ala Ser Gly Val
 1               5                  10                  15

Xaa Ser Tyr Ser Ala Cys Cys His Pro Ser Val Arg Lys Gly Leu Pro
                20                  25                  30

Arg Gly His
         35
```

(2) INFORMATION FOR SEQ ID NO:528:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:528:

```
Gly Cys Leu Asp Trp Ser Gly Ser
 1               5
```

(2) INFORMATION FOR SEQ ID NO:529:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:529:

```
Leu Thr Pro Arg Lys Arg His Gly Phe Gly Asp Gly Tyr Leu Ala Gln
 1               5                  10                  15

His Gly Asn Val Leu Lys Arg Val Ala Val His Asp Ile Pro Trp Gly
                20                  25                  30

Phe Phe Pro Asn His Cys Asp Thr Cys Gly Gly Pro
                35                  40
```

(2) INFORMATION FOR SEQ ID NO:530:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:530:

```
Pro Lys Val Val Val Gly Gln
 1               5
```

(2) INFORMATION FOR SEQ ID NO:531:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:531:

```
Arg His Gly Leu Ser Pro Pro Arg Trp Ser
 1               5                  10
```

(2) INFORMATION FOR SEQ ID NO:532:

(i) SEQUENCE CHARACTERISTICS:

(A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:532:

Leu Val Gly Ser Leu Leu Val Ser Gly
 1               5

(2) INFORMATION FOR SEQ ID NO:533:

(i) SEQUENCE CHARACTERISTICS:
            (A) LENGTH: 30 amino acids
            (B) TYPE: amino acid
            (D) TOPOLOGY: linear (ii) MOLECULE TYPE: protein (xi) SEQUENCE DESCRIPTION: SEQ ID NO:533:

Val Leu Leu Gly His Xaa Ile Arg Trp Gly Ser Leu Pro Trp Leu Glu
 1               5                  10                  15

Gln Gly Gly Gln Gly Arg Thr Gly Arg Gly His Gly Gly Cys
            20                  25                  30

(2) INFORMATION FOR SEQ ID NO:534:

(i) SEQUENCE CHARACTERISTICS:
            (A) LENGTH: 50 amino acids
            (B) TYPE: amino acid
            (D) TOPOLOGY: linear (ii) MOLECULE TYPE: protein (xi) SEQUENCE DESCRIPTION: SEQ ID NO:534:

Leu Ser Trp Val Val Trp Val Ser Cys Pro Met Arg Arg Gly Ala Arg
 1               5                  10                  15

Cys Arg Asn Ala Arg Val Arg Pro Ser Phe Gly Gly Glu Gly Asp Arg
                20                  25                  30

Gly Ser Ile His Ser Ala Val Asp Pro Ser Pro Asn Arg Arg Gln Asp
            35                  40                  45

Tyr His
    50

(2) INFORMATION FOR SEQ ID NO:535:

(i) SEQUENCE CHARACTERISTICS:
            (A) LENGTH: 6 amino acids
            (B) TYPE: amino acid
            (D) TOPOLOGY: linear (ii) MOLECULE TYPE: protein (xi) SEQUENCE DESCRIPTION: SEQ ID NO:535:

Ala Thr Pro Gly Ala Ser
 1               5

(2) INFORMATION FOR SEQ ID NO:536:

(i) SEQUENCE CHARACTERISTICS:
            (A) LENGTH: 56 amino acids
            (B) TYPE: amino acid
            (D) TOPOLOGY: linear (ii) MOLECULE TYPE: protein (xi) SEQUENCE DESCRIPTION: SEQ ID NO:536:

```
Arg Gly Phe Gln Arg Gly Ser Ser Phe His Ala Asn Arg Gly Gly Glu
 1               5                  10                  15

Lys His Thr Arg Pro Phe Gly Val Trp Lys His Gly Ala Gln Gly Pro
                20                  25                  30

Asp Ser Gln Pro Val Gly Cys His Cys Glu Gly His Gly Pro Leu His
            35                  40                  45

Gly Glu Ala Gly Gly Glu Thr Ser
        50                  55
```

(2) INFORMATION FOR SEQ ID NO:537:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:537:

```
His Phe Leu Trp Thr Arg His Asn Ser Phe His Thr Asp His Gly Leu
 1               5                  10                  15

Ser Ile Asp Val Leu Tyr Leu Trp Glu Val Ser Gly Gln Pro Glu Ala
                20                  25                  30

Asp Ala Glu Gly Ser Phe Arg Gly His Leu
            35                  40
```

(2) INFORMATION FOR SEQ ID NO:538:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:538:

```
Val Pro Gln Ser
 1
```

(2) INFORMATION FOR SEQ ID NO:539:

(i) SEQUENCE CHARACTERISTICS:
        (A) LENGTH: 41 amino acids
        (B) TYPE: amino acid
        (D) TOPOLOGY: linear (ii) MOLECULE TYPE: protein (xi) SEQUENCE DESCRIPTION: SEQ ID NO:539:

```
Leu Asn Cys Val Ala Gly Tyr Arg Gln Gly Gln Gly Arg Gly Ala Gly
 1               5                  10                  15

Val Trp Ser Ala Ile Ser Ala Leu Arg Tyr Cys Asp Ser Pro Gly Leu
                20                  25                  30

Ala Tyr Asp Ser Ala Ser Ile His Asn
            35                  40
```

(2) INFORMATION FOR SEQ ID NO:540:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:540:

Asp Lys Ala Gly Arg Trp
1               5

(2) INFORMATION FOR SEQ ID NO:541:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:541:

Asp Pro Leu Leu Trp Ala Trp Tyr Pro Pro Arg Ala Tyr Glu Asp Trp
1               5                   10                  15

Ser Pro Pro Cys Ile Leu Pro Phe Gln Gly Gly Val Arg Glu Ile Gly
            20                  25                  30

Arg Pro Val Leu Arg Ala Gly Gly
            35                  40

(2) INFORMATION FOR SEQ ID NO:542:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:542:

Cys His Arg Leu Leu
1               5

(2) INFORMATION FOR SEQ ID NO:543:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:543:

Gly Gln Phe His His Gln Arg Arg Pro Gly Gly Leu Cys Asp Arg
1               5                   10                  15

Arg Ala Leu Tyr Arg Val His Arg Lys Leu Arg Phe Cys His Arg Leu
            20                  25                  30

Trp Val Gly Gly Gly Gly Gly Arg
            35                  40

(2) INFORMATION FOR SEQ ID NO:544:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:544:

Ser His His Tyr His Phe Leu Ala Asp Cys Pro Cys Phe Gly
1               5                   10

(2) INFORMATION FOR SEQ ID NO:545:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:545:

Ile Val Asp Ala Ala Ala Arg Thr His Gly Glu Arg Ser Val Gly Pro
 1               5                  10                  15

Leu Leu Leu Arg Trp Gly Arg
            20

(2) INFORMATION FOR SEQ ID NO:546:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:546:

Gly Ser Arg Gly Gly Gly Ala Val Trp Ser Gly Leu Val Gly Ser Gly
 1               5                  10                  15

Ser Trp Ser Asp Leu Val Trp Asn Gly Thr
            20                  25

(2) INFORMATION FOR SEQ ID NO:547:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:547:

Leu Asp Ser Lys Pro Ser Glu Thr Leu Arg Arg Leu Pro Leu His Arg
 1               5                  10                  15

Ser Arg Arg Ser
            20

(2) INFORMATION FOR SEQ ID NO:548:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:548:

Ser Arg Gly Val Leu Cys Gly Pro Arg Ala Pro Gln Asp Ala Ser Arg
 1               5                  10                  15

Cys (2) INFORMATION FOR SEQ ID NO:549:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:549:

Leu Gly Lys Ser Ser Arg Arg Gln Leu Ala Pro Pro Gly Gly Cys Ser
 1               5                  10                  15

Ala Asp Asp Val Ser Gly Asn Thr Val Ser Arg Pro Val Gly Arg Pro
                20                  25                  30

Ser Val Gly Arg Ser Glu Arg Pro Glu Ser Cys Pro Thr Thr Ala Glu
            35                  40                  45

Val Gly Gln
    50

(2) INFORMATION FOR SEQ ID NO:550:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:550:

Phe Ala Ile Lys Ser Gly Arg Pro Pro His Ser
 1               5                  10

(2) INFORMATION FOR SEQ ID NO:551:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:551:

Arg Ser Gly Pro Ser Ala Arg Cys Gly Gly Gly Ile Arg Ala Leu
 1               5                  10                  15

(2) INFORMATION FOR SEQ ID NO:552:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO:552:

Cys Trp Xaa His Pro His Gly Gly Leu Gly His Ser Gly Arg His Asp
 1               5                  10                  15

Leu Arg Leu Leu His Trp Val Ala Ser Gly Gly Asn Arg Leu Gly Cys
                20                  25                  30

Glu Gly Arg Trp Gln Ser Pro Leu
            35                  40

(2) INFORMATION FOR SEQ ID NO:553:

(i) SEQUENCE CHARACTERISTICS:
    (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO:553:

Pro Gly His Pro Ser Thr Arg Gly Ala Gly Pro Pro Gly Arg Pro Ser

```
                1               5                  10                 15
Ala Gly Gly Gly Val Cys Ala Thr Gly Cys Gln Asp Ser Asp Arg Cys
                       20                  25                 30

Gly Gly Ser His Pro Gly Glu Leu Arg Leu Val Cys Asp Asp Pro Val
               35                  40                  45

Asp Arg Gly Ser Pro His Leu Gly Ser Gly
        50                  55
```

(2) INFORMATION FOR SEQ ID NO:554:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:554:

```
Asp Ser Arg Gly Leu Arg Ser Tyr Phe Gln Val Ala Arg Trp Leu Leu
 1               5                  10                 15

His Gly Asp Ala Gly Arg Pro His Cys Ile Asn Cys
                20                  25
```

(2) INFORMATION FOR SEQ ID NO:555:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:555:

```
Gln Ala Leu Arg Arg Gly Leu Gly Arg Gly Gly Ser Leu Ser Gln
 1               5                  10                 15

Arg His Cys Cys Gly Gly Gly Cys Leu Trp Ser Phe Ser Lys Ser Ser
                20                  25                 30

Thr Gly Arg Gly Gly Val Leu Pro His Gly Val Gly Arg Arg Gln
            35                  40                  45

Arg Thr Gly Ala Leu Gly Phe Ser Ser Ser Thr Gly Gly Cys Trp Tyr
        50                  55                  60

Gly Ser Gly Asp Pro Cys Arg Gly Thr His His Gly Gly Leu His
65                  70                  75                  80

Gly Arg Cys Gln Arg Val Pro Leu Pro Arg His Cys Pro Thr Trp Gly
                85                  90                  95

Cys Gly Arg Leu Gly Gly Arg Cys Gln Arg Cys Gln Ser Arg Leu Arg
               100                 105                 110

Leu His Gly Trp Glu Thr Phe Asn Arg Arg Pro Leu Val Cys His Pro
           115                 120                 125

Gly Thr His
       130
```

(2) INFORMATION FOR SEQ ID NO:556:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:556:

```
Ser Trp Xaa Gly Pro Arg Gly Asp Cys Pro Trp Ser Gly Phe Val Leu
 1               5                  10                  15

Ser Lys Gln Leu Trp His Tyr His Met Ala Glu Pro Ser Ala Asp Asp
                20                  25                  30

Val Ala Thr Val Ile Leu His Thr Arg Gln Leu Leu Pro Thr Gly
                35                  40                  45
```

(2) INFORMATION FOR SEQ ID NO:557:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:557:

```
Leu Leu Arg Gln Gly Leu Gly Asn Arg Ala Pro Pro Glu Pro Tyr Ser
 1               5                  10                  15

His Arg Gly Gly Pro Gly Gln Gln Gly Ala
                20                  25
```

(2) INFORMATION FOR SEQ ID NO:558:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:558:

```
Gly Pro Gly Gly Val Arg Leu Gly Ser Val Gly Val Gly Asp Ala Pro
 1               5                  10                  15

Gly Ala His Gly Asp Val
                20
```

(2) INFORMATION FOR SEQ ID NO:559:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:559:

```
Thr Pro Gly Pro Leu Pro Cys Gly Val Thr Pro Leu Val Ala Leu Arg
 1               5                  10                  15

Gly Gly Val Val Arg
                20
```

(2) INFORMATION FOR SEQ ID NO:560:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:560:

```
Met Ala Ser Arg Trp Ala Arg Gly Glu Ser Leu Ser Val Arg Val Cys
 1               5                  10                  15
```

```
Asn His Arg Arg Arg Pro Gln Trp Ala Thr Gln Arg Ser Ser Leu Leu
             20                  25                  30

Tyr Gln Ala Val Gln Ala Leu Leu Asp Gly Asn Cys Ala Gly Gln His
         35                  40                  45

Ala Gly Leu Arg Gly Asn Leu Thr Ser Ser Arg Leu
     50                  55                  60
```

(2) INFORMATION FOR SEQ ID NO:561:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:561:

```
His Pro Glu Gly Gly Thr Leu Arg Asp Val Gly Val Gly
 1               5                  10
```

(2) INFORMATION FOR SEQ ID NO:562:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:562:

```
Gly Gly Gly Asp Pro Tyr Pro Arg Gly Asp Gln Ala His Val Leu Leu
 1               5                  10                  15

Gln Thr Ala Ser Pro Ala Asn Ser Phe Ser Ser Cys Ser
             20                  25
```

(2) INFORMATION FOR SEQ ID NO:563:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:563:

```
Ala Leu Leu Arg
 1
```

(2) INFORMATION FOR SEQ ID NO:564:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:564:

```
Trp His Ser Gly Leu Leu Gly Gly
 1               5
```

(2) INFORMATION FOR SEQ ID NO:565:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:565:

Arg Glu Ser Ala Gly His Gly Leu Arg Ser Gly Pro Lys Cys Tyr His
 1               5                  10                  15

(2) INFORMATION FOR SEQ ID NO:566:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:566:

Trp Gly Ala Leu His Pro Ser Ala Pro Val Ala Asp Ala Glu Cys Gly
 1               5                  10                  15

Ala Leu (2) INFORMATION FOR SEQ ID NO:567:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:567:

Gly Gln His Arg Asp Arg Asp Gly Asp
 1               5

(2) INFORMATION FOR SEQ ID NO:568:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:568:

Arg Leu Arg Thr Asp
 1               5

(2) INFORMATION FOR SEQ ID NO:569:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:569:

Gly Arg Phe Ala Thr Ser Gly Cys Cys Pro Pro Ser Asp Arg Glu Cys
 1               5                  10                  15

Cys Glu Asn Ser Arg Thr Ala His Arg Cys Xaa His Gly Gly Leu Gln
                20                  25                  30

Tyr Thr Leu Ser Leu Trp
            35

(2) INFORMATION FOR SEQ ID NO:570:

(i) SEQUENCE CHARACTERISTICS:
            (A) LENGTH:  27 amino acids
            (B) TYPE:  amino acid
            (D) TOPOLOGY:  linear (ii) MOLECULE TYPE:  protein (xi) SEQUENCE DESCRIPTION: SEQ ID NO:570:

Pro Arg Asp Ala Cys Val Gly Arg Arg His Thr Pro His Ser Ile Ala
 1               5                  10                  15

Cys Thr Tyr Leu Gly Tyr Gly Glu Gln Leu Arg
                20                  25

(2) INFORMATION FOR SEQ ID NO:571:

(i) SEQUENCE CHARACTERISTICS:
            (A) LENGTH:  18 amino acids
            (B) TYPE:  amino acid
            (D) TOPOLOGY:  linear (ii) MOLECULE TYPE:  protein (xi) SEQUENCE DESCRIPTION: SEQ ID NO:571:

Glu Asp Pro Val Gly Asp Leu Leu Ala Gly Gly His Pro Val Leu Arg
 1               5                  10                  15

Leu Ile (2) INFORMATION FOR SEQ ID NO:572:

(i) SEQUENCE CHARACTERISTICS:
            (A) LENGTH:  5 amino acids
            (B) TYPE:  amino acid
            (D) TOPOLOGY:  linear (ii) MOLECULE TYPE:  protein (xi) SEQUENCE DESCRIPTION: SEQ ID NO:572:

Ser His Pro Arg Val
 1               5

(2) INFORMATION FOR SEQ ID NO:573:

(i) SEQUENCE CHARACTERISTICS:
            (A) LENGTH:  28 amino acids
            (B) TYPE:  amino acid
            (D) TOPOLOGY:  linear (ii) MOLECULE TYPE:  protein (xi) SEQUENCE DESCRIPTION: SEQ ID NO:573:

Ile Arg Gly Lys Arg Leu Gln Arg Gly Ser Phe Arg Thr Lys Ser Leu
 1               5                  10                  15

Ile Ser Thr Glu Arg Cys His Thr Lys Ala Asn Gly
                20                  25

(2) INFORMATION FOR SEQ ID NO:574:

(i) SEQUENCE CHARACTERISTICS:
            (A) LENGTH:  5 amino acids
            (B) TYPE:  amino acid
            (D) TOPOLOGY:  linear (ii) MOLECULE TYPE:  protein (xi) SEQUENCE DESCRIPTION: SEQ ID NO:574:

Asp Val Leu Leu Cys
 1               5

(2) INFORMATION FOR SEQ ID NO:575:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:575:

```
Glu Glu Arg Asn Thr Leu Leu Phe Phe Arg Val Asp Arg Gly
 1               5                  10
```

(2) INFORMATION FOR SEQ ID NO:576:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:576:

```
Asp Gly Asp Pro Glu Pro Tyr Ser Leu Leu
 1               5                  10
```

(2) INFORMATION FOR SEQ ID NO:577:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:577:

```
Gln Gly Ala His Ser Ala Arg Ile Ala Ser Trp Val Leu Gly Gly Gln
 1               5                  10                  15
```

(2) INFORMATION FOR SEQ ID NO:578:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:578:

```
Gly Thr Pro Arg Asp Pro Cys Leu Leu Leu His Met Val Arg Gly
 1               5                  10                  15

Pro Thr Tyr Ser Gly His Ser Gly Gln Thr Thr Ser Gly Glu Ala Gly
                20                  25                  30

Gly Val Leu Val Gly Gly Arg His His Gln Gly Leu Arg Asp Gln Ser
             35                  40                  45

Gly Gln Cys Trp Glu Glu Gly
             50                  55
```

(2) INFORMATION FOR SEQ ID NO:579:

(i) SEQUENCE CHARACTERISTICS:
        (A) LENGTH: 36 amino acids
        (B) TYPE: amino acid
        (D) TOPOLOGY: linear (ii) MOLECULE TYPE: protein -continued (xi) SEQUENCE DESCRIPTION: SEQ ID NO:579:

Gln Gly Asp Phe Leu Ala Arg Ser Ser Gly Thr Arg Gln Val Pro Arg
1               5                   10                  15

Gly Leu Asp Arg Ala Arg Ser Glu Ser Cys Ser Arg Leu Pro Lys His
                20                  25                  30

Gly Leu His Leu
        35

(2) INFORMATION FOR SEQ ID NO:580:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:580:

Gly Gly Asn Lys Asp Cys
1               5

(2) INFORMATION FOR SEQ ID NO:581:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:581:

Ala Ala Cys Cys His Gly Leu Gly Ile
1               5

(2) INFORMATION FOR SEQ ID NO:582:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:582:

Gly Val Gly Gln Gly Leu Gly His Pro Cys Gly Glu Asp Gly Cys Ser
1               5                   10                  15

(2) INFORMATION FOR SEQ ID NO:583:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:583:

Pro Ala Ser Gly Asp Thr
1               5

(2) INFORMATION FOR SEQ ID NO:584:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:584:

Arg Asp Ser Gly Pro Phe Tyr Pro Asp Cys Gln Lys Gly Gly Val Leu
 1               5                  10                  15

Gln Arg Ser (2) INFORMATION FOR SEQ ID NO:585:

(i) SEQUENCE CHARACTERISTICS:
            (A) LENGTH: 18 amino acids
            (B) TYPE: amino acid
            (D) TOPOLOGY: linear (ii) MOLECULE TYPE: protein (xi) SEQUENCE DESCRIPTION: SEQ ID NO:585:

Gly Gly Glu Gly Pro Pro Pro His Cys Val Pro Pro Gly Leu Pro
 1               5                  10                  15

Asp Ser (2) INFORMATION FOR SEQ ID NO:586:

(i) SEQUENCE CHARACTERISTICS:
            (A) LENGTH: 29 amino acids
            (B) TYPE: amino acid
            (D) TOPOLOGY: linear (ii) MOLECULE TYPE: protein (xi) SEQUENCE DESCRIPTION: SEQ ID NO:586:

Lys Ala His Ser Gly Arg Pro Gly Ala Gly Cys Lys Gly Arg Cys Trp
 1               5                  10                  15

Gly Gly Leu Arg Leu Pro Val His Pro Gln Pro Ala Gly
                20                  25

(2) INFORMATION FOR SEQ ID NO:587:

(i) SEQUENCE CHARACTERISTICS:
            (A) LENGTH: 24 amino acids
            (B) TYPE: amino acid
            (D) TOPOLOGY: linear (ii) MOLECULE TYPE: protein (xi) SEQUENCE DESCRIPTION: SEQ ID NO:587:

Gly Asp Ala Lys Ala Val Gly Ile Lys Glu Asp Pro Val Arg His Leu
 1               5                  10                  15

Cys Gly Cys His Leu Leu Arg Gln
                20

(2) INFORMATION FOR SEQ ID NO:588:

(i) SEQUENCE CHARACTERISTICS:
            (A) LENGTH: 45 amino acids
            (B) TYPE: amino acid
            (D) TOPOLOGY: linear (ii) MOLECULE TYPE: protein (xi) SEQUENCE DESCRIPTION: SEQ ID NO:588:

Xaa Gly Arg Gly Thr Arg Asp Arg Ala Leu Arg Pro Gly Leu Gly Pro
 1               5                  10                  15

Ser Arg Met Gly Ala Arg Pro Gly Glu Ile Xaa Cys Leu Trp His Asn

```
                    20                  25                  30
Gly Asp Pro Gly Arg Gly Ala Ser Gly Arg Glu Val Leu
        35                  40                  45
```

(2) INFORMATION FOR SEQ ID NO:589:

(i) SEQUENCE CHARACTERISTICS:
        (A) LENGTH:  9 amino acids
        (B) TYPE: amino acid
        (D) TOPOLOGY: linear (ii) MOLECULE TYPE: protein (xi) SEQUENCE DESCRIPTION: SEQ ID NO:589:

```
Val Leu Gly Cys Val Asp His Lys Cys
 1               5
```

(2) INFORMATION FOR SEQ ID NO:590:

(i) SEQUENCE CHARACTERISTICS:
        (A) LENGTH:  13 amino acids
        (B) TYPE: amino acid
        (D) TOPOLOGY: linear (ii) MOLECULE TYPE: protein (xi) SEQUENCE DESCRIPTION: SEQ ID NO:590:

```
Gln Leu Phe Asp Leu Leu His Gln Ser Glu Ser Arg Leu
 1               5                  10
```

(2) INFORMATION FOR SEQ ID NO:591:

(i) SEQUENCE CHARACTERISTICS:
        (A) LENGTH:  14 amino acids
        (B) TYPE: amino acid
        (D) TOPOLOGY: linear (ii) MOLECULE TYPE: protein (xi) SEQUENCE DESCRIPTION: SEQ ID NO:591:

```
Glu Asp Arg Thr Glu Lys Cys Leu Ala Ser His Arg Gly Arg
 1               5                  10
```

(2) INFORMATION FOR SEQ ID NO:592:

(i) SEQUENCE CHARACTERISTICS:
        (A) LENGTH:  27 amino acids
        (B) TYPE: amino acid
        (D) TOPOLOGY: linear (ii) MOLECULE TYPE: protein (xi) SEQUENCE DESCRIPTION: SEQ ID NO:592:

```
Leu Leu Asn Cys Val Arg Glu Ala Cys Met Arg Pro Leu Arg Gly Pro
 1               5                  10                  15
Gly Pro Asn Pro Gly Phe Val Arg Val Arg Val
            20                  25
```

(2) INFORMATION FOR SEQ ID NO:593:

(i) SEQUENCE CHARACTERISTICS:
        (A) LENGTH:  18 amino acids
        (B) TYPE: amino acid
        (D) TOPOLOGY: linear (ii) MOLECULE TYPE: protein (xi) SEQUENCE DESCRIPTION: SEQ ID NO:593:

```
Ala Leu Val Ser Arg Phe Thr Gly His Ser Pro Leu Leu Leu His Leu
 1               5                  10                  15
Ala Arg
```

(2) INFORMATION FOR SEQ ID NO:594:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:594:

```
Val Gln Cys Gly Trp Xaa Lys Ala Phe Leu Pro Asp His Gly Leu Ser
 1               5                  10                  15
Glu Thr Thr Arg Ser His Val Glu Arg Val Gln
                20                  25
```

(2) INFORMATION FOR SEQ ID NO:595:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:595:

```
Pro Tyr Gly Phe Gly His Trp Leu His Ser Pro Leu Pro Leu Xaa Ser
 1               5                  10                  15
His His Thr Val Gly His His Pro Ala Cys Ala Asn Met Arg Phe Phe
                20                  25                  30
Pro Gly Trp Trp His Xaa Val
                35
```

(2) INFORMATION FOR SEQ ID NO:596:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:596:

```
Ser Gly Leu Val Ser Gly Ser Trp
 1               5
```

(2) INFORMATION FOR SEQ ID NO:597:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:597:

```
Leu Leu Gln Val Ser Pro Gly Gln Thr Ala
 1               5                  10
```

(2) INFORMATION FOR SEQ ID NO:598:

(i) SEQUENCE CHARACTERISTICS:

(A) LENGTH: 60 amino acids
          (B) TYPE: amino acid
          (D) TOPOLOGY: linear (ii) MOLECULE TYPE: protein (xi) SEQUENCE DESCRIPTION: SEQ ID NO:598:

His His Arg Gly Pro Pro Arg Thr Ser Ser Val Glu Gly Tyr Arg Arg
1               5                   10                  15

His Asn Gln Asn Lys Asp Gly Gly Trp Glu Gly Ser Glu Arg Pro Gln
            20                  25                  30

Ala Pro Trp Ser Ser Arg Pro Pro Gln Glu Gly Arg Gly Ile Ala Asn
        35                  40                  45

Thr His Ala Pro Val Ala Arg Leu Gly Gly Val Gly
    50                  55                  60

(2) INFORMATION FOR SEQ ID NO:599:

(i) SEQUENCE CHARACTERISTICS:
          (A) LENGTH: 13 amino acids
          (B) TYPE: amino acid
          (D) TOPOLOGY: linear (ii) MOLECULE TYPE: protein (xi) SEQUENCE DESCRIPTION: SEQ ID NO:599:

Gly Pro Val Val Ala Ser Arg Thr Pro Ala Ser Ser Pro
1               5                   10

(2) INFORMATION FOR SEQ ID NO:600:

(i) SEQUENCE CHARACTERISTICS:
          (A) LENGTH: 47 amino acids
          (B) TYPE: amino acid
          (D) TOPOLOGY: linear (ii) MOLECULE TYPE: protein (xi) SEQUENCE DESCRIPTION: SEQ ID NO:600:

Asp Cys Trp Tyr Pro Arg Gly Phe Pro Ser Val Pro Pro Leu His Gly
1               5                   10                  15

Gly Gly Ser Ser Ile Gly Phe His Ser Xaa Ala Glu Ser Leu Ala Val
            20                  25                  30

Val Gly Val Leu Ser Pro Ala His Arg Ser Ala Leu Trp Val Asn
        35                  40                  45

(2) INFORMATION FOR SEQ ID NO:601:

(i) SEQUENCE CHARACTERISTICS:
          (A) LENGTH: 18 amino acids
          (B) TYPE: amino acid
          (D) TOPOLOGY: linear (ii) MOLECULE TYPE: protein (xi) SEQUENCE DESCRIPTION: SEQ ID NO:601:

Ile His Leu Leu Arg Pro Glu Ser Asp Leu Ser Pro Val Gln Lys Gly
1               5                   10                  15

Ile Glu (2) INFORMATION FOR SEQ ID NO:602:

(i) SEQUENCE CHARACTERISTICS:
          (A) LENGTH: 36 base pairs
          (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:602:

GCCGCTGAAT TCATGCCTTG TTATTTCTAC TCAAAC                                  36

(2) INFORMATION FOR SEQ ID NO:603:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:603:

GCCGCAGGAT CCTCGAACGA CCGCTCCTGC CAC                                     33

(2) INFORMATION FOR SEQ ID NO:604:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:604:

GCCGCAGGAA TTCATGGCTT GGCTGTGGTT GCTG                                    34

(2) INFORMATION FOR SEQ ID NO:605:

(i) SEQUENCE CHARACTERISTICS:
            (A) LENGTH: 507 amino acids
            (B) TYPE: amino acid
            (C) STRANDEDNESS: double
            (D) TOPOLOGY: linear (ii) MOLECULE TYPE: protein (xi) SEQUENCE DESCRIPTION: SEQ ID NO:605:

Tyr Ser Thr Tyr Gly Met Tyr Leu Thr Gly Arg Cys Ser Arg Asn Tyr
1               5                   10                  15

Asp Val Ile Ile Cys Asp Glu Cys His Ala Thr Asp Arg Thr Thr Val
            20                  25                  30

Leu Gly Ile Gly Lys Val Leu Thr Glu Ala Pro Ser Lys Asn Val Arg
        35                  40                  45

Leu Val Val Leu Ala Thr Ala Thr Pro Pro Gly Val Ile Pro Thr Pro
    50                  55                  60

His Ala Asn Ile Thr Glu Ile Gln Leu Thr Asp Gly Thr Ile Pro
65                  70                  75                  80

Phe His Gly Lys Lys Ile Lys Glu Glu Asn Leu Lys Lys Gly Arg His
                85                  90                  95

Leu Ile Phe Glu Ala Thr Lys Lys His Cys Asp Glu Leu Ala Asn Glu
            100                 105                 110

Leu Ala Arg Lys Gly Ile Thr Ala Val Ser Tyr Tyr Arg Gly Cys Asp
        115                 120                 125

Ile Ser Lys Met Pro Glu Gly Asp Cys Val Val Val Ala Thr Asp Ala
    130                 135                 140

```
Leu Cys Thr Gly Tyr Thr Gly Asp Phe Asp Ser Val Tyr Asp Cys Ser
145                 150                 155                 160

Leu Met Val Glu Gly Thr Cys His Val Asp Leu Asp Pro Thr Phe Thr
                165                 170                 175

Met Gly Val Arg Val Cys Gly Val Ser Ala Ile Val Lys Gly Gln Arg
                180                 185                 190

Arg Gly Arg Thr Gly Arg Gly Arg Ala Gly Ile Tyr Tyr Tyr Val Asp
                195                 200                 205

Gly Ser Cys Thr Pro Ser Gly Met Val Pro Glu Cys Asn Ile Val Glu
            210                 215                 220

Ala Phe Asp Ala Ala Lys Ala Trp Tyr Gly Leu Ser Ser Thr Glu Ala
225                 230                 235                 240

Gln Thr Ile Leu Asp Thr Tyr Arg Thr Gln Pro Gly Leu Pro Ala Ile
                245                 250                 255

Gly Ala Asn Leu Asp Glu Trp Ala Asp Leu Phe Ser Met Val Asn Pro
                260                 265                 270

Glu Pro Ser Phe Val Asn Thr Ala Lys Arg Thr Ala Asp Asn Tyr Val
                275                 280                 285

Leu Leu Thr Ala Ala Gln Leu Gln Leu Cys His Gln Tyr Gly Tyr Ala
290                 295                 300

Ala Pro Asn Asp Ala Pro Arg Trp Gln Gly Ala Arg Leu Gly Lys Lys
305                 310                 315                 320

Pro Cys Gly Val Leu Trp Arg Leu Asp Gly Cys Asp Ala Cys Pro Gly
                325                 330                 335

Pro Glu Pro Ser Glu Val Thr Arg Tyr Gln Met Cys Phe Thr Glu Val
                340                 345                 350

Asn Thr Ser Gly Thr Ala Ala Leu Ala Val Gly Val Gly Val Ala Met
                355                 360                 365

Ala Tyr Leu Ala Ile Asp Thr Phe Gly Ala Thr Cys Val Arg Arg Cys
370                 375                 380

Trp Ser Ile Thr Ser Val Pro Thr Gly Ala Thr Val Ala Pro Val Val
385                 390                 395                 400

Asp Glu Glu Glu Ile Val Glu Glu Cys Ala Ser Phe Ile Pro Leu Glu
                405                 410                 415

Ala Met Val Ala Ala Ile Asp Lys Leu Lys Ser Thr Ile Thr Thr Thr
                420                 425                 430

Ser Pro Phe Thr Leu Glu Thr Ala Leu Glu Lys Leu Asn Thr Phe Leu
                435                 440                 445

Gly Pro His Ala Ala Thr Ile Leu Ala Ile Ile Glu Tyr Cys Cys Gly
                450                 455                 460

Leu Val Thr Leu Pro Asp Asn Pro Phe Ala Ser Cys Val Phe Ala Phe
465                 470                 475                 480

Ile Ala Gly Ile Thr Thr Pro Leu Pro His Lys Ile Lys Met Phe Leu
                485                 490                 495

Ser Leu Phe Gly Gly Ala Ile Ala Ser Lys Leu
                500                 505
```

(2) INFORMATION FOR SEQ ID NO:606:

(i) SEQUENCE CHARACTERISTICS:
        (A) LENGTH: 522 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:606:

| | | | | | | | | | | | | | | |
|---|---|---|---|---|---|---|---|---|---|---|---|---|---|---|
| Cys | Gln | Lys | Gly | Tyr | Lys | Gly | Pro | Trp | Ile | Gly | Ser | Gly | Met | Leu | Gln |
| 1 | | | | 5 | | | | | 10 | | | | | 15 | |

Ala Arg Cys Pro Cys Gly Ala Glu Leu Ile Phe Ser Val Glu Asn Gly
                20                      25                      30

Phe Ala Lys Leu Tyr Lys Gly Pro Arg Thr Cys Ser Asn Tyr Trp Arg
            35                      40                      45

Gly Ala Val Pro Val Asn Ala Arg Leu Cys Gly Ser Ala Arg Pro Asp
        50                      55                      60

Pro Thr Asp Trp Thr Ser Leu Val Val Asn Tyr Gly Val Arg Asp Tyr
65                      70                      75                      80

Cys Lys Tyr Glu Lys Leu Gly Asp His Ile Phe Val Thr Ala Val Ser
                85                      90                      95

Ser Pro Asn Val Cys Phe Thr Gln Val Pro Pro Thr Leu Arg Ala Ala
                100                     105                     110

Val Ala Val Asp Arg Val Gln Val Gln Xaa Tyr Leu Gly Glu Pro Lys
            115                     120                     125

Thr Pro Trp Thr Thr Ser Ala Cys Cys Tyr Gly Pro Asp Gly Lys Gly
        130                     135                     140

Lys Thr Val Lys Leu Pro Phe Arg Val Asp Gly His Thr Pro Gly Gly
145                     150                     155                     160

Arg Met Gln Leu Asn Leu Arg Asp Arg Leu Glu Ala Asn Asp Cys Asn
                165                     170                     175

Ser Ile Asn Asn Thr Pro Ser Asp Glu Ala Ala Val Ser Ala Leu Val
                180                     185                     190

Phe Lys Gln Glu Leu Arg Arg Thr Asn Gln Leu Leu Glu Ala Ile Ser
            195                     200                     205

Ala Gly Val Asp Thr Thr Lys Leu Pro Ala Pro Ser Gln Ile Glu Glu
        210                     215                     220

Val Val Val Arg Lys Arg Gln Phe Arg Ala Arg Thr Gly Ser Leu Thr
225                     230                     235                     240

Leu Pro Pro Pro Pro Arg Ser Val Pro Gly Val Ser Cys Pro Glu Ser
                245                     250                     255

Leu Gln Arg Ser Asp Pro Leu Glu Gly Pro Ser Xaa Leu Pro Ser Ser
                260                     265                     270

Pro Pro Val Leu Gln Leu Ala Met Pro Met Pro Leu Leu Gly Ala Gly
            275                     280                     285

Glu Cys Asn Pro Phe Thr Ala Ile Gly Cys Ala Met Thr Glu Thr Xaa
        290                     295                     300

Gly Xaa Pro Xaa Xaa Leu Pro Ser Tyr Pro Pro Lys Lys Glu Val Ser
305                     310                     315                     320

Glu Trp Ser Asp Glu Ser Trp Ser Thr Thr Thr Ala Ser Ser Tyr
                325                     330                     335

Val Thr Gly Pro Pro Tyr Pro Lys Ile Arg Gly Lys Asp Ser Thr Gln
            340                     345                     350

Ser Ala Thr Ala Lys Arg Pro Thr Lys Lys Leu Gly Lys Ser Glu
        355                     360                     365

Phe Ser Cys Ser Met Ser Tyr Thr Trp Thr Asp Val Ile Ser Phe Lys
        370                     375                     380

Thr Ala Ser Lys Val Leu Ser Ala Thr Arg Ala Ile Thr Ser Gly Phe
385                     390                     395                     400

Leu Lys Gln Arg Ser Leu Val Tyr Val Thr Glu Pro Arg Asp Ala Glu 405                 410                 415
Leu Arg Lys Gln Lys Val Thr Ile Asn Arg Gln Pro Leu Phe Pro Pro
            420                 425                 430

Ser Tyr His Lys Gln Val Arg Leu Ala Lys Glu Lys Ala Ser Lys Val
            435                 440                 445

Val Gly Val Met Trp Asp Tyr Asp Glu Val Ala Ala His Thr Pro Ser
    450                 455                 460

Lys Ser Ala Lys Ser His Ile Thr Gly Leu Arg Gly Thr Asp Val Leu
465                 470                 475                 480

Asp Leu Gln Lys Cys Val Glu Ala Gly Glu Ile Pro Ser His Tyr Arg
                485                 490                 495

Gln Thr Val Ile Val Pro Lys Glu Glu Val Phe Val Lys Thr Pro Gln
            500                 505                 510

Lys Pro Thr Lys Lys Pro Pro Arg Leu Ile
        515                 520

(2) INFORMATION FOR SEQ ID NO:607:

(i) SEQUENCE CHARACTERISTICS:
        (A) LENGTH: 118 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:607:

Met Pro Val Ile Ser Thr Gln Thr Ser Pro Val Pro Ala Pro Arg Thr
1               5                   10                  15

Arg Lys Asn Lys Gln Thr Gln Ala Ser Tyr Pro Val Ser Ile Lys Thr
            20                  25                  30

Ser Val Glu Arg Gly Gln Arg Ala Xaa Arg Lys Val Gln Arg Asp Ala
        35                  40                  45

Arg Pro Arg Asn Tyr Lys Ile Ala Gly Ile His Asp Gly Leu Gln Thr
    50                  55                  60

Leu Ala Gln Ala Ala Leu Pro Ala His Gly Trp Gly Arg Gln Asp Pro
65                  70                  75                  80

Arg His Lys Ser Arg Asn Leu Gly Ile Leu Leu Asp Tyr Pro Leu Gly
                85                  90                  95

Trp Ile Gly Asp Val Thr Thr His Thr Pro Leu Val Gly Pro Leu Val
            100                 105                 110

Ala Gly Ala Val Val Arg
        115

(2) INFORMATION FOR SEQ ID NO:608:

(i) SEQUENCE CHARACTERISTICS:
        (A) LENGTH: 343 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:608:

Gly Ser Gly Trp Thr Asp Glu Asp Glu Arg Asp Leu Val Glu Thr Lys
1               5                   10                  15

Ala Ala Ala Ile Glu Ala Ile Gly Ala Ala Leu His Leu Pro Ser Pro
            20                  25                  30

```
Glu Ala Ala Gln Ala Ala Leu Glu Ala Leu Glu Ala Ala Val Ser
            35                  40                  45

Leu Leu Pro His Val Pro Val Ile Met Gly Asp Asp Cys Ser Cys Arg
        50                  55                  60

Asp Glu Ala Phe Gln Gly His Phe Ile Pro Glu Pro Asn Val Thr Glu
65                      70                  75                  80

Val Pro Ile Glu Pro Thr Val Gly Asp Val Glu Ala Leu Lys Leu Arg
                85                  90                  95

Ala Ala Asp Leu Thr Ala Arg Leu Gln Asp Leu Glu Ala Met Ala Leu
                100                 105                 110

Ala Arg Ala Glu Ser Ile Glu Asp Ala Arg Ala Ala Ser Met Pro Ser
        115                 120                 125

Leu Thr Glu Val Asp Ser Met Pro Ser Leu Glu Ser Ser Pro Cys Ser
        130                 135                 140

Ser Phe Glu Gln Ile Ser Leu Thr Glu Ser Asp Pro Glu Thr Val Val
145                 150                 155                 160

Glu Ala Gly Xaa Pro Leu Glu Phe Val Asn Ser Asn Thr Gly Xaa Ser
                165                 170                 175

Pro Ala Arg Arg Ile Val Arg Ile Arg Gln Ala Cys Cys Cys Asp Arg
                180                 185                 190

Ser Thr Met Lys Ala Met Pro Leu Ser Phe Thr Val Gly Glu Cys Leu
        195                 200                 205

Phe Val Thr Arg Tyr Asp Pro Asp Gly His Gln Leu Phe Asp Glu Arg
        210                 215                 220

Gly Pro Ile Glu Val Ser Thr Pro Ile Cys Glu Val Ile Gly Asp Ile
225                 230                 235                 240

Arg Leu Gln Cys Asp Gln Ile Glu Glu Thr Pro Thr Ser Tyr Ser Tyr
                245                 250                 255

Ile Trp Ser Gly Ala Pro Leu Gly Thr Gly Arg Ser Val Pro Gln Pro
                260                 265                 270

Met Thr Arg Pro Ile Gly Thr His Leu Thr Cys Asp Thr Thr Lys Val
        275                 280                 285

Tyr Val Thr Asp Pro Asp Arg Ala Ala Glu Arg Ala Glu Lys Val Thr
        290                 295                 300

Ile Trp Arg Gly Asp Arg Lys Tyr Asp Lys His Tyr Glu Ala Val Val
305                 310                 315                 320

Glu Ala Val Leu Lys Lys Ala Ala Thr Lys Ser His Gly Trp Thr
                325                 330                 335

Tyr Ser Gln Ala Ile Ala Lys
                340
```

(2) INFORMATION FOR SEQ ID NO:609:

(i) SEQUENCE CHARACTERISTICS:
        (A) LENGTH: 222 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:609:

```
Tyr Ser Gln Ala Ile Ala Lys Val Arg Arg Arg Ala Ala Ala Gly Tyr
1               5                   10                  15

Gly Ser Lys Val Thr Ala Ser Thr Leu Ala Thr Gly Trp Pro His Val
                20                  25                  30
```

```
Glu Glu Met Leu Asp Lys Ile Ala Arg Gly Gln Glu Val Pro Phe Thr
         35                  40                  45

Phe Val Thr Lys Arg Glu Val Phe Phe Ser Lys Thr Thr Arg Lys Pro
 50                  55                  60

Pro Arg Phe Ile Val Phe Pro Pro Leu Asp Phe Arg Ile Ala Glu Lys
 65              70                  75                  80

Met Ile Leu Gly Asp Pro Gly Ile Val Ala Lys Ser Ile Leu Gly Asp
                 85                  90                  95

Ala Tyr Leu Phe Gln Tyr Thr Pro Asn Gln Arg Val Lys Ala Leu Val
                100                 105                 110

Lys Ala Trp Glu Gly Lys Leu His Pro Ala Ala Ile Thr Val Xaa Ala
            115                 120                 125

Thr Cys Phe Asp Ser Ser Ile Asp Glu His Asp Met Gln Val Glu Ala
        130                 135                 140

Ser Val Phe Ala Ala Ala Ser Asp Asn Pro Ser Met Val His Ala Leu
145                 150                 155                 160

Cys Lys Tyr Tyr Ser Gly Gly Pro Met Val Ser Pro Asp Gly Val Pro
                165                 170                 175

Leu Gly Tyr Arg Gln Cys Arg Ser Ser Gly Val Leu Thr Thr Ser Ser
                180                 185                 190

Ala Asn Ser Ile Thr Cys Tyr Ile Lys Val Ser Ala Ala Cys Arg Arg
            195                 200                 205

Val Gly Ile Lys Ala Pro Ser Phe Phe Ile Ala Gly Asp Asp
210                 215                 220
```

(2) INFORMATION FOR SEQ ID NO:610:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:610:

GGGGCCGAAT TCTACAGCAC ATATGGCATG TAC                                       33

(2) INFORMATION FOR SEQ ID NO:611:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:611:

GGGGAAAAGC TTATTAGTGT TTTTTGGTAG CCTCAAAG                             38

(2) INFORMATION FOR SEQ ID NO:612:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:612:

-continued

```
GGGGCCGAAT TCATCTTTGA GGCTACCAAA AAAC                                  34
```

(2) INFORMATION FOR SEQ ID NO:613:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:613:

```
GGGGAAAAGC TTATTAATAG TAGTATATGC CAGCTCTC                              38
```

(2) INFORMATION FOR SEQ ID NO:614:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:614:

```
GGGGCCGAAT TCGGGAGAGC TGGCATATAC TAC                                   33
```

(2) INFORMATION FOR SEQ ID NO:615:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:615:

```
GGGGAAAAGC TTATTAGTCA TTGGGAGCAG CATAGCC                               37
```

(2) INFORMATION FOR SEQ ID NO:616:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:616:

```
GGGGCCGAAT TCTATGGCTA TGCTGCTCCC AATG                                  34
```

(2) INFORMATION FOR SEQ ID NO:617:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:617:

```
GGGGAAAAGC TTATTATGCA CACTCCTCCA CGATTTC                               37
```

(2) INFORMATION FOR SEQ ID NO:618:

```
    (i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:618:

GGGGCCGAAT TCGAGGAAAT CGTGGAGGAG TGT                                      33

(2) INFORMATION FOR SEQ ID NO:619:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:619:

GGGGAAAAGC TTATTACTTG GACGCAATTG CGCCTCC                                  37

(2) INFORMATION FOR SEQ ID NO:620:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:620:

GAAT TCTCAGCAAT AGTTAAAGGC CAG                                            33

(2) INFORMATION FOR SEQ ID NO:621:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:621:

GGGGAAAAGC TTATTAATTT GCTCCTATCG CAGGTAAC                                 38

(2) INFORMATION FOR SEQ ID NO:622:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:622:

GGGGCCGAAT TCCCTGGGTT ACCTGCGATA GGA                                      33

(2) INFORMATION FOR SEQ ID NO:623:

(i) SEQUENCE CHARACTERISTICS:
        (A) LENGTH: 38 base pairs
        (B) TYPE: nucleic acid
```

```
        (C) STRANDEDNESS: single
        (D) TOPOLOGY: linear (ii) MOLECULE TYPE: DNA (genomic)

(xi) SEQUENCE DESCRIPTION: SEQ ID NO:623:

GGGGAAAAGC TTATTACAGA ACCCCACAAG GTTTTTTC                              38

(2) INFORMATION FOR SEQ ID NO:624:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:624:

GGGGAAGAAT TCTGCCAGAA GGGGTACAAG GGC                                   33

(2) INFORMATION FOR SEQ ID NO:625:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:625:

GGAAAAGGAT CCTTAACAGC AAGCAGATGT CGTCCA                                36

(2) INFORMATION FOR SEQ ID NO:626:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:626:

GGGGAAGAAT TCACTCCTTG GACGACATCT GCT                                   33

(2) INFORMATION FOR SEQ ID NO:627:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:627:

GGAAAAGGAT CCTTAACCTT CTAACGGGTC ACTTCG                                36

(2) INFORMATION FOR SEQ ID NO:628:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:628:

GGGGAAGAAT TCCTGCAACG AAGTGACCCG TTA                33

(2) INFORMATION FOR SEQ ID NO:629:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:629:

GGGGAAGGAT CCTTAAGTTG CAGACAGAAC TTTAGA             36

(2) INFORMATION FOR SEQ ID NO:630:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:630:

GGGGCCGAAT TCACTGCTTC TAAAGTTCTG TCT                33

(2) INFORMATION FOR SEQ ID NO:631:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:631:

GGAAAAGGAT CCTTAGATAA GCCTTGGGGG TTTCTT             36

(2) INFORMATION FOR SEQ ID NO:632:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:632:

GGGGAAGAAT TCTACGGTCC TGACGGTAAG GGT                33

(2) INFORMATION FOR SEQ ID NO:633:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:633:

GGAAAAGGAT CCTTAGTCAA CGCCAGCTGA AATTGC             36

(2) INFORMATION FOR SEQ ID NO:634:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:634:

GGGGAAGAAT TCCTTGAGGC AATTTCAGCT GGC                          33

(2) INFORMATION FOR SEQ ID NO:635:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:635:

GGAAAAGGAT CCTTACAACT GCAGAACAGG TGGTGA                       36

(2) INFORMATION FOR SEQ ID NO:636:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:636:

GGAAAAGGAT CCAGTGACGC TTGGTGCCTG GTC                          33

(2) INFORMATION FOR SEQ ID NO:637:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:637:

GGGGAAAAGC TTAAAGTTTA TTGTACAGGA ACCG                         34

(2) INFORMATION FOR SEQ ID NO:638:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:638:

GGGGAAGAAT TCCGGCTAGG TCGGTTCCTG TAC                          33

(2) INFORMATION FOR SEQ ID NO:639:

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:639:

GGAAAAGGAT CCTTATGTCC CATGCACGAC CACAGC                              36

(2) INFORMATION FOR SEQ ID NO:640:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:640:

GGGGAAGAAT TCTGGTTTGA GGCTGTGGTC GTG                                 33

(2) INFORMATION FOR SEQ ID NO:641:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:641:

GGAAAAGGAT CCTTACAAGG CCGCCCCAAT GGCCTC                              36

(2) INFORMATION FOR SEQ ID NO:642:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:642:

GGGGAAGAAT TCGCCGCCAT CGAGGCCATT GGG                                 33

(2) INFORMATION FOR SEQ ID NO:643:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:643:

GGAAAAGGAT CCTTACACCT CGGTGAGCGA AGGCATC                             37

(2) INFORMATION FOR SEQ ID NO:644:

(i) SEQUENCE CHARACTERISTICS:
        (A) LENGTH: 33 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:644:

GGGGAAGAAT TCGCAGCTTC GATGCCTTCG CTC                                         33

(2) INFORMATION FOR SEQ ID NO:645:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:645:

GGAAAAGGAT CCTTAAATCA CTTCACATAT AGGAGTAG                                    38

(2) INFORMATION FOR SEQ ID NO:646:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:646:

GGGGAAGAAT TCGAGGTATC TACTCCTATA TGTG                                        34

(2) INFORMATION FOR SEQ ID NO:647:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:647:

GGAAAAGGAT CCTTATTTAG CTATAGCCTG GGAATAG                                     37

(2) INFORMATION FOR SEQ ID NO:648:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:648:

CTCT GAACACCGCC GCAC                                                         24

(2) INFORMATION FOR SEQ ID NO:649:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:649:

AAGC ATGCAGTTGT TAAGG                                                                25

(2) INFORMATION FOR SEQ ID NO:650:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:650:

TGTT CAGTCCATCT CC                                                                   22

(2) INFORMATION FOR SEQ ID NO:651:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:651:

CTCTACTGCA CACGTCAGGT TCGG                                                           24

(2) INFORMATION FOR SEQ ID NO:652:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:652:

CCAGAGCCAC CAGGCATCCG C                                                              21

(2) INFORMATION FOR SEQ ID NO:653:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:653:

CAGGCAGAAG CCTATGTCCT CCAGG                                                          25

(2) INFORMATION FOR SEQ ID NO:654:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:654:

GTGGTAGTAG CCGAGAGATG CCTG                                                           24

(2) INFORMATION FOR SEQ ID NO:655:

(i) SEQUENCE CHARACTERISTICS:
  (A) LENGTH: 25 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:655:

CACTCCATCG CCTGCACTTA TCTCG  25

(2) INFORMATION FOR SEQ ID NO:656:

(i) SEQUENCE CHARACTERISTICS:
  (A) LENGTH: 25 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:656:

CTCGAATTGC AAGTTGGGTG CTTGG  25

(2) INFORMATION FOR SEQ ID NO:657:

(i) SEQUENCE CHARACTERISTICS:
  (A) LENGTH: 23 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:657:

GAATGTGACA AGTGTGAGGC ACG  23

(2) INFORMATION FOR SEQ ID NO:658:

(i) SEQUENCE CHARACTERISTICS:
  (A) LENGTH: 24 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:658:

GGAGATGCTA AAGCTGTGGG AATC  24

(2) INFORMATION FOR SEQ ID NO:659:

(i) SEQUENCE CHARACTERISTICS:
  (A) LENGTH: 24 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:659:

GAGGACGTGG CACTAGAGAC AGAG  24

(2) INFORMATION FOR SEQ ID NO:660:

(i) SEQUENCE CHARACTERISTICS:

(A) LENGTH: 34 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:660:

CAGTTCAAGC TTGTCCAGGA ATTCNNNNNG CGCA                                34

(2) INFORMATION FOR SEQ ID NO:661:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:661:

GCTTCGGCCA TTGGTTACAT TCTCC                                          25

(2) INFORMATION FOR SEQ ID NO:662:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:662:

GGTCATCATC CCGCATGTGC TAAC                                           24

(2) INFORMATION FOR SEQ ID NO:663:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:663:

GGGATTTAGG ACCAAGACCT C                                              21

(2) INFORMATION FOR SEQ ID NO:664:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:664:

CCAAAAGTCG AAAGGCACCT TCC                                            23

(2) INFORMATION FOR SEQ ID NO:665:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:665:

CAACCGTGCC TCTGCCAGCT TC                                                    22

(2) INFORMATION FOR SEQ ID NO:666:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:666:

TYGCYACKGC KACCCCHCCK G                                                     21

(2) INFORMATION FOR SEQ ID NO:667:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:667:

TGCCMGCTYT CCCMCKGCC                                                        19

(2) INFORMATION FOR SEQ ID NO:668:

(i) SEQUENCE CHARACTERISTICS:
            (A) LENGTH: 5091 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:668:

TACGTTTGGG TTCTTCCCAG GAGTCCCCCC CCTTAACAAC TGCATGCTTC TCGGCACTGA           60

GGTGTCAGAG GTATTGGGTG GGGCGGGCCT CACTGGGGGG TTTTACGAAC CTCTGGTGCG          120

GCGGTGTTCA GAGCTGATGG GTCGGCGGAA TCCGGTCTGC CCGGGGTTTG CATGGCTCTC         180

TTCGGGACGG CCTGATGGGT TCATACATGT TCAGGGCCAC TTGCAGGAGG TGGATGCGGG         240

CAACTTCATT CCGCCCCCAC GCTGGTTGCT CTTGGACTTT GTATTTGTCC TGTTATACCT         300

GATGAAGCTG GCAGAGGCAC GGTTGGTCCC GCTGATCCTC CTCCTGCTAT GGTGGTGGGT         360

GAACCAGTTG GCGGTCCTTG KTGTGSCGGC TGCKCRCGCC GCCGTGGCTG GAGAGGTGTT         420

TGCGGGCCCT GCCTTGTCCT GGTGTCTGGG CCTACCCTTC GTGAGTATGA TCCTGGGGCT         480

AGCAAACCTG GTGTTGTACT TCCGCTGGAT GGGTCCTCAA CGCCTGATGT TCCTCGTGTT         540

GTGGAAGCTC GCTCGGGGGG CTTTCCCGCT GGCATTACTG ATGGGGATTT CCGCCACTCG         600

CGGCCGCACC TCTGTGCTTG GCGCCGAATT CTGCTTTGAT GTCACCTTTG AAGTGGACAC         660

GTCAGTCTTG GGTTGGGTGG TTGCTAGTGT GGTGGCTTGG GCCATAGCGC TCCTGAGCTC         720

TATGAGCGCG GGGGGGTGGA AGCACAAAGC CATAATCTAT AGGACGTGGT GTAAAGGGTA         780

CCAGGCYCTT CGCCAGCGCG TGGTGCGTAG CCCCCTCGGG AGGGGCGGCC CACCAAGCCG         840

CTGACGATAR GCCTGGTGTC TGGCCTCTTA CATCTGGCCG GACGCTGTGA TGTTGGTGGT         900

```
TGTGGCCATG GTCCTCCTCT TCGGCCTTTT CGACGCGCTC GATTGGGCCT TGGAGGAGCT    960
CCTTGTGTCG CGGCCTTCGT TGCGTCGTTT GGCAAGGGTG GTGGAGTGTT GTGTGATGGC   1020
GGGCGAGAAG GCCACTACCG TCCGGCTTGT GTCCAAGATG TGCGCGAGAG GGGCCTACCT   1080
GTTTGACCAC ATGGGGTCGT TCTCGCGCGC GGTCAAGGAG CGCTTGCTGG AGTGGGACGC   1140
GGCTTTGGAG MCCCTGTCAT TCACTAGGAC GGACTGTCGC ATCATACGAG ACGCCGCCAG   1200
ACCCTGAGCT GCGGCCAATG CGTCATGGGC TTGCGTGGTG GCTAGGCGCG GCGATGAGGT   1260
CCTGATTGGG GTCTTTCAGG ATGTGAACCA CTTGCCTCCG GGGTTTGYTC CTACAGCGCC   1320
TGTTGTCATC CGTCGGTGCG GAAAGGGCTT CCTCGGGGTC ACTAAGGCTG CCTTGACTGG   1380
TCGGGATCCT GACTTACACC CAGGAAACGT CATGGTTTTG GGGACGGCTA CCTCGCGCAG   1440
CATGGGAACG TGCTTAAACG GGTTGCTGTT CACGACATTC CATGGGCTT CTTCCCGAAC   1500
CATTGCGACA CCTGTGGGGG CCCTTAACCC AAGGTGGTGG TCGGCCAGTG ATGACGTCAC   1560
GGTCTATCCC CTCCCCGATG GAGCTAACTC GTTGGTTCCC TGCTCGTGTC AGGCTGAGTC   1620
CTGTTGGGTC ATYCGATCCG ATGGGGCTCT TTGCCATGGC TTGAGCAAGG GGGACAAGGT   1680
AGAACTGGAC GTGGCCATGG AGGTTGCTGA CTTTCGTGGG TCGTCTGGGT CTCCTGTCCT   1740
ATGCGACGAG GGGCACGCTG TAGGAATGCT CGTGTCCGTC CTTCATTCGG GGGGAGGGT   1800
GACCGCGGCT CGATTCACTC GGCCGTGGAC CCAAGTCCCA ACAGACGCCA AGACTACCAC   1860
TGAGCCACCC CCGGTGCCAG CTAAAGGGGT TTTCAAAGAG GCTCCTCTTT TCATGCCAAC   1920
AGGGGCGGGG AAAAGCACAC GCGTCCCTTT GGAGTATGGA AACATGGGGC ACAAGGTCCT   1980
GATTCTCAAC CCGTCGGTTG CCACTGTGAG GGCCATGGGC CCTTACATGG AGAGGCTGGC   2040
GGGGAAACAT CCTAGCATTT TCTGTGGACA CGACACAACA GCTTTCACAC GGATCACGGA   2100
CTCTCCATTG ACGTACTCTA CCTATGGGAG GTTTCTGGCC AACCCGAGGC AGATGCTGAG   2160
GGGAGTTTCC GTGGTCATCT GTGATGAGTG CCACAGTCAT GACTCAACTG TGTTGCTGGG   2220
TATAGGCAGG GTCAGGGACG TGGCGCGGGG GTGTGGAGTG CAATTAGTGC TCTAGCCTAC   2280
TGCGACTCCC CCGGGCTCGC CTATGACTCA GCATCCATCC ATAATTGAGA CAAAGCTGGA   2340
CGTTGGTGAG ATCCCCTTTT ATGGGCATGG TATCCCCCTC GAGCGTATGA GGACTGGTCG   2400
CCACCTTGTA TTCTGCCATT CCAAGGCGGA GTGCGAGAGA TTGGCCGGCC AGTTCTCCGC   2460
GCGGGGGTT AATGCCATCG CCTATTATAG GGGTAAGGAC AGTTCCATCA TCAAAGACGG   2520
AGACCTGGTG GTTTGTGCGA CAGACGCGCT CTCTACCGGG TACACAGGAA ACTTCGATTC   2580
TGTCACCGAC TGTGGGTTGG TGGTGGAGGA GGTCGTTGAG GTGACCCTTG ATCCCACCAT   2640
TACCATTTCC TTGCGGACTG TCCCTGCTTC GGCTGAATTG TCGATGCAGC GGCGCGGACG   2700
CACGGGGAGA GGTCGGTCGG GCCGCTACTA CTACGCTGGG GTCGGTAAGG CTCCCGCGGG   2760
GGTGGTGCGG TCTGGTCCGG TCTGGTCGGC AGTGGAAGCT GGAGTGACCT GGTATGGAAT   2820
GGAACCTGAC TTGACAGCAA ACCTTCTGAG ACTTTACGAC GACTGCCCTT ACACCGCAGC   2880
CGTCGCAGCT GACATTGGTG AAGCCGCGGT GTTCTTTGCG GGCCTCGCGC CCCTCAGGAT   2940
GCATCCCGAT GTTAGCTGGG CAAAAGTTCG CGGCGTCAAT TGGCCCCTCC TGGTGGGTGT   3000
TCAGCGGACG ATGTGTCGGG AAACACTGTC TCCCGGCCCG TCGACGACC CTCAGTGGGC   3060
AGGTCTGAAA GGCCCGAATC CTGTCCCACT ACTGCTGAGG TGGGGCAATG ATTTGCCATC   3120
AAAAGTGGCC GGCCACCACA TAGTTGACGA TCTGGTCCGT CGGCTCGGTG TGGCGGAGGG   3180
ATACGTGCGC TGTGATGCTG GRCCCATCCT CATGGTGGGC TTGCCATAG CGGGCGGCAT   3240
```

```
GATCTACGCC TCTTACACTG GGTCGCTAGT GGTGGTAACA GACTGGGATG TGAAGGGAGG      3300

TGGCAATCCC CTTTATAGGA GTGGTGACCA GGCCACCCCT CAACCCGTGG TGCAGGTCCC      3360

CCCGGTAGAC CATCGGCCGG GGGGGAGTC TGCGCCACGG GATGCCAAGA CAGTGACAGA       3420

TGCGGTGGCA GCCATCCAGG TGAACTGCGA TTGGTCTGTG ATGACCCTGT CGATCGGGGA      3480

AGTCCTCACC TTGGCTCAGG CTAAGACAGC CGAGGCCTAC GCAGCTACTT CCAGGTGGCT      3540

CGCTGGCTGC TACACGGGGA CGCGGGCCGT CCCCACTGTA TCAATTGTTG ACAAGCTCTT      3600

CGCCGGGGGT TGGGCCGCCG TGGTGGGTCA CTGTCACAGC GTCATTGCTG CGGCGGTGGC      3660

TGCCTATGGA GCTTCTCGAA GTCCTCCACT GGCCGCGGCG GCGTCCTACC TCATGGGGTT      3720

GGGCGTCGGA GGCAACGCAC AGGCGCGCTT GGCTTCAGCT CTTCTACTGG GGGCTGCTGG      3780

GTACGGCTCT GGGGGACCCC TGTCAGTGGG ACTCACCATG GCGGGGGCCT TCATGGGACA      3840

GGTGCCAGCG TGTCCCCTCC CTCGTCACTG TCCTACTTGG GGCTGTGGGA GGTTGGGAGG      3900

GCGTTGTCAA CGCTGCCAGT CTCGTCTTCG ACTTCATGGC TGGGAAACTT TCAACAGAAG      3960

ACCTTTGGTA TGCCATCCCG GTACTCACTA GTCCTGGRGC GGGCCTCGCG GGGATTGCCC      4020

TTGGTCTGGT TTTGTACTCA GCAAACAACT CTGGCACTAC CACATGGCTG AACCGTCTGC      4080

TGACGACGTT GCCACGGTCA TCTTGCATAC CCGACAGCTA CTTCCAACAG CTGACTACT      4140

GCGACAAGGT CTCGGCAATC GTGCGCCGCC TGAGCCTTAC TCGCACCGTG GTGGCCCTGG      4200

TCAACAGGGA GCCTAAGGTG GATGAGGTCC AGGTGGGGTA CGTCTGGGAT CTGTGGGAGT      4260

GGGTGATGCG CCAGGTGCGC ATGGTGATGT CTAGACTCCG GGCCCTCTGC CCTGTGGTGT      4320

CACTCCCCTT GTGGCACTGC GGGGAGGGGT GGTCCGGTGA ATGGCTTCTC GATGGGCACG      4380

TGGAGAGTCG TTGTCTGTGC GGGTGTGTAA TCACCGGCGA CGTCCTCAAT GGGCAACTCA      4440

AAGATCCAGT TTACTCTACC AAGCTGTGCA GGCACTACTG GATGGGAACT GTGCCGGTCA      4500

ACATGCTGGG CTACGGGGAA ACCTCACCTC TTCTCGCCTC TGACACCCCG AAGGTGGTAC      4560

CCTTCGGGAC GTCGGGGTGG GCTGAGGTGG TGGTGACCCC TACCCACGTG GTGATCAGGC      4620

GCACGTCCTG TTACAAACTG CTTCGCCAGC AAATTCTTTC AGCAGCTGTA GCTGAGCCCT      4680

ACTACGTTGA TGGCATTCCG GTCTCTTGGG AGGCTGACGC GAGAGCGCCG GCCATGGTCT      4740

ACGGTCCGGG CCAAAGTGTT ACCATTGATG GGGAGCGCTA CACCCTTCCG CACCAGTTGC      4800

GGATGCGGAA TGTGGCGCCC TCTGAGGTTT CATCTGAGGT CAGCATCGAG ATCGGGACGG      4860

AGACTGAAGA CTCAGAACTG ACTGAGGCCG ATTTGCCACC AGCGGCTGCT GCCCTCCAAG      4920

CGATAGAGAA TGCTGCGAGA ATTCTCGAAC CGCACATCGA TGTCAYCATG GAGGATTGCA      4980

GTACACCCTC TCTCTGTGGT AGTAGCCGAG AGATGCCTGT GTGGGAGAA GACATACCCC       5040

GCACTCCATC GCCTGCACTT ATCTCGGTTA CGGAGAGCAG CTCAGATGAG A               5091
```

(2) INFORMATION FOR SEQ ID NO:669:

(i) SEQUENCE CHARACTERISTICS:
        (A) LENGTH: 373 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:669:

```
TCGCCACTGC TACCCCTCCG GGCTCCGTCA CTGTGTCCCA TCCTAACATC GAGGAGGTTG       60

CTCTGTCCAC CACCGGAGAG ATCCCCTTTT ACGGCAAGGC TATCCCCCTC GAGGTGATCA      120
```

```
AGGGGGGAAG ACATCTCATC TTCTGCCACT CAAAGAAGAA GTGCGACGAG CTCGCCGCGA      180

AGCTGGTCGC ATTGGGCATC AATGCCGTGG CCTACTACCG CGGTCTTGAC GTGTCTGTCA      240

TCCCGACCAG CGGCGATGTT GTCGTCGTGT CGACCGATGC TCTCATGACT GGCTTTACCG      300

GCGACTTCGA CTCTGTGATA GACTGCAACA CGTGTGTCAC TCAGACAGTC GATTTTAGCC      360

TTGACCCTAC CTT                                                         373

(2) INFORMATION FOR SEQ ID NO:670:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:670:

GACGTTGGTG AGATCCCCTT                                                   20

(2) INFORMATION FOR SEQ ID NO:671:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:671:

CGAAGTTTCC TGTGTACCC                                                    19

(2) INFORMATION FOR SEQ ID NO:672:

(i) SEQUENCE CHARACTERISTICS:
        (A) LENGTH: 156 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:672:

ATCCCCTTTT ATGGGCATGG CATACCCCTG GAGAGGATGC GGACCGGCAG GCACCTCGTA       60

ATCCCCTTTT ATGGGCATGG CATACCCCTG GAGAGGATGC GGACCGGCAG GCACCTCGTA      120

AATGCCATTG CCTATTATAG GGGGAAAGAC AGTTCT                                156

(2) INFORMATION FOR SEQ ID NO:673:

(i) SEQUENCE CHARACTERISTICS:
        (A) LENGTH: 156 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:673:

ATCCCCTTTT ATGGGCATGG AATCCCCCTC GAGCGGATGC GGACCGGGCG CCACCTCGTG       60

TTCTGCCATT CAAAGGCGGA GTGCGAGCGG TTGGCTGGCC AGTTCTCTTC GCGGGGGGTG      120

AATGCCATTG CCTATTACAG GGGGAAAGAC AGTTCC                                156
```

-continued (2) INFORMATION FOR SEQ ID NO:674:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:674:

CCAATCTCTC GCACTCCGCC TTG                                              23

(2) INFORMATION FOR SEQ ID NO:675:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:675:

CTCACCAACG TCCAGCTTTG TCTC                                           24

(2) INFORMATION FOR SEQ ID NO:676:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:676:

CTCGTATGAT GCGACAGTCC GTCC                                           24

(2) INFORMATION FOR SEQ ID NO:677:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:677:

GTAGTGGCCT TCTCGCCCGC CATC                                           24

(2) INFORMATION FOR SEQ ID NO:678:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:678:

CACTCCACCA CCCTTGCCAA ACG                                              23

(2) INFORMATION FOR SEQ ID NO:679:

(i) SEQUENCE CHARACTERISTICS:
        (A) LENGTH: 24 base pairs (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:679:

CCTGGTACCC TTTACACCAC GTCC                                              24

(2) INFORMATION FOR SEQ ID NO:680:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:680:

GATTATGGCC TTTGTGCTTC CACCC                                             25

(2) INFORMATION FOR SEQ ID NO:681:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:681:

CTCCAAAGCC GCGTCCCACT CCAGC                                             25

(2) INFORMATION FOR SEQ ID NO:682:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:682:

CATCATCAAA GACGGAGACC TGGTGG                                            26

(2) INFORMATION FOR SEQ ID NO:683:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:683:

GCATGATCTA CGCCTCTTAC ACTGG                                             25

(2) INFORMATION FOR SEQ ID NO:684:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:684:

GTCGCTAGTG GTGGTAACAG ACTGG                                           25

(2) INFORMATION FOR SEQ ID NO:685:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:685:

GGTGCGCATG GTGATGTCTA GACTC                                           25

(2) INFORMATION FOR SEQ ID NO:686:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:686:

GGTCCGGTGA ATGGCTTCTC GATGG                                           25

(2) INFORMATION FOR SEQ ID NO:687:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:687:

ACCAGTTGCG GATGCGGAAT GTG                                             23

(2) INFORMATION FOR SEQ ID NO:688:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:688:

GCATCGAGAT CGGGACGGAG ACTG                                            24

(2) INFORMATION FOR SEQ ID NO:689:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:689:

```
CAGTTCAAGC TTGTCCAGGA ATTCNNNNNG GCCA                                    34

(2) INFORMATION FOR SEQ ID NO:690:

(i) SEQUENCE CHARACTERISTICS:
          (A) LENGTH: 34 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:690:

CAGTTCAAGC TTGTCCAGGA ATTCNNNNNC CGGA                                    34

(2) INFORMATION FOR SEQ ID NO:691:

(i) SEQUENCE CHARACTERISTICS:
          (A) LENGTH: 24 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:691:

CATCAGCTCT GAACACCGCC GCAC                                               24

(2) INFORMATION FOR SEQ ID NO:692:

(i) SEQUENCE CHARACTERISTICS:
          (A) LENGTH: 25 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:692:

GCCGAGAAGC ATGCAGTTGT TAAGG                                              25

(2) INFORMATION FOR SEQ ID NO:693:

(i) SEQUENCE CHARACTERISTICS:
          (A) LENGTH: 22 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:693:

GCCAGCTGTT CAGTCCATCT CC                                                 22

(2) INFORMATION FOR SEQ ID NO:694:

(i) SEQUENCE CHARACTERISTICS:
          (A) LENGTH: 24 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:694:

CTCTACTGCA CACGTCAGGT TCGG                                               24

(2) INFORMATION FOR SEQ ID NO:695:
```

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:695:

CCAGAGCCAC CAGGCATCCG C                                         21

(2) INFORMATION FOR SEQ ID NO:696:

(i) SEQUENCE CHARACTERISTICS:
       (A) LENGTH: 25 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:696:

CAGGCAGAAG CCTATGTCCT CCAGG                                     25

(2) INFORMATION FOR SEQ ID NO:697:

(i) SEQUENCE CHARACTERISTICS:
       (A) LENGTH: 24 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:697:

GTGGTAGTAG CCGAGAGATG CCTG                                      24

(2) INFORMATION FOR SEQ ID NO:698:

(i) SEQUENCE CHARACTERISTICS:
       (A) LENGTH: 25 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:698:

CACTCCATCG CCTGCACTTA TCTCG                                     25

(2) INFORMATION FOR SEQ ID NO:699:

(i) SEQUENCE CHARACTERISTICS:
       (A) LENGTH: 25 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:699:

CTCGAATTGC AAGTTGGGTG CTTGG                                     25

(2) INFORMATION FOR SEQ ID NO:700:

(i) SEQUENCE CHARACTERISTICS:
       (A) LENGTH: 23 base pairs
       (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO:700:

GAATGTGACA AGTGTGAGGC ACG                                         23

(2) INFORMATION FOR SEQ ID NO:701:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:701:

GGAGATGCTA AAGCTGTGGG AATC                                        24

(2) INFORMATION FOR SEQ ID NO:702:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:702:

GAGGACGTGG CACTAGAGAC AGAG                                        24

(2) INFORMATION FOR SEQ ID NO:703:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:703:

GCCGCTGAAT TCATGCCTTG TTATTTCTAC TCAAAC                           36

(2) INFORMATION FOR SEQ ID NO:704:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:704:

GCCGCAGGAT CCTCGAACGA CCGCTCCTGC CAC                              33

(2) INFORMATION FOR SEQ ID NO:705:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:705:

GCCGCAGGAA TTCATGGCTT GGCTGTGGTT GCTG                                   34

(2) INFORMATION FOR SEQ ID NO:706:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: Modified site
             (B) LOCATION: 3
             (D) OTHER INFORMATION: /label= N
                 /note= "N = Inosine"

(ix) FEATURE:
             (A) NAME/KEY: Modified site
             (B) LOCATION: 6
             (D) OTHER INFORMATION: /label= N
                 /note= "N = Inosine"

(ix) FEATURE:
             (A) NAME/KEY: Modified site
             (B) LOCATION: 9
             (D) OTHER INFORMATION: /label= N
                 /note= "N = Inosine"

(xi) SEQUENCE DESCRIPTION: SEQ ID NO:706:

GCNACNGCNA CNCCNCCNGG                                                   20

(2) INFORMATION FOR SEQ ID NO:707:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: Modified site
             (B) LOCATION: 6
             (D) OTHER INFORMATION: /label= N
                 /note= "N = Inosine"

(ix) FEATURE:
             (A) NAME/KEY: Modified site
             (B) LOCATION: 8
             (D) OTHER INFORMATION: /label= N
                 /note= "N = Inosine"

(ix) FEATURE:
             (A) NAME/KEY: Modified site
             (B) LOCATION: 9
             (D) OTHER INFORMATION: /label= N
                 /note= "N = Inosine"

(xi) SEQUENCE DESCRIPTION: SEQ ID NO:707:

ATGGTNANNG TNGGRTCHAR R                                                 21

(2) INFORMATION FOR SEQ ID NO:708:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:708:

ATGGGCATGG CATCCCCCTG GA                                                22

(2) INFORMATION FOR SEQ ID NO:709:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:709:

TCCTTGATGA TTGAACTGTC                                                   20

(2) INFORMATION FOR SEQ ID NO:710:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:710:

GGCACCTCGT GTTCTGCCA                                                    19

(2) INFORMATION FOR SEQ ID NO:711:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:711:

AGGTCTCCGT CCTTGATGAT                                                   20

(2) INFORMATION FOR SEQ ID NO:712:

(i) SEQUENCE CHARACTERISTICS:
        (A) LENGTH: 199 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:712:

TTATGGGCAT GGCATCCCCC TGGAGCGGAT GAGGACCGGT AGGCACCTGG TATTCTGCCA        60

CTCAAAGGCG GAGTGTGAGA GGCTGGCCGG CCAATTCTCC TCACGGGGG TTAATGCTGT        120

TGCCTATTAT AGGGGTAAGG ACAGTTCAAT CATCAAGGAT GGTGACCTGG TGGTGTGCGC       180

TACTGACGCG CTATCTACC                                                   199

(2) INFORMATION FOR SEQ ID NO:713:

(i) SEQUENCE CHARACTERISTICS:
        (A) LENGTH: 199 base pairs
        (B) TYPE: nucleic acid -continued

```
            (C) STRANDEDNESS: double
            (D) TOPOLOGY: linear (ii) MOLECULE TYPE: DNA (gen full complement, wherein said HGBV comprises a positive stranded RNA viral genome comprising an open reading frame encoding a polyprotein, wherein said polyprotein
(i) has an amino acid sequence having at least 35% identity to a polyprotein sequence selected from the group consisting of SEQ ID NO:387, SEQ ID NO:394, and SEQ ID NO:401 wherein said % identity is determined by using the computer program GAP of the Wisconsin Package, Version 8 with the gap penalty set to 3 and the gap extension penalty set to 0.1; and
(ii) is not immunoreactive with an antibody that specifically reacts with a protein encoded by a virus selected from the group consisting of hepatitis A virus, hepatitis B virus, hepatitis C virus, hepatitis delta virus and hepatitis E virus, under conditions and for a time which allows the formation of a complex between the probe and the target HGBV nucleic acid in the test sample; and
(b) detecting the complex that contains the target HGBV nucleic acid wherein the presence of the complex is indicative of the presence of the target HGBV.

2. The method of claim 1, wherein the target HGBV is amplified prior to performing step (a).

3. The method of claim 2, wherein said amplifying is performed by the polymerase chain reaction or the ligase chain reaction.

4. The method of claim 1, wherein said polynucleotide probe further comprises a measurable signal generating compound.

5. The method of claim 4, wherein said signal generating compound is selected from the group consisting of a chemiluminescent compound, fluorescein, an enzyme, and a radioactive element.

6. The method of claim 2, wherein said target is immobilized on a solid phase.

7. The method of claim 4, wherein said target is immobilized on a solid phase.

8. The method of claim 2, wherein said amplifying further comprises utilizing a primer conjugated to a first hapten.

9. The method of claim 8, further comprising contacting said complex with said primer-first hapten under conditions and for a time which allows the formation of a complex between the probe/target and the primer-first hapten.

10. The method of claim 9, further comprising contacting said probe/target/first hapten complex with an anti-first hapten antibody conjugated to a detectable signal generating compound prior to performing step (b).

11. The method of claim 10, wherein said signal generating compound is selected from the group consisting of a chemiluminescent compound, fluorescein, an enzyme, and a radioactive element.

12. The method of claim 1, wherein said probe is immobilized on a solid phase.

13. The method of claim 12, wherein said probe is immobilized to said solid phase prior to performing step (a).

14. The method of claim 8, wherein said first hapten is selected from the group consisting of adamatane, carbazole, fluorescein, and biotin.

15. The method of claim 14, wherein said polynucleotide probe is conjugated to a second hapten, with the proviso that the second hapten is different than the first hapten.

16. The method of claim 15, further comprising reacting said probe with a solid phase to which an anti-second hapten antibody conjugated to said probe is immobilized, prior to performing step (b).

17. The method of claim 16, further comprising contacting an anti-first hapten antibody conjugated to a measurable signal generating compound with said probe/target complex prior to performing step (b).

18. The method of claim 17, wherein said signal generating compound is selected from the group consisting of a chemiluminescent compound, fluorescein an enzyme, and a radioactive element.

19. The method of claim 2, wherein said polynucleotide probe is conjugated to a hapten.

20. The method of claim 19, wherein said hapten is selected from the group consisting of adamatane, carbazole, fluorescein, and biotin.

21. The method of claim 19, further comprising immobilizing said target to a solid phase prior to performing step (b).

22. A test kit useful for determining the presence of target hepatitis GB virus (HGBV) nucleic acid in a test sample, comprising a container containing a polynucleotide probe wherein said polynucleotide probe comprises a sequence of at least 15 contiguous nucleotides, and wherein said polynucleotide probe selectively hybridizes to a genome of hepatitis GB (HGBV) or its full complement, wherein said HGBV comprises a positive stranded RNA viral genome comprising an open reading frame encoding a polyprotein, wherein said polyprotein
(a) has an amino acid sequence having at least 35% identity to a polyprotein sequence selected from the group consisting of SEQ ID NO:387, SEQ ID NO:394, and SEQ ID NO:401 wherein said % identity is determined by using the computer program GAP of the Wisconsin Package, Version 8 with the gap penalty set to 3 and the gap extension penalty set to 0.1; and
(b) is not immunoreactive with an antibody that specifically reacts with a protein encoded by a virus selected from the group consisting of hepatitis A virus, hepatitis B virus, hepatitis C virus, hepatitis delta virus, and hepatitis E virus.

23. The test kit of claim 22, wherein said polynucleotide probe further comprises a measurable signal generating compound.

24. The test kit of claim 22, wherein said signal generating compound is selected from the group consisting of a chemiluminescent compound, fluorescein an enzyme, and a radioactive element.

25. The test kit of claim 22, wherein said polynucleotide probe further comprises a hapten.

26. The test kit of claim 25, wherein said hapten is selected from the group consisting of adamatane, carbazole, fluorescein, and biotin.

27. The test kit of claim 22, further comprising a container containing at least one primer.

28. The test kit of claim 27, wherein said primer further comprises a hapten.

29. The test kit of claim 28, wherein said hapten is selected from the group consisting of adamatane, carbazole, fluorescein, and biotin.

30. The test kit of claim 28 wherein said test kit further comprises a solid phase to which a second hapten is immobilized.

31. The test kit of claim 30, wherein said second hapten is selected from the group consisting of adamatane, carbazole, fluorescein, and biotin, with the proviso that the second hapten is different than the first hapten.

32. The method of claim 1, wherein said encoded polyprotein has an amino acid sequence having at least 40% identity to a polyprotein selected from the group consisting of SEQ ID NO:387, SEQ ID NO:394, and SEQ ID NO:401.

33. The test kit of claim 22, wherein said encoded polyprotein has an amino acid sequence having at least 40% identity to a polyprotein selected from the group consisting of SEQ ID NO:387, SEQ ID NO:394, and SEQ ID NO:401.

34. The method of claim 1, wherein said encoded polyprotein has an amino acid sequence having at least 60% identity to a polyprotein selected from the group consisting of SEQ ID NO:387, SEQ ID NO:394, and SEQ ID NO:401.

35. The test kit of claim 22, wherein said encoded polyprotein has an amino acid sequence having at least 60% identity to a polyprotein selected from the group consisting of SEQ ID NO:387, SEQ ID NO: 394, and SEQ ID NO:401.

* * * * *